US011761967B2

(12) United States Patent
Anderberg et al.

(10) Patent No.: US 11,761,967 B2
(45) Date of Patent: *Sep. 19, 2023

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/085,351

(22) Filed: Oct. 30, 2020

(65) Prior Publication Data

US 2021/0080474 A1 Mar. 18, 2021

Related U.S. Application Data

(60) Continuation of application No. 15/589,836, filed on May 8, 2017, now Pat. No. 10,823,742, which is a division of application No. 13/806,760, filed as application No. PCT/US2011/001128 on Jun. 23, 2011, now abandoned.

(60) Provisional application No. 61/364,297, filed on Jul. 14, 2010, provisional application No. 61/364,305, filed on Jul. 14, 2010, provisional application No. 61/357,965, filed on Jun. 23, 2010, provisional application No. 61/357,966, filed on Jun. 23, 2010.

(51) Int. Cl.
   *G01N 33/68* (2006.01)

(52) U.S. Cl.
   CPC ... *G01N 33/6893* (2013.01); *G01N 2333/475* (2013.01); *G01N 2333/49* (2013.01); *G01N 2333/52* (2013.01); *G01N 2333/521* (2013.01); *G01N 2333/54* (2013.01); *G01N 2333/5418* (2013.01); *G01N 2333/71* (2013.01); *G01N 2333/7155* (2013.01); *G01N 2333/96494* (2013.01); *G01N 2800/347* (2013.01); *G01N 2800/50* (2013.01); *G01N 2800/52* (2013.01); *G01N 2800/56* (2013.01)

(58) Field of Classification Search
   CPC . G01N 2333/8146; G01N 2333/96494; G01N 33/6893; G01N 2800/52; G01N 2333/521; G01N 2800/347; G01N 2800/50; G01N 2800/56

See application file for complete search history.

(56) References Cited

U.S. PATENT DOCUMENTS

| | | |
|---|---|---|
| 5,324,634 A | 6/1994 | Zucker |
| 5,480,792 A | 1/1996 | Buechler et al. |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler |
| 6,143,576 A | 11/2000 | Buechler |
| 6,218,122 B1 | 4/2001 | Friend et al. |

(Continued)

FOREIGN PATENT DOCUMENTS

| | | |
|---|---|---|
| CN | 1791797 | 6/2006 |
| CN | 101010001 A | 8/2007 |

(Continued)

OTHER PUBLICATIONS

Askenazi et al. American Journal of Kidney Diseases 53.4: A27. W.B. Saunders. (Apr. 2009) (Year: 2009).*

(Continued)

*Primary Examiner* — Vanessa L. Ford
*Assistant Examiner* — Sandra Dillahunt
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using a one or more assays configured to detect a kidney injury marker selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor A/B dimer, Platelet-derived growth factor A/A dimer, and MMP9: TIMP2 complex as diagnostic and prognostic biomarkers in renal injuries.

20 Claims, No Drawings

Specification includes a Sequence Listing.

(56) References Cited

U.S. PATENT DOCUMENTS

| | | |
|---|---|---|
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,662,578 B2 | 2/2010 | Devarajan |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 8,252,905 B2 | 8/2012 | Furusako et al. |
| 8,778,615 B2 | 7/2014 | Anderberg et al. |
| 8,871,459 B2 | 10/2014 | Anderberg et al. |
| 8,993,250 B2 | 3/2015 | Anderberg et al. |
| 9,029,093 B2 | 5/2015 | Anderberg et al. |
| 9,057,735 B2 | 6/2015 | Anderberg et al. |
| 9,229,010 B2 | 1/2016 | Anderberg et al. |
| 9,360,488 B2 | 6/2016 | Anderberg et al. |
| 9,459,261 B2 | 10/2016 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | McPherson et al. |
| 2003/0003588 A1 | 1/2003 | Comper |
| 2004/0029200 A1 | 2/2004 | Weimbs |
| 2004/0053309 A1 | 3/2004 | Holt et al. |
| 2004/0106155 A1 | 6/2004 | Comper |
| 2004/0219603 A1 | 11/2004 | Devarajan et al. |
| 2004/0241744 A1 | 12/2004 | Kohno et al. |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0166779 A1 | 7/2007 | Belkowski et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0111427 A1 | 5/2011 | Kadomatsu et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0142754 A1 | 6/2012 | Niitsu et al. |
| 2012/0190044 A1 | 7/2012 | Anderberg et al. |
| 2012/0190051 A1 | 7/2012 | Anderberg et al. |
| 2012/0283128 A1 | 11/2012 | Anderberg et al. |
| 2013/0035290 A1 | 2/2013 | Elias et al. |
| 2013/0065239 A1 | 3/2013 | Bodavilla Sandoval et al. |
| 2013/0157881 A1 | 6/2013 | Anderberg et al. |
| 2013/0210041 A1 | 8/2013 | Anderberg et al. |
| 2013/0210043 A1 | 8/2013 | Anderberg et al. |
| 2014/0323594 A1 | 10/2014 | Anderberg et al. |
| 2014/0377777 A1 | 12/2014 | Anderberg et al. |
| 2015/0355196 A1 | 12/2015 | Anderberg et al. |
| 2016/0146832 A1 | 5/2016 | Chawla et al. |
| 2016/0274128 A1 | 9/2016 | Anderberg et al. |
| 2016/0281083 A1 | 9/2016 | Niitsu et al. |
| 2016/0297893 A1 | 10/2016 | Vijayendran et al. |
| 2016/0303187 A1 | 10/2016 | McPherson et al. |
| 2017/0248613 A1 | 8/2017 | Anderberg et al. |
| 2018/0074054 A1 | 3/2018 | McPherson et al. |
| 2019/0263926 A1 | 8/2019 | McPherson et al. |

FOREIGN PATENT DOCUMENTS

| | | |
|---|---|---|
| CN | 101358976 | 2/2009 |
| CN | 102539745 | 7/2012 |
| CN | 103080743 | 7/2015 |
| EP | 0828159 | 3/1998 |
| EP | 1905846 | 4/2008 |
| EP | 1970709 | 9/2008 |
| EP | 2261660 | 12/2010 |
| EP | 2479564 | 7/2012 |
| EP | 2480882 | 8/2012 |
| EP | 2513649 | 10/2012 |
| JP | H09-072906 | 3/1997 |
| JP | H09-274036 | 10/1997 |
| JP | 2005-120070 | 5/2005 |
| JP | 2008-224526 | 9/2008 |
| JP | 2008-537875 | 10/2008 |
| JP | 2012-508382 | 4/2012 |
| JP | 2012-510058 | 4/2012 |
| RU | 2180965 | 3/2002 |
| SU | 1429031 | 10/1988 |
| WO | WO 1998/055508 | 12/1998 |
| WO | WO 2001/028500 A2 | 4/2001 |
| WO | WO 2001/090421 | 11/2001 |
| WO | WO 2003/054004 | 7/2003 |
| WO | WO 2003/075016 | 9/2003 |
| WO | WO 2004/005934 | 1/2004 |
| WO | WO 2004/088276 | 10/2004 |
| WO | WO 2005/002416 | 1/2005 |
| WO | WO 2005/087264 | 9/2005 |
| WO | WO 2005/121788 | 12/2005 |
| WO | WO 2006/044779 | 4/2006 |
| WO | WO 2006/083986 | 8/2006 |
| WO | WO 2007/013919 | 2/2007 |
| WO | WO 2007/024743 | 3/2007 |
| WO | WO 2007/039109 | 4/2007 |
| WO | WO 2007/041623 | 4/2007 |
| WO | WO 2007/084397 A2 | 7/2007 |
| WO | WO 2007/093183 A2 | 8/2007 |
| WO | WO 2007/121922 | 11/2007 |
| WO | WO 2007/144781 | 12/2007 |

(56) References Cited

FOREIGN PATENT DOCUMENTS

| | | |
|---|---|---|
| WO | WO 2008/060607 | 5/2008 |
| WO | WO 2008/084331 | 7/2008 |
| WO | WO 2008/104804 | 9/2008 |
| WO | WO 2008/116867 | 10/2008 |
| WO | WO 2008/122670 | 10/2008 |
| WO | WO 2008/154238 | 12/2008 |
| WO | WO 2009/038742 | 3/2009 |
| WO | WO 2009/062520 | 5/2009 |
| WO | WO 2010/025424 | 3/2010 |
| WO | WO 2010/025434 | 3/2010 |
| WO | WO 2010/048346 | 4/2010 |
| WO | WO 2010/048347 | 4/2010 |
| WO | WO 2010/054389 | 5/2010 |
| WO | WO 2010/059996 | 5/2010 |
| WO | WO 2010/091236 | 8/2010 |
| WO | WO 2010/111746 | 10/2010 |
| WO | WO 2010/128158 | 11/2010 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Kallakury et al. Clinical Cancer Research, 2001; 7:3113-3119 (Year: 2001).*

"3-reactive Protein," MedlinePlus Medical Encyclopedia. National Institutes of Health/US National Library of Medicine, Feb. 11, 2013, Web Jul. 31, 2015 http://www.nlm.nih.gov/medlineplus/ency/article/003356.htm.

Abd El Latif et al., "Urinary epidermal growth factor excretion: a useful prognostic marker for progression of renal damage in children," J Med Sci, Oct. 2007, 7(7):1171-1176.

Abou-Shousha et al., "Interleukin-2 Regulatory Effect on P-Selectin and Interleukin-8 Production in Patients with Chronic Renal Failure," Egypt J Immunol, 2006, 13(1):11-18.

Akcay et al., "Mediators of Inflammation in Acute Kidney Injury," Mediators Inflamm, 2009, 2009:137072 (12 pp).

Alatas et al., "Beneficial Effects of Allopurinol on Glutathione Levels and Glutathione Peroxidase Activity in Rat Ischaemic Acute Renal Failure," The Journal of International Medical Research, 1996, 24:33-39.

Albright, "Acute Renal Failure: A Practical Update," Mayo Clin Proc, Jan. 2001, 76(1):67-74.

Alere Triage BNP Test Product Insert, Rapid Quantitative Test for B-type Natriuretic Peptide, 2011, 28 pages.

Allakhverdi et al., "Thymic stromal lymphopoietin is released by human epithelial cells in response to microbes, trauma, or inflammation arid potently activates mast cells," J Exp Med, Feb. 19, 2007, 204(2):253-258.

Amar et al., "Potential clinical implications of recent matrix metalloproteinase inhibitor design strategies," Expert Rev Proteomics, 2015, 12(5):445-447.

Anders et al., "Chemokines and chemokine receptors are involved in the resolution or progression of renal disease," Kidney Int, Feb. 2003, 63(2):401-415.

Anilkumar et al., "Trimeric assembly of the C-terminal region of Thrombospondin-1 or Thrombospondin-2 is necessary for cell spreading and fascin spike organisation," J Cell Sci, Jun. 1, 2002, 115(Pt 11):2357-2366.

Arribas et al., "ADAM17 as a Therapeutic Target in Multiple Diseases," Curr Pharm Des, 2009,15(20):2319-2335.

Arrizabalaga et al., "Tubular and Interstitial Expression of ICAM-1 as a Marker of Renal Injury in IgA Nephropathy," Am J Nephrol, May-Jun. 2003, 23(3):121-128.

Arthur et al., "Diagnostic and Prognostic Biomarkers in Acute Renal Failure," Contributions to Nephrology, Karger, Jan. 2008, 160:53-64.

Asanuma et al., "Selective modulation of the secretion of proteinases and their inhibitors by growth factors in cultured differentiated podocytes," Kidney Int, 2002, 62:822-831.

Atkins et al., "Heat Shock Proteins in Renal Cell Carcinomas," Contrib Nephrol, 2005, 148:35-56.

Bagshaw et al., "A multi-centre evaluation of the Rifle criteria for early acute kidney injury in critically ill patients," Nephrol Dial Transplant, 2008, 23:1203-1210.

Bagshaw et al., "Urinary biomarkers in septic acute kidney injury," Intensive Care Med, Jul. 2007, 33(7):1285-1296.

Bajwa et al., "Immune Mechanisms and Novel Pharmacological Therapies of Acute Kidney Injury," Curr Drug Targets, Dec. 2009, 10(12):1196-1204.

Barrera-Chimal et al., "Hsp72 is an early and sensitive biomarker to detect acute kidney injury," EMBO Mol Med, Jan. 2011, 3(1):5-20.

Basile et al., "Angiostatin and matrix metalloprotease expression following ischemic acute renal failure," Am J Physiol Renal Physiol, May 2004, 286:F893-F902.

Bauer et al., Gawaz, "Sensitive Cardiac Troponin Assays," The New England Journal of Medicine, 2009, 361(26):2575-2577.

Bellomo et al., "Acute renal failure—definition, outcome measures, animal models, fluid therapy and information technology needs: the Second International Consensus Conference of the Acute Dialysis Quality Initiative (ADQI) Group," Crit Care, Aug. 2004, 8(4):R204-R212.

Berahovich et al., "Proteolytic activation of alternative CCR1 ligands in inflammation," J Immunol, Jun. 1, 2005, 174(11):7341-7351.

Berthier et al., "Metzincins, including matrix metalloproteinases and meprin, in kidney transplantation," Swiss Med Wkly, Dec. 23, 2006, 136(49-50):789-794.

Beushausen, "NWG Biomarker Objectives," ILSI Health and Environmental Sciences Institute, ILSI-HESI Annual Meeting, 2006:17 pp.

Bicik et al., "Role of Transforming Growth Factor-.beta.2 in, and a Possible Transforming Growth Factor-beta2 Gene Polymorphism as a Marker of, Renal Dysfunction in Essential Hypertension: A Study in Turkish Patients," Current Therapeutic Research, 2005, 44(4):266-278.

Biotrin International, "Biotrin Biomarkers: How late do you want to detect preclinical kidney damage?," Biotrin's acute kidney injury test (AKI Test), Biotrin's Preclinical Kidney Biomarkers: 8 pp.

Bonomini et al., "Serum Levels of Soluble Adhesion Molecules in Chronic Renal Failure and Dialysis Patients," Nephron. Aug. 1998, 79(4):399-407.

Bonventre, "Dedifferentiation and Proliferation of Surviving Epithelial Cells in Acute Renal Failure," J Am Soc Nephrol, Jun. 2003, 14 Suppl 1:S55-S61.

Bonventre, "Pathophysiology of Acute Kidney Injury: Roles of Potential Inhibitors of Inflammation," Contrib Nephrol, 2007, 156:39-46.

Bonventre et al., "Ischemic acute renal failure: An inflammatory disease?," Kidney Int, Aug. 2004, 66(2):480-485.

Briasoulis et al., "A Retrospective Analysis of Serum CA 15-3 Concentrations in Patients with Localised or Metastatic Renal Cancer and its Impact on Prognosis and Follow-up. A Single-centre Experience," UroOncology, 2002, 2(4):179-184.

Brook et al., "Fibrosis-associated gene expression in renal transplant glomeruli after acute renal allograft rejection," Br J Surg, 2003, 90:1009-1014.

(56) References Cited

OTHER PUBLICATIONS

Burne et al., "IL-1 and TNF independent pathways mediate ICAM-1NCAM-1 up-regulation in ischemia repertusion injury," J Leukoc Biol, Aug. 2001, 70(2):192-198.
Burne-Taney et al., "The role of adhesion molecules and T cells in ischemic renal injury," Curr Opin Nephrol Hypertens, Jan. 2003, 12(1):85-90.
Bussieres et al., "Fetal Urinary Insulin-Like Growth Factor I and Binding Protein 3 in Bilateral Obstructive Uropathies," Prenat Diagn, 1995, 15:1047-1055.
Cai, "Detection and Application for the biomarker of Rental Injury in Early Stage," Laboratory Med Clinic, Jun. 2005, 2(3):124-127—includes English translation abstract only.
Calabrese et al., "Oxidative stress and cellular stress response in diabetic nephropathy," Database Biosis [Online], Biosciences Information Service Jan. 2007; XP002705326. Database accession No. PREV200800097004 (abstract):3 pages & Cell Stress Chaperones. 2007 Winter; 12(4):299-306.
Canani et al., "The Fatty Acid-Binding Protein-2 A54T Polymorphism Is Associated With Renal Disease in Patients With Type 2 Diabetes," Diabetes, Nov. 2005, 54(11):3326-3330.
Caron et al. "Ischemic injury alters endothelial cell properties of kidney cortex:stimulation of MMP-9," Exp Cell Res, Oct. 2005, 301:105-116.
Caron et al., "Ischemia-reperfusion injury stimulates gelatinase expression and activity in kidney glomeruli," Can J Physiol Pharmacol, 2005, 83(3):287-300.
Casset et al., "A peptide mimetic of an anti-CD4 monoclonal antibody by rational design," Biochemical and Biophysical Research Communications, 2003, 307:198-205.
Catania et al., "Role of matrix metalloproteinases in renal pathophysiologies," Am J Physiol Renal Physiol, Mar. 2007, 292(3):F905-F911.
Chang et al., "Levels in the Serum of Tissue Inhibitors of Metalloproteinase-1 (TIMP-1) from Patients with Primary Nephrotic Syndrome," Chin J Integr Trad Western Nephrol, 2007, 10:600-601—English translation, abstract only.
Chawla et al., "Identifying critically ill patients at high risk for developing acute renal failure: a pilot study," Kidney Int, Nov. 2005, 68(5):2274-2280.
Chatterjee et al., "Tempol, a membrane-permeable radical scavenger, reduces oxidant stress-mediated renal dysfunction and injury in the rat," Kidney Int, 2000, 58:658-673.
Chertow et al., "Acute Kidney Injury, Mortality, Length of Stay, and Costs in Hospitalized Patients," J Am Soc Nephrol, 2005, 16:3365-3370.
Choi et al., "Expression of Vascular Endothelial Growth Factor-C and Its Receptor mRNA In The Rat Kidney With Ischemia-Reperfusion Injury," Clinical Kidney J, Jun. 2, 2011, 4(Suppl 2):2 pages.
Christenson et al., "Standardization of cardiac troponin I assays: round Robin of ten candidate reference materials," Clin Chem, Mar. 2001, 47(3):431-437.
Coca et al., "Biomarkers for the diagnosis and risk stratification of acute kidney injury: A systematic review," Kidney Int, May 2008, 73(9):1008-1016.
Colomer et al., "Circulating CA 15-3 levels in the postsurgical follow-up of breast cancer patients and in non-malignant diseases," Breast Cancer Res Treat, Mar. 1989, 13(2):123-133.
Constantin et al., "Plasma neutrophil gelatinase-associated lipocalin is an early marker of acute kidney injury in adult critically ill patients: a prospective study," Journal of Cirical Care, 2010, 25:176.e1-176.e6.
Cooper, "Effect Of Tobacco Smoking On Renal Function," Indian J Med Res, Sep. 2006, 124(3):261-268.
Correale et al., "Activation of humoral immunity and eosinophils in neuromyelitis optica," Neurology, Dec. 28, 2004, 63(12):2363-2370.
Cottone et al., "Endothelin-1 and F2-isoprostane relate to and predict renal dysfunction in hypertensive patients," Nephrol Dial Transpl, Feb. 2009, 24(2):497-503.
Cruz et al., "North East Italian Prospective Hospital Renal Outcome Survey on Acute Kidney Injury (NEiPHROS-AKI): Targeting the Problem with the Rifle Criteria," Clin J Amer. Soc. Nephrol, May 2007, 2(3):418-425.
Cuadrado et al., "Vascular MMP-9/TIMP-2 and Neuronal MMP-10 Up-Regulation in Human Brain after Stroke: A Combined Laser Microdissection and Protein Array Study," J Proteome Res, 2009, 8:3191-3197.
Cwirla et al., "Peptides on phage: A vast library of peptides for identifying ligands," Proc Natl Arad Sci USA, Aug. 1990, 87:6378-6382.
Daha et al., "Is the proximal tubular cell a proinflammatory cell?," Nephrol Dial Transplant, 2000, 15 Suppl 6:41-43.
De Sa et al., "Leukocyte, platelet and endothelial activation in patients with acute renal failure treated by intermittent hemodialysis," Am J Nephrol, Jul.-Aug. 2001, 21(4):264-273.
Devarajan, "Cellular and molecular derangements in acute tubular necrosis," Curr Opin Pediatr, Apr. 2005, 17(2):193-199.
Devarajan, "Neutrophil gelatinase-associated lipocalin (NGAL): A new marker of kidney disease," Scand J Clin Lab Invest Suppl, 2008, 69(5241):89-94.
Devarajan, "Novel biomarkers for the early prediction of acute kidney injury," Cancer Therapy, Sep. 2005, 3:477-488.
Devarajan, "Update on Mechanisms of Ischemic Acute Kidney Injury," J Am Soc Nephrol, Jun. 2006, 17(6):1503-1520.
Devarajan et al., "Proteomics for Biomarker Discovery in Acute Kidney Injury," Semin Nephrol, Nov. 2007, 27(6):637-651.
Devlin et al., "Random Peptide Libraries: A Source of Specific Protein Binding Molecules," Science, 1990, 249:404-406.
Domanski et al., "Purine and Cytokine Concentrations in the Renal Vein of the Allograft During Reperfusion," Transplant Proc, Jun. 2007, 39(5):1319-1322.
Edelstein, "Biomarkers of Acute Kidney Injury," Adv Chronic Kidney Dis, Jul. 2008, 15(3)222-234.
Eissa et al., "Noninvasive Diagnosis of Bladder Cancer by Detection of Matrix Metalloproteinases (MMP-2 and MMP-9) and Their Inhibitor (TIMP-2) in Urine," European Urology, 2007, 52:1388-1397.
Engers et al., "Rac Affects Invasion of Human Renal Cell Carcinomas by Up-regulating Tissue Inhibitor of Metalloproteinases (TIMP)-1 and TIMP-2 Expression," J Biol Chem, Nov. 9, 2001, 276(45):41889-41897.
Eremina et al., "Glomerular-specific alterations of VEGF-A expression lead to distinct congenital and acquired renal diseases," The Journal of Clinical Investigation, Mar. 2003, 111(5):707-716.
FDA, "European Medicines Agency to Consider Additional Test Results When Assessing New Drug Safety—Collaborative effort by FDA and EMEA expected to yield additional safety data," http://www.natap.org/2008/newsUpdates/071608_01.htm dated Jun. 12, 2008.
Ferguson et al., "Biomarkers of nephrotoxic acute kidney injury," Toxicology, Mar. 20, 2008, 245(3):182-193.
Ferrara et al., "Recombinant renewable polyclonal antibodies," mABs, 2015, 7(1):32-41.
Fischer et al., "A readers' guide to the interpretation of diagnostic test properties: clinical example of sepsis," Intensive Care Med, 2003, 29:1043-1051.
Flynn et al., "Urinary excretion of beta2-glycoprotein-1 (apolipoprotein H) and other markers of tubular malfunction in "non-tubular" renal disease," J Clin Pathol, Jul. 1992, 45(7):561-567.
Frangogiannis, "Chemokines in ischemia and reperfusion," Thromb Haemost, May 2007, 97(5):738-747.
Fried et al., "Inflammatory and Prothrombotic Markers and the Progression of Renal Disease in Elderly Individuals," J Am Soc Nephrol, Dec. 2004, 15(12):3184-3191.
Fry et al., "Management of acute renal failure," Postgrad Med J, 2006, 82:106-116.
Fu et al., "Study on the expression of VEGF, MMP-2 and TIMP-2 in the progression of IgA nephropathy," J Clin Exp Pathol 2008, 24(5):573-576—includes English translation abstract only.
Fujisaki et al., "Infusion of radiocontrast agents induces exaggerated release of urinary endothelin in patients with impaired renal function," Clin Exp Nephrol, Dec. 2003, 7(4):279-283.

(56) References Cited

OTHER PUBLICATIONS

Furuichi et al., "Chemokine/chemokine receptor-mediated inflammation regulates pathologic changes from acute kidney injury to chronic kidney disease," Clin Exp Nephrol, Feb. 2009, 13(1):9-14.
Furuichi et al., "Roles of chemokines in renal ischemia/reperfusion injury," Front Biosci, May 1, 2008, 13:4021-4028.
Gaggar et al., "Matrix metalloprotease-9 dysregulation in lower airway secretions of cystic fibrosis patients," Am J Physiol Lung Cell Mol Physiol, 2007, 293:L96-L104.
Galkina et al., "Leukocyte Recruitment and Vascular Injury in Diabetic Nephropathy," J Am Soc Nephrol, Feb. 2006, 17(2):368-377.
Garcia et al., "Adenosine A2A receptor activation and macrophagemediated experimental glomerulonephritis," FASEB J, Feb. 2008, 22(2):445-454.
Gbadegesin et al., "Plasma and urinary soluble adhesion molecule expression is increased during first documented acute pyelonephritis," Arch Dis Child, Mar. 2002, 86(3):218-221.
Gharagozlian et al., "Matrix metalloproteinases in subjects with type 1 diabetes," BMC Clin Pathol, 2009, 9:7.
Giasson et al., "Neutrophil Gelatinase-Associated Lipocalin (NGAL) as a New Biomarker for Non-Acute Kidney Injury (AKI) Diseases," Inflammation & Allergy—Drug Targets, 2011, 10:272-282.
Goes et al., "Effect of Recombinant Human Insulin-Like Growth Factor-1 on the Inflammatory Response to Acute Renal Injury," J Am Soc Nephrol, May 1996, 7(5):710-720.
Goldstein et al., "Renal Angina," Clin J Am Soc Nephrol, 2010, 5:943-949.
Grankvist et al., "Evaluation of Five Glycoprotein Tumour Markers (Cea, Ca-50, Ca-19-9, Ca-125, Ca-15-3) for the Prognosis of Renal-Cell Carcinoma," Int J Cancer, Apr. 22, 1997, 74(2):233-236.
Grigoryev et al., "The Local and Systemic Inflammatory Transcriptome after Acute Kidney Injury," J Am Soc Nephrol, Mar. 2008, 19(3):547-558.
Grobmeyer et al., "Secretory leukocyte protease inhibitor, an inhibitor of neutrophil activiation, is elevated in serum in human sepsis and experimental endotoxema," Critical Care Medicine, May 2000, 28(5):1276-1282.
Gumus et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001, 27(2):133-135.
Gupta et al., "Role of Protein C in Renal Dysfunction after Polymicrobial Sepsis," J Am Soc Nephrol, Mar. 2007, 18(3):860-867.
Haase et al., "A comparison of the Rifle and Acute Kidney Injury Network classifications for cardiac surgery-associated acute kidney injury: A prospective cohort study," J Thorac Cardiovasc Surg, Dec. 2009, 138(6):1370-1376.
Han, "Biomarkers for Early Detection of Acute Kidney Injury," Nephrology Rounds, Apr. 2008, 6(4):6 pp.
Han et al., "An imbalance between matrix metalloproteinase-2 and tissue inhibitor of matrix metalloproteinase-2 contributes to the development of early diabetic nephropathy," Nephrol Dial Transplant, 2006, 21:2406-2416.
Han et al., Upregulation of hyaluronan and its binding receptors in an experimental model of chronic cyclosporine nephropathy. Nephrology (Carlton). Mar. 2010;15(2):216-224.
Han et al., "Urinary biomarkers in the early diagnosis of acute kidney injury," Kidney Int, Apr. 2008, 73(7):863-869.
Hanley et al., "The Meaning and Use of the Area Under a Receiver Operating Characteristic (ROC) Curve," Radiology, Apr. 1982, 143:29-36.
Harpur et al., "Biological Qualification of Biomarkers of Chemical-Induced Renal Toxicity in Two Strains of Male Rat," Toxicol Sci, Aug. 2011, 122(2):235-252.
Harris et al., "Growth Factors and Cytokines in Acute Renal Failure," Adv Ren Replace Ther, Apr. 1997, 4(2 Suppl):43-53.
Hatta et al., "Cytokine Array Comparisons of Plasma from Cycling Fertile Women on Cycle Day 5 and Ovulation," Am J Reprod Immunol, Sep. 2009, 62(3):158-164.

Hayashi et al., "Enhanced Expression of Membrane Type-1 Matrix Metalloproteinase in Mesangial Proliferative Glomerulonephritis," J Am Soc Nephrol, 1998, 9:2262-2271.
He et al., "Interleukin-18 binding protein transgenic mice are protected against ischemic acute kidney injury," Am J Physiol Renal Physiol, Nov. 2008, 295(5):F1414-F1421.
Herget-Rosenthal et al., "Early detection of acute renal failure by serum cystatin," C Kidney Int, Sep. 2004, 66(3):1115-1122.
Hidaka et al., "Urinary clusterin levels in the rat correlate with the severity of tubular damage and may help to differentiate between glomerular and tubular injuries," Cell Tissue Res, Dec. 2002, 310(3):289-296.
Hiemstra, "Novel roles of protease inhibitors in infection and inflammation," Biochem Soc Trans, Apr. 2002, 30(2):116-120.
Hirai et al., "Plasma endothelin-1(ET-1) is a useful marker for renal dysfunction," Atheroscler Suppl, Jun. 19, 2006, 7(3):60[Mo-P1:65].
Hirschberg et al., "Factors Predicting Poor Outcome in Patients with Acute Renal Failure (ARF)," J Am Soc Nephrol, Sep. 1, 1996, 7(9):1374.
Hollander et al., "Serum and bronchial lavage fluid concentrations of IL-8, SLPI, sCD14 and sICAM-1 in patients with COPD and Asthma," Respiratory Medicine, 2007, 101:1947-1953.
Horstrup et al., "Elevation of serum and urine levels of TIMP-1 and tenascin in patients with renal disease," Nephrol Dial Transplant, 2002, 17:1005-1013.
Hoste et al., "Rifle criteria for acute kidney injury are associated with hospital mortality in critically ill patients: a cohort analysis," Crit Care, 2006, 10(3):R73 (10 pp).
Hugo et al., "Thrombospondin in Renal Disease," Nephron Exp Nephrol, 2009, 111(3):e61-e66.
Hugo et al., "Thrombospondin 1 precedes and predicts the development of tubulointerstitial fibrosis in glomerular disease in the rat," Kidney Int, Feb. 1998, 53(2):302-311.
Iglesias et al., "Thyroid Dysfunction and Kidney Disease," Revised version, Eur J Endocrinol. Dec. 18, 2008, 32 pp retrieved from URL://www.eje.org/content!early/2008/12/18/EJE-08-0837.full.pdf.
Iyoda et al., "Imatinib Suppresses Cryoglobulinemia and Secondary Membranoproliferative Glomerulonephritis," J Am Soc of Nephrol, Jan. 2009, 20(1):68-77.
Journal of the Kanazawa University Juzen Medical Society, Hisada, "Expression of Matrix metalloproteinase-2 in Anti-Thy1.1 Glomerulonephritis in Rats," 1995;104:36-45—includes English translation abstract only.
Jalalah et al., "Inactive matrix metalloproteinase 2 in a normal constituent of human glomerular basement membrane. An immunoelectron microscopic study," J Pathol, 2000, 191:61-66.
Jang et al., "The innate immune response in ischemic acute kidney injury," Clin Immunol, Jan. 2009, 130(1):41-50.
Jang et al., "B Cells Limit Repair after Ischemic Acute Kidney Injury," J Am Soc Nephrol, Apr. 2010, 21(4):654-665.
Jin et al., "Correlation between Pathological Classification and Levels of TNF and sTNF-R in Sera from Patients with Lupus Nephritis," Clin Med J China, 2002, 9(1):7-8—English translation, abstract only.
Jo et al., "Heat Preconditioning Attenuates Renal Injury in Ischemic ARF in Rats: Role of Heat-Shock Protein 70 on NF-kappa B-Mediated Inflammation and on Tubular Cell Injury," J Am Soc Nephrology, 2006, 17:3082-3092.
Jo et al., "Pharmacological Treatment of Acute Kidney Injury: Why Drugs Haven't Worked and What Is on the Horizon," Clin J Am Soc Nephrol, 2007, 2:356-365.
Jonsson, "The role of fibroblast growth factor 23 in renal disease," Nephrol Dial Transplant, Mar. 2005, 20(3):479-482.
Julian et al., "Sources of Urinary Proteins and their Analysis by Urinary Proteomics for the Detection of Biomarkers of Disease," Proteomics Clin Appl., 2009, 3(9):1029-1043.
Jung et al., "Diagnostic significance of urinary enzymes in detecting acute rejection crises in renal transplant recipients depending on expression of results illustrated through the example of alanine aminopeptidase," Clin Biochem, Aug. 1985, 18(4):257-260.

(56) References Cited

OTHER PUBLICATIONS

Kadiroglu et al., "The Evaluation of Effects of Demographic Features, Biochemical Parameters, and Cytokines on Clinical Outcomes in Patients with Acute Renal Failure," Ren Fail, 2007, 29(4):503-508.
Kallakury et al., "Increased Expression of Matrix Metalloproteinases 2 and 9 and Tissue Inhibitors of Metalloproteinases 1 and 2 Correlate with Poor Prognostic Variables in Renal Cell Carcinoma," Clin Cancer Res, 2001, 7:3113-3119.
Kalousova et al., "Soluble Receptor for Advanced Glycation End Products in Patients With Decreased Renal Function," Am J Kidney Dis, Mar. 2006, 47(3):406-411.
Kamata et al., "Up-regulation of glomerular extracellular matrix and transforming growth factor-beta expression in RF/J mice," Kidney Int, Mar. 1999, 55(3):864-876.
Kasahara et al., "Clinical Significance of Serum Oxidized Low-Density Lipoprotein/beta2-Giycoprotein I Complexes in Patients with Chronic Renal Diseases," Nephron Clin Pract, 2004, 98(1):15-24.
Kawata et al., "Significant Relationship of Matrix Metalloproteinase 9 with Nuclear Grade and Prognostic Impact of Tissue Inhibitor of Metalloproteinase 2 for Incidental Clear Cell Renal Cell Carcinoma," Urology, 2007, 69(6):1049-1053.
Kehoe et al., "Elevated Plasma Renin Activity Associated with Renal Dysfunction," Nephron, 1986, 44:51-57 (abstract only).
Kellum, "Acute kidney injury," Crit Care Med, 2008, 36(4):5141-5145.
Kellum et al., "Definition and Classification of Acute Kdney Injury," Nephron Clin Pract, 2008, 109(4):c182-c187.
Keyes et al., "Early diagnosis of acute kidney injury in critically ill patients," Expert Rev Mol Diagn, Jul. 2008, 8(4):455-464.
Khanna et al., "Expression of TGF-beta and fibrogenic genes in transplant recipients with tacrolimus and cyclosporine nephrotoxicity," Kidney Int, Dec. 2002, 62(6):2257-2263.
Kharasch et al., "Gene Expression Profiling of Nephrotoxicity from the Sevoflurane Degradation Product Fluoromethy1-2,2-difluoro-1-(trifluoromethyl)vinyl Ether ("Compound A") in Rats," Toxicol Sci, Apr. 2006, 90(2):419-431.
Kiley et al., "Urinary biomarkers: The future looks promising," Kidney Int, Jul. 2009, 76(2):133-134.
Kilis-Pstrusinska et al., "Levels of selected soluble adhesion molecules in blood serum of children with chronic glomerulonephritis," Pol Merkur Lekarski, Apr. 2001, 10(58):247-249.
Kilis-Pstrusinska et al., "Serum levels of soluble adhesion molecules in children with glomerulonephritis (GN)," Nephrol Dialysis Transplant, Jun. 2001, 16(6):A62.
Kimmel et al., "Immunologic function and survival in hemodialysis patients," Kidney Int, Jul. 1998, 54(1):236-244.
Kinsey et al., "Inflammation in Acute Kidney Injury," Nephron Exp Nephrol, 2008, 109(4):e102-e107.
Kolkenbrock et al., "Biochemical Characterization of the Catalytic Domain of Membrane-Type 4 Matrix Metalloproteinase," Biol Chem, Sep. 1999, 380:1103-1108.
Koo et al., "Cadaver versus living donor kidneys: Impact of donor factors on antigen induction before transplantation," Kidney Int, Oct. 1999, 56(4):1551-1559.
Kos et al., "Cathepsins B,H and L and Their Inhibitors Stefin A and Cystatin C in Sera of Melanoma Patients," Clin Cancer Res, Oct. 1997, 3(10):1815-1822.
Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004, 43(2):244-253.
Lang et al., "Heat Shock Protein 60 Is Released in Immune-Mediated Glomerulonephritis and Aggravates Disease: In Vivo Evidence for an Immunologic Danger Signal," J Am Soc Nephrol, Feb. 2005, 16(2):383-391.
Laplante et al., "Modulation of matrix gelatinases and metalloproteinase-activating process in acute kidney rejection," Transpl Int, 2003, 16:262-269.
Lapsley et al., "Beta2-glycoprotein-1 (apolipoprotein H) excretion in chronic renal tubular disorders: Comparison with other protein markers of tubular malfunction," J Clin Pathol, Oct. 1991, 44(10):812-816.
Larsson et al., "Circulating concentration of FGF-23 increases as renal function declines in patients with chronic kidney disease, but does not change in response to variation in Phosphate intake in healthy volunteers," Kidney Int, De 2003, 64(6):2272-2279.
Lassnigg et al., "Minimal Changes of Serum Creatinine Predict Prognosis in Patients after Cardiothoracic Surgery: A Prospective Cohort Study," J Am Soc Nephrol, 2004, 15:1597-1605.
Lemancewicz et al., "Matrix metalloproteinase-2 and tissue inhibitor of metalloproteinase-2 urine levels in preterm laboring patients," Archives of Perinatal Medicine, 2007, 13(2):50-52.
Lenz et al., "Matrix Metalloproteinases in Renal Development and Disease," J Am Soc Nephrol, 2000, 11:574-581.
Li et al., "Predictive value of Rifle classification on prognosis of critically ill patients with acute kidney injury treated with continuous renal replacement therapy," Chin Med J (Engl), May 5, 2009, 122(9):1020-1025.
Lichte et al., "The recombinant catalytic domain of membrane-type matrix metalloproteinase-1 (MT1-MMP) induces activation of progelatinase A and progelatinase A complexed with TIMP-2," FEBS Lett, 1996, 397:277-282.
Liu et al., "Predictive and pathogenetic value of plasma biomarkers for acute kidney injury in patients with acute lung injury," Crit Care Med, Dec. 2007, 35(12):2755-2761.
Liu et al., "Serum Interleukin-6 and interleukin-8 are early biomarkers of acute kidney injury and predict prolonged mechanical ventilation in children undergoing cardiac surgery: a case-control study," Critical Care, 2009, 13(4):R104 (9 Pi).
Lopes et al., "The Rifle an AKIN classifications for acute kidney injury: a critical and comprehensive review," Clin Kidney J, 2013, 6:8-14.
Lopes-Virella et al., "Urinary high density lipoprotein in minimal change glomerular disease and chronic glomerulopathies," Clin Chim Acta, May 16, 1979, 94(1):73-81.
Lu et al., "Increased Macrophage Infiltration and Fractalkine Expression in Cisplatin-Induced Acute Renal Failure in Mice," J Pharmacol Exp Ther, Jan. 2008, 324(1):111-117.
MacCallum et al., "Antibody-antigen Interactions: Contact Analysis and Binding Site Topography," J Mol Biol, 1996, 262:732-745.
Maddens et al., "Chitinase-like Proteins are Candidate Biomarkers for Sepsis-induced Acute Kidney Injury," Mol Cell Proteomics, Jan. 10, 2012, 11(6):1-13.
Malm et al., "Changes in the plasma levels of vitamin K-dependent proteins C and S and of C4b-binding protein during pregnancy and oral contraception," Br J Haematol, Apr. 1988, 68(4):437-443.
Malyszko et al., "Visfatin and apelin, new adipocytokines, and their relation to endothelial function in patients with chronic renal failure," Adv Med Sci, 2008, 53(1):32-36.
Mast et al., "Clinical utility of the soluble transferrin receptor and comparison with serum ferritin in several populations," Clin Chem, Jan. 1998, 44(1):45-51.
Matousovic et al., "IgA-containing immune complexes in the urine of IgA nephropathy patients," Nephrol Dial Transplant, Sep. 2006, 21(9):2478-2484.
Matsuda et al., "Beta 2-Glycoprotein l-Dependent and -Independent Anticardiolipin Antibody in Patients with End-Stage Renal Disease," Thromb Res, Oct. 15, 1993, 72(2):109-117.
Matsuzaka et al., "Relationship between vitamin K dependent coagulation factors and anticoagulants (protein C and protein S) in neonatal vitamin K deficiency," Arch Dis Child, Mar. 1993, 68(3 Spec No):297-302.
Mattes, "Experience With a Biomarker Consortium," CPath Predictive Safety Training Consortium, Critical Path Institute, 48 pp.
McCullough et al., "Contrast-Induced Nephropathy (CIN) Consensus Working Panel: Executive Summary," Rev Cardiovasc Med, 2006, 7(4):177-197.
Mehran et al., "A Simple Risk Score for Prediction of Contrast-Induced Nephropathy After Percutaneous Coronary Intervention: Development and Initial Validation," J Am Col Cardiology, 2004, 44(7):1393-1399.

(56) References Cited

OTHER PUBLICATIONS

Mehta et al., "Acute Kidney Injury Network: report of an initiative to improve outcomes in acute kidney injury," Crit Care, 2007,11:R31.
Melnikov et al., "Impaired IL-18 processing protects caspase-1-deficient mice from ischemic acute renal failure," J Clin Invest, May 2001, 107(9):1145-1152.
Mezzano et al., "Endothelial Cell Markers in Chronic Uremia: Relationship with Hemostatic Defects and Severity of Renal Failure," Thromb Res, Dec. 15, 1997, 88(6):465-472.
Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991, 6(4):232-237.
Mills et al., "Implications of lowering threshold of plasma troponin concentration in diagnosis of myocardial infarction: cohort study," BMJ, 2012, 344:e1533 doi: 10.1136/bmj.e1533 (Published Mar. 16, 2012).
Mishra et al., "Neutrophil gelatinase-associated lipocalin (NGAL) as a biomarker for acute renal injury after cardiac surgery," Lancet, Apr. 2-8, 2005, 365(9466):1231-1238.
Montagna et al., "Impairment of cellular redox status and membrane protein activities in kidneys from rats with ischemic acute renal failure," Biochim Biophys Acta, Aug. 14, 1998, 1407(2):99-108.
Muhlfeld et al., "Overexpression of complement inhibitor Crry does not prevent cryoglobulin-associated membranoproliferative glomerulonephritis," Kidney International, 2004, 65:1214-1223.
Musial et al., "Soluble adhesion molecules in chronic renal failure (CRF) children treated conservatively," Nephrol Dialysis Transplant, 2002, 17(Abstracts Suppl 1):232.
Musial et al., "The Heat Shock Protein Profile in Children with Chronic Kidney Disease," Pent Dial Int, Mar.-Apr. 2010, 30(2):227-232.
Nambi et al., "Down regulation of kidney neutral endopeptidase mRNA, protein and activity during acute renal failure: possible mechanism for ischemia-induced acute renal failure in rats?," Mol Cell Biochem, Jul. 1999, 197(12):53-59.
Nelson et al., "A computer program for calculating antibody affinity constants," Computer Methods Programs in Biomed, 1988, 27:65-68.
Neziri et al., "Cloning and molecular characterization of Dashurin encoded by C20orf116, a PCI-domain containing protein," Biochim Biophys Acta, Apr. 2010, 1800(4):430-438.
Nguyen et al, "Biomarkers for the early detection of acute kidney injury," Pediatr Nephrol, 2008, 23(12):2151-2157.
Nguyen et al., "Heparin-Binding EGF-Like Growth Factor Is Up-Regulated in the Obstructed Kidney in a Cell- and Region-Specific Manner and Acts to Inhibit Apoptosis," Am J Pathol, Mar. 2000, 156(3):889-898.
Nishiyama et al., "Up-Regulation of Galectin-3 in Acute Renal Failure of the Rat," Am J Pathol, Sep. 2000, 157(3):815-823.
Norman et al., "Progressive Renal Disease: Fibroblasts, Extracellular Matrix, and Integrins," Exp Nephrol, Mar.-Apr. 1999, 7(2):167-177.
Obata et al., "A one-step sandwich enzyme immunoassay for human matrix metalloproteinase 3 (stromelysin-1) using monoclonal antibodies," Clin Chim Acta, 1992, 211:59-72.
Obuchowski et al., "ROC Curves in Clinical Chemistry: Uses, Misuses, and Possible Solutions," Clin Chem, 2004, 50(7):1118-1125.
Ohno et al., "Prognostic significance of tenascin-C expression in clear cell renal cell carcinoma," Oncol Rep, 2008, 20(3):511-516.
Ostermann et al., "Acute kidney injury 2016: diagnosis and diagnostic workup," Crit Care, 2016, 20(1):299.
Ozer et al., "A panel of urinary biomarkers to monitor reversibility of renal injury and a serum marker with improved potential to assess renal function," Nat Biotechnol, May 2010, 28(5):486-494.
Parikh et al., "New biomarkers of acute kidney injury," Crit Care Med, 2008, 36(4 Suppl):S159-S165.
Parikh et al., "Urinary IL-18 is an early predictive biomarker of acute kidney injury after cardiac surgery," Kidney Int, 2006, 70(1):199-203.
Paul, Fundamental Immunology, 3rd Edition, Raven Press, New York, 1993, Chapter 8, pp. 292-295.
Perco et al., "Protein biomarkers associated with acute renal failure and chronic kidney disease," Eur J Clin Invest, Nov. 2006, 36(11):753-763.
Picard et al., "Origin of renal myofibroblasts in the model of unilateral ureter obstruction in the rat," Histochem Cell Biol, Jul. 2008, 130(1):141-155.
Powell et al., "Characterization of Insulin-Like Growth Factor Binding Protein-3 in Chronic Renal Failure Serum," Pediatr Res, 1993, 33(2):136-143.
Praught et al., "Are small changes in serum creatinine an important risk factor?," Curr Opin Nephrol Hypertens, 2005, 14:265-270.
Price, "Abrupt Changes in Prostate-Specific Antigen Concentration in Acute Renal Failure," Clin Chem, Jan. 1993, 39(1):161-162.
Prozialeck et al., "Cell Adhesion Molecules in Chemically-Induced Renal Injury," Pharmacol Ther, Apr. 2007, 114(1):74-93.
Radford et al., "Predicting renal outcome in IgA nephropathy," J Am Soc Nephrol, Feb. 1997, 8(2):199-207.
Rajashekar et al., "Systemic diseases with renal manifestations," Prim Care, Jun. 2008, 35(2):297-328, abstract retrieved from URL:www.ncbi.nlm.nih.gov/pubmed/18486717.
Ramesh et al., "Endotoxin and cisplatin synergistically induce renal dysfunction and cytokine production in mice," Am J Physiol Renal Physiol, Jul. 2007, 293(1):F325-F332.
Ramesh et al., "INF-a mediates chemokine and cytokine expression and renal injury in cisplatin nephrotoxicity," J Clin Invest, Sep. 2002, 110(6):835-842.
Ramirez et al., "Prospective Study on Autoantibodies Against Apolipoprotein H (beta2GPl) in Several Clinical Parameters From Patients With Terminal Renal Failure and Functioning Renal Transplants," Transplant Proc, 2009, 41:2370-2372.
Ramp et al., "Expression of heat shock protein 70 in renal cell carcinoma and its relation to tumor progression and prognosis," Histol Histopathol, 2007, 22:1099-1107.
Ricci et al., "The Rifle criteria and mortality in acute kidney injury: A systematic review," Kidney Int, Mar. 2008, 73(5):538-546.
Ridker, "C-Reactive Protein: A Simple Test to Help Predict Risk of Heart Attack and Stroke," Circulation, 2003, 108:e81-e85.
Ridker, "Clinical Application of C-Reactive Protein for Cardiovascular Disease Detection and Prevention," Circulation, 2003, 107:363-369.
Rini et al., "Renal cell carcinoma," Lancet, Mar. 28, 2009, 373(9669):1119-1132.
Rosenkranz et al., "P-selectin deficiency exacerbates experimental glomerulonephritis: a protective role for endothelial P-selectin in inflammation," J Clin Invest, Mar. 1999, 103(5):649-659.
Rouschop et al., "Pre-transplant plasma and cellular levels of CD44 correlate with acute renal allograft rejection," Nephrol Dial Transplant, Oct. 2005, 20(10):2248-2254.
Rouschop et al., "Renal expression of CD44 correlates with acute renal allograft rejection," Kidney Int, Sep. 2006, 70(6):1127-1134.
Roy et al., "Urinary TIMP-1 and MMP-2 levels detect the presence of pancreatic malignancies," British Journal of Cancer, Aug. 19, 2014, 111(9):1772-1779.
Rysz et al., "Serum matrix metalloproteinases MMP-2 and MMP-9 and metalloproteinase tissue inhibitors TIMP-1 and TIMP-2 in diabetic nephropathy," J Nephrol, 2007, 20:444-452.
Schaefer et al., "Tubular gelatinase a (MMP-2) and its tissue inhibitors in polycystic kidney disease in the Han:SPRD rat," Kidney Int, 1996, 49:75-81.
Schaefer et al., "Urinary excretion of cathepsin B and cystatins as parameters of tubular damage," Kidney Int Suppl, Nov. 1994, 47:S64-S67.
Schena et al., "EGF and MCP-1 Urinary Excretion Is a Suitable Prognostic Marker in Iga Nephropathy," J Am Soc of Nephrology, Meeting of the American Society of Nephrology, Sep. 1, 2002, 13 (Program and Abstracts Issue):458A.

(56) References Cited

OTHER PUBLICATIONS

Schiffer et al., "Activated Renal Macrophages Are Markers of Disease Onset and Disease Remission in Lupus Nephritis," J Immunol, Feb. 1, 2008, 180(3):1938-1947.
Schmaldienst et al., "Angiogenin: a novel inhibitor of neutrophil-lactoferrin release during extracorporeal circulation," Kidney Blood Press Res, 2003, 26(2):107-112.
Schmidt et al., "Sexual hormone abnormalities in male patients with renal failure," Nephrol Dial Transplant, Mar. 2002, 17(3):368-371.
Schrijvers et al., "The role of vascular endothelial factor (VEGF) in renal pathophysiology," Kidney International, 2004, 65:2003-2017.
Schulz et al., "Endothelin-1 as an early prognostic marker in acute renal failure (ARF) and sepsis," Kidney Blood Press Res, 2000, 23(3-5):341-342.
Scott et al., "Searching for Peptide Ligands with an Epitope Library," Science, Jul. 27, 1990, 249:386-390.
Segawa et al., "In situ expression and soluble form of P-selectin in human glomerulonephritis," Kidney Int, Oct. 1997, 52(4)1054-1063.
Segerer et al., "Chemokines, Chemokine Receptors, and Renal Disease: From Basic Science To Pathophysiologic and Therapeutic Studies," J Am Soc Nephrol, Jan. 2000, 11(1):152-176.
Senatorski et al., "Urine activity of cathepsin B, collagenase and urine excretion of TGF-beta1 and fibronectin in membranous glomerulonephritis," Res Exp Med (Berl), Dec. 1998, 198(4):199-206.
Seo et al., "TIMP-2 Mediated Inhibition of Angiogenesis: An MMP-Independent Mechanism," Cell, Jul. 25, 2003, 114:171-180.
Severini et al., "Diagnostic significance of urinary enzymes: Development of a high performance liquid chromatographic method for the measurement of urinary lysozyme," Clin Chim Acta, Feb. 27, 1987, 163(1):97-103.
Sharma et al.,"Two-dimensional fluorescence difference gel electrophoresis analysis of the urine proteome in human diabetic nephropathy," Proteomics, Jul. 2005, 5(10):2648-2655.
Shiba et al., "Chronic kidney disease and heart failure—Bidirectional close link and common therapeutic goal," J Cardiol, 2011, 57(1):8-17.
Shlipak et al., "Elevations of Inflammatory and Procoagulant Biomarkers in Elderly Persons With Renal Insufficiency," Circulation, Jan. 2003, 107(1):87-92.
Shoji et al., "Plasma angiopoietin-like protein 3 (ANGPTL3) concentration is associated with uremic dyslipidemia. Atherosclerosis," Dec. 2009, 207(2):579-584.
Simmons et al., "Plasma cytokine levels predict mortality in patients with acute renal failure," Kidney Int, Apr. 2004, 65(4):1357-1365.
Song et al., "Expression of Trail, DR4, and DR5 in kidney and serum from patients receiving renal transplantation," Transplant Proc, Jun. 2004, 36(5):1340-1343.
Stafford-Smith et al., "Acute Kidney Injury and Chronic Kidney Disease After Cardiac Surgery. Adv Chronic Kidney Dis," Jul. 2008, 15(3):257-277.
Stasko et al., "Soluble P-Selectin During a Single Hemodialysis Session in Patients With Chronic Renal Failure and Erythropoietin Treatment," Clin Appl Thromb Hemost, Oct. 2007, 13(4):410-415.
Stenvinkel et al., "High Serum Hyaluronan Indicates Poor Survival in Renal Replacement Therapy," Am J Kidney Dis, Dec. 1999, 34(6):1083-1088.
Stuard et al., "Soluble adhesion molecules in chronic renal failure patients," Nephrol Dialysis Transplant, 1997, 12(9):A100.
Sun et al., "A Survey on the Relationship between the Epidermal Growth Factor and Renal Function," Int J Transpl Hemopurific, Dec. 31, 2006, 4(1):41-44 (abstract English translation).
Supavekin et al., "Differential gene expression following early renal ischemia/repertusion," Kidney Int, May 2003, 63(5):1714-1724.
Sutton, "Alteration of microvascular permeability in acute kidney injury," Microvasc Res, Jan. 2009, 77(1):4-7.
Sutton et al., "Injury of the renal microvascular endothelium alters barrier function after ischemia," Am J Physiol Renal Physiol, Aug. 2003, 285(2):F191-F198.
Sutton et al., "Microvascular endothelial injury and dysfunction during ischemic acute renal failure," Kidney Int, Nov. 2002, 62(5):1539-1549.
Sykes et al., "Analytical relationships among Biosite, Bayer, and Roche methods for BNP and NT-proBNP," Am J Clin Pathol, Apr. 2005, 123(4):584-590.
Symon et al., "The endogenous insulin-like growth factor system in radiocontrast nephropathy," Am J Physiol Renal Physiol, Mar. 1998, 274(3 Pt 2):F490-F497.
Takada et al., "The Cytokine-adhesion Molecule Cascade in Ischemia/Reperfusion Injury of the Rat Kidney, Inhibition by a Soluble P-selectin Ligand," J Clin Invest, Jun. 1997, 99(11):2682-2690.
Tan et al., "The level of urinary secretory immunoglobulin A (sIgA) of patients with IgA nephropathy is elevated and associated with pathological phenotypes," Clin Exp Immunol, Apr. 2009, 156(1):111-116.
Taneda et al., "Cryoglobulinemic Glomerulonephritis in Thymic Stromal Lymphopoietin Transgenic Mice," Am J Path, 2001, 159(6):2355-2369.
Tao et al., "Expression of 60-kDa and Inducible 70-kDa Stress Proteins in Gentamicin-Induced Acute Renal Failure," Clin Exp Nephrol, Jul. 1997, 1:254-260.
Tary-Lehmann et al., "Enzyme-Linked Immunosorbent Assay Spot Detection of Interferon-Gamma and Interleukin 5-Producing Cells as a Predictive Marker for Renal Allograft Failure," Transplantation, Jul. 27, 1998, 66(2):219-224.
Taulan et al., "Comprehensive analysis of the renal transcriptional response to acute uranyl nitrate exposure," BMC Genomics, Jan. 11, 2006, 7(2) 14 pp.
Teppo et al., "Soluble Intercellular Adhesion Molecule-1 (Sicam-1) after Kidney Transplantation: The Origin and Role of Urinary Sicam-1?," Transplantation, Apr. 27, 2001, 71(8):1113-1119.
Thakar et al., "A Clinical Score to Predict Acute Renal Failure after Cardiac Surgery," J Am Soc Nephrol, 2005, 16:162-168.
Thakar et al., "Identification of thrombospondin 1 (TSP-1) as a novel mediator of cell injury in kidney ischemia," J Clin Invest, Dec. 2005, 115(12):3451-3458.
Thiemermann et al., "High Density Lipoprotein (HDL) Reduces Renal Ischemia/Reperfusion Injury," J Am Soc Nephrol, 2003, 14:1833-1843.
Thorburn et al., "CXC and CC chemokines induced in human renal epithelial cells by inflammatory cytokines," APMIS, Jul. 2009, 117(7):477-487.
Thrailkill et al., "Matrix Metalloproteinase-2 Dysregulation in Type 1 Diabetes," Diabetes Care, Sep. 2007, 30(9):2321-2326.
Timoshanko et al., "Interleukin-12 from Intrinsic Cells Is an Effector of Renal Injury in Crescentic Glomerulonephritis," J Am Soc Nephrol, Mar. 2001, 12(3):464-471.
Torres et al., "The ratio of epidermal growth factor to monocyte chemotactic peptide-1 in the urine predicts renal prognosis in IgA nephropathy," Kidney Int, Feb. 2008, 73(3):327-333.
Tzitzikos et al., "Measurement of Tumor Markers in Chronic Hemodialysis Patients," Saudi J Kidney Dis Transpl, Jan. 2010, 21(1):50-53.
Uchio-Yamada et al., "Decreased Expression of Matrix Metalloproteinases and Tissue Inhibitors of Metalloproteinase in the Kidneys of Hereditary Nephrotic (ICGN) Mice," J Vet Med Sci, 2005, 67(1):35-41.
Vaidya et al., "Mechanistic biomarkers for cytotoxic acute kidney injury," Expert Opin Drug Metab Toxicol, Oct. 2006, 2(5):697-713.
Vaidya et al., "Biomarkers of Acute Kidney Injury," Annu Rev Pharmacol Toxicol, Feb. 2008, 48:463-493.
Vijayan et al., "Clinical Use of the Urine Biomarker [TIMP-2] x [IGFBP7] for Acute Kidney Injury Risk Assessment," Am J Kidney Dis, 2016, 68(1):19-28.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Van Erp et al., "Application of a Sol Particle Immunoassay to the Determination of Affinity Constants of Monoclonal Antibodies," J Immunoassay, 1991, 12(3):425-443.

(56) References Cited

OTHER PUBLICATIONS

Vanhoutte et al., "Biomarker discovery with SELDI-TOF MS in human urine associated with early renal injury: evaluation with computational analytical tools," Nephrol Dial Transplant, Oct. 2007, 22(10):2932-2943.
Vasala, "Matrix Metalloproteinase MMP-2 and MMP-9 and Their Inhibitors TIMP-1 and TIMP-2 in Bladder Carcinoma," Acta Univ Oul, 2008, D 983:1-76.
Vasala et al., "Serum tissue inhibitor of metalloproteinase-2 (TIMP-2) and matrix metalloproteinase-2 in complex with the inhibitor (MMP-2:TIMP-2) as prognostic markers in bladder cancer," Clin Biochem, Jun. 1, 2007, 40(9-10):640-644.
Villanueva et al., "Ischemic acute renal failure induces the expression of a wide range of nephrogenic proteins," Am J Physiol Regul Integr Comp Physiol, Apr. 2006, 290(4):R861-R870.
Vonderscher, "Biomarker of Drug Induced Kidney Injury Qualification for Regulatory Decision Making (CRADA)," IOM/FDA, Silver Spring, MD, Apr. 23, 2007, 31 pp.
Voshol et al., "Evaluation of Biomarker Discovery Approaches to Detect Protein Biomarkers of Acute Renal Allograft Rejection," J Proteome Res, Jul.-Aug. 2005, 4(4):1192-1199.
Wagrowska-Danilewicz et al., "Aberrant Tubulointerstitial Immunoexpression of Matrix Metalloproteinases MMP-2, MMP-9 and Tissue Inhibitor of Matrix Proteinase-2 (TIMP-2) in Acute Cellular Rejection of Human Renal Allograft," Pol J Pathol, 2008, 59:189-194.
Waikar et al., "Diagnosis, Epidemiology and Outcomes of Acute Kidney Injury," Clin J Am Soc Nephrol, May 2008, 3(3):844-861.
Waku et al., "Serum Level of Human Tissue Inhibitor Metalloproteinase-1 in Various Glomerulonephritides," J Kyorin Med Soc, 1997, 28:441-447—English translation, abstract only.
Wan et al., "The pathogenesis of septic acute renal failure," Curr Opin Crit Care, Dec. 2003, 9(6):496-502.
Wang et al., "Induction of heat shock protein 70 inhibits ischemic renal injury," International Society of Nephrology, 2011, 79:861-870.
Wang et al., "Netrin-1 and kidney injury. I. Netrin-1 protects against ischemia-repertusion injury of the kidney." Am J Physiol Renal Physiol, Apr. 2008, 294(4):F739-F747.
Wang et al., "Validation of putative genomic biomarkers of nephrotoxicity in rats," Toxicology, Apr. 18, 2008, 246(2-3):91-100.
Ward et al., "Binding activities of a repertoire of single immunoglobulin variable domains secreted from *Escherichia coli*," Nature, Oct. 12, 1989, 341:544-546.
Wasileska et al., "Urinary levels of matrix metalloproteinases and their tissue inhibitors in nephrotic children," Pediatr Nephrol, Jul. 2, 2008, 23(10):1795-1802.
Weinzimer et al., "Elevated Urinary Insulin-Like Growth Factor Binding Protein-3 Predicts Renal Outcome in Fetuses with Lower Urinary Tract Obstruction," Am J Obst Gyn, 2001, 184(1):5132.
When et al., "The expression and Significance of Serum TGF-beta$_1$), MMP-9 and TIMP-1 in Patients with Chronic renal failure," Wanfang Data Knowledge Service Platform, 2007—English translation, abstract only.
Wijeysundera et al., "Derivation and Validation of a Simplified Predictive Index for Renal Replacement Therapy After Cardiac Surgery," JAMA, Apr. 25, 2007, 297:1801-1809.
Williamson et al., "Comparison of Biomarkers in Blood and Saliva in Healthy Adults," Nursing Research and Practice, 2012, vol. 2012, Article ID 246178, pp. 1-4.
Wilson et al., "Simplified conjugation chemistry for coupling peptides to F(ab') fragments: autologous red cell agglutination assay for HIV-1 antibodies," J Immunol Methods, 1994, 175:267-273.
Wilson et al., "Urinary lysozyme," J Pediatr, Feb. 1950, 36(2):199-211.
Winchester et al., "Sorbents in Acute Renal Failure and End-Stage Renal Disease: Middle Molecule and Cytokine Removal," Blood Purif, 2004, 22(1):73-77.
Xiaofang et al., "Serum tumour markers in patients with chronic kidney disease," Scand J Clin Lab Invest, 2007, 67(6):661-667.
Yan et al., "Expression of MMP-2 and TIMP-1 in Renal Tissue of Patients with Chronic Active Antibody-mediated Renal Graft Rejection," Diagn Pathol, 2012, 7:141.
Yang et al., "Frequency of anti-bactericidal/permeability-increasing protein (BPI) and anti-azurocidin in patients with renal disease," Clin Exp Immunol, Jul. 1996, 105(1):125-131.
Yarmush et al., "Coupling of antibody-binding fragments to solid-phase supports: site-directed binding of F(ab')2 fragments," J Biochem Biophys Methods, 1992, 25:285-297.
Yu et al., "Urinary biomarkers trefoil factor 3 and albumin enable early detection of kidney tubular injury," Nat Biotechnol, May 2010, 128(5):470-477.
Yuen et al., "Ischemic and Nephrotoxic Acute Renal Failure are Distinguished by their Broad Transcriptomic Responses," Physiol Genomics, May 16, 2006, 25(3):375-386.
Zaffanello et al., "Early diagnosis of acute kidney injury with urinary biomarkers in the newborn," J Matern Fetal Neonatal Med, 2009, 22(Suppl 3):62-66.
Zager et al., "Proximal tubular cytochrome c efflux: Determinant, and potential marker, of mitochondrial injury," Kidney Int, Jun. 2004, 65(6):2123-2134.
Zhang et al., "Significance of MMP-2 and TIMP-2 mRNA Expressions on Glomerular Cells in the Development of Giomerulosclerosis," Chin Med Sci J, Jun. 2004, 19(2):84-88.
Zhang et al., "The level of serum secretory IgA of patients with IgA nephropathy is elevated and associated with pathological phenotypes," Nephrol Dial Transplant, Jan. 2008, 23(1):207-212.
Zheng et al., "Antiphospholipid antibody profiles in lupus nephritis with glomerular microthrombosis: a prospective study of 124 cases," Arthritis Res Ther, 2009, 11(3):1-9.
Zhu et al., "Expression of Urinary Epidermal Growth Factor and Renal Function," J Clin Urol, Dec. 31, 1998, 13(8):374-379 (abstract English translation).
Office Action dated Sep. 13, 2013 in AU 2011269775.
Office Action dated May 1, 2017 in CA 2804297.
Office Action dated Jul. 18, 2013 in CN 201080057014.7—includes English translation.
Office Action and Search Report dated Apr. 23, 2013 in CN 200980140805.3—includes English translation.
Office Action dated May 29, 2013 in CN 2009801406946—includes English translation.
Office Action dated Jul. 1, 2013 in CN 200980149555.X—includes English translation.
Office Action dated Jul. 1, 2013 in CN 200980149636.X—includes English translation.
Office Action and Search Report dated Dec. 17, 2013 in CN 2011800388045—includes English translation.
Office Action and Search Report dated May 22, 2016 in CN 2015104280932—includes English translation.
Non-final Office Action dated Dec. 17, 2012 in CN 2009801542245.
Office Action dated Jun. 25, 2013 in CN 201080014932.1—includes English translation.
Office Action dated Dec. 16, 2019 in EP 18151593.3.
Non-final Office Action dated Jan. 19, 2019 in in 2811/MUMNP/2012.
Non-final Office Action dated Feb. 5, 2013 in JP 2011-525262.
Non-final Office Action dated Feb. 5, 2013 in JP 2011-525262—includes English translation.
Office Action and Search Report dated Jan. 20, 2014 in JP 2013-516566—includes English translation.
Office Action dated Nov. 2, 2015 in JP 2013-516566—includes English translation.
Office Action dated Jan. 24, 2017 in JP 2016-040339—includes English translation.
Office Action dated Nov. 20, 2015 in MX MX/a/2013/000220—includes English translation.
Office Action dated Dec. 7, 2017 in MX/a/2016/002060—includes English translation summary.
Non-final Office Action dated Feb. 1, 2013 in U.S. Appl. No. 13/508,363.
Non-final Office Action dated Nov. 16, 2012 in U.S. Appl. No. 13/389,351.

(56) References Cited

OTHER PUBLICATIONS

Non-final Office Action dated Apr. 18, 2013 in U.S. Appl. No. 13/389,363.
Non-final Office Action dated Jan. 2, 2013 in U.S. Appl. No. 13/061,413.
Final Office Action dated Aug. 23, 2013 in U.S. Appl. No. 13/061,413.
Final Office Action dated Jun. 7, 2013 in U.S. Appl. No. 13/061,446.
Non-final Office Action dated Oct. 12, 2012 in U.S. Appl. No. 13/061,446.
Non-final Office Action dated Jun. 20, 2013 in U.S. Appl. No. 13/577,242.
Non-final Office Action dated Feb. 14, 2013 in U.S. Appl. No. 13/577,243.
Non-final Office Action dated Jan. 24, 2013 in U.S. Appl. No. 13/125,360.
Non-final Office Action dated Aug. 27, 2013 in U.S. Appl. No. 13/125,360.
Non-final Office Action dated Mar. 5, 2013 in U.S. Appl. No. 13/125,454.
Non-final Office Action dated Dec. 18, 2012 in U.S. Appl. No. 13/164,768.
Non-final Office Action dated Apr. 27, 2015 in U.S. Appl. No. 13/806,759.
Non-final Office Action dated Nov. 27, 2012 in U.S. Appl. No. 13/130,474.
Non-final Office Action dated May 1, 2013 in U.S. Appl. No. 13/148,030.
Non-final Office Action dated Jul. 2, 2018 in U.S. Appl. No. 15/604,573.
Restriction Requirement dated Sep. 5, 2012 in U.S. Appl. No. 13/061,413.
Restriction Requirement dated Mar. 20, 2013 in U.S. Appl. No. 13/148,031.
Restriction Requirement dated Jul. 1, 2013 in U.S. Appl. No. 13/517,244.
Extended European Search Report and Written Opinion dated Jul. 16, 2013 in EP 10812639.
Extended European Search Report and Written Opinion dated Aug. 23, 2012 in EP 09822670.7.
Extended European Search Report and Written Opinion dated Jun. 8, 2012 in 09825600.1.
Extended European Search Report and Written Opinion dated Apr. 15, 2013 in EP 10817878.
Extended European Search Report and Written Opinion dated May 24, 2013 in EP 10829191.
Extended European Search Report and Written Opinion dated Mar. 20, 2018 in EP 18151593.
Extended European Search Report and Written Opinion dated May 21, 2013 in EP 2010829198.
Extended European Search Report and Written Opinion dated Dec. 3, 2012 in EP 2010807254.
Extended European Search Report and Written Opinion dated Dec. 3, 2012 in EP 2010807232.
Extended European Search Report and Written Opinion dated Oct. 21, 2011 in EP 09810695.8.
Extended European Search Report and Written Opinion dated Feb. 22, 2012 in EP 2009810705.
Extended European Search Report and Written Opinion dated Jun. 13, 2013 in EP 11740468.
Extended European Search Report and Written Opinion dated Jun. 13, 2013 in EP 11740469.
Extended European Search Report and Written Opinion dated Jun. 18, 2013 in EP 11740470.
Extended European Search Report and Written Opinion dated Aug. 16, 2013 in EP 11748210.
Extended European Search Report and Written Opinion dated Aug. 13, 2013 in EP 11751238.
Extended European Search Report and Written Opinion dated Jun. 6, 2013 in EP 10818036.
Extended European Search Report and Written Opinion dated Jul. 6, 2012 in EP 2009822669.
Extended European Search Report dated May 22, 2015 in EP 15151607.
Extended European Search Report dated Nov. 4, 2013 in EP 11798516.
Extended European Search Report and Written Opinion dated Feb. 23, 2012 in EP 2009828325.
Extended European Search Report and Written Opinion dated Jun. 3, 2013 in EP 10838357.
Extended European Search Report and Written Opinion dated Jul. 9, 2012 in EP 2010739150.
Extended European Search Report and Written Opinion dated Jul. 27, 2012 in EP 10739152.6.
Extended European Search Report and Written Opinion dated Aug. 23, 2012 in EP 2010739155.
Extended European Search Report and Written Opinion dated Mar. 15, 2013 in EP 18817878.
Response to Extended European Search Report and Written Opinion dated May 16, 2012 in PCT/US2009/055449.
International Preliminary Report on Patentability dated May 5, 2011 in PCT/US2009/061562.
International Preliminary Report on Patentability dated Mar. 29, 2011 in PCT/US2010/049234.
International Preliminary Report on Patentability dated May 24, 2013 in PCT/US2011/055055.
International Preliminary Report on Patentability dated May 18, 2012 in PCT/US2010/055730.
International Preliminary Report on Patentability dated Mar. 10, 2011 in PCT/US2009/055449.
International Preliminary Report on Patentability dated Mar. 10, 2011 in PCT/US2009/055460.
International Preliminary Report on Patentability dated Aug. 16, 2012 in PCT/US2011/023830.
International Preliminary Report on Patentability dated Aug. 16, 2012 in PCT/US2011/023831.
International Preliminary Report on Patentability dated Aug. 16, 2012 in PCT/US2011/023832.
International Preliminary Report on Patentability dated Sep. 7, 2012 in PCT/US2011/026384.
International Preliminary Report on Patentability dated Apr. 5, 2012 in PCT/US2010/049695.
International Preliminary Report on Patentability dated Jun. 3, 2011 in PCT/US2009/065419.
International Preliminary Report on Patentability dated Jul. 5, 2012 in PCT/US2010/061377.
International Preliminary Report on Patentability dated Aug. 18, 2011 in PCT/US2010/023292.
International Preliminary Report on Patentability dated Aug. 18, 2011 in PCT/US2010/023294.
International Preliminary Report on Patentability dated Oct. 21, 2011 in PCT/US2010/023297.
International Preliminary Report on Patentability dated May 10, 2011 in PCT/US2009/063906.
International Search Report and Written Opinion dated Apr. 13, 2010 in PCT/US2009/061562.
International Search Report and Written Opinion dated Jan. 15, 2010 in PCT/US2009/063906.
International Search Report and Written Opinion dated Nov. 18, 2010 in PCT/US2010/046910.
International Search Report and Written Opinion dated Dec. 3, 2010 in PCT/US2010/049234.
International Search Report and Written Opinion dated Jan. 18, 2012 in PCT/US2011/053015.
International Search Report and Written Opinion dated Feb. 24, 2012 in PCT/US2011/055055.
International Search Report and Written Opinion dated Jan. 19, 2011 in PCT/US2010/055721.
International Search Report and Written Opinion dated Feb. 8, 2011 in PCT/US2010/055730.
International Search Report and Written Opinion dated May 10, 2012 in PCT/US2012/020571.

(56) References Cited

OTHER PUBLICATIONS

International Search Report and Written Opinion dated Oct. 28, 2010 in PCT/US2010/044772.
International Search Report and Written Opinion dated Oct. 8, 2010 in PCT/US2010/044708.
International Search Report and Written Opinion dated Dec. 10, 2009 in PCT/US2009/055449.
International Search Report and Written Opinion dated Dec. 31, 2009 in PCT/US2009/055460.
International Search Report and Written Opinion dated Apr. 27, 2011 in PCT/US2011/023830.
International Search Report and Written Opinion dated Apr. 27, 2011 in PCT/US2011/023831.
International Search Report and Written Opinion dated Apr. 29, 2011 in PCT/US2011/023832.
International Search Report and Written Opinion dated May 17, 2011 in PCT/US2011/026384.
International Search Report and Written Opinion dated Jun. 3, 2011 in PCT/US2011/026759.
International Search Report and Written Opinion dated Dec. 3, 2010 in PCT/US2010/049695.
International Search Report and Written Opinion dated Jan. 20, 2010 in PCT/US2009/061561.
International Search Report and Written Opinion dated Sep. 7, 2012 in PCT/US2012/043279.
International Search Report and Written Opinion dated Dec. 15, 2011 in PCT/US2011/001126.
International Search Report and Written Opinion dated Nov. 25, 2011 in PCT/US2011/001127.
International Search Report and Written Opinion dated Nov. 25, 2011 in PCT/US2011/001128.
International Search Report and Written Opinion dated Nov. 25, 2011 in PCT/US2011/001125.
International Search Report and Written Opinion dated Sep. 21, 2012 in PCT/US2012/045583.
International Search Report and Written Opinion dated Mar. 30, 2010 in PCT/US2009/065419.
International Search Report and Written Opinion dated Mar. 8, 2011 in PCT/US2010/061377.
International Search Report and Written Opinion dated Apr. 30, 2010 in PCT/US2010/023292.
International Search Report and Written Opinion dated Apr. 22, 2010 in PCT/US2010/023294.
International Search Report and Written Opinion dated Jun. 3, 2010 in PCT/US2010/023297.
International Search Report and Written Opinion dated Jun. 20, 2012 in PCT/US2012/020572.
International Search Report and Written Opinion dated May 2, 2012 in PCT/US2012/022926.
International Search Report and Written Opinion dated Jun. 18, 2013 in PCT/US2013/028005.
International Search Report and Written Opinion dated Mar. 15, 2013 in PCT/US2012/066152.
International Search Report and Written Opinion May 15, 2013 in PCT/US2013/023479.
Response to Non-final Office Action dated Jul. 2, 2013 in U.S. Appl. No. 13/061,413.
Response to Restriction Requirement dated Oct. 16, 2012 in U.S. Appl. No. 13/061,413.
Search Report and Written Opinion dated Apr. 15, 2013 in CN 2009801406946—includes English translation.
Search Report dated Jul. 8, 2013 in CN 201080057014.7—includes English translation.
Search Report dated May 23, 2013 in CN 200980149555.X—includes English translation.
Search Report dated Jun. 17, 2013 in CN 200980149636.X—includes English translation.
Search Report dated Nov. 23, 2012 in CN 200980154224.5—includes English translation.
Search Report dated Jun. 9, 2013 in CN 201080014932.1—includes English translation.
Anonymous, "Granulomatosis with polyangiitis", Wikipedia, Jan. 2, 2021, Retrieved from the Internet: https://en.wikipedia.org/wiki/Granulomatosis_with_polyangitis.
Daubin et al., "Urinary Biomarkers IGFBP7 and TIMP-2 for the Diagnostic Assessment of Transient and Persistent Acute Kidney Injury in Critically Ill Patients," PLoS One, 2017, 12(1):e0169674.
Huang et al., "Chymase is Upregulated in Diabetic Nephropathy: Implications for an Alternative Pathway of Angiotensin II-Mediated Diabetic Renal and Vascular Disease," J Am Soc Nephrol, 2003, 14:1738-1747.
Koyner et al., "Tissue Inhibitor Metalloproteinase-2 (TIMP-2) IGF-Binding Protein-7 (IGFBP7) Levels Are Associated with Adverse Long-Term Outcomes in Patients with AKI," J Am Soc Nephrol, 2015, 26:1747-1754.
Malhotra et al., "Biomarkers for the Early Detection and Prognosis of Acute Kidney Injury," Clin J Am Soc Nephrol, 2017, 12:149-173.
Ohlsson et al., "Increased expression of the secretory leukocyte proteinase inhibitor in Wegener's granulomatosis," Clin Exp Immunol, 2003, 131:190-196.
Official Action dated Oct. 28, 2022 issued in EP Application No. 18151593.3.

* cited by examiner

SEQUENCE LISTING

<160> NUMBER OF SEQ ID NOS: 17

<210> SEQ ID NO 1
<211> LENGTH: 96
<212> TYPE: PRT
<213> ORGANISM: Homo sapiens

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

<210> SEQ ID NO 2
<211> LENGTH: 94
<212> TYPE: PRT
<213> ORGANISM: Homo sapiens

<400> SEQUENCE: 2

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90

<210> SEQ ID NO 3
<211> LENGTH: 112
<212> TYPE: PRT
<213> ORGANISM: Homo sapiens

<400> SEQUENCE: 3

Met Lys Gly Pro Pro Thr Phe Cys Ser Leu Leu Leu Ser Leu Leu
1               5                   10                  15

Leu Ser Pro Asp Pro Thr Ala Ala Phe Leu Leu Pro Pro Ser Thr Ala
            20                  25                  30

Cys Cys Thr Gln Leu Tyr Arg Lys Pro Leu Ser Asp Lys Leu Leu Arg
        35                  40                  45

Lys Val Ile Gln Val Glu Leu Gln Glu Ala Asp Gly Asp Cys His Leu
    50                  55                  60

Gln Ala Phe Val Leu His Leu Ala Gln Arg Ser Ile Cys Ile His Pro
65                  70                  75                  80

Gln Asn Pro Ser Leu Ser Gln Trp Phe Glu His Gln Glu Arg Lys Leu
                85                  90                  95

```
His Gly Thr Leu Pro Lys Leu Asn Phe Gly Met Leu Arg Lys Met Gly
                100                 105                 110

<210> SEQ ID NO 4
<211> LENGTH: 235
<212> TYPE: PRT
<213> ORGANISM: Homo sapiens

<400> SEQUENCE: 4

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
                180                 185                 190

Pro Val Gly Leu Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
210                 215                 220

Pro Ser Pro Gln Asp Leu Leu Leu Val Glu His
225                 230                 235

<210> SEQ ID NO 5
<211> LENGTH: 569
<212> TYPE: PRT
<213> ORGANISM: Homo sapiens

<400> SEQUENCE: 5

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80
```

```
Leu Trp Phe Val Pro Ala Lys Val Glu Asp Ser Gly His Tyr Tyr Cys
                85                  90                  95
Val Val Arg Asn Ser Ser Tyr Cys Leu Arg Ile Lys Ile Ser Ala Lys
                100                 105                 110
Phe Val Glu Asn Glu Pro Asn Leu Cys Tyr Asn Ala Gln Ala Ile Phe
                115                 120                 125
Lys Gln Lys Leu Pro Val Ala Gly Asp Gly Gly Leu Val Cys Pro Tyr
        130                 135                 140
Met Glu Phe Phe Lys Asn Glu Asn Asn Glu Leu Pro Lys Leu Gln Trp
145                 150                 155                 160
Tyr Lys Asp Cys Lys Pro Leu Leu Leu Asp Asn Ile His Phe Ser Gly
                165                 170                 175
Val Lys Asp Arg Leu Ile Val Met Asn Val Ala Glu Lys His Arg Gly
                180                 185                 190
Asn Tyr Thr Cys His Ala Ser Tyr Thr Tyr Leu Gly Lys Gln Tyr Pro
        195                 200                 205
Ile Thr Arg Val Ile Glu Phe Ile Thr Leu Glu Glu Asn Lys Pro Thr
        210                 215                 220
Arg Pro Val Ile Val Ser Pro Ala Asn Glu Thr Met Glu Val Asp Leu
225                 230                 235                 240
Gly Ser Gln Ile Gln Leu Ile Cys Asn Val Thr Gly Gln Leu Ser Asp
                245                 250                 255
Ile Ala Tyr Trp Lys Trp Asn Gly Ser Val Ile Asp Glu Asp Asp Pro
                260                 265                 270
Val Leu Gly Glu Asp Tyr Tyr Ser Val Glu Asn Pro Ala Asn Lys Arg
                275                 280                 285
Arg Ser Thr Leu Ile Thr Val Leu Asn Ile Ser Glu Ile Glu Ser Arg
        290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                325                 330                 335
His Met Ile Gly Ile Cys Val Thr Leu Thr Val Ile Ile Val Cys Ser
                340                 345                 350
Val Phe Ile Tyr Lys Ile Phe Lys Ile Asp Ile Val Leu Trp Tyr Arg
                355                 360                 365
Asp Ser Cys Tyr Asp Phe Leu Pro Ile Lys Ala Ser Asp Gly Lys Thr
        370                 375                 380
Tyr Asp Ala Tyr Ile Leu Tyr Pro Lys Thr Val Gly Glu Gly Ser Thr
385                 390                 395                 400
Ser Asp Cys Asp Ile Phe Val Phe Lys Val Leu Pro Glu Val Leu Glu
                405                 410                 415
Lys Gln Cys Gly Tyr Lys Leu Phe Ile Tyr Gly Arg Asp Asp Tyr Val
                420                 425                 430
Gly Glu Asp Ile Val Glu Val Ile Asn Glu Asn Val Lys Lys Ser Arg
        435                 440                 445
Arg Leu Ile Ile Ile Leu Val Arg Glu Thr Ser Gly Phe Ser Trp Leu
450                 455                 460
Gly Gly Ser Ser Glu Glu Gln Ile Ala Met Tyr Asn Ala Leu Val Gln
465                 470                 475                 480
Asp Gly Ile Lys Val Val Leu Leu Glu Leu Glu Lys Ile Gln Asp Tyr
                485                 490                 495
```

```
Glu Lys Met Pro Glu Ser Ile Lys Phe Ile Lys Gln Lys His Gly Ala
                500                 505                 510
Ile Arg Trp Ser Gly Asp Phe Thr Gln Gly Pro Gln Ser Ala Lys Thr
            515                 520                 525
Arg Phe Trp Lys Asn Val Arg Tyr His Met Pro Val Gln Arg Arg Ser
        530                 535                 540
Pro Ser Ser Lys His Gln Leu Leu Ser Pro Ala Thr Lys Glu Lys Leu
545                 550                 555                 560
Gln Arg Glu Ala His Val Pro Leu Gly
                565

<210> SEQ ID NO 6
<211> LENGTH: 200
<212> TYPE: PRT
<213> ORGANISM: Homo sapiens

<400> SEQUENCE: 6

Met Ala Ala Ala Trp Thr Val Val Leu Val Thr Leu Val Leu Gly Leu
1               5                   10                  15
Ala Val Ala Gly Pro Val Pro Thr Ser Lys Pro Thr Thr Thr Gly Lys
            20                  25                  30
Gly Cys His Ile Gly Arg Phe Lys Ser Leu Ser Pro Gln Glu Leu Ala
        35                  40                  45
Ser Phe Lys Lys Ala Arg Asp Ala Leu Glu Glu Ser Leu Lys Leu Lys
    50                  55                  60
Asn Trp Ser Cys Ser Ser Pro Val Phe Pro Gly Asn Trp Asp Leu Arg
65                  70                  75                  80
Leu Leu Gln Val Arg Glu Arg Pro Val Ala Leu Glu Ala Glu Leu Ala
                85                  90                  95
Leu Thr Leu Lys Val Leu Glu Ala Ala Gly Pro Ala Leu Glu Asp
            100                 105                 110
Val Leu Asp Gln Pro Leu His Thr Leu His His Ile Leu Ser Gln Leu
        115                 120                 125
Gln Ala Cys Ile Gln Pro Gln Pro Thr Ala Gly Pro Arg Pro Arg Gly
    130                 135                 140
Arg Leu His His Trp Leu His Arg Leu Gln Glu Ala Pro Lys Lys Glu
145                 150                 155                 160
Ser Ala Gly Cys Leu Glu Ala Ser Val Thr Phe Asn Leu Phe Arg Leu
                165                 170                 175
Leu Thr Arg Asp Leu Lys Tyr Val Ala Asp Gly Asn Leu Cys Leu Arg
            180                 185                 190
Thr Ser Thr His Pro Glu Ser Thr
        195                 200

<210> SEQ ID NO 7
<211> LENGTH: 159
<212> TYPE: PRT
<213> ORGANISM: Homo sapiens

<400> SEQUENCE: 7

Met Phe Pro Phe Ala Leu Leu Tyr Val Leu Ser Val Ser Phe Arg Lys
1               5                   10                  15
Ile Phe Ile Leu Gln Leu Val Gly Leu Val Leu Thr Tyr Asp Phe Thr
            20                  25                  30
Asn Cys Asp Phe Glu Lys Ile Lys Ala Ala Tyr Leu Ser Thr Ile Ser
        35                  40                  45
```

```
Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Ala Leu Ala Ile Trp Cys Pro Gly
             100                 105                 110

Tyr Ser Glu Thr Gln Ile Asn Ala Thr Gln Ala Met Lys Lys Arg Arg
             115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 8
<211> LENGTH: 1338
<212> TYPE: PRT
<213> ORGANISM: Homo sapiens

<400> SEQUENCE: 8

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
             20                  25                  30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
 50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270
```

```
Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685
```

-continued

```
Glu Pro Gln Ile Thr Trp Phe Lys Asn Asn His Lys Ile Gln Gln Glu
    690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
                740                 745                 750
Asp Lys Ser Asn Leu Glu Leu Ile Thr Leu Thr Cys Thr Cys Val Ala
            755                 760                 765
Ala Thr Leu Phe Trp Leu Leu Leu Thr Leu Phe Ile Arg Lys Met Lys
770                 775                 780
Arg Ser Ser Ser Glu Ile Lys Thr Asp Tyr Leu Ser Ile Ile Met Asp
785                 790                 795                 800
Pro Asp Glu Val Pro Leu Asp Glu Gln Cys Glu Arg Leu Pro Tyr Asp
                805                 810                 815
Ala Ser Lys Trp Glu Phe Ala Arg Glu Arg Leu Lys Leu Gly Lys Ser
                820                 825                 830
Leu Gly Arg Gly Ala Phe Gly Lys Val Val Gln Ala Ser Ala Phe Gly
            835                 840                 845
Ile Lys Lys Ser Pro Thr Cys Arg Thr Val Ala Val Lys Met Leu Lys
850                 855                 860
Glu Gly Ala Thr Ala Ser Glu Tyr Lys Ala Leu Met Thr Glu Leu Lys
865                 870                 875                 880
Ile Leu Thr His Ile Gly His His Leu Asn Val Val Asn Leu Leu Gly
                885                 890                 895
Ala Cys Thr Lys Gln Gly Gly Pro Leu Met Val Ile Val Glu Tyr Cys
                900                 905                 910
Lys Tyr Gly Asn Leu Ser Asn Tyr Leu Lys Ser Lys Arg Asp Leu Phe
            915                 920                 925
Phe Leu Asn Lys Asp Ala Ala Leu His Met Glu Pro Lys Lys Glu Lys
930                 935                 940
Met Glu Pro Gly Leu Glu Gln Gly Lys Lys Pro Arg Leu Asp Ser Val
945                 950                 955                 960
Thr Ser Ser Glu Ser Phe Ala Ser Ser Gly Phe Gln Glu Asp Lys Ser
                965                 970                 975
Leu Ser Asp Val Glu Glu Glu Asp Ser Asp Gly Phe Tyr Lys Glu
            980                 985                 990
Pro Ile Thr Met Glu Asp Leu Ile Ser Tyr Ser Phe Gln Val Ala Arg
            995                 1000                1005
Gly Met Glu Phe Leu Ser Ser Arg Lys Cys Ile His Arg Asp Leu
    1010                1015                1020
Ala Ala Arg Asn Ile Leu Leu Ser Glu Asn Asn Val Val Lys Ile
    1025                1030                1035
Cys Asp Phe Gly Leu Ala Arg Asp Ile Tyr Lys Asn Pro Asp Tyr
    1040                1045                1050
Val Arg Lys Gly Asp Thr Arg Leu Pro Leu Lys Trp Met Ala Pro
    1055                1060                1065
Glu Ser Ile Phe Asp Lys Ile Tyr Ser Thr Lys Ser Asp Val Trp
    1070                1075                1080
Ser Tyr Gly Val Leu Leu Trp Glu Ile Phe Ser Leu Gly Gly Ser
    1085                1090                1095
Pro Tyr Pro Gly Val Gln Met Asp Glu Asp Phe Cys Ser Arg Leu
```

```
            1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 9
<211> LENGTH: 31
<212> TYPE: PRT
<213> ORGANISM: Homo sapiens

<400> SEQUENCE: 9

Asp Gln Glu Ala Pro Tyr Leu Leu Arg Asn Leu Ser Asp His Thr Val
1               5                   10                  15

Ala Ile Ser Ser Ser Thr Thr Leu Asp Cys His Ala Asn Gly Val
            20                  25                  30

<210> SEQ ID NO 10
<211> LENGTH: 31
<212> TYPE: PRT
<213> ORGANISM: Homo sapiens

<400> SEQUENCE: 10

Gly Glu His Cys Asn Lys Lys Ala Val Phe Ser Arg Ile Ser Lys Phe
1               5                   10                  15

Lys Ser Thr Arg Asn Asp Cys Thr Thr Gln Ser Asn Val Lys His
            20                  25                  30

<210> SEQ ID NO 11
<211> LENGTH: 134
<212> TYPE: PRT
```

-continued

<213> ORGANISM: Homo sapiens

<400> SEQUENCE: 11

Met Ala Gln Ser Leu Ala Leu Ser Leu Leu Ile Leu Val Leu Ala Phe
1               5                   10                  15

Gly Ile Pro Arg Thr Gln Gly Ser Asp Gly Ala Gln Asp Cys Cys
            20                  25                  30

Leu Lys Tyr Ser Gln Arg Lys Ile Pro Ala Lys Val Val Arg Ser Tyr
            35                  40                  45

Arg Lys Gln Glu Pro Ser Leu Gly Cys Ser Ile Pro Ala Ile Leu Phe
        50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 12
<211> LENGTH: 176
<212> TYPE: PRT
<213> ORGANISM: Homo sapiens

<400> SEQUENCE: 12

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
            35                  40                  45

Ile Arg Gly Ser Val Gln Ala Lys Asp Gly Asn Ile Asp Ile Arg Ile
        50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 13
<211> LENGTH: 211
<212> TYPE: PRT
<213> ORGANISM: Homo sapiens

<400> SEQUENCE: 13

```
Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
            195                 200                 205

Lys Pro Thr
210

<210> SEQ ID NO 14
<211> LENGTH: 241
<212> TYPE: PRT
<213> ORGANISM: Homo sapiens

<400> SEQUENCE: 14

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
130                 135                 140

Gln Val Gln Leu Arg Pro Val Gln Val Arg Lys Ile Glu Ile Val Arg
```

```
                    145                 150                 155                 160
Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
                180                 185                 190

Pro Gly Gly Ser Gln Glu Gln Arg Ala Lys Thr Pro Gln Thr Arg Val
                195                 200                 205

Thr Ile Arg Thr Val Arg Val Arg Arg Pro Pro Lys Gly Lys His Arg
            210                 215                 220

Lys Phe Lys His Thr His Asp Lys Thr Ala Leu Lys Glu Thr Leu Gly
225                 230                 235                 240

Ala

<210> SEQ ID NO 15
<211> LENGTH: 177
<212> TYPE: PRT
<213> ORGANISM: Homo sapiens

<400> SEQUENCE: 15

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
                100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
        130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 16
<211> LENGTH: 707
<212> TYPE: PRT
<213> ORGANISM: Homo sapiens

<400> SEQUENCE: 16

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45
```

```
Leu Tyr Arg Tyr Gly Tyr Thr Arg Val Ala Glu Met Arg Gly Glu Ser
    50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Thr Pro Gln Pro Thr Ala Pro
450                 455                 460

Pro Thr Val Cys Pro Thr Gly Pro Pro Thr Val His Pro Ser Glu Arg
```

```
            465                 470                 475                 480
Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
                530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705

<210> SEQ ID NO 17
<211> LENGTH: 220
<212> TYPE: PRT
<213> ORGANISM: Homo sapiens

<400> SEQUENCE: 17

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
                35                  40                  45

Ala Val Ser Glu Lys Glu Val Asp Ser Gly Asn Asp Ile Tyr Gly Asn
                50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
                100                 105                 110

Ala Gly Lys Ala Glu Gly Asp Gly Lys Met His Ile Thr Leu Cys Asp
                115                 120                 125
```

```
Phe Ile Val Pro Trp Asp Thr Leu Ser Thr Thr Gln Lys Lys Ser Leu
    130             135             140

Asn His Arg Tyr Gln Met Gly Cys Glu Cys Lys Ile Thr Arg Cys Pro
145             150             155             160

Met Ile Pro Cys Tyr Ile Ser Ser Pro Asp Glu Cys Leu Trp Met Asp
            165             170             175

Trp Val Thr Glu Lys Asn Ile Asn Gly His Gln Ala Lys Phe Phe Ala
            180             185             190

Cys Ile Lys Arg Ser Asp Gly Ser Cys Ala Trp Tyr Arg Gly Ala Ala
        195             200             205

Pro Pro Lys Gln Glu Phe Leu Asp Ile Glu Asp Pro
    210             215             220
```

METHODS AND COMPOSITIONS FOR DIAGNOSIS AND PROGNOSIS OF RENAL INJURY AND RENAL FAILURE

The present application claims priority to U.S. Provisional Patent Application No. 61/357,965 filed Jun. 23, 2010; U.S. Provisional Patent Application No. 61/357,956 filed Jun. 23, 2010; U.S. Provisional Patent Application No. 61/357,966 filed Jun. 23, 2010; U.S. Provisional Patent Application No. 61/364,305 filed Jul. 14, 2010; and U.S. Provisional Patent Application No. 61/364,297 filed Jul. 14, 2010, each of which is hereby incorporated in its entirety including all tables, figures, and claims.

SEQUENCE LISTING

The instant application contains a Sequence Listing which has been submitted via EFS-Web and is hereby incorporated by reference in its entirety. Said ASCII copy, created on Aug. 4, 2011, is named AST1930PC_SeqList.txt, and is 41,964 bytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and' increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 µmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 µmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 µmol/L accompanied by an acute increase of at least 44 µmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor A/B dimer, Platelet-derived growth factor A/A dimer, and MMP9:TIMP2 complex (each referred to herein as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

The kidney injury markers of the present invention may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor AB dimer, Platelet-derived growth factor A/A dimer, and MMP9:TIMP2 complex complex is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example measured concentration(s) of one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor A/B dimer, Platelet-derived growth factor A/A dimer, and MMP9:TIMP2 complex is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s) is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example measured concentration(s) of one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor AB dimer, Platelet-derived growth factor A/A dimer, and MMP9: TIMP2 complex is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example measured concentration(s) of one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor AB dimer, Platelet-derived growth factor A/A dimer, and MMP9:TIMP2 complex is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the 75th, 85th, 90th, 95th, or 99th percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the 75th, 85th, 90th, 95th, or 99th percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more biomarkers selected from the group consisting of Thymic stromal lymphopoietin, Vascular endothelial growth factor receptor 1, C—C motif chemokine 1, C—C motif chemokine 17, C—C motif chemokine 21, C—C motif chemokine 27, FLT-3 Ligand, Immunoglobulin G subclass 3, Interleukin-1 receptor type I, Interleukin-20, Interleukin-29, Interleukin-7, Platelet-derived growth factor AB dimer, Platelet-derived growth factor A/A dimer, and MMP9:TIMP2 complex or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq 8.8$ µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq 26.4$ µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "C—C motif chemokine 1" refers to one or more polypeptides present in a biological sample that are derived from the C—C motif chemokine 1 precursor (human precursor Swiss-Prot P22362 (SEQ ID NO: 1)).

```
           10         20         30         40         50         60
    MQIITTALVC LLLAGMWPED VDSKSMQVPF SRCCFSFAEQ EIPLRAILCY RNTSSICSNE 70         80         90
    GLIFKLKRGK EACALDTVGW VQRHRKMLRH CPSKRK
```

The following domains have been identified in C—C motif chemokine 1:

| Residues | Length | Domain ID |
|---|---|---|
| 1-23 | 23 | Signal peptide |
| 24-96 | 73 | C-C motif chemokine 1 |

As used herein, the term "C—C motif chemokine 17" refers to one or more polypeptides present in a biological sample that are derived from the C—C motif chemokine 17 precursor (human precursor Swiss-Prot Q92583 (SEQ ID NO: 2)).

```
            10          20          30          40          50          60
MAPLKMLALV  TLLLGASLQH  IHAARGTNVG  RECCLEYFKG  AIPLRKLKTW  YQTSEDCSRD 70          80          90
AIVFVTVQGR  AICSDPNNKR  VKNAVKYLQS  LERS
```

The following domains have been identified in C—C motif chemokine 17:

| Residues | Length | Domain ID |
|---|---|---|
| 1-23 | 23 | Signal peptide |
| 24-94 | 71 | C-C motif chemokine 17 |

As used herein, the term "C—C motif chemokine 27" refers to one or more polypeptides present in a biological sample that are derived from the C—C motif chemokine 27 precursor (human precursor Swiss-Prot Q9Y4X3 (SEQ ID NO: 3)).

```
            10          20          30          40          50          60
MKGPPTFCSL  LLLSLLLSPD  PTAAFLLPPS  TACCTQLYRK  PLSDKLLRKV  IQVELQEADG 70          80          90         100         110
DCHLQAFVLH  LAQRSICIHP  QNPSLSQWFE  HQERKLHGTL  PKLNFGMLRK  MG
```

The following domains have been identified in C—C motif chemokine 27:

| Residues | Length | Domain ID |
|---|---|---|
| 1-24 | 24 | Signal peptide |
| 25-112 | 88 | C-C motif chemokine 27 |

As used herein, the term "SL Cytokine" (also known as FLT-3 ligand) refers to one or more polypeptides present in a biological sample that are derived from the SL Cytokine precursor (human precursor Swiss-Prot P49771 (SEQ ID NO: 4)).

```
            10          20          30          40          50          60
MTVLAPAWSP  TTYLLLLLLL  SSGLSGTQDC  SFQHSPISSD  FAVKIRELSD  YLLQDYPVTV 70          80          90         100         110         120
ASNLQDEELC  GGLWRLVLAQ  RWMERLKTVA  GSKMQGLLER  VNTEIHFVTK  CAFQPPPSCL 130         140         150         160         170         180
RFVQTNISRL  LQETSEQLVA  LKPWITRQNF  SRCLELQCQP  DSSTLPPPWS  PRPLEATAPT 190         200         210         220         230
APQPPLLLLL  LLPVGLLLLA  AAWCLHWQRT  RRRTPRPGEQ  VPPVPSPQDL  LLVEH
```

The following domains have been identified in SL Cytokine:

| Residues | Length | Domain ID |
|---|---|---|
| 1-26 | 26 | Signal peptide |
| 27-235 | 209 | SL Cytokine |

As used herein, the term "Interleukin-1 receptor type 1" refers to one or more polypeptides present in a biological sample that are derived from the Interleukin-1 receptor type 1 precursor (human precursor Swiss-Prot P14778 (SEQ ID NO: 5):

```
            10         20         30         40         50         60
    MKVLLRLICF IALLISSLEA DKCKEREEKI ILVSSANEID VRPCPLNPNE HKGTITWYKD 70         80         90        100        110        120
    DSKTPVSTEQ ASRIHQHKEK LWFVPAKVED SGHYYCVVRN SSYCLRIKIS AKFVENEPNL 130        140        150        160        170        180
    CYNAQAIFKQ KLPVAGDGGL VCPYMEFFKN ENNELPKLQW YKDCKPLLLD NIHFSGVKDR 190        200        210        220        230        240
    LIVMNVAEKH RGNYTCHASY TYLGKQYPIT RVIEFITLEE NKPTRPVIVS PANETMEVDL 250        260        270        280        290        300
    GSQIQLICNV TGQLSDIAYW KWNGSVIDED DPVLGEDYYS VENPANKRRS TLITVLNISE 310        320        330        340        350        360
    IESRFYKHPF TCFAKNTHGI DAAYIQLIYP VTNFQKHMIG ICVTLTVIIV CSVFIYKIFK 370        380        390        400        410        420
    IDIVLWYRDS CYDFLPIKAS DGKTYDAYIL YPKTVGEGST SDCDIFVFKV LPEVLEKQCG 430        440        450        460        470        480
    YKLFIYGRDD YVGEDIVEVI NENVKKSRRL IIILVRETSG FSWLGGSSEE QIAMYNALVQ 490        500        510        520        530        540
    DGIKVVLLEL EKIQDYEKMP ESIKFIKQKH GAIRWSGDFT QGPQSAKTRF WKNVRYHMPV 550        560
    QRRSPSSKHQ LLSPATKEKL QREAHVPLG
```

Interleukin-1 receptor type 1 is a single-pass type I membrane protein having a large extracellular domain, some or all of which is present in soluble forms of Interleukin-1 receptor type 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Interleukin-1 receptor type 1:

| Residues | Length | Domain ID |
|---|---|---|
| 1-17 | 17 | Signal peptide |
| 18-569 | 552 | Interleukin-2 receptor subunit alpha |

| Residues | Length | Domain ID |
|---|---|---|
| 18-336 | 319 | Extracellular domain |
| 337-356 | 20 | Transmembrane domain |
| 357-569 | 213 | Cytoplasmic domain |

As used herein, the term "Interleukin-29" refers to one or more polypeptides present in a biological sample that are derived from the Interleukin-29 precursor (human precursor Swiss-Prot Q8IU54 (SEQ ID NO: 6)).

```
            10         20         30         40         50         60
    MAAAWTVVLV TLVLGLAVAG PVPTSKPTTT GKGCHIGRFK SLSPQELASF KKARDALEES 70         80         90        100        110        120
    LKLKNWSCSS PVFPGNWDLR LLQVRERPVA LEAELALTLK VLEAAAGPAL EDVLDQPLHT 130        140        150        160        170        180
    LHHILSQLQA CIQPQPTAGP RPRGRLHHWL HRLQEAPKKE SAGCLEASVT FNLFRLLTRD 190        200
    LKYVADGNLC LRTSTHPEST
```

The following domains have been identified in Interleukin-29:

| Residues | Length | Domain ID |
|---|---|---|
| 1-19 | 19 | Signal peptide |

As used herein, the term "Thymic stromal lymphopoietin" refers to one or more polypeptides present in a biological sample that are derived from the Thymic stromal lymphopoietin precursor (human precursor Swiss-Prot Q969D9 (SEQ ID NO: 7)).

```
         10         20         30         40         50         60
 MFPFALLYVL SVSFRKIFIL QLVGLVLTYD FTNCDFEKIK AAYLSTISKD LITYMSGTKS 70         80         90        100        110        120
 TEFNNTVSCS NRPHCLTEIQ SLTFNPTAGC ASLAKEMFAM KTKAALAIWC PGYSETQINA 130        140        150
 TQAMKKRRKR KVTTNKCLEQ VSQLQGLWRR FNRPLLKQQ
```

The following domains have been identified in Thymic stromal lymphopoietin:

| Residues | Length | Domain ID |
|---|---|---|
| 1-28 | 28 | Signal peptide |
| 29-159 | 131 | Thymic stromal lymphopoietin |

As used herein, the term "Vascular endothelial growth factor receptor 1" refers to one or more polypeptides present in a biological sample that are derived from the Vascular endothelial growth factor receptor 1 precursor (human precursor Swiss-Prot P17948 (SEQ ID NO: 8):

```
         10         20         30         40         50         60
 MVSYWDTGVL LCALLSCLLL TGSSSGSKLK DPELSLKGTQ HIMQAGQTLH LQCRGEAAHK 70         80         90        100        110        120
 WSLPEMVSKE SERLSITKSA CGRNGKQFCS TLTLNTAQAN HTGFYSCKYL AVPTSKKKET 130        140        150        160        170        180
 ESAIYIFISD TGRPFVEMYS EIPEIIHMTE GRELVIPCRV TSPNITVTLK KFPLDTLIPD 190        200        210        220        230        240
 GKRIIWDSRK GFIISNATYK EIGLLTCEAT VNGHLYKTNY LTHRQTNTII DVQISTPRPV 250        260        270        280        290        300
 KLLRGHTLVL NCTATTPLNT RVQMTWSYPD EKNKRASVRR RIDQSNSHAN IFYSVLTIDK 310        320        330        340        350        360
 MQNKDKGLYT CRVRSGPSFK SVNTSVHIYD KAFITVKHRK QQVLETVAGK RSYRLSMKVK 370        380        390        400        410        420
 AFPSPEVVWL KDGLPATEKS ARYLTRGYSL IIKDVTEEDA GNYTILLSIK QSNVFKNLTA 430        440        450        460        470        480
 TLIVNVKPQI YEKAVSSFPD PALYPLGSRQ ILTCTAYGIP QPTIKWFWHP CNHNHSEARC 490        500        510        520        530        540
 DFCSNNEESF ILDADSNMGN RIESITQRMA IIEGKNKMAS TLVVADSRIS GIYICIASNK 550        560        570        580        590        600
 VGTVGRNISF YITDVPNGFH VNLEKMPTEG EDLKLSCTVN KFLYRDVTWI LLRTVNNRTM 610        620        630        640        650        660
 HYSISKQKMA ITKEHSITLN LTIMNVSLQD SGTYACRARN VYTGEEILQK KEITIRDQEA 670        680        690        700        710        720
 PYLLRNLSDH TVAISSSTTL DCHANGVPEP QITWFKNNHK IQQEPGIILG PGSSTLFIER
```

```
               730        740        750        760        770        780
        VTEEDEGVYH CKATNQKGSV ESSAYLTVQG TSDKSNLELI TLTCTCVAAT LFWLLLTLFI 790        800        810        820        830        840
        RKMKRSSSEI KTDYLSIIMD PDEVPLDEQC ERLPYDASKW EFARERLKLG KSLGRGAFGK 850        860        870        880        890        900
        VVQASAFGIK KSPTCRTVAV KMLKEGATAS EYKALMTELK ILTHIGHHLN VVNLLGACTK 910        920        930        940        950        960
        QGGPLMVIVE YCKYGNLSNY LKSKRDLFFL NKDAALHMEP KKEKMEPGLE QGKKPRLDSV 970        980        990       1000       1010       1020
        TSSESFASSG FQEDKSLSDV EEEEDSDGFY KEPITMEDLI SYSFQVARGM EFLSSRKCIH 1030       1040       1050       1060       1070       1080
        RDLAARNILL SENNVVKICD FGLARDIYKN PDYVRKGDTR LPLKWMAPES IFDKIYSTKS 1090       1100       1110       1120       1130       1140
        DVWSYGVLLW EIFSLGGSPY PGVQMDEDFC SRLREGMRMR APEYSTPEIY QIMLDCWHRD 1150       1160       1170       1180       1190       1200
        PKERPRFAEL VEKLGDLLQA NVQQDGKDYI PINAILTGNS GFTYSTPAFS EDFFKESISA 1210       1220       1230       1240       1250       1260
        PKFNSGSSDD VRYVNAFKFM SLERIKTFEE LLPNATSMFD DYQGDSSTLL ASPMLKRFTW 1270       1280       1290       1300       1310       1320
        TDSKPKASLK IDLRVTSKSK ESGLSDVSRP SFCHSSCGHV SEGKRRFTYD HAELERKIAC

1330
        CSPPPDYNSV VLYSTPPI
```

Vascular endothelial growth factor receptor 1 is a single-pass type I membrane protein having a large extracellular domain, some or all of which is present in soluble forms of Vascular endothelial growth factor receptor 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Vascular endothelial growth factor receptor 1:

| Residues | Length | Domain ID |
|---|---|---|
| 1-26 | 26 | Signal peptide |
| 27-1338 | 1312 | Vascular endothelial growth factor receptor 1 |
| 27-758 | 732 | Extracellular domain |
| 759-780 | 22 | Transmembrane domain |
| 781-1338 | 558 | Cytoplasmic domain |
| 688-1338 | | Missing in isoform 2 |
| 657-687 | | DQEAPYLLRNLSDHTVAISSST TLDCHANGV (SEQ ID NO: 9) → GEHCNKKAVFSRISKFKSTRND CTTQSNVICH (SEQ ID NO: 10) in isoform 2 |

As used herein, the term "C—C motif chemokine 21" refers to one or more polypeptides present in a biological sample that are derived from the C—C motif chemokine 21 precursor (human precursor Swiss-Prot O00585 (SEQ ID NO: 11)).

```
                        10         20         30         40         50         60
                MAQSLALSLL ILVLAFGIPR TQGSDGGAQD CCLKYSQRKI PAKVVRSYRK QEPSLGCSIP 70         80         90        100        110        120
                AILFLPRKRS QAELCADPKE LWVQQLMQHL DKTPSPQKPA QGCRKDRGAS KTGKKGKGSK

130
                GCKRTERSQT PKGP
```

The following domains have been identified in C—C motif chemokine 21:

| Residues | Length | Domain ID |
|---|---|---|
| 1-23 | 23 | Signal peptide |
| 24-134 | 111 | C-C motif chemokine 21 |

As used herein, the term "Interleukin-20" refers to one or more polypeptides present in a biological sample that are derived from the Interleukin-20 precursor (human precursor Swiss-Prot Q9NYY1 (SEQ ID NO: 12)).

```
         10         20         30         40         50         60
    MKASSLAFSL LSAAFYLLWT PSTGLKTLNL GSCVIATNLQ EIRNGFSEIR GSVQAKDGNI 70         80         90        100        110        120
    DIRILRRTES LQDTKPANRC CLLRHLLRLY LDRVFKNYQT PDHYTLRKIS SLANSFLTIK 130        140        150        160        170
    KDLRLCHAHM TCHCGEEAMK KYSQILSHFE KLEPQAAVVK ALGELDILLQ WMEETE
```

The following domains have been identified in Interleukin-20:

| Residues | Length | Domain ID |
|---|---|---|
| 1-24 | 24 | Signal peptide |
| 25-176 | 152 | Interleukin-20 |

As used herein, the term "Platelet-derived Growth Factor A/B dimer" refers to one or more polypeptides present in a biological sample that are derived from the Platelet-derived Growth Factor A precursor in a complex with one or more polypeptides present in a biological sample that are derived from the Platelet-derived Growth Factor B precursor. Similarly, the term "Platelet-derived Growth Factor A/B dimer" refers to one or more polypeptides present in a biological sample that are derived from the Platelet-derived Growth Factor A precursor in a homodimeric complex.

The sequences of these precursors are Swiss-Prot P04085 (SEQ ID NO: 13)

```
         10         20         30         40         50         60
    MRTLACLLLL GCGYLAHVLA EEAEIPREVI ERLARSQIHS IRDLQRLLEI DSVGSEDSLD 70         80         90        100        110        120
    TSLRAHGVHA TKHVPEKRPL PIRRKRSIEE AVPAVCKTRT VIYEIPRSQV DPTSANFLIW 130        140        150        160        170        180
    PPCVEVKRCT GCCNTSSVKC QPSRVHHRSV KVAKVEYVRK KPKLKEVQVR LEEHLECACA 190        200        210
    TTSLNPDYRE EDTGRPRESG KKRKRKRLKP T
```

And Swiss-Prot P01127 (SEQ ID NO: 14)

```
         10         20         30         40         50         60
    MNRCWALFLS LCCYLRLVSA EGDPIPEELY EMLSDHSIRS FDDLQRLLHG DPGEEDGAEL 70         80         90        100        110        120
    DLNMTRSHSG GELESLARGR RSLGSLTIAE PAMIAECKTR TEVFEISRRL IDRTNANFLV 130        140        150        160        170        180
    WPPCVEVQRC SGCCNNRNVQ CRPTQVQLRP VQVRKIEIVR KKPIFKKATV TLEDHLACKC 190        200        210        220        230        240
    ETVAAARPVT RSPGGSQEQR AKTPQTRVTI RTVRVRRPPK GKHRKFKHTH DKTALKETLG
```

A

The following domains have been identified in Platelet-derived Growth Factor A:

| Residues | Length | Domain ID |
|---|---|---|
| 1-20 | 20 | Signal peptide |
| 21-86 | 66 | Propeptide |
| 87-211 | 125 | Platelet-derived Growth Factor A |
| 194-196 | 3 | GRP → DVR in short isoform |
| 197-211 | 15 | Missing in short isoform. |

The following domains have been identified in Platelet-derived Growth Factor B:

| Residues | Length | Domain ID |
|---|---|---|
| 1-20 | 20 | Signal peptide |
| 21-81 | 61 | Propeptide |
| 82-190 | 109 | Platelet-derived Growth Factor B |
| 191-241 | 51 | Propeptide |

As used herein, the term "Interleukin 7" refers to one or more polypeptides present a biological sample that are derived from the Interleukin 7 precursor (human precursor Swiss-Prot P13232 (SEQ ID NO: 15)).

```
              10         20         30         40         50         60
      MFHVSFRYIF GLPPLILVLL PVASSDCDIE GKDGKQYESV LMVSIDQLLD SMKEIGSNCL 70         80         90        100        110        120
      NNEFNFFKRH ICDANKEGMF LFRAARKLRQ FLKMNSTGDF DLHLLKVSEG TTILLNCTGQ 130        140        150        160        170
      VKGRKPAALG EAQPTKSLEE NKSLKEQKKL NDLCFLKRLL QEIKTCWNKI LMGTKEH
```

The following domains have been identified in Interleukin 7:

| Residues | Length | Domain ID |
|---|---|---|
| 1-25 | 25 | Signal peptide |
| 26-177 | 152 | Interleukin 7 |

As used herein, the term "MMP9-TIMP2 complex" refers to a complex present in a biological sample comprising one or more polypeptides that are derived from the MMP9 precursor (human precursor Swiss-Prot P14780) and one or more polypeptides that are derived from the TIMP2 precursor (human precursor Swiss-Prot P16035). TIMP2 interacts (via its C-terminal region) with MMP2 (via its C-terminal PEX domain); the interaction inhibits the MMP2 activity. Immunoassays may be formulated that detect the MMP9-TIMP2 complex, but not the individual MMP9 and TIMP2 components thereof.

The MMP9 human human precursor has the following structure (SEQ ID NO: 16):

```
              10         20         30         40         50         60
      MSLWQPLVLV LLVLGCCFAA PRQRQSTLVL FPGDLRTNLT DRQLAEEYLY RYGYTRVAEM 70         80         90        100        110        120
      RGESKSLGPA LLLLQKQLSL PETGELDSAT LKAMRTPRCG VPDLGRFQTF EGDLKWHHHN 130        140        150        160        170        180
      ITYWIQNYSE DLPRAVIDDA FARAFALWSA VTPLTFTRVY SRDADIVIQF GVAEHGDGYP 190        200        210        220        230        240
      FDGKDGLLAH AFPPGPGIQG DAHFDDDELW SLGKGVVVPT RFGNADGAAC HFPFIFEGRS 250        260        270        280        290        300
      YSACTTDGRS DGLPWCSTTA NYDTDDRFGF CPSERLYTQD GNADGKPCQF PFIFQGQSYS 310        320        330        340        350        360
      ACTTDGRSDG YRWCATTANY DRDKLFGFCP TRADSTVMGG NSAGELCVFP FTFLGKEYST 370        380        390        400        410        420
      CTSEGRGDGR LWCATTSNFD SDKKWGFCPD QGYSLFLVAA HEFGHALGLD HSSVPEALMY 430        440        450        460        470        480
      PMYRFTEGPP LHKDDVNGIR HLYGPRPEPE PRPPTTTTPQ PTAPPTVCPT GPPTVHPSER
```

```
           490        500        510        520        530        540
     PTAGPTGPPS AGPTGPPTAG PSTATTVPLS PVDDACNVNI FDAIAEIGNQ LYLFKDGKYW 550        560        570        580        590        600
     RFSEGRGSRP QGPFLIADKW PALPRKLDSV FEERLSKKLF FFSGRQVWVY TGASVLGPRR 610        620        630        640        650        660
     LDKLGLGADV AQVTGALRSG RGKMLLFSGR RLWRFDVKAQ MVDPRSASEV DRMFPGVPLD 670        680        690        700
     THDVFQYREK AYFCQDRFYW RVSSRSELNQ VDQVGYVTYD ILQCPED
```

The following domains have been identified in MMP9:

| Residues | Length | Domain ID |
| --- | --- | --- |
| 1-19 | 19 | Signal peptide |
| 20-93 | 74 | Activation peptide |
| 107-707 | 896 | 82 kDa MMP9 |

The TIMP2 human precursor has the following structure (SEQ ID NO: 17):

```
            10         20         30         40         50         60
     MGAAARTLRL ALGLLLLATL LRPADACSCS PVHPQQAFCN ADVVIRAKAV SEKEVDSGND 70         80         90        100        110        120
     IYGNPIKRIQ YEIKQIKMFK GPEKDIEFIY TAPSSAVCGV SLDVGGKKEY LIAGKAEGDG 130        140        150        160        170        180
     KMHITLCDFI VPWDTLSTTQ KKSLNHRYQM GCECKITRCP MIPCYISSPD ECLWMDWVTE 190        200        210        220
     KNINGHQAKF FACIKRSDGS CAWYRGAAPP KQEFLDIEDP
```

The following domains have been identified in TIMP2:

| Residues | Length | Domain ID |
| --- | --- | --- |
| 1-26 | 26 | Signal peptide |
| 27-220 | 194 | TIMP2 |
| 27-31 and 95-96 | | Involved in MMP9 binding |

As used herein, the terms "IgG3" and "immunoglobulin G subclass 3" refer to subclass 3 of the glycoprotein immunoglobulin G (IgG), a major effector molecule of the humoral immune response in man. Antibodies of the IgG class express their predominant activity during a secondary antibody response. The basic immunoglobulin G molecule has a four-chain structure, comprising two identical heavy (H) chains and two identical light (L) chains, linked together by inter-chain disulfide bonds. Each heavy chain is encoded by 4 distinct types of gene segments, designated $V_H$ (variable), D (diversity), $J_H$ (joining) and $C_H$ (constant). The variable region of the heavy chain is encoded by the $V_H$, D and $J_H$ segments. The light chains are encoded by the 3 gene segments, $V_L$, $J_L$ and $C_L$. The variable region of the light chains is encoded by the VL and JL segments.

As used herein, the term "IgG4" refers to subclass 4 of the glycoprotein immunoglobulin G (IgG), a major effector molecule of the humoral immune response in man. Antibodies of the IgG class express their predominant activity during a secondary antibody response. The basic immunoglobulin G molecule has a four-chain structure, comprising two identical heavy (H) chains and two identical light (L) chains, linked together by inter-chain disulfide bonds. Each heavy chain is encoded by 4 distinct types of gene segments, designated $V_H$ (variable), D (diversity), $J_H$ (joining) and $C_H$ (constant). The variable region of the heavy chain is encoded by the $V_H$, D and $J_H$ segments. The light chains are encoded by the 3 gene segments, $V_L$, $J_L$ and $C_L$. The variable region of the light chains is encoded by the $V_L$ and $J_L$ segments.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges (23). IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule (24). IgG3 differs from the other subclasses by its unique extended hinge region (about four times as long as the IgG1 hinge), containing 62 amino acids (including 21 prolines and 11 cysteines), forming an inflexible poly-proline double helix (25,26). In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

The four IgG subclasses also differ with respect to the number of inter-heavy chain disulfide bonds in the hinge region (26). The structural differences between the IgG subclasses are also reflected in their susceptibility to proteolytic enzymes. IgG3 is very susceptible to cleavage by these enzymes, whereas IgG2 is relatively resistant. IgG1 and IgG4 exhibit an intermediary sensitivity, depending upon the enzyme used. Since these proteolytic enzymes all cleave IgG molecules near or within the hinge region, it is likely that the high sensitivity of IgG3 to enzyme digestion is related to its accessible hinge. Another structural difference between the human IgG subclasses is the linkage of the heavy and light chain by a disulfide bond. This bond links the carboxy-terminal of the light chain with the cysteine residue at position 220 (in IgG) or at position 131 (in IgG2, IgG3 and IgG4) of the CHI sequence of the heavy chain.

As a consequence of the structural differences, the four IgG subclasses may be distinguished from one another, for example using antibodies that are specific for differences between the isoforms. In the present application, a level of IgG1 is determined using an assay which distinguishes this subclass, relative to the other subclasses.

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TENTAGEL™ resins (Rapp Polymere GmbH), AGROGEL™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the latter case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably at least 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1 alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of F1FO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin- 18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PM-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

ARF can often be prevented by proper maintenance of normal fluid balance, blood volume, and BP during and after major surgery; by adequate isotonic NaCl infusions in patients with severe burns; and by prompt transfusion in hemorrhagic hypotension. When a vasopressor drug is required, dopamine 1 to 3 µg/kg/min IV may augment renal blood flow, and urine output, but there is no clinical evidence that ARF is averted. In incipient ARF, furosemide with mannitol or dopamine may, reestablish normal urine flow or convert oliguric to nonoliguric ARF, but little evidence exists that the mortality rate is reduced.

Dehydration and ECF depletion should be avoided in patients requiring cholecystography or in patients with renal insufficiency requiring urography, particularly those with multiple myeloma. Urography and angiography should be avoided in any patient with renal insufficiency because of the high incidence of renal deterioration. The higher incidence in elderly patients correlates with the natural fall in GFR with aging. Before cytolytic therapy in patients with certain neoplastic diseases (e.g., lymphoma, leukemia), treatment with allopurinol should be considered along with alkalinizing the urine (oral sodium bicarbonate or acetazolamide) and increasing urine flow with increased oral or IV fluids to reduce urate crystalluria.

Dialysis improves fluid and electrolyte imbalances and allows adequate nutrition. No consensus exists as to when to begin dialysis, how frequently to perform it, or whether it even improves recovery or survival. However, hemodialysis with biocompatible membranes (e.g., polysulfone, polyacrylonitrile, polymethylmethacrylate) rather than cuprophane membranes may improve the recovery of renal function and reduce the mortality rate.

ARF should be managed without dialysis only when dialysis is unavailable or the course of ARF is uncomplicated and has existed <5 days. All renally excreted substances (e.g., digoxin, some antibiotics) must be adjusted. Water intake should be restricted to a volume equal to urine output plus measured extrarenal losses plus 500 mL/day for insensible loss. Water intake can be further modified to keep the serum Na concentration in the normal range. Body weight is an indication of fluid intake; weight loss of up to 0.5 kg/day is expected in patients not meeting basal caloric needs, and any weight gain must be attributed to excess fluid. Na and K intake is minimized, except when prior deficiencies or GI losses occurred. To reduce nitrogen loss; oral or IV administration of essential amino acids with glucose or a highly concentrated carbohydrate has been advocated, but risks include fluid overload, hyperosmolality, and infection. Ca salts (carbonate, acetate) before meals help maintain serum phosphorus at <5.5 mg/dL (<1.78 mmol/L). To help maintain serum K at <6 mmol/L in the absence of dialysis, a cation-exchange resin, sodium polystyrene sulfonate, is given 15 g po or rectally 1 to 4 times/day as a suspension in water or in a syrup (e.g., 70% sorbitol). An indwelling bladder catheter is rarely needed and should be used only when necessary because of an increased risk of UTI and urosepsis.

When obstruction is relieved, polyuria characterized by excretion of large amounts of Na, K, Mg, and other solutes may result. Self-limited hypokalemia; hyponatremia, hypernatremia, hypomagnesemia, or marked contraction of ECF volume with peripheral vascular collapse can occur. In many patients, a brisk diuresis after relief of obstruction is a physiologic response to the expansion of ECF during obstruction and does not compromise volume status. Overzealous administration of salt and water after relief of obstruction can prolong the diuresis.

In the postoliguric phase, close attention to fluid and electrolyte balance is mandatory to present potentially serious or lethal disturbances in extracellular volume, osmolality, acid-base balance, and K balance.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;

undergoing a radiographic/angiographic procedure (such as a CT scan or coronary intervention) involving the intravascular administration of contrast media;

expected to be hospitalized for at least 48 hours after contrast administration.

able and willing to provide written informed consent for study participation and to comply with all study procedures.

Exclusion Criteria renal transplant recipients;

acutely worsening renal function prior to the contrast procedure;

already receiving dialysis (either acute or chronic) or in imminent need of dialysis at enrollment;

expected to undergo a major surgical procedure (such as involving cardiopulmonary bypass) or an additional imaging procedure with contrast media with significant risk for further renal insult within the 48 hrs following contrast administration;

participation in an interventional clinical study with an experimental therapy within the previous 30 days;

known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level<39% for men, <35% for women=3 points; diabetes=3 points; contrast media volume=1 point for each 100 mL; serum creatinine level>1.5 g/dL=4 points OR estimated GFR 40-60 mL/min/1.73 m$^2$=2 points, 20-40 mL/min/1.73 m$^2$=4 points, <20 mL/min/1.73 m$^2$=6 points.

The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria males and females 18 years of age or older;

undergoing cardiovascular surgery;

Toronto/Ottawa Predictive Risk Index for Renal Replacement risk score of at least 2 (Wijeysundera et al., *JAMA* 297: 1801-9, 2007); and able and willing to provide written informed consent for study participation and to comply with all study procedures.

Exclusion Criteria known pregnancy;

previous renal transplantation; acutely worsening renal function prior to enrollment (e.g., any category of RIFLE criteria);

already receiving dialysis (either acute or chronic) or in imminent need of dialysis at enrollment;

currently enrolled in another clinical study or expected to be enrolled in another clinical study within 7 days of cardiac surgery that involves drug infusion or a therapeutic intervention for AKI;

known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 1900 adults expected to be in the ICU for at least 48 hours will be enrolled. To be enrolled in the study, each patient must meet all of the following inclusion criteria and none of the following exclusion criteria:

Inclusion Criteria males and females 18 years of age or older;

Study population 1: approximately 300 patients that have at least one of:

shock (SBP<90 mmHg and/or need for vasopressor support to maintain MAP>60 mmHg and/or documented drop in SBP of at least 40 mmHg); and sepsis;

Study population 2: approximately 300 patients that have at least one of:

IV antibiotics ordered in computerized physician order entry (CPOE) within 24 hours of enrollment;

contrast media exposure within 24 hours of enrollment;

increased Intra-Abdominal Pressure with acute decompensated heart failure; and severe trauma as the primary reason for ICU admission and likely to be hospitalized in the ICU for 48 hours after enrollment;

Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment;

Study population 4: approximately 1000 patients that are 21 years of age or older, within 24 hours of being admitted into the ICU, expected to have an indwelling urinary catheter for at least 48 hours after enrollment, and have at least one of the following acute conditions within 24 hours prior to enrollment:

(i) respiratory SOFA score of ≥2 (PaO2/FiO2<300), (ii) cardiovascular SOFA score of ≥1 (MAP<70 mm Hg and/or any vasopressor required).

Exclusion Criteria known pregnancy;

institutionalized individuals;

previous renal transplantation;

known acutely worsening renal function prior to enrollment (e.g., any category of RIFLE criteria);

received dialysis (either acute or chronic) within 5 days prior to enrollment or in imminent need of dialysis at the time of enrollment;

known infection with human immunodeficiency virus (HIV) or a hepatitis virus;

meets any of the following:

(i) active bleeding with an anticipated need for >4 units PRBC in a day;

(ii) hemoglobin <7 g/dL;

(iii) any other condition that in the physician's opinion would contraindicate drawing serial blood samples for clinical study purposes;

meets only the SBP <90 mmHg inclusion criterion set forth above, and does not have shock in the attending physician's or principal investigator's opinion;

After obtaining informed consent, an EDTA anti-coagulated blood sample (10 mL) and a urine sample (25-50 mL) are collected from each patient. Blood and urine samples are then collected at 4 (±0.5) and 8 (±1) hours after contrast administration (if applicable); at 12 (±1), 24 (±2), 36 (±2), 48 (±2), 60 (±2), 72 (±2), and 84 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards. In the case of kidney injury markers that are membrane proteins, assays are directed to soluble forms thereof as described above.

Commercially-available reagents were sourced from the following vendors:

| Analyte | Assay Source | Catalog number |
| --- | --- | --- |
| Thymic stromal lymphopoietin | Millipore | Cat. # MPXHCYP2-62K |
| Vascular endothelial growth factor receptor 1 | Millipore | Cat. # HSCR-32K |
| C-C motif chemokine 1 | Millipore | Cat. # MPXHCYP2-62K |
| C-C motif chemokine 17 | Millipore | Cat. # MPXHCYP2-62K |
| C-C motif chemokine 21 | Millipore | Cat. # MPXHCYP2-62K |
| C-C motif chemokine 27 | Millipore | Cat. # MPXHCYP2-62K |
| FLT-3 Ligand | Millipore | Cat. # MPXHCYTO-60K |
| Immunoglobulin G, subclass 3 | Millipore | Cat. # HGAM-301 |
| Interleukin-1 receptor type I | Millipore | Cat. # HSCR-32K |
| Interleukin-20 | Millipore | Cat. # MPXHCYP2-62K |
| Interleukin-29 | Millipore | Cat. # MPXHCYP3-63K |
| Interleukin-7 | Millipore | Cat. # MPXHCYTO-60K |
| Matrix Metalloproteinase-9: Tissue Inhibitor of Metalloproteinase 2 Complex | R&D Systems Moss | Calibrator Cat #841177; Detect Ab Cat # BAF911 |

Units for the concentrations reported in the following data tables are as follows: C—C Motif chemokine 21—pg/mL, Interleukin-20—pg/mL, Platelet-derived Growth Factor A/B dimer—pg/mL, Interleukin 7—pg/mL, C—C motif chemokine 1—pg/mL, C—C motif chemokine 17—pg/mL, C—C motif chemokine 27—pg/mL, FLT-3 Ligand—pg/mL, Interferon alpha-2—pg/mL, Interleukin-1 receptor type I—pg/mL, Interleukin-29—pg/mL, Platelet-derived growth factor subunit A (AA-dimer)—pg/mL, Thymic stromal lymphopoietin—pg/mL, Vascular endothelial growth factor receptor 1—pg/mL, IgG3—ng/mL, and MMP9:TIMP2 complex—pg/mL.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Use of Kidney Injury Markers for Evaluating Renal Status in Patients

Patients from the intensive care unit (ICU) were enrolled in the following study. Each patient was classified by kidney status as non-injury (0), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined. Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 are determined. OR is the odds ratio calculated for the particular cutoff concentration, and 95% CI is the confidence interval for the odds ratio.

TABLE 1

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | C-C motif chemokine 1 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 0.0132 | 0.0161 | 0.0132 | 0.0151 | 0.0132 | 0.0141 |
| Average | 1.33 | 1.52 | 1.33 | 1.41 | 1.33 | 1.46 |
| Stdev | 8.92 | 7.21 | 8.92 | 5.99 | 8.92 | 6.24 |
| p(t-test) | | 0.82 | | 0.92 | | 0.92 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | |
|---|---|---|---|---|---|---|
| Min | 0.00501 | 0.00547 | 0.00501 | 0.00501 | 0.00501 | 0.00547 |
| Max | 99.1 | 70.8 | 99.1 | 51.4 | 99.1 | 38.2 |
| n (Samp) | 463 | 120 | 463 | 130 | 463 | 47 |
| n (Patient) | 223 | 120 | 223 | 130 | 223 | 47 | sCr only

| | | | | | | |
|---|---|---|---|---|---|---|
| Median | 0.0140 | 0.0174 | 0.0140 | 0.0208 | 0.0140 | 0.0161 |
| Average | 0.819 | 3.53 | 0.819 | 4.50 | 0.819 | 2.04 |
| Stdev | 6.18 | 11.9 | 6.18 | 11.8 | 6.18 | 7.47 |
| p(t-test) | | 0.0097 | | 1.9E4 | | 0.32 |
| Min | 0.00501 | 0.00595 | 0.00501 | 0.00547 | 0.00501 | 0.00595 |
| Max | 99.1 | 70.8 | 99.1 | 51.4 | 99.1 | 38.2 |
| n (Samp) | 1019 | 40 | 1019 | 46 | 1019 | 26 |
| n (Patient) | 375 | 40 | 375 | 46 | 375 | 26 |

UO only

| | | | | | | |
|---|---|---|---|---|---|---|
| Median | 0.0140 | 0.0161 | 0.0140 | 0.0151 | 0.0140 | 0.0146 |
| Average | 2.11 | 1.33 | 2.11 | 3.17 | 2.11 | 1.10 |
| Stdev | 10.7 | 3.82 | 10.7 | 21.3 | 10.7 | 3.97 |
| p(t-test) | | 0.46 | | 0.45 | | 0.54 |
| Min | 0.00501 | 0.00547 | 0.00501 | 0.00501 | 0.00501 | 0.00547 |
| Max | 99.1 | 26.5 | 99.1 | 228 | 99.1 | 20.1 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.66 | 0.59 | 0.59 | 0.65 | 0.57 | 0.58 | 0.62 | 0.57 |
| SE | 0.030 | 0.048 | 0.032 | 0.029 | 0.045 | 0.030 | 0.045 | 0.059 | 0.047 |
| p | 3.2E−4 | 0.0011 | 0.0063 | 0.0014 | 0.0012 | 0.023 | 0.080 | 0.036 | 0.16 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 0.0128 | 0.0140 | 0.0128 | 0.0128 | 0.0133 | 0.0128 | 0.0116 | 0.0105 | 0.0122 |
| Sens 1 | 74% | 70% | 73% | 72% | 74% | 71% | 70% | 73% | 70% |
| Spec 1 | 48% | 53% | 44% | 48% | 50% | 44% | 43% | 35% | 43% |
| Cutoff 2 | 0.00936 | 0.0128 | 0.00936 | 0.00997 | 0.00928 | 0.00997 | 0.00936 | 0.00997 | 0.0105 |
| Sens 2 | 83% | 82% | 81% | 80% | 80% | 81% | 85% | 81% | 82% |
| Spec 2 | 32% | 46% | 29% | 32% | 26% | 29% | 32% | 31% | 38% |
| Cutoff 3 | 0.00637 | 0.00637 | 0.00637 | 0.00547 | 0.00547 | 0.00595 | 0.00637 | 0.00764 | 0.00637 |
| Sens 3 | 92% | 95% | 91% | 93% | 91% | 91% | 96% | 92% | 98% |
| Spec 3 | 10% | 11% | 9% | 5% | 8% | 9% | 10% | 19% | 9% |
| Cutoff 4 | 0.0186 | 0.0186 | 0.0223 | 0.0186 | 0.0186 | 0.0223 | 0.0186 | 0.0186 | 0.0223 |
| Sens 4 | 38% | 48% | 31% | 38% | 52% | 31% | 30% | 42% | 23% |
| Spec 4 | 73% | 71% | 74% | 73% | 71% | 74% | 73% | 71% | 74% |
| Cutoff 5 | 0.0250 | 0.0224 | 0.0250 | 0.0250 | 0.0224 | 0.0250 | 0.0250 | 0.0224 | 0.0250 |
| Sens 5 | 24% | 32% | 28% | 25% | 41% | 24% | 23% | 38% | 20% |
| Spec 5 | 83% | 80% | 81% | 83% | 80% | 81% | 83% | 80% | 81% |
| Cutoff 6 | 0.351 | 0.305 | 0.890 | 0.351 | 0.305 | 0.890 | 0.351 | 0.305 | 0.890 |
| Sens 6 | 18% | 28% | 16% | 16% | 33% | 17% | 15% | 27% | 14% |
| Spec 6 | 90% | 90% | 90% | 90% | 90% | 90% | 90% | 90% | 90% |
| OR Quart 2 | 1.4 | 1.00 | 1.1 | 1.0 | 0.33 | 1.0 | 1.6 | 1.3 | 2.3 |
| p Value | 0.33 | 1.00 | 0.76 | 1.0 | 0.095 | 0.89 | 0.34 | 0.74 | 0.13 |
| 95% CI of | 0.72 | 0.28 | 0.57 | 0.53 | 0.087 | 0.55 | 0.60 | 0.33 | 0.77 |
| OR Quart 2 | 2.7 | 3.5 | 2.1 | 1.9 | 1.2 | 2.0 | 4.3 | 4.7 | 6.8 |
| OR Quart 3 | 2.6 | 2.9 | 2.1 | 2.3 | 1.7 | 2.2 | 2.6 | 1.8 | 4.0 |
| p Value | 0.0026 | 0.045 | 0.019 | 0.0040 | 0.21 | 0.0072 | 0.037 | 0.37 | 0.0078 |
| 95% CI of | 1.4 | 1.0 | 1.1 | 1.3 | 0.73 | 1.2 | 1.1 | 0.51 | 1.4 |
| OR Quart | 34.8 | 8.1 | 3.8 | 4.1 | 4.0 | 4.0 | 6.6 | 6.1 | 11 |
| OR Quart 4 | 2.6 | 3.3 | 1.6 | 2.0 | 2.2 | 1.6 | 1.8 | 2.5 | 2.1 |
| p Value | 0.0026 | 0.021 | 0.13 | 0.018 | 0.059 | 0.11 | 0.25 | 0.12 | 0.20 |
| 95% CI of | 1.4 | 1.2 | 0.87 | 1.1 | 0.97 | 0.90 | 0.67 | 0.79 | 0.69 |
| OR Quart 4 | 4.8 | 9.2 | 3.0 | 3.5 | 4.9 | 3.0 | 4.7 | 8.2 | 6.3 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

C-C motif chemokine 17

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| *sCr or UO* | | | | | | |
| Median | 0.00503 | 0.0114 | 0.00503 | 0.00730 | 0.00503 | 0.00977 |
| Average | 0.115 | 0.384 | 0.115 | 0.305 | 0.115 | 0.239 |
| Stdev | 0.619 | 1.68 | 0.619 | 1.04 | 0.619 | 0.898 |
| *sCr or UO* | | | | | | |
| p(t-test) |  | 0.0052 |  | 0.0090 |  | 0.21 |
| Min | 0.00114 | 0.00114 | 0.00114 | 0.00114 | 0.00114 | 0.00114 |
| Max | 9.18 | 16.3 | 9.18 | 7.18 | 9.18 | 5.98 |
| n (Samp) | 463 | 120 | 463 | 130 | 463 | 47 |
| n (Patient) | 223 | 120 | 223 | 130 | 223 | 47 |
| *sCr only* | | | | | | |
| Median | 0.00507 | 0.0114 | 0.00507 | 0.0114 | 0.00507 | 0.0114 |
| Average | 0.210 | 0.505 | 0.210 | 0.457 | 0.210 | 0.305 |
| Stdev | 1.14 | 1.28 | 1.14 | 1.10 | 1.14 | 0.895 |
| p(t-test) |  | 0.11 |  | 0.15 |  | 0.67 |
| Min | 0.00114 | 0.00114 | 0.00114 | 0.00114 | 0.00114 | 0.00114 |
| Max | 20.4 | 6.33 | 20.4 | 5.96 | 20.4 | 4.45 |
| n (Samp) | 1019 | 40 | 1019 | 46 | 1019 | 26 |
| n (Patient) | 375 | 40 | 375 | 46 | 375 | 26 |
| *UO only* | | | | | | |
| Median | 0.00503 | 0.0114 | 0.00503 | 0.00781 | 0.00503 | 0.00909 |
| Average | 0.143 | 0.643 | 0.143 | 0.747 | 0.143 | 0.261 |
| Stdev | 0.654 | 3.09 | 0.654 | 3.50 | 0.654 | 0.930 |
| p(t-test) |  | 0.0020 |  | 7.3E−4 |  | 0.28 |
| Min | 0.00114 | 0.00114 | 0.00114 | 0.00114 | 0.00114 | 0.00114 |
| Max | 7.83 | 26.9 | 7.83 | 31.5 | 7.83 | 5.98 |
| n (Samp) | 435 | 108 | 435 | 119 | 435 | 44 |
| n (Patient) | 173 | 108 | 173 | 119 | 173 | 44 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.59 | 0.61 | 0.60 | 0.56 | 0.62 | 0.57 | 0.64 | 0.61 | 0.63 |
| SE | 0.030 | 0.048 | 0.031 | 0.029 | 0.045 | 0.030 | 0.045 | 0.059 | 0.047 |
| p | 0.0024 | 0.026 | 8.6E−4 | 0.037 | 0.0087 | 0.021 | 0.0016 | 0.065 | 0.0048 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 0.00442 | 0.00443 | 0.00443 | 0.00442 | 0.00449 | 0.00442 | 0.00503 | 0.00449 | 0.00503 |
| Sens 1 | 70% | 70% | 71% | 70% | 72% | 71% | 77% | 73% | 73% |
| Spec 1 | 40% | 41% | 42% | 40% | 46% | 40% | 52% | 46% | 51% |
| Cutoff 2 | 0.00249 | 0.00388 | 0.00249 | 0.00304 | 0.00249 | 0.00308 | 0.00449 | 0.00388 | 0.00449 |
| Sens 2 | 82% | 80% | 82% | 80% | 83% | 82% | 85% | 85% | 82% |
| Spec 2 | 16% | 30% | 16% | 21% | 15% | 24% | 46% | 30% | 48% |
| Cutoff 3 | 0.00114 | 0.00249 | 0.00114 | 0.00241 | 0.00241 | 0.00241 | 0.00388 | 0.00249 | 0.00388 |
| Sens 3 | 93% | 90% | 94% | 92% | 96% | 92% | 94% | 92% | 93% |
| Spec 3 | 4% | 15% | 4% | 7% | 7% | 8% | 31% | 15% | 32% |
| Cutoff 4 | 0.00977 | 0.0114 | 0.00977 | 0.00977 | 0.0114 | 0.00977 | 0.00977 | 0.0114 | 0.00977 |
| Sens 4 | 53% | 48% | 56% | 46% | 48% | 47% | 49% | 38% | 45% |
| Spec 4 | 71% | 72% | 71% | 71% | 72% | 71% | 71% | 72% | 71% |
| Cutoff 5 | 0.0130 | 0.0130 | 0.0130 | 0.0130 | 0.0130 | 0.0130 | 0.0130 | 0.0130 | 0.0130 |
| Sens 5 | 40% | 42% | 41% | 26% | 37% | 29% | 19% | 23% | 20% |
| Spec 5 | 84% | 80% | 81% | 84% | 80% | 81% | 84% | 80% | 81% |
| Cutoff 6 | 0.0234 | 0.216 | 0.0498 | 0.0234 | 0.216 | 0.0498 | 0.0234 | 0.216 | 0.0498 |
| Sens 6 | 19% | 25% | 21% | 18% | 24% | 20% | 17% | 19% | 18% |
| Spec 6 | 92% | 90% | 90% | 92% | 90% | 90% | 92% | 90% | 90% |
| OR Quart 2 | 0.54 | 1.3 | 0.57 | 1.1 | 0.59 | 1.6 | 3.1 | 1.0 | 5.9 |
| p Value | 0.057 | 0.62 | 0.12 | 0.66 | 0.32 | 0.13 | 0.093 | 1.0 | 0.023 |
| 95% CI of | 0.29 | 0.47 | 0.29 | 0.64 | 0.21 | 0.87 | 0.83 | 0.25 | 1.3 |
| OR Quart 2 | 1.0 | 3.5 | 1.1 | 2.0 | 1.6 | 3.0 | 12 | 4.0 | 27 |
| OR Quart 3 | 0.68 | 0.85 | 0.94 | 1.3 | 1.1 | 1.5 | 8.7 | 2.6 | 12 |
| p Value | 0.21 | 0.77 | 0.85 | 0.32 | 0.82 | 0.21 | 6.1E−4 | 0.12 | 8.2E−4 |
| 95% CI of | 0.37 | 0.28 | 0.50 | 0.76 | 0.46 | 0.80 | 2.5 | 0.79 | 2.8 |
| OR Quart 3 | 1.2 | 2.6 | 1.8 | 2.4 | 2.6 | 2.8 | 30 | 8.3 | 54 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart 4 | 2.0 | 2.7 | 2.4 | 1.6 | 2.0 | 2.1 | 4.7 | 2.0 | 5.3 |
| p Value | 0.010 | 0.030 | 0.0029 | 0.10 | 0.093 | 0.015 | 0.018 | 0.25 | 0.033 |
| 95% CI of | 1.2 | 1.1 | 1.3 | 0.91 | 0.89 | 1.2 | 1.3 | 0.60 | 1.1 |
| OR Quart 4 | 3.4 | 6.5 | 4.2 | 2.8 | 4.3 | 3.8 | 17 | 6.8 | 25 |

C-C motif chemokine 21

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 1.60 | 1.79 | 1.60 | 5.63 | 1.60 | 11.9 |
| Average | 462 | 211 | 462 | 251 | 462 | 734 |
| Stdev | 3100 | 692 | 3100 | 1180 | 3100 | 4500 |
| p(t-test) | | 0.38 | | 0.45 | | 0.59 |
| Min | 0.327 | 0.327 | 0.327 | 0.327 | 0.327 | 0.327 |
| Max | 36200 | 4860 | 36200 | 10700 | 36200 | 30900 |
| n (Samp) | 463 | 120 | 463 | 130 | 463 | 47 |
| n (Patient) | 223 | 120 | 223 | 130 | 223 | 47 | sCr only

| | | | | | | |
|---|---|---|---|---|---|---|
| Median | 1.77 | 7.75 | 1.77 | 22.9 | 1.77 | 17.6 |
| Average | 317 | 211 | 317 | 257 | 317 | 254 |
| Stdev | 2370 | 681 | 2370 | 768 | 2370 | 487 |
| p(t-test) | | 0.78 | | 0.86 | | 0.89 |
| Min | 0.327 | 0.327 | 0.327 | 0.371 | 0.327 | 0.327 |
| Max | 36200 | 4070 | 36200 | 4860 | 36200 | 1820 |
| n (Samp) | 1019 | 40 | 1019 | 46 | 1019 | 26 |
| n (Patient) | 375 | 40 | 375 | 46 | 375 | 26 |

UO only

| | | | | | | |
|---|---|---|---|---|---|---|
| Median | 1.60 | 1.79 | 1.60 | 4.37 | 1.60 | 6.31 |
| Average | 492 | 252 | 492 | 305 | 492 | 737 |
| Stdev | 3190 | 781 | 3190 | 1270 | 3190 | 4650 |
| p(t-test) | | 0.44 | | 0.53 | | 0.64 |
| Min | 0.327 | 0.371 | 0.327 | 0.327 | 0.327 | 0.327 |
| Max | 36200 | 4860 | 36200 | 10700 | 36200 | 30900 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | 0.56 | 0.56 | 0.56 | 0.61 | 0.57 | 0.59 | 0.64 | 0.55 |
| SE | 0.030 | 0.048 | 0.032 | 0.029 | 0.045 | 0.030 | 0.045 | 0.059 | 0.047 |
| p | 0.25 | 0.18 | 0.047 | 0.036 | 0.015 | 0.018 | 0.054 | 0.017 | 0.30 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 0.979 | 0.922 | 0.979 | 0.979 | 0.979 | 1.07 | 1.31 | 1.60 | 0.979 |
| Sens 1 | 73% | 78% | 77% | 73% | 72% | 71% | 70% | 73% | 70% |
| Spec 1 | 35% | 25% | 36% | 35% | 34% | 40% | 48% | 50% | 36% |
| Cutoff 2 | 0.922 | 0.832 | 0.979 | 0.939 | 0.979 | 0.922 | 0.939 | 1.07 | 0.832 |
| Sens 2 | 81% | 85% | 81% | 80% | 80% | 85% | 81% | 81% | 86% |
| Spec 2 | 25% | 19% | 33% | 28% | 30% | 26% | 28% | 38% | 19% |
| Cutoff 3 | 0.327 | 0.647 | 0.611 | 0.647 | 0.647 | 0.611 | 0.601 | 0.832 | 0.601 |
| Sens 3 | 98% | 90% | 92% | 90% | 93% | 91% | 94% | 92% | 93% |
| Spec 3 | 2% | 13% | 10% | 13% | 13% | 10% | 6% | 19% | 7% |
| Cutoff 4 | 13.0 | 12.9 | 12.9 | 13.0 | 12.9 | 12.9 | 13.0 | 12.9 | 12.9 |
| Sens 4 | 34% | 45% | 38% | 36% | 52% | 35% | 49% | 54% | 39% |
| Spec 4 | 70% | 71% | 71% | 70% | 71% | 71% | 70% | 71% | 71% |
| Cutoff 5 | 54.6 | 42.5 | 76.2 | 54.6 | 42.5 | 76.2 | 54.6 | 42.5 | 76.2 |
| Sens 5 | 23% | 32% | 23% | 21% | 35% | 20% | 23% | 31% | 16% |
| Spec 5 | 80% | 80% | 80% | 80% | 80% | 80% | 80% | 80% | 80% |
| Cutoff 6 | 194 | 170 | 285 | 194 | 170 | 285 | 194 | 170 | 285 |
| Sens 6 | 15% | 20% | 11% | 15% | 28% | 13% | 11% | 23% | 5% |
| Spec 6 | 90% | 90% | 90% | 90% | 90% | 90% | 90% | 90% | 90% |
| OR Quart 2 | 1.1 | 0.77 | 2.1 | 1.8 | 1.9 | 1.6 | 0.64 | 1.3 | 0.87 |
| p Value | 0.79 | 0.61 | 0.021 | 0.054 | 0.18 | 0.15 | 0.42 | 0.70 | 0.79 |
| 95% CI of | 0.61 | 0.28 | 1.1 | 0.99 | 0.75 | 0.84 | 0.22 | 0.30 | 0.33 |
| OR Quart 2 | 1.9 | 2.1 | 4.1 | 3.3 | 4.8 | 3.1 | 1.9 | 6.0 | 2.3 |
| OR Quart 3 | 0.99 | 0.88 | 1.8 | 2.0 | 0.85 | 2.9 | 2.2 | 3.4 | 1.7 |
| p Value | 0.98 | 0.80 | 0.080 | 0.020 | 0.78 | 6.3E−4 | 0.072 | 0.064 | 0.21 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| 95% CI of | 0.55 | 0.34 | 0.93 | 1.1 | 0.28 | 1.6 | 0.93 | 0.93 | 0.73 |
| OR Quart 3 | 1.8 | 2.3 | 3.5 | 3.6 | 2.6 | 5.4 | 5.0 | 13 | 4.2 |
| OR Quart 4 | 1.3 | 1.8 | 2.0 | 2.1 | 3.0 | 2.0 | 1.6 | 3.1 | 1.4 |
| p Value | 0.41 | 0.16 | 0.030 | 0.016 | 0.014 | 0.033 | 0.29 | 0.096 | 0.51 |
| 95% CI of | 0.72 | 0.79 | 1.1 | 1.1 | 1.2 | 1.1 | 0.67 | 0.82 | 0.55 |
| OR Quart 4 | 2.2 | 4.2 | 3.9 | 3.7 | 7.2 | 3.8 | 3.9 | 11 | 3.4 |

C-C motif chemokine 27

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 1.78 | 2.47 | 1.78 | 2.71 | 1.78 | 1.35 |
| Average | 4.25 | 4.45 | 4.25 | 5.19 | 4.25 | 4.74 |
| Stdev | 14.7 | 8.51 | 14.7 | 12.2 | 14.7 | 13.3 |
| p(t-test) | | 0.89 | | 0.50 | | 0.82 |
| Min | 0.00255 | 0.00333 | 0.00255 | 0.00333 | 0.00255 | 0.00333 |
| Max | 230 | 67.0 | 230 | 109 | 230 | 87.0 |
| n (Samp) | 463 | 120 | 463 | 130 | 463 | 47 |
| n (Patient) | 223 | 120 | 223 | 130 | 223 | 47 | sCr only

| | | | | | | |
|---|---|---|---|---|---|---|
| Median | 1.95 | 2.53 | 1.95 | 3.27 | 1.95 | 1.75 |
| Average | 4.06 | 4.57 | 4.06 | 4.68 | 4.06 | 3.94 |
| Stdev | 11.8 | 7.63 | 11.8 | 6.29 | 11.8 | 6.54 |
| p(t-test) | | 0.79 | | 0.72 | | 0.96 |
| Min | 0.00255 | 0.00333 | 0.00255 | 0.00668 | 0.00255 | 0.00333 |
| Max | 230 | 45.2 | 230 | 38.4 | 230 | 31.3 |
| n (Samp) | 1018 | 40 | 1018 | 46 | 1018 | 26 |
| n (Patient) | 375 | 40 | 375 | 46 | 375 | 26 |

UO only

| | | | | | | |
|---|---|---|---|---|---|---|
| Median | 1.85 | 2.53 | 1.85 | 2.71 | 1.85 | 1.35 |
| Average | 4.81 | 7.78 | 4.81 | 6.93 | 4.81 | 5.41 |
| Stdev | 15.3 | 25.8 | 15.3 | 21.6 | 15.3 | 15.3 |
| p(t-test) | | 0.12 | | 0.22 | | 0.80 |
| Min | 0.00255 | 0.00668 | 0.00255 | 0.00333 | 0.00255 | 0.00912 |
| Max | 230 | 234 | 230 | 198 | 230 | 87.0 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.56 | 0.57 | 0.58 | 0.61 | 0.57 | 0.48 | 0.50 | 0.49 |
| SE | 0.030 | 0.048 | 0.032 | 0.029 | 0.045 | 0.030 | 0.045 | 0.057 | 0.046 |
| p | 0.053 | 0.22 | 0.025 | 0.0091 | 0.013 | 0.030 | 0.63 | 0.98 | 0.75 |
| nCohort 1 | 463 | 1018 | 435 | 463 | 1018 | 435 | 463 | 1018 | 435 |
| nCohort 2 | 120 | 40 | 108 | 130 | 46 | 119 | 47 | 26 | 44 |
| Cutoff 1 | 1.11 | 1.37 | 1.28 | 1.32 | 2.16 | 1.28 | 0.554 | 0.506 | 0.774 |
| Sens 1 | 70% | 70% | 70% | 70% | 72% | 71% | 70% | 73% | 70% |
| Spec 1 | 41% | 42% | 42% | 44% | 54% | 42% | 28% | 26% | 33% |
| Cutoff 2 | 0.648 | 0.521 | 0.729 | 0.697 | 1.32 | 0.697 | 0.405 | 0.185 | 0.396 |
| Sens 2 | 80% | 80% | 81% | 80% | 80% | 81% | 81% | 81% | 82% |
| Spec 2 | 30% | 26% | 31% | 32% | 41% | 31% | 27% | 21% | 26% |
| Cutoff 3 | 0.0149 | 0.0115 | 0.0337 | 0.0149 | 0.00986 | 0.116 | 0.0100 | 0.00333 | 0.0203 |
| Sens 3 | 90% | 90% | 91% | 90% | 91% | 91% | 91% | 92% | 91% |
| Spec 3 | 18% | 14% | 20% | 18% | 13% | 21% | 14% | 1% | 20% |
| Cutoff 4 | 3.52 | 3.46 | 3.88 | 3.52 | 3.46 | 3.88 | 3.52 | 3.46 | 3.88 |
| Sens 4 | 32% | 32% | 34% | 35% | 39% | 34% | 23% | 42% | 23% |
| Spec 4 | 70% | 70% | 70% | 70% | 70% | 70% | 70% | 70% | 70% |
| Cutoff 5 | 4.61 | 4.56 | 5.22 | 4.61 | 4.56 | 5.22 | 4.61 | 4.56 | 5.22 |
| Sens 5 | 23% | 30% | 21% | 25% | 30% | 23% | 17% | 27% | 16% |
| Spec 5 | 80% | 80% | 80% | 80% | 80% | 80% | 80% | 80% | 80% |
| Cutoff 6 | 7.37 | 7.16 | 8.58 | 7.37 | 7.16 | 8.58 | 7.37 | 7.16 | 8.58 |
| Sens 6 | 12% | 18% | 14% | 12% | 15% | 13% | 13% | 12% | 7% |
| Spec 6 | 90% | 90% | 90% | 90% | 90% | 90% | 90% | 90% | 90% |
| OR Quart 2 | 1.6 | 1.1 | 1.6 | 1.3 | 0.33 | 1.6 | 0.90 | 1.5 | 1.3 |
| p Value | 0.13 | 0.81 | 0.14 | 0.35 | 0.095 | 0.13 | 0.83 | 0.43 | 0.62 |
| 95% CI of | 0.87 | 0.43 | 0.84 | 0.72 | 0.087 | 0.87 | 0.35 | 0.53 | 0.48 |
| OR Quart 2 | 3.0 | 3.0 | 3.2 | 2.5 | 1.2 | 3.0 | 2.3 | 4.3 | 3.3 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart 3 | 2.1 | 1.4 | 2.3 | 2.5 | 2.2 | 2.1 | 2.2 | 0.49 | 2.6 |
| p Value | 0.014 | 0.49 | 0.010 | 0.0017 | 0.058 | 0.018 | 0.056 | 0.32 | 0.029 |
| 95% CI of | 1.2 | 0.55 | 1.2 | 1.4 | 0.98 | 1.1 | 0.98 | 0.12 | 1.1 |
| OR Quart 3 | 3.9 | 3.5 | 4.4 | 4.4 | 4.9 | 3.8 | 4.9 | 2.0 | 6.3 |
| OR Quart 4 | 1.8 | 1.5 | 2.0 | 1.8 | 1.7 | 1.8 | 0.79 | 1.3 | 0.88 |
| p Value | 0.054 | 0.37 | 0.030 | 0.061 | 0.21 | 0.052 | 0.64 | 0.59 | 0.80 |
| 95% CI of | 0.99 | 0.61 | 1.1 | 0.97 | 0.73 | 0.99 | 0.30 | 0.46 | 0.31 |
| OR Quart 4 | 3.4 | 3.8 | 3.9 | 3.2 | 4.0 | 3.4 | 2.1 | 3.9 | 2.5 |

Vascular endothelial growth factor receptor 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| | sCr or UO | | | | | |
| Median | 3.72 | 36.8 | 3.72 | 13.6 | 3.72 | 37.5 |
| Average | 46.7 | 140 | 46.7 | 120 | 46.7 | 73.5 |
| Stdev | 97.8 | 723 | 97.8 | 502 | 97.8 | 116 |
| p(t-test) | | 0.065 | | 0.040 | | 0.16 |
| Min | 0.169 | 0.169 | 0.169 | 0.169 | 0.169 | 0.169 |
| Max | 809 | 6850 | 809 | 4630 | 809 | 563 |
| n (Samp) | 215 | 89 | 215 | 95 | 215 | 32 |
| n (Patient) | 126 | 89 | 126 | 95 | 126 | 32 |
| | sCr only | | | | | |
| Median | 19.5 | 26.5 | 19.5 | 8.62 | 19.5 | 8.05 |
| Average | 82.8 | 56.1 | 82.8 | 61.6 | 82.8 | 33.5 |
| Stdev | 379 | 88.7 | 379 | 128 | 379 | 40.2 |
| p(t-test) | | 0.71 | | 0.75 | | 0.58 |
| Min | 0.169 | 0.169 | 0.169 | 0.242 | 0.169 | 0.169 |
| Max | 6850 | 417 | 6850 | 673 | 6850 | 132 |
| n (Samp) | 512 | 28 | 512 | 33 | 512 | 18 |
| n (Patient) | 239 | 28 | 239 | 33 | 239 | 18 |
| | UO only | | | | | |
| Median | 5.82 | 38.1 | 5.82 | 8.62 | 5.82 | 38.1 |
| Average | 46.6 | 168 | 46.6 | 122 | 46.6 | 78.1 |
| Stdev | 94.8 | 769 | 94.8 | 526 | 94.8 | 118 |
| p(t-test) | | 0.020 | | 0.039 | | 0.094 |
| Min | 0.169 | 0.169 | 0.169 | 0.169 | 0.169 | 0.281 |
| Max | 809 | 6850 | 809 | 4630 | 809 | 563 |
| n (Samp) | 227 | 79 | 227 | 85 | 227 | 31 |
| n (Patient) | 122 | 79 | 122 | 85 | 122 | 31 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.66 | 0.54 | 0.68 | 0.55 | 0.49 | 0.54 | 0.62 | 0.46 | 0.64 |
| SE | 0.036 | 0.057 | 0.037 | 0.036 | 0.052 | 0.037 | 0.056 | 0.071 | 0.056 |
| p | 3.8E−6 | 0.52 | 1.3E−6 | 0.15 | 0.84 | 0.31 | 0.032 | 0.53 | 0.016 |
| nCohort 1 | 215 | 512 | 227 | 215 | 512 | 227 | 215 | 512 | 227 |
| nCohort 2 | 89 | 28 | 79 | 95 | 33 | 85 | 32 | 18 | 31 |
| Cutoff 1 | 9.67 | 9.67 | 10.1 | 0.455 | 0.480 | 0.455 | 2.27 | 0.568 | 2.27 |
| Sens 1 | 73% | 75% | 71% | 74% | 79% | 73% | 75% | 72% | 81% |
| Spec 1 | 60% | 46% | 58% | 28% | 26% | 24% | 47% | 34% | 43% |
| Cutoff 2 | 0.526 | 0.521 | 2.27 | 0.281 | 0.455 | 0.388 | 0.526 | 0.281 | 2.27 |
| Sens 2 | 81% | 82% | 82% | 80% | 82% | 80% | 81% | 83% | 81% |
| Spec 2 | 43% | 31% | 43% | 16% | 21% | 20% | 43% | 12% | 43% |
| Cutoff 3 | 0.455 | 0.215 | 0.455 | 0.169 | 0.242 | 0.169 | 0.429 | 0.169 | 0.429 |
| Sens 3 | 96% | 96% | 96% | 94% | 97% | 93% | 91% | 94% | 94% |
| Spec 3 | 28% | 6% | 24% | 7% | 9% | 6% | 26% | 3% | 22% |
| Cutoff 4 | 31.0 | 65.7 | 36.8 | 31.0 | 65.7 | 36.8 | 31.0 | 65.7 | 36.8 |
| Sens 4 | 57% | 21% | 54% | 44% | 21% | 39% | 53% | 17% | 52% |
| Spec 4 | 70% | 71% | 70% | 70% | 71% | 70% | 70% | 71% | 70% |
| Cutoff 5 | 75.5 | 102 | 80.7 | 75.5 | 102 | 80.7 | 75.5 | 102 | 80.7 |
| Sens 5 | 28% | 14% | 33% | 24% | 18% | 24% | 31% | 6% | 29% |
| Spec 5 | 80% | 80% | 80% | 80% | 80% | 80% | 80% | 80% | 80% |
| Cutoff 6 | 152 | 179 | 129 | 152 | 179 | 129 | 152 | 179 | 129 |
| Sens 6 | 16% | 7% | 23% | 13% | 6% | 14% | 16% | 0% | 19% |
| Spec 6 | 90% | 90% | 90% | 90% | 90% | 90% | 90% | 90% | 90% |
| OR Quart 2 | 3.6 | 1.2 | 4.3 | 0.80 | 1.3 | 0.48 | 2.1 | 1.7 | 0.98 |
| p Value | 0.011 | 0.76 | 0.0062 | 0.55 | 0.60 | 0.060 | 0.24 | 0.47 | 0.98 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| 95% CI of | 1.3 | 0.36 | 1.5 | 0.39 | 0.48 | 0.22 | 0.60 | 0.40 | 0.27 |
| OR Quart 2 | 9.7 | 4.1 | 12 | 1.7 | 3.6 | 1.0 | 7.4 | 7.3 | 3.6 |
| OR Quart 3 | 10 | 2.3 | 7.8 | 1.4 | 1.6 | 1.1 | 1.5 | 1.7 | 1.7 |
| p Value | 1.2E−6 | 0.13 | 7.9E−5 | 0.30 | 0.33 | 0.86 | 0.53 | 0.48 | 0.38 |
| 95% CI of | 4.1 | 0.78 | 2.8 | 0.73 | 0.61 | 0.54 | 0.41 | 0.40 | 0.52 |
| OR Quart 3 | 27 | 6.8 | 22 | 2.9 | 4.3 | 2.1 | 5.7 | 7.2 | 5.5 |
| OR Quart 4 | 7.2 | 1.2 | 8.6 | 1.6 | 0.86 | 1.1 | 4.2 | 1.7 | 3.0 |
| p Value | 5.0E−5 | 0.76 | 3.5E−5 | 0.19 | 0.79 | 0.73 | 0.018 | 0.47 | 0.053 |
| 95% CI of | 2.8 | 0.36 | 3.1 | 0.80 | 0.28 | 0.57 | 1.3 | 0.40 | 0.99 |
| OR Quart 4 | 19 | 4.1 | 24 | 3.1 | 2.6 | 2.2 | 13 | 7.3 | 8.8 |

SL cytokine

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 0.0627 | 0.0869 | 0.0627 | 0.0818 | 0.0627 | 0.0908 |
| Average | 2.51 | 0.905 | 2.51 | 2.00 | 2.51 | 0.275 |
| Stdev | 29.2 | 5.65 | 29.2 | 9.44 | 29.2 | 1.18 |
| p(t-test) | | 0.55 | | 0.84 | | 0.60 |
| Min | 0.0336 | 0.0336 | 0.0336 | 0.0336 | 0.0336 | 0.0336 |
| Max | 527 | 57.6 | 527 | 76.7 | 527 | 8.15 |
| n (Samp) | 462 | 120 | 462 | 130 | 462 | 47 |
| n (Patient) | 223 | 120 | 223 | 130 | 223 | 47 | sCr only

| | | | | | | |
|---|---|---|---|---|---|---|
| Median | 0.0627 | 0.0554 | 0.0627 | 0.0914 | 0.0627 | 0.0911 |
| Average | 1.59 | 0.554 | 1.59 | 1.82 | 1.59 | 0.127 |
| Stdev | 20.1 | 2.96 | 20.1 | 7.71 | 20.1 | 0.0887 |
| p(t-test) | | 0.74 | | 0.94 | | 0.71 |
| Min | 0.0336 | 0.0336 | 0.0336 | 0.0336 | 0.0336 | 0.0336 |
| Max | 527 | 18.8 | 527 | 50.2 | 527 | 0.288 |
| n (Samp) | 1019 | 40 | 1019 | 46 | 1019 | 26 |
| n (Patient) | 375 | 40 | 375 | 46 | 375 | 26 |

UO only

| | | | | | | |
|---|---|---|---|---|---|---|
| Median | 0.0627 | 0.0869 | 0.0627 | 0.0747 | 0.0627 | 0.0747 |
| Average | 2.64 | 1.64 | 2.64 | 1.93 | 2.64 | 0.275 |
| Stdev | 30.0 | 8.81 | 30.0 | 9.08 | 30.0 | 1.22 |
| p(t-test) | | 0.73 | | 0.80 | | 0.60 |
| Min | 0.0336 | 0.0449 | 0.0336 | 0.0336 | 0.0336 | 0.0336 |
| Max | 527 | 68.6 | 527 | 76.7 | 527 | 8.15 |
| n (Samp) | 436 | 108 | 436 | 119 | 436 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.43 | 0.59 | 0.56 | 0.65 | 0.54 | 0.57 | 0.61 | 0.53 |
| SE | 0.030 | 0.048 | 0.032 | 0.029 | 0.045 | 0.030 | 0.045 | 0.059 | 0.046 |
| p | 0.037 | 0.12 | 0.0029 | 0.035 | 9.9E−4 | 0.23 | 0.10 | 0.067 | 0.46 |
| nCohort 1 | 462 | 1019 | 436 | 462 | 1019 | 436 | 462 | 1019 | 436 |
| nCohort 2 | 120 | 40 | 108 | 130 | 46 | 119 | 47 | 26 | 44 |
| Cutoff 1 | 0.0537 | 0.0455 | 0.0579 | 0.0541 | 0.0651 | 0.0541 | 0.0579 | 0.0541 | 0.0537 |
| Sens 1 | 70% | 75% | 71% | 73% | 72% | 71% | 70% | 81% | 73% |
| Spec 1 | 28% | 16% | 39% | 28% | 51% | 30% | 37% | 29% | 30% |
| Cutoff 2 | 0.0455 | 0.0449 | 0.0514 | 0.0527 | 0.0579 | 0.0511 | 0.0455 | 0.0541 | 0.0487 |
| Sens 2 | 87% | 85% | 81% | 81% | 83% | 85% | 83% | 81% | 82% |
| Spec 2 | 19% | 13% | 21% | 26% | 37% | 21% | 19% | 29% | 17% |
| Cutoff 3 | 0.0449 | 0.0445 | 0.0449 | 0.0445 | 0.0445 | 0.0445 | 0.0445 | 0.0455 | 0.0435 |
| Sens 3 | 95% | 92% | 96% | 94% | 96% | 94% | 91% | 92% | 91% |
| Spec 3 | 15% | 9% | 13% | 9% | 9% | 7% | 9% | 16% | 7% |
| Cutoff 4 | 0.0914 | 0.0914 | 0.0914 | 0.0914 | 0.0914 | 0.0914 | 0.0914 | 0.0914 | 0.0914 |
| Sens 4 | 34% | 20% | 39% | 32% | 48% | 28% | 34% | 42% | 25% |
| Spec 4 | 72% | 72% | 71% | 72% | 72% | 71% | 72% | 72% | 71% |
| Cutoff 5 | 0.109 | 0.109 | 0.109 | 0.109 | 0.109 | 0.109 | 0.109 | 0.109 | 0.109 |
| Sens 5 | 31% | 20% | 33% | 28% | 39% | 24% | 28% | 35% | 20% |
| Spec 5 | 83% | 82% | 81% | 83% | 82% | 81% | 83% | 82% | 81% |
| Cutoff 6 | 0.154 | 0.186 | 0.154 | 0.154 | 0.186 | 0.154 | 0.154 | 0.186 | 0.154 |
| Sens 6 | 19% | 15% | 22% | 18% | 30% | 16% | 19% | 23% | 16% |
| Spec 6 | 90% | 90% | 90% | 90% | 90% | 90% | 90% | 90% | 90% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart 2 | 0.52 | 0.87 | 0.58 | 0.96 | 1.3 | 1.2 | 0.43 | 0.80 | 0.58 |
| p Value | 0.041 | 0.79 | 0.12 | 0.88 | 0.59 | 0.56 | 0.13 | 0.74 | 0.31 |
| 95% CI of | 0.27 | 0.31 | 0.29 | 0.53 | 0.46 | 0.65 | 0.15 | 0.21 | 0.20 |
| OR Quart 2 | 0.97 | 2.4 | 1.2 | 1.7 | 3.9 | 2.2 | 1.3 | 3.0 | 1.6 |
| OR Quart 3 | 1.1 | 1.0 | 1.5 | 1.5 | 2.2 | 1.6 | 1.5 | 1.4 | 1.8 |
| p Value | 0.67 | 1.0 | 0.18 | 0.12 | 0.11 | 0.12 | 0.31 | 0.56 | 0.16 |
| 95% CI of | 0.65 | 0.37 | 0.83 | 0.89 | 0.83 | 0.89 | 0.68 | 0.44 | 0.79 |
| OR Quart 3 | 2.0 | 2.7 | 2.7 | 2.7 | 5.9 | 2.9 | 3.4 | 4.5 | 4.1 |
| OR Quart 4 | 1.2 | 2.2 | 1.7 | 1.6 | 3.3 | 1.4 | 1.4 | 2.0 | 1.1 |
| p Value | 0.42 | 0.070 | 0.081 | 0.095 | 0.012 | 0.24 | 0.42 | 0.20 | 0.82 |
| 95% CI of | 0.72 | 0.94 | 0.94 | 0.92 | 1.3 | 0.79 | 0.62 | 0.68 | 0.45 |
| OR Quart 4 | 2.2 | 5.2 | 3.0 | 2.8 | 8.4 | 2.6 | 3.2 | 6.0 | 2.7 |

Immunoglogulin G3

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 82.9 | 132 | 82.9 | 119 | 82.9 | 104 |
| Average | 195 | 194 | 195 | 238 | 195 | 166 |
| Stdev | 301 | 247 | 301 | 314 | 301 | 200 |
| p(t-test) | | 0.97 | | 0.16 | | 0.51 |
| Min | 0.833 | 10.0 | 0.833 | 4.58 | 0.833 | 8.91 |
| Max | 1200 | 1200 | 1200 | 1200 | 1200 | 884 |
| n (Samp) | 461 | 119 | 461 | 126 | 461 | 47 |
| n (Patient) | 222 | 119 | 222 | 126 | 222 | 47 | sCr only

| | | | | | | |
|---|---|---|---|---|---|---|
| Median | 91.7 | 155 | 91.7 | 131 | 91.7 | 159 |
| Average | 196 | 229 | 196 | 268 | 196 | 196 |
| Stdev | 282 | 294 | 282 | 335 | 282 | 220 |
| p(t-test) | | 0.48 | | 0.093 | | 1.00 |
| Min | 0.833 | 10.8 | 0.833 | 13.0 | 0.833 | 8.91 |
| Max | 1200 | 1200 | 1200 | 1200 | 1200 | 884 |
| n (Samp) | 1011 | 40 | 1011 | 46 | 1011 | 26 |
| n (Patient) | 373 | 40 | 373 | 46 | 373 | 26 |

UO only

| | | | | | | |
|---|---|---|---|---|---|---|
| Median | 97.9 | 147 | 97.9 | 136 | 97.9 | 112 |
| Average | 199 | 250 | 199 | 273 | 199 | 208 |
| Stdev | 293 | 316 | 293 | 353 | 293 | 260 |
| p(t-test) | | 0.12 | | 0.023 | | 0.86 |
| Min | 0.833 | 10.0 | 0.833 | 4.58 | 0.833 | 15.8 |
| Max | 1200 | 1200 | 1200 | 1200 | 1200 | 1200 |
| n (Samp) | 433 | 107 | 433 | 115 | 433 | 44 |
| n (Patient) | 171 | 107 | 171 | 115 | 171 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.60 | 0.60 | 0.57 | 0.58 | 0.57 | 0.53 | 0.57 | 0.55 |
| SE | 0.030 | 0.048 | 0.032 | 0.029 | 0.045 | 0.031 | 0.045 | 0.059 | 0.047 |
| p | 0.0039 | 0.029 | 0.0023 | 0.027 | 0.060 | 0.025 | 0.50 | 0.27 | 0.32 |
| nCohort 1 | 461 | 1011 | 433 | 461 | 1011 | 433 | 461 | 1011 | 433 |
| nCohort 2 | 119 | 40 | 107 | 126 | 46 | 115 | 47 | 26 | 44 |
| Cutoff 1 | 68.7 | 94.9 | 77.4 | 54.9 | 66.3 | 56.0 | 52.5 | 95.8 | 65.4 |
| Sens 1 | 71% | 70% | 70% | 71% | 72% | 70% | 70% | 73% | 70% |
| Spec 1 | 43% | 51% | 42% | 36% | 39% | 33% | 34% | 52% | 37% |
| Cutoff 2 | 53.7 | 62.0 | 58.5 | 42.7 | 45.4 | 45.1 | 42.4 | 42.4 | 50.1 |
| Sens 2 | 81% | 80% | 80% | 80% | 80% | 80% | 81% | 81% | 82% |
| Spec 2 | 34% | 37% | 33% | 28% | 27% | 26% | 28% | 25% | 29% |
| Cutoff 3 | 31.8 | 31.8 | 39.2 | 23.9 | 27.7 | 28.8 | 23.7 | 18.0 | 31.7 |
| Sens 3 | 91% | 90% | 91% | 90% | 91% | 90% | 91% | 92% | 91% |
| Spec 3 | 19% | 17% | 22% | 13% | 14% | 16% | 13% | 8% | 17% |
| Cutoff 4 | 152 | 171 | 164 | 152 | 171 | 164 | 152 | 171 | 164 |
| Sens 4 | 45% | 38% | 42% | 40% | 41% | 42% | 34% | 46% | 27% |
| Spec 4 | 70% | 70% | 70% | 70% | 70% | 70% | 70% | 70% | 70% |
| Cutoff 5 | 239 | 270 | 243 | 239 | 270 | 243 | 239 | 270 | 243 |
| Sens 5 | 21% | 18% | 29% | 26% | 26% | 28% | 19% | 12% | 27% |
| Spec 5 | 80% | 80% | 80% | 80% | 80% | 80% | 80% | 80% | 80% |
| Cutoff 6 | 447 | 403 | 408 | 447 | 403 | 408 | 447 | 403 | 408 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Sens 6 | 7% | 10% | 12% | 13% | 20% | 19% | 9% | 8% | 14% |
| Spec 6 | 90% | 90% | 90% | 90% | 90% | 90% | 90% | 90% | 90% |
| OR Quart 2 | 1.9 | 1.4 | 2.1 | 1.2 | 1.3 | 1.0 | 1.7 | 0.16 | 1.6 |
| p Value | 0.056 | 0.57 | 0.033 | 0.47 | 0.63 | 1.0 | 0.26 | 0.095 | 0.33 |
| 95% CI of | 0.98 | 0.44 | 1.1 | 0.69 | 0.49 | 0.54 | 0.68 | 0.020 | 0.61 |
| OR Quart 2 | 3.6 | 4.5 | 4.1 | 2.3 | 3.2 | 1.9 | 4.2 | 1.4 | 4.4 |
| OR Quart 3 | 2.7 | 3.3 | 2.0 | 1.4 | 1.3 | 1.2 | 2.0 | 2.2 | 2.1 |
| p Value | 0.0021 | 0.021 | 0.047 | 0.25 | 0.63 | 0.54 | 0.13 | 0.11 | 0.12 |
| 95% CI of | 1.4 | 1.2 | 1.0 | 0.79 | 0.49 | 0.66 | 0.81 | 0.83 | 0.83 |
| OR Quart 3 | 5.0 | 9.2 | 4.0 | 2.5 | 3.2 | 2.2 | 4.9 | 6.0 | 5.5 |
| OR Quart 4 | 2.4 | 2.5 | 3.0 | 2.0 | 2.3 | 1.9 | 1.4 | 1.00 | 1.8 |
| p Value | 0.0068 | 0.096 | 9.7E-4 | 0.019 | 0.051 | 0.033 | 0.48 | 0.99 | 0.24 |
| 95% CI of | 1.3 | 0.85 | 1.6 | 1.1 | 1.00 | 1.1 | 0.55 | 0.32 | 0.67 |
| OR Quart 4 | 4.5 | 7.1 | 5.8 | 3.5 | 5.5 | 3.3 | 3.6 | 3.1 | 4.7 |

Interleukin-1 receptor type I

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 4.25 | 7.23 | 4.25 | 6.24 | 4.25 | 7.49 |
| Average | 5.20 | 7.14 | 5.20 | 7.31 | 5.20 | 6.97 |
| Stdev | 5.07 | 5.22 | 5.07 | 9.00 | 5.07 | 5.33 |
| p(t-test) | | 0.0027 | | 0.0088 | | 0.068 |
| Min | 0.0147 | 0.0147 | 0.0147 | 0.0147 | 0.0147 | 0.0177 |
| Max | 27.4 | 33.9 | 27.4 | 78.1 | 27.4 | 16.8 |
| n (Samp) | 217 | 90 | 217 | 96 | 217 | 32 |
| n (Patient) | 128 | 90 | 128 | 96 | 128 | 32 | sCr only

| | | | | | | |
|---|---|---|---|---|---|---|
| Median | 5.40 | 5.09 | 5.40 | 7.75 | 5.40 | 6.82 |
| Average | 6.28 | 5.40 | 6.28 | 6.78 | 6.28 | 6.21 |
| Stdev | 6.14 | 4.29 | 6.14 | 5.25 | 6.14 | 5.03 |
| p(t-test) | | 0.45 | | 0.65 | | 0.96 |
| Min | 0.0141 | 0.0147 | 0.0141 | 0.0177 | 0.0141 | 0.0147 |
| Max | 78.1 | 16.5 | 78.1 | 16.8 | 78.1 | 15.9 |
| n (Samp) | 517 | 28 | 517 | 33 | 517 | 18 |
| n (Patient) | 242 | 28 | 242 | 33 | 242 | 18 |

UO only

| | | | | | | |
|---|---|---|---|---|---|---|
| Median | 4.02 | 7.91 | 4.02 | 6.57 | 4.02 | 8.46 |
| Average | 5.04 | 8.32 | 5.04 | 7.55 | 5.04 | 7.07 |
| Stdev | 5.00 | 5.64 | 5.00 | 9.19 | 5.00 | 5.01 |
| p(t-test) | | 1.8E-6 | | 0.0022 | | 0.035 |
| Min | 0.0147 | 0.203 | 0.0147 | 0.0147 | 0.0147 | 0.0177 |
| Max | 27.4 | 33.9 | 27.4 | 78.1 | 27.4 | 16.8 |
| n (Samp) | 227 | 80 | 227 | 86 | 227 | 31 |
| n (Patient) | 122 | 80 | 122 | 86 | 122 | 31 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | 0.47 | 0.71 | 0.59 | 0.54 | 0.62 | 0.60 | 0.51 | 0.63 |
| SE | 0.036 | 0.057 | 0.036 | 0.036 | 0.053 | 0.037 | 0.056 | 0.070 | 0.057 |
| p | 1.7E-4 | 0.62 | 9.2E-9 | 0.012 | 0.42 | 0.0013 | 0.063 | 0.86 | 0.022 |
| nCohort 1 | 217 | 517 | 227 | 217 | 517 | 227 | 217 | 517 | 227 |
| nCohort 2 | 90 | 28 | 80 | 96 | 33 | 86 | 32 | 18 | 31 |
| Cutoff 1 | 4.13 | 2.88 | 5.69 | 2.88 | 2.40 | 3.66 | 2.81 | 2.81 | 2.81 |
| Sens 1 | 70% | 71% | 70% | 71% | 73% | 71% | 75% | 72% | 77% |
| Spec 1 | 49% | 32% | 62% | 45% | 28% | 49% | 44% | 31% | 44% |
| Cutoff 2 | 2.79 | 0.617 | 3.49 | 1.45 | 1.04 | 2.41 | 0.709 | 0.355 | 2.26 |
| Sens 2 | 80% | 82% | 81% | 80% | 82% | 80% | 81% | 83% | 81% |
| Spec 2 | 44% | 14% | 48% | 29% | 18% | 41% | 22% | 13% | 39% |
| Cutoff 3 | 1.06 | 0.0231 | 2.40 | 0.143 | 0.0231 | 0.289 | 0.100 | 0.100 | 0.0299 |
| Sens 3 | 90% | 93% | 90% | 92% | 91% | 92% | 91% | 94% | 90% |
| Spec 3 | 24% | 7% | 41% | 16% | 7% | 17% | 15% | 10% | 14% |
| Cutoff 4 | 7.15 | 8.15 | 7.01 | 7.15 | 8.15 | 7.01 | 7.15 | 8.15 | 7.01 |
| Sens 4 | 51% | 32% | 60% | 44% | 45% | 45% | 50% | 33% | 55% |
| Spec 4 | 70% | 70% | 70% | 70% | 70% | 70% | 70% | 70% | 70% |
| Cutoff 5 | 8.64 | 9.72 | 8.49 | 8.64 | 9.72 | 8.49 | 8.64 | 9.72 | 8.49 |
| Sens 5 | 33% | 11% | 40% | 28% | 30% | 31% | 44% | 28% | 48% |
| Spec 5 | 80% | 80% | 80% | 80% | 80% | 80% | 80% | 80% | 80% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 6 | 11.3 | 12.4 | 11.3 | 11.3 | 12.4 | 11.3 | 11.3 | 12.4 | 11.3 |
| Sens 6 | 11% | 4% | 16% | 17% | 18% | 14% | 19% | 11% | 16% |
| Spec 6 | 91% | 90% | 90% | 91% | 90% | 90% | 91% | 90% | 90% |
| OR Quart 2 | 1.9 | 0.74 | 4.4 | 1.3 | 0.61 | 2.0 | 0.59 | 0.59 | 0.98 |
| p Value | 0.12 | 0.59 | 0.012 | 0.46 | 0.39 | 0.081 | 0.38 | 0.47 | 0.98 |
| 95% CI of | 0.85 | 0.25 | 1.4 | 0.64 | 0.19 | 0.92 | 0.18 | 0.14 | 0.30 |
| OR Quart 2 | 4.4 | 2.2 | 14 | 2.7 | 1.9 | 4.5 | 1.9 | 2.5 | 3.2 |
| OR Quart 3 | 3.8 | 0.88 | 11 | 1.7 | 1.1 | 2.4 | 0.47 | 0.99 | 0.31 |
| p Value | 9.3E−4 | 0.80 | 2.4E−5 | 0.16 | 0.80 | 0.025 | 0.23 | 0.99 | 0.16 |
| 95% CI of | 1.7 | 0.31 | 3.6 | 0.82 | 0.42 | 1.1 | 0.13 | 0.28 | 0.060 |
| OR Quart 3 | 8.3 | 2.5 | 33 | 3.4 | 3.0 | 5.3 | 1.6 | 3.5 | 1.6 |
| OR Quart 4 | 3.8 | 0.88 | 13 | 2.0 | 1.4 | 3.2 | 2.1 | 0.99 | 3.4 |
| p Value | 9.3E−4 | 0.80 | 6.0E−6 | 0.044 | 0.49 | 0.0030 | 0.12 | 0.99 | 0.017 |
| 95% CI of | 1.7 | 0.31 | 4.2 | 1.0 | 0.54 | 1.5 | 0.82 | 0.28 | 1.3 |
| OR Quart 4 | 8.3 | 2.5 | 39 | 4.1 | 3.6 | 6.9 | 5.4 | 3.5 | 9.4 |

Interleukin-20

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 13.0 | 15.7 | 13.0 | 15.6 | 13.0 | 15.6 |
| Average | 72.1 | 75.6 | 72.1 | 111 | 72.1 | 90.7 |
| Stdev | 116 | 116 | 116 | 187 | 116 | 139 |
| p(t-test) | | 0.77 | | 0.0040 | | 0.30 |
| Min | 0.368 | 0.412 | 0.368 | 0.368 | 0.368 | 0.488 |
| Max | 811 | 561 | 811 | 1080 | 811 | 658 |
| n (Samp) | 463 | 120 | 463 | 130 | 463 | 47 |
| n (Patient) | 223 | 120 | 223 | 130 | 223 | 47 | sCr only

| | Cohort 1 | Cohort 2 | Cohort 1 | Cohort 2 | Cohort 1 | Cohort 2 |
|---|---|---|---|---|---|---|
| Median | 9.54 | 18.6 | 9.54 | 81.3 | 9.54 | 12.7 |
| Average | 72.5 | 117 | 72.5 | 137 | 72.5 | 136 |
| Stdev | 120 | 189 | 120 | 181 | 120 | 209 |
| p(t-test) | | 0.026 | | 5.3E−4 | | 0.0094 |
| Min | 0.368 | 0.488 | 0.368 | 0.412 | 0.368 | 0.488 |
| Max | 1080 | 677 | 1080 | 798 | 1080 | 811 |
| n (Samp) | 1018 | 40 | 1018 | 46 | 1018 | 26 |
| n (Patient) | 375 | 40 | 375 | 46 | 375 | 26 |

UO only

| | Cohort 1 | Cohort 2 | Cohort 1 | Cohort 2 | Cohort 1 | Cohort 2 |
|---|---|---|---|---|---|---|
| Median | 13.0 | 15.8 | 13.0 | 15.6 | 13.0 | 15.6 |
| Average | 79.4 | 76.6 | 79.4 | 103 | 79.4 | 74.8 |
| Stdev | 128 | 104 | 128 | 182 | 128 | 115 |
| p(t-test) | | 0.83 | | 0.10 | | 0.82 |
| Min | 0.368 | 0.412 | 0.368 | 0.368 | 0.368 | 0.412 |
| Max | 811 | 431 | 811 | 1080 | 811 | 509 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | 0.56 | 0.54 | 0.55 | 0.59 | 0.52 | 0.55 | 0.57 | 0.52 |
| SE | 0.030 | 0.048 | 0.031 | 0.029 | 0.045 | 0.030 | 0.045 | 0.059 | 0.046 |
| p | 0.17 | 0.18 | 0.26 | 0.10 | 0.047 | 0.48 | 0.24 | 0.21 | 0.69 |
| nCohort 1 | 463 | 1018 | 435 | 463 | 1018 | 435 | 463 | 1018 | 435 |
| nCohort 2 | 120 | 40 | 108 | 130 | 46 | 119 | 47 | 26 | 44 |
| Cutoff 1 | 1.56 | 2.71 | 1.56 | 1.37 | 1.37 | 1.37 | 1.62 | 1.47 | 1.62 |
| Sens 1 | 71% | 70% | 71% | 74% | 76% | 73% | 74% | 73% | 70% |
| Spec 1 | 37% | 43% | 34% | 29% | 28% | 25% | 38% | 31% | 37% |
| Cutoff 2 | 1.33 | 1.37 | 1.33 | 1.32 | 1.33 | 1.32 | 1.33 | 1.33 | 1.33 |
| Sens 2 | 88% | 80% | 88% | 83% | 80% | 82% | 81% | 81% | 82% |
| Spec 2 | 25% | 28% | 21% | 23% | 24% | 19% | 25% | 24% | 21% |
| Cutoff 3 | 1.32 | 0.541 | 1.32 | 0.488 | 0.488 | 0.488 | 0.488 | 0.541 | 0.488 |
| Sens 3 | 91% | 92% | 91% | 93% | 93% | 92% | 94% | 92% | 93% |
| Spec 3 | 23% | 11% | 19% | 9% | 9% | 7% | 9% | 11% | 7% |
| Cutoff 4 | 77.5 | 78.9 | 85.6 | 77.5 | 78.9 | 85.6 | 77.5 | 78.9 | 85.6 |
| Sens 4 | 33% | 32% | 37% | 38% | 50% | 34% | 38% | 46% | 30% |
| Spec 4 | 70% | 70% | 70% | 70% | 70% | 70% | 70% | 70% | 70% |
| Cutoff 5 | 125 | 139 | 149 | 125 | 139 | 149 | 125 | 139 | 149 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Sens 5 | 24% | 28% | 24% | 31% | 39% | 24% | 30% | 38% | 20% |
| Spec 5 | 80% | 80% | 80% | 80% | 80% | 80% | 80% | 80% | 80% |
| Cutoff 6 | 235 | 233 | 260 | 235 | 233 | 260 | 235 | 233 | 260 |
| Sens 6 | 10% | 18% | 7% | 14% | 20% | 10% | 9% | 15% | 9% |
| Spec 6 | 90% | 90% | 90% | 90% | 90% | 90% | 90% | 90% | 90% |
| OR Quart 2 | 2.9 | 2.7 | 1.2 | 1.1 | 1.1 | 0.66 | 1.2 | 1.6 | 0.88 |
| p Value | 6.7E−4 | 0.065 | 0.54 | 0.67 | 0.82 | 0.17 | 0.65 | 0.40 | 0.80 |
| 95% CI of | 1.6 | 0.94 | 0.65 | 0.64 | 0.45 | 0.36 | 0.49 | 0.52 | 0.35 |
| OR Quart 2 | 5.5 | 7.6 | 2.3 | 2.0 | 2.8 | 1.2 | 3.1 | 5.0 | 2.3 |
| OR Quart 3 | 1.9 | 2.0 | 1.5 | 0.83 | 0.77 | 0.88 | 1.2 | 0.20 | 1.4 |
| p Value | 0.060 | 0.20 | 0.23 | 0.55 | 0.61 | 0.66 | 0.64 | 0.14 | 0.40 |
| 95% CI of | 0.98 | 0.69 | 0.79 | 0.46 | 0.28 | 0.50 | 0.50 | 0.023 | 0.61 |
| OR Quart 3 | 3.6 | 6.0 | 2.7 | 1.5 | 2.1 | 1.6 | 3.1 | 1.7 | 3.4 |
| OR Quart 4 | 2.2 | 2.5 | 1.5 | 1.7 | 2.3 | 1.1 | 1.9 | 2.5 | 1.1 |
| p Value | 0.015 | 0.096 | 0.23 | 0.048 | 0.041 | 0.70 | 0.15 | 0.094 | 0.83 |
| 95% CI of | 1.2 | 0.85 | 0.79 | 1.0 | 1.0 | 0.64 | 0.80 | 0.86 | 0.45 |
| OR Quart 4 | 4.2 | 7.1 | 2.7 | 2.9 | 5.2 | 1.9 | 4.4 | 7.1 | 2.7 |

Interleukin-29

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 24.7 | 80.7 | 24.7 | 69.2 | 24.7 | 39.1 |
| Average | 66.0 | 108 | 66.0 | 97.2 | 66.0 | 61.0 |
| Stdev | 98.3 | 110 | 98.3 | 107 | 98.3 | 64.7 |
| p(t-test) | | 6.2E−5 | | 0.0019 | | 0.73 |
| Min | 0.114 | 0.114 | 0.114 | 0.170 | 0.114 | 0.170 |
| Max | 675 | 597 | 675 | 612 | 675 | 249 |
| n (Samp) | 461 | 119 | 461 | 129 | 461 | 47 |
| n (Patient) | 223 | 119 | 223 | 129 | 223 | 47 | sCr only

| | Cohort 1 | Cohort 2 | Cohort 1 | Cohort 2 | Cohort 1 | Cohort 2 |
|---|---|---|---|---|---|---|
| Median | 35.4 | 84.5 | 35.4 | 82.8 | 35.4 | 35.5 |
| Average | 78.6 | 105 | 78.6 | 109 | 78.6 | 58.9 |
| Stdev | 103 | 97.0 | 103 | 123 | 103 | 65.4 |
| p(t-test) | | 0.12 | | 0.049 | | 0.33 |
| Min | 0.114 | 0.114 | 0.114 | 0.170 | 0.114 | 0.173 |
| Max | 675 | 274 | 675 | 612 | 675 | 247 |
| n (Samp) | 1017 | 40 | 1017 | 46 | 1017 | 26 |
| n (Patient) | 375 | 40 | 375 | 46 | 375 | 26 |

UO only

| | Cohort 1 | Cohort 2 | Cohort 1 | Cohort 2 | Cohort 1 | Cohort 2 |
|---|---|---|---|---|---|---|
| Median | 30.5 | 80.7 | 30.5 | 67.8 | 30.5 | 47.0 |
| Average | 70.8 | 129 | 70.8 | 100 | 70.8 | 74.4 |
| Stdev | 96.2 | 142 | 96.2 | 112 | 96.2 | 95.6 |
| p(t-test) | | 5.7E−7 | | 0.0047 | | 0.81 |
| Min | 0.114 | 0.173 | 0.114 | 0.172 | 0.114 | 0.114 |
| Max | 675 | 635 | 675 | 613 | 675 | 510 |
| n (Samp) | 434 | 107 | 434 | 118 | 434 | 44 |
| n (Patient) | 173 | 107 | 173 | 118 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | 0.57 | 0.65 | 0.62 | 0.59 | 0.60 | 0.56 | 0.48 | 0.52 |
| SE | 0.030 | 0.048 | 0.031 | 0.029 | 0.045 | 0.030 | 0.045 | 0.058 | 0.046 |
| p | 3.0E−6 | 0.15 | 2.5E−6 | 2.2E−5 | 0.049 | 0.0011 | 0.22 | 0.78 | 0.62 |
| nCohort 1 | 461 | 1017 | 434 | 461 | 1017 | 434 | 461 | 1017 | 434 |
| nCohort 2 | 119 | 40 | 107 | 129 | 46 | 118 | 47 | 26 | 44 |
| Cutoff 1 | 24.3 | 12.3 | 38.1 | 24.7 | 25.1 | 25.5 | 16.2 | 2.79 | 12.8 |
| Sens! | 71% | 70% | 70% | 71% | 72% | 70% | 70% | 73% | 70% |
| Spec 1 | 49% | 32% | 54% | 50% | 43% | 46% | 41% | 22% | 33% |
| Cutoff 2 | 5.37 | 5.25 | 16.2 | 8.42 | 8.42 | 8.21 | 5.25 | 2.69 | 0.571 |
| Sens 2 | 82% | 80% | 80% | 81% | 80% | 81% | 81% | 81% | 82% |
| Spec 2 | 32% | 24% | 35% | 34% | 28% | 28% | 31% | 22% | 16% |
| Cutoff 3 | 0.553 | 0.172 | 1.41 | 0.553 | 0.187 | 1.07 | 0.232 | 0.228 | 0.232 |
| Sens 3 | 92% | 92% | 91% | 91% | 93% | 91% | 91% | 92% | 91% |
| Spec 3 | 21% | 5% | 21% | 21% | 9% | 19% | 17% | 11% | 13% |
| Cutoff 4 | 66.4 | 91.9 | 80.7 | 66.4 | 91.9 | 80.7 | 66.4 | 91.9 | 80.7 |
| Sens 4 | 54% | 48% | 50% | 50% | 48% | 42% | 34% | 27% | 27% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Spec 4 | 71% | 71% | 70% | 71% | 71% | 70% | 71% | 71% | 70% |
| Cutoff 5 | 119 | 143 | 128 | 119 | 143 | 128 | 119 | 143 | 128 |
| Sens 5 | 39% | 40% | 37% | 32% | 28% | 27% | 17% | 12% | 18% |
| Spec 5 | 80% | 80% | 81% | 80% | 80% | 81% | 80% | 80% | 81% |
| Cutoff 6 | 196 | 218 | 186 | 196 | 218 | 186 | 196 | 218 | 186 |
| Sens 6 | 22% | 12% | 26% | 13% | 9% | 17% | 4% | 4% | 9% |
| Spec 6 | 90% | 90% | 90% | 90% | 90% | 90% | 90% | 90% | 90% |
| OR Quart 2 | 1.1 | 0.59 | 1.0 | 1.4 | 1.3 | 1.4 | 1.5 | 1.6 | 0.61 |
| p Value | 0.73 | 0.31 | 1.0 | 0.27 | 0.62 | 0.33 | 0.45 | 0.40 | 0.32 |
| 95% CI of | 0.58 | 0.21 | 0.49 | 0.76 | 0.47 | 0.72 | 0.54 | 0.52 | 0.23 |
| OR Quart 2 | 2.2 | 1.6 | 2.1 | 2.7 | 3.5 | 2.6 | 4.0 | 5.0 | 1.6 |
| OR Quart 3 | 1.9 | 0.59 | 2.1 | 2.3 | 1.6 | 1.9 | 3.0 | 1.0 | 1.4 |
| p Value | 0.047 | 0.31 | 0.028 | 0.0058 | 0.35 | 0.035 | 0.017 | 1.0 | 0.41 |
| 95% CI of | 1.0 | 0.21 | 1.1 | 1.3 | 0.61 | 1.0 | 1.2 | 0.29 | 0.62 |
| OR Quart 3 | 3.5 | 1.6 | 4.0 | 4.3 | 4.2 | 3.6 | 7.5 | 3.5 | 3.2 |
| OR Quart 4 | 3.2 | 1.9 | 3.1 | 3.0 | 2.8 | 2.2 | 1.6 | 1.6 | 0.99 |
| p Value | 1.4E-4 | 0.13 | 3.9E-4 | 2.5E-4 | 0.021 | 0.0087 | 0.33 | 0.40 | 0.98 |
| 95% CI of | 1.8 | 0.84 | 1.7 | 1.7 | 1.2 | 1.2 | 0.61 | 0.52 | 0.41 |
| OR Quart 4 | 5.8 | 4.1 | 5.8 | 5.5 | 6.9 | 4.1 | 4.3 | 5.0 | 2.4 |

Interleukin-7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 0.0110 | 0.0156 | 0.0110 | 0.0135 | 0.0110 | 0.0128 |
| Average | 0.485 | 0.445 | 0.485 | 0.526 | 0.485 | 0.241 |
| Stdev | 4.37 | 2.33 | 4.37 | 3.22 | 4.37 | 1.07 |
| p(t-test) | | 0.93 | | 0.92 | | 0.70 |
| Min | 0.00316 | 0.00316 | 0.00316 | 0.00316 | 0.00316 | 0.00316 |
| Max | 64.2 | 18.1 | 64.2 | 31.8 | 64.2 | 6.25 |
| n (Samp) | 462 | 118 | 462 | 130 | 462 | 47 |
| n (Patient) | 223 | 118 | 223 | 130 | 223 | 47 | sCr only

| | Cohort 1 | Cohort 2 | Cohort 1 | Cohort 2 | Cohort 1 | Cohort 2 |
|---|---|---|---|---|---|---|
| Median | 0.0110 | 0.0142 | 0.0110 | 0.0128 | 0.0110 | 0.0128 |
| Average | 0.356 | 0.322 | 0.356 | 0.214 | 0.356 | 0.0200 |
| Stdev | 3.26 | 1.35 | 3.26 | 1.01 | 3.26 | 0.0180 |
| p(t-test) | | 0.95 | | 0.77 | | 0.60 |
| Min | 0.00316 | 0.00316 | 0.00316 | 0.00316 | 0.00316 | 0.00316 |
| Max | 64.2 | 7.74 | 64.2 | 6.38 | 64.2 | 0.0655 |
| n (Samp) | 1017 | 40 | 1017 | 46 | 1017 | 26 |
| n (Patient) | 375 | 40 | 375 | 46 | 375 | 26 |

UO only

| | Cohort 1 | Cohort 2 | Cohort 1 | Cohort 2 | Cohort 1 | Cohort 2 |
|---|---|---|---|---|---|---|
| Median | 0.0123 | 0.0156 | 0.0123 | 0.0128 | 0.0123 | 0.0139 |
| Average | 0.384 | 0.584 | 0.384 | 0.643 | 0.384 | 0.295 |
| Stdev | 3.40 | 2.56 | 3.40 | 3.43 | 3.40 | 1.13 |
| p(t-test) | | 0.57 | | 0.46 | | 0.86 |
| Min | 0.00316 | 0.00451 | 0.00316 | 0.00316 | 0.00316 | 0.00316 |
| Max | 64.2 | 18.1 | 64.2 | 31.8 | 64.2 | 6.25 |
| n (Samp) | 436 | 106 | 436 | 119 | 436 | 44 |
| n (Patient) | 173 | 106 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.58 | 0.61 | 0.57 | 0.55 | 0.55 | 0.58 | 0.58 | 0.54 |
| SE | 0.030 | 0.048 | 0.032 | 0.029 | 0.045 | 0.030 | 0.045 | 0.059 | 0.047 |
| p | 1.9E-5 | 0.081 | 3.3E-4 | 0.010 | 0.30 | 0.080 | 0.071 | 0.20 | 0.35 |
| nCohort 1 | 462 | 1017 | 436 | 462 | 1017 | 436 | 462 | 1017 | 436 |
| nCohort 2 | 118 | 40 | 106 | 130 | 46 | 119 | 47 | 26 | 44 |
| Cutoff 1 | 0.0119 | 0.0107 | 0.0119 | 0.0105 | 0.00822 | 0.0104 | 0.0107 | 0.0107 | 0.0105 |
| Sens 1 | 71% | 70% | 72% | 71% | 78% | 71% | 74% | 81% | 70% |
| Spec 1 | 52% | 46% | 50% | 44% | 29% | 42% | 46% | 46% | 42% |
| Cutoff 2 | 0.00822 | 0.00487 | 0.00822 | 0.00801 | 0.00584 | 0.00584 | 0.00901 | 0.0107 | 0.00487 |
| Sens 2 | 85% | 88% | 85% | 80% | 83% | 82% | 81% | 81% | 82% |
| Spec 2 | 33% | 13% | 30% | 29% | 21% | 22% | 37% | 46% | 13% |
| Cutoff 3 | 0.00487 | 0.00451 | 0.00584 | 0.00451 | 0.00316 | 0.00451 | 0.00451 | 0.00487 | 0.00451 |
| Sens 3 | 94% | 95% | 91% | 92% | 93% | 93% | 94% | 92% | 91% |
| Spec 3 | 17% | 9% | 22% | 12% | 4% | 8% | 12% | 13% | 8% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 4 | 0.0186 | 0.0156 | 0.0226 | 0.0186 | 0.0156 | 0.0226 | 0.0186 | 0.0156 | 0.0226 |
| Sens 4 | 46% | 45% | 41% | 42% | 35% | 34% | 36% | 35% | 27% |
| Spec 4 | 70% | 71% | 74% | 70% | 71% | 74% | 70% | 71% | 74% |
| Cutoff 5 | 0.0303 | 0.0280 | 0.0315 | 0.0303 | 0.0280 | 0.0315 | 0.0303 | 0.0280 | 0.0315 |
| Sens 5 | 35% | 32% | 25% | 25% | 17% | 18% | 17% | 15% | 14% |
| Spec 5 | 80% | 80% | 83% | 80% | 80% | 83% | 80% | 80% | 83% |
| Cutoff 6 | 0.0478 | 0.0478 | 0.0478 | 0.0478 | 0.0478 | 0.0478 | 0.0478 | 0.0478 | 0.0478 |
| Sens 6 | 6% | 10% | 8% | 11% | 9% | 11% | 13% | 12% | 11% |
| Spec 6 | 92% | 93% | 91% | 92% | 93% | 91% | 92% | 93% | 91% |
| OR Quart 2 | 1.7 | 0.29 | 1.5 | 1.3 | 0.59 | 0.99 | 1.3 | 1.00 | 1.0 |
| p Value | 0.12 | 0.064 | 0.30 | 0.45 | 0.31 | 0.98 | 0.61 | 1.00 | 1.0 |
| 95% CI of | 0.86 | 0.079 | 0.72 | 0.69 | 0.21 | 0.54 | 0.47 | 0.25 | 0.38 |
| OR Quart 2 | 3.4 | 1.1 | 3.0 | 2.3 | 1.6 | 1.8 | 3.6 | 4.0 | 2.6 |
| OR Quart 3 | 2.8 | 1.2 | 2.5 | 1.5 | 1.7 | 1.3 | 2.6 | 3.1 | 1.8 |
| p Value | 0.0024 | 0.66 | 0.0075 | 0.14 | 0.17 | 0.39 | 0.037 | 0.054 | 0.20 |
| 95% CI of | 1.4 | 0.51 | 1.3 | 0.86 | 0.78 | 0.72 | 1.1 | 0.98 | 0.74 |
| OR Quart 3 | 5.3 | 2.9 | 4.8 | 2.8 | 3.9 | 2.3 | 6.6 | 9.7 | 4.2 |
| OR Quart 4 | 3.8 | 1.5 | 3.1 | 2.1 | 1.3 | 1.4 | 2.1 | 1.5 | 1.2 |
| p Value | 4.9E−5 | 0.31 | 7.0E−4 | 0.0091 | 0.53 | 0.20 | 0.12 | 0.53 | 0.64 |
| 95% CI of | 2.0 | 0.67 | 1.6 | 1.2 | 0.56 | 0.82 | 0.82 | 0.42 | 0.50 |
| OR Quart 4 | 7.2 | 3.5 | 6.0 | 3.7 | 3.0 | 2.6 | 5.4 | 5.4 | 3.1 |

Matrix metallo-proteinase-9: Metalloproteinase inhibitor 2 complex

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| | | | sCr or UO | | | |
| Median | 252 | 329 | 252 | 477 | 252 | 440 |
| Average | 3150 | 3390 | 3150 | 5090 | 3150 | 6790 |
| Stdev | 7450 | 7980 | 7450 | 9450 | 7450 | 10700 |
| p(t-test) | | 0.85 | | 0.15 | | 0.040 |
| Min | 0.227 | 0.227 | 0.227 | 0.227 | 0.227 | 1.03 |
| Max | 24000 | 24000 | 24000 | 24000 | 24000 | 24000 |
| n (Samp) | 121 | 47 | 121 | 51 | 121 | 26 |
| n (Patient) | 98 | 47 | 98 | 51 | 98 | 26 |
| | | | sCr only | | | |
| Median | 261 | 577 | 261 | 959 | 261 | 2030 |
| Average | 3590 | 5470 | 3590 | 9170 | 3590 | 9740 |
| Stdev | 8000 | 10000 | 8000 | 11600 | 8000 | 11800 |
| p(t-test) | | 0.40 | | 0.0050 | | 0.0089 |
| Min | 0.227 | 2.00 | 0.227 | 0.227 | 0.227 | 42.8 |
| Max | 24000 | 24000 | 24000 | 24000 | 24000 | 24000 |
| n (Samp) | 261 | 14 | 261 | 19 | 261 | 13 |
| n (Patient) | 159 | 14 | 159 | 19 | 159 | 13 |
| | | | UO only | | | |
| Median | 237 | 371 | 237 | 457 | 237 | 164 |
| Average | 2380 | 4150 | 2380 | 4490 | 2380 | 5530 |
| Stdev | 6330 | 8740 | 6330 | 8950 | 6330 | 9970 |
| p(t-test) | | 0.16 | | 0.096 | | 0.054 |
| Min | 0.227 | 0.227 | 0.227 | 0.227 | 0.227 | 1.03 |
| Max | 24000 | 24000 | 24000 | 24000 | 24000 | 24000 |
| n (Samp) | 110 | 44 | 110 | 47 | 110 | 23 |
| n (Patient) | 85 | 44 | 85 | 47 | 85 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.58 | 0.55 | 0.57 | 0.64 | 0.59 | 0.54 | 0.71 | 0.50 |
| SE | 0.050 | 0.082 | 0.052 | 0.049 | 0.071 | 0.051 | 0.063 | 0.082 | 0.067 |
| p | 0.63 | 0.34 | 0.32 | 0.14 | 0.052 | 0.093 | 0.52 | 0.012 | 0.96 |
| nCohort 1 | 121 | 261 | 110 | 121 | 261 | 110 | 121 | 261 | 110 |
| nCohort 2 | 47 | 14 | 44 | 51 | 19 | 47 | 26 | 13 | 23 |
| Cutoff 1 | 108 | 194 | 126 | 119 | 181 | 150 | 55.7 | 316 | 60.4 |
| Sens 1 | 70% | 71% | 70% | 71% | 74% | 70% | 73% | 77% | 74% |
| Spec 1 | 31% | 44% | 34% | 31% | 43% | 38% | 21% | 55% | 23% |
| Cutoff 2 | 44.6 | 88.0 | 44.6 | 81.4 | 55.7 | 91.9 | 41.3 | 173 | 10.0 |
| Sens 2 | 81% | 86% | 82% | 80% | 84% | 81% | 81% | 85% | 83% |
| Spec 2 | 20% | 25% | 20% | 26% | 21% | 27% | 17% | 41% | 10% |
| Cutoff 3 | 3.86 | 3.86 | 18.8 | 10.0 | 10.8 | 10.0 | 0.227 | 63.1 | 0.227 |
| Sens 3 | 91% | 93% | 91% | 92% | 95% | 94% | 100% | 92% | 100% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Spec 3 | 9% | 10% | 12% | 10% | 12% | 10% | 2% | 21% | 2% |
| Cutoff 4 | 515 | 666 | 523 | 515 | 666 | 523 | 515 | 666 | 523 |
| Sens 4 | 38% | 50% | 39% | 49% | 53% | 45% | 50% | 69% | 43% |
| Spec 4 | 70% | 70% | 70% | 70% | 70% | 70% | 70% | 70% | 70% |
| Cutoff 5 | 1020 | 1610 | 866 | 1020 | 1610 | 866 | 1020 | 1610 | 866 |
| Sens 5 | 19% | 21% | 27% | 29% | 42% | 32% | 35% | 54% | 35% |
| Spec 5 | 80% | 80% | 80% | 80% | 80% | 80% | 80% | 80% | 80% |
| Cutoff 6 | 24000 | 24000 | 3410 | 24000 | 24000 | 3410 | 24000 | 24000 | 3410 |
| Sens 6 | 0% | 0% | 16% | 0% | 0% | 17% | 0% | 0% | 22% |
| Spec 6 | 100% | 100% | 90% | 100% | 100% | 90% | 100% | 100% | 90% |
| OR Quart 2 | 1.0 | 2.0 | 1.1 | 1.0 | 0.49 | 1.3 | 0.36 | 0.49 | 0.56 |
| p Value | 1.0 | 0.42 | 0.84 | 1.0 | 0.41 | 0.60 | 0.12 | 0.56 | 0.36 |
| 95% CI of | 0.38 | 0.36 | 0.39 | 0.38 | 0.086 | 0.47 | 0.10 | 0.043 | 0.16 |
| OR Quart 2 | 2.6 | 11 | 3.1 | 2.6 | 2.7 | 3.6 | 1.3 | 5.5 | 1.9 |
| OR Quart 3 | 1.3 | 1.5 | 1.5 | 1.0 | 1.0 | 1.3 | 0.083 | 1.0 | 0.098 |
| p Value | 0.63 | 0.66 | 0.44 | 1.0 | 1.0 | 0.60 | 0.022 | 1.0 | 0.033 |
| 95% CI of | 0.49 | 0.24 | 0.54 | 0.38 | 0.24 | 0.47 | 0.0099 | 0.14 | 0.011 |
| OR Quart 3 | 3.3 | 9.3 | 4.1 | 2.6 | 4.2 | 3.6 | 0.70 | 7.3 | 0.83 |
| OR Quart 4 | 1.1 | 2.6 | 1.6 | 2.1 | 2.4 | 2.2 | 1.4 | 4.3 | 1.1 |
| p Value | 0.81 | 0.27 | 0.35 | 0.11 | 0.16 | 0.11 | 0.48 | 0.071 | 0.83 |
| 95% CI of | 0.43 | 0.48 | 0.59 | 0.84 | 0.71 | 0.84 | 0.52 | 0.88 | 0.37 |
| OR Quart 4 | 2.9 | 14 | 4.4 | 5.2 | 8.3 | 5.9 | 4.0 | 21 | 3.4 |

Platelet-derived growth factor subunit A (dimer)

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 84.7 | 107 | 84.7 | 85.6 | 84.7 | 101 |
| Average | 132 | 178 | 132 | 224 | 132 | 167 |
| Stdev | 170 | 391 | 170 | 778 | 170 | 181 |
| p(t-test) | | 0.055 | | 0.019 | | 0.19 |
| Min | 0.994 | 4.55 | 0.994 | 4.13 | 0.994 | 11.9 |
| Max | 1830 | 4020 | 1830 | 8310 | 1830 | 806 |
| n (Samp) | 463 | 119 | 463 | 128 | 463 | 47 |
| n (Patient) | 223 | 119 | 223 | 128 | 223 | 47 | sCr only

| | | | | | | |
|---|---|---|---|---|---|---|
| Median | 91.8 | 65.5 | 91.8 | 92.2 | 91.8 | 123 |
| Average | 144 | 244 | 144 | 206 | 144 | 161 |
| Stdev | 301 | 649 | 301 | 450 | 301 | 136 |
| p(t-test) | | 0.053 | | 0.18 | | 0.78 |
| Min | 0.994 | 4.55 | 0.994 | 6.32 | 0.994 | 12.2 |
| Max | 8310 | 4020 | 8310 | 3020 | 8310 | 533 |
| n (Samp) | 1015 | 40 | 1015 | 46 | 1015 | 26 |
| n (Patient) | 374 | 40 | 374 | 46 | 374 | 26 |

UO only

| | | | | | | |
|---|---|---|---|---|---|---|
| Median | 84.5 | 115 | 84.5 | 94.1 | 84.5 | 82.8 |
| Average | 128 | 219 | 128 | 255 | 128 | 168 |
| Stdev | 151 | 491 | 151 | 838 | 151 | 195 |
| p(t-test) | | 0.0010 | | 0.0029 | | 0.11 |
| Min | 2.61 | 5.66 | 2.61 | 4.13 | 2.61 | 3.37 |
| Max | 1190 | 4020 | 1190 | 8310 | 1190 | 806 |
| n (Samp) | 436 | 107 | 436 | 117 | 436 | 44 |
| n (Patient) | 173 | 107 | 173 | 117 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.47 | 0.58 | 0.52 | 0.54 | 0.53 | 0.56 | 0.57 | 0.53 |
| SE | 0.030 | 0.047 | 0.032 | 0.029 | 0.044 | 0.030 | 0.045 | 0.059 | 0.046 |
| p | 0.058 | 0.59 | 0.010 | 0.47 | 0.41 | 0.34 | 0.21 | 0.21 | 0.56 |
| nCohort 1 | 463 | 1015 | 436 | 463 | 1015 | 436 | 463 | 1015 | 436 |
| nCohort 2 | 119 | 40 | 107 | 128 | 46 | 117 | 47 | 26 | 44 |
| Cutoff 1 | 52.9 | 47.3 | 58.0 | 47.2 | 53.2 | 50.2 | 54.9 | 48.2 | 45.8 |
| Sens 1 | 71% | 70% | 70% | 70% | 72% | 70% | 70% | 73% | 70% |
| Spec 1 | 34% | 27% | 36% | 29% | 31% | 31% | 35% | 28% | 27% |
| Cutoff 2 | 36.6 | 36.4 | 45.7 | 29.8 | 41.0 | 29.8 | 31.5 | 31.5 | 22.0 |
| Sens 2 | 81% | 80% | 80% | 80% | 80% | 80% | 81% | 81% | 82% |
| Spec 2 | 23% | 22% | 27% | 18% | 24% | 17% | 19% | 18% | 11% |
| Cutoff 3 | 27.6 | 26.2 | 28.9 | 17.7 | 26.7 | 15.8 | 19.3 | 24.9 | 18.8 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Sens 3 | 91% | 90% | 91% | 91% | 91% | 91% | 91% | 92% | 91% |
| Spec 3 | 17% | 15% | 16% | 9% | 15% | 6% | 10% | 14% | 7% |
| Cutoff 4 | 127 | 142 | 129 | 127 | 142 | 129 | 127 | 142 | 129 |
| Sens 4 | 42% | 28% | 46% | 36% | 39% | 37% | 43% | 46% | 41% |
| Spec 4 | 70% | 70% | 70% | 70% | 70% | 70% | 70% | 70% | 70% |
| Cutoff 5 | 184 | 204 | 184 | 184 | 204 | 184 | 184 | 204 | 184 |
| Sens 5 | 29% | 15% | 33% | 27% | 26% | 26% | 38% | 27% | 36% |
| Spec 5 | 80% | 80% | 80% | 80% | 80% | 80% | 80% | 80% | 80% |
| Cutoff 6 | 293 | 298 | 272 | 293 | 298 | 272 | 293 | 298 | 272 |
| Sens 6 | 10% | 15% | 15% | 15% | 13% | 18% | 17% | 19% | 18% |
| Spec 6 | 90% | 90% | 90% | 90% | 90% | 90% | 90% | 90% | 90% |
| OR Quart 2 | 0.99 | 0.69 | 1.0 | 0.81 | 1.3 | 0.64 | 1.3 | 0.28 | 1.1 |
| p Value | 0.98 | 0.46 | 0.89 | 0.46 | 0.52 | 0.14 | 0.53 | 0.11 | 0.83 |
| 95% CI of | 0.54 | 0.26 | 0.55 | 0.46 | 0.57 | 0.35 | 0.56 | 0.058 | 0.47 |
| OR Quart 2 | 1.8 | 1.8 | 2.0 | 1.4 | 3.1 | 1.2 | 3.1 | 1.4 | 2.6 |
| OR Quart 3 | 1.3 | 1.3 | 1.2 | 0.74 | 0.79 | 0.70 | 0.48 | 0.85 | 0.34 |
| p Value | 0.45 | 0.52 | 0.64 | 0.30 | 0.63 | 0.24 | 0.19 | 0.78 | 0.073 |
| 95% CI of | 0.69 | 0.57 | 0.61 | 0.42 | 0.31 | 0.39 | 0.16 | 0.28 | 0.11 |
| OR Quart 3 | 2.3 | 3.1 | 2.2 | 1.3 | 2.0 | 1.3 | 1.4 | 2.6 | 1.1 |
| OR Quart 4 | 1.7 | 1.0 | 2.3 | 1.1 | 1.5 | 1.1 | 2.0 | 1.6 | 1.6 |
| p Value | 0.053 | 0.99 | 0.0071 | 0.61 | 0.31 | 0.70 | 0.084 | 0.35 | 0.23 |
| 95% CI of | 0.99 | 0.41 | 1.2 | 0.67 | 0.67 | 0.64 | 0.91 | 0.61 | 0.73 |
| OR Quart 4 | 3.1 | 2.5 | 4.1 | 2.0 | 3.5 | 1.9 | 4.6 | 4.2 | 3.7 |

Platelet-derived growth factor A

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| | sCr or UO | | | | | |
| Median | 3.39 | 3.33 | 3.39 | 4.69 | 3.39 | 3.97 |
| Average | 35.7 | 16.3 | 35.7 | 52.6 | 35.7 | 22.3 |
| Stdev | 492 | 39.5 | 492 | 430 | 492 | 70.5 |
| p(t-test) | | 0.67 | | 0.72 | | 0.85 |
| Min | 0.0141 | 0.0141 | 0.0141 | 0.0161 | 0.0141 | 0.0161 |
| Max | 10600 | 344 | 10600 | 4860 | 10600 | 376 |
| n (Samp) | 463 | 119 | 463 | 128 | 463 | 47 |
| n (Patient) | 223 | 119 | 223 | 128 | 223 | 47 |
| | sCr only | | | | | |
| Median | 3.43 | 3.28 | 3.43 | 7.56 | 3.43 | 6.73 |
| Average | 36.2 | 11.9 | 36.2 | 17.2 | 36.2 | 9.33 |
| Stdev | 387 | 17.6 | 387 | 28.2 | 387 | 12.1 |
| p(t-test) | | 0.69 | | 0.74 | | 0.72 |
| Min | 0.0141 | 0.0288 | 0.0141 | 0.0161 | 0.0141 | 0.0184 |
| Max | 10600 | 75.5 | 10600 | 153 | 10600 | 56.2 |
| n (Samp) | 1015 | 40 | 1015 | 46 | 1015 | 26 |
| n (Patient) | 374 | 40 | 374 | 46 | 374 | 26 |
| | UO only | | | | | |
| Median | 3.53 | 6.35 | 3.53 | 4.43 | 3.53 | 3.80 |
| Average | 14.7 | 61.6 | 14.7 | 119 | 14.7 | 30.7 |
| Stdev | 48.5 | 410 | 48.5 | 773 | 48.5 | 82.2 |
| p(t-test) | | 0.020 | | 0.0053 | | 0.054 |
| Min | 0.0141 | 0.0141 | 0.0141 | 0.0161 | 0.0141 | 0.0161 |
| Max | 632 | 4230 | 632 | 6850 | 632 | 376 |
| n (Samp) | 436 | 107 | 436 | 117 | 436 | 44 |
| n (Patient) | 173 | 107 | 173 | 117 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | 0.54 | 0.56 | 0.56 | 0.60 | 0.55 | 0.52 | 0.57 | 0.50 |
| SE | 0.030 | 0.048 | 0.032 | 0.029 | 0.045 | 0.030 | 0.045 | 0.059 | 0.046 |
| p | 0.21 | 0.39 | 0.051 | 0.036 | 0.034 | 0.11 | 0.65 | 0.25 | 0.92 |
| nCohort 1 | 463 | 1015 | 436 | 463 | 1015 | 436 | 463 | 1015 | 436 |
| nCohort 2 | 119 | 40 | 107 | 128 | 46 | 117 | 47 | 26 | 44 |
| Cutoff 1 | 0.756 | 0.756 | 1.07 | 0.998 | 1.13 | 0.756 | 1.07 | 2.26 | 0.756 |
| Sens 1 | 71% | 72% | 70% | 70% | 72% | 73% | 70% | 73% | 73% |
| Spec 1 | 32% | 34% | 37% | 37% | 40% | 31% | 38% | 44% | 31% |
| Cutoff 2 | 0.123 | 0.257 | 0.143 | 0.143 | 0.756 | 0.143 | 0.143 | 0.756 | 0.0890 |
| Sens 2 | 82% | 80% | 80% | 81% | 80% | 81% | 81% | 81% | 82% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Spec 2 | 24% | 30% | 25% | 27% | 34% | 25% | 27% | 34% | 16% |
| Cutoff 3 | 0.0604 | 0.123 | 0.0649 | 0.0649 | 0.0604 | 0.0649 | 0.0568 | 0.0649 | 0.0568 |
| Sens 3 | 91% | 90% | 91% | 91% | 91% | 91% | 94% | 96% | 93% |
| Spec 3 | 8% | 25% | 10% | 12% | 10% | 10% | 6% | 14% | 6% |
| Cutoff 4 | 8.15 | 9.40 | 9.40 | 8.15 | 9.40 | 9.40 | 8.15 | 9.40 | 9.40 |
| Sens 4 | 39% | 35% | 38% | 36% | 43% | 36% | 26% | 27% | 25% |
| Spec 4 | 71% | 71% | 70% | 71% | 71% | 70% | 71% | 71% | 70% |
| Cutoff 5 | 12.4 | 14.2 | 14.2 | 12.4 | 14.2 | 14.2 | 12.4 | 14.2 | 14.2 |
| Sens 5 | 29% | 30% | 32% | 29% | 35% | 28% | 19% | 19% | 23% |
| Spec 5 | 80% | 80% | 80% | 80% | 80% | 80% | 80% | 80% | 80% |
| Cutoff 6 | 26.3 | 29.8 | 28.9 | 26.3 | 29.8 | 28.9 | 26.3 | 29.8 | 28.9 |
| Sens 6 | 15% | 15% | 18% | 13% | 13% | 15% | 13% | 8% | 20% |
| Spec 6 | 90% | 90% | 90% | 90% | 90% | 90% | 90% | 90% | 90% |
| OR Quart 2 | 2.0 | 4.2 | 1.2 | 1.2 | 1.0 | 1.2 | 1.1 | 1.7 | 1.0 |
| p Value | 0.023 | 0.012 | 0.54 | 0.47 | 1.0 | 0.64 | 0.83 | 0.48 | 1.0 |
| 95% CI of | 1.1 | 1.4 | 0.65 | 0.69 | 0.37 | 0.63 | 0.44 | 0.40 | 0.40 |
| OR Quart 2 | 3.5 | 13 | 2.3 | 2.3 | 2.7 | 2.1 | 2.8 | 7.1 | 2.5 |
| OR Quart 3 | 0.95 | 1.5 | 1.1 | 1.5 | 1.5 | 1.3 | 2.2 | 4.5 | 1.3 |
| p Value | 0.87 | 0.53 | 0.77 | 0.20 | 0.37 | 0.36 | 0.072 | 0.020 | 0.51 |
| 95% CI of | 0.50 | 0.42 | 0.58 | 0.82 | 0.61 | 0.73 | 0.93 | 1.3 | 0.56 |
| OR Quart 3 | 1.8 | 5.4 | 2.1 | 2.6 | 3.8 | 2.4 | 5.0 | 16 | 3.2 |
| OR Quart 4 | 2.0 | 3.6 | 1.8 | 2.0 | 2.3 | 1.7 | 1.1 | 1.7 | 1.1 |
| p Value | 0.023 | 0.025 | 0.058 | 0.014 | 0.051 | 0.087 | 0.83 | 0.48 | 0.82 |
| 95% CI of | 1.1 | 1.2 | 0.98 | 1.2 | 1.00 | 0.93 | 0.44 | 0.40 | 0.45 |
| OR Quart 4 | 3.5 | 11 | 3.2 | 3.6 | 5.5 | 3.0 | 2.8 | 7.1 | 2.7 |

Thymic stromal lymphopoietin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 85.3 | 56.9 | 85.3 | 69.7 | 85.3 | 52.6 |
| Average | 104 | 77.0 | 104 | 87.6 | 104 | 63.4 |
| Stdev | 87.3 | 86.3 | 87.3 | 83.7 | 87.3 | 51.2 |
| p(t-test) | | 0.0023 | | 0.052 | | 0.0017 |
| Min | 0.00642 | 0.00579 | 0.00642 | 0.00960 | 0.00642 | 0.868 |
| Max | 559 | 695 | 559 | 659 | 559 | 266 |
| n (Samp) | 463 | 120 | 463 | 129 | 463 | 47 |
| n (Patient) | 223 | 120 | 223 | 129 | 223 | 47 | sCr only

| | | | | | | |
|---|---|---|---|---|---|---|
| Median | 74.1 | 60.3 | 74.1 | 68.2 | 74.1 | 60.1 |
| Average | 96.0 | 90.4 | 96.0 | 83.6 | 96.0 | 71.0 |
| Stdev | 80.7 | 115 | 80.7 | 100 | 80.7 | 58.0 |
| p(t-test) | | 0.67 | | 0.31 | | 0.12 |
| Min | 0.00579 | 11.9 | 0.00579 | 0.0163 | 0.00579 | 0.868 |
| Max | 559 | 695 | 559 | 659 | 559 | 252 |
| n (Samp) | 1016 | 40 | 1016 | 46 | 1016 | 26 |
| n (Patient) | 375 | 40 | 375 | 46 | 375 | 26 |

UO only

| | | | | | | |
|---|---|---|---|---|---|---|
| Median | 86.2 | 50.2 | 86.2 | 63.3 | 86.2 | 50.9 |
| Average | 108 | 65.6 | 108 | 81.7 | 108 | 62.5 |
| Stdev | 94.5 | 62.4 | 94.5 | 70.0 | 94.5 | 49.7 |
| p(t-test) | | 1.2E−5 | | 0.0052 | | 0.0018 |
| Min | 0.00667 | 0.00579 | 0.00667 | 0.00960 | 0.00667 | 5.43 |
| Max | 695 | 331 | 695 | 361 | 695 | 266 |
| n (Samp) | 435 | 108 | 435 | 118 | 435 | 44 |
| n (Patient) | 173 | 108 | 173 | 118 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.38 | 0.44 | 0.34 | 0.43 | 0.44 | 0.41 | 0.35 | 0.40 | 0.33 |
| SE | 0.030 | 0.048 | 0.031 | 0.029 | 0.045 | 0.030 | 0.045 | 0.059 | 0.046 |
| p | 5.8E−5 | 0.19 | 1.2E−7 | 0.024 | 0.15 | 0.0019 | 7.4E−4 | 0.099 | 2.9E−4 |
| nCohort 1 | 463 | 1016 | 435 | 463 | 1016 | 435 | 463 | 1016 | 435 |
| nCohort 2 | 120 | 40 | 108 | 129 | 46 | 118 | 47 | 26 | 44 |
| Cutoff 1 | 32.5 | 45.4 | 30.0 | 45.2 | 36.1 | 41.8 | 30.2 | 39.0 | 30.2 |
| Sens 1 | 70% | 70% | 70% | 71% | 72% | 70% | 70% | 73% | 70% |
| Spec 1 | 17% | 27% | 14% | 25% | 20% | 21% | 16% | 22% | 14% |
| Cutoff 2 | 21.0 | 29.7 | 17.3 | 32.5 | 23.1 | 26.9 | 25.0 | 33.7 | 23.7 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Sens 2 | 80% | 80% | 81% | 81% | 80% | 81% | 81% | 81% | 82% |
| Spec 2 | 11% | 17% | 10% | 18% | 13% | 12% | 13% | 19% | 11% |
| Cutoff 3 | 13.8 | 22.8 | 10.0 | 16.8 | 10.7 | 17.0 | 13.6 | 25.6 | 13.8 |
| Sens 3 | 90% | 90% | 91% | 91% | 91% | 91% | 91% | 92% | 91% |
| Spec 3 | 8% | 12% | 5% | 10% | 6% | 10% | 8% | 14% | 8% |
| Cutoff 4 | 125 | 113 | 124 | 125 | 113 | 124 | 125 | 113 | 124 |
| Sens 4 | 15% | 18% | 13% | 19% | 17% | 19% | 13% | 15% | 9% |
| Spec 4 | 70% | 70% | 70% | 70% | 70% | 70% | 70% | 70% | 70% |
| Cutoff 5 | 150 | 142 | 153 | 150 | 142 | 153 | 150 | 142 | 153 |
| Sens 5 | 11% | 12% | 8% | 13% | 9% | 14% | 6% | 12% | 5% |
| Spec 5 | 80% | 80% | 80% | 80% | 80% | 80% | 80% | 80% | 80% |
| Cutoff 6 | 221 | 199 | 234 | 221 | 199 | 234 | 221 | 199 | 234 |
| Sens 6 | 6% | 5% | 4% | 7% | 4% | 5% | 2% | 8% | 2% |
| Spec 6 | 90% | 90% | 90% | 90% | 90% | 90% | 90% | 90% | 90% |
| OR Quart 2 | 1.3 | 1.9 | 1.3 | 1.4 | 3.1 | 0.95 | 1.0 | 1.5 | 2.1 |
| p Value | 0.40 | 0.22 | 0.45 | 0.28 | 0.029 | 0.89 | 0.99 | 0.52 | 0.25 |
| 95% CI of | 0.68 | 0.68 | 0.63 | 0.76 | 1.1 | 0.50 | 0.32 | 0.42 | 0.61 |
| OR Quart 2 | 2.6 | 5.1 | 2.8 | 2.6 | 8.7 | 1.8 | 3.2 | 5.4 | 7.1 |
| OR Quart 3 | 2.3 | 2.0 | 2.5 | 2.2 | 2.3 | 1.9 | 2.9 | 1.5 | 3.5 |
| p Value | 0.0076 | 0.16 | 0.0099 | 0.0077 | 0.14 | 0.037 | 0.032 | 0.53 | 0.032 |
| 95% CI of | 1.3 | 0.76 | 1.2 | 1.2 | 0.77 | 1.0 | 1.1 | 0.42 | 1.1 |
| OR Quart 3 | 4.3 | 5.5 | 4.9 | 3.9 | 6.6 | 3.4 | 7.7 | 5.4 | 11 |
| OR Quart 4 | 3.0 | 1.9 | 4.5 | 1.9 | 3.1 | 2.1 | 3.6 | 2.6 | 5.5 |
| p Value | 4.1E−4 | 0.22 | 7.3E−6 | 0.031 | 0.029 | 0.014 | 0.0088 | 0.11 | 0.0026 |
| 95% CI of | 1.6 | 0.68 | 2.3 | 1.1 | 1.1 | 1.2 | 1.4 | 0.80 | 1.8 |
| OR Quart 4 | 5.5 | 5.1 | 8.7 | 3.4 | 8.7 | 3.8 | 9.3 | 8.3 | 17 |

TABLE 2

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

C-C motif chemokine 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0140 | 0.0156 | 0.0140 | 0.0156 | 0.0140 | 0.0151 |
| Average | 1.33 | 1.75 | 1.33 | 2.28 | 1.33 | 0.922 |
| Stdev | 10.4 | 4.86 | 10.4 | 6.00 | 10.4 | 3.04 |
| p(t-test) | | 0.75 | | 0.45 | | 0.81 |
| Min | 0.00501 | 0.00547 | 0.00501 | 0.00547 | 0.00501 | 0.00595 |
| Max | 228 | 26.5 | 228 | 35.4 | 228 | 17.3 |
| n (Samp) | 928 | 62 | 928 | 70 | 928 | 39 |
| n (Patient) | 361 | 62 | 361 | 70 | 361 | 39 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0140 | 0.0151 | 0.0140 | 0.0437 | 0.0140 | 0.0186 |
| Average | 1.28 | 4.21 | 1.28 | 7.10 | 1.28 | 3.09 |
| Stdev | 9.32 | 8.08 | 9.32 | 13.6 | 9.32 | 6.13 |
| p(t-test) | | 0.23 | | 0.0091 | | 0.43 |
| Min | 0.00501 | 0.00501 | 0.00501 | 0.00547 | 0.00501 | 0.00595 |
| Max | 228 | 26.5 | 228 | 49.3 | 228 | 24.6 |
| n (Samp) | 1232 | 15 | 1232 | 18 | 1232 | 17 |
| n (Patient) | 441 | 15 | 441 | 18 | 441 | 17 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0140 | 0.0161 | 0.0140 | 0.0151 | 0.0140 | 0.0151 |
| Average | 1.62 | 1.83 | 1.62 | 2.32 | 1.62 | 1.42 |
| Stdev | 11.3 | 4.63 | 11.3 | 6.21 | 11.3 | 4.31 |
| p(t-test) | | 0.89 | | 0.63 | | 0.92 |
| Min | 0.00501 | 0.00547 | 0.00501 | 0.00547 | 0.00501 | 0.00595 |
| Max | 228 | 26.5 | 228 | 35.4 | 228 | 18.2 |
| n (Samp) | 817 | 57 | 817 | 63 | 817 | 34 |
| n (Patient) | 283 | 57 | 283 | 63 | 283 | 34 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.62 | 0.60 | 0.64 | 0.59 | 0.71 | 0.58 |
| SE | 0.039 | 0.078 | 0.041 | 0.037 | 0.069 | 0.039 |
| p | 0.0019 | 0.20 | 4.9E-4 | 0.014 | 0.0028 | 0.037 |
| nCohort 1 | 928 | 1232 | 817 | 928 | 1232 | 817 |
| nCohort 2 | 62 | 15 | 57 | 70 | 18 | 63 |
| Cutoff 1 | 0.0134 | 0.0134 | 0.0140 | 0.0112 | 0.0140 | 0.0112 |
| Sens 1 | 79% | 80% | 75% | 70% | 72% | 71% |
| Spec 1 | 50% | 48% | 54% | 40% | 56% | 38% |
| Cutoff 2 | 0.0128 | 0.0134 | 0.0134 | 0.00928 | 0.0116 | 0.00928 |
| Sens 2 | 81% | 80% | 81% | 80% | 83% | 81% |
| Spec 2 | 45% | 48% | 48% | 25% | 39% | 25% |
| Cutoff 3 | 0.00637 | 0.00501 | 0.00928 | 0.00764 | 0.00501 | 0.00764 |
| Sens 3 | 90% | 93% | 91% | 90% | 100% | 92% |
| Spec 3 | 10% | 3% | 25% | 18% | 3% | 18% |
| Cutoff 4 | 0.0198 | 0.0206 | 0.0223 | 0.0198 | 0.0206 | 0.0223 |
| Sens 4 | 34% | 33% | 33% | 40% | 61% | 32% |
| Spec 4 | 70% | 70% | 74% | 70% | 70% | 74% |
| Cutoff 5 | 0.0250 | 0.0250 | 0.0250 | 0.0250 | 0.0250 | 0.0250 |
| Sens 5 | 26% | 33% | 32% | 33% | 56% | 32% |
| Spec 5 | 83% | 83% | 82% | 83% | 83% | 82% |
| Cutoff 6 | 0.568 | 0.671 | 0.783 | 0.568 | 0.671 | 0.783 |
| Sens 6 | 19% | 33% | 19% | 21% | 44% | 22% |
| Spec 6 | 90% | 90% | 90% | 90% | 90% | 90% |
| OR Quart 2 | 1.7 | 0.66 | 1.3 | 0.85 | 1.5 | 1.0 |
| p Value | 0.25 | 0.65 | 0.59 | 0.68 | 0.66 | 1.0 |
| 95% CI of | 0.67 | 0.11 | 0.46 | 0.38 | 0.25 | 0.44 |
| OR Quart2 | 4.5 | 4.0 | 3.9 | 1.9 | 9.0 | 2.3 |
| OR Quart 3 | 3.9 | 1.7 | 4.6 | 1.5 | 1.5 | 1.6 |
| p Value | 0.0020 | 0.48 | 0.0011 | 0.22 | 0.66 | 0.20 |
| 95% CI of | 1.6 | 0.40 | 1.8 | 0.77 | 0.25 | 0.78 |
| OR Quart3 | 9.1 | 7.1 | 11 | 3.1 | 9.1 | 3.5 |
| OR Quart 4 | 2.7 | 1.7 | 3.2 | 1.7 | 5.1 | 1.7 |
| p Value | 0.030 | 0.48 | 0.017 | 0.13 | 0.036 | 0.15 |
| 95% CI of | 1.1 | 0.40 | 1.2 | 0.85 | 1.1 | 0.83 |
| OR Quart4 | 6.5 | 7.1 | 8.1 | 3.4 | 24 | 3.6 |

|  | 48 hr prior to AKI stage | | |
|---|---|---|---|
|  | sCr or UO | sCr only | UO only |
| AUC | 0.62 | 0.67 | 0.62 |
| SE | 0.049 | 0.072 | 0.052 |
| p | 0.011 | 0.017 | 0.023 |
| nCohort 1 | 928 | 1232 | 817 |
| nCohort 2 | 39 | 17 | 34 |
| Cutoff 1 | 0.0140 | 0.0150 | 0.0140 |
| Sens 1 | 74% | 71% | 79% |
| Spec 1 | 53% | 60% | 52% |
| Cutoff 2 | 0.0127 | 0.0105 | 0.0134 |
| Sens 2 | 82% | 82% | 82% |
| Spec 2 | 44% | 34% | 48% |
| Cutoff 3 | 0.00997 | 0.00908 | 0.0112 |
| Sens 3 | 95% | 94% | 91% |
| Spec 3 | 30% | 22% | 38% |
| Cutoff 4 | 0.0198 | 0.0206 | 0.0223 |
| Sens 4 | 28% | 47% | 24% |
| Spec 4 | 70% | 70% | 74% |
| Cutoff 5 | 0.0250 | 0.0250 | 0.0250 |
| Sens 5 | 21% | 41% | 21% |
| Spec 5 | 83% | 83% | 82% |
| Cutoff 6 | 0.568 | 0.671 | 0.783 |
| Sens 6 | 15% | 35% | 18% |
| Spec 6 | 90% | 90% | 90% |
| OR Quart 2 | 4.1 | 1.5 | 2.5 |
| p Value | 0.077 | 0.66 | 0.27 |
| 95% CI of | 0.86 | 0.25 | 0.48 |
| OR Quart2 | 19 | 9.1 | 13 |
| OR Quart 3 | 11 | 2.5 | 10 |
| p Value | 0.0015 | 0.27 | 0.0019 |
| 95% CI of | 2.5 | 0.49 | 2.4 |
| OR Quart3 | 47 | 13 | 45 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  | OR Quart 4 | 4.6 | 3.5 | 4.1 |
|---|---|---|---|---|
|  | p Value | 0.052 | 0.12 | 0.077 |
|  | 95% CI of | 0.99 | 0.73 | 0.86 |
|  | OR Quart4 | 22 | 17 | 20 |

C-C motif chemokine 17

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.00505 | 0.0114 | 0.00505 | 0.0111 | 0.00505 | 0.00781 |
| Average | 0.208 | 0.238 | 0.208 | 0.339 | 0.208 | 0.200 |
| Stdev | 1.38 | 0.525 | 1.38 | 1.08 | 1.38 | 0.736 |
| p(t-test) |  | 0.86 |  | 0.43 |  | 0.97 |
| Min | 0.00114 | 0.00114 | 0.00114 | 0.00114 | 0.00114 | 0.00114 |
| Max | 31.5 | 2.38 | 31.5 | 6.36 | 31.5 | 4.45 |
| n (Samp) | 928 | 62 | 928 | 70 | 928 | 39 |
| n (Patient) | 361 | 62 | 361 | 70 | 361 | 39 |

|  | 0 hr prior to AKI stage | | 24 hr prior to AKI stage | | 48 hr prior to AK stage | |
|---|---|---|---|---|---|---|
| sCr only | Cohort 1 | Cohort 2 | Cohort 1 | Cohort 2 | Cohort 1 | Cohort 2 |
| Median | 0.00507 | 0.00309 | 0.00507 | 0.0176 | 0.00507 | 0.0104 |
| Average | 0.249 | 0.153 | 0.249 | 0.367 | 0.249 | 0.454 |
| Stdev | 1.41 | 0.483 | 1.41 | 0.752 | 1.41 | 1.45 |
| p(t-test) |  | 0.79 |  | 0.72 |  | 0.55 |
| Min | 0.00114 | 0.00114 | 0.00114 | 0.00241 | 0.00114 | 0.00114 |
| Max | 31.5 | 1.88 | 31.5 | 2.38 | 31.5 | 5.96 |
| n (Samp) | 1232 | 15 | 1232 | 18 | 1232 | 17 |
| n (Patient) | 441 | 15 | 441 | 18 | 441 | 17 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.00503 | 0.0117 | 0.00503 | 0.0114 | 0.00503 | 0.00751 |
| Average | 0.216 | 0.784 | 0.216 | 0.708 | 0.216 | 0.231 |
| Stdev | 1.43 | 3.59 | 1.43 | 2.65 | 1.43 | 0.785 |
| p(t-test) |  | 0.012 |  | 0.015 |  | 0.95 |
| Min | 0.00114 | 0.00114 | 0.00114 | 0.00114 | 0.00114 | 0.00114 |
| Max | 31.5 | 26.9 | 31.5 | 19.4 | 31.5 | 4.45 |
| n (Samp) | 817 | 57 | 817 | 63 | 817 | 34 |
| n (Patient) | 283 | 57 | 283 | 63 | 283 | 34 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.58 | 0.39 | 0.66 | 0.59 | 0.61 | 0.63 |
| SE | 0.039 | 0.078 | 0.040 | 0.037 | 0.071 | 0.039 |
| p | 0.033 | 0.17 | 7.1E−5 | 0.015 | 11 | 9.7E−4 |
| nCohort 1 | 928 | 1232 | 817 | 928 | 1232 | 817 |
| nCohort 2 | 62 | 15 | 57 | 70 | 18 | 63 |
| Cutoff 1 | 0.00442 | 0.00241 | 0.00503 | 0.00442 | 0.00442 | 0.00443 |
| Sens 1 | 71% | 73% | 72% | 71% | 72% | 73% |
| Spec 1 | 38% | 7% | 50% | 38% | 37% | 42% |
| Cutoff 2 | 0.00249 | 0.00114 | 0.00442 | 0.00308 | 0.00246 | 0.00388 |
| Sens 2 | 82% | 93% | 81% | 81% | 83% | 81% |
| Spec 2 | 15% | 4% | 39% | 23% | 10% | 32% |
| Cutoff 3 | 0.00114 | 0.00114 | 0.00246 | 0.00241 | 0.00241 | 0.00246 |
| Sens 3 | 95% | 93% | 93% | 91% | 94% | 90% |
| Spec 3 | 4% | 4% | 12% | 7% | 7% | 12% |
| Cutoff 4 | 0.0106 | 0.0114 | 0.0105 | 0.0106 | 0.0114 | 0.0105 |
| Sens 4 | 58% | 33% | 67% | 51% | 56% | 56% |
| Spec 4 | 70% | 71% | 70% | 70% | 71% | 70% |
| Cutoff 5 | 0.0138 | 0.0162 | 0.0161 | 0.0138 | 0.0162 | 0.0161 |
| Sens 5 | 31% | 20% | 37% | 34% | 50% | 35% |
| Spec 5 | 80% | 83% | 80% | 80% | 83% | 80% |
| Cutoff 6 | 0.109 | 0.348 | 0.109 | 0.109 | 0.348 | 0.109 |
| Sens 6 | 23% | 7% | 28% | 23% | 22% | 27% |
| Spec 6 | 90% | 90% | 90% | 90% | 90% | 90% |
| OR Quart 2 | 0.58 | 0.66 | 1.3 | 0.67 | 0.75 | 0.83 |
| p Value | 0.21 | 0.66 | 0.62 | 0.32 | 0.70 | 0.66 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| 95% CI of | 0.25 | 0.11 | 0.47 | 0.30 | 0.17 | 0.35 |
| OR Quart2 | 1.4 | 4.0 | 3.5 | 1.5 | 3.4 | 2.0 |
| OR Quart 3 | 1.3 | 0.66 | 2.7 | 0.80 | 0.50 | 1.1 |
| p Value | 0.48 | 0.66 | 0.029 | 0.57 | 0.42 | 0.84 |
| 95% CI of | 0.64 | 0.11 | 1.1 | 0.38 | 0.090 | 0.49 |
| OR Quart3 | 2.6 | 4.0 | 6.6 | 1.7 | 2.7 | 2.4 |
| OR Quart 4 | 1.3 | 2.7 | 3.5 | 2.0 | 2.3 | 2.5 |
| p Value | 0.49 | 0.14 | 0.0043 | 0.034 | 0.17 | 0.0098 |
| 95% CI of | 0.64 | 0.71 | 1.5 | 1.1 | 0.69 | 1.3 |
| OR Quart4 | 2.6 | 10 | 8.4 | 3.7 | 7.5 | 5.1 |

| | | 48 hr prior to AKI stage | | |
|---|---|---|---|---|
| | | sCr or UO | sCr only | UO only |
| | AUC | 0.54 | 0.56 | 0.57 |
| | SE | 0.048 | 0.073 | 0.052 |
| | p | 0.37 | 0.41 | 0.18 |
| | nCohort 1 | 928 | 1232 | 817 |
| | nCohort 2 | 39 | 17 | 34 |
| | Cutoff 1 | 0.00442 | 0.00869 | 0.00443 |
| | Sens 1 | 74% | 71% | 71% |
| | Spec 1 | 38% | 55% | 42% |
| | Cutoff 2 | 0.00308 | 0.00304 | 0.00308 |
| | Sens 2 | 85% | 82% | 85% |
| | Spec 2 | 23% | 18% | 24% |
| | Cutoff 3 | 0.00114 | 0.00114 | 0.00249 |
| | Sens 3 | 95% | 94% | 91% |
| | Spec 3 | 4% | 4% | 16% |
| | Cutoff 4 | 0.0106 | 0.0114 | 0.0105 |
| | Sens 4 | 36% | 29% | 47% |
| | Spec 4 | 70% | 71% | 70% |
| | Cutoff 5 | 0.0138 | 0.0162 | 0.0161 |
| | Sens 5 | 18% | 18% | 21% |
| | Spec 5 | 80% | 83% | 80% |
| | Cutoff 6 | 0.109 | 0.348 | 0.109 |
| | Sens 6 | 15% | 12% | 18% |
| | Spec 6 | 90% | 90% | 90% |
| | OR Quart 2 | 1.6 | 0.25 | 1.3 |
| | p Value | 0.35 | 0.21 | 0.62 |
| | 95% CI of | 0.61 | 0.028 | 0.47 |
| | OR Quart2 | 4.2 | 2.2 | 3.5 |
| | OR Quart 3 | 1.9 | 2.3 | 1.4 |
| | p Value | 0.18 | 0.17 | 0.47 |
| | 95% CI of | 0.74 | 0.70 | 0.54 |
| | OR Quart3 | 4.8 | 7.5 | 3.9 |
| | OR Quart 4 | 1.1 | 0.75 | 1.1 |
| | p Value | 0.80 | 0.70 | 0.80 |
| | 95% CI of | 0.41 | 0.17 | 0.41 |
| | OR Quart4 | 3.2 | 3.4 | 3.2 |

C-C motif chemokine 21

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1.60 | 12.9 | 1.60 | 6.34 | 1.60 | 7.82 |
| Average | 349 | 206 | 349 | 195 | 349 | 115 |
| Stdev | 2490 | 591 | 2490 | 679 | 2490 | 311 |
| p(t-test) | | 0.65 | | 0.61 | | 0.56 |
| Min | 0.327 | 0.371 | 0.327 | 0.327 | 0.327 | 0.647 |
| Max | 36200 | 4070 | 36200 | 4860 | 36200 | 1680 |
| n (Samp) | 928 | 62 | 928 | 70 | 928 | 39 |
| n (Patient) | 361 | 62 | 361 | 70 | 361 | 39 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1.77 | 1.60 | 1.77 | 27.4 | 1.77 | 19.5 |
| Average | 374 | 113 | 374 | 285 | 374 | 131 |
| Stdev | 2560 | 223 | 2560 | 580 | 2560 | 206 |
| p(t-test) | | 0.69 | | 0.88 | | 0.70 |
| Min | 0.327 | 0.762 | 0.327 | 0.611 | 0.327 | 0.762 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Max | 36200 | 760 | 36200 | 2190 | 36200 | 650 |
| n (Samp) | 1232 | 15 | 1232 | 18 | 1232 | 17 |
| n (Patient) | 441 | 15 | 441 | 18 | 441 | 17 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1.60 | 12.9 | 1.60 | 6.89 | 1.60 | 9.85 |
| Average | 373 | 267 | 373 | 213 | 373 | 187 |
| Stdev | 2640 | 736 | 2640 | 715 | 2640 | 481 |
| p(t-test) | | 0.76 | | 0.63 | | 0.68 |
| Min | 0.327 | 0.371 | 0.327 | 0.327 | 0.327 | 0.647 |
| Max | 36200 | 4070 | 36200 | 4860 | 36200 | 2190 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.62 | 0.53 | 0.64 | 0.59 | 0.62 | 0.60 |
| SE | 0.039 | 0.076 | 0.041 | 0.037 | 0.071 | 0.039 |
| P | 0.0016 | 0.72 | 6.3E-4 | 0.011 | 0.099 | 0.011 |
| nCohort 1 | 928 | 1232 | 817 | 928 | 1232 | 817 |
| nCohort 2 | 62 | 15 | 57 | 70 | 18 | 63 |
| Cutoff 1 | 1.20 | 0.939 | 1.31 | 1.20 | 0.979 | 1.20 |
| Sens 1 | 73% | 73% | 70% | 73% | 78% | 73% |
| Spec 1 | 43% | 27% | 49% | 43% | 30% | 43% |
| Cutoff 2 | 0.979 | 0.922 | 0.979 | 0.979 | 0.939 | 0.979 |
| Sens 2 | 81% | 80% | 82% | 80% | 83% | 81% |
| Spec 2 | 35% | 24% | 35% | 35% | 27% | 35% |
| Cutoff 3 | 0.832 | 0.762 | 0.832 | 0.647 | 0.611 | 0.647 |
| Sens 3 | 90% | 93% | 91% | 91% | 94% | 90% |
| Spec 3 | 20% | 15% | 20% | 14% | 9% | 14% |
| Cutoff 4 | 12.9 | 13.0 | 12.0 | 12.9 | 13.0 | 12.0 |
| Sens 4 | 48% | 40% | 53% | 39% | 50% | 41% |
| Spec 4 | 71% | 70% | 70% | 71% | 70% | 70% |
| Cutoff 5 | 43.5 | 51.8 | 43.5 | 43.5 | 51.8 | 43.5 |
| Sens 5 | 27% | 27% | 26% | 29% | 39% | 30% |
| Spec 5 | 80% | 80% | 80% | 80% | 80% | 80% |
| Cutoff 6 | 194 | 213 | 194 | 194 | 213 | 194 |
| Sens 6 | 23% | 20% | 23% | 14% | 28% | 16% |
| Spec 6 | 90% | 90% | 90% | 90% | 90% | 90% |
| OR Quart 2 | 2.5 | 1.00 | 2.4 | 2.2 | 1.3 | 1.8 |
| p Value | 0.044 | 1.00 | 0.077 | 0.072 | 0.71 | 0.19 |
| 95% CI of OR Quart2 | 1.0 | 0.25 | 0.91 | 0.93 | 0.30 | 0.74 |
| | 6.2 | 4.0 | 6.4 | 5.2 | 6.0 | 4.4 |
| OR Quart 3 | 2.2 | 0.25 | 2.1 | 2.6 | 0.66 | 2.4 |
| p Value | 0.088 | 0.21 | 0.16 | 0.024 | 0.66 | 0.049 |
| 95% CI of OR Quart3 | 0.89 | 0.027 | 0.76 | 1.1 | 0.11 | 1.0 |
| | 5.5 | 2.2 | 5.6 | 6.1 | 4.0 | 5.6 |
| OR Quart 4 | 3.5 | 1.5 | 4.6 | 3.3 | 3.0 | 3.1 |
| p Value | 0.0045 | 0.53 | 0.0011 | 0.0037 | 0.097 | 0.0075 |
| 95% CI of OR Quart4 | 1.5 | 0.42 | 1.8 | 1.5 | 0.82 | 1.4 |
| | 8.3 | 5.4 | 11 | 7.6 | 11 | 7.1 |

| | 48 hr prior to AKI stage | | |
|---|---|---|---|
| | sCr or UO | sCr only | UO only |
| AUC | 0.61 | 0.67 | 0.63 |
| SE | 0.049 | 0.073 | 0.052 |
| p | 0.030 | 0.023 | 0.014 |
| nCohort 1 | 928 | 1232 | 817 |
| nCohort 2 | 39 | 17 | 34 |
| Cutoff 1 | 1.07 | 1.60 | 1.31 |
| Sens 1 | 72% | 71% | 71% |
| Spec 1 | 39% | 49% | 49% |
| Cutoff 2 | 0.939 | 1.20 | 0.939 |
| Sens 2 | 87% | 82% | 85% |
| Spec 2 | 29% | 41% | 30% |
| Cutoff 3 | 0.922 | 0.979 | 0.922 |
| Sens 3 | 95% | 94% | 94% |
| Spec 3 | 25% | 34% | 26% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  |  |  |  |
|---|---|---|---|
| Cutoff 4 | 12.9 | 13.0 | 12.0 |
| Sens 4 | 38% | 53% | 44% |
| Spec 4 | 71% | 70% | 70% |
| Cutoff 5 | 43.5 | 51.8 | 43.5 |
| Sens 5 | 26% | 41% | 29% |
| Spec 5 | 80% | 80% | 80% |
| Cutoff 6 | 194 | 213 | 194 |
| Sens 6 | 15% | 24% | 18% |
| Spec 6 | 90% | 90% | 90% |
| OR Quart 2 | 6.8 | 5.1 | 4.6 |
| p Value | 0.012 | 0.14 | 0.052 |
| 95% CI of | 1.5 | 0.59 | 0.99 |
| OR Quart2 | 30 | 44 | 22 |
| OR Quart 3 | 5.7 | 3.0 | 4.6 |
| p Value | 0.025 | 0.34 | 0.052 |
| 95% CI of | 1.2 | 0.31 | 0.99 |
| OR Quart3 | 26 | 29 | 22 |
| OR Quart 4 | 6.8 | 8.2 | 7.4 |
| p Value | 0.012 | 0.048 | 0.0087 |
| 95% CI of | 1.5 | 1.0 | 1.7 |
| OR Quart4 | 30 | 66 | 33 |

C-C motif chemokine 27

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1.87 | 2.53 | 1.87 | 3.30 | 1.87 | 2.17 |
| Average | 4.03 | 6.49 | 4.03 | 6.61 | 4.03 | 4.00 |
| Stdev | 11.7 | 15.9 | 11.7 | 15.1 | 11.7 | 9.24 |
| p(t-test) |  | 0.12 |  | 0.083 |  | 0.99 |
| Min | 0.00255 | 0.00668 | 0.00255 | 0.00333 | 0.00255 | 0.00333 |
| Max | 230 | 118 | 230 | 109 | 230 | 57.4 |
| n (Samp) | 928 | 62 | 928 | 70 | 928 | 38 |
| n (Patient) | 361 | 62 | 361 | 70 | 361 | 38 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1.99 | 1.94 | 1.99 | 3.56 | 1.99 | 4.65 |
| Average | 4.34 | 3.25 | 4.34 | 5.53 | 4.34 | 4.86 |
| Stdev | 12.1 | 3.53 | 12.1 | 6.63 | 12.1 | 3.64 |
| p(t-test) |  | 0.73 |  | 0.68 |  | 0.86 |
| Min | 0.00255 | 0.00668 | 0.00255 | 0.00983 | 0.00255 | 0.00333 |
| Max | 230 | 11.9 | 230 | 27.8 | 230 | 12.8 |
| n (Samp) | 1231 | 15 | 1231 | 18 | 1231 | 17 |
| n (Patient) | 441 | 15 | 441 | 18 | 441 | 17 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1.89 | 2.84 | 1.89 | 3.08 | 1.89 | 2.27 |
| Average | 4.29 | 11.1 | 4.29 | 10.1 | 4.29 | 4.39 |
| Stdev | 12.4 | 34.3 | 12.4 | 28.9 | 12.4 | 9.85 |
| p(t-test) |  | 8.1E-4 |  | 0.0018 |  | 0.96 |
| Min | 0.00255 | 0.00696 | 0.00255 | 0.00333 | 0.00255 | 0.00668 |
| Max | 230 | 234 | 230 | 198 | 230 | 57.4 |
| n (Samp) | 817 | 57 | 817 | 63 | 817 | 33 |
| n (Patient) | 283 | 57 | 283 | 63 | 283 | 33 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.57 | 0.52 | 0.59 | 0.62 | 0.67 | 0.61 |
| SE | 0.039 | 0.076 | 0.041 | 0.037 | 0.071 | 0.039 |
| P | 0.070 | 0.81 | 0.020 | 9.2E-4 | 0.018 | 0.0064 |
| nCohort 1 | 928 | 1231 | 817 | 928 | 1231 | 817 |
| nCohort 2 | 62 | 15 | 57 | 70 | 18 | 63 |
| Cutoff 1 | 1.48 | 0.527 | 1.89 | 2.02 | 2.86 | 1.60 |
| Sens 1 | 71% | 73% | 70% | 70% | 72% | 71% |
| Spec 1 | 45% | 26% | 50% | 52% | 62% | 46% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Cutoff 2 | 0.658 | 0.292 | 0.856 | 1.22 | 2.02 | 0.697 |
| Sens 2 | 81% | 80% | 81% | 80% | 83% | 81% |
| Spec 2 | 29% | 22% | 33% | 40% | 51% | 30% |
| Cutoff 3 | 0.0115 | 0.00883 | 0.0115 | 0.400 | 0.723 | 0.280 |
| Sens 3 | 90% | 93% | 91% | 90% | 94% | 90% |
| Spec 3 | 14% | 9% | 14% | 24% | 29% | 23% |
| Cutoff 4 | 3.46 | 3.59 | 3.62 | 3.46 | 3.59 | 3.62 |
| Sens 4 | 34% | 40% | 37% | 49% | 44% | 48% |
| Spec 4 | 70% | 70% | 70% | 70% | 70% | 70% |
| Cutoff 5 | 4.63 | 4.76 | 5.03 | 4.63 | 4.76 | 5.03 |
| Sens 5 | 29% | 27% | 26% | 34% | 28% | 30% |
| Spec 5 | 80% | 80% | 80% | 80% | 80% | 80% |
| Cutoff 6 | 7.19 | 7.44 | 7.79 | 7.19 | 7.44 | 7.79 |
| Sens 6 | 16% | 13% | 19% | 16% | 17% | 17% |
| Spec 6 | 90% | 90% | 90% | 90% | 90% | 90% |
| OR Quart 2 | 0.82 | 1.00 | 1.00 | 1.1 | 2.0 | 1.1 |
| p Value | 0.66 | 1.00 | 0.99 | 0.83 | 0.57 | 0.82 |
| 95% CI of OR Quart2 | 0.35 1.9 | 0.25 4.0 | 0.39 2.6 | 0.46 2.6 | 0.18 22 | 0.46 2.7 |
| OR Quart 3 | 1.8 | 0.25 | 2.3 | 2.3 | 9.2 | 2.0 |
| p Value | 0.11 | 0.21 | 0.039 | 0.032 | 0.035 | 0.089 |
| 95% CI of OR Quart3 | 0.87 3.8 | 0.028 2.2 | 1.0 5.3 | 1.1 5.0 | 1.2 73 | 0.90 4.4 |
| OR Quart 4 | 1.6 | 1.5 | 2.2 | 2.9 | 6.1 | 2.5 |
| p Value | 0.20 | 0.53 | 0.058 | 0.0054 | 0.096 | 0.022 |
| 95% CI of OR Quart4 | 0.77 3.4 | 0.42 5.4 | 0.98 5.0 | 1.4 6.1 | 0.73 51 | 1.1 5.3 |

| | 48 hr prior to AKI stage | | |
|---|---|---|---|
| | sCr or UO | sCr only | UO only |
| AUC | 0.51 | 0.67 | 0.52 |
| SE | 0.048 | 0.073 | 0.052 |
| p | 0.91 | 0.018 | 0.68 |
| nCohort 1 | 928 | 1231 | 817 |
| nCohort 2 | 38 | 17 | 33 |
| Cutoff 1 | 0.774 | 3.07 | 0.903 |
| Sens 1 | 71% | 71% | 73% |
| Spec 1 | 31% | 64% | 34% |
| Cutoff 2 | 0.0105 | 1.48 | 0.0105 |
| Sens 2 | 82% | 82% | 82% |
| Spec 2 | 13% | 43% | 14% |
| Cutoff 3 | 0.00786 | 0.0149 | 0.00983 |
| Sens 3 | 92% | 94% | 91% |
| Spec 3 | 6% | 17% | 12% |
| Cutoff 4 | 3.46 | 3.59 | 3.62 |
| Sens 4 | 34% | 59% | 36% |
| Spec 4 | 70% | 70% | 70% |
| Cutoff 5 | 4.63 | 4.76 | 5.03 |
| Sens 5 | 26% | 47% | 15% |
| Spec 5 | 80% | 80% | 80% |
| Cutoff 6 | 7.19 | 7.44 | 7.79 |
| Sens 6 | 8% | 24% | 9% |
| Spec 6 | 90% | 90% | 90% |
| OR Quart 2 | 0.59 | 1.0 | 0.49 |
| p Value | 0.31 | 1.0 | 0.25 |
| 95% CI of OR Quart2 | 0.21 1.6 | 0.14 7.1 | 0.14 1.6 |
| OR Quart 3 | 1.1 | 2.0 | 1.4 |
| p Value | 0.82 | 0.42 | 0.48 |
| 95% CI of OR Quart3 | 0.46 2.7 | 0.37 11 | 0.55 3.5 |
| OR Quart 4 | 1.1 | 4.6 | 1.3 |
| p Value | 0.83 | 0.052 | 0.64 |
| 95% CI of OR Quart4 | 0.46 2.6 | 0.99 21 | 0.49 3.2 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

Vascular endothelial growth factor receptor 1

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 10.1 | 40.7 | 10.1 | 44.5 | 10.1 | 9.07 |
| Average | 67.5 | 100 | 67.5 | 181 | 67.5 | 40.5 |
| Stdev | 333 | 120 | 333 | 634 | 333 | 60.4 |
| p(t-test) | | 0.51 | | 0.035 | | 0.67 |
| Min | 0.169 | 0.242 | 0.169 | 0.169 | 0.169 | 0.169 |
| Max | 6850 | 529 | 6850 | 4630 | 6850 | 219 |
| n (Samp) | 469 | 46 | 469 | 54 | 469 | 28 |
| n (Patient) | 237 | 46 | 237 | 54 | 237 | 28 |

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 19.5 | 0.363 | 19.5 | 56.8 | 19.5 | 36.8 |
| Average | 78.1 | 40.8 | 78.1 | 118 | 78.1 | 70.9 |
| Stdev | 345 | 62.2 | 345 | 193 | 345 | 103 |
| p(t-test) | | 0.75 | | 0.70 | | 0.95 |
| Min | 0.169 | 0.169 | 0.169 | 0.281 | 0.169 | 0.242 |
| Max | 6850 | 149 | 6850 | 673 | 6850 | 294 |
| n (Samp) | 628 | 9 | 628 | 11 | 628 | 11 |
| n (Patient) | 292 | 9 | 292 | 11 | 292 | 11 |

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 10.1 | 54.0 | 10.1 | 40.7 | 10.1 | 35.8 |
| Average | 69.1 | 119 | 69.1 | 183 | 69.1 | 49.0 |
| Stdev | 343 | 145 | 343 | 668 | 343 | 61.2 |
| p(t-test) | | 0.35 | | 0.054 | | 0.77 |
| Min | 0.169 | 0.454 | 0.169 | 0.169 | 0.169 | 0.169 |
| Max | 6850 | 605 | 6850 | 4630 | 6850 | 219 |
| n (Samp) | 439 | 42 | 439 | 48 | 439 | 25 |
| n (Patient) | 209 | 42 | 209 | 48 | 209 | 25 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.64 | 0.37 | 0.68 | 0.63 | 0.64 | 0.62 |
| SE | 0.046 | 0.10 | 0.047 | 0.043 | 0.091 | 0.045 |
| p | 0.0015 | 0.18 | 1.6E-4 | 0.0028 | 0.11 | 0.010 |
| nCohort 1 | 469 | 628 | 439 | 469 | 628 | 439 |
| nCohort 2 | 46 | 9 | 42 | 54 | 11 | 48 |
| Cutoff 1 | 5.82 | 0.215 | 8.62 | 5.82 | 36.8 | 5.82 |
| Sens 1 | 74% | 89% | 71% | 72% | 73% | 71% |
| Spec 1 | 45% | 6% | 49% | 45% | 60% | 44% |
| Cutoff 2 | 2.27 | 0.215 | 2.27 | 2.27 | 19.5 | 0.521 |
| Sens 2 | 80% | 89% | 83% | 81% | 82% | 81% |
| Spec 2 | 39% | 6% | 39% | 39% | 51% | 34% |
| Cutoff 3 | 0.429 | 0 | 0.455 | 0.429 | 2.27 | 0.429 |
| Sens 3 | 91% | 100% | 90% | 91% | 91% | 92% |
| Spec 3 | 20% | 0% | 22% | 20% | 35% | 20% |
| Cutoff 4 | 53.5 | 59.8 | 54.1 | 53.5 | 59.8 | 54.1 |
| Sens 4 | 46% | 22% | 50% | 46% | 36% | 42% |
| Spec 4 | 70% | 70% | 71% | 70% | 70% | 71% |
| Cutoff 5 | 93.9 | 99.9 | 90.5 | 93.9 | 99.9 | 90.5 |
| Sens 5 | 39% | 22% | 43% | 33% | 27% | 33% |
| Spec 5 | 81% | 80% | 80% | 81% | 80% | 80% |
| Cutoff 6 | 159 | 178 | 152 | 159 | 178 | 152 |
| Sens 6 | 28% | 0% | 33% | 22% | 18% | 21% |
| Spec 6 | 90% | 90% | 90% | 90% | 90% | 90% |
| OR Quart 2 | 0.99 | 1.0 | 2.4 | 1.3 | 0.99 | 2.5 |
| p Value | 0.99 | 0.99 | 0.16 | 0.64 | 1.00 | 0.091 |
| 95% CI of | 0.34 | 0.14 | 0.70 | 0.48 | 0.062 | 0.86 |
| OR Quart2 | 2.9 | 7.2 | 7.9 | 3.3 | 16 | 7.4 |
| OR Quart 3 | 1.8 | 0 | 2.4 | 2.3 | 6.2 | 3.0 |
| p Value | 0.25 | na | 0.16 | 0.067 | 0.094 | 0.041 |
| 95% CI of | 0.67 | na | 0.70 | 0.94 | 0.73 | 1.0 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| OR Quart3 | 4.7 | na | 7.9 | 5.5 | 52 | 8.6 |
| OR Quart 4 | 3.2 | 2.6 | 5.7 | 2.6 | 3.0 | 3.8 |
| p Value | 0.012 | 0.26 | 0.0020 | 0.031 | 0.34 | 0.012 |
| 95% CI of | 1.3 | 0.49 | 1.9 | 1.1 | 0.31 | 1.3 |
| OR Quart4 | 7.8 | 13 | 17 | 6.1 | 29 | 11 |

| | 48 hr prior to AKI stage | | |
|---|---|---|---|
| | sCr or UO | sCr only | UO only |
| AUC | 0.46 | 0.52 | 0.52 |
| SE | 0.057 | 0.089 | 0.060 |
| p | 0.47 | 0.80 | 0.79 |
| nCohort 1 | 469 | 628 | 439 |
| nCohort 2 | 28 | 11 | 25 |
| Cutoff 1 | 0.429 | 0.568 | 0.429 |
| Sens 1 | 79% | 73% | 84% |
| Spec 1 | 20% | 33% | 20% |
| Cutoff 2 | 0.281 | 0.429 | 0.429 |
| Sens 2 | 82% | 82% | 84% |
| Spec 2 | 14% | 18% | 20% |
| Cutoff 3 | 0 | 0.281 | 0 |
| Sens 3 | 100% | 91% | 100% |
| Spec 3 | 0% | 12% | 0% |
| Cutoff 4 | 53.5 | 59.8 | 54.1 |
| Sens 4 | 29% | 36% | 36% |
| Spec 4 | 70% | 70% | 71% |
| Cutoff 5 | 93.9 | 99.9 | 90.5 |
| Sens 5 | 14% | 18% | 16% |
| Spec 5 | 81% | 80% | 80% |
| Cutoff 6 | 159 | 178 | 152 |
| Sens 6 | 7% | 18% | 8% |
| Spec 6 | 90% | 90% | 90% |
| OR Quart 2 | 1.4 | 0.66 | 0.12 |
| p Value | 0.57 | 0.65 | 0.045 |
| 95% CI of | 0.46 | 0.11 | 0.014 |
| OR Quart2 | 4.1 | 4.0 | 0.95 |
| OR Quart 3 | 0.49 | 0.99 | 1.3 |
| p Value | 0.32 | 0.99 | 0.62 |
| 95% CI of | 0.12 | 0.20 | 0.48 |
| OR Quart3 | 2.0 | 5.0 | 3.4 |
| OR Quart 4 | 1.9 | 0.99 | 0.74 |
| p Value | 0.21 | 0.99 | 0.58 |
| 95% CI of | 0.69 | 0.20 | 0.25 |
| OR Quart4 | 5.4 | 5.0 | 2.2 |

SL cytokine

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0627 | 0.0869 | 0.0627 | 0.0908 | 0.0627 | 0.0747 |
| Average | 1.56 | 2.84 | 1.56 | 2.77 | 1.56 | 0.303 |
| Stdev | 20.8 | 11.8 | 20.8 | 9.51 | 20.8 | 1.29 |
| p(t-test) | | 0.63 | | 0.63 | | 0.71 |
| Min | 0.0336 | 0.0336 | 0.0336 | 0.0445 | 0.0336 | 0.0336 |
| Max | 527 | 68.6 | 527 | 50.2 | 527 | 8.15 |
| n (Samp) | 930 | 62 | 930 | 70 | 930 | 39 |
| n (Patient) | 361 | 62 | 361 | 70 | 361 | 39 |

| | 0 hr prior to AKI stage | | 24 hr prior to AKI stage | | 48 hr prior to AK stage | |
|---|---|---|---|---|---|---|
| sCr only | Cohort 1 | Cohort 2 | Cohort 1 | Cohort 2 | Cohort 1 | Cohort 2 |
| Median | 0.0627 | 0.0598 | 0.0627 | 0.0764 | 0.0627 | 0.0997 |
| Average | 1.71 | 1.31 | 1.71 | 4.99 | 1.71 | 0.723 |
| Stdev | 19.7 | 4.84 | 19.7 | 13.0 | 19.7 | 2.39 |
| p(t-test) | | 0.94 | | 0.48 | | 0.84 |
| Min | 0.0336 | 0.0336 | 0.0336 | 0.0336 | 0.0336 | 0.0511 |
| Max | 527 | 18.8 | 527 | 50.2 | 527 | 9.98 |
| n (Samp) | 1234 | 15 | 1234 | 18 | 1234 | 17 |
| n (Patient) | 441 | 15 | 441 | 18 | 441 | 17 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.0660 | 0.0914 | 0.0660 | 0.0908 | 0.0660 | 0.0745 |
| Average | 1.73 | 3.10 | 1.73 | 2.27 | 1.73 | 0.329 |
| Stdev | 22.2 | 12.3 | 22.2 | 7.97 | 22.2 | 1.38 |
| p(t-test) | | 0.65 | | 0.85 | | 0.71 |
| Min | 0.0336 | 0.0336 | 0.0336 | 0.0445 | 0.0336 | 0.0336 |
| Max | 527 | 68.6 | 527 | 45.6 | 527 | 8.15 |
| n (Samp) | 819 | 57 | 819 | 63 | 819 | 34 |
| n (Patient) | 283 | 57 | 283 | 63 | 283 | 34 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.57 | 0.43 | 0.59 | 0.61 | 0.58 | 0.60 |
| SE | 0.039 | 0.077 | 0.041 | 0.037 | 0.071 | 0.039 |
| p | 0.064 | 0.39 | 0.024 | 0.0043 | 0.28 | 0.011 |
| nCohort 1 | 930 | 1234 | 819 | 930 | 1234 | 819 |
| nCohort 2 | 62 | 15 | 57 | 70 | 18 | 63 |
| Cutoff 1 | 0.0541 | 0.0487 | 0.0541 | 0.0598 | 0.0598 | 0.0579 |
| Sens 1 | 71% | 87% | 72% | 70% | 72% | 73% |
| Spec 1 | 28% | 17% | 29% | 42% | 43% | 37% |
| Cutoff 2 | 0.0514 | 0.0487 | 0.0514 | 0.0541 | 0.0527 | 0.0527 |
| Sens 2 | 81% | 87% | 84% | 80% | 83% | 81% |
| Spec 2 | 20% | 17% | 20% | 28% | 25% | 25% |
| Cutoff 3 | 0.0487 | 0.0396 | 0.0449 | 0.0487 | 0.0487 | 0.0487 |
| Sens 3 | 90% | 93% | 95% | 94% | 94% | 92% |
| Spec 3 | 17% | 5% | 12% | 17% | 17% | 16% |
| Cutoff 4 | 0.0914 | 0.0914 | 0.0914 | 0.0914 | 0.0914 | 0.0914 |
| Sens 4 | 32% | 13% | 37% | 37% | 28% | 38% |
| Spec 4 | 72% | 72% | 71% | 72% | 72% | 71% |
| Cutoff 5 | 0.109 | 0.109 | 0.109 | 0.109 | 0.109 | 0.109 |
| Sens 5 | 31% | 7% | 35% | 29% | 28% | 29% |
| Spec 5 | 81% | 82% | 81% | 81% | 82% | 81% |
| Cutoff 6 | 0.167 | 0.188 | 0.170 | 0.167 | 0.188 | 0.170 |
| Sens 6 | 24% | 7% | 28% | 20% | 17% | 21% |
| Spec 6 | 90% | 95% | 90% | 90% | 95% | 90% |
| OR Quart 2 | 0.45 | 2.5 | 0.63 | 0.84 | 1.0 | 0.82 |
| p Value | 0.071 | 0.27 | 0.29 | 0.68 | 1.0 | 0.65 |
| 95% CI of OR Quart2 | 0.19 1.1 | 0.49 13 | 0.27 1.5 | 0.37 1.9 | 0.20 5.0 | 0.35 1.9 |
| OR Quart 3 | 1.1 | 1.0 | 1.0 | 1.8 | 2.4 | 1.7 |
| p Value | 0.86 | 1.00 | 1.0 | 0.088 | 0.22 | 0.15 |
| 95% CI of OR Quart3 | 0.53 2.1 | 0.14 7.2 | 0.47 2.2 | 0.91 3.7 | 0.61 9.2 | 0.83 3.6 |
| OR Quart 4 | 1.1 | 3.0 | 1.5 | 1.8 | 1.7 | 1.8 |
| p Value | 0.73 | 0.17 | 0.29 | 0.088 | 0.48 | 0.11 |
| 95% CI of OR Quart4 | 0.57 2.2 | 0.61 15 | 0.72 3.0 | 0.91 3.7 | 0.40 7.1 | 0.87 3.8 |

| | 48 hr prior to AKI stage | | |
|---|---|---|---|
| | sCr or UO | sCr only | UO only |
| AUC | 0.51 | 0.72 | 0.49 |
| SE | 0.047 | 0.071 | 0.051 |
| p | 0.85 | 0.0015 | 0.81 |
| nCohort 1 | 930 | 1234 | 819 |
| nCohort 2 | 39 | 17 | 34 |
| Cutoff 1 | 0.0514 | 0.0847 | 0.0514 |
| Sens 1 | 77% | 76% | 76% |
| Spec 1 | 20% | 61% | 20% |
| Cutoff 2 | 0.0487 | 0.0845 | 0.0449 |
| Sens 2 | 82% | 82% | 82% |
| Spec 2 | 17% | 57% | 12% |
| Cutoff 3 | 0 | 0.0569 | 0 |
| Sens 3 | 100% | 94% | 100% |
| Spec 3 | 0% | 30% | 0% |
| Cutoff 4 | 0.0914 | 0.0914 | 0.0914 |
| Sens 4 | 31% | 59% | 26% |
| Spec 4 | 72% | 72% | 71% |
| Cutoff 5 | 0.109 | 0.109 | 0.109 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | |
|---|---|---|---|---|
| Sens 5 | 23% | 41% | 24% |
| Spec 5 | 81% | 82% | 81% |
| Cutoff 6 | 0.167 | 0.188 | 0.170 |
| Sens 6 | 21% | 29% | 21% |
| Spec 6 | 90% | 95% | 90% |
| OR Quart 2 | 0.49 | 2.0 | 1.0 |
| p Value | 0.16 | 0.57 | 0.99 |
| 95% CI of | 0.18 | 0.18 | 0.39 |
| OR Quart2 | 1.3 | 22 | 2.6 |
| OR Quart 3 | 0.74 | 6.1 | 0.55 |
| p Value | 0.50 | 0.096. | 0.29 |
| 95% CI of | 0.31 | 0.73 | 0.18 |
| OR Quart3 | 1.8 | 51 | 1.7 |
| OR Quart 4 | 1.00 | 8.2 | 1.2 |
| p Value | 0.99 | 0.048 | 0.64 |
| 95% CI of | 0.44 | 1.0 | 0.50 |
| OR Quart4 | 2.3 | 66 | 3.1 |

Immunoglogulin G3

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 94.9 | 154 | 94.9 | 173 | 94.9 | 118 |
| Average | 190 | 295 | 190 | 321 | 190 | 191 |
| Stdev | 272 | 357 | 272 | 368 | 272 | 256 |
| p(t-test) | | 0.0039 | | 1.6E-4 | | 0.97 |
| Min | 0.833 | 10.6 | 0.833 | 5.93 | 0.833 | 2.02 |
| Max | 1200 | 1200 | 1200 | 1200 | 1200 | 1200 |
| n (Samp) | 922 | 62 | 922 | 70 | 922 | 39 |
| n (Patient) | 358 | 62 | 358 | 70 | 358 | 39 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 101 | 211 | 101 | 129 | 101 | 213 |
| Average | 204 | 441 | 204 | 369 | 204 | 336 |
| Stdev | 285 | 484 | 285 | 443 | 285 | 431 |
| p(t-test) | | 0.0015 | | 0.016 | | 0.059 |
| Min | 0.833 | 29.9 | 0.833 | 14.4 | 0.833 | 8.91 |
| Max | 1200 | 1200 | 1200 | 1200 | 1200 | 1200 |
| n (Samp) | 1225 | 15 | 1225 | 18 | 1225 | 17 |
| n (Patient) | 438 | 15 | 438 | 18 | 438 | 17 |

| | 0 hr prior to AKI stage | | 24 hr prior to AKI stage | | 48 hr prior to AK stage | |
|---|---|---|---|---|---|---|
| UO only | Cohort 1 | Cohort 2 | Cohort 1 | Cohort 2 | Cohort 1 | Cohort 2 |
| Median | 99.4 | 160 | 99.4 | 191 | 99.4 | 121 |
| Average | 191 | 345 | 191 | 371 | 191 | 216 |
| Stdev | 270 | 403 | 270 | 402 | 270 | 266 |
| p(t-test) | | 7.3E-5 | | 1.3E-6 | | 0.60 |
| Min | 0.833 | 10.6 | 0.833 | 5.93 | 0.833 | 2.02 |
| Max | 1200 | 1200 | 1200 | 1200 | 1200 | 1200 |
| n (Samp) | 810 | 57 | 810 | 63 | 810 | 34 |
| n (Patient) | 280 | 57 | 280 | 63 | 280 | 34 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.62 | 0.68 | 0.63 | 0.62 | 0.57 | 0.65 |
| SE | 0.039 | 0.077 | 0.041 | 0.037 | 0.071 | 0.039 |
| p | 0.0026 | 0.017 | 0.0019 | 0.0016 | 0.32 | 8.6E-5 |
| nCohort 1 | 922 | 1225 | 810 | 922 | 1225 | 810 |
| nCohort 2 | 62 | 15 | 57 | 70 | 18 | 63 |
| Cutoff 1 | 74.7 | 98.1 | 69.6 | 82.8 | 64.8 | 88.7 |
| Sens 1 | 71% | 73% | 70% | 70% | 72% | 71% |
| Spec 1 | 42% | 49% | 39% | 46% | 35% | 46% |
| Cutoff 2 | 54.9 | 90.6 | 54.9 | 52.4 | 27.1 | 68.8 |
| Sens 2 | 81% | 80% | 81% | 80% | 83% | 81% |
| Spec 2 | 31% | 46% | 31% | 29% | 12% | 38% |
| Cutoff 3 | 46.5 | 52.1 | 46.5 | 27.1 | 15.3 | 42.4 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Sens 3 | 90% | 93% | 91% | 90% | 94% | 90% |
| Spec 3 | 26% | 27% | 26% | 13% | 6% | 22% |
| Cutoff 4 | 163 | 182 | 167 | 163 | 182 | 167 |
| Sens 4 | 47% | 60% | 49% | 53% | 44% | 57% |
| Spec 4 | 70% | 70% | 70% | 70% | 70% | 70% |
| Cutoff 5 | 249 | 271 | 256 | 249 | 271 | 256 |
| Sens 5 | 35% | 33% | 40% | 39% | 39% | 40% |
| Spec 5 | 80% | 80% | 80% | 80% | 80% | 80% |
| Cutoff 6 | 397 | 426 | 401 | 397 | 426 | 401 |
| Sens 6 | 18% | 33% | 23% | 24% | 33% | 29% |
| Spec 6 | 90% | 90% | 90% | 90% | 90% | 90% |
| OR Quart 2 | 2.5 | 4.0 | 2.2 | 1.0 | 0.75 | 1.6 |
| p Value | 0.043 | 0.21 | 0.089 | 1.0 | 0.70 | 0.29 |
| 95% CI of OR Quart2 | 1.0 | 0.45 | 0.89 | 0.45 | 0.17 | 0.67 |
| | 6.2 | 36 | 5.6 | 2.2 | 3.4 | 3.8 |
| OR Quart 3 | 1.6 | 4.0 | 1.3 | 1.1 | 1.00 | 1.2 |
| p Value | 0.34 | 0.21 | 0.62 | 0.84 | 1.00 | 0.65 |
| 95% CI of OR Quart3 | 0.61 | 0.45 | 0.47 | 0.50 | 0.25 | 0.50 |
| | 4.2 | 36 | 3.5 | 2.4 | 4.0 | 3.0 |
| OR Quart 4 | 4.2 | 6.1 | 4.1 | 2.5 | 1.8 | 3.5 |
| p Value | 9.4E−4 | 0.095 | 0.0013 | 0.0083 | 0.37 | 0.0013 |
| 95% CI of OR Quart4 | 1.8 | 0.73 | 1.7 | 1.3 | 0.51 | 1.6 |
| | 9.9 | 51 | 9.6 | 4.9 | 6.1 | 7.7 |

| | 48 hr prior to AKI stage | | |
|---|---|---|---|
| | sCr or UO | sCr only | UO only |
| AUC | 0.49 | 0.57 | 0.55 |
| SE | 0.047 | 0.073 | 0.052 |
| p | 0.88 | 0.36 | 0.38 |
| nCohort 1 | 922 | 1225 | 810 |
| nCohort 2 | 39 | 17 | 34 |
| Cutoff 1 | 38.2 | 58.2 | 62.9 |
| Sens 1 | 72% | 71% | 71% |
| Spec 1 | 20% | 31% | 35% |
| Cutoff 2 | 30.0 | 27.0 | 32.5 |
| Sens 2 | 82% | 82% | 82% |
| Spec 2 | 15% | 12% | 17% |
| Cutoff 3 | 14.4 | 14.5 | 30.0 |
| Sens 3 | 92% | 94% | 91% |
| Spec 3 | 6% | 6% | 16% |
| Cutoff 4 | 163 | 182 | 167 |
| Sens 4 | 36% | 53% | 38% |
| Spec 4 | 70% | 70% | 70% |
| Cutoff 5 | 249 | 271 | 256 |
| Sens 5 | 23% | 29% | 26% |
| Spec 5 | 80% | 80% | 80% |
| Cutoff 6 | 397 | 426 | 401 |
| Sens 6 | 8% | 24% | 9% |
| Spec 6 | 90% | 90% | 90% |
| OR Quart 2 | 0.74 | 0.75 | 0.74 |
| p Value | 0.51 | 0.70 | 0.59 |
| 95% CI of OR Quart2 | 0.31 | 0.17 | 0.25 |
| | 1.8 | 3.4 | 2.2 |
| OR Quart 3 | 0.49 | 0.50 | 1.0 |
| p Value | 0.16 | 0.42 | 1.0 |
| 95% CI of OR Quart3 | 0.18 | 0.090 | 0.37 |
| | 1.3 | 2.7 | 2.7 |
| OR Quart 4 | 1.0 | 2.0 | 1.5 |
| p Value | 0.99 | 0.26 | 0.36 |
| 95% CI of OR Quart4 | 0.44 | 0.60 | 0.61 |
| | 2.3 | 6.8 | 3.8 |

Interleukin-1 receptor type I

| | 0 hr prior to AKI stage | | 24 hr prior to AKI stage | | 48 hr prior to AK stage | |
|---|---|---|---|---|---|---|
| sCr or UO | Cohort 1 | Cohort 2 | Cohort 1 | Cohort 2 | Cohort 1 | Cohort 2 |
| Median | 4.52 | 6.94 | 4.52 | 6.49 | 4.52 | 6.21 |
| Average | 5.52 | 8.16 | 5.52 | 8.94 | 5.52 | 5.82 |
| Stdev | 4.87 | 5.99 | 4.87 | 11.6 | 4.87 | 4.86 |
| p(t-test) | | 6.5E−4 | | 6.3E−5 | | 0.75 |
| Min | 0.0141 | 0.0200 | 0.0141 | 0.203 | 0.0141 | 0.0147 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Max | 33.9 | 29.6 | 33.9 | 78.1 | 33.9 | 14.7 |
| n (Samp) | 473 | 46 | 473 | 54 | 473 | 28 |
| n (Patient) | 240 | 46 | 240 | 54 | 240 | 28 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 5.40 | 3.39 | 5.40 | 7.41 | 5.40 | 6.52 |
| Average | 6.22 | 6.49 | 6.22 | 7.46 | 6.22 | 7.71 |
| Stdev | 6.08 | 6.25 | 6.08 | 4.87 | 6.08 | 5.57 |
| p(t-test) | | 0.89 | | 0.50 | | 0.42 |
| Min | 0.0141 | 1.95 | 0.0141 | 1.09 | 0.0141 | 0.355 |
| Max | 78.1 | 20.6 | 78.1 | 16.5 | 78.1 | 16.8 |
| n (Samp) | 633 | 9 | 633 | 11 | 633 | 11 |
| n (Patient) | 295 | 9 | 295 | 11 | 295 | 11 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 4.47 | 8.36 | 4.47 | 6.57 | 4.47 | 7.43 |
| Average | 5.57 | 8.75 | 5.57 | 9.37 | 5.57 | 6.42 |
| Stdev | 4.98 | 6.03 | 4.98 | 12.1 | 4.98 | 4.77 |
| p(t-test) | | 1.2E−4 | | 4.3E−5 | | 0.41 |
| Min | 0.0141 | 0.0200 | 0.0141 | 0.203 | 0.0141 | 0.0147 |
| Max | 33.9 | 29.6 | 33.9 | 78.1 | 33.9 | 14.7 |
| n (Samp) | 441 | 42 | 441 | 48 | 441 | 25 |
| n (Patient) | 210 | 42 | 210 | 48 | 210 | 25 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.64 | 0.51 | 0.67 | 0.61 | 0.60 | 0.62 |
| SE | 0.046 | 0.097 | 0.047 | 0.043 | 0.091 | 0.045 |
| p | 0.0018 | 0.96 | 2.9E−4 | 0.010 | 0.28 | 0.0082 |
| nCohort 1 | 473 | 633 | 441 | 473 | 633 | 441 |
| nCohort 2 | 46 | 9 | 42 | 54 | 11 | 48 |
| Cutoff 1 | 4.14 | 2.68 | 4.91 | 3.99 | 3.99 | 4.04 |
| Sens 1 | 72% | 78% | 71% | 70% | 73% | 71% |
| Spec 1 | 47% | 31% | 52% | 44% | 39% | 46% |
| Cutoff 2 | 3.03 | 2.19 | 3.67 | 2.61 | 2.87 | 2.61 |
| Sens 2 | 80% | 89% | 81% | 81% | 82% | 81% |
| Spec 2 | 39% | 26% | 44% | 35% | 32% | 35% |
| Cutoff 3 | 2.19 | 1.93 | 2.41 | 1.38 | 2.55 | 1.38 |
| Sens 3 | 91% | 100% | 90% | 91% | 91% | 92% |
| Spec 3 | 31% | 24% | 33% | 25% | 30% | 24% |
| Cutoff 4 | 7.97 | 8.18 | 7.97 | 7.97 | 8.18 | 7.97 |
| Sens 4 | 48% | 33% | 52% | 31% | 36% | 35% |
| Spec 4 | 70% | 70% | 70% | 70% | 70% | 70% |
| Cutoff 5 | 9.21 | 9.72 | 9.18 | 9.21 | 9.72 | 9.18 |
| Sens 5 | 41% | 22% | 48% | 26% | 27% | 29% |
| Spec 5 | 80% | 80% | 80% | 80% | 80% | 80% |
| Cutoff 6 | 11.2 | 12.1 | 11.3 | 11.2 | 12.1 | 11.3 |
| Sens 6 | 22% | 11% | 24% | 22% | 18% | 23% |
| Spec 6 | 90% | 90% | 90% | 90% | 90% | 90% |
| OR Quart 2 | 4.7 | 5.1 | 3.1 | 2.3 | 3.0 | 2.3 |
| p Value | 0.018 | 0.14 | 0.093 | 0.11 | 0.34 | 0.13 |
| 95% CI of OR Quart2 | 1.3 | 0.59 | 0.83 | 0.84 | 0.31 | 0.78 |
| | 17 | 44 | 12 | 6.2 | 30 | 6.9 |
| OR Quart 3 | 3.1 | 0 | 3.1 | 3.3 | 3.0 | 3.3 |
| p Value | 0.093 | na | 0.093 | 0.015 | 0.34 | 0.026 |
| 95% CI of OR Quart3 | 0.83 | na | 0.83 | 1.3 | 0.31 | 1.2 |
| | 12 | na | 12 | 8.6 | 30 | 9.3 |
| OR Quart 4 | 8.1 | 3.0 | 8.2 | 3.1 | 4.1 | 3.8 |
| p Value | 9.2E−4 | 0.34 | 8.8E−4 | 0.022 | 0.21 | 0.012 |
| 95% CI of OR Quart4 | 2.3 | 0.31 | 2.4 | 1.2 | 0.45 | 1.3 |
| | 28 | 29 | 28 | 8.1 | 37 | 11 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | 48 hr prior to AKI stage | | |
|---|---|---|---|---|
| | | sCr or UO | sCr only | UO only |
| | AUC | 0.52 | 0.60 | 0.55 |
| | SE | 0.057 | 0.091 | 0.061 |
| | p | 0.78 | 0.26 | 0.38 |
| | nCohort 1 | 473 | 633 | 441 |
| | nCohort 2 | 28 | 11 | 25 |
| | Cutoff 1 | 1.04 | 5.68 | 3.49 |
| | Sens 1 | 71% | 73% | 72% |
| | Spec 1 | 21% | 52% | 41% |
| | Cutoff 2 | 0.289 | 1.04 | 0.289 |
| | Sens 2 | 82% | 82% | 80% |
| | Spec 2 | 15% | 18% | 14% |
| | Cutoff 3 | 0.0179 | 0.900 | 0.0179 |
| | Sens 3 | 93% | 91% | 92% |
| | Spec 3 | 3% | 17% | 2% |
| | Cutoff 4 | 7.97 | 8.18 | 7.97 |
| | Sens 4 | 39% | 45% | 44% |
| | Spec 4 | 70% | 70% | 70% |
| | Cutoff 5 | 9.21 | 9.72 | 9.18 |
| | Sens 5 | 25% | 45% | 32% |
| | Spec 5 | 80% | 80% | 80% |
| | Cutoff 6 | 11.2 | 12.1 | 11.3 |
| | Sens 6 | 11% | 36% | 12% |
| | Spec 6 | 90% | 90% | 90% |
| | OR Quart 2 | 0.32 | 0 | 0.48 |
| | p Value | 0.091 | na | 0.31 |
| | 95% CI of | 0.084 | na | 0.12 |
| | OR Quart2 | 1.2 | na | 2.0 |
| | OR Quart 3 | 0.76 | 1.0 | 1.2 |
| | p Value | 0.61 | 1.0 | 0.78 |
| | 95% CI of | 0.28 | 0.20 | 0.38 |
| | OR Quart3 | 2.1 | 5.0 | 3.6 |
| | OR Quart 4 | 0.99 | 1.7 | 1.5 |
| | p Value | 0.99 | 0.48 | 0.44 |
| | 95% CI of | 0.38 | 0.40 | 0.53 |
| | OR Quart4 | 2.6 | 7.2 | 4.4 |

| Interleukin-20 | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 13.0 | 18.5 | 13.0 | 36.7 | 13.0 | 15.6 |
| Average | 76.5 | 97.4 | 76.5 | 125 | 76.5 | 70.5 |
| Stdev | 124 | 132 | 124 | 184 | 124 | 121 |
| p(t-test) | | 0.20 | | 0.0027 | | 0.77 |
| Min | 0.368 | 0.412 | 0.368 | 0.412 | 0.368 | 0.412 |
| Max | 811 | 677 | 811 | 1080 | 811 | 534 |
| n (Samp) | 928 | 62 | 928 | 70 | 928 | 38 |
| n (Patient) | 361 | 62 | 361 | 70 | 361 | 38 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 9.54 | 41.3 | 9.54 | 42.2 | 9.54 | 136 |
| Average | 74.0 | 122 | 74.0 | 152 | 74.0 | 157 |
| Stdev | 123 | 187 | 123 | 190 | 123 | 170 |
| p(t-test) | | 0.14 | | 0.0088 | | 0.0063 |
| Min | 0.368 | 0.552 | 0.368 | 0.412 | 0.368 | 0.898 |
| Max | 1080 | 677 | 1080 | 583 | 1080 | 534 |
| n (Samp) | 1231 | 15 | 1231 | 18 | 1231 | 17 |
| n (Patient) | 441 | 15 | 441 | 18 | 441 | 17 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 13.0 | 15.6 | 13.0 | 15.8 | 13.0 | 15.6 |
| Average | 79.7 | 86.9 | 79.7 | 106 | 79.7 | 49.3 |
| Stdev | 127 | 117 | 127 | 175 | 127 | 86.7 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| p(t-test) | | 0.68 | | 0.12 | | 0.17 |
| Min | 0.368 | 0.412 | 0.368 | 0.488 | 0.368 | 0.412 |
| Max | 811 | 482 | 811 | 1080 | 811 | 392 |
| n (Samp) | 817 | 57 | 817 | 63 | 817 | 33 |
| n (Patient) | 283 | 57 | 283 | 63 | 283 | 33 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.57 | 0.62 | 0.54 | 0.60 | 0.61 | 0.55 |
| SE | 0.039 | 0.078 | 0.040 | 0.037 | 0.071 | 0.039 |
| p | 0.068 | 0.13 | 0.28 | 0.0079 | 0.13 | 0.17 |
| nCohort 1 | 928 | 1231 | 817 | 928 | 1231 | 817 |
| nCohort 2 | 62 | 15 | 57 | 70 | 18 | 63 |
| Cutoff 1 | 1.62 | 3.75 | 1.62 | 3.75 | 2.13 | 1.56 |
| Sens 1 | 74% | 73% | 72% | 70% | 72% | 71% |
| Spec 1 | 38% | 46% | 37% | 44% | 40% | 35% |
| Cutoff 2 | 1.37 | 2.13 | 1.37 | 1.47 | 1.33 | 1.37 |
| Sens 2 | 81% | 80% | 81% | 80% | 83% | 83% |
| Spec 2 | 27% | 40% | 25% | 30% | 24% | 25% |
| Cutoff 3 | 1.32 | 1.33 | 0.898 | 1.33 | 0.488 | 0.898 |
| Sens 3 | 90% | 93% | 91% | 91% | 94% | 90% |
| Spec 3 | 20% | 24% | 14% | 23% | 9% | 14% |
| Cutoff 4 | 89.8 | 85.2 | 96.2 | 89.8 | 85.2 | 96.2 |
| Sens 4 | 40% | 33% | 39% | 43% | 44% | 37% |
| Spec 4 | 70% | 70% | 70% | 70% | 70% | 70% |
| Cutoff 5 | 140 | 140 | 153 | 140 | 140 | 153 |
| Sens 5 | 32% | 27% | 21% | 33% | 39% | 24% |
| Spec 5 | 80% | 80% | 81% | 80% | 80% | 81% |
| Cutoff 6 | 234 | 232 | 244 | 234 | 232 | 244 |
| Sens 6 | 13% | 20% | 11% | 19% | 33% | 14% |
| Spec 6 | 90% | 90% | 90% | 90% | 90% | 90% |
| OR Quart 2 | 1.3 | 4.0 | 1.3 | 2.2 | 0.75 | 1.2 |
| p Value | 0.56 | 0.21 | 0.55 | 0.058 | 0.70 | 0.56 |
| 95% CI of OR Quart2 | 0.58 2.8 | 0.45 36 | 0.57 2.9 | 0.97 4.9 | 0.17 3.4 | 0.59 2.7 |
| OR Quart 3 | 1.1 | 5.1 | 1.3 | 1.5 | 0.75 | 0.84 |
| p Value | 0.84 | 0.14 | 0.54 | 0.39 | 0.70 | 0.67 |
| 95% CI of OR Quart3 | 0.49 2.4 | 0.59 44 | 0.57 2.9 | 0.62 3.5 | 0.17 3.4 | 0.37 1.9 |
| OR Quart 4 | 1.9 | 5.0 | 1.7 | 3.5 | 2.0 | 1.9 |
| p Value | 0.082 | 0.14 | 0.19 | 0.0014 | 0.26 | 0.086 |
| 95% CI of OR Quart4 | 0.92 3.9 | 0.59 43 | 0.78 3.7 | 1.6 7.6 | 0.60 6.8 | 0.92 3.8 |

| | 48 hr prior to AKI stage | | |
|---|---|---|---|
| | sCr or UO | sCr only | UO only |
| AUC | 0.49 | 0.65 | 0.46 |
| SE | 0.048 | 0.073 | 0.052 |
| p | 0.91 | 0.042 | 0.40 |
| nCohort 1 | 928 | 1231 | 817 |
| nCohort 2 | 38 | 17 | 33 |
| Cutoff 1 | 1.47 | 1.47 | 1.33 |
| Sens 1 | 71% | 76% | 76% |
| Spec 1 | 30% | 31% | 21% |
| Cutoff 2 | 0.898 | 1.37 | 0.541 |
| Sens 2 | 82% | 82% | 82% |
| Spec 2 | 15% | 28% | 9% |
| Cutoff 3 | 0.488 | 1.33 | 0.488 |
| Sens 3 | 97% | 94% | 97% |
| Spec 3 | 9% | 24% | 8% |
| Cutoff 4 | 89.8 | 85.2 | 96.2 |
| Sens 4 | 21% | 53% | 12% |
| Spec 4 | 70% | 70% | 70% |
| Cutoff 5 | 140 | 140 | 153 |
| Sens 5 | 16% | 47% | 9% |
| Spec 5 | 80% | 80% | 81% |
| Cutoff 6 | 234 | 232 | 244 |
| Sens 6 | 11% | 24% | 6% |
| Spec 6 | 90% | 90% | 90% |
| OR Quart 2 | 1.9 | 5.1 | 4.9 |
| p Value | 0.17 | 0.14 | 0.013 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  |  | 95% CI of OR Quart2 | 0.75 4.9 | 0.59 44 | 1.4 17 |
|---|---|---|---|---|---|
|  |  | OR Quart 3 | 1.3 | 2.0 | 2.0 |
|  |  | p Value | 0.61 | 0.57 | 0.32 |
|  |  | 95% CI of OR Quart3 | 0.48 3.5 | 0.18 22 | 0.50 8.2 |
|  |  | OR Quart 4 | 1.3 | 9.2 | 3.5 |
|  |  | p Value | 0.61 | 0.035 | 0.062 |
|  |  | 95% CI of OR Quart4 | 0.48 3.6 | 1.2 73 | 0.94 13 |

Interleukin-29

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 32.2 | 95.6 | 32.2 | 85.6 | 32.2 | 36.4 |
| Average | 76.3 | 122 | 76.3 | 117 | 76.3 | 68.1 |
| Stdev | 105 | 117 | 105 | 113 | 105 | 92.3 |
| p(t-test) |  | 0.0011 |  | 0.0021 |  | 0.63 |
| Min | 0.114 | 0.172 | 0.114 | 0.173 | 0.114 | 0.170 |
| Max | 675 | 635 | 675 | 613 | 675 | 510 |
| n (Samp) | 929 | 62 | 929 | 69 | 929 | 39 |
| n (Patient) | 361 | 62 | 361 | 69 | 361 | 39 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 36.3 | 66.4 | 36.3 | 105 | 36.3 | 54.5 |
| Average | 82.1 | 118 | 82.1 | 103 | 82.1 | 85.6 |
| Stdev | 110 | 133 | 110 | 73.6 | 110 | 104 |
| p(t-test) |  | 0.22 |  | 0.43 |  | 0.90 |
| Min | 0.114 | 0.173 | 0.114 | 0.228 | 0.114 | 0.173 |
| Max | 827 | 468 | 827 | 274 | 827 | 408 |
| n (Samp) | 1232 | 15 | 1232 | 18 | 1232' | 17 |
| n (Patient) | 441 | 15 | 441 | 18 | 441 | 17 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 36.1 | 100 | 36.1 | 85.1 | 36.1 | 40.7 |
| Average | 79.4 | 137 | 79.4 | 121 | 79.4 | 70.2 |
| Stdev | 105 | 138 | 105 | 118 | 105 | 95.5 |
| p(t-test) |  | 1.0E−4 |  | 0.0030 |  | 0.62 |
| Min | 0.114 | 0.172 | 0.114 | 0.173 | 0.114 | 0.170 |
| Max | 675 | 635 | 675 | 613 | 675 | 510 |
| n (Samp) | 817 | 57 | 817 | 62 | 817 | 34 |
| n (Patient) | 283 | 57 | 283 | 62 | 283 | 34 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.65 | 0.60 | 0.66 | 0.66 | 0.65 | 0.64 |
| SE | 0.039 | 0.078 | 0.040 | 0.037 | 0.071 | 0.039 |
| p | 1.3E−4 | 0.18 | 8.5E−5 | 2.1E−5 | 0.037 | 2.6E−4 |
| nCohort 1 | 929 | 1232 | 817 | 929 | 1232 | 817 |
| nCohort 2 | 62 | 15 | 57 | 69 | 18 | 62 |
| Cutoff 1 | 38.5 | 25.1 | 59.7 | 38.9 | 38.9 | 38.9 |
| Sens 1 | 71% | 73% | 72% | 71% | 72% | 71% |
| Spec 1 | 54% | 43% | 61% | 54% | 52% | 51% |
| Cutoff 2 | 16.2 | 16.3 | 24.3 | 25.8 | 29.9 | 25.5 |
| Sens 2 | 81% | 80% | 82% | 81% | 83% | 81% |
| Spec 2 | 38% | 35% | 41% | 47% | 46% | 43% |
| Cutoff 3 | 2.69 | 2.69 | 2.69 | 6.75 | 24.9 | 6.75 |
| Sens 3 | 90% | 93% | 91% | 91% | 94% | 90% |
| Spec 3 | 22% | 21% | 19% | 28% | 42% | 26% |
| Cutoff 4 | 85.3 | 98.4 | 95.2 | 85.3 | 98.4 | 95.2 |
| Sens 4 | 55% | 33% | 53% | 51% | 61% | 47% |
| Spec 4 | 70% | 70% | 70% | 70% | 70% | 70% |
| Cutoff 5 | 139 | 150 | 143 | 139 | 150 | 143 |
| Sens 5 | 37% | 27% | 37% | 30% | 17% | 32% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Spec 5 | 80% | 80% | 80% | 80% | 80% | 80% |
| Cutoff 6 | 211 | 218 | 211 | 211 | 218 | 211 |
| Sens 6 | 21% | 27% | 21% | 13% | 6% | 15% |
| Spec 6 | 90% | 90% | 90% | 90% | 90% | 90% |
| OR Quart 2 | 1.3 | 1.5 | 1.1 | 1.9 | 4.0 | 2.0 |
| p Value | 0.64 | 0.66 | 0.80 | 0.23 | 0.21 | 0.16 |
| 95% CI of | 0.49 | 0.25 | 0.41 | 0.68 | 0.45 | 0.75 |
| OR Quart2 | 3.2 | 9.0 | 3.2 | 5.1 | 36 | 5.6 |
| OR Quart 3 | 2.6 | 2.5 | 3.0 | 4.3 | 5.1 | 3.7 |
| p Value | 0.025 | 0.27 | 0.013 | 0.0017 | 0.14 | 0.0053 |
| 95% CI of | 1.1 | 0.48 | 1.3 | 1.7 | 0.59 | 1.5 |
| OR Quart 3 | 6.1 | 13 | 7.4 | 11 | 44 | 9.5 |
| OR Quart 4 | 3.2 | 2.5 | 3.4 | 5.1 | 8.2 | 4.1 |
| p Value | 0.0055 | 0.27 | 0.0064 | 3.8E-4 | 0.048 | 0.0024 |
| 95% CI of | 1.4 | 0.48 | 1.4 | 2.1 | 1.0 | 1.7 |
| OR Quart4 | 73 | 13 | 8.1 | 13 | 66 | 10 |

| | 48 hr prior to AKI stage | | |
|---|---|---|---|
| | sCr or UO | sCr only | UO only |
| AUC | 0.49 | 0.53 | 0.49 |
| SE | 0.047 | 0.072 | 0.051 |
| p | 0.89 | 0.70 | 0.87 |
| nCohort 1 | 929 | 1232 | 817 |
| nCohort 2 | 39 | 17 | 34 |
| Cutoff 1 | 2.79 | 22.5 | 13.9 |
| Sens 1 | 72% | 71% | 71% |
| Spec 1 | 23% | 39% | 32% |
| Cutoff 2 | 0.571 | 2.69 | 2.78 |
| Sens 2 | 82% | 82% | 82% |
| Spec 2 | 17% | 21% | 20% |
| Cutoff 3 | 0.454 | 0.173 | 0.547 |
| Sens 3 | 92% | 94% | 94% |
| Spec 3 | 16% | 7% | 14% |
| Cutoff 4 | 85.3 | 98.4 | 95.2 |
| Sens 4 | 38% | 35% | 35% |
| Spec 4 | 70% | 70% | 70% |
| Cutoff 5 | 139 | 150 | 143 |
| Sens 5 | 8% | 18% | 9% |
| Spec 5 | 80% | 80% | 80% |
| Cutoff 6 | 211 | 218 | 211 |
| Sens 6 | 3% | 6% | 3% |
| Spec 6 | 90% | 90% | 90% |
| OR Quart 2 | 0.81 | 0.75 | 1.4 |
| p Value | 0.65 | 0.70 | 0.48 |
| 95% CI of | 0.33 | 0.17 | 0.55 |
| OR Quart2 | 2.0 | 3.4 | 3.5 |
| OR Quart 3 | 0.63 | 1.5 | 0.62 |
| p Value | 0.34 | 0.53 | 0.40 |
| 95% CI of | 0.24 | 0.42 | 0.20 |
| OR Quart3 | 1.6 | 5.4 | 1.9 |
| OR Quart 4 | 1.1 | 1.00 | 1.3 |
| p Value | 0.83 | 1.00 | 0.62 |
| 95% CI of | 0.47 | 0.25 | 0.49 |
| OR Quart4 | 2.5 | 4.0 | 3.3 |

| | Interleukin-7 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 0.0110 | 0.0128 | 0.0110 | 0.0208 | 0.0110 | 0.0127 |
| Average | 0.380 | 0.0743 | 0.380 | 0.651 | 0.380 | 0.0698 |
| Stdev | 3.29 | 0.291 | 3.29 | 3.89 | 3.29 | 0.294 |
| p(t-test) | | 0.46 | | 0.51 | | 0.56 |
| Min | 0.00316 | 0.00316 | 0.00316 | 0.00316 | 0.00316 | 0.00316 |
| Max | 64.2 | 2.11 | 64.2 | 31.8 | 64.2 | 1.84 |
| n (Samp) | 928 | 62 | 928 | 70 | 928 | 39 |
| n (Patient) | 361 | 62 | 361 | 70 | 361 | 39 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.0110 | 0.0123 | 0.0110 | 0.0109 | 0.0110 | 0.0128 |
| Average | 0.341 | 0.715 | 0.341 | 0.0180 | 0.341 | 0.393 |
| Stdev | 3.00 | 2.59 | 3.00 | 0.0169 | 3.00 | 1.54 |
| p(t-test) | | 0.63 | | 0.65 | | 0.94 |
| Min | 0.00316 | 0.00316 | 0.00316 | 0.00316 | 0.00316 | 0.00742 |
| Max | 64.2 | 10.1 | 64.2 | 0.0655. | 64.2 | 6.38 |
| n (Samp) | 1232 | 15 | 1232 | 18 | 1232 | 17 |
| n (Patient) | 441 | 15 | 441 | 18 | 441 | 17 |

| UO only | 0 hr prior to AKI stage | | 24 hr prior to AKI stage | | 48 hr prior to AK stage | |
|---|---|---|---|---|---|---|
| | Cohort 1 | Cohort 2 | Cohort 1 | Cohort 2 | Cohort 1 | Cohort 2 |
| Median | 0.0123 | 0.0128 | 0.0123 | 0.0226 | 0.0123 | 0.0126 |
| Average | 0.357 | 0.0707 | 0.357 | 0.720 | 0.357 | 0.0764 |
| Stdev | 2.76 | 0.298 | 2.76 | 4.10 | 2.76 | 0.314 |
| p(t-test) | | 0.43 | | 0.33 | | 0.55 |
| Min | 0.00316 | 0.00316 | 0.00316 | 0.00316 | 0.00316 | 0.00316 |
| Max | 64.2 | 2.11 | 64.2 | 31.8 | 64.2 | 1.84 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.56 | 0.49 | 0.53 | 0.62 | 0.47 | 0.60 |
| SE | 0.039 | 0.075 | 0.040 | 0.037 | 0.070 | 0.039 |
| P | 0.14 | 0.93 | 0.45 | 0.0015 | 0.68 | 0.0076 |
| nCohort 1 | 928 | 1232 | 817 | 928 | 1232 | 817 |
| nCohort 2 | 62 | 15 | 57 | 70 | 18 | 63 |
| Cutoff 1 | 0.0104 | 0.00801 | 0.0104 | 0.0119 | 0.00822 | *0.0119 |
| Sens 1 | 71% | 73% | 70% | 70% | 72% | 71% |
| Spec 1 | 42% | 25% | 40% | 51% | 29% | 49% |
| Cutoff 2 | 0.00584 | 0.00517 | 0.00487 | 0.0104 | 0.00316 | 0.00822 |
| Sens 2 | 81% | 80% | 86% | 80% | 89% | 83% |
| Spec 2 | 21% | 17% | 12% | 42% | 4% | 27% |
| Cutoff 3 | 0.00451 | 0.00451 | 0.00451 | 0.00487 | 0 | 0.00487 |
| Sens 3 | 94% | 93% | 91% | 94% | 100% | 94% |
| Spec 3 | 9% | 9% | 7% | 14% | 0% | 12% |
| Cutoff 4 | 0.0174 | 0.0156 | 0.0226 | 0.0174 | 0.0156 | 0.0226 |
| Sens 4 | 37% | 33% | 37% | 51% | 39% | 37% |
| Spec 4 | 70% | 71% | 73% | 70% | 71% | 73% |
| Cutoff 5 | 0.0315 | 0.0288 | 0.0315 | 0.0315 | 0.0288 | 0.0315 |
| Sens 5 | 16% | 20% | 16% | 20% | 17% | 21% |
| Spec 5 | 84% | 80% | 82% | 84% | 80% | 82% |
| Cutoff 6 | 0.0478 | 0.0478 | 0.0478 | 0.0478 | 0.0478 | 0.0478 |
| Sens 6 | 10% | 13% | 9% | 9% | 6% | 8% |
| Spec 6 | 92% | 92% | 92% | 92% | 92% | 92% |
| OR Quart 2 | 0.48 | 0.60 | 0.45 | 1.1 | 0.60 | 0.72 |
| p Value | 0.12 | 0.48 | 0.085 | 0.83 | 0.48 | 0.48 |
| 95% CI of | 0.19 | 0.14 | 0.18 | 0.46 | 0.14 | 0.28 |
| OR Quart2 | 1.2 | 2.5 | 1.1 | 2.6 | 2.5 | 1.8 |
| OR Quart 3 | 1.3 | 0.60 | 1.4 | 2.5 | 1.0 | 2.2 |
| p Value | 0.47 | 0.48 | 0.38 | 0.016 | 1.0 | 0.036 |
| 95% CI of | 0.64 | 0.14 | 0.68 | 1.2 | 0.29 | 1.1 |
| OR Quart3 | 2.7 | 2.5 | 2.7 | 5.5 | 3.5 | 4.7 |
| OR Quart 4 | 1.7 | 0.80 | 1.00 | 2.7 | 1.0 | 2.0 |
| p Value | 0.13 | 0.74 | 0.99 | 0.011 | 1.00 | 0.071 |
| 95% CI of | 0.85 | 0.21 | 0.47 | 1.2 | 0.29 | 0.94 |
| OR Quart4 | 3.4 | 3.0 | 2.1 | 5.7 | 3.5 | 4.3 |

| | 48 hr prior to AKI stage | | |
|---|---|---|---|
| | sCr or UO | sCr only | UO only |
| AUC | 0.53 | 0.63 | 0.49 |
| SE | 0.048 | 0.073 | 0.051 |
| p | 0.58 | 0.080 | 0.84 |
| nCohort 1 | 928 | 1232 | 817 |
| nCohort 2 | 39 | 17 | 34 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | |
|---|---|---|---|
| Cutoff 1 | 0.0105 | 0.0123 | 0.00801 |
| Sens 1 | 72% | 76% | 71% |
| Spec 1 | 42% | 55% | 24% |
| Cutoff 2 | 0.00487 | 0.0119 | 0.00487 |
| Sens 2 | 85% | 82% | 82% |
| Spec 2 | 14% | 51% | 12% |
| Cutoff 3 | 0 | 0.00801 | 0 |
| Sens 3 | 100% | 94% | 100% |
| Spec 3 | 0% | 25% | 0% |
| Cutoff 4 | 0.0174 | 0.0156 | 0.0226 |
| Sens 4 | 33% | 29% | 32% |
| Spec 4 | 70% | 71%, | 73% |
| Cutoff 5 | 0.0315 | 0.0288 | 0.0315 |
| Sens 5 | 13% | 24% | 12% |
| Spec 5 | 84% | 80% | 82% |
| Cutoff 6 | 0.0478 | 0.0478 | 0.0478 |
| Sens 6 | 8% | 12% | 6% |
| Spec 6 | 92% | 92% | 92% |
| OR Quart 2 | 0.66 | 2.0 | 1.6 |
| p Value | 0.43 | 0.57 | 0.34 |
| 95% CI of | 0.23 | 0.18 | 0.61 |
| OR Quart2 | 1.9 | 22 | 4.2 |
| OR Quart 3 | 1.3 | 9.2 | 0.85 |
| p Value | 0.51 | 0.035 | 0.78 |
| 95% CI of | 0.56 | 1.2 | 0.28 |
| OR Quart3 | 3.3 | 73 | 2.6 |
| OR Quart 4 | 1.3 | 5.0 | 1.5 |
| p Value | 0.51 | 0.14 | 0.45 |
| 95% CI of | 0.56 | 0.59 | 0.54 |
| OR Quart4 | 3.3 | 43 | 3.9 |

Matrix metalloproteinase-9:Metalloproteinase inhibitor 2 complex

| | 0 hr prior to AKI stage | | 24 hr prior to AKI stage | | 48 hr prior to AK stage | |
|---|---|---|---|---|---|---|
| sCr or UO | Cohort 1 | Cohort 2 | Cohort 1 | Cohort 2 | Cohort 1 | Cohort 2 |
| Median | 225 | 375 | 225 | 672 | 225 | 1430 |
| Average | 2980 | 7890 | 2980 | 3700 | 2980 | 9470 |
| Stdev | 7310 | 11300 | 7310 | 7830 | 7310 | 11600 |
| p(t-test) | | 0.0045 | | 0.61 | | 0.0011 |
| Min | 0.227 | 0.227 | 0.227 | 0.227 | 0.227 | 1.03 |
| Max | 24000 | 24000 | 24000 | 24000 | 24000 | 24000 |
| n (Samp) | 248 | 22 | 248 | 32 | 248 | 16 |
| n (Patient) | 161 | 22 | 161 | 32 | 161 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | nd | nd | 280 | 396 | 280 | 24000 |
| Average | nd | nd | 3680 | 420 | 3680 | 17200 |
| Stdev | nd | nd | 8080 | 407 | 8080 | 11700 |
| p(t-test) | nd | nd | | 0.32 | | 2.1E−5 |
| Min | nd | nd | 0.227 | 18.2 | 0.227 | 42.8 |
| Max | nd | nd | 24000 | 1070 | 24000 | 24000 |
| n (Samp) | nd | nd | 314 | 6 | 314 | 7 |
| n (Patient) | nd | nd | 188 | 6 | 188 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 222 | 375 | 222 | 714 | 222 | 1210 |
| Average | 2710 | 7890 | 2710 | 4030 | 2710 | 8530 |
| Stdev | 6940 | 11300 | 6940 | 8160 | 6940 | 11300 |
| p(t-test) | | 0.0021 | | 0.35 | | 0.0031 |
| Min | 0.227 | 0.227 | 0.227 | 0.227 | 0.227 | 1.03 |
| Max | 24000 | 24000 | 24000 | 24000 | 24000 | 24000 |
| n (Samp) | 216 | 22 | 216 | 29 | 216 | 15 |
| n (Patient) | 134 | 22 | 134 | 29 | 134 | 15 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.63 | nd | 0.63 | 0.64 | 0.46 | 0.66 |
| SE | 0.066 | nd | 0.066 | 0.055 | 0.12 | 0.058 |
| p | 0.058 | nd | 0.055 | 0.014 | 0.77 | 0.0070 |
| nCohort 1 | 248 | nd | 216 | 248 | 314 | 216 |
| nCohort 2 | 22 | nd | 22 | 32 | 6 | 29 |
| Cutoff 1 | 261 | nd | 269 | 280 | 18.8 | 384 |
| Sens 1 | 73% | nd | 73% | 72% | 83% | 72% |
| Spec 1 | 54% | nd | 56% | 56% | 12% | 62% |
| Cutoff 2 | 128 | nd | 128 | 102 | 18.8 | 102 |
| Sens 2 | 82% | nd | 82% | 81% | 83% | 83% |
| Spec 2 | 35% | nd | 35% | 30% | 12% | 30% |
| Cutoff 3 | 29.2 | nd | 29.2 | 18.8 | 10.8 | 29.2 |
| Sens 3 | 95% | nd | 91% | 91% | 100% | 93% |
| Spec 3 | 17% | nd | 16% | 14% | 11% | 16% |
| Cutoff 4 | 539 | nd | 539 | 539 | 708 | 539 |
| Sens 4 | 41% | nd | 41% | 56% | 17% | 55% |
| Spec 4 | 70% | nd | 70% | 70% | 70% | 70% |
| Cutoff 5 | 980 | nd | 959 | 980 | 1630 | 959 |
| Sens 5 | 41% | nd | 41% | 41% | 0% | 41% |
| Spec 5 | 80% | nd | 80% | 80% | 80% | 80% |
| Cutoff 6 | 24000 | nd | 12000 | 24000 | 24000 | 12000 |
| Sens 6 | 0% | nd | 32% | 0% | 0% | 14% |
| Spec 6 | 100% | nd | 90% | 100% | 100% | 90% |
| OR Quart 2 | 0.24 | nd | 0.23 | 1.3 | 2.0 | 1.4 |
| p Value | 0.20 | nd | 0.20 | 0.73 | 0.57 | 0.70 |
| 95% CI of | 0.026 | nd | 0.025 | 0.33 | 0.18 | 0.29 |
| OR Quart2 | 2.2 | nd | 2.1 | 4.9 | 23 | 6.3 |
| OR Quart 3 | 2.1 | nd | 2.2 | 2.1 | 1.0 | 2.9 |
| p Value | 0.23 | nd | 0.23 | 0.24 | 1.0 | 0.13 |
| 95% CI of | 0.61 | nd | 0.61 | 0.61 | 0.061 | 0.74 |
| OR Quart3 | 7.5 | nd | 7.6 | 7.4 | 16 | 12 |
| OR Quart 4 | 2.4 | nd | 2.4 | 4.5 | 2.0 | 5.6 |
| p Value | 0.16 | nd | 0.16 | 0.011 | 0.57 | 0.0093 |
| 95% CI of | 0.70 | nd | 0.70 | 1.4 | 0.18 | 1.5 |
| OR Quart4 | 8.2 | nd | 8.4 | 14 | 23 | 21 |

|  | 48 hr prior to AKI stage | | |
|---|---|---|---|
|  | sCr or UO | sCr only | UO only |
| AUC | 0.70 | 0.72 | 0.73 |
| SE | 0.075 | 0.11 | 0.076 |
| p | 0.0095 | 0.044 | 0.0029 |
| nCohort 1 | 248 | 314 | 216 |
| nCohort 2 | 16 | 7 | 15 |
| Cutoff 1 | 445 | 12500 | 443 |
| Sens 1 | 75% | 71% | 73% |
| Spec 1 | 65% | 87% | 66% |
| Cutoff 2 | 94.3 | 63.1 | 261 |
| Sens 2 | 81% | 86% | 80% |
| Spec 2 | 29% | 21% | 55% |
| Cutoff 3 | 41.3 | 41.3 | 90.1 |
| Sens 3 | 94% | 100% | 93% |
| Spec 3 | 19% | 17% | 28% |
| Cutoff 4 | 539 | 708 | 539 |
| Sens 4 | 69% | 71% | 67% |
| Spec 4 | 70% | 70% | 70% |
| Cutoff 5 | 980 | 1630 | 959 |
| Sens 5 | 56% | 71% | 53% |
| Spec 5 | 80% | 80% | 80% |
| Cutoff 6 | 24000 | 24000 | 12000 |
| Sens 6 | 0% | 0% | 33% |
| Spec 6 | 100% | 100% | 90% |
| OR Quart 2 | 0.32 | 0 | 2.0 |
| p Value | 0.33 | na | 0.58 |
| 95% CI of | 0.033 | na | 0.18 |
| OR Quart2 | 3.2 | na | 23 |
| OR Quart 3 | 1.0 | 0 | 4.1 |
| p Value | 1.0 | na | 0.21 |
| 95% CI of | 0.19 | na | 0.45 |
| OR Quart3 | 5.1 | na | 38 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  |  |  |  |
|---|---|---|---|
| OR Quart 4 | 3.3 | 2.6 | 9.0 |
| p Value | 0.083 | 0.27 | 0.042 |
| 95% CI of | 0.86 | 0.48 | 1.1 |
| OR Quart4 | 13 | 14 | 74 |

Platelet-derived growth factor subunit A (dimer)

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 89.0 | 114 | 89.0 | 138 | 89.0 | 108 |
| Average | 139 | 482 | 139 | 347 | 139 | 162 |
| Stdev | 203 | 2530 | 203 | 1040 | 203 | 172 |
| p(t-test) |  | 7.3E−5 |  | 6.8E−7 |  | 0.49 |
| Min | 0.994 | 5.66 | 0.994 | 1.31 | 0.994 | 5.73 |
| Max | 4020 | 20000 | 4020 | 8310 | 4020 | 730 |
| n (Samp) | 927 | 62 | 927 | 70 | 927 | 39 |
| n (Patient) | 360 | 62 | 360 | 70 | 360 | 39 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 92.7 | 62.8 | 92.7 | 180 | 92.7 | 69.2 |
| Average | 149 | 363 | 149 | 1270 | 149 | 287 |
| Stdev | 304 | 924 | 304 | 4680 | 304 | 716 |
| p(t-test) |  | 0.0096 |  | 6.6E−14 |  | 0.071 |
| Min | 0.994 | 22.3 | 0.994 | 11.8 | 0.994 | 12.2 |
| Max | 8310 | 3640 | 8310 | 20000 | 8310 | 3020 |
| n (Samp) | 1230 | 15 | 1230 | 18 | 1230 | 17 |
| n (Patient) | 440 | 15 | 440 | 18 | 440 | 17 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 89.6 | 124 | 89.6 | 136 | 89.6 | 111 |
| Average | 137 | 565 | 137 | 400 | 137 | 173 |
| Stdev | 202 | 2650 | 202 | 1130 | 202 | 181 |
| p(t-test) |  | 9.4E−6 |  | 2.4E−8 |  | 0.30 |
| Min | 2.61 | 5.66 | 2.61 | 1.31 | 2.61 | 5.73 |
| Max | 4020 | 20000 | 4020 | 8310 | 4020 | 730 |
| n (Samp) | 815 | 57 | 815 | 63 | 815 | 34 |
| n (Patient) | 282 | 57 | 282 | 63 | 282 | 34 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.56 | 0.48 | 0.59 | 0.62 | 0.64 | 0.62 |
| SE | 0.039 | 0.076 | 0.041 | 0.037 | 0.071 | 0.039 |
| P | 0.13 | 0.78 | 0.031 | 8.8E−4 | 0.044 | 0.0024 |
| nCohort 1 | 927 | 1230 | 815 | 927 | 1230 | 815 |
| nCohort 2 | 62 | 15 | 57 | 70 | 18 | 63 |
| Cutoff 1 | 53.7 | 47.6 | 56.8 | 84.7 | 104 | 69.6 |
| Sens 1 | 71% | 73% | 70% | 70% | 72% | 71% |
| Spec 1 | 32% | 27% | 33% | 48% | 55% | 40% |
| Cutoff 2 | 47.4 | 36.4 | 50.4 | 58.7 | 53.2 | 58.7 |
| Sens 2 | 81% | 80% | 81% | 80% | 83% | 81% |
| Spec 2 | 28% | 22% | 30% | 36% | 31% | 35% |
| Cutoff 3 | 30.3 | 28.3 | 31.8 | 27.3 | 14.0 | 27.3 |
| Sens 3 | 90% | 93% | 91% | 90% | 94% | 90% |
| Spec 3 | 18% | 16% | 19% | 16% | 7% | 16% |
| Cutoff 4 | 140 | 150 | 139 | 140 | 150 | 139 |
| Sens 4 | 40% | 27% | 47% | 49% | 56% | 49% |
| Spec 4 | 70% | 70% | 70% | 70% | 70% | 70% |
| Cutoff 5 | 201 | 210 | 197 | 201 | 210 | 197 |
| Sens 5 | 23% | 20% | 26% | 37% | 39% | 38% |
| Spec 5 | 80% | 80% | 80% | 80% | 80% | 80% |
| Cutoff 6 | 300 | 301 | 291 | 300 | 301 | 291 |
| Sens 6 | 13% | 13% | 16% | 21% | 22% | 25% |
| Spec 6 | 90% | 90% | 90% | 90% | 90% | 90% |
| OR Quart 2 | 1.4 | 0.50 | 1.8 | 1.0 | 0.33 | 0.90 |
| p Value | 0.42 | 0.42 | 0.19 | 1.0 | 0.34 | 0.81 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| 95% CI of | 0.62 | 0.091 | 0.74 | 0.43 | 0.034 | 0.37 |
| OR Quart2 | 3.1 | 2.7 | 4.4 | 2.4 | 3.2 | 2.2 |
| OR Quart 3 | 1.6 | 1.3 | 1.9 | 1.8 | 1.7 | 1.6 |
| p Value | 0.25 | 0.73 | 0.14 | 0.14 | 0.48 | 0.24 |
| 95% CI of | 0.73 | 0.33 | 0.80 | 0.83 | 0.40 | 0.73 |
| OR Quart3 | 3.5 | 4.7 | 4.7 | 3.8 | 7.1 | 3.5 |
| OR Quart 4 | 1.8 | 1.0 | 2.7 | 2.8 | 3.1 | 2.4 |
| p Value | 0.14 | 1.00 | 0.023 | 0.0044 | 0.096 | 0.018 |
| 95% CI of | 0.83 | 0.25 | 1.1 | 1.4 | 0.82 | 1.2 |
| OR Quart4 | 3.8 | 4.0 | 6.2 | 5.8 | 11 | 5.1 |

| | 48 hr prior to AKI stage | | |
|---|---|---|---|
| | sCr or UO | sCr only | UO only |
| AUC | 0.53 | 0.48 | 0.55 |
| SE | 0.048 | 0.071 | 0.052 |
| p | 0.51 | 0.78 | 0.32 |
| nCohort 1 | 927 | 1230 | 815 |
| nCohort 2 | 39 | 17 | 34 |
| Cutoff 1 | 31.5 | 48.2 | 38.8 |
| Sens 1 | 72% | 71% | 71% |
| Spec 1 | 19% | 28% | 24% |
| Cutoff 2 | 28.9 | 29.8 | 28.9 |
| Sens 2 | 82% | 82% | 82% |
| Spec 2 | 17% | 17% | 17% |
| Cutoff 3 | 24.9 | 15.9 | 24.9 |
| Sens 3 | 92% | 94% | 91% |
| Spec 3 | 14% | 7% | 14% |
| Cutoff 4 | 140 | 150 | 139 |
| Sens 4 | 44% | 29% | 41% |
| Spec 4 | 70% | 70% | 70% |
| Cutoff 5 | 201 | 210 | 197 |
| Sens 5 | 28% | 18% | 32% |
| Spec 5 | 80% | 80% | 80% |
| Cutoff 6 | 300 | 301 | 291 |
| Sens 6 | 13% | 12% | 21% |
| Spec 6 | 90% | 90% | 90% |
| OR Quart 2 | 0.27 | 0.40 | 0.35 |
| p Value | 0.024 | 0.27 | 0.077 |
| 95% CI of | 0.088 | 0.076 | 0.11 |
| OR Quart2 | 0.84 | 2.1 | 1.1 |
| OR Quart 3 | 0.49 | 1.0 | 0.62 |
| p Value | 0.13 | 1.0 | 0.34 |
| 95% CI of | 0.19 | 0.29 | 0.24 |
| OR Quart3 | 1.2 | 3.5 | 1.6 |
| OR Quart 4 | 1.00 | 1.0 | 1.1 |
| p Value | 0.99 | 1.00 | 0.84 |
| 95% CI of | 0.46 | 0.29 | 0.47 |
| OR Quart4 | 2.1 | 3.5 | 2.5 |

Platelet-derived growth factor A

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 3.43 | 4.33 | 3.43 | 7.50 | 3.43 | 3.55 |
| Average | 28.7 | 19.6 | 28.7 | 92.1 | 28.7 | 16.2 |
| Stdev | 356 | 43.4 | 356 | 581 | 356 | 44.7 |
| p(t-test) | | 0.84 | | 0.17 | | 0.83 |
| Min | 0.0141 | 0.0184 | 0.0141 | 0.0161 | 0.0141 | 0.0161 |
| Max | 10600 | 266 | 10600 | 4860 | 10600 | 277 |
| n (Samp) | 27 | 62 | 927 | 70 | 927 | 39 |
| n (Patient) | 360 | 62 | 360 | 70 | 360 | 39 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 3.43 | 10.6 | 3.43 | 11.0 | 3.43 | 14.9 |
| Average | 33.6 | 24.9 | 33.6 | 53.1 | 33.6 | 22.5 |
| Stdev | 353 | 44.8 | 353 | 127 | 353 | 27.7 |
| p(t-test) | | 0.92 | | 0.81 | | 0.90 |
| Min | 0.0141 | 0.0764 | 0.0141 | 0.0161 | 0.0141 | 0.0184 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| Max | 10600 | 174 | 10600 | 540 | 10600 | 90.7 |
| n (Samp) | 1230 | 15 | 1230 | 18 | 1230 | 17 |
| n (Patient) | 440 | 15 | 440 | 18 | 440 | 17 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3.53 | 4.69 | 3.53 | 7.67 | 3.53 | 3.59 |
| Average | 18.5 | 96.8 | 18.5 | 209 | 18.5 | 19.2 |
| Stdev | 87.3 | 560 | 87.3 | 1050 | 87.3 | 47.9 |
| p(t-test) | | 5.7E-4 | | 6.7E-7 | | 0.96 |
| Min | 0.0141 | 0.0184 | 0.0141 | 0.0184 | 0.0141 | 0.0161 |
| Max | 2000 | 4230 | 2000 | 6850 | 2000 | 277 |
| n (Samp) | 815 | 57 | 815 | 63 | 815 | 34 |
| n (Patient) | 282 | 57 | 282 | 63 | 282 | 34 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.55 | 0.60 | 0.56 | 0.60 | 0.64 | 0.60 |
| SE | 0.039 | 0.078 | 0.041 | 0.037 | 0.071 | 0.039 |
| p | 0.17 | 0.22 | 0.15 | 0.0095 | 0.057 | 0.012 |
| nCohort 1 | 927 | 1230 | 815 | 927 | 1230 | 815 |
| nCohort 2 | 62 | 15 | 57 | 70 | 18 | 63 |
| Cutoff 1 | 0.661 | 0.257 | 0.756 | 2.12 | 2.12 | 1.72 |
| Sens 1 | 71% | 73% | 70% | 70% | 72% | 71% |
| Spec 1 | 32% | 29% | 33% | 42% | 42% | 40% |
| Cutoff 2 | 0.123 | 0.143 | 0.123 | 0.123 | 0.143 | 0.123 |
| Sens 2 | 87% | 87% | 88% | 84% | 83% | 84% |
| Spec 2 | 23% | 27% | 22% | 23% | 27% | 22% |
| Cutoff 3 | 0.0785 | 0.123 | 0.0785 | 0.0742 | 0.0604 | 0.0742 |
| Sens 3 | 92% | 93% | 93% | 90% | 94% | 90% |
| Spec 3 | 15% | 23% | 14% | 13% | 10% | 13% |
| Cutoff 4 | 9.39 | 9.40 | 9.81 | 9.39 | 9.40 | 9.81 |
| Sens 4 | 40% | 53% | 39% | 44% | 56% | 44% |
| Spec 4 | 70% | 70% | 70% | 70% | 70% | 70% |
| Cutoff 5 | 14.2 | 15.6 | 15.3 | 14.2 | 15.6 | 15.3 |
| Sens 5 | 29% | 40% | 30% | 37% | 44% | 38% |
| Spec 5 | 80% | 80% | 80% | 80% | 80% | 80% |
| Cutoff 6 | 29.4 | 31.0 | 29.8 | 29.4 | 31.0 | 29.8 |
| Sens 6 | 16% | 27% | 18% | 23% | 28% | 24% |
| Spec 6 | 90% | 90% | 90% | 90% | 90% | 90% |
| OR Quart 2 | 1.6 | 6.1 | 1.5 | 1.1 | 2.0 | 0.70 |
| p Value | 0.25 | 0.095 | 0.31 | 0.84 | 0.42 | 0.40 |
| 95% CI of OR Quart2 | 0.73 3.5 | 0.73 51 | 0.67 3.5 | 0.50 2.4 | 0.37 11 | 0.30 1.6 |
| OR Quart 3 | 1.1 | 2.0 | 1.2 | 1.2 | 2.0 | 1.0 |
| p Value | 0.83 | 0.57 | 0.66 | 0.57 | 0.42 | 1.0 |
| 95% CI of OR Quart3 | 0.47 2.5 | 0.18 22 | 0.51 2.9 | 0.59 2.6 | 0.37 11 | 0.47 2.2 |
| OR Quart 4 | 2.1 | 6.1 | 2.1 | 2.2 | 4.1 | 1.9 |
| p Value | 0.053 | 0.096 | 0.063 | 0.025 | 0.077 | 0.071 |
| 95% CI of OR Quart4 | 0.99 4.4 | 0.73 51 | 0.96 4.6 | 1.1 4.4 | 0.86 19 | 0.95 3.7 |

| | 48 hr prior to AKI stage | | |
|---|---|---|---|
| | sCr or UO | sCr only | UO only |
| AUC | 0.54 | 0.68 | 0.56 |
| SE | 0.048 | 0.072 | 0.052 |
| p | 0.39 | 0.013 | 0.24 |
| nCohort 1 | 927 | 1230 | 815 |
| nCohort 2 | 39 | 17 | 34 |
| Cutoff 1 | 1.17 | 6.21 | 1.78 |
| Sens 1 | 72% | 76% | 71% |
| Spec 1 | 40% | 61% | 40% |
| Cutoff 2 | 0.143 | 3.43 | 0.173 |
| Sens 2 | 82% | 82% | 82% |
| Spec 2 | 27% | 49% | 28% |
| Cutoff 3 | 0.0604 | 0.143 | 0.0823 |
| Sens 3 | 92% | 94% | 91% |
| Spec 3 | 9% | 27% | 15% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

|  |  | Cutoff 4 | 9.39 | 9.40 | 9.81 |
|---|---|---|---|---|---|
|  |  | Sens 4 | 31% | 53% | 35% |
|  |  | Spec 4 | 70% | 70% | 70% |
|  |  | Cutoff 5 | 14.2 | 15.6 | 15.3 |
|  |  | Sens 5 | 28% | 47% | 29% |
|  |  | Spec 5 | 80% | 80% | 80% |
|  |  | Cutoff 6 | 29.4 | 31.0 | 29.8 |
|  |  | Sens 6 | 15% | 18% | 18% |
|  |  | Spec 6 | 90% | 90% | 90% |
|  |  | OR Quart 2 | 1.4 | 3.0 | 1.5 |
|  |  | p Value | 0.47 | 0.34 | 0.43 |
|  |  | 95% CI of | 0.54 | 0.31 | 0.53 |
|  |  | OR Quart2 | 3.9 | 29 | 4.4 |
|  |  | OR Quart 3 | 1.4 | 4.0 | 1.2 |
|  |  | p Value | 0.46 | 0.21 | 0.78 |
|  |  | 95% CI of | 0.54 | 0.45 | 0.39 |
|  |  | OR Quart3 | 3.9 | 36 | 3.5 |
|  |  | OR Quart 4 | 1.7 | 9.2 | 2.0 |
|  |  | p Value | 0.25 | 0.036 | 0.16 |
|  |  | 95% CI of | 0.67 | 1.2 | 0.75 |
|  |  | OR Quart4 | 4.5 | 73 | 5.6 |

Thymic stromal lymphopoietin

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 77.7 | 51.2 | 77.7 | 55.7 | 77.7 | 65.2 |
| Average | 98.2 | 64.6 | 98.2 | 74.0 | 98.2 | 80.3 |
| Stdev | 85.4 | 52.5 | 85.4 | 60.1 | 85.4 | 64.9 |
| p(t-test) |  | 0.0023 |  | 0.021 |  | 0.20 |
| Min | 0.00642 | 0.00579 | 0.00642 | 0.0163 | 0.00642 | 3.01 |
| Max | 695 | 211 | 695 | 254 | 695 | 266 |
| n (Samp) | 927 | 62 | 927 | 69 | 927 | 38 |
| n (Patient) | 361 | 62 | 361 | 69 | 361 | 38 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 73.1 | 59.9 | 73.1 | 58.6 | 73.1 | 69.4 |
| Average | 93.7 | 72.8 | 93.7 | 69.8 | 93.7 | 75.2 |
| Stdev | 80.7 | 47.2 | 80.7 | 46.7 | 80.7 | 61.2 |
| p(t-test) |  | 0.32 |  | 0.21 |  | 0.34 |
| Min | 0.00579 | 10.2 | 0.00579 | 0.0266 | 0.00579 | 0.0163 |
| Max | 695 | 163 | 695 | 184 | 695 | 238 |
| n (Samp) | 1229 | 15 | 1229 | 18 | 1229 | 17 |
| n (Patient) | 441 | 15 | 441 | 18 | 441 | 17 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 79.1 | 42.7 | 79.1 | 52.5 | 79.1 | 61.3 |
| Average | 99.9 | 59.1 | 99.9 | 76.7 | 99.9 | 79.5 |
| Stdev | 87.0 | 51.3 | 87.0 | 76.2 | 87.0 | 68.2 |
| p(t-test) |  | 4.8E−4 |  | 0.041 |  | 0.18 |
| Min | 0.00667 | 0.00579 | 0.00667 | 0.0163 | 0.00667 | 3.01 |
| Max | 695 | 211 | 695 | 439 | 695 | 266 |
| n (Samp) | 816 | 57 | 816 | 62 | 816 | 33 |
| n (Patient) | 283 | 57 | 283 | 62 | 283 | 33 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.37 | 0.44 | 0.33 | 0.41 | 0.43 | 0.39 |
| SE | 0.039 | 0.077 | 0.040 | 0.037 | 0.071 | 0.039 |
| p | 6.5E−4 | 0.47 | 2.0E−5 | 0.015 | 0.31 | 0.0062 |
| nCohort 1 | 927 | 1229 | 816 | 927 | 1229 | 816 |
| nCohort 2 | 62 | 15 | 57 | 69 | 18 | 62 |
| Cutoff 1 | 31.6 | 32.8 | 30.9 | 34.5 | 46.5 | 31.1 |
| Sens 1 | 71% | 73% | 70% | 71% | 72% | 71% |
| Spec 1 | 17% | 19% | 16% | 19% | 29% | 17% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| Cutoff 2 | 24.4 | 32.1 | 18.5 | 27.5 | 29.5 | 26.5 |
|---|---|---|---|---|---|---|
| Sens 2 | 81% | 80% | 81% | 81% | 83% | 81% |
| Spec 2 | 13% | 18% | 10% | 15% | 17% | 14% |
| Cutoff 3 | 15.7 | 24.7 | 10.8 | 10.0 | 6.81 | 10.8 |
| Sens 3 | 90% | 93% | 91% | 91% | 94% | 90% |
| Spec 3 | 8% | 14% | 5% | 5% | 4% | 5% |
| Cutoff 4 | 114 | 110 | 116 | 114 | 110 | 116 |
| Sens 4 | 16% | 20% | 14% | 23% | 22% | 19% |
| Spec 4 | 70% | 70% | 70% | 70% | 70% | 70% |
| Cutoff 5 | 143 | 139 | 144 | 143 | 139 | 144 |
| Sens 5 | 11% | 13% | 9% | 16% | 6% | 15% |
| Spec 5 | 80% | 80% | 80% | 80% | 80% | 80% |
| Cutoff 6 | 200 | 192 | 208 | 200 | 192 | 208 |
| Sens 6 | 5% | 0% | 5% | 4% | 0% | 6% |
| Spec 6 | 90% | 90% | 90% | 90% | 90% | 90% |
| OR Quart 2 | 0.80 | 2.0 | 0.49 | 0.92 | 3.0 | 0.57 |
| p Value | 0.64 | 0.42 | 0.25 | 0.84 | 0.18 | 0.25 |
| 95% CI of OR Quart2 | 0.31 2.1 | 0.37 11 | 0.15 1.7 | 0.41 2.1 | 0.61 15 | 0.22 1.5 |
| OR Quart 3 | 1.8 | 2.0 | 2.2 | 1.6 | 2.5 | 1.6 |
| p Value | 0.17 | 0.42 | 0.068 | 0.21 | 0.27 | 0.20 |
| 95% CI of OR Quart3 | 0.79 3.9 | 0.37 11 | 0.94 5.3 | 0.77 3.3 | 0.49 13 | 0.78 3.5 |
| OR Quart 4 | 2.9 | 2.5 | 3.9 | 1.9 | 2.5 | 2.1 |
| p Value | 0.0050 | 0.27 | 0.0010 | 0.064 | 0.27 | 0.039 |
| 95% CI of OR Quart4 | 1.4 6.2 | 0.49 13 | 1.7 8.7 | 0.96 3.9 | 0.49 13 | 1.0 4.4 |

| | 48 hr prior to AKI stage | | |
|---|---|---|---|
| | sCr or UO | sCr only | UO only |
| AUC | 0.44 | 0.44 | 0.42 |
| SE | 0.049 | 0.073 | 0.053 |
| p | 0.20 | 0.38 | 0.12 |
| nCohort 1 | 927 | 1229 | 816 |
| nCohort 2 | 38 | 17 | 33 |
| Cutoff 1 | 45.5 | 30.9 | 32.1 |
| Sens 1 | 71% | 71% | 73% |
| Spec 1 | 27% | 18% | 17% |
| Cutoff 2 | 26.1 | 23.0 | 29.0 |
| Sens 2 | 82% | 82% | 82% |
| Spec 2 | 14% | 13% | 15% |
| Cutoff 3 | 14.5 | 10.7 | 16.0 |
| Sens 3 | 92% | 94% | 91% |
| Spec 3 | 8% | 6% | 8% |
| Cutoff 4 | 114 | 110 | 116 |
| Sens 4 | 18% | 18% | 18% |
| Spec 4 | 70% | 70% | 70% |
| Cutoff 5 | 143 | 139 | 144 |
| Sens 5 | 16% | 12% | 18% |
| Spec 5 | 80% | 80% | 80% |
| Cutoff 6 | 200 | 192 | 208 |
| Sens 6 | 8% | 6% | 9% |
| Spec 6 | 90% | 90% | 90% |
| OR Quart 2 | 1.2 | 1.7 | 0.83 |
| p Value | 0.79 | 0.48 | 0.77 |
| 95% CI of OR Quart2 | 0.41 3.2 | 0.40 7.1 | 0.25 2.8 |
| OR Quart 3 | 1.8 | 1.0 | 1.9 |
| p Value | 0.24 | 1.0 | 0.22 |
| 95% CI of OR Quart3 | 0.68 4.5 | 0.20 5.0 | 0.69 5.2 |
| OR Quart 4 | 1.6 | 2.0 | 1.9 |
| p Value | 0.34 | 0.32 | 0.22 |
| 95% CI of OR Quart4 | 0.61 4.2 | 0.50 8.2 | 0.69 5.2 |

TABLE 3

Comparison of marker levels in urine samples collected within 12 hours of reaching stage R from Cohort 1 (patients that reached, but did not progress beyond, RIFLE stage R) and from Cohort 2 (patients that reached RIFLE stage I or F).

C-C motif chemokine 21

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 1.60 | 1.79 | 2.56 | 2.17 | 1.79 | 1.79 |
| Average | 130 | 218 | 187 | 332 | 123 | 232 |
| Stdev | 524 | 815 | 676 | 657 | 535 | 910 |
| p(t-test) |  | 0.41 |  | 0.48 |  | 0.41 |
| Min | 0.327 | 0.371 | 0.327 | 0.371 | 0.371 | 0.371 |
| Max | 4130 | 4860 | 4070 | 2190 | 4130 | 4860 |
| n (Samp) | 124 | 45 | 49 | 14 | 97 | 31 |
| n (Patient) | 124 | 45 | 49 | 14 | 97 | 31 |

At Enrollment

|  | sCr or UO | sCr only | UO only |
| --- | --- | --- | --- |
| AUC | 0.56 | 0.57 | 0.54 |
| SE | 0.051 | 0.089 | 0.060 |
| P | 0.25 | 0.45 | 0.54 |
| nCohort 1 | 124 | 49 | 97 |
| nCohort 2 | 45 | 14 | 31 |
| Cutoff 1 | 1.07 | 1.36 | 1.06 |
| Sens 1 | 71% | 71% | 71% |
| Spec 1 | 37% | 43% | 33% |
| Cutoff 2 | 0.979 | 0.647 | 0.939 |
| Sens 2 | 80% | 93% | 81% |
| Spec 2 | 32% | 18% | 20% |
| Cutoff 3 | 0.647 | 0.647 | 0.647 |
| Sens 3 | 93% | 93% | 94% |
| Spec 3 | 18% | 18% | 13% |
| Cutoff 4 | 12.9 | 23.1 | 12.9 |
| Sens 4 | 33% | 43% | 35% |
| Spec 4 | 74% | 71% | 74% |
| Cutoff 5 | 23.1 | 86.1 | 23.1 |
| Sens 5 | 27% | 36% | 26% |
| Spec 5 | 81% | 82% | 80% |
| Cutoff 6 | 125 | 248 | 99.6 |
| Sens 6 | 13% | 29% | 16% |
| Spec 6 | 90% | 92% | 91% |
| OR Quart 2 | 1.3 | 1.8 | 1.2 |
| p Value | 0.61 | 0.48 | 0.77 |
| 95% CI of | 0.47 | 0.35 | 0.37 |
| OR Quart2 | 3.6 | 9.5 | 3.8 |
| OR Quart 3 | 1.1 | 0.27 | 0.66 |
| p Value | 0.79 | 0.28 | 0.52 |
| 95% CI of | 0.41 | 0.025 | 0.19 |
| OR Quart3 | 3.2 | 2.9 | 2.4 |
| OR Quart 4 | 2.0 | 1.8 | 1.9 |
| p Value | 0.17 | 0.48 | 0.27 |
| 95% CI of | 0.75 | 0.35 | 0.62 |
| OR Quart4 | 5.2 | 9.5 | 5.7 |

Interleukin-20

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 15.8 | 17.3 | 13.0 | 29.7 | 17.3 | 15.8 |
| Average | 78.6 | 93.4 | 73.9 | 163 | 80.3 | 95.7 |
| Stdev | 114 | 143 | 127 | 218 | 104 | 139 |
| p(t-test) |  | 0.49 |  | 0.057 |  | 0.51 |
| Min | 0.412 | 0.541 | 0.412 | 0.541 | 0.412 | 0.541 |
| Max | 561 | 547 | 561 | 583 | 431 | 547 |
| n (Samp) | 124 | 45 | 49 | 14 | 97 | 31 |
| n (Patient) | 124 | 45 | 49 | 14 | 97 | 31 |

At Enrollment

|  | sCr or UO | sCr only | UO only |
| --- | --- | --- | --- |
| AUC | 0.52 | 0.60 | 0.50 |
| SE | 0.051 | 0.089 | 0.060 |
| P | 0.63 | 0.25 | 0.96 |
| nCohort 1 | 124 | 49 | 97 |
| nCohort 2 | 45 | 14 | 31 |
| Cutoff 1 | 1.62 | 2.84 | 1.62 |
| Sens 1 | 76% | 71% | 71% |
| Spec 1 | 31% | 41% | 28% |
| Cutoff 2 | 1.47 | 1.33 | 1.47 |
| Sens 2 | 82% | 86% | 81% |
| Spec 2 | 23% | 16% | 21% |
| Cutoff 3 | 0.552 | 0.541 | 0.552 |
| Sens 3 | 91% | 93% | 90% |
| Spec 3 | 7% | 12% | 6% |
| Cutoff 4 | 98.7 | 83.3 | 102 |
| Sens 4 | 29% | 36% | 35% |
| Spec 4 | 70% | 71% | 70% |
| Cutoff 5 | 163 | 153 | 163 |
| Sens 5 | 16% | 36% | 16% |
| Spec 5 | 81% | 82% | 80% |
| Cutoff 6 | 242 | 220 | 242 |
| Sens 6 | 16% | 36% | 16% |
| Spec 6 | 90% | 92% | 91% |
| OR Quart 2 | 1.3 | 0.57 | 1.2 |
| p Value | 0.62 | 0.57 | 0.78 |
| 95% CI of | 0.48 | 0.081 | 0.39 |
| OR Quart2 | 3.4 | 4.0 | 3.6 |
| OR Quart 3 | 1.1 | 1.3 | 0.69 |
| p Value | 0.80 | 0.74 | 0.55 |
| 95% CI of | 0.42 | 0.24 | 0.21 |
| OR Quart3 | 3.1 | 7.3 | 2.3 |
| OR Quart 4 | 1.2 | 1.8 | 1.0 |
| p Value | 0.67 | 0.48 | 1.0 |
| 95% CI of | 0.47 | 0.35 | 0.32 |
| OR Quart4 | 3.3 | 9.5 | 3.1 |

Matrix metalloproteinase-9:Metalloproteinase inhibitor 2 complex

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 197 | 755 | nd | nd | 221 | 693 |
| Average | 2100 | 2820 | nd | nd | 2010 | 3670 |
| Stdev | 6330 | 6720 | nd | nd | 6110 | 7970 |
| p(t-test) |  | 0.65 | nd | nd |  | 0.40 |
| Min | 0.227 | 3.10 | nd | nd | 0.227 | 3.10 |
| Max | 24000 | 24000 | nd | nd | 24000 | 24000 |
| n (Samp) | 53 | 23 | nd | nd | 43 | 16 |
| n (Patient) | 53 | 23 | nd | nd | 43 | 16 |

At Enrollment

|  | sCr or UO | sCr only | UO only |
| --- | --- | --- | --- |
| AUC | 0.64 | nd | 0.61 |
| SE | 0.072 | nd | 0.085 |
| P | 0.053 | nd | 0.18 |
| nCohort 1 | 53 | nd | 43 |
| nCohort 2 | 23 | nd | 16 |
| Cutoff 1 | 101 | nd | 101 |
| Sens 1 | 74% | nd | 75% |
| Spec 1 | 34% | nd | 30% |
| Cutoff 2 | 52.9 | nd | 29.2 |
| Sens 2 | 83% | nd | 81% |
| Spec 2 | 23% | nd | 12% |
| Cutoff 3 | 18.8 | nd | 3.86 |
| Sens 3 | 91% | nd | 94% |
| Spec 3 | 11% | nd | 7% |
| Cutoff 4 | 426 | nd | 426 |
| Sens 4 | 61% | nd | 62% |

TABLE 3-continued

Comparison of marker levels in urine samples collected within 12 hours of reaching stage R from Cohort 1 (patients that reached, but did not progress beyond, RIFLE stage R) and from Cohort 2 (patients that reached RIFLE stage I or F).

| | | | |
|---|---|---|---|
| Spec 4 | 72% | nd | 72% |
| Cutoff 5 | 668 | nd | 666 |
| Sens 5 | 52% | nd | 50% |
| Spec 5 | 81% | nd | 81% |
| Cutoff 6 | 1380 | nd | 1380 |
| Sens 6 | 30%. | nd | 31% |
| Spec 6 | 91% | nd | 91% |
| OR Quart 2 | 0.75 | nd | 0.38 |
| p Value | 0.70 | nd | 0.32 |
| 95% CI of | 0.17 | nd | 0.058 |
| OR Quart2 | 3.4 | nd | 2.5 |
| OR Quart 3 | 0.52 | nd | 0.62 |
| p Value | 0.43 | nd | 0.59 |
| 95% CI of | 0.11 | nd | 0.11 |
| OR Quart3 | 2.6 | nd | 3.5 |
| OR Quart 4 | 3.8 | nd | 2.2 |
| p Value | 0.053 | nd | 0.32 |
| 95% CI of | 0.98 | nd | 0.47 |
| OR Quart4 | 15 | nd | 10 |

TABLE 4

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

C—C motif chemokine 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0140 | 0.314 | 0.0140 | 0.314 | 0.0140 | 0.0224 |
| Average | 1.05 | 7.06 | 1.05 | 6.26 | 1.05 | 2.05 |
| Stdev | 7.73 | 11.7 | 7.73 | 11.5 | 7.73 | 4.62 |
| p (t-test) | | 2.3E-4 | | 0.0013 | | 0.61 |
| Min | 0.00595 | 0.00547 | 0.00595 | 0.00547 | 0.00595 | 0.00929 |
| Max | 99.1 | 49.3 | 99.1 | 49.3 | 99.1 | 17.3 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0161 | 0.351 | 0.0161 | 0.351 | 0.0161 | 6.03 |
| Average | 1.05 | 14.9 | 1.05 | 10.1 | 1.05 | 10.5 |
| Stdev | 6.29 | 26.3 | 6.29 | 16.1 | 6.29 | 14.0 |
| p (t-test) | | 6.3E-10 | | 3.2E-6 | | 1.7E-4 |
| Min | 0.00501 | 0.00547 | 0.00501 | 0.00547 | 0.00501 | 0.00929 |
| Max | 99.1 | 87.8 | 99.1 | 49.3 | 99.1 | 35.4 |
| n (Samp) | 375 | 13 | 375 | 13 | 375 | 7 |
| n (Patient) | 375 | 13 | 375 | 13 | 375 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0186 | 2.88 | 0.0186 | 1.47 | 0.0186 | 0.0205 |
| Average | 1.99 | 6.30 | 1.99 | 5.50 | 1.99 | 1.91 |
| Stdev | 10.8 | 8.99 | 10.8 | 9.01 | 10.8 | 4.80 |
| p (t-test) | | 0.068 | | 0.14 | | 0.98 |
| Min | 0.00595 | 0.00547 | 0.00595 | 0.00547 | 0.00595 | 0.00547 |
| Max | 99.1 | 35.4 | 99.1 | 35.4 | 99.1 | 17.3 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.73 | 0.64 | 0.75 | 0.73 | 0.63 | 0.74 | 0.71 | 0.78 | 0.60 |
| SE | 0.054 | 0.084 | 0.061 | 0.055 | 0.084 | 0.061 | 0.075 | 0.10 | 0.083 |
| p | 1.6E-5 | 0.090 | 5.9E-5 | 3.6E-5 | 0.13 | 7.4E-5 | 0.0056 | 0.0060 | 0.21 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 0.0161 | 0.0105 | 0.0223 | 0.0161 | 0.0105 | 0.0223 | 0.0151 | 0.333 | 0.0151 |
| Sens 1 | 73% | 77% | 74% | 70% | 77% | 74% | 75% | 71% | 71% |
| Spec 1 | 62% | 26% | 63% | 62% | 26% | 63% | 59% | 84% | 47% |
| Cutoff 2 | 0.0151 | 0.00928 | 0.0151 | 0.0150 | 0.00928 | 0.0151 | 0.0150 | 0.0200 | 0.0140 |
| Sens 2 | 80% | 85% | 87% | 80% | 85% | 87% | 81% | 86% | 86% |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| Spec 2 | 59% | 11% | 47% | 57% | 11% | 47% | 57% | 56% | 43% |
| Cutoff 3 | 0.00773 | 0.00679 | 0.0150 | 0.00773 | 0.00679 | 0.0150 | 0.0140 | 0.00928 | 0.0140 |
| Sens 3 | 90% | 92% | 91% | 90% | 92% | 91% | 94% | 100% | 93% |
| Spec 3 | 13% | 7% | 45% | 13% | 7% | 45% | 45% | 11% | 36% |
| Cutoff 4 | 0.0223 | 0.0250 | 0.0250 | 0.0223 | 0.0250 | 0.0250 | 0.0223 | 0.0250 | 0.0250 |
| Sens 4 | 63% | 54% | 61% | 63% | 54% | 61% | 50% | 71% | 29% |
| Spec 4 | 71% | 74% | 72% | 71% | 74% | 72% | 71% | 74% | 72% |
| Cutoff 5 | 0.0291 | 0.0338 | 0.0291 | 0.0291 | 0.0338 | 0.0291 | 0.0291 | 0.0338 | 0.0291 |
| Sens 5 | 53% | 54% | 61% | 53% | 54% | 61% | 31% | 71% | 29% |
| Spec 5 | 83% | 80% | 80% | 83% | 80% | 80% | 83% | 80% | 80% |
| Cutoff 6 | 0.552 | 1.35 | 1.35 | 0.552 | 1.35 | 1.35 | 0.552 | 1.35 | 1.35 |
| Sens 6 | 47% | 46% | 52% | 47% | 46% | 52% | 25% | 57% | 21% |
| Spec 6 | 90% | 90% | 90% | 90% | 90% | 90% | 90% | 90% | 90% |
| OR Quart 2 | 0.24 | 0.33 | 2.1 | 0.48 | 0.66 | 2.1 | 0.98 | 0 | 5.4 |
| p Value | 0.20 | 0.34 | 0.41 | 0.41 | 0.65 | 0.41 | 0.99 | na | 0.13 |
| 95% CI of OR Quart 2 | 0.026 | 0.033 | 0.36 | 0.085 | 0.11 | 0.36 | 0.060 | na | 0.60 |
| | 2.2 | 3.2 | 12 | 2.7 | 4.0 | 12 | 16 | na | 48 |
| OR Quart 3 | 2.5 | 0.66 | 1.5 | 2.1 | 0.33 | 1.5 | 10 | 1.0 | 4.2 |
| p Value | 0.15 | 0.65 | 0.65 | 0.23 | 0.34 | 0.65 | 0.030 | 1.0 | 0.21 |
| 95% CI of OR Quart 3 | 0.72 | 0.11 | 0.24 | 0.61 | 0.033 | 0.24 | 1.3 | 0.062 | 0.45 |
| | 8.4 | 4.0 | 9.6 | 7.5 | 3.2 | 9.6 | 84 | 16 | 39 |
| OR Quart 4 | 4.9 | 2.4 | 9.4 | 4.9 | 2.4 | 9.4 | 5.3 | 5.2 | 4.2 |
| p Value | 0.0071 | 0.21 | 0.0045 | 0.0071 | 0.21 | 0.0045 | 0.13 | 0.14 | 0.21 |
| 95% CI of OR Quart 4 | 1.5 | 0.61 | 2.0 | 1.5 | 0.61 | 2.0 | 0.60 | 0.59 | 0.45 |
| | 16 | 9.7 | 44 | 16 | 9.7 | 44 | 47 | 45 | 39 |

C—C motif chemokine 17

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.00885 | 0.192 | 0.00885 | 0.0417 | 0.00885 | 0.0110 |
| Average | 0.191 | 1.49 | 0.191 | 1.18 | 0.191 | 0.359 |
| Stdev | 0.835 | 4.96 | 0.835 | 3.65 | 0.835 | 0.631 |
| p (t-test) | | 3.8E−4 | | 5.8E−4 | | 0.43 |
| Min | 0.00241 | 0.00246 | 0.00241 | 0.00114 | 0.00241 | 0.00114 |
| Max | 9.18 | 26.9 | 9.18 | 19.4 | 9.18 | 2.32 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.00977 | 0.135 | 0.00977 | 0.00762 | 0.00977 | 0.00503 |
| Average | 0.398 | 0.365 | 0.398 | 0.155 | 0.398 | 0.0559 |
| Stdev | 1.70 | 0.555 | 1.70 | 0.257 | 1.70 | 0.129 |
| p (t-test) | | 0.94 | | 0.61 | | 0.60 |
| Min | 0.00114 | 0.00249 | 0.00114 | 0.00241 | 0.00114 | 0.00249 |
| Max | 20.4 | 2.00 | 20.4 | 0.771 | 20.4 | 0.348 |
| n (Samp) | 375 | 13 | 375 | 13 | 375 | 7 |
| n (Patient) | 375 | 13 | 375 | 13 | 375 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0114 | 0.348 | 0.0114 | 0.295 | 0.0114 | 0.153 |
| Average | 0.257 | 2.02 | 0.257 | 1.60 | 0.257 | 0.463 |
| Stdev | 0.915 | 5.62 | 0.915 | 4.12 | 0.915 | 0.658 |
| p (t-test) | | 1.9E−4 | | 2.7E−4 | | 0.41 |
| Min | 0.00241 | 0.00246 | 0.00241 | 0.00114 | 0.00241 | 0.00114 |
| Max | 7.83 | 26.9 | 7.83 | 19.4 | 7.83 | 2.32 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.68 | 0.63 | 0.69 | 0.63 | 0.49 | 0.67 | 0.57 | 0.44 | 0.60 |
| SE | 0.057 | 0.084 | 0.064 | 0.057 | 0.082 | 0.065 | 0.077 | 0.11 | 0.083 |
| p | 0.0019 | 0.14 | 0.0024 | 0.029 | 0.90 | 0.0091 | 0.36 | 0.60 | 0.21 |
| nCohort 1 | 223 | 375 | 173 | 223 | 375 | 173 | 223 | 375 | 173 |

TABLE 4-continued

Comparison of the maximum marker levels in urine samples collected from
Cohort 1 (patients that did not progress beyond RIFLE stage 0) and the maximum
values in urine samples collected from subjects between enrollment and 0, 24 hours,
and 48 hours prior to reaching stage F in Cohort 2.

| nCohort 2 | 30 | 13 | 23 | 30 | 13 | 23 | 16 | 7 | 14 |
|---|---|---|---|---|---|---|---|---|---|
| Cutoff 1 | 0.00722 | 0.00449 | 0.0109 | 0.00449 | 0.00443 | 0.00869 | 0.00449 | 0.00449 | 0.00449 |
| Sens 1 | 70% | 77% | 74% | 77% | 77% | 74% | 75% | 71% | 86% |
| Spec 1 | 44% | 30% | 50% | 30% | 23% | 39% | 30% | 30% | 29% |
| Cutoff 2 | 0.00449 | 0.00443 | 0.00449 | 0.00443 | 0.00308 | 0.00449 | 0.00443 | 0.00443 | 0.00449 |
| Sens 2 | 80% | 85% | 87% | 80% | 85% | 87% | 81% | 86% | 86% |
| Spec 2 | 30% | 23% | 29% | 25% | 13% | 29% | 25% | 23% | 29% |
| Cutoff 3 | 0.00421 | 0.00308 | 0.00421 | 0.00304 | 0.00246 | 0.00421 | 0.00246 | 0.00246 | 0.00421 |
| Sens 3 | 90% | 92% | 96% | 90% | 92% | 96% | 94% | 100% | 93% |
| Spec 3 | 22% | 13% | 15% | 15% | 5% | 15% | 4% | 5% | 15% |
| Cutoff 4 | 0.0130 | 0.0162 | 0.0162 | 0.0130 | 0.0162 | 0.0162 | 0.0130 | 0.0162 | 0.0162 |
| Sens 4 | 57% | 62% | 61% | 50% | 38% | 57% | 44% | 29% | 50% |
| Spec 4 | 74% | 74% | 76% | 74% | 74% | 76% | 74% | 74% | 76% |
| Cutoff 5 | 0.0162 | 0.0234 | 0.0234 | 0.0162 | 0.0234 | 0.0234 | 0.0162 | 0.0234 | 0.0234 |
| Sens 5 | 57% | 62% | 61% | 50% | 38% | 57% . | 44% | 14% | 50% |
| Spec 5 | 80% | 80% | 83% | 80% | 80% | 83% | 80% | 80% | 83% |
| Cutoff 6 | 0.198 | 0.767 | 0.587 | 0.198 | 0.767 | 0.587 | 0.198 | 0.767 | 0.587 |
| Sens 6 | 47% | 15% | 43% | 40% | 8% | 43% | 38% | 0% | 36% |
| Spec 6 | 91% | 90% | 91% | 91% | 90% | 91% | 91% | 90% | 91% |
| OR Quart | 21.0 | 0.66 | 1.7 | 0.69 | 0.19 | 2.1 | 1.3 | 2.0 | 2.0 |
| p Value | 1.0 | 0.65 | 0.47 | 0.55 | 0.13 | 0.30 | 0.71 | 0.56 | 0.42 |
| 95% CI of | 0.27 | 0.11 | 0.39 | 0.21 | 0.022 | 0.50 | 0.29 | 0.18 | 0.36 |
| OR Quart 2 | 3.6 | 4.0 | 7.7 | 2.3 | 1.7 | 9.1 | 6.2 | 23 | 12 |
| OR Quart 3 | 0.58 | 0 | 0.32 | 0.40 | 0.79 | 0.32 | 0.64 | 2.0 | 0.48 |
| p Value | 0.47 | na | 0.33 | 0.20 | 0.73 | 0.33 | 0.64 | 0.57 | 0.55 |
| 95% CI of | 0.13 | na | 0.032 | 0.099 | 0.21 | 0.032 | 0.10 | 0.18 | 0.042 |
| OR Quart 3 | 2.5 | na | 3.2 | 1.6 | 3.0 | 3.2 | 4.0 | 23 | 5.5 |
| OR Quart 4 | 4.2 | 2.8 | 6.1 | 2.4 | 0.59 | 5.5 | 2.5 | 2.0 | 3.8 |
| p Value | 0.0085 | 0.14 | 0.0072 | 0.072 | 0.47 | 0.012 | 0.21 | 0.56 | 0.10 |
| 95% CI of | 1.4 | 0.72 | 1.6 | 0.92 | 0.14 | 1.5 | 0.61 | 0.18 | 0.76 |
| OR Quart 4 | 12 | 11 | 23 | 6.5 | 2.5 | 21 | 10 | 23 | 20 |

C—C motif chemokine 21

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 7.71 | 161 | 7.71 | 135 | 7.71 | 61.9 |
| Average | 443 | 451 | 443 | 378 | 443 | 361 |
| Stdev | 3000 | 674 | 3000 | 646 | 3000 | 679 |
| p (t-test) |  | 0.99 |  | 0.91 |  | 0.91 |
| Min | 0.327 | 0.979 | 0.327 | 0.327 | 0.327 | 1.06 |
| Max | 36200 | 2190 | 36200 | 2190 | 36200 | 2150 |
| n (Samp) | 223 | 30 | 223 | 30 | 223 | 16 |
| n (Patient) | 223 | 30 | 223 | 30 | 223 | 16 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 9.69 | 269 | 9.69 | 225 | 9.69 | 378 |
| Average | 457 | 664 | 457 | 644 | 457 | 798 |
| Stdev | 2860 | 838 | 2860 | 845 | 2860 | 876 |
| p (t-test) |  | 0.79 |  | 0.81 |  | 0.75 |
| Min | 0.327 | 0.979 | 0.327 | 0.979 | 0.327 | 1.23 |
| Max | 36200 | 2190 | 36200 | 2190 | 36200 | 2150 |
| n (Samp) | 375 | 13 | 375 | 13 | 375 | 7 |
| n (Patient) | 375 | 13 | 375 | 13 | 375 | 7 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 10.7 | 125 | 10.7 | 86.1 | 10.7 | 36.8 |
| Average | 547 | 495 | 547 | 366 | 547 | 243 |
| Stdev | 3380 | 816 | 3380 | 631 | 3380 | 520 |
| p (t-test) |  | 0.94 |  | 0.80 |  | 0.74 |
| Min | 0.327 | 0.979 | 0.327 | 0.327 | 0.327 | 0.979 |
| Max | 36200 | 3280 | 36200 | 2240 | 36200 | 1820 |
| n (Samp) | 173 | 23 | 173 | 23 | 173 | 14 |
| n (Patient) | 173 | 23 | 173 | 23 | 173 | 14 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.75 | 0.76 | 0.72 | 0.72 | 0.76 | 0.67 | 0.66 | 0.80 | 0.58 |
| SE | 0.053 | 0.078 | 0.063 | 0.055 | 0.078 | 0.065 | 0.076 | 0.10 | 0.083 |
| p | 1.8E−6 | 7.4E−4 | 5.0E−4 | 7.0E−5 | 9.0E−4 | 0.0074 | 0.032 | 0.0024 | 0.31 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 42.7 | 42.7 | 37.0 | 37.0 | 42.7 | 11.7 | 1.79 | 224 | 1.79 |
| Sens 1 | 70% | 77% | 74% | 70% | 77% | 74% | 81% | 71% | 79% |
| Spec 1 | 73% | 71% | 67% | 71% | 71% | 54% | 45% | 87% | 40% |
| Cutoff 2 | 11.7 | 12.0 | 1.79 | 1.79 | 12.0 | 1.79 | 1.79 | 42.7 | 0.979 |
| Sens 2 | 80% | 85% | 91% | 87% | 85% | 87% | 81% | 86% | 93% |
| Spec 2 | 56% | 53% | 40% | 45% | 53% | 40% | 45% | 71% | 18% |
| Cutoff 3 | 1.79 | 1.17 | 1.79 | 1.17 | 1.17 | 0.979 | 0.979 | 1.17 | 0.979 |
| Sens 3 | 90% | 92% | 91% | 90% | 92% | 91% | 100% | 100% | 93% |
| Spec 3 | 45% | 27% | 40% | 32% | 27% | 18% | 24% | 27% | 18% |
| Cutoff 4 | 28.6 | 42.0 | 63.0 | 28.6 | 42.0 | 63.0 | 28.6 | 42.0 | 63.0 |
| Sens 4 | 73% | 77% | 57% | 70% | 77% | 52% | 56% | 86% | 36% |
| Spec 4 | 70% | 70% | 71% | 70% | 70% | 71% | 70% | 70% | 71% |
| Cutoff 5 | 86.1 | 93.4 | 121 | 86.1 | 93.4 | 121 | 86.1 | 93.4 | 121 |
| Sens 5 | 57% | 69% | 52% | 53% | 69% | 48% | 38% | 71% | 29% |
| Spec 5 | 81% | 80% | 80% | 81% | 80% | 80% | 81% | 80% | 80% |
| Cutoff 6 | 257 | 374 | 568 | 257 | 374 | 568 | 257 | 374 | 568 |
| Sens 6 | 40% | 46% | 22% | 30% | 38% | 17% | 25% | 57% | 14% |
| Spec 6 | 90% | 90% | 90% | 90% | 90% | 90% | 90% | 90% | 90% |
| OR Quart 2 | 2.1 | 1.0 | 1.5 | 1.4 | 1.0 | 1.0 | 1.5 | >1.0 | 0.98 |
| p Value | 0.41 | 1.0 | 0.65 | 0.70 | 1.0 | 1.0 | 0.66 | <1.0 | 0.98 |
| 95% CI of | 0.36 | 0.062 | 0.24 | 0.29 | 0.062 | 0.19 | 0.24 | >0.062 | 0.19 |
| OR Quart 2 | 12 | 16 | 9.6 | 6.3 | 16 | 5.2 | 9.3 | na | 5.1 |
| OR Quart 3 | 3.2 | 2.0 | 3.3 | 2.5 | 2.0 | 2.1 | 2.0 | >1.0 | 0.98 |
| p Value | 0.16 | 0.57 | 0.16 | 0.20 | 0.57 | 0.30 | 0.42 | <0.99 | 0.98 |
| 95% CI of | 0.62 | 0.18 | 0.63 | 0.62 | 0.18 | 0.50 | 0.36 | >0.062 | 0.19 |
| OR Quart 3 | 17 | 23 | 17 | 10 | 23 | 9.1 | 12 | na | 5.1 |
| OR Quart 4 | 12 | 9.8 | 7.6 | 6.7 | 9.8 | 4.4 | 3.8 | >5.2 | 1.7 |
| p Value | 0.0013 | 0.032 | 0.011 | 0.0040 | 0.032 | 0.030 | 0.11 | <0.13 | 0.48 |
| 95% CI of | 2.6 | 1.2 | 1.6 | 1.8 | 1.2 | 1.2 | 0.75 | >0.60 | 0.38 |
| OR Quart 4 | 54 | 79 | 36 | 24 | 79 | 17 | 19 | na | 7.6 |

C—C motif chemokine 27

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 2.71 | 6.17 | 2.71 | 5.75 | 2.71 | 4.91 |
| Average | 5.24 | 15.4 | 5.24 | 12.5 | 5.24 | 7.89 |
| Stdev | 16.8 | 28.7 | 16.8 | 22.7 | 16.8 | 13.6 |
| p (t-test) |  | 0.0050 |  | 0.034 |  | 0.54 |
| Min | 0.00668 | 0.0130 | 0.00668 | 0.00333 | 0.00668 | 0.0102 |
| Max | 230 | 118 | 230 | 109 | 230 | 57.4 |
| n (Samp) | 223 | 30 | 223 | 30 | 223 | 16 |
| n (Patient) | 223 | 30 | 223 | 30 | 223 | 16 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 3.43 | 6.61 | 3.43 | 4.23 | 3.43 | 3.08 |
| Average | 6.23 | 5.82 | 6.23 | 5.25 | 6.23 | 5.23 |
| Stdev | 15.8 | 4.00 | 15.8 | 4.00 | 15.8 | 4.90 |
| p (t-test) |  | 0.93 |  | 0.82 |  | 0.87 |
| Min | 0.00668 | 0.0130 | 0.00668 | 0.0130 | 0.00668 | 0.0130 |
| Max | 230 | 12.8 | 230 | 12.8 | 230 | 12.8 |
| n (Samp) | 375 | 13 | 375 | 13 | 375 | 7 |
| n (Patient) | 375 | 13 | 375 | 13 | 375 | 7 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3.65 | 6.58 | 3.65 | 6.58 | 3.65 | 5.73 |
| Average | 6.48 | 28.8 | 6.48 | 23.5 | 6.48 | 8.96 |
| Stdev | 19.0 | 55.0 | 19.0 | 45.7 | 19.0 | 14.3 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| p (t-test) | | 1.3E−4 | | 0.0013 | | | 0.63 | | |
| Min | 0.00668 | 0.393 | 0.00668 | 0.00333 | 0.00668 | | 0.0102 | | |
| Max | 230 | 234 | 230 | 198 | 230 | | 57.4 | | |
| n (Samp) | 173 | 23 | 173 | 23 | 173 | | 14 | | |
| n (Patient) | 173 | 23 | 173 | 23 | 173 | | 14 | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.72 | 0.63 | 0.73 | 0.68 | 0.58 | 0.69 | 0.63 | 0.54 | 0.63 |
| SE | 0.055 | 0.084 | 0.062 | 0.056 | 0.084 | 0.064 | 0.077 | 0.11 | 0.083 |
| p | 6.6E−5 | 0.13 | 3.0E−4 | 0.0010 | 0.34 | 0.0027 | 0.100 | 0.74 | 0.13 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 3.84 | 2.34 | 4.45 | 3.61 | 2.34 | 3.83 | 2.31 | 2.34 | 3.83 |
| Sens 1 | 70% | 77% | 74% | 70% | 77% | 74% | 75% | 71% | 71% |
| Spec 1 | 65% | 37% | 61% | 61% | 37% | 54% | 46% | 37% | 54% |
| Cutoff 2 | 3.07 | 1.40 | 3.54 | 2.31 | 1.40 | 3.07 | 1.40 | 1.40 | 1.40 |
| Sens 2 | 80% | 85% | 83% | 80% | 85% | 83% | 81% | 86% | 86% |
| Spec 2 | 55% | 23% | 50% | 46% | 23% | 45% | 30% | 23% | 24% |
| Cutoff 3 | 1.29 | 0.800 | 1.40 | 0.800 | 0.800 | 1.28 | 0.0102 | 0.0100 | 0.353 |
| Sens 3 | 90% | 92% | 91% | 90% | 92% | 91% | 94% | 100% | 93% |
| Spec 3 | 29% | 17% | 24% | 22% | 17% | 22% | 10% | 7% | 12% |
| Cutoff 4 | 4.41 | 5.23 | 5.58 | 4.41 | 5.23 | 5.58 | 4.41 | 5.23 | 5.58 |
| Sens 4 | 67% | 62% | 61% | 60% | 46% | 61% | 56% | 43% | 50% |
| Spec 4 | 70% | 70% | 71% | 70% | 70% | 71% | 70% | 70% | 71% |
| Cutoff 5 | 5.88 | 6.38 | 7.00 | 5.88 | 6.38 | 7.00 | 5.88 | 6.38 | 7.00 |
| Sens 5 | 53% | 54% | 48% | 50% | 38% | 48% | 44% | 29% | 36% |
| Spec 5 | 80% | 80% | 80% | 80% | 80% | 80% | 80% | 80% | 80% |
| Cutoff 6 | 8.44 | 9.68 | 9.69 | 8.44 | 9.68 | 9.69 | 8.44 | 9.68 | 9.69 |
| Sens 6 | 30% | 15% | 39% | 30% | 15% | 39% | 19% | 29% | 21% |
| Spec 6 | 90% | 90% | 90% | 90% | 90% | 90% | 90% | 90% | 90% |
| OR Quart | 21.0 | 0.33 | 0.65 | 0.74 | 0.66 | 0.48 | 0.64 | 0.99 | 0.31 |
| p Value | 1.0 | 0.34 | 0.65 | 0.70 | 0.65 | 0.41 | 0.64 | 0.99 | 0.32 |
| 95% CI of | 0.19 | 0.033 | 0.10 | 0.16 | 0.11 | 0.084 | 0.10 | 0.14 | 0.031 |
| OR Quart 2 | 5.2 | 3.2 | 4.1 | 3.4 | 4.0 | 2.7 | 4.0 | 7.2 | 3.1 |
| OR Quart 3 | 2.9 | 0.66 | 2.1 | 2.1 | 1.0 | 1.3 | 1.3 | 0 | 1.3 |
| p Value | 0.13 | 0.65 | 0.30 | 0.23 | 1.0 | 0.73 | 0.71 | na | 0.72 |
| 95% CI of | 0.73 | 0.11 | 0.50 | 0.61 | 0.20 | 0.32 | 0.29 | na | 0.28 |
| OR Quart 3 | 12 | 4.0 | 9.1 | 7.5 | 5.1 | 5.1 | 6.2 | na | 6.3 |
| OR Quart 4 | 6.7 | 2.4 | 5.0 | 4.5 | 1.7 | 3.6 | 2.5 | 1.5 | 2.1 |
| p Value | 0.0040 | 0.21 | 0.019 | 0.011 | 0.47 | 0.036 | 0.21 | 0.66 | 0.32 |
| 95% CI of | 1.8 | 0.61 | 1.3 | 1.4 | 0.40 | 1.1 | 0.61 | 0.24 | 0.49 |
| OR Quart 4 | 24 | 9.7 | 19 | 14 | 7.3 | 12 | 10 | 9.2 | 8.9 |

Vascular endothelial growth factor receptor 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 9.88 | 188 | 9.88 | 107 | 9.88 | 107 |
| Average | 61.3 | 389 | 61.3 | 357 | 61.3 | 137 |
| Stdev | 114 | 921 | 114 | 945 | 114 | 109 |
| p (t-test) | | 1.5E−4 | | 7.9E−4 | | 0.023 |
| Min | 0.169 | 0.526 | 0.169 | 0.242 | 0.169 | 8.05 |
| Max | 809 | 4630 | 809 | 4630 | 809 | 394 |
| n (Samp) | 126 | 24 | 126 | 23 | 126 | 13 |
| n (Patient) | 126 | 24 | 126 | 23 | 126 | 13 |

| | 0 hr prior to AKI stage | | 24 hr prior to AKI stage | | 48 hr prior to AK stage | |
|---|---|---|---|---|---|---|
| sCr only | Cohort 1 | Cohort 2 | Cohort 1 | Cohort 2 | Cohort 1 | Cohort 2 |
| Median | 38.3 | 81.0 | 38.3 | 65.7 | nd | nd |
| Average | 131 | 136 | 131 | 133 | nd | nd |
| Stdev | 538 | 153 | 538 | 155 | nd | nd |
| p (t-test) | | 0.98 | | 0.99 | nd | nd |
| Min | 0.169 | 0.526 | 0.169 | 0.242 | nd | nd |
| Max | 6850 | 432 | 6850 | 432 | nd | nd |
| n (Samp) | 239 | 9 | 239 | 9 | nd | nd |
| n (Patient) | 239 | 9 | 239 | 9 | nd | nd |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 11.8 | 239 | 11.8 | 188 | 11.8 | 112 |
| Average | 63.8 | 500 | 63.8 | 465 | 63.8 | 171 |
| Stdev | 114 | 1050 | 114 | 1090 | 114 | 135 |
| p (t-test) | | 1.3E−5 | | 9.8E−5 | | 0.0028 |
| Min | 0.169 | 38.1 | 0.169 | 38.1 | 0.169 | 38.1 |
| Max | 809 | 4630 | 809 | 4630 | 809 | 432 |
| n (Samp) | 122 | 18 | 122 | 17 | 122 | 12 |
| n (Patient) | 122 | 18 | 122 | 17 | 122 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.82 | 0.62 | 0.89 | 0.78 | 0.57 | 0.86 | 0.80 | nd | 0.82 |
| SE | 0.054 | 0.10 | 0.052 | 0.060 | 0.10 | 0.059 | 0.076 | nd | 0.076 |
| p | 1.8E−9 | 0.24 | 1.2E−13 | 3.5E−6 | 0.47 | 1.1E−9 | 1.1E−4 | nd | 2.8E−5 |
| nCohort 1 | 126 | 239 | 122 | 126 | 239 | 122 | 126 | nd | 122 |
| nCohort 2 | 24 | 9 | 18 | 23 | 9 | 17 | 13 | nd | 12 |
| Cutoff 1 | 59.8 | 19.5 | 181 | 56.8 | 19.5 | 107 | 56.8 | nd | 62.2 |
| Sens 1 | 71% | 78% | 72% | 74% | 78% | 71% | 77% | nd | 75% |
| Spec 1 | 71% | 37% | 91% | 71% | 37% | 82% | 71% | nd | 70% |
| Cutoff 2 | 54.1 | 13.6 | 62.2 | 54.1 | 0.521 | 62.2 | 54.1 | nd | 56.8 |
| Sens 2 | 83% | 89% | 83% | 83% | 89% | 82% | 85% | nd | 83% |
| Spec 2 | 70% | 36% | 70% | 70% | 16% | 70% | 70% | nd | 67% |
| Cutoff 3 | 19.5 | 0.521 | 54.1 | 19.5 | 0.169 | 54.1 | 36.8 | nd | 54.1 |
| Sens 3 | 92% | 100% | 94% | 91% | 100% | 94% | 92% | nd | 92% |
| Spec 3 | 56% | 16% | 66% | 56% | 3% | 66% | 66% | nd | 66% |
| Cutoff 4 | 56.8 | 102 | 65.7 | 56.8 | 102 | 65.7 | 56.8 | nd | 65.7 |
| Sens 4 | 75% | 44% | 78% | 74% | 44% | 76% | 77% | nd | 67% |
| Spec 4 | 71% | 71% | 70% | 71% | 71% | 70% | 71% | nd | 70% |
| Cutoff 5 | 104 | 162 | 104 | 104 | 162 | 104 | 104 | nd | 104 |
| Sens 5 | −62% | 22% | 78% | 61% | 22% | 76% | 54% | nd | 58% |
| Spec 5 | 80% | 80% | 80% | 80% | 80% | 80% | 80% | nd | 80% |
| Cutoff 6 | 181 | 215 | 181 | 181 | 215 | 181 | 181 | nd | 181 |
| Sens 6 | 54% | 22% | 72% | 39% | 22% | 53% | 31% | nd | 42% |
| Spec 6 | 91% | 90% | 91% | 91% | 90% | 91% | 91% | nd | 91% |
| OR Quart 2 | 2.0 | 2.0 | >0 | 0.49 | 0.49 | >0 | >1.0 | nd | >0 |
| p Value | 0.58 | 0.57 | <na | 0.56 | 0.57 | <na | <1.0 | nd | <na |
| 95% CI of | 0.17 | 0.18 | >na | 0.042 | 0.043 | >na | >0.060 | nd | >na |
| OR Quart 2 | 23 | 23 | na | 5.6 | 5.6 | na | na | nd | na |
| OR Quart 3 | 7.0 | 3.1 | >4.5 | 3.4 | 1.5 | >4.4 | >5.7 | nd | >5.9 |
| p Value | 0.080 | 0.33 | <0.19 | 0.15 | 0.65 | <0.20 | <0.12 | nd | <0.11 |
| 95% CI of | 0.79 | 0.31 | >0.48 | 0.64 | 0.25 | >0.46 | >0.63 | nd | >0.65 |
| OR Quart 3 | 61 | 31 | na | 18 | 9.5 | na | na | nd | na |
| OR Quart 4 | 23 | 3.1 | >23 | 10 | 1.5 | >20 | >8.5 | nd | >8.6 |
| p Value | 0.0031 | 0.33 | <0.0033 | 0.0037 | 0.65 | <0.0052 | <0.052 | nd | <0.051 |
| 95% CI of | 2.9 | 0.31 | >2.9 | 2.1 | 0.25 | >2.5 | >0.99 | nd | >0.99 |
| OR Quart 4 | 190 | 31 | na | 49 | 9.5 | na | na | nd | na |

SL cytokine

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.0908 | 0.165 | 0.0908 | 0.113 | 0.0908 | 0.133 |
| Average | 3.01 | 9.23 | 3.01 | 6.42 | 3.01 | 3.90 |
| Stdev | 35.6 | 19.0 | 35.6 | 14.1 | 35.6 | 13.0 |
| p (t-test) | | 0.35 | | 0.60 | | 0.92 |
| Min | 0.0336 | 0.0537 | 0.0336 | 0.0449 | 0.0336 | 0.0336 |
| Max | 527 | 68.6 | 527 | 52.2 | 527 | 52.2 |
| n (Samp) | 223 | 30 | 223 | 30 | 223 | 16 |
| n (Patient) | 223 | 30 | 223 | 30 | 223 | 16 |

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.0908 | 0.154 | 0.0908 | 0.117 | 0.0908 | 0.288 |
| Average | 2.75 | 2.34 | 2.75 | 2.33 | 2.75 | 3.47 |
| Stdev | 28.1 | 5.64 | 28.1 | 5.65 | 28.1 | 5.71 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

|  |  | 0.96 |  | 0.96 |  |  | 0.95 |  |
|---|---|---|---|---|---|---|---|---|
| p (t-test) |  |  |  |  |  |  |  |  |
| Min | 0.0336 | 0.0598 | 0.0336 | 0.0511 | 0.0336 |  | 0.0598 |  |
| Max | 527 | 18.8 | 527 | 18.8 | 527 |  | 13.4 |  |
| n (Samp) | 375 | 13 | 375 | 13 | 375 |  | 7 |  |
| n (Patient) | 375 | 13 | 375 | 13 | 375 |  | 7 |  |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0997 | 0.288 | 0.0997 | 0.0997 | 0.0997 | 0.0891 |
| Average | 3.83 | 12.0 | 3.83 | 8.32 | 3.83 | 4.43 |
| Stdev | 40.4 | 21.0 | 40.4 | 15.7 | 40.4 | 13.9 |
| p (t-test) |  | 0.34 |  | 0.60 |  | 0.96 |
| Min | 0.0336 | 0.0537 | 0.0336 | 0.0449 | 0.0336 | 0.0336 |
| Max | 527 | 68.6 | 527 | 52.2 | 527 | 52.2 |
| n (Samp) | 173 | 23 | 173 | 23 | 173 | 14 |
| n (Patient) | 173 | 23 | 173 | 23 | 173 | 14 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.69 | 0.67 | 0.66 | 0.66 | 0.64 | 0.60 | 0.64 | 0.74 | 0.56 |
| SE | 0.056 | 0.084 | 0.065 | 0.057 | 0.084 | 0.066 | 0.077 | 0.11 | 0.082 |
| p | 8.8E−4 | 0.039 | 0.013 | 0.0049 | 0.091 | 0.11 | 0.060 | 0.029 | 0.44 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 0.0747 | 0.0847 | 0.0747 | 0.0747 | 0.0627 | 0.0627 | 0.0747 | 0.175 | 0.0747 |
| Sens 1 | 77% | 77% | 74% | 73% | 77% | 74% | 75% | 71% | 71% |
| Spec 1 | 42% | 38% | 32% | 42% | 33% | 29% | 42% | 83% | 32% |
| Cutoff 2 | 0.0627 | 0.0627 | 0.0572 | 0.0598 | 0.0598 | 0.0572 | 0.0598 | 0.0598 | 0.0572 |
| Sens 2 | 80% | 85% | 83% | 80% | 85% | 83% | 81% | 86% | 86% |
| Spec 2 | 39% | 33% | 18% | 31% | 26% | 18% | 31% | 26% | 18% |
| Cutoff 3 | 0.0537 | 0.0598 | 0.0527 | 0.0527 | 0.0579 | 0.0527 | 0.0527 | 0.0579 | 0.0527 |
| Sens 3 | 90% | 92% | 100% | 93% | 92% | 96% | 94% | 100% | 93% |
| Spec 3 | 18% | 26% | 13% | 18% | 20% | 13% | 18% | 20% | 13% |
| Cutoff 4 | 0.109 | 0.125 | 0.125 | 0.109 | 0.125 | 0.125 | 0.109 | 0.125 | 0.125 |
| Sens 4 | 53% | 54% | 57% | 50% | 46% | 48% | 50% | 71% | 43% |
| Spec 4 | 73% | 75% | 74% | 73% | 75% | 74% | 73% | 75% | 74% |
| Cutoff 5 | 0.154 | 0.154 | 0.154 | 0.154 | 0.154 | 0.154 | 0.154 | 0.154 | 0.154 |
| Sens 5 | 50% | 46% | 57% | 47% | 46% | 48% | 50% | 71% | 43% |
| Spec 5 | 85% | 80% | 83% | 85% | 80% | 83% | 85% | 80% | 83% |
| Cutoff 6 | 0.188 | 0.288 | 0.188 | 0.188 | 0.288 | 0.188 | 0.188 | 0.288 | 0.188 |
| Sens 6 | 43% | 15% | 52% | 40% | 15% | 43% | 38% | 29% | 36% |
| Spec 6 | 93% | 94% | 94% | 93% | 94% | 94% | 93% | 94% | 94% |
| OR Quart 2 | 2.1 | 3.1 | 1.0 | 1.4 | 1.5 | 0.81 | 1.3 | 0.99 | 1.7 |
| p Value | 0.23 | 0.34 | 1.0 | 0.55 | 0.65 | 0.75 | 0.71 | 0.99 | 0.48 |
| 95% CI of | 0.61 | 0.31 | 0.27 | 0.43 | 0.25 | 0.23 | 0.29 | 0.061 | 0.38 |
| OR Quart 2 | 7.5 | 30 | 3.7 | 4.8 | 9.3 | 2.9 | 6.2 | 16 | 7.6 |
| OR Quart 3 | 0.48 | 2.0 | 0 | 0.79 | 1.0 | 0.15 | 0.32 | 0 | 0 |
| p Value | 0.41 | 0.57 | na | 0.73 | 1.0 | 0.084 | 0.33 | na | na |
| 95% CI of | 0.085 | 0.18 | na | 0.20 | 0.14 | 0.017 | 0.032 | na | na |
| OR Quart 3 | 2.7 | 23 | na | 3.1 | 7.2 | 1.3 | 3.1 | na | na |
| OR Quart 4 | 4.9 | 7.5 | 3.2 | 3.2 | 3.1 | 2.1 | 2.9 | 5.2 | 2.1 |
| p Value | 0.0071 | 0.062 | 0.043 | 0.034 | 0.17 | 0.19 | 0.13 | 0.14 | 0.32 |
| 95% CI of | 1.5 | 0.90 | 1.0 | 1.1 | 0.62 | 0.70 | 0.72 | 0.59 | 0.49 |
| OR Quart 4 | 16 | 62 | 9.8 | 9.7 | 16 | 6.1 | 11 | 45 | 8.9 |

Immunoglobulin G3

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 120 | 321 | 120 | 283 | 120 | 260 |
| Average | 237 | 534 | 237 | 471 | 237 | 401 |
| Stdev | 330 | 447 | 330 | 415 | 330 | 367 |
| p (t-test) |  | 1.5E−5 |  | 5.0E−4 |  | 0.058 |
| Min | 0.833 | 34.7 | 0.833 | 34.7 | 0.833 | 107 |
| Max | 1200 | 1200 | 1200 | 1200 | 1200 | 1200 |
| n (Samp) | 222 | 30 | 222 | 30 | 222 | 16 |
| n (Patient) | 222 | 30 | 222 | 30 | 222 | 16 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 139 | 255 | 139 | 255 | 139 | 255 |
| Average | 286 | 434 | 286 | 426 | 286 | 292 |
| Stdev | 354 | 449 | 354 | 455 | 354 | 130 |
| p (t-test) | | 0.14 | | 0.17 | | 0.97 |
| Min | 0.833 | 34.7 | 0.833 | 34.7 | 0.833 | 107 |
| Max | 1200 | 1200 | 1200 | 1200 | 1200 | 461 |
| n (Samp) | 373 | 13 | 373 | 13 | 373 | 7 |
| n (Patient) | 373 | 13 | 373 | 13 | 373 | 7 |

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 136 | 381 | 136 | 326 | 136 | 251 |
| Average | 250 | 634 | 250 | 557 | 250 | 407 |
| Stdev | 329 | 461 | 329 | 433 | 329 | 392 |
| p (t-test) | | 1.3E−6 | | 7.7E−5 | | 0.092 |
| Min | 0.833 | 107 | 0.833 | 107 | 0.833 | 107 |
| Max | 1200 | 1200 | 1200 | 1200 | 1200 | 1200 |
| n (Samp) | 171 | 23 | 171 | 23 | 171 | 14 |
| n (Patient) | 171 | 23 | 171 | 23 | 171 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.77 | 0.65 | 0.81 | 0.75 | 0.62 | 0.79 | 0.75 | 0.69 | 0.71 |
| SE | 0.052 | 0.084 | 0.056 | 0.053 | 0.084 | 0.058 | 0.072 | 0.11 | 0.080 |
| p | 1.7E−7 | 0.082 | 4.6E−8 | 2.8E−6 | 0.15 | 4.3E−7 | 6.2E−4 | 0.094 | 0.0091 |
| nCohort 1 | 222 | 373 | 171 | 222 | 373 | 171 | 222 | 373 | 171 |
| nCohort 2 | 30 | 13 | 23 | 30 | 13 | 23 | 16 | 7 | 14 |
| Cutoff 1 | 232 | 135 | 263 | 232 | 105 | 235 | 162 | 234 | 163 |
| Sens 1 | 70% | 77% | 74% | 70% | 77% | 74% | 75% | 71% | 71% |
| Spec 1 | 76% | 49% | 76% | 76% | 39% | 73% | 65% | 67% | 60% |
| Cutoff 2 | 138 | 126 | 198 | 135 | 90.6 | 198 | 147 | 210 | 117 |
| Sens 2 | 80% | 85% | 83% | 80% | 85% | 83% | 81% | 86% | 86% |
| Spec 2 | 57% | 46% | 68% | 56% | 35% | 68% | 60% | 65% | 43% |
| Cutoff 3 | 114 | 105 | 117 | 105 | 76.3 | 117 | 112 | 105 | 112 |
| Sens 3 | 90% | 92% | 91% | 90% | 92% | 91% | 94% | 100% | 93% |
| Spec 3 | 49% | 39% | 43% | 46% | 30% | 43% | 49% | 39% | 43% |
| Cutoff 4 | 190 | 266 | 207 | 190 | 266 | 207 | 190 | 266 | 207 |
| Sens 4 | 73% | 46% | 78% | 73% | 46% | 78% | 69% | 43% | 57% |
| Spec 4 | 70% | 70% | 70% | 70% | 70% | 70% | 70% | 70% | 70% |
| Cutoff 5 | 273 | 382 | 280 | 273 | 382 | 280 | 273 | 382 | 280 |
| Sens 5 | 57% | 31% | 70% | 53% | 31% | 61% | 44% | 29% | 43% |
| Spec 5 | 80% | 80% | 80% | 80% | 80% | 80% | 80% | 80% | 80% |
| Cutoff 6 | 792 | 1050 | 747 | 792 | 1050 | 747 | 792 | 1050 | 747 |
| Sens 6 | 30% | 23% | 43% | 23% | 23% | 35% | 19% | 0% | 21% |
| Spec 6 | 90% | 90% | 90% | 90% | 90% | 90% | 90% | 90% | 90% |
| OR Quart 2 | 4.2 | 4.1 | >3.1 | 5.3 | 4.1 | >3.1 | >3.1 | >1.0 | >3.2 |
| p Value | 0.20 | 0.21 | <0.33 | 0.13 | 0.21 | <0.33 | <0.33 | <0.99 | <0.32 |
| 95% CI of | 0.46 | 0.45 | >0.31 | 0.61 | 0.45 | >0.31 | >0.31 | >0.062 | >0.32 |
| OR Quart 2 | 39 | 37 | na | 47 | 37 | na | na | na | na |
| OR Quart 3 | 7.8 | 4.1 | >4.4 | 7.8 | 4.1 | >6.9 | >4.3 | >4.2 | >5.6 |
| p Value | 0.059 | 0.21 | <0.20 | 0.059 | 0.21 | <0.080 | <0.20 | <0.20 | <0.12 |
| 95% CI of | 0.92 | 0.45 | >0.47 | 0.92 | 0.45 | >0.79 | >0.47 | >0.46 | >0.63 |
| OR Quart 3 | 65 | 38 | na | 65 | 38 | na | na | na | na |
| OR Quart | 425 | 4.1 | >23 | 23 | 4.1 | >19 | >10 | >2.0 | >6.7 |
| p Value | 0.0021 | 0.21 | <0.0029 | 0.0028 | 0.21 | <0.0053 | <0.029 | <0.56 | <0.083 |
| 95% CI of | 3.2 | 0.45 | >2.9 | 2.9 | 0.45 | >2.4 | >1.3 | >0.18 | >0.78 |
| OR Quart 4 | 190 | 37 | na | 180 | 37 | na | na | na | na |

Interleukin-1 receptor type I

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 6.06 | 10.3 | 6.06 | 9.31 | 6.06 | 9.18 |
| Average | 6.56 | 13.5 | 6.56 | 12.3 | 6.56 | 8.52 |
| Stdev | 5.40 | 15.1 | 5.40 | 15.1 | 5.40 | 4.28 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | |
|---|---|---|---|---|---|---|
| p (t-test) | | 8.0E−5 | | 0.0011 | | 0.21 |
| Min | 0.0179 | 0.0214 | 0.0179 | 0.0214 | 0.0179 | 0.355 |
| Max | 27.4 | 78.1 | 27.4 | 78.1 | 27.4 | 14.7 |
| n (Samp) | 128 | 24 | 128 | 23 | 128 | 13 |
| n (Patient) | 128 | 24 | 128 | 23 | 128 | 13 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 7.35 | 9.31 | 7.35 | 9.31 | nd | nd |
| Average | 8.27 | 8.70 | 8.27 | 8.38 | nd | nd |
| Stdev | 7.33 | 4.76 | 7.33 | 4.99 | nd | nd |
| p (t-test) | | 0.86 | | 0.96 | nd | nd |
| Min | 0.0179 | 0.0214 | 0.0179 | 0.0214 | nd | nd |
| Max | 78.1 | 16.8 | 78.1 | 16.8 | nd | nd |
| n (Samp) | 242 | 9 | 242 | 9 | nd | nd |
| n (Patient) | 242 | 9 | 242 | 9 | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 6.01 | 12.1 | 6.01 | 10.1 | 6.01 | 9.25 |
| Average | 6.69 | 15.8 | 6.69 | 14.5 | 6.69 | 8.62 |
| Stdev | 5.41 | 16.7 | 5.41 | 17.0 | 5.41 | 4.40 |
| p (t-test) | | 7.8E−6 | | 1.6E−4 | | 0.24 |
| Min | 0.0179 | 3.33 | 0.0179 | 3.33 | 0.0179 | 0.355 |
| Max | 27.4 | 78.1 | 27.4 | 78.1 | 27.4 | 14.7 |
| n (Samp) | 122 | 18 | 122 | 17 | 122 | 12 |
| n (Patient) | 122 | 18 | 122 | 17 | 122 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.73 | 0.58 | 0.78 | 0.69 | 0.56 | 0.75 | 0.65 | nd | 0.66 |
| SE | 0.062 | 0.10 | 0.066 | 0.065 | 0.10 | 0.071 | 0.086 | nd | 0.089 |
| p | 2.2E−4 | 0.42 | 1.9E−5 | 0.0027 | 0.55 | 3.8E−4 | 0.074 | nd | 0.081 |
| nCohort 1 | 128 | 242 | 122 | 128 | 242 | 122 | 128 | nd | 122 |
| nCohort 2 | 24 | 9 | 18 | 23 | 9 | 17 | 13 | nd | 12 |
| Cutoff 1 | 8.18 | 6.39 | 8.90 | 6.56 | 6.39 | 8.18 | 4.81 | nd | 4.81 |
| Sens 1 | 71% | 78% | 72% | 74% | 78% | 71% | 85% | nd | 83% |
| Spec 1 | 70% | 40% | 75% | 55% | 40% | 70% | 45% | nd | 44% |
| Cutoff 2 | 6.39 | 4.41 | 6.56 | 6.39 | 2.67 | 6.56 | 4.81 | nd | 4.81 |
| Sens 2 | 83% | 89% | 83% | 83% | 89% | 82% | 85% | nd | 83% |
| Spec 2 | 52% | 27% | 54% | 52% | 18% | 54% | 45% | nd | 44% |
| Cutoff 3 | 4.41 | 0.0213 | 4.81 | 3.17 | 0.0213 | 4.81 | 3.17 | nd | 3.17 |
| Sens 3 | 92% | 100% | 94% | 91% | 100% | 94% | 92% | nd | 92% |
| Spec 3 | 41% | 2% | 44% | 34% | 2% | 44% | 34% | nd | 30% |
| Cutoff 4 | 8.46 | 9.72 | 8.46 | 8.46 | 9.72 | 8.46 | 8.46 | nd | 8.46 |
| Sens 4 | 67% | 44% | 72% | 57% | 44% | 65% | 54% | nd | 58% |
| Spec 4 | 70% | 71% | 70% | 70% | 71% | 70% | 70% | nd | 70% |
| Cutoff 5 | 10.9 | 11.3 | 10.9 | 10.9 | 11.3 | 10.9 | 10.9 | nd | 10.9 |
| Sens 5 | 46% | 22% | 61% | 35% | 22% | 47% | 38% | nd | 42% |
| Spec 5 | 80% | 80% | 80% | 80% | 80% | 80% | 80% | nd | 80% |
| Cutoff 6 | 13.0 | 14.7 | 13.7 | 13.0 | 14.7 | 13.7 | 13.0 | nd | 13.7 |
| Sens 6 | 29% | 11% | 28% | 22% | 11% | 24% | 15% | nd | 8% |
| Spec 6 | 91% | 90% | 90% | 91% | 90% | 90% | 91% | nd | 90% |
| OR Quart 2 | 5.6 | 2.0 | >3.3 | 4.2 | 0.48 | >3.2 | 3.2 | nd | 3.1 |
| p Value | 0.12 | 0.58 | <0.31 | 0.21 | 0.56 | <0.33 | 0.33 | nd | 0.34 |
| 95% CI of | 0.62 | 0.18 | >0.32 | 0.45 | 0.043 | >0.32 | 0.32 | nd | 0.31 |
| OR Quart 2 | 50 | 23 | na | 40 | 5.5 | na | 32 | nd | 31 |
| OR Quart 3 | 8.4 | 4.1 | >4.5 | 9.6 | 2.0 | >5.7 | 3.2 | nd | 3.2 |
| p Value | 0.053 | 0.21 | <0.19 | 0.038 | 0.42 | <0.12 | 0.33 | nd | 0.33 |
| 95% CI of | 0.97 | 0.45 | >0.48 | 1.1 | 0.36 | >0.63 | 0.32 | nd | 0.32 |
| OR Quart 3 | 72 | 38 | na | 81 | 12 | na | 32 | nd | 32 |
| OR Quart 4 | 15 | 2.0 | >16 | 13 | 0.98 | >12 | 6.8 | nd | 5.5 |
| p Value | 0.012 | 0.58 | <0.010 | 0.018 | 0.99 | <0.023 | 0.084 | nd | 0.13 |
| 95% CI of | 1.8 | 0.18 | >1.9 | 1.6 | 0.13 | >1.4 | 0.77 | nd | 0.61 |
| OR Quart 4 | 120 | 23 | na | 110 | 7.2 | na | 60 | nd | 50 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

Interleukin-29

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 34.9 | 152 | 34.9 | 131 | 34.9 | 114 |
| Average | 81.6 | 192 | 81.6 | 172 | 81.6 | 158 |
| Stdev | 112 | 153 | 112 | 148 | 112 | 141 |
| p (t-test) | | 2.3E−6 | | 9.1E−5 | | 0.010 |
| Min | 0.114 | 19.5 | 0.114 | 19.5 | 0.114 | 14.3 |
| Max | 675 | 635 | 675 | 613 | 675 | 510 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 65.3 | 135 | 65.3 | 107 | 65.3 | 107 |
| Average | 113 | 137 | 113 | 122 | 113 | 88.8 |
| Stdev | 128 | 111 | 128 | 116 | 128 | 67.7 |
| p (t-test) | | 0.51 | | 0.80 | | 0.62 |
| Min | 0.114 | 19.5 | 0.114 | 19.5 | 0.114 | 20.2 |
| Max | 675 | 423 | 675 | 423 | 675 | 204 |
| n (Samp) | 375 | 13 | 375 | 13 | 375 | 7 |
| n (Patient) | 375 | 13 | 375 | 13 | 375 | 7 |

| | 0 hr prior to AKI stage | | 24 hr prior to AKI stage | | 48 hr prior to AK stage | |
|---|---|---|---|---|---|---|
| UO only | Cohort 1 | Cohort 2 | Cohort 1 | Cohort 2 | Cohort 1 | Cohort 2 |
| Median | 69.2 | 194 | 69.2 | 165 | 69.2 | 146 |
| Average | 102 | 237 | 102 | 202 | 102 | 192 |
| Stdev | 112 | 181 | 112 | 158 | 112 | 159 |
| p (t-test) | | 1.4E−6 | | 2.0E−4 | | 0.0060 |
| Min | 0.114 | 25.6 | 0.114 | 25.6 | 0.114 | 14.3 |
| Max | 675 | 635 | 675 | 613 | 675 | 510 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.77 | 0.61 | 0.75 | 0.74 | 0.57 | 0.72 | 0.72 | 0.52 | 0.69 |
| SE | 0.052 | 0.084 | 0.061 | 0.054 | 0.084 | 0.063 | 0.074 | 0.11 | 0.081 |
| p | 3.3E−7 | 0.18 | 3.5E−5 | 8.6E−6 | 0.41 | 5.7E−4 | 0.0026 | 0.84 | 0.017 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 105 | 50.4 | 105 | 72.7 | 29.8 | 77.0 | 72.7 | 29.8 | 95.5 |
| Sens 1 | 70% | 77% | 74% | 70% | 77% | 74% | 75% | 71% | 71% |
| Spec 1 | 71% | 44% | 60% | 65% | 35% | 55% | 65% | 35% | 59% |
| Cutoff 2 | 50.4 | 29.8 | 76.8 | 39.4 | 25.4 | 54.1 | 46.5 | 25.4 | 46.5 |
| Sens 2 | 80% | 85% | 83% | 80% | 85% | 83% | 81% | 86% | 86% |
| Spec 2 | 57% | 35% | 54% | 53% | 33% | 45% | 55% | 33% | 39% |
| Cutoff 3 | 25.6 | 19.5 | 29.8 | 25.6 | 19.5 | 29.8 | 19.5 | 19.5 | 29.8 |
| Sens 3 | 90% | 92% | 91% | 90% | 92% | 91% | 94% | 100% | 93% |
| Spec 3 | 47% | 29% | 33% | 47% | 29% | 33% | 42% | 29% | 33% |
| Cutoff 4 | 105 | 148 | 139 | 105 | 148 | 139 | 105 | 148 | 139 |
| Sens 4 | 70% | 38% | 65% | 60% | 31% | 57% | 62% | 14% | 50% |
| Spec 4 | 70% | 70% | 71% | 70% | 70% | 71% | 70% | 70% | 71% |
| Cutoff 5 | 150 | 211 | 176 | 150 | 211 | 176 | 150 | 211 | 176 |
| Sens 5 | 50% | 15% | 57% | 43% | 15% | 48% | 38% | 0% | 43% |
| Spec 5 | 80% | 80% | 81% | 80% | 80% | 81% | 80% | 80% | 81% |
| Cutoff 6 | 222 | 293 | 218 | 222 | 293 | 218 | 222 | 293 | 218 |
| Sens 6 | 33% | 8% | 43% | 30% | 8% | 39% | 19% | 0% | 29% |
| Spec 6 | 90% | 90% | 90% | 90% | 90% | 90% | 90% | 90% | 90% |
| OR Quart 2 | >6.6 | >5.3 | >4.4 | >7.9 | >6.4 | >5.6 | >3.1 | >3.1 | 2.0 |
| p Value | <0.084 | <0.13 | <0.20 | <0.089 | <0.12 | <0.33 | <0.34 | 0.58 |
| 95% CI of | >0.77 | >0.60 | >0.47 | >0.94 | >0.76 | >0.63 | >0.31 | >0.31 | 0.18 |
| OR Quart 2 | na | na | na | na | na | na | na | na | 23 |
| OR Quart 3 | >7.9 | >5.3 | >6.8 | >10 | >4.2 | >6.8 | >7.8 | >3.1 | 4.2 |
| p Value | <0.057 | <0.13 | <0.081 | <0.028 | <0.21 | <0.081 | <0.059 | <0.33 | 0.21 |
| 95% CI of | >0.94 | >0.60 | >0.79 | >1.3 | >0.46 | >0.79 | >0.93 | >0.32 | 0.45 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| OR Quart 3 | na | na | na | na | na | na | na | na | 39 |
| OR Quart 4 | >23 | >3.1 | >18 | >18 | >3.1 | >16 | >6.6 | >1.0 | 7.9 |
| p Value | <0.0028 | <0.33 | <0.0068 | <0.0064 | <0.33 | <0.0093 | <0.086 | <1.0 | 0.059 |
| 95% CI of | >2.9 | >0.32 | >2.2 | >2.2 | >0.32 | >2.0 | >0.76 | >0.062 | 0.93 |
| OR Quart 4 | na | na | na | na | na | na | na | na | 67 |

Interleukin-7

| | 0 hr prior to AKI stage | | 24 hr prior to AKI stage | | 48 hr prior to AK stage | |
|---|---|---|---|---|---|---|
| sCr or UO | Cohort 1 | Cohort 2 | Cohort 1 | Cohort 2 | Cohort 1 | Cohort 2 |
| Median | 0.0156 | 0.0226 | 0.0156 | 0.0226 | 0.0156 | 0.0226 |
| Average | 0.765 | 1.93 | 0.765 | 1.72 | 0.765 | 0.754 |
| Stdev | 6.07 | 6.21 | 6.07 | 6.06 | 6.07 | 2.49 |
| p (t-test) | | 0.33 | | 0.42 | | 0.99 |
| Min | 0.00316 | 0.00451 | 0.00316 | 0.00316 | 0.00316 | 0.00316 |
| Max | 64.2 | 31.8 | 64.2 | 31.8 | 64.2 | 9.95 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0156 | 0.0226 | 0.0156 | 0.0135 | 0.0156 | 0.0156 |
| Average | 0.745 | 0.989 | 0.745 | 0.833 | 0.745 | 0.924 |
| Stdev | 5.12 | 2.94 | 5.12 | 2.95 | 5.12 | 2.41 |
| p (t-test) | | 0.86 | | 0.95 | | 0.93 |
| Min | 0.00316 | 0.00451 | 0.00316 | 0.00451 | 0.00316 | 0.00316 |
| Max | 64.2 | 10.6 | 64.2 | 10.6 | 64.2 | 6.38 |
| n (Samp) | 375 | 13 | 375 | 13 | 375 | 7 |
| n (Patient) | 375 | 13 | 375 | 13 | 375 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0226 | 0.0226 | 0.0226 | 0.0226 | 0.0226 | 0.0226 |
| Average | 0.659 | 2.44 | 0.659 | 2.24 | 0.659 | 0.859 |
| Stdev | 5.06 | 7.05 | 5.06 | 6.87 | 5.06 | 2.66 |
| p (t-test) | | 0.13 | | 0.18 | | 0.88 |
| Min | 0.00316 | 0.00487 | 0.00316 | 0.00316 | 0.00316 | 0.00316 |
| Max | 64.2 | 31.8 | 64.2 | 31.8 | 64.2 | 9.95 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.54 | 0.50 | 0.55 | 0.43 | 0.49 | 0.55 | 0.43 | 0.47 |
| SE | 0.058 | 0.083 | 0.064 | 0.057 | 0.084 | 0.065 | 0.076 | 0.11 | 0.082 |
| p | 0.15 | 0.60 | 0.96 | 0.36 | 0.40 | 0.88 | 0.54 | 0.52 | 0.72 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 0.0127 | 0.0128 | 0.0107 | 0.0123 | 0.0107 | 0.0107 | 0.0110 | 0.0107 | 0.0110 |
| Sens 1 | 70% | 77% | 74% | 70% | 77% | 74% | 75% | 71% | 71% |
| Spec 1 | 44% | 42% | 18% | 36% | 24% | 18% | 35% | 24% | 23% |
| Cutoff 2 | 0.0107 | 0.0107 | 0.00980 | 0.0107 | 0.00822 | 0.00801 | 0.0107 | 0.00316 | 0.00980 |
| Sens 2 | 80% | 85% | 83% | 80% | 85% | 87% | 81% | 86% | 86% |
| Spec 2 | 28% | 24% | 16% | 28% | 18% | 14% | 28% | 6% | 16% |
| Cutoff 3 | 0.00801 | 0.00822 | 0.00801 | 0.00801 | 0.00451 | 0.00487 | 0.00316 | 0 | 0.00801 |
| Sens 3 | 93% | 92% | 91% | 90% | 92% | 91% | 94% | 100% | 93% |
| Spec 3 | 25% | 18% | 14% | 25% | 10% | 11% | 9% | 0% | 14% |
| Cutoff 4 | 0.0315 | 0.0315 | 0.0423 | 0.0315 | 0.0315 | 0.0423 | 0.0315 | 0.0315 | 0.0423 |
| Sens 4 | 23% | 23% | 26% | 20% | 8% | 26% | 19% | 14% | 21% |
| Spec 4 | 75% | 71% | 76% | 75% | 71% | 76% | 75% | 71% | 76% |
| Cutoff 5 | 0.0423 | 0.0478 | 0.0478 | 0.0423 | 0.0478 | 0.0478 | 0.0423 | 0.0478 | 0.0478 |
| Sens 5 | 23% | 23% | 22% | 20% | 8% | 22% | 19% | 14% | 14% |
| Spec 5 | 82% | 85% | 83% | 82% | 85% | 83% | 82% | 85% | 83% |
| Cutoff 6 | 0.0655 | 0.0655 | 0.0655 | 0.0655 | 0.0655 | 0.0655 | 0.0655 | 0.0655 | 0.0655 |
| Sens 6 | 20% | 23% | 22% | 17% | 8% | 22% | 12% | 14% | 14% |
| Spec 6 | 93% | 91% | 92% | 93% | 91% | 92% | 93% | 91% | 92% |
| OR Quart 2 | 2.1 | 2.0 | 0.64 | 1.9 | 4.1 | 0.64 | 2.6 | 2.0 | 1.0 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| p Value | 0.23 | 0.42 | 0.51 | 0.26 | 0.21 | 0.51 | 0.27 | 0.56 | 1.0 |
| 95% CI of | 0.61 | 0.37 | 0.17 | 0.61 | 0.45 | 0.17 | 0.48 | 0.18 | 0.19 |
| OR Quart 2 | 7.5 | 11 | 2.4 | 6.1 | 38 | 2.4 | 14 | 23 | 5.2 |
| OR Quart 3 | 3.1 | 2.0 | 0.81 | 2.2 | 5.2 | 0.81 | 3.2 | 2.0 | 1.0 |
| p Value | 0.064 | 0.42 | 0.75 | 0.18 | 0.13 | 0.75 | 0.17 | 0.57 | 1.0 |
| 95% CI of | 0.94 | 0.37 | 0.23 | 0.70 | 0.60 | 0.23 | 0.61 | 0.18 | 0.19 |
| OR Quart 3 | 10 | 11 | 2.9 | 6.8 | 46 | 2.9 | 16 | 23 | 5.2 |
| OR Quart 4 | 1.8 | 1.5 | 1.4 | 1.2 | 3.1 | 1.4 | 1.5 | 2.0 | 1.8 |
| p Value | 0.36 | 0.65 | 0.56 | 0.77 | 0.34 | 0.56 | 0.66 | 0.56 | 0.45 |
| 95% CI of | 0.50 | 0.25 | 0.45 | 0.35 | 0.31 | 0.45 | 0.24 | 0.18 | 0.40 |
| OR Quart 4 | 6.5 | 9.3 | 4.4 | 4.2 | 30 | 4.4 | 9.3 | 23 | 8.0 |

Matrix metalloproteinase-9: Metalloproteinase inhibitor 2 complex

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 310 | 24000 | 310 | 24000 | 310 | 24000 |
| Average | 3840 | 14500 | 3840 | 14500 | 3840 | 17500 |
| Stdev | 8130 | 11800 | 8130 | 11800 | 8130 | 11000 |
| p (t-test) | | 9.5E−5 | | 9.5E−5 | | 5.6E−5 |
| Min | 0.227 | 244 | 0.227 | 244 | 0.227 | 705 |
| Max | 24000 | 24000 | 24000 | 24000 | 24000 | 24000 |
| n (Samp) | 98 | 12 | 98 | 12 | 98 | 7 |
| n (Patient) | 98 | 12 | 98 | 12 | 98 | 7 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 415 | 24000 | 415 | 24000 | nd | nd |
| Average | 4500 | 16100 | 4500 | 16100 | nd | nd |
| Stdev | 8770 | 12200 | 8770 | 12200 | nd | nd |
| p (t-test) | | 0.0020 | | 0.0020 | nd | nd |
| Min | 0.227 | 244 | 0.227 | 244 | nd | nd |
| Max | 24000 | 24000 | 24000 | 24000 | nd | nd |
| n (Samp) | 159 | 6 | 159 | 6 | nd | nd |
| n (Patient) | 159 | 6 | 159 | 6 | nd | nd |

| | 0 hr prior to AKI stage | | 24 hr prior to AKI stage | | 48 hr prior to AK stage | |
|---|---|---|---|---|---|---|
| UO only | Cohort 1 | Cohort 2 | Cohort 1 | Cohort 2 | Cohort 1 | Cohort 2 |
| Median | 269 | 24000 | 269 | 24000 | 269 | 24000 |
| Average | 2990 | 15600 | 2990 | 15600 | 2990 | 16500 |
| Stdev | 7090 | 11600 | 7090 | 11600 | 7090 | 11700 |
| p (t-test) | | 1.8E−5 | | 1.8E−5 | | 4.5E−5 |
| Min | 0.227 | 705 | 0.227 | 705 | 0.227 | 705 |
| Max | 24000 | 24000 | 24000 | 24000 | 24000 | 24000 |
| n (Samp) | 85 | 8 | 85 | 8 | 85 | 6 |
| n (Patient) | 85 | 8 | 85 | 8 | 85 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.83 | 0.78 | 0.89 | 0.83 | 0.78 | 0.89 | 0.88 | nd | 0.89 |
| SE | 0.075 | 0.11 | 0.077 | 0.075 | 0.11 | 0.077 | 0.085 | nd | 0.088 |
| P | 1.1E−5 | 0.013 | 3.4E−7 | 1.1E−5 | 0.013 | 3.4E−7 | 6.9E−6 | nd | 8.4E−6 |
| nCohort 1 | 98 | 159 | 85 | 98 | 159 | 85 | 98 | nd | 85 |
| nCohort 2 | 12 | 6 | 8 | 12 | 6 | 8 | 7 | nd | 6 |
| Cutoff 1 | 1610 | 571 | 2030 | 1610 | 571 | 2030 | 12500 | nd | 1610 |
| Sens 1 | 75% | 83% | 75% | 75% | 83% | 75% | 71% | nd | 83% |
| Spec 1 | 80% | 63% | 82% | 80% | 63% | 82% | 87% | nd | 82% |
| Cutoff 2 | 697 | 571 | 1610 | 697 | 571 | 1610 | 1610 | nd | 1610 |
| Sens 2 | 83% | 83% | 88% | 83% | 83% | 88% | 86% | nd | 83% |
| Spec 2 | 70% | 63% | 82% | 70% | 63% | 82% | 80% | nd | 82% |
| Cutoff 3 | 571 | 228 | 697 | 571 | 228 | 697 | 697 | nd | 697 |
| Sens 3 | 92% | 100% | 100% | 92% | 100% | 100% | 100% | nd | 100% |
| Spec 3 | 68% | 38% | 72% | 68% | 38% | 72% | 70% | nd | 72% |
| Cutoff 4 | 697 | 796 | 697 | 697 | 796 | 697 | 697 | nd | 697 |
| Sens 4 | 83% | 67% | 100% | 83% | 67% | 100% | 100% | nd | 100% |
| Spec 4 | 70% | 70% | 71% | 70% | 70% | 71% | 70% | nd | 71% |
| Cutoff 5 | 2130 | 2830 | 1090 | 2130 | 2830 | 1090 | 2130 | nd | 1090 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| Sens 5 | 58% | 67% | 88% | 58% | 67% | 88% | 71% | nd | 83% |
|---|---|---|---|---|---|---|---|---|---|
| Spec 5 | 81% | 81% | 80% | 81% | 81% | 80% | 81% | nd | 80% |
| Cutoff 6 | 24000 | 24000 | 12500 | 24000 | 24000 | 12500 | 24000 | nd | 12500 |
| Sens 6 | 0% | 0% | 62% | 0% | 0% | 62% | 0% | nd | 67% |
| Spec 6 | 100% | 100% | 91% | 100% | 100% | 91% | 100% | nd | 91% |
| OR Quart 2 | >1.0 | >1.0 | >0 | >1.0 | >1.0 | >0 | >0 | nd | >0 |
| p Value | <1.0 | <0.99 | <na | <1.0 | <0.99 | <na | <na | nd | <na |
| 95% CI of | >0.059 | >0.062 | >na | >0.059 | >0.062 | >na | >na | nd | >na |
| OR Quart 2 | na | na | na | na | na | na | na | nd | na |
| OR Quart 3 | >3.4 | >1.0 | >1.0 | >3.4 | >1.0 | >1.0 | >1.0 | nd | >1.0 |
| p Value | <0.31 | <0.99 | <0.98 | <0.31 | <0.99 | <0.98 | <0.98 | nd | <1.0 |
| 95% CI of | >0.33 | >0.062 | >0.062 | >0.33 | >0.062 | >0.062 | >0.062 | nd | >0.059 |
| OR Quart 3 | na | na | na | na | na | na | na | nd | na |
| OR Quart 4 | >11 | >4.3 | >9.5 | >11 | >4.3 | >9.5 | >7.4 | nd | >6.1 |
| p Value | <0.031 | <0.20 | <0.044 | <0.031 | <0.20 | <0.044 | <0.073 | nd | <0.11 |
| 95% CI of | >1.2 | >0.46 | >1.1 | >1.2 | >0.46 | >1.1 | >0.83 | nd | >0.65 |
| OR Quart 4 | na | na | na | na | na | na | na | nd | na |

Platelet-derived growth factor subunit A (dimer)

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 102 | 243 | 102 | 243 | 102 | 226 |
| Average | 175 | 1610 | 175 | 698 | 175 | 250 |
| Stdev | 216 | 4170 | 216 | 1580 | 216 | 187 |
| p (t-test) | | 5.2E−7 | | 4.7E−6 | | 0.18 |
| Min | 0.994 | 22.8 | 0.994 | 14.9 | 0.994 | 29.1 |
| Max | 1830 | 20000 | 1830 | 8310 | 1830 | 730 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 127 | 217 | 127 | 202 | 127 | 232 |
| Average | 221 | 981 | 221 | 944 | 221 | 611 |
| Stdev | 472 | 2740 | 472 | 2750 | 472 | 1070 |
| p (t-test) | | 7.0E−5 | | 1.6E−4 | | 0.036 |
| Min | 0.994 | 22.8 | 0.994 | 14.9 | 0.994 | 101 |
| Max | 8310 | 10100 | 8310 | 10100 | 8310 | 3020 |
| n (Samp) | 374 | 13 | 374 | 13 | 374 | 7 |
| n (Patient) | 374 | 13 | 374 | 13 | 374 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 112 | 300 | 112 | 300 | 112 | 211 |
| Average | 182 | 2050 | 182 | 868 | 182 | 255 |
| Stdev | 201 | 4700 | 201 | 1780 | 201 | 196 |
| p (t-test) | | 3.3E−7 | | 1.8E−6 | | 0.19 |
| Min | 4.08 | 48.3 | 4.08 | 48.3 | 4.08 | 29.1 |
| Max | 1190 | 20000 | 1190 | 8310 | 1190 | 730 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.76 | 0.66 | 0.80 | 0.73 | 0.59 | 0.78 | 0.69 | 0.70 | 0.66 |
| SE | 0.053 | 0.084 | 0.057 | 0.054 | 0.084 | 0.059 | 0.076 | 0.11 | 0.082 |
| p | 5.2E−7 | 0.056 | 1.4E−7 | 1.9E−5 | 0.26 | 1.6E−6 | 0.014 | 0.078 | 0.045 |
| nCohort 1 | 223 | 374 | 173 | 223 | 374 | 173 | 223 | 374 | 173 |
| nCohort 2 | 30 | 13 | 23 | 30 | 13 | 23 | 16 | 7 | 14 |
| Cutoff 1 | 192 | 133 | 209 | 161 | 133 | 192 | 125 | 161 | 161 |
| Sens 1 | 70% | 77% | 74% | 70% | 77% | 74% | 75% | 71% | 71% |
| Spec 1 | 73% | 52% | 72% | 68% | 52% | 71% | 59% | 59% | 64% |
| Cutoff 2 | 135 | 130 | 172 | 125 | 100 | 135 | 113 | 137 | 113 |
| Sens 2 | 80% | 85% | 83% | 80% | 85% | 83% | 81% | 86% | 86% |
| Spec 2 | 63% | 51% | 66% | 59% | 41% | 58% | 55% | 54% | 51% |
| Cutoff 3 | 125 | 100 | 135 | 100 | 35.5 | 116 | 46.0 | 100 | 43.1 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| Sens 3 | 90% | 92% | 91% | 90% | 92% | 91% | 94% | 100% | 93% |
|---|---|---|---|---|---|---|---|---|---|
| Spec 3 | 59% | 41% | 58% | 50% | 13% | 52% | 19% | 41% | 17% |
| Cutoff 4 | 182 | 228 | 192 | 182 | 228 | 192 | 182 | 228 | 192 |
| Sens 4 | 70% | 46% | 78% | 67% | 38% | 74% | 56% | 57% | 57% |
| Spec 4 | 70% | 70% | 71% | 70% | 70% | 71% | 70% | 70% | 71% |
| Cutoff 5 | 251 | 299 | 259 | 251 | 299 | 259 | 251 | 299 | 259 |
| Sens 5 | 50% | 38% | 57% | 50% | 31% | 57% | 44% | 43% | 36% |
| Spec 5 | 80% | 80% | 80% | 80% | 80% | 80% | 80% | 80% | 80% |
| Cutoff 6 | 397 | 438 | 385 | 397 | 438 | 385 | 397 | 438 | 385 |
| Sens 6 | 30% | 15% | 43% | 30% | 8% | 43% | 12% | 14% | 14% |
| Spec 6 | 90% | 90% | 90% | 90% | 90% | 90% | 90% | 90% | 90% |
| OR Quart 2 | 0.49 | 0.99 | 1.0 | 0.32 | 0.49 | 2.0 | 0.48 | >1.0 | 0.48 |
| p Value | 0.57 | 0.99 | 1.0 | 0.33 | 0.56 | 0.57 | 0.56 | <0.99 | 0.55 |
| 95% CI of OR Quart 2 | 0.043 | 0.061 | 0.061 | 0.033 | 0.044 | 0.18 | 0.043 | >0.062 | 0.042 |
|  | 5.6 | 16 | 16 | 3.2 | 5.5 | 23 | 5.5 | na | 5.5 |
| OR Quart 3 | 7.2 | 6.3 | 8.0 | 4.2 | 3.1 | 6.7 | 2.6 | >3.1 | 2.6 |
| p Value | 0.012 | 0.092 | 0.056 | 0.033 | 0.17 | 0.084 | 0.27 | <0.33 | 0.27 |
| 95% CI of OR Quart 3 | 1.5 | 0.74 | 0.95 | 1.1 | 0.61 | 0.77 | 0.48 | >0.32 | 0.48 |
|  | 34 | 53 | 68 | 16 | 16 | 58 | 14 | na | 14 |
| OR Quart 4 | 9.3 | 5.2 | 19 | 6.1 | 2.0 | 19 | 4.4 | >3.1 | 3.2 |
| p Value | 0.0040 | 0.14 | 0.0053 | 0.0061 | 0.42 | 0.0053 | 0.069 | <0.34 | 0.17 |
| 95% CI of OR Quart 4 | 2.0 | 0.59 | 2.4 | 1.7 | 0.36 | 2.4 | 0.89 | >0.31 | 0.61 |
|  | 43 | 45 | 150 | 22 | 11 | 150 | 22 | na | 17 |

Platelet-derived growth factor A

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 4.66 | 23.1 | 4.66 | 21.0 | 4.66 | 18.5 |
| Average | 64.8 | 429 | 64.8 | 424 | 64.8 | 34.9 |
| Stdev | 708 | 1500 | 708 | 1500 | 708 | 65.7 |
| p (t-test) |  | 0.026 |  | 0.028 |  | 0.87 |
| Min | 0.0161 | 0.0450 | 0.0161 | 0.0450 | 0.0161 | 0.0910 |
| Max | 10600 | 6850 | 10600 | 6850 | 10600 | 277 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 7.50 | 23.5 | 7.50 | 19.8 | 7.50 | 19.8 |
| Average | 81.5 | 55.2 | 81.5 | 24.8 | 81.5 | 26.5 |
| Stdev | 634 | 81.2 | 634 | 29.4 | 634 | 32.5 |
| p (t-test) |  | 0.88 |  | 0.75 |  | 0.82 |
| Min | 0.0141 | 0.0910 | 0.0141 | 0.0910 | 0.0141 | 0.0625 |
| Max | 10600 | 280 | 10600 | 103 | 10600 | 90.7 |
| n (Samp) | 374 | 13 | 374 | 13 | 374 | 7 |
| n (Patient) | 374 | 13 | 374 | 13 | 374 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 7.67 | 29.5 | 7.67 | 28.7 | 7.67 | 19.2 |
| Average | 22.7 | 558 | 22.7 | 554 | 22.7 | 38.2 |
| Stdev | 63.9 | 1700 | 63.9 | 1700 | 63.9 | 69.6 |
| p (t-test) |  | 4.2E−5 |  | 4.9E−5 |  | 0.39 |
| Min | 0.0161 | 0.0450 | 0.0161 | 0.0450 | 0.0161 | 5.31 |
| Max | 632 | 6850 | 632 | 6850 | 632 | 277 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.75 | 0.71 | 0.74 | 0.71 | 0.60 | 0.73 | 0.74 | 0.58 | 0.72 |
| SE | 0.054 | 0.082 | 0.062 | 0.055 | 0.084 | 0.062 | 0.073 | 0.11 | 0.079 |
| P | 4.0E−6 | 0.0091 | 9.4E−5 | 1.4E−4 | 0.26 | 2.8E−4 | 9.3E−4 | 0.51 | 0.0047 |
| nCohort 1 | 223 | 374 | 173 | 223 | 374 | 173 | 223 | 374 | 173 |
| nCohort 2 | 30 | 13 | 23 | 30 | 13 | 23 | 16 | 7 | 14 |
| Cutoff 1 | 16.6 | 7.33 | 16.6 | 8.37 | 4.61 | 16.6 | 8.37 | 7.33 | 15.6 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| Sens 1 | 70% | 77% | 74% | 70% | 77% | 74% | 75% | 71% | 71% |
|---|---|---|---|---|---|---|---|---|---|
| Spec 1 | 80% | 50% | 74% | 63% | 41% | 74% | 63% | 50% | 69% |
| Cutoff 2 | 6.68 | 7.03 | 7.33 | 5.22 | 0.756 | 7.33 | 7.33 | 0.0890 | 7.33 |
| Sens 2 | 80% | 85% | 83% | 80% | 85% | 83% | 81% | 86% | 86% |
| Spec 2 | 56% | 48% | 50% | 51% | 19% | 50% | 59% | 10% | 50% |
| Cutoff 3 | 0.756 | 4.61 | 0.756 | 0.0911 | 0.143 | 0.173 | 5.22 | 0.0604 | 6.11 |
| Sens 3 | 90% | 92% | 91% | 90% | 92% | 91% | 94% | 100% | 93% |
| Spec 3 | 21% | 41% | 18% | 17% | 15% | 15% | 51% | 4% | 46% |
| Cutoff 4 | 11.0 | 15.6 | 15.8 | 11.0 | 15.6 | 15.8 | 11.0 | 15.6 | 15.8 |
| Sens 4 | 70% | 69% | 74% | 67% | 54% | 74% | 69% | 57% | 57% |
| Spec 4 | 71% | 70% | 71% | 71% | 70% | 71% | 71% | 70% | 71% |
| Cutoff 5 | 18.3 | 25.7 | 23.8 | 18.3 | 25.7 | 23.8 | 18.3 | 25.7 | 23.8 |
| Sens 5 | 63% | 46% | 52% | 60% | 31% | 52% | 50% | 29% | 36% |
| Spec 5 | 81% | 80% | 80% | 81% | 80% | 80% | 81% | 80% | 80% |
| Cutoff 6 | 31.0 | 52.2 | 37.9 | 31.0 | 52.2 | 37.9 | 31.0 | 52.2 | 37.9 |
| Sens 6 | 43% | 23% | 48% | 33% | 8% | 39% | 19% | 14% | 14% |
| Spec 6 | 90% | 90% | 90% | 90% | 90% | 90% | 90% | 90% | 90% |
| OR Quart 2 | 0.48 | 2.0 | 1.0 | 0.38 | 0.99 | 1.0 | 0.98 | 0 | >3.1 |
| p Value | 0.41 | 0.57 | 1.0 | 0.26 | 0.99 | 1.0 | 0.99 | na | <0.33 |
| 95% CI of | 0.085 | 0.18 | 0.19 | 0.071 | 0.19 | 0.19 | 0.060 | na | >0.31 |
| OR Quart 2 | 2.7 | 22 | 5.2 | 2.0 | 5.0 | 5.2 | 16 | na | na |
| OR Quart 3 | 1.3 | 2.0 | 1.7 | 0.79 | 0.65 | 1.7 | 5.3 | 1.0 | >4.3 |
| p Value | 0.73 | 0.57 | 0.47 | 0.73 | 0.64 | 0.47 | 0.13 | 1.0 | <0.20 |
| 95% CI of | 0.33 | 0.18 | 0.39 | 0.20 | 0.11 | 0.39 | 0.60 | 0.14 | >0.46 |
| OR Quart 3 | 5.0 | 22 | 7.7 | 3.1 | 4.0 | 7.7 | 47 | 7.2 | na |
| OR Quart 4 | 6.2 | 8.5 | 5.0 | 4.9 | 1.7 | 5.0 | 10 | 1.5 | >8.0 |
| p Value | 0.0018 | 0.045 | 0.019 | 0.0033 | 0.48 | 0.019 | 0.030 | 0.66 | <0.056 |
| 95% CI of | 2.0 | 1.0 | 1.3 | 1.7 | 0.39 | 1.3 | 1.3 | 0.24 | >0.95 |
| OR Quart 4 | 20 | 70 | 19 | 14 | 7.3 | 19 | 84 | 9.2 | na |

Thymic stromal lymphopoietin

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 97.9 | 56.6 | 97.9 | 52.9 | 97.9 | 61.5 |
| Average | 127 | 86.5 | 127 | 78.3 | 127 | 85.8 |
| Stdev | 103 | 75.8 | 103 | 74.4 | 103 | 65.4 |
| p (t-test) | | 0.040 | | 0.014 | | 0.12 |
| Min | 0.00642 | 4.01 | 0.00642 | 4.01 | 0.00642 | 23.2 |
| Max | 559 | 356 | 559 | 356 | 559 | 266 |
| n (Samp) | 223 | 30 | 223 | 30 | 223 | 16 |
| n (Patient) | 223 | 30 | 223 | 30 | 223 | 16 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 98.8 | 53.4 | 98.8 | 52.4 | 98.8 | 53.4 |
| Average | 130 | 89.9 | 130 | 78.3 | 130 | 66.8 |
| Stdev | 100 | 89.8 | 100 | 89.5 | 100 | 40.3 |
| p (t-test) | | 0.15 | | 0.067 | | 0.096 |
| Min | 0.00642 | 29.1 | 0.00642 | 17.1 | 0.00642 | 17.1 |
| Max | 559 | 356 | 559 | 356 | 559 | 143 |
| n (Patient) | 375 | 13 | 375 | 13 | 375 | 7 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 112 | 50.7 | 112 | 50.7 | 112 | 48.6 |
| Average | 144 | 73.7 | 144 | 68.8 | 144 | 80.6 |
| Stdev | 121 | 59.4 | 121 | 57.2 | 121 | 68.7 |
| p (t-test) | | 0.0068 | | 0.0038 | | 0.055 |
| Min | 0.0112 | 4.01 | 0.0112 | 4.01 | 0.0112 | 23.2 |
| Max | 695 | 266 | 695 | 266 | 695 | 266 |
| n (Samp) | 173 | 23 | 173 | 23 | 173 | 14 |
| n (Patient) | 173 | 23 | 173 | 23 | 173 | 14 |

TABLE 4-continued

Comparison of the maximum marker levels in urine samples collected from
Cohort 1 (patients that did not progress beyond RIFLE stage 0) and the maximum
values in urine samples collected from subjects between enrollment and 0, 24 hours,
and 48 hours prior to reaching stage F in Cohort 2.

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.36 | 0.34 | 0.29 | 0.32 | 0.28 | 0.26 | 0.37 | 0.29 | 0.30 |
| SE | 0.057 | 0.084 | 0.063 | 0.057 | 0.082 | 0.062 | 0.077 | 0.11 | 0.081 |
| p | 0.017 | 0.053 | 6.7E−4 | 0.0018 | 0.0079 | 1.5E−4 | 0.089 | 0.059 | 0.013 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 45.4 | 39.5 | 40.8 | 42.7 | 34.8 | 40.8 | 45.4 | 51.8 | 40.8 |
| Sens 1 | 70% | 77% | 74% | 70% | 77% | 74% | 75% | 71% | 71% |
| Spec 1 | 17% | 13% | 12% | 15% | 11% | 12% | 17% | 21% | 12% |
| Cutoff 2 | 39.5 | 34.8 | 33.5 | 34.1 | 29.5 | 26.6 | 42.5 | 42.8 | 29.5 |
| Sens 2 | 80% | 85% | 83% | 80% | 85% | 83% | 81% | 86% | 86% |
| Spec 2 | 14% | 11% | 9% | 12% | 9% | 8% | 15% | 14% | 8% |
| Cutoff 3 | 26.6 | 32.8 | 22.5 | 25.8 | 27.3 | 22.5 | 25.0 | 16.8 | 23.2 |
| Sens 3 | 90% | 92% | 91% | 90% | 92% | 91% | 94% | 100% | 93% |
| Spec 3 | 10% | 10% | 7% | 9% | 9% | 7% | 9% | 5% | 7% |
| Cutoff 4 | 150 | 154 | 177 | 150 | 154 | 177 | 150 | 154 | 177 |
| Sens 4 | 13% | 15% | 4% | 10% | 8% | 4% | 12% | 0% | 7% |
| Spec 4 | 70% | 70% | 71% | 70% | 70% | 71% | 70% | 70% | 71% |
| Cutoff 5 | 194 | 200 | 227 | 194 | 200 | 227 | 194 | 200 | 227 |
| Sens 5 | 7% | 8% | 4% | 7% | 8% | 4% | 6% | 0% | 7% |
| Spec 5 | 80% | 80% | 80% | 80% | 80% | 80% | 80% | 80% | 80% |
| Cutoff 6 | 275 | 267 | 288 | 275 | 267 | 288 | 275 | 267 | 288 |
| Sens 6 | 3% | 8% | 0% | 3% | 8% | 0% | 0% | 0% | 0% |
| Spec 6 | 90% | 90% | 90% | 90% | 90% | 90% | 90% | 90% | 90% |
| OR Quart 2 | 2.1 | 2.0 | 4.3 | 0.67 | 1.0 | 2.0 | 1.0 | >1.0 | 2.0 |
| p Value | 0.30 | 0.57 | 0.20 | 0.66 | 1.0 | 0.57 | 1.0 | <0.99 | 0.56 |
| 95% CI of | 0.51 | 0.18 | 0.46 | 0.11 | 0.062 | 0.18 | 0.14 | >0.063 | 0.18 |
| OR Quart 2 | 9.0 | 23 | 40 | 4.1 | 16 | 23 | 7.3 | na | 23 |
| OR Quart 3 | 3.0 | 3.1 | 6.7 | 4.3 | 3.1 | 9.4 | 2.6 | >2.0 | 3.1 |
| p Value | 0.12 | 0.34 | 0.084 | 0.031 | 0.34 | 0.039 | 0.26 | <0.56 | 0.33 |
| 95% CI of | 0.75 | 0.31 | 0.77 | 1.1 | 0.31 | 1.1 | 0.49 | >0.18 | 0.31 |
| OR Quart 3 | 12 | 30 | 58 | 16 | 30 | 78 | 14 | na | 31 |
| OR Quart 4 | 5.3 | 7.5 | 16 | 5.8 | 8.6 | 16 | 3.9 | >4.2 | 9.7 |
| p Value | 0.013 | 0.062 | 0.0098 | 0.0081 | 0.044 | 0.0098 | 0.098 | <0.20 | 0.036 |
| 95% CI of | 1.4 | 0.90 | 1.9 | 1.6 | 1.1 | 1.9 | 0.78 | >0.46 | 1.2 |
| OR Quart 4 | 20 | 62 | 130 | 21 | 70 | 130 | 20 | na | 81 |

TABLE 5

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

C—C motif chemokine 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1.82 | 2.05 | 1.82 | 2.44 | 1.82 | 1.54 |
| Average | 3.15 | 2.28 | 3.15 | 3.93 | 3.15 | 3.71 |
| Stdev | 7.74 | 1.73 | 7.74 | 8.80 | 7.74 | 5.07 |
| p (t-test) | | 0.46 | | 0.61 | | 0.77 |
| Min | 0.00831 | 0.00552 | 0.00831 | 0.00831 | 0.00831 | 0.0143 |
| Max | 62.2 | 8.54 | 62.2 | 57.3 | 62.2 | 18.0 |
| n (Samp) | 93 | 45 | 93 | 42 | 93 | 18 |
| n (Patient) | 64 | 45 | 64 | 42 | 64 | 18 |

| | 0 hr prior to AKI stage | | 24 hr prior to AKI stage | | 48 hr prior to AK stage | |
|---|---|---|---|---|---|---|
| sCr only | Cohort 1 | Cohort 2 | Cohort 1 | Cohort 2 | Cohort 1 | Cohort 2 |
| Median | 1.82 | 2.29 | 1.82 | 2.73 | 1.82 | 2.38 |
| Average | 3.04 | 2.32 | 3.04 | 3.55 | 3.04 | 3.85 |
| Stdev | 6.52 | 2.09 | 6.52 | 3.08 | 6.52 | 4.69 |
| p (t-test) | | 0.68 | | 0.74 | | 0.71 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| | | | | | | | |
|---|---|---|---|---|---|---|---|
| Min | 0.00552 | 0.00552 | 0.00552 | 0.00552 | 0.00552 | 0.0143 | |
| Max | 62.2 | 6.68 | 62.2 | 12.6 | 62.2 | 15.3 | |
| n (Samp) | 224 | 14 | 224 | 18 | 224 | 9 | |
| n (Patient) | 131 | 14 | 131 | 18 | 131 | 9 | |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1.88 | 2.05 | 1.88 | 2.03 | 1.88 | 1.48 |
| Average | 3.17 | 2.20 | 3.17 | 8.81 | 3.17 | 3.16 |
| Stdev | 7.41 | 1.56 | 7.41 | 33.7 | 7.41 | 4.61 |
| p (t-test) | | 0.43 | | 0.11 | | 1.00 |
| Min | 0.00831 | 0.00552 | 0.00831 | 0.00831 | 0.00831 | 0.00831 |
| Max | 62.2 | 8.54 | 62.2 | 212 | 62.2 | 18.0 |
| n (Samp) | 102 | 37 | 102 | 41 | 102 | 15 |
| n (Patient) | 63 | 37 | 63 | 41 | 63 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | 0.50 | 0.53 | 0.58 | 0.64 | 0.55 | 0.55 | 0.59 | 0.50 |
| SE | 0.053 | 0.080 | 0.056 | 0.054 | 0.073 | 0.054 | 0.076 | 0.10 | 0.080 |
| P | 0.35 | 0.97 | 0.63 | 0.13 | 0.050 | 0.34 | 0.48 | 0.37 | 0.96 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 1.32 | 1.06 | 1.33 | 1.10 | 2.13 | 1.10 | 1.26 | 1.29 | 1.12 |
| Sens 1 | 73% | 71% | 70% | 71% | 72% | 71% | 78% | 78% | 73% |
| Spec 1 | 42% | 29% | 41% | 38% | 60% | 36% | 40% | 37% | 37% |
| Cutoff 2 | 1.10 | 0.00552 | 1.12 | 0.855 | 1.10 | 0.939 | 1.12 | 1.26 | 0.784 |
| Sens 2 | 80% | 93% | 81% | 81% | 83% | 80% | 83% | 89% | 80% |
| Spec 2 | 38% | 1% | 37% | 32% | 31% | 32% | 39% | 34% | 31% |
| Cutoff 3 | 0.00883 | 0.00552 | 0.486 | 0.570 | 0.00883 | 0.570 | 0.570 | 0.00883 | 0.00883 |
| Sens 3 | 93% | 93% | 92% | 90% | 94% | 90% | 94% | 100% | 93% |
| Spec 3 | 15% | 1% | 26% | 29% | 11% | 28% | 29% | 11% | 16% |
| Cutoff 4 | 2.66 | 2.75 | 3.13 | 2.66 | 2.75 | 3.13 | 2.66 | 2.75 | 3.13 |
| Sens 4 | 33% | 36% | 16% | 45% | 50% | 32% | 28% | 44% | 27% |
| Spec 4 | 72% | 70% | 71% | 72% | 70% | 71% | 72% | 70% | 71% |
| Cutoff 5 | 3.57 | 3.57 | 3.81 | 3.57 | 3.57 | 3.81 | 3.57 | 3.57 | 3.81 |
| Sens 5 | 20% | 29% | 8% | 24% | 33% | 20% | 22% | 22% | 20% |
| Spec 5 | 81% | 80% | 80% | 81% | 80% | 80% | 81% | 80% | 80% |
| Cutoff 6 | 5.13 | 5.13 | 5.18 | 5.13 | 5.13 | 5.18 | 5.13 | 5.13 | 5.18 |
| Sens 6 | 7% | 14% | 3% | 10% | 17% | 10% | 22% | 22% | 20% |
| Spec 6 | 90% | 90% | 90% | 90% | 90% | 90% | 90% | 90% | 90% |
| OR Quart 2 | 2.3 | 0.47 | 3.0 | 3.9 | 1.5 | 4.3 | 12 | 2.0 | 4.3 |
| p Value | 0.13 | 0.40 | 0.065 | 0.022 | 0.66 | 0.014 | 0.022 | 0.57 | 0.087 |
| 95% CI of | 0.78 | 0.083 | 0.93 | 1.2 | 0.24 | 1.3 | 1.4 | 0.18 | 0.81 |
| OR Quart 2 | 6.7 | 2.7 | 9.8 | 13 | 9.3 | 14 | 110 | 23 | 23 |
| OR Quart 3 | 2.7 | 1.0 | 3.9 | 2.7 | 2.6 | 2.3 | 3.1 | 4.2 | 1.6 |
| p Value | 0.070 | 1.0 | 0.023 | 0.11 | 0.26 | 0.17 | 0.34 | 0.20 | 0.64 |
| 95% CI of | 0.92 | 0.24 | 1.2 | 0.81 | 0.49 | 0.70 | 0.30 | 0.46 | 0.24 |
| OR Quart 3 | 7.9 | 4.2 | 12 | 8.8 | 14 | 7.6 | 32 | 39 | 10 |
| OR Quart 4 | 1.8 | 0.98 | 1.2 | 3.1 | 4.4 | 2.6 | 5.7 | 2.0 | 1.5 |
| p Value | 0.31 | 0.98 | 0.78 | 0.064 | 0.069 | 0.11 | 0.13 | 0.58 | 0.67 |
| 95% CI of | 0.59 | 0.23 | 0.33 | 0.94 | 0.89 | 0.81 | 0.61 | 0.18 | 0.23 |
| OR Quart 4 | 5.3 | 4.1 | 4.4 | 10.0 | 22 | 8.6 | 52 | 23 | 9.7 |

C—C motif chemokine 17

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 14.7 | 19.1 | 14.7 | 19.7 | 14.7 | 21.7 |
| Average | 36.5 | 41.7 | 36.5 | 65.1 | 36.5 | 86.7 |
| Stdev | 48.9 | 70.5 | 48.9 | 156 | 48.9 | 178 |
| p (t-test) | | 0.62 | | 0.11 | | 0.021 |
| Min | 2.05 | 0.0212 | 2.05 | 0.0212 | 2.05 | 1.95 |
| Max | 258 | 438 | 258 | 871 | 258 | 737 |
| n (Samp) | 93 | 45 | 93 | 42 | 93 | 18 |
| n (Patient) | 64 | 45 | 64 | 42 | 64 | 18 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 16.0 | 14.7 | 16.0 | 20.5 | 16.0 | 32.9 |
| Average | 37.5 | 46.5 | 37.5 | 75.9 | 37.5 | 165 |
| Stdev | 74.5 | 75.9 | 74.5 | 132 | 74.5 | 281 |
| p (t-test) | | 0.66 | | 0.051 | | 4.4E−5 |
| Min | 0.0212 | 5.54 | 0.0212 | 1.98 | 0.0212 | 13.2 |
| Max | 737 | 279 | 737 | 438 | 737 | 871 |
| n (Samp) | 224 | 14 | 224 | 18 | 224 | 9 |
| n (Patient) | 131 | 14 | 131 | 18 | 131 | 9 |

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 13.0 | 19.1 | 13.0 | 19.7 | 13.0 | 21.3 |
| Average | 31.3 | 42.2 | 31.3 | 61.2 | 31.3 | 69.9 |
| Stdev | 47.6 | 75.3 | 47.6 | 156 | 47.6 | 186 |
| p (t-test) | | 0.31 | | 0.081 | | 0.079 |
| Min | 2.05 | 0.0212 | 2.05 | 0.0212 | 2.05 | 1.95 |
| Max | 285 | 438 | 285 | 871 | 285 | 737 |
| n (Samp) | 102 | 37 | 102 | 41 | 102 | 15 |
| n (Patient) | 63 | 37 | 63 | 41 | 63 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | 0.52 | 0.57 | 0.52 | 0.55 | 0.58 | 0.58 | 0.73 | 0.56 |
| SE | 0.053 | 0.081 | 0.056 | 0.054 | 0.072 | 0.054 | 0.076 | 0.097 | 0.082 |
| p | 0.63 | 0.81 | 0.22 | 0.64 | 0.50 | 0.13 | 0.32 | 0.017 | 0.50 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 11.0 | 9.29 | 11.2 | 9.69 | 9.66 | 11.0 | 12.7 | 20.0 | 11.0 |
| Sens 1 | 71% | 71% | 70% | 71% | 72% | 71% | 72% | 78% | 73% |
| Spec 1 | 39% | 32% | 46% | 37% | 34% | 46% | 44% | 58% | 46% |
| Cutoff 2 | 7.37 | 7.64 | 6.89 | 7.88 | 5.44 | 9.14 | 9.53 | 19.1 | 9.53 |
| Sens 2 | 80% | 86% | 81% | 81% | 83% | 80% | 83% | 89% | 80% |
| Spec 2 | 27% | 25% | 27% | 29% | 15% | 40% | 35% | 56% | 42% |
| Cutoff 3 | 4.63 | 6.89 | 4.20 | 4.63 | 4.87 | 7.72 | 4.63 | 12.7 | 4.63 |
| Sens 3 | 91% | 93% | 92% | 90% | 94% | 90% | 94% | 100% | 93% |
| Spec 3 | 12% | 23% | 11% | 12% | 12% | 31% | 12% | 44% | 13% |
| Cutoff 4 | 34.4 | 30.7 | 24.4 | 34.4 | 30.7 | 24.4 | 34.4 | 30.7 | 24.4 |
| Sens 4 | 31% | 29% | 38% | 26% | 33% | 39% | 28% | 56% | 33% |
| Spec 4 | 71% | 70% | 71% | 71% | 70% | 71% | 71% | 70% | 71% |
| Cutoff 5 | 54.2 | 42.0 | 38.5 | 54.2 | 42.0 | 38.5 | 54.2 | 42.0 | 38.5 |
| Sens 5 | 22% | 21% | 30% | 17% | 33% | 20% | 22% | 33% | 20% |
| Spec 5 | 81% | 80% | 80% | 81% | 80% | 80% | 81% | 80% | 80% |
| Cutoff 6 | 98.8 | 81.0 | 81.0 | 98.8 | 81.0 | 81.0 | 98.8 | 81.0 | 81.0 |
| Sens 6 | 11% | 21% | 14% | 10% | 17% | 7% | 17% | 33% | 7% |
| Spec 6 | 90% | 90% | 90% | 90% | 90% | 90% | 90% | 90% | 90% |
| OR Quart 2 | 1.3 | 3.2 | 1.3 | 1.5 | 0.37 | 4.4 | 0.96 | >1.0 | 1.4 |
| p Value | 0.65 | 0.17 | 0.61 | 0.46 | 0.25 | 0.020 | 0.96 | <0.99 | 0.69 |
| 95% CI of | 0.45 | 0.61 | 0.43 | 0.51 | 0.069 | 1.3 | 0.18 | >0.062 | 0.28 |
| OR Quart 2 | 3.6 | 16 | 4.1 | 4.4 | 2.0 | 15 | 5.2 | na | 6.8 |
| OR Quart 3 | 1.5 | 1.5 | 1.3 | 1.9 | 1.0 | 4.9 | 2.7 | >5.5 | 1.8 |
| p Value | 0.43 | 0.65 | 0.61 | 0.22 | 1.0 | 0.012 | 0.19 | <0.13 | 0.45 |
| 95% CI of | 0.54 | 0.25 | 0.43 | 0.67 | 0.27 | 1.4 | 0.61 | >0.62 | 0.39 |
| OR Quart 3 | 4.3 | 9.5 | 4.1 | 5.6 | 3.7 | 17 | 12 | na | 8.4 |
| OR Quart 4 | 1.6 | 1.5 | 2.0 | 1.3 | 1.2 | 3.0 | 1.7 | >3.1 | 0.96 |
| p Value | 0.34 | 0.66 | 0.21 | 0.63 | 0.77 | 0.092 | 0.48 | <0.33 | 0.97 |
| 95% CI of | 0.59 | 0.24 | 0.68 | 0.44 | 0.35 | 0.84 | 0.37 | >0.31 | 0.18 |
| OR Quart 4 | 4.6 | 9.3 | 6.0 | 3.9 | 4.2 | 11 | 8.1 | na | 5.2 |

C—C motif chemokine 21

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 414 | 497 | 414 | 597 | 414 | 591 |
| Average | 773 | 712 | 773 | 819 | 773 | 942 |
| Stdev | 1500 | 687 | 1500 | 1020 | 1500 | 858 |
| p (t-test) | | 0.80 | | 0.85 | | 0.64 |

TABLE 5-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

|  |  |  |  |  |  |  |
|---|---|---|---|---|---|---|
| Min | 0.303 | 83.1 | 0.303 | 0.999 | 0.303 | 56.1 |
| Max | 12300 | 3130 | 12300 | 5980 | 12300 | 2860 |
| n (Samp) | 94 | 45 | 94 | 42 | 94 | 18 |
| n (Patient) | 65 | 45 | 65 | 42 | 65 | 18 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 455 | 583 | 455 | 465 | 455 | 337 |
| Average | 677 | 979 | 677 | 1630 | 677 | 823 |
| Stdev | 1090 | 1040 | 1090 | 3760 | 1090 | 971 |
| p (t-test) |  | 0.31 |  | 0.0081 |  | 0.69 |
| Min | 0.303 | 26.8 | 0.303 | 26.8 | 0.303 | 56.1 |
| Max | 12300 | 3130 | 12300 | 16300 | 12300 | 2860 |
| n (Samp) | 225 | 14 | 225 | 18 | 225 | 9 |
| n (Patient) | 132 | 14 | 132 | 18 | 132 | 9 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 425 | 457 | 425 | 602 | 425 | 716 |
| Average | 825 | 616 | 825 | 791 | 825 | 983 |
| Stdev | 1480 | 466 | 1480 | 960 | 1480 | 713 |
| p (t-test) |  | 0.40 |  | 0.89 |  | 0.68 |
| Min | 0.303 | 83.1 | 0.999 | 0.999 | 0.303 | 395 |
| Max | 12300 | 2230 | 12300 | 5980 | 12300 | 2610 |
| n (Samp) | 103 | 37 | 103 | 41 | 103 | 15 |
| n (Patient) | 64 | 37 | 64 | 41 | 64 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.57 | 0.59 | 0.54 | 0.58 | 0.53 | 0.57 | 0.65 | 0.51 | 0.70 |
| SE | 0.053 | 0.082 | 0.056 | 0.054 | 0.072 | 0.054 | 0.075 | 0.099 | 0.079 |
| p | 0.17 | 0.28 | 0.45 | 0.15 | 0.68 | 0.16 | 0.054 | 0.88 | 0.013 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 299 | 339 | 299 | 287 | 168 | 369 | 474 | 247 | 500 |
| Sens 1 | 71% | 71% | 70% | 71% | 72% | 71% | 72% | 78% | 73% |
| Spec 1 | 40% | 40% | 39% | 39% | 19% | 44% | 56% | 28% | 56% |
| Cutoff 2 | 272 | 277 | 272 | 218 | 105 | 231 | 336 | 227 | 497 |
| Sens 2 | 80% | 86% | 81% | 81% | 83% | 80% | 83% | 89% | 80% |
| Spec 2 | 36% | 35% | 32% | 28% | 12% | 28% | 43% | 26% | 56% |
| Cutoff 3 | 227 | 218 | 227 | 62.0 | 61.1 | 168 | 247 | 46.0 | 430 |
| Sens 3 | 91% | 93% | 92% | 90% | 94% | 90% | 94% | 100% | 93% |
| Spec 3 | 29% | 23% | 27% | 13% | 9% | 18% | 31% | 8% | 53% |
| Cutoff 4 | 709 | 716 | 785 | 709 | 716 | 785 | 709 | 716 | 785 |
| Sens 4 | 31% | 29% | 27% | 40% | 33% | 37% | 44% | 33% | 33% |
| Spec 4 | 70% | 71% | 72% | 70% | 71% | 72% | 70% | 71% | 72% |
| Cutoff 5 | 914 | 866 | 933 | 914 | 866 | 933 | 914 | 866 | 933 |
| Sens 5 | 18% | 29% | 16% | 24% | 33% | 22% | 28% | 22% | 33% |
| Spec 5 | 81% | 80% | 81% | 81% | 80% | 81% | 81% | 80% | 81% |
| Cutoff 6 | 1460 | 1210 | 1560 | 1460 | 1210 | 1560 | 1460 | 1210 | 1560 |
| Sens 6 | 9% | 29% | 5% | 12% | 28% | 5% | 22% | 22% | 13% |
| Spec 6 | 90% | 90% | 90% | 90% | 90% | 90% | 90% | 90% | 90% |
| OR Quart 2 | 3.5 | 2.0 | 3.5 | 1.0 | 0.47 | 0.84 | 4.5 | 4.1 | >2.1 |
| p Value | 0.027 | 0.42 | 0.034 | 1.0 | 0.30 | 0.77 | 0.19 | 0.21 | <0.56 |
| 95% CI of | 1.2 | 0.36 | 1.1 | 0.33 | 0.11 | 0.27 | 0.47 | 0.45 | >0.18 |
| OR Quart 2 | 11 | 12 | 11 | 3.1 | 2.0 | -2.6 | 43 | 38 | na |
| OR Quart 3 | 2.4 | 2.0 | 2.1 | 2.0 | 0.47 | 2.2 | 11 | 1.0 | >11 |
| p Value | 0.12 | 0.42 | 0.24 | 0.19 | 0.30 | 0.13 | 0.031 | 1.0 | <0.029 |
| 95% CI of | 0.79 | 0.36 | 0.62 | 0.70 | 0.11 | 0.79 | 1.2 | 0.061 | >1.3 |
| OR Quart 3 | 7.5 | 12 | 7.0 | 5.8 | 2.0 | 6.3 | 93 | 16 | na |
| OR Quart 4 | 2.4 | 2.0 | 2.4 | 2.0 | 0.98 | 1.8 | 5.9 | 3.1 | >5.8 |
| p Value | 0.12 | 0.42 | 0.15 | 0.19 | 0.98 | 0.30 | 0.12 | 0.34 | <0.12 |
| 95% CI of | 0.79 | 0.36 | 0.72 | 0.70 | 0.30 | 0.61 | 0.64 | 0.31 | >0.63 |
| OR Quart 4 | 7.5 | 12 | 7.9 | 5.8 | 3.2 | 5.0 | 54 | 30 | na |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

C—C motif chemokine 27

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 305 | 382 | 305 | 318 | 305 | 387 |
| Average | 373 | 381 | 373 | 333 | 373 | 405 |
| Stdev | 219 | 149 | 219 | 165 | 219 | 138 |
| p (t-test) |  | 0.84 |  | 0.29 |  | 0.55 |
| Min | 29.4 | 88.8 | 29.4 | 36.9 | 29.4 | 144 |
| Max | 973 | 847 | 973 | 855 | 973 | 698 |
| n (Samp) | 94 | 45 | 94 | 42 | 94 | 18 |
| n (Patient) | 65 | 45 | 65 | 42 | 65 | 18 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 328 | 412 | 328 | 338 | 328 | 375 |
| Average | 361 | 452 | 361 | 367 | 361 | 437 |
| Stdev | 190 | 169 | 190 | 175 | 190 | 205 |
| p (t-test) |  | 0.082 |  | 0.90 |  | 0.25 |
| Min | 29.4 | 219 | 29.4 | 164 | 29.4 | 202 |
| Max | 973 | 847 | 973 | 855 | 973 | 935 |
| n (Samp) | 225 | 14 | 225 | 18 | 225 | 9 |
| n (Patient) | 132 | 14 | 132 | 18 | 132 | 9 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 337 | 328 | 337 | 324 | 337 | 400 |
| Average | 407 | 348 | 407 | 333 | 407 | 408 |
| Stdev | 229 | 125 | 229 | 153 | 229 | 150 |
| p (t-test) |  | 0.14 |  | 0.059 |  | 0.99 |
| Min | 29.4 | 88.8 | 29.4 | 36.9 | 29.4 | 144 |
| Max | 973 | 576 | 973 | 812 | 973 | 698 |
| n (Samp) | 103 | 37 | 103 | 41 | 103 | 15 |
| n (Patient) | 64 | 37 | 64 | 41 | 64 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.56 | 0.65 | 0.47 | 0.47 | 0.51 | 0.44 | 0.59 | 0.62 | 0.54 |
| SE | 0.053 | 0.082 | 0.056 | 0.054 | 0.071 | 0.054 | 0.076 | 0.10 | 0.081 |
| p | 0.25 | 0.062 | 0.53 | 0.61 | 0.88 | 0.26 | 0.23 | 0.26 | 0.59 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 287 | 377 | 273 | 221 | 253 | 250 | 347 | 355 | 347 |
| Sens 1 | 71% | 71% | 70% | 71% | 72% | 71% | 72% | 78% | 73% |
| Spec 1 | 46% | 59% | 38% | 29% | 34% | 33% | 55% | 54% | 52% |
| Cutoff 2 | 263 | 296 | 232 | 179 | 220 | 205 | 318 | 322 | 273 |
| Sens 2 | 80% | 86% | 81% | 81% | 83% | 80% | 83% | 89% | 80% |
| Spec 2 | 43% | 43% | 25% | 17% | 24% | 19% | 54% | 49% | 38% |
| Cutoff 3 | 212 | 288 | 195 | 166 | 178 | 166 | 201 | 201 | 230 |
| Sens 3 | 91% | 93% | 92% | 90% | 94% | 90% | 94% | 100% | 93% |
| Spec 3 | 28% | 41% | 17% | 16% | 16% | 13% | 24% | 21% | 25% |
| Cutoff 4 | 484 | 450 | 512 | 484 | 450 | 512 | 484 | 450 | 512 |
| Sens 4 | 24% | 43% | 14% | 14% | 22% | 7% | 22% | 22% | 20% |
| Spec 4 | 70% | 70% | 71% | 70% | 70% | 71% | 70% | 70% | 71% |
| Cutoff 5 | 582 | 507 | 651 | 582 | 507 | 651 | 582 | 507 | 651 |
| Sens 5 | 7% | 21% | 0% | 7% | 22% | 5% | 11% | 22% | 7% |
| Spec 5 | 81% | 80% | 81% | 81% | 80% | 81% | 81% | 80% | 81% |
| Cutoff 6 | 705 | 651 | 739 | 705 | 651 | 739 | 705 | 651 | 739 |
| Sens 6 | 2% | 14% | 0% | 2% | 6% | 2% | 0% | 11% | 0% |
| Spec 6 | 90% | 90% | 90% | 90% | 90% | 90% | 90% | 90% | 90% |
| OR Quart | 22.4 | 2.0 | 3.5 | 4.7 | 1.2 | 5.7 | 1.0 | 0.98 | 1.5 |
| p Value | 0.12 | 0.58 | 0.034 | 0.0065 | 0.75 | 0.0056 | 1.0 | 0.99 | 0.67 |
| 95% CI of | 0.79 | 0.18 | 1.1 | 1.5 | 0.32 | 1.7 | 0.13 | 0.060 | 0.23 |
| OR Quart 2 | 7.5 | 23 | 11 | 14 | 4.9 | 20 | 7.6 | 16 | 9.7 |
| OR Quart 3 | 4.4 | 7.7 | 2.8 | 1.7 | 1.2 | 4.0 | 7.2 | 5.4 | 4.3 |
| p Value | 0.0084 | 0.061 | 0.094 | 0.38 | 0.75 | 0.030 | 0.018 | 0.13 | 0.087 |
| 95% CI of | 1.5 | 0.91 | 0.84 | 0.52 | 0.32 | 1.1 | 1.4 | 0.61 | 0.81 |
| OR Quart 3 | 13 | 64 | 9.0 | 5.4 | 4.9 | 14 | 37 | 48 | 23 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| | | | | | | | | | |
|---|---|---|---|---|---|---|---|---|---|
| OR Quart 4 | 1.9 | 4.1 | 1.8 | 1.9 | 0.98 | 3.1 | 2.2 | 2.0 | 1.5 |
| p Value | 0.29 | 0.21 | 0.36 | 0.26 | 0.98 | 0.083 | 0.40 | 0.58 | 0.67 |
| 95% CI of | 0.59 | 0.45 | 0.52 | 0.62 | 0.23 | 0.86 | 0.36 | 0.18 | 0.23 |
| OR Quart 4 | 5.9 | 38 | 6.1 | 6.1 | 4.1 | 11 | 13 | 23 | 9.7 |

Vascular endothelial growth factor receptor 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 728 | 697 | 728 | 842 | 728 | 1080 |
| Average | 1090 | 1030 | 1090 | 1660 | 1090 | 1720 |
| Stdev | 1460 | 1060 | 1460 | 2770 | 1460 | 1810 |
| p (t-test) | | 0.82 | | 0.11 | | 0.11 |
| Min | 173 | 152 | 173 | 259 | 173 | 206 |
| Max | 12800 | 5940 | 12800 | 15600 | 12800 | 7250 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 765 | 588 | 765 | 1210 | 765 | 829 |
| Average | 1220 | 897 | 1220 | 4510 | 1220 | 801 |
| Stdev | 1680 | 848 | 1680 | 11700 | 1680 | 541 |
| p (t-test) | | 0.48 | | 1.7E−4 | | 0.46 |
| Min | 73.4 | 162 | 73.4 | 152 | 73.4 | 206 |
| Max | 15600 | 3480 | 15600 | 50500 | 15600 | 1930 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 713 | 752 | 713 | 811 | 713 | 1250 |
| Average | 1120 | 2000 | 1120 | 1720 | 1120 | 2010 |
| Stdev | 1450 | 5980 | 1450 | 2820 | 1450 | 1890 |
| p (t-test) | | 0.17 | | 0.092 | | 0.036 |
| Min | 162 | 152 | 162 | 238 | 162 | 403 |
| Max | 12800 | 36800 | 12800 | 15600 | 12800 | 7250 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.43 | 0.50 | 0.58 | 0.61 | 0.56 | 0.64 | 0.43 | 0.71 |
| SE | 0.053 | 0.082 | 0.056 | 0.054 | 0.073 | 0.054 | 0.075 | 0.10 | 0.079 |
| p | 0.85 | 0.37 | 0.96 | 0.16 | 0.12 | 0.28 | 0.055 | 0.50 | 0.0088 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 427 | 481 | 416 | 534 | 662 | 551 | 782 | 388 | 782 |
| Sens 1 | 71% | 71% | 73% | 71% | 72% | 71% | 72% | 78% | 73% |
| Spec 1 | 24% | 26% | 26% | 36% | 42% | 43% | 55% | 19% | 55% |
| Cutoff 2 | 396 | 455 | 386 | 404 | 427 | 404 | 570 | 326 | 685 |
| Sens 2 | 80% | 86% | 81% | 81% | 89% | 80% | 83% | 89% | 80% |
| Spec 2 | 23% | 24% | 25% | 24% | 22% | 26% | 39% | 12% | 50% |
| Cutoff 3 | 296 | 225 | 296 | 356 | 356 | 296 | 380 | 173 | 551 |
| Sens 3 | 91% | 93% | 92% | 90% | 94% | 90% | 94% | 100% | 93% |
| Spec 3 | 13% | 4% | 14% | 17% | 14% | 14% | 23% | 2% | 43% |
| Cutoff 4 | 1050 | 1160 | 1100 | 1050 | 1160 | 1100 | 1050 | 1160 | 1100 |
| Sens 4 | 31% | 29% | 30% | 45% | 50% | 37% | 50% | 11% | 60% |
| Spec 4 | 70% | 70% | 71% | 70% | 70% | 71% | 70% | 70% | 71% |
| Cutoff 5 | 1400 | 1540 | 1580 | 1400 | 1540 | 1580 | 1400 | 1540 | 1580 |
| Sens 5 | 20% | 14% | 19% | 33% | 33% | 27% | 28% | 11% | 40% |
| Spec 5 | 81% | 80% | 81% | 81% | 80% | 81% | 81% | 80% | 81% |
| Cutoff 6 | 2070 | 2390 | 2440 | 2070 | 2390 | 2440 | 2070 | 2390 | 2440 |
| Sens 6 | 11% | 7% | 8% | 14% | 17% | 15% | 22% | 0% | 27% |
| Spec 6 | 90% | 90% | 90% | 90% | 90% | 90% | 90% | 90% | 90% |
| OR Quart 2 | 0.59 | 1.0 | 1.0 | 0.86 | 0.47 | 1.3 | 0.64 | 4.3 | 3.1 |
| p Value | 0.31 | 1.0 | 1.0 | 0.79 | 0.40 | 0.60 | 0.64 | 0.20 | 0.34 |
| 95% CI of | 0.21 | 0.14 | 0.34 | 0.30 | 0.084 | 0.47 | 0.099 | 0.47 | 0.30 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| | | | | | | | | | |
|---|---|---|---|---|---|---|---|---|---|
| OR Quart 2 | 1.6 | 7.3 | 2.9 | 2.5 | 2.7 | 3.7 | 4.2 | 40 | 32 |
| OR Quart 3 | 0.88 | 3.8 | 1.0 | 0.86 | 1.2 | 1.0 | 2.3 | 0 | 5.8 |
| p Value | 0.80 | 0.10 | 1.0 | 0.79 | 0.75 | 1.0 | 0.28 | na | 0.12 |
| 95% CI of | 0.33 | 0.76 | 0.34 | 0.30 | 0.32 | 0.34 | 0.51 | na | 0.64 |
| OR Quart 3 | 2.3 | 19 | 2.9 | 2.5 | 4.9 | 2.9 | 10 | na | 53 |
| OR Quart 4 | 0.81 | 1.6 | 1.2 | 1.7 | 1.8 | 1.5 | 2.8 | 4.3 | 7.0 |
| p Value | 0.68 | 0.64 | 0.79 | 0.31 | 0.36 | 0.44 | 0.17 | 0.20 | 0.081 |
| 95% CI of | 0.30 | 0.25 | 0.40 | 0.61 | 0.50 | 0.54 | 0.64 | 0.47 | 0.79 |
| OR Quart 4 | 2.2 | 9.7 | 3.3 | 4.6 | 6.6 | 4.2 | 12 | 40 | 62 |

SL cytokine

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0696 | 0.0548 | 0.0696 | 0.0696 | 0.0696 | 0.0206 |
| Average | 9.85 | 3.17 | 9.85 | 14.8 | 9.85 | 9.82 |
| Stdev | 43.5 | 10.1 | 43.5 | 52.0 | 43.5 | 38.4 |
| p (t-test) | | 0.31 | | 0.56 | | 1.00 |
| Min | 0.0206 | 0.0206 | 0.0206 | 0.0206 | 0.0206 | 0.0206 |
| Max | 400 | 43.1 | 400 | 294 | 400 | 163 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0548 | 0.0548 | 0.0548 | 0.0696 | 0.0548 | 0.0548 |
| Average | 9.19 | 6.86 | 9.19 | 11.5 | 9.19 | 0.726 |
| Stdev | 39.7 | 15.2 | 39.7 | 26.1 | 39.7 | 2.03 |
| p (t-test) | | 0.83 | | 0.81 | | 0.52 |
| Min | 0.0206 | 0.0206 | 0.0206 | 0.0206 | 0.0206 | 0.0206 |
| Max | 400 | 43.1 | 400 | 101 | 400 | 6.14 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0548 | 0.0548 | 0.0548 | 0.0696 | 0.0548 | 0.0275 |
| Average | 9.80 | 1.27 | 9.80 | 14.3 | 9.80 | 16.2 |
| Stdev | 41.8 | 5.87 | 41.8 | 52.5 | 41.8 | 44.8 |
| p (t-test) | | 0.22 | | 0.59 | | 0.58 |
| Min | 0.0206 | 0.0206 | 0.0206 | 0.0206 | 0.0206 | 0.0206 |
| Max | 400 | 35.4 | 400 | 294 | 400 | 163 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.44 | 0.49 | 0.44 | 0.52 | 0.63 | 0.51 | 0.31 | 0.42 | 0.36 |
| SE | 0.053 | 0.080 | 0.056 | 0.054 | 0.073 | 0.054 | 0.074 | 0.10 | 0.082 |
| p | 0.23 | 0.89 | 0.27 | 0.72 | 0.076 | 0.85 | 0.0098 | 0.44 | 0.097 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.0206 | 0.0206 | 0.0206 | 0.0486 | 0.0486 | 0.0206 | 0 | 0 | 0 |
| Sens 1 | 82% | 86% | 78% | 71% | 89% | 83% | 100% | 100% | 100% |
| Spec 1 | 9% | 16% | 10% | 28% | 35% | 10% | 0% | 0% | 0% |
| Cutoff 2 | 0.0206 | 0.0206 | 0 | 0.0206 | 0.0486 | 0.0206 | 0 | 0 | 0 |
| Sens 2 | 82% | 86% | 100% | 86% | 89% | 83% | 100% | 100% | 100% |
| Spec 2 | 9% | 16% | 0% | 9% | 35% | 10% | 0% | 0% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 0.114 | 0.114 | 0.114 | 0.114 | 0.114 | 0.114 | 0.114 | 0.114 | 0.114 |
| Sens 4 | 13% | 21% | 8% | 26% | 28% | 24% | 22% | 11% | 27% |
| Spec 4 | 80% | 82% | 80% | 80% | 82% | 80% | 80% | 82% | 80% |
| Cutoff 5 | 7.12 | 0.114 | 7.88 | 7.12 | 0.114 | 7.88 | 7.12 | 0.114 | 7.88 |
| Sens 5 | 9% | 21% | 3% | 19% | 28% | 17% | 6% | 11% | 13% |
| Spec 5 | 81% | 82% | 81% | 81% | 82% | 81% | 81% | 82% | 81% |
| Cutoff 6 | 21.6 | 15.2 | 26.5 | 21.6 | 15.2 | 26.5 | 21.6 | 15.2 | 26.5 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| | | | | | | | | | |
|---|---|---|---|---|---|---|---|---|---|
| Sens 6 | 7% | 14% | 3% | 12% | 22% | 7% | 6% | 0% | 13% |
| Spec 6 | 90% | 90% | 90% | 90% | 90% | 90% | 90% | 90% | 90% |
| OR Quart 2 | 1.3 | 1.4 | 7.1 | 1.0 | 2.0 | 1.3 | 0.46 | 1.0 | 0.23 |
| p Value | 0.60 | 0.70 | 0.0048 | 1.0 | 0.42 | 0.59 | 0.40 | 0.99 | 0.20 |
| 95% CI of | 0.47 | 0.29 | 1.8 | 0.35 | 0.36 | 0.46 | 0.077 | 0.14 | 0.024 |
| OR Quart 2 | 3.8 | 6.3 | 28 | 2.8 | 12 | 3.9 | 2.8 | 7.5 | 2.2 |
| OR Quart 3 | 1.3 | 0.32 | 4.9 | 1.1 | 2.0 | 2.0 | 0.46 | 1.0 | 0.46 |
| p Value | 0.60 | 0.33 | 0.024 | 0.79 | 0.42 | 0.20 | 0.40 | 1.0 | 0.40 |
| 95% CI of | 0.47 | 0.033 | 1.2 | 0.41 | 0.36 | 0.70 | 0.077 | 0.14 | 0.078 |
| OR Quart 3 | 3.8 | 3.2 | 19 | 3.2 | 12 | 5.6 | 2.8 | 7.3 | 2.8 |
| OR Quart 4 | 2.0 | 2.2 | 3.7 | 1.1 | 4.4 | 1.3 | 3.3 | 1.6 | 2.5 |
| p Value | 0.18 | 0.30 | 0.068 | 0.79 | 0.069 | 0.59 | 0.072 | 0.64 | 0.18 |
| 95% CI of | 0.73 | 0.51 | 0.91 | 0.41 | 0.89 | 0.46 | 0.90 | 0.25 | 0.65 |
| OR Quart 4 | 5.6 | 9.0 | 15 | 3.2 | 22 | 3.9 | 12 | 9.7 | 9.4 |

Immunoglogulin G3

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 557000 | 488000 | 557000 | 556000 | 557000 | 448000 |
| Average | 704000 | 651000 | 704000 | 838000 | 704000 | 762000 |
| Stdev | 520000 | 439000 | 520000 | 701000 | 520000 | 812000 |
| p (t-test) | | 0.59 | | 0.23 | | 0.75 |
| Min | 94000 | 231000 | 94000 | 161000 | 94000 | 248000 |
| Max | 2920000 | 2310000 | 2920000 | 3750000 | 2920000 | 2930000 |
| n (Samp) | 94 | 35 | 94 | 37 | 94 | 10 |
| n (Patient) | 67 | 35 | 67 | 37 | 67 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 559000 | 546000 | 559000 | 976000 | nd | nd |
| Average | 688000 | 722000 | 688000 | 1020000 | nd | nd |
| Stdev | 471000 | 597000 | 471000 | 623000 | nd | nd |
| p (t-test) | | 0.82 | | 0.056 | nd | nd |
| Min | 94000 | 243000 | 94000 | 280000 | nd | nd |
| Max | 2930000 | 2310000 | 2930000 | 2090000 | nd | nd |
| n (Samp) | 205 | 10 | 205 | 8 | nd | nd |
| n (Patient) | 126 | 10 | 126 | 8 | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 526000 | 498000 | 526000 | 553000 | 526000 | 472000 |
| Average | 679000 | 635000 | 679000 | 804000 | 679000 | 867000 |
| Stdev | 492000 | 370000 | 492000 | 680000 | 492000 | 867000 |
| p (t-test) | | 0.66 | | 0.24 | | 0.26 |
| Min | 94000 | 231000 | 94000 | 161000 | 94000 | 248000 |
| Max | 2920000 | 1790000 | 2920000 | 3750000 | 2920000 | 2930000 |
| n (Samp) | 101 | 28 | 101 | 36 | 101 | 12 |
| n (Patient) | 65 | 28 | 65 | 36 | 65 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | 0.50 | 0.50 | 0.56 | 0.67 | 0.56 | 0.45 | nd | 0.50 |
| SE | 0.058 | 0.094 | 0.062 | 0.057 | 0.11 | 0.057 | 0.098 | nd | 0.089 |
| P | 0.75 | 0.98 | 0.95 | 0.30 | 0.11 | 0.29 | 0.63 | nd | 0.99 |
| nCohort 1 | 94 | 205 | 101 | 94 | 205 | 101 | 94 | nd | 101 |
| nCohort 2 | 35 | 10 | 28 | 37 | 8 | 36 | 10 | nd | 12 |
| Cutoff 1 | 396000 | 458000 | 396000 | 447000 | 514000 | 428000 | 385000 | nd | 385000 |
| Sens 1 | 71% | 70% | 71% | 70% | 75% | 72% | 70% | nd | 75% |
| Spec 1 | 32% | 38% | 32% | 37% | 44% | 37% | 30% | nd | 30% |
| Cutoff 2 | 365000 | 372000 | 339000 | 396000 | 436000 | 386000 | 339000 | nd | 339000 |
| Sens 2 | 80% | 80% | 82% | 81% | 88% | 81% | 80% | nd | 83% |
| Spec 2 | 26% | 25% | 21% | 32% | 37% | 30% | 19% | nd | 21% |
| Cutoff 3 | 334000 | 365000 | 312000 | 342000 | 277000 | 342000 | 249000 | nd | 249000 |
| Sens 3 | 91% | 90% | 93% | 92% | 100% | 92% | 90% | nd | 92% |
| Spec 3 | 18% | 24% | 17% | 19% | 9% | 21% | 7% | nd | 7% |
| Cutoff 4 | 755000 | 765000 | 745000 | 755000 | 765000 | 745000 | 755000 | nd | 745000 |
| Sens 4 | 26% | 20% | 32% | 35% | 62% | 33% | 20% | nd | 25% |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| | | | | | | | | | |
|---|---|---|---|---|---|---|---|---|---|
| Spec 4 | 70% | 70% | 70% | 70% | 70% | 70% | 70% | nd | 70% |
| Cutoff 5 | 943000 | 931000 | 917000 | 943000 | 931000 | 917000 | 943000 | nd | 917000 |
| Sens 5 | 14% | 20% | 21% | 27% | 50% | 28% | 20% | nd | 25% |
| Spec 5 | 81% | 80% | 80% | 81% | 80% | 80% | 81% | nd | 80% |
| Cutoff 6 | 1410000 | 1260000 | 1300000 | 1410000 | 1260000 | 1300000 | 1410000 | nd | 1300000 |
| Sens 6 | 9% | 10% | 7% | 14% | 25% | 11% | 10% | nd | 17% |
| Spec 6 | 90% | 90% | 90% | 90% | 90% | 90% | 90% | nd | 90% |
| OR Quart 2 | 1.0 | 1.5 | 0.72 | 4.0 | 2.0 | 2.2 | 1.0 | nd | 1.4 |
| p Value | 0.94 | 0.65 | 0.59 | 0.022 | 0.57 | 0.17 | 1.0 | nd | 0.69 |
| 95% CI of | 0.34 | 0.25 | 0.22 | 1.2 | 0.18 | 0.72 | 0.13 | nd | 0.28 |
| OR Quart 2 | 3.2 | 9.5 | 2.4 | 13 | 23 | 7.0 | 7.7 | nd | 6.9 |
| OR Quart 3 | 1.6 | 1.5 | 0.88 | 1.2 | 0 | 1.4 | 1.6 | nd | 0.64 |
| p Value | 0.37 | 0.65 | 0.82 | 0.78 | na | 0.55 | 0.64 | nd | 0.64 |
| 95% CI of | 0.56 | 0.25 | 0.28 | 0.33 | na | 0.44 | 0.24 | nd | 0.099 |
| OR Quart 3 | 4.8 | 9.5 | 2.8 | 4.4 | na | 4.7 | 10 | nd | 4.2 |
| OR Quart 4 | 1.0 | 1.0 | 0.88 | 3.1 | 5.3 | 2.1 | 1.6 | nd | 0.96 |
| p Value | 0.94 | 0.98 | 0.82 | 0.063 | 0.13 | 0.19 | 0.64 | nd | 0.96 |
| 95% CI of | 0.34 | 0.14 | 0.28 | 0.94 | 0.60 | 0.69 | 0.24 | nd | 0.18 |
| OR Quart 4 | 3.2 | 7.5 | 2.8 | 10 | 47 | 6.7 | 10 | nd | 5.2 |

Interleukin-1 receptor type I

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 60.2 | 66.7 | 60.2 | 65.8 | 60.2 | 55.2 |
| Average | 69.6 | 75.1 | 69.6 | 71.0 | 69.6 | 63.4 |
| Stdev | 58.4 | 47.2 | 58.4 | 27.8 | 58.4 | 25.8 |
| p (t-test) | | 0.58 | | 0.88 | | 0.66 |
| Min | 25.4 | 27.1 | 25.4 | 25.8 | 25.4 | 37.7 |
| Max | 502 | 322 | 502 | 197 | 502 | 141 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 63.6 | 61.0 | 63.6 | 66.8 | 63.6 | 56.0 |
| Average | 71.5 | 76.6 | 71.5 | 83.7 | 71.5 | 63.7 |
| Stdev | 47.6 | 41.0 | 47.6 | 39.0 | 47.6 | 30.2 |
| p (t-test) | | 0.69 | | 0.29 | | 0.63 |
| Min | 25.4 | 47.2 | 25.4 | 50.9 | 25.4 | 37.7 |
| Max | 502 | 200 | 502 | 197 | 502 | 141 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 62.9 | 66.7 | 62.9 | 63.9 | 62.9 | 56.8 |
| Average | 75.8 | 72.8 | 75.8 | 66.0 | 75.8 | 63.7 |
| Stdev | 63.2 | 46.4 | 63.2 | 19.9 | 63.2 | 19.1 |
| p (t-test) | | 0.79 | | 0.33 | | 0.46 |
| Min | 29.0 | 27.1 | 29.0 | 25.8 | 29.0 | 38.7 |
| Max | 502 | 322 | 502 | 123 | 502 | 93.4 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.53 | 0.53 | 0.59 | 0.62 | 0.50 | 0.47 | 0.41 | 0.47 |
| SE | 0.053 | 0.081 | 0.056 | 0.054 | 0.073 | 0.054 | 0.075 | 0.10 | 0.081 |
| p | 0.17 | 0.68 | 0.62 | 0.083 | 0.086 | 0.93 | 0.72 | 0.36 | 0.75 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 53.0 | 53.4 | 53.0 | 58.6 | 60.2 | 51.6 | 49.0 | 51.0 | 50.1 |
| Sens 1 | 71% | 71% | 70% | 71% | 72% | 73% | 72% | 78% | 73% |
| Spec 1 | 33% | 31% | 28% | 49% | 44% | 27% | 27% | 27% | 26% |
| Cutoff 2 | 49.9 | 50.1 | 49.0 | 52.9 | 57.0 | 50.0 | 43.5 | 49.0 | 44.9 |
| Sens 2 | 80% | 86% | 81% | 81% | 83% | 80% | 83% | 89% | 80% |
| Spec 2 | 27% | 26% | 22% | 33% | 41% | 25% | 19% | 23% | 18% |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| Cutoff 3 | 44.9 | 49.9 | 44.2 | 49.0 | 53.8 | 47.4 | 38.2 | 36.5 | 39.9 |
|---|---|---|---|---|---|---|---|---|---|
| Sens 3 | 91% | 93% | 92% | 90% | 94% | 90% | 94% | 100% | 93% |
| Spec 3 | 23% | 24% | 17% | 27% | 32% | 21% | 13% | 8% | 11% |
| Cutoff 4 | 71.3 | 74.1 | 74.1 | 71.3 | 74.1 | 74.1 | 71.3 | 74.1 | 74.1 |
| Sens 4 | 40% | 36% | 32% | 36% | 33% | 32% | 28% | 11% | 40% |
| Spec 4 | 70% | 70% | 71% | 70% | 70% | 71% | 70% | 70% | 71% |
| Cutoff 5 | 81.6 | 86.3 | 84.4 | 81.6 | 86.3 | 84.4 | 81.6 | 86.3 | 84.4 |
| Sens 5 | 27% | 14% | 22% | 21% | 28% | 20% | 17% | 11% | 20% |
| Spec 5 | 81% | 80% | 81% | 81% | 80% | 81% | 81% | 80% | 81% |
| Cutoff 6 | 88.2 | 96.4 | 93.5 | 88.2 | 96.4 | 93.5 | 88.2 | 96.4 | 93.5 |
| Sens 6 | 18% | 14% | 14% | 14% | 28% | 7% | 17% | 11% | 0% |
| Spec 6 | 90% | 91% | 90% | 90% | 91% | 90% | 90% | 91% | 90% |
| OR Quart 2 | 1.3 | 2.6 | 1.0 | 2.2 | 6.4 | 1.2 | 0.35 | 1.0 | 1.4 |
| p Value | 0.65 | 0.27 | 1.0 | 0.17 | 0.089 | 0.79 | 0.24 | 0.99 | 0.65 |
| 95% CI of | 0.45 | 0.48 | 0.33 | 0.72 | 0.75 | 0.40 | 0.063 | 0.062 | 0.29 |
| OR Quart 2 | 3.6 | 14 | 3.1 | 7.0 | 55 | 3.3 | 2.0 | 17 | 7.1 |
| OR Quart 3 | 1.3 | 1.5 | 1.8 | 2.9 | 6.4 | 1.7 | 1.3 | 5.4 | 1.4 |
| p Value | 0.65 | 0.66 | 0.29 | 0.064 | 0.089 | 0.31 | 0.74 | 0.13 | 0.69 |
| 95% CI of | 0.45 | 0.24 | 0.61 | 0.94 | 0.75 | 0.61 | 0.33 | 0.61 | 0.28 |
| OR Quart 3 | 3.6 | 9.3 | 5.0 | 8.9 | 55 | 4.7 | 4.7 | 47 | 6.8 |
| OR Quart 4 | 1.9 | 2.0 | 1.2 | 2.5 | 5.3 | 1.0 | 1.0 | 2.1 | 1.4 |
| p Value | 0.24 | 0.42 | 0.78 | 0.10 | 0.13 | 1.0 | 1.0 | 0.56 | 0.65 |
| 95% CI of | 0.67 | 0.36 | 0.39 | 0.82 | 0.60 | 0.34 | 0.25 | 0.18 | 0.29 |
| OR Quart 4 | 5.1 | 12 | 3.5 | 7.9 | 47 | 2.9 | 3.9 | 23 | 7.1 |

Interleukin-20

| | 0 hr prior to AKI stage | | 24 hr prior to AKI stage | | 48 hr prior to AKI stage | |
|---|---|---|---|---|---|---|
| sCr orUO | Cohort 1 | Cohort 2 | Cohort 1 | Cohort 2 | Cohort 1 | Cohort 2 |
| Median | 5.54 | 12.1 | 5.54 | 12.1 | 5.54 | 58.1 |
| Average | 159 | 69.7 | 159 | 67:1 | 159 | 115 |
| Stdev | 895 | 174 | 895 | 138 | 895 | 252 |
| p (t-test) | | 0.51 | | 0.51 | | 0.84 |
| Min | 0.990 | 0.990 | 0.990 | 0.990 | 0.990 | 0.990 |
| Max | 8230 | 1090 | 8230 | 732 | 8230 | 1100 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 5.54 | 8.82 | 5.54 | 14.9 | 5.54 | 37.9 |
| Average | 97.2 | 116 | 97.2 | 137 | 97.2 | 163 |
| Stdev | 583 | 285 | 583 | 277 | 583 | 354 |
| p (t-test) | | 0.91 | | 0.77 | | 0.74 |
| Min | 0.990 | 0.990 | 0.990 | 0.990 | 0.990 | 0.990 |
| Max | 8230 | 1090 | 8230 | 1000 | 8230 | 1100 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3.83 | 5.54 | 3.83 | 12.1 | 3.83 | 50.0 |
| Average | 144 | 46.4 | 144 | 45.5 | 144 | 51.3 |
| Stdev | 856 | 81.4 | 856 | 85.1 | 856 | 55.3 |
| p (t-test) | | 0.49 | | 0.46 | | 0.68 |
| Min | 0.990 | 0.990 | 0.990 | 0.990 | 0.990 | 0.990 |
| Max | 8230 | 412 | 8230 | 504 | 8230 | 192 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | 0.53 | 0.53 | 0.57 | 0.62 | 0.58 | 0.66 | 0.64 | 0.64 |
| SE | 0.053 | 0.081 | 0.056 | 0.054 | 0.073 | 0.054 | 0.075 | 0.10 | 0.081 |
| p | 0.81 | 0.70 | 0.60 | 0.19 | 0.098 | 0.15 | 0.030 | 0.16 | 0.081 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.990 | 0.990 | 0.990 | 3.83 | 6.98 | 3.83 | 5.54 | 6.98 | 3.83 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| Sens 1 | 78% | 86% | 78% | 74% | 72% | 71% | 72% | 78% | 80% |
|---|---|---|---|---|---|---|---|---|---|
| Spec 1 | 20% | 19% | 21% | 48% | 52% | 51% | 54% | 52% | 51% |
| Cutoff 2 | 0 | 0.990 | 0 | 0.990 | 3.83 | 0.990 | 3.83 | 3.83 | 3.83 |
| Sens 2 | 100% | 86% | 100% | 88% | 83% | 90% | 89% | 89% | 80% |
| Spec 2 | 0% | 19% | 0% | 20% | 43% | 21% | 48% | 43% | 51% |
| Cutoff 3 | 0 | 0 | 0 | 0 | 0 | 0.990 | 2.41 | 0 | 0.990 |
| Sens 3 | 100% | 100% | 100% | 100% | 100% | 90% | 94% | 100% | 93% |
| Spec 3 | 0% | 0% | 0% | 0% | 0% | 21% | 39% | 0% | 21% |
| Cutoff 4 | 50.0 | 50.0 | 45.2 | 50.0 | 50.0 | 45.2 | 50.0 | 50.0 | 45.2 |
| Sens 4 | 31% | 43% | 30% | 31% | 33% | 34% | 56% | 44% | 53% |
| Spec 4 | 72% | 71% | 71% | 72% | 71% | 71% | 72% | 71% | 71% |
| Cutoff 5 | 99.9 | 99.9 | 99.9 | 99.9 | 99.9 | 99.9 | 99.9 | 99.9 | 99.9 |
| Sens 5 | 13% | 21% | 16% | 14% | 28% | 10% | 22% | 22% | 13% |
| Spec 5 | 84% | 82% | 82% | 84% | 82% | 82% | 84% | 82% | 82% |
| Cutoff 6 | 150 | 150 | 141 | 150 | 150 | 141 | 150 | 150 | 141 |
| Sens 6 | 11% | 14% | 8% | 10% | 17% | 5% | 11% | 11% | 7% |
| Spec 6 | 90% | 90% | 90% | 90% | 90% | 90% | 90% | 90% | 90% |
| OR Quart 2 | 0.84 | 1.3 | 0.86 | 1.6 | 1.5 | 1.4 | 4.5 | 0.98 | 0.96 |
| p Value | 0.73 | 0.71 | 0.78 | 0.40 | 0.66 | 0.57 | 0.19 | 0.99 | 0.97 |
| 95% CI of | 0.30 | 0.29 | 0.29 | 0.53 | 0.24 | 0.45 | 0.47 | 0.060 | 0.13 |
| OR Quart 2 | 2.3 | 6.2 | 2.6 | 4.9 | 9.3 | 4.2 | 43 | 16 | 7.3 |
| OR Quart 3 | 1.4 | 0.98 | 1.2 | 3.4 | 4.4 | 2.6 | 13 | 4.2 | 3.5 |
| p Value | 0.51 | 0.98 | 0.79 | 0.024 | 0.069 | 0.074 | 0.020 | 0.20 | 0.15 |
| 95% CI of | 0.52 | 0.19 | 0.40 | 1.2 | 0.89 | 0.91 | 1.5 | 0.46 | 0.65 |
| OR Quart 3 | 33 | 5.1 | 3.3 | 10.0 | 22 | 7.6 | 110 | 39 | 19 |
| OR Quart 4 | 0.84 | 1.3 | 1.2 | 1.4 | 2.6 | 1.8 | 4.5 | 3.1 | 2.7 |
| p Value | 0.73 | 0.71 | 0.79 | 0.57 | 0.27 | 0.28 | 0.19 | 0.34 | 0.26 |
| 95% CI of | 0.30 | 0.29 | 0.40 | 0.45 | 0.48 | 0.61 | 0.47 | 0.31 | 0.48 |
| OR Quart 4 | 2.3 | 6.2 | 3.3 | 4.3 | 14 | 5.4 | 43 | 30 | 15 |

Interleukin-29

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 20.7 | 52.7 | 20.7 | 36.3 | 20.7 | 79.8 |
| Average | 251 | 140 | 251 | 72.7 | 251 | 131 |
| Stdev | 1320 | 466 | 1320 | 91.8 | 1320 | 175 |
| p (t-test) | | 0.59 | | 0.38 | | 0.70 |
| Min | 0.690 | 0.690 | 0.690 | 0.690 | 0.690 | 1.31 |
| Max | 10500 | 3150 | 10500 | 412 | 10500 | 735 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 25.8 | 62.9 | 25.8 | 113 | 25.8 | 134 |
| Average | 146 | 295 | 146 | 701 | 146 | 188 |
| Stdev | 857 | 826 | 857 | 2430 | 857 | 227 |
| p (t-test) | | 0.53 | | 0.032 | | 0.88 |
| Min | 0.690 | 0.690 | 0.690 | 0.690 | 0.690 | 0.690 |
| Max | 10500 | 3150 | 10500 | 10400 | 10500 | 735 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 20.7 | 52.7 | 20.7 | 49.5 | 20.7 | 59.3 |
| Average | 235 | 68.3 | 235 | 116 | 235 | 75.2 |
| Stdev | 1260 | 76.8 | 1260 | 249 | 1260 | 68.7 |
| p (t-test) | | 0.42 | | 0.55 | | 0.62 |
| Min | 0.690 | 0.690 | 0.690 | 0.690 | 0.690 | 1.31 |
| Max | 10500 | 379 | 10500 | 1520 | 10500 | 276 |
| n (Samp) | 103 | 37 | 103 | 41 | 103 | 15 |
| n (Patient) | 64 | 37 | 64 | 41 | 64 | 15 |

TABLE 5-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.59 | 0.58 | 0.57 | 0.55 | 0.68 | 0.57 | 0.71 | 0.70 | 0.67 |
| SE | 0.053 | 0.082 | 0.056 | 0.054 | 0.072 | 0.054 | 0.072 | 0.100 | 0.080 |
| p | 0.080 | 0.35 | 0.19 | 0.34 | 0.010 | 0.20 | 0.0032 | 0.050 | 0.030 |
| nCohort 1 | 94 | 225 | 103 | 94 | 225 | 103 | 94 | 225 | 103 |
| nCohort | 2 45 | 14 | 37 | 42 | 18 | 41 | 18 | 9 | 15 |
| Cutoff 1 | 4.53 | 15.6 | 4.53 | 2.05 | 59.3 | 2.46 | 51.5 | 73.6 | 49.5 |
| Sens 1 | 71% | 71% | 70% | 76% | 72% | 71% | 72% | 78% | 73% |
| Spec 1 | 45% | 44% | 45% | 24% | 61% | 35% | 66% | 63% | 64% |
| Cutoff 2 | 2.05 | 2.05 | 1.31 | 0.823 | 15.6 | 2.05 | 4.53 | 0.823 | 25.8 |
| Sens 2 | 80% | 86% | 84% | 81% | 83% | 80% | 89% | 89% | 80% |
| Spec 2 | 24% | 21% | 18% | 19% | 44% | 22% | 45% | 14% | 62% |
| Cutoff 3 | 0 | 0 | 0 | 0 | 0 | 0 | 0.823 | 0 | 4.53 |
| Sens 3 | 100% | 100% | 100% | 100% | 100% | 100% | 100% | 100% | 93% |
| Spec 3 | 0% | 0% | 0% | 0% | 0% | 0% | 19% | 0% | 45% |
| Cutoff 4 | 52.7 | 80.9 | 59.3 | 52.7 | 80.9 | 59.3 | 52.7 | 80.9 | 59.3 |
| Sens 4 | 49% | 36% | 49% | 40% | 61% | 41% | 67% | 67% | 47% |
| Spec 4 | 70% | 74% | 71% | 70% | 74% | 71% | 70% | 74% | 71% |
| Cutoff 5 | 86.3 | 108 | 92.5 | 86.3 | 108 | 92.5 | 86.3 | 108 | 92.5 |
| Sens 5 | 33% | 29% | 24% | 38% | 56% | 37% | 44% | 56% | 27% |
| Spec 5 | 81% | 81% | 81% | 81% | 81% | 81% | 81% | 81% | 81% |
| Cutoff 6 | 121 | 178 | 178 | 121 | 178 | 178 | 121 | 178 | 178 |
| Sens 6 | 20% | 21% | 8% | 21% | 28% | 15% | 39% | 22% | 7% |
| Spec 6 | 90% | 91% | 90% | 90% | 91% | 90% | 90% | 91% | 90% |
| OR Quart 2 | 0.43 | 0.64 | 0.70 | 1.0 | 0.32 | 1.3 | 1.0 | 0 | 2.0 |
| p Value | 0.15 | 0.64 | 0.55 | 1.0 | 0.33 | 0.59 | 1.0 | na | 0.58 |
| 95% CI of | 0.14 | 0.10 | 0.21 | 0.35 | 0.032 | 0.46 | 0.13 | na | 0.17 |
| OR Quart 2 | 1.3 | 4.0 | 2.3 | 2.8 | 3.1 | 3.9 | 7.6 | na | 23 |
| OR Quart 3 | 1.2 | 1.3 | 1.8 | 0.51 | 1.3 | 1.0 | 3.5 | 0.49 | 11 |
| p Value | 0.68 | 0.71 | 0.29 | 0.26 | 0.71 | 1.0 | 0.14 | 0.57 | 0.031 |
| 95% CI of | 0.46 | 0.29 | 0.61 | 0.16 | 0.29 | 0.33 | 0.65 | 0.043 | 1.2 |
| OR Quart 3 | 3.3 | 6.2 | 5.0 | 1.6 | 6.2 | 3.0 | 19 | 5.6 | 92 |
| OR Quart 4 | 1.6 | 1.7 | 1.5 | 2.1 | 3.7 | 2.5 | 5.2 | 3.2 | 4.3 |
| p Value | 0.37 | 0.48 | 0.42 | 0.14 | 0.055 | 0.081 | 0.051 | 0.17 | 0.20 |
| 95% CI of | 0.59 | 0.39 | 0.53 | 0.79 | 0.97 | 0.89 | 0.99 | 0.61 | 0.45 |
| OR Quart 4 | 4.2 | 7.4 | 4.5 | 5.8 | 14 | 7.0 | 27 | 16 | 41 |

Interleukin-7

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0293 | 0.464 | 0.0293 | 1.31 | 0.0293 | 2.59 |
| Average | 6.96 | 1.96 | 6.96 | 3.74 | 6.96 | 2.76 |
| Stdev | 26.3 | 2.63 | 26.3 | 7.84 | 26.3 | 2.08 |
| p (t-test) |  | 0.21 |  | 0.44 |  | 0.50 |
| Min | 0.00806 | 0.00806 | 0.00806 | 0.00806 | 0.00806 | 0.0119 |
| Max | 153 | 10.0 | 153 | 48.8 | 153 | 7.47 |
| n (Samp) | 94 | 45 | 94 | 42 | 94 | 18 |
| n (Patient) | 65 | 45 | 65 | 42 | 65 | 18 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0301 | 0.0269 | 0.0301 | 2.27 | 0.0301 | 1.10 |
| Average | 4.36 | 1.77 | 4.36 | 6.84 | 4.36 | 1.53 |
| Stdev | 17.6 | 2.88 | 17.6 | 12.7 | 17.6 | 1.59 |
| p (t-test) |  | 0.58 |  | 0.56 |  | 0.63 |
| Min | 0.00806 | 0.00806 | 0.00806 | 0.0144 | 0.00806 | 0.00806 |
| Max | 153 | 9.97 | 153 | 48.8 | 153 | 3.69 |
| n (Samp) | 225 | 14 | 225 | 18 | 225 | 9 |
| n (Patient) | 132 | 14 | 132 | 18 | 132 | 9 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0293 | 0.464 | 0.0293 | 1.33 | 0.0293 | 2.29 |
| Average | 6.42 | 2.07 | 6.42 | 2.74 | 6.42 | 2.40 |
| Stdev | 25.3 | 2.77 | 25.3 | 3.36 | 25.3 | 2.43 |
| p (t-test) |  | 0.30 |  | 0.36 |  | 0.54 |

TABLE 5-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

|  | | | | | | | | | |
|---|---|---|---|---|---|---|---|---|---|
| Min | 0.00806 | 0.00806 | 0.00806 | 0.00806 | 0.00806 | | 0.00806 | | |
| Max | 153 | 10.0 | 153 | 12.0 | 153 | | 7.47 | | |
| n (Samp) | 103 | 37 | 103 | 41 | 103 | | 15 | | |
| n (Patient) | 64 | 37 | 64 | 41 | 64 | | 15 | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | 0.45 | 0.59 | 0.58 | 0.62 | 0.61 | 0.68 | 0.53 | 0.65 |
| SE | 0.053 | 0.081 | 0.056 | 0.054 | 0.073 | 0.054 | 0.074 | 0.100 | 0.081 |
| p | 0.54 | 0.56 | 0.13 | 0.12 | 0.090 | 0.039 | 0.015 | 0.76 | 0.062 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.0119 | 0.0119 | 0.0119 | 0.0245 | 0.0245 | 0.0245 | 1.09 | 0.0163 | 0.131 |
| Sens 1 | 89% | 71% | 92% | 71% | 72% | 71% | 78% | 78% | 73% |
| Spec 1 | 18% | 18% | 21% | 45% | 43% | 49% | 64% | 38% | 60% |
| Cutoff 2 | 0.0119 | 0 | 0.0119 | 0.0119 | 0.0119 | 0.0119 | 0.815 | 0.0119 | 0.0245 |
| Sens 2 | 89% | 100% | 92% | 88% | 100% | 83% | 83% | 89% | 80% |
| Spec 2 | 18% | 0% | 21% | 18% | 18% | 21% | 62% | 18% | 49% |
| Cutoff 3 | 0.00806 | 0 | 0.0119 | 0.00806 | 0.0119 | 0 | 0.0119 | 0 | 0.00806 |
| Sens 3 | 93% | 100% | 92% | 90% | 100% | 100% | 94% | 100% | 93% |
| Spec 3 | 17% | 0% | 21% | 17% | 18% | 0% | 18% | 0% | 19% |
| Cutoff 4 | 1.97 | 2.41 | 1.47 | 1.97 | 2.41 | 1.47 | 1.97 | 2.41 | 1.47 |
| Sens 4 | 40% | 29% | 43% | 45% | 44% | 49% | 67% | 44% | 53% |
| Spec 4 | 71% | 70% | 71% | 71% | 70% | 71% | 71% | 70% | 71% |
| Cutoff 5 | 3.77 | 4.33 | 3.29 | 3.77 | 4.33 | 3.29 | 3.77 | 4.33 | 3.29 |
| Sens 5 | 24% | 14% | 30% | 29% | 28% | 32% | 22% | 0% | 27% |
| Spec 5 | 81% | 81% | 81% | 81% | 81% | 81% | 81% | 81% | 81% |
| Cutoff 6 | 9.36 | 7.47 | 7.46 | 9.36 | 7.47 | 7.46 | 9.36 | 7.47 | 7.46 |
| Sens 6 | 4% | 7% | 5% | 7% | 22% | 15% | 0% | 0% | 7% |
| Spec 6 | 90% | 90% | 90% | 90% | 90% | 90% | 90% | 90% | 90% |
| OR Quart 2 | 1.7 | 1.0 | 4.0 | 1.2 | >9.1 | 1.2 | 1.0 | 3.1 | 0.96 |
| p Value | 0.33 | 1.0 | 0.029 | 0.78 | <0.041 | 0.77 | 1.0 | 0.34 | 0.97 |
| 95% CI of | 0.59 | 0.19 | 1.2 | 0.39 | >1.1 | 0.38 | 0.059 | 0.31 | 0.13 |
| OR Quart 2 | 4.9 | 5.2 | 14 | 3.5 | na | 3.7 | 17 | 30 | 7.3 |
| OR Quart 3 | 1.7 | 0.66 | 2.3 | 1.6 | >4.2 | 2.1 | 17 | 4.2 | 2.2 |
| p Value | 0.33 | 0.65 | 0.21 | 0.42 | <0.20 | 0.19 | 0.0086 | 0.20 | 0.40 |
| 95% CI of | 0.59 | 0.11 | 0.62 | 0.53 | >0.46 | 0.71 | 2.1 | 0.46 | 0.36 |
| OR Quart 3 | 4.9 | 4.1 | 8.5 | 4.5 | na | 6.1 | 150 | 39 | 13 |
| OR Quart 4 | 1.9 | 2.2 | 4.6 | 2.3 | >6.5 | 2.6 | 5.9 | 0.98 | 4.1 |
| p Value | 0.22 | 0.30 | 0.017 | 0.12 | <0.087 | 0.074 | 0.12 | 0.99 | 0.097 |
| 95% CI of | 0.67 | 0.51 | 1.3 | 0.80 | >0.76 | 0.91 | 0.64 | 0.060 | 0.78 |
| OR Quart 4 | 5.5 | 9.0 | 16 | 6.5 | na | 7.6 | 54 | 16 | 22 |

Platelet-derived growth factor subunit A (dimer)

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1510 | 1310 | 1510 | 1220 | 1510 | 2850 |
| Average | 2620 | 2630 | 2620 | 3830 | 2620 | 3340 |
| Stdev | 2980 | 3220 | 2980 | 7860 | 2980 | 2550 |
| p (t-test) | | 0.98 | | 0.14 | | 0.25 |
| Min | 0.479 | 0.268 | 0.479 | 0.735 | 0.479 | 51.0 |
| Max | 13500 | 14000 | 13500 | 51400 | 13500 | 10200 |
| n (Samp) | 120 | 53 | 120 | 53 | 120 | 26 |
| n (Patient) | 86 | 53 | 86 | 53 | 86 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1220 | 1270 | 1220 | 2710 | 1220 | 2150 |
| Average | 2480 | 2760 | 2480 | 7330 | 2480 | 3470 |
| Stdev | 3110 | 3300 | 3110 | 13100 | 3110 | 3330 |
| p (t-test) | | 0.72 | | 1.4E−5 | | 0.32 |
| Min | 0.268 | 0.479 | 0.268 | 15.3 | 0.268 | 332 |
| Max | 17600 | 10500 | 17600 | 51400 | 17600 | 10200 |
| n (Samp) | 287 | 16 | 287 | 15 | 287 | 10 |
| n (Patient) | 160 | 16 | 160 | 15 | 160 | 10 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 944 | 1280 | 944 | 1180 | 944 | 2980 |
| Average | 1900 | 2560 | 1900 | 2900 | 1900 | 3530 |
| Stdev | 2250 | 3220 | 2250 | 4170 | 2250 | 3070 |
| p (t-test) | | 0.14 | | 0.040 | | 0.0031 |
| Min | 0.479 | 0.268 | 0.479 | 0.735 | 0.479 | 51.0 |
| Max | 12100 | 14000 | 12100 | 17600 | 12100 | 10500 |
| n (Samp) | 124 | 43 | 124 | 54 | 124 | 23 |
| n (Patient) | 79 | 43 | 79 | 54 | 79 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | 0.51 | 0.54 | 0.50 | 0.61 | 0.56 | 0.62 | 0.62 | 0.68 |
| SE | 0.048 | 0.075 | 0.052 | 0.048 | 0.079 | 0.048 | 0.063 | 0.096 | 0.065 |
| p | 0.74 | 0.87 | 0.44 | 0.93 | 0.15 | 0.21 | 0.050 | 0.20 | 0.0056 |
| nCohort 1 | 120 | 287 | 124 | 120 | 287 | 124 | 120 | 287 | 124 |
| nCohort 2 | 53 | 16 | 43 | 53 | 15 | 54 | 26 | 10 | 23 |
| Cutoff 1 | 388 | 417 | 367 | 456 | 450 | 468 | 1550 | 1470 | 1200 |
| Sens 1 | 72% | 75% | 72% | 72% | 73% | 70%. | 73% | 70% | 74% |
| Spec 1 | 29% | 31% | 34% | 30% | 32% | 37% | 51% | 54% | 54% |
| Cutoff 2 | 182 | 376 | 182 | 289 | 381 | 258 | 1170 | 469 | 555 |
| Sens 2 | 81% | 81% | 81% | 81% | 80% | 81% | 81% | 80% | 83% |
| Spec 2 | 20% | 29% | 25% | 24% | 30% | 28% | 46% | 33% | 40% |
| Cutoff 3 | 15.3 | 5.98 | 38.2 | 97.4 | 75.0 | 87.1 | 235 | 438 | 209 |
| Sens 3 | 92% | 94% | 93% | 91% | 93% | 91% | 92% | 90% | 91% |
| Spec 3 | 3% | 3% | 7% | 12% | 9% | 16% | 22% | 31% | 26% |
| Cutoff 4 | 3500 | 2860 | 2430 | 3500 | 2860 | 2430 | 3500 | 2860 | 2430 |
| Sens 4 | 28% | 38% | 37% | 26% | 47% | 37% | 42% | 40% | 57% |
| Spec 4 | 70% | 70% | 70% | 70% | 70% | 70% | 70% | 70% | 70% |
| Cutoff 5 | 4530 | 4370 | 3790 | 4530 | 4370 | 3790 | 4530 | 4370 | 3790 |
| Sens 5 | 21% | 25% | 26% | 25% | 47% | 22% | 31% | 40% | 39% |
| Spec 5 | 80% | 80% | 81% | 80% | 80% | 81% | 80% | 80% | 81% |
| Cutoff 6 | 6480 | 6700 | 4780 | 6480 | 6700 | 4780 | 6480 | 6700 | 4780 |
| Sens 6 | 17% | 12% | 21% | 13% | 27% | 17% | 12% | 20% | 30% |
| Spec 6 | 90% | 90% | 90% | 90% | 90% | 90% | 90% | 90% | 90% |
| OR Quart 2 | 1.3 | 1.7 | 1.3 | 1.7 | 0.99 | 1.7 | 1.7 | >3.1 | 0.97 |
| p Value | 0.59 | 0.48 | 0.65 | 0.25 | 0.99 | 0.27 | 0.48 | <0.33 | 0.97 |
| 95% CI of | 0.51 | 0.39 | 0.46 | 0.69 | 0.19 | 0.66 | 0.38 | >0.32 | 0.18 |
| OR Quart 2 | 3.2 | 7.3 | 3.5 | 4.3 | 5.0 | 4.3 | 7.8 | na | 5.2 |
| OR Quart 3 | 1.2 | 0.65 | 1.1 | 1.3 | 0.66 | 1.6 | 4.2 | >3.1 | 2.6 |
| p Value | 0.76 | 0.64 | 0.84 | 0.63 | 0.65 | 0.34 | 0.042 | <0.33 | 0.20 |
| 95% CI of | 0.46 | 0.11 | 0.40 | 0.49 | 0.11 | 0.61 | 1.1 | >0.32 | 0.61 |
| OR Quart 3 | 2.9 | 4.0 | 3.1 | 3.2 | 4.1 | 4.1 | 17 | na | 11 |
| OR Quart 4 | 1.3 | 2.1 | 1.6 | 1.2 | 2.4 | 1.7 | 3.0 | >4.2 | 4.1 |
| p Value | 0.59 | 0.32 | 0.35 | 0.68 | 0.21 | 0.27 | 0.12 | <0.21 | 0.047 |
| 95% CI of | 0.51 | 0.50 | 0.59 | 0.48 | 0.61 | 0.66 | 0.74 | >0.45 | 1.0 |
| OR Quart 4 | 3.2 | 8.5 | 4.3 | 3.1 | 9.8 | 4.3 | 13 | na | 16 |

Platelet-derived growth factor A

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 5270 | 4080 | 5270 | 4380 | 5270 | 8890 |
| Average | 9680 | 9330 | 9680 | 11900 | 9680 | 11100 |
| Stdev | 13400 | 11800 | 13400 | 26100 | 13400 | 9670 |
| p (t-test) | | 0.87 | | 0.46 | | 0.60 |
| Min | 2.22 | 6.64 | 2.22 | 1.99 | 2.22 | 303 |
| Max | 94900 | 64400 | 94900 | 170000 | 94900 | 33400 |
| n (Samp) | 120 | 53 | 120 | 53 | 120 | 26 |
| n (Patient) | 86 | 53 | 86 | 53 | 86 | 26 |

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 4080 | 4000 | 4080 | 8690 | 4080 | 8450 |
| Average | 9040 | 7550 | 9040 | 20800 | 9040 | 11100 |
| Stdev | 13000 | 7900 | 13000 | 42300 | 13000 | 8460 |
| p (t-test) | | 0.65 | | 0.0049 | | 0.62 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

|  |  |  |  |  |  |  |
|---|---|---|---|---|---|---|
| Min | 1.99 | 6.64 | 1.99 | 333 | 1.99 | 1770 |
| Max | 94900 | 23400 | 94900 | 170000 | 94900 | 25300 |
| n (Samp) | 287 | 16 | 287 | 15 | 287 | 10 |
| n (Patient) | 160 | 16 | 160 | 15 | 160 | 10 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3380 | 4080 | 3380 | 4380 | 3380 | 7560 |
| Average | 6780 | 9500 | 6780 | 9050 | 6780 | 10700 |
| Stdev | 8950 | 12500 | 8950 | 14700 | 8950 | 10000 |
| p (t-test) |  | 0.12 |  | 0.21 |  | 0.062 |
| Min | 2.22 | 6.64 | 2.22 | 1.99 | 2.22 | 9.75 |
| Max | 49900 | 64400 | 49900 | 88200 | 49900 | 33400 |
| n (Samp) | 124 | 43 | 124 | 54 | 124 | 23 |
| n (Patient) | 79 | 43 | 79 | 54 | 79 | 23 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.50 | 0.49 | 0.57 | 0.49 | 0.59 | 0.54 | 0.60 | 0.65 | 0.63 |
| SE | 0.048 | 0.075 | 0.052 | 0.048 | 0.079 | 0.047 | 0.064 | 0.096 | 0.067 |
| P | 0.98 | 0.92 | 0.20 | 0.76 | 0.26 | 0.43 | 0.12 | 0.11 | 0.046 |
| nCohort 1 | 120 | 287 | 124 | 120 | 287 | 124 | 120 | 287 | 124 |
| nCohort 2 | 53 | 16 | 43 | 53 | 15 | 54 | 26 | 10 | 23 |
| Cutoff 1 | 2180 | 1840 | 2180 | 1600 | 2650 | 1700 | 4720 | 4950 | 3240 |
| Sens 1 | 72% | 75% | 72% | 72% | 73% | 70% | 73% | 70% | 74% |
| Spec 1 | 37% | 32% | 42% | 32% | 38% | 37% | 48% | 56% | 50% |
| Cutoff 2 | 867 | 333 | 1400 | 1080 | 1170 | 1080 | 2650 | 4000 | 1600 |
| Sens 2 | 81% | 81% | 81% | 83% | 80% | 81% | 81% | 80% | 83% |
| Spec 2 | 20% | 11% | 35% | 22% | 23% | 28% | 40% | 50% | 37% |
| Cutoff 3 | 176 | 6.64 | 303 | 303 | 333 | 57.8 | 369 | 2570 | 333 |
| Sens 3 | 91% | 94% | 91% | 91% | 93% | 93% | 92% | 90% | 91% |
| Spec 3 | 7% | 2% | 10% | 8% | 11% | 7% | 11% | 36% | 11% |
| Cutoff 4 | 10000 | 8580 | 8070 | 10000 | 8580 | 8070 | 10000 | 8580 | 8070 |
| Sens 4 | 30% | 38% | 35% | 28% | 53% | 30% | 50% | 50% | 48% |
| Spec 4 | 70% | 70% | 70% | 70% | 70% | 70% | 70% | 70% | 70% |
| Cutoff 5 | 14200 | 13600 | 10800 | 14200 | 13600 | 10800 | 14200 | 13600 | 10800 |
| Sens 5 | 26% | 31% | 28% | 21% | 33% | 26% | 23% | 40% | 39% |
| Spec 5 | 80% | 80% | 81% | 80% | 80% | 81% | 80% | 80% | 81% |
| Cutoff 6 | 23800 | 24900 | 18000 | 23800 | 24900 | 18000 | 23800 | 24900 | 18000 |
| Sens 6 | 9% | 0% | 16% | 11% | 20% | 17% | 15% | 10% | 17% |
| Spec 6 | 90% | 90% | 90% | 90% | 90% | 90% | 90% | 90% | 90% |
| OR Quart 2 | 0.40 | 0.58 | 1.5 | 0.72 | 0.48 | 1.5 | 3.0 | >3.1 | 0.71 |
| p Value | 0.068 | 0.47 | 0.47 | 0.51 | 0.40 | 0.37 | 0.12 | <0.33 | 0.66 |
| 95% CI of | 0.15 | 0.13 | 0.52 | 0.28 | 0.085 | 0.60 | 0.74 | >0.32 | 0.15 |
| OR Quart 2 | 1.1 | 2.5 | 4.1 | 1.9 | 2.7 | 4.0 | 13 | na | 3.4 |
| OR Quart 3 | 1.3 | 0.79 | 1.5 | 1.7 | 0.49 | 1.9 | 2.2 | >2.1 | 1.2 |
| p Value | 0.60 | 0.73 | 0.47 | 0.23 | 0.41 | 0.16 | 0.29 | <0.56 | 0.76 |
| 95% CI of | 0.53 | 0.20 | 0.52 | 0.71 | 0.086 | 0.76 | 0.51 | >0.18 | 0.31 |
| OR Quart 3 | 3.0 | 3.1 | 4.1 | 4.2 | 2.7 | 4.9 | 9.6 | na | 5.1 |
| OR Quart 4 | 0.60 | 0.80 | 1.8 | 0.92 | 1.8 | 1.5 | 3.5 | >5.3 | 3.4 |
| p Value | 0.28 | 0.75 | 0.23 | 0.87 | 0.36 | 0.37 | 0.077 | <0.13 | 0.057 |
| 95% CI of | 0.24 | 0.21 | 0.67 | 0.36 | 0.50 | 0.60 | 0.87 | >0.60 | 0.96 |
| OR Quart 4 | 1.5 | 3.1 | 5.1 | 2.3 | 6.4 | 4.0 | 14 | na | 12 |

Thymic stromal lymphopoietin

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0181 | 0.0181 | 0.0181 | 1.09 | 0.0181 | 1.55 |
| Average | 226 | 75.6 | 226 | 81.5 | 226 | 26.3 |
| Stdev | 2070 | 334 | 2070 | 340 | 2070 | 75.8 |
| p (t-test) |  | 0.63 |  | 0.65 |  | 0.68 |
| Min | 0.00640 | 0.00640 | 0.00640 | 0.00640 | 0.00640 | 0.0129 |
| Max | 20000 | 2170 | 20000 | 2170 | 20000 | 314 |
| n (Samp) | 93 | 45 | 93 | 42 | 93 | 18 |
| n (Patient) | 64 | 45 | 64 | 42 | 64 | 18 |

TABLE 5-continued

Comparison of marker levels in EDTA samples collected from Cohort 1
(patients that did not progress beyond RIFLE stage 0) and in EDTA samples collected
from subjects at 0, 24 hours, and 48 hours prior to reaching stage R, I or F in Cohort 2.

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.0503 | 0.0174 | 0.0503 | 0.0181 | 0.0503 | 0.0825 |
| Average | 216 | 77.4 | 216 | 1160 | 216 | 35.2 |
| Stdev | 1900 | 168 | 1900 | 4700 | 1900 | 105 |
| p (t-test) | | 0.79 | | 0.083 | | 0.78 |
| Min | 0.00640 | 0.00640 | 0.00640 | 0.0129 | 0.00640 | 0.0129 |
| Max | 20000 | 565 | 20000 | 20000 | 20000 | 314 |
| n (Samp) | 224 | 14 | 224 | 18 | 224 | 9 |
| n (Patient) | 131 | 14 | 131 | 18 | 131 | 9 |

| UO only | 0 hr prior to AKI stage | | 24 hr prior to AKI stage | | 48 hr prior to AK stage | |
|---|---|---|---|---|---|---|
| | Cohort 1 | Cohort 2 | Cohort 1 | Cohort 2 | Cohort 1 | Cohort 2 |
| Median | 0.0167 | 0.0181 | 0.0167 | 1.55 | 0.0167 | 2.92 |
| Average | 225 | 62.7 | 225 | 64.8 | 225 | 11.1 |
| Stdev | 1980 | 356 | 1980 | 338 | 1980 | 26.4 |
| p (t-test) | | 0.62 | | 0.61 | | 0.68 |
| Min | 0.00640 | 0.00640 | 0.00640 | 0.00640 | 0.00640 | 0.00640 |
| Max | 20000 | 2170 | 20000 | 2170 | 20000 | 105 |
| n (Samp) | 102 | 37 | 102 | 41 | 102 | 15 |
| n (Patient) | 63 | 37 | 63 | 41 | 63 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.47 | 0.52 | 0.60 | 0.58 | 0.59 | 0.61 | 0.45 | 0.66 |
| SE | 0.053 | 0.081 | 0.056 | 0.054 | 0.073 | 0.054 | 0.076 | 0.10 | 0.081 |
| P | 0.71 | 0.72 | 0.75 | 0.060 | 0.24 | 0.10 | 0.13 | 0.62 | 0.049 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 0.0129 | 0.0129 | 0.0129 | 0.0150 | 0.0150 | 0.0150 | 0.0167 | 0.0123 | 0.353 |
| Sens 1 | 82% | 79% | 81% | 74% | 78% | 71% | 72% | 100% | 73% |
| Spec 1 | 16% | 17% | 19% | 32% | 29% | 35% | 49% | 11% | 65% |
| Cutoff 2 | 0.0129 | 0.0123 | 0.0129 | 0.0129 | 0.0129 | 0.0129 | 0.0123 | 0.0123 | 0.0167 |
| Sens 2 | 82% | 86% | 81% | 90% | 94% | 83% | 100% | 100% | 80% |
| Spec 2 | 16% | 11% | 19% | 16% | 17% | 19% | 12% | 11% | 54% |
| Cutoff 3 | 0 | 0 | 0 | 0.0129 | 0.0129 | 0.0123 | 0.0123 | 0.0123 | 0.00640 |
| Sens 3 | 100% | 100% | 100% | 90% | 94% | 90% | 100% | 100% | 93% |
| Spec 3 | 0% | 0% | 0% | 16% | 17% | 16% | 12% | 11% | 16% |
| Cutoff 4 | 1.88 | 4.53 | 1.40 | 1.88 | 4.53 | 1.40 | 1.88 | 4.53 | 1.40 |
| Sens 4 | 36% | 29% | 35% | 48% | 39% | 51% | 50% | 11% | 60% |
| Spec 4 | 71% | 71% | 71% | 71% | 71% | 71% | 71% | 71% | 71% |
| Cutoff 5 | 5.02 | 7.01 | 6.32 | 5.02 | 7.01 | 6.32 | 5.02 | 7.01 | 6.32 |
| Sens 5 | 27% | 29% | 11% | 36% | 39% | 29% | 39% | 11% | 27% |
| Spec 5 | 81% | 80% | 80% | 81% | 80% | 80% | 81% | 80% | 80% |
| Cutoff 6 | 20.8 | 18.6 | 29.6 | 20.8 | 18.6 | 29.6 | 20.8 | 18.6 | 29.6 |
| Sens 6 | 11% | 21% | 5% | 17% | 28% | 10% | 11% | 11% | 7% |
| Spec 6 | 90% | 90% | 90% | 90% | 90% | 90% | 90% | 90% | 90% |
| OR Quart 2 | 0.84 | 0.24 | 0.60 | 0.49 | 1.5 | 0.70 | 0.44 | 4.3 | 0.48 |
| p Value | 0.73 | 0.21 | 0.37 | 0.23 | 0.53 | 0.53 | 0.37 | 0.20 | 0.56 |
| 95% CI of | 0.31 | 0.026 | 0.20 | 0.16 | 0.41 | 0.23 | 0.074 | 0.47 | 0.041 |
| OR Quart 2 | 2.3 | 2.2 | 1.8 | 1.6 | 5.7 | 2.1 | 2.6 | 40 | 5.6 |
| OR Quart 3 | 0.56 | 1.0 | 0.96 | 1.1 | 0.24 | 1.1 | 1.2 | 1.0 | 2.8 |
| p Value | 0.29 | 1.0 | 0.94 | 0.86 | 0.20 | 0.84 | 0.76 | 0.99 | 0.24 |
| 95% CI of | 0.20 | 0.24 | 0.34 | 0.39 | 0.026 | 0.39 | 0.30 | 0.062 | 0.50 |
| OR Quart 3 | 1.6 | 4.2 | 2.7 | 3.1 | 2.2 | 3.2 | 5.3 | 17 | 16 |
| OR Quart 4 | 1.2 | 1.3 | 0.96 | 1.8 | 1.8 | 2.1 | 1.9 | 3.2 | 4.1 |
| p Value | 0.69 | 0.71 | 0.94 | 0.24 | 0.36 | 0.16 | 0.35 | 0.32 | 0.097 |
| 95% CI of | 0.46 | 0.33 | 0.34 | 0.66 | 0.50 | 0.75 | 0.49 | 0.32 | 0.78 |
| OR Quart 4 | 3.2 | 5.1 | 2.7 | 5.0 | 6.6 | 5.6 | 7.5 | 31 | 22 |

TABLE 6

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | C—C motif chemokine 1 | | | | | | |
|---|---|---|---|---|---|---|---|
| | 0 hr prior to AKI stage | | 24 hr prior to AKI stage | | 48 hr prior to AKI stage | | |
| | Cohort 1 | Cohort 2 | Cohort 1 | Cohort 2 | Cohort 1 | Cohort 2 | |
| sCr or UO | | | | | | | |
| Median | 1.79 | 2.29 | 1.79 | 2.52 | 1.79 | 2.29 | |
| Average | 3.93 | 2.37 | 3.93 | 2.78 | 3.93 | 3.66 | |
| Stdev | 15.6 | 1.82 | 15.6 | 1.95 | 15.6 | 4.26 | |
| p(t-test) | | 0.69 | | 0.70 | | 0.94 | |
| Min | 0.00552 | 0.00831 | 0.00552 | 0.00831 | 0.00552 | 0.00831 | |
| Max | 212 | 6.68 | 212 | 8.54 | 212 | 18.0 | |
| n (Samp) | 216 | 16 | 216 | 28 | 216 | 17 | |
| n (Patient) | 132 | 16 | 132 | 28 | 132 | 17 | |
| UO only | | | | | | | |
| Median | 1.82 | 1.83 | 1.82 | 2.38 | 1.82 | 2.05 | |
| Average | 4.24 | 1.99 | 4.24 | 2.62 | 4.24 | 3.57 | |
| Stdev | 16.3 | 1.56 | 16.3 | 1.82 | 16.3 | 4.46 | |
| p(t-test) | | 0.62 | | 0.59 | | 0.87 | |
| Min | 0.00552 | 0.00831 | 0.00552 | 0.00831 | 0.00552 | 0.00831 | |
| Max | 212 | 4.69 | 212 | 8.54 | 212 | 18.0 | |
| n (Samp) | 198 | 13 | 198 | 29 | 198 | 15 | |
| n (Patient) | 117 | 13 | 117 | 29 | 117 | 15 | |

| | 0 hr prior to AKI stage | | 24 hr prior to AKI stage | | | 48 hr prior to AKI stage | | |
|---|---|---|---|---|---|---|---|---|
| | sCr or UO | sCr only | UO only | sCr or UO | sCr only | UO only | sCr or UO | sCr only | UO only |
| AUC | 0.54 | nd | 0.48 | 0.60 | nd | 0.58 | 0.60 | nd | 0.57 |
| SE | 0.076 | nd | 0.084 | 0.060 | nd | 0.059 | 0.075 | nd | 0.080 |
| p | 0.57 | nd | 0.82 | 0.079 | nd | 0.17 | 0.17 | nd | 0.35 |
| nCohort 1 | 216 | nd | 198 | 216 | nd | 198 | 216 | nd | 198 |
| nCohort 2 | 16 | nd | 13 | 28 | nd | 29 | 17 | nd | 15 |
| Cutoff 1 | 1.32 | nd | 0.509 | 1.63 | nd | 1.62 | 1.48 | nd | 1.48 |
| Sens 1 | 75% | nd | 77% | 71% | nd | 76% | 71% | nd | 73% |
| Spec 1 | 39% | nd | 20% | 46% | nd | 45% | 44% | nd | 43% |
| Cutoff 2 | 0.509 | nd | 0.506 | 1.47 | nd | 1.33 | 1.29 | nd | 1.47 |
| Sens 2 | 81% | nd | 85% | 82% | nd | 83% | 82% | nd | 80% |
| Spec 2 | 21% | nd | 20% | 44% | nd | 39% | 39% | nd | 43% |
| Cutoff 3 | 0.00552 | nd | 0.00552 | 0.305 | nd | 0.266 | 0.00883 | nd | 0.00883 |
| Sens 3 | 100% | nd | 100% | 93% | nd | 93% | 94% | nd | 93% |
| Spec 3 | 0% | nd | 1% | 20% | nd | 19% | 12% | nd | 12% |
| Cutoff 4 | 2.75 | nd | 2.75 | 2.75 | nd | 2.75 | 2.75 | nd | 2.75 |
| Sens 4 | 38% | nd | 31% | 43% | nd | 41% | 41% | nd | 40% |
| Spec 4 | 71% | nd | 70% | 71% | nd | 70% | 71% | nd | 70% |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| Cutoff 5 | 3.45 | nd | 3.45 | nd | 3.45 | nd |
|  | | | | | 3.69 | nd |
| Sens 5 | 25% | nd | 23% | nd | 29% | nd |
|  | | | 21% | | 27% | |
| Spec 5 | 80% | nd | 80% | nd | 80% | nd |
| Cutoff 6 | 5.18 | nd | 6.77 | nd | 5.18 | nd |
|  | | | 6.77 | | 6.77 | |
| Sens 6 | 6% | nd | 0% | nd | 24% | nd |
|  | | | 3% | | 13% | |
| Spec 6 | 90% | nd | 90% | nd | 90% | nd |
| OR Quart 2 | 0.48 | nd | 2.5 | nd | 2.1 | nd |
|  | | | 2.9 | | 2.1 | |
| p Value | 0.41 | nd | 0.20 | nd | 0.41 | nd |
|  | | | 0.13 | | 0.41 | |
| 95% CI of OR Quart 2 | 0.085 | nd | 0.62 | nd | 0.36 | nd |
|  | | | 0.72 | | 0.36 | |
| OR Quart | 2.7 | nd | 10 | nd | 12 | nd |
|  | 31.6 | | 11 | | 12 | |
| p Value | 0.51 | nd | 3.3 | nd | 3.2 | nd |
|  | | | 4.2 | | 2.7 | |
| 95% CI of OR Quart | 0.42 | nd | 0.082 | nd | 0.16 | nd |
|  | | | 0.035 | | 0.26 | |
| OR Quart3 | 5.8 | nd | 0.86 | nd | 0.62 | nd |
|  | | | 1.1 | | 0.49 | |
| p Value | 1.0 | nd | 4.1 | nd | 17 | nd |
|  | | | 16 | | 14 | |
| 95% CI of OR Quart 4 | 1.0 | nd | 1.4 | nd | 2.6 | nd |
|  | | | 2.5 | | 2.0 | |
| OR Quart 4 | 0.24 | nd | 0.68 | nd | 0.27 | nd |
|  | | | 0.21 | | 0.42 | |
| p Value | 4.2 | nd | 0.30 | nd | 0.48 | nd |
|  | | | 0.61 | | 0.36 | |
| 95% CI of OR Quart4 | | | 6.5 | | 14 | |
|  | | | 13 | | 12 | |

C—C motif chemokine 17

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 19.1 | 12.8 | 19.1 | 14.5 | 19.1 | 13.2 |
| Average | 49.4 | 39.4 | 49.4 | 42.7 | 49.4 | 76.9 |
| Stdev | 88.9 | 70.0 | 88.9 | 92.5 | 88.9 | 208 |
| p(t-test) |  | 0.66 |  | 0.71 |  | 0.28 |
| Min | 1.57 | 0.0212 | 1.57 | 0.0212 | 1.57 | 1.95 |
| Max | 737 | 279 | 737 | 438 | 737 | 871 |
| n (Samp) | 216 | 16 | 216 | 28 | 216 | 17 |
| n (Patient) | 132 | 16 | 132 | 28 | 132 | 17 |
| UO only | | | | | | |
| Median | 18.2 | 11.4 | 18.2 | 13.6 | 18.2 | 13.2 |
| Average | 41.3 | 36.3 | 41.3 | 41.2 | 41.3 | 84.0 |
| Stdev | 82.1 | 75.0 | 82.1 | 90.9 | 82.1 | 221 |
| p(t-test) | 0.83 | 1.00 | 0.10 |  |  |  |
| Min | 1.57 | 0.0212 | 1.57 | 0.0212 | 1.57 | 1.95 |
| Max | 737 | 279 | 737 | 438 | 737 | 871 |
| n (Samp) | 198 | 13 | 198 | 29 | 198 | 15 |
| n (Patient) | 117 | 13 | 117 | 29 | 117 | 15 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.43 | nd | 0.40 | 0.43 | nd | 0.45 | 0.46 | nd | 0.48 |
| SE | 0.077 | nd | 0.085 | 0.059 | nd | 0.059 | 0.074 | nd | 0.078 |
| p | 0.36 | nd | 0.22 | 0.27 | nd | 0.44 | 0.63 | nd | 0.79 |
| nCohort 1 | 216 | | 198 | 216 | | 198 | 216 | | 198 |
| nCohort 2 | 16 | | 13 | 28 | | 29 | 17 | | 15 |
| Cutoff 1 | 6.89 | nd | 5.85 | 7.72 | nd | 7.72 | 9.69 | nd | 7.80 |
| Sens 1 | 75% | nd | 77% | 71% | nd | 72% | 71% | nd | 73% |
| Spec 1 | 18% | nd | 13% | 20% | nd | 22% | 30% | nd | 23% |
| Cutoff 2 | 5.85 | nd | 5.54 | 6.26 | nd | 6.26 | 5.93 | nd | 5.93 |
| Sens 2 | 81% | nd | 85% | 82% | nd | 83% | 82% | nd | 80% |
| Spec 2 | 12% | nd | 13% | 14% | nd | 15% | 12% | nd | 13% |
| Cutoff 3 | 5.07 | nd | 5.07 | 0.0212 | nd | 0.0212 | 4.63 | nd | 4.63 |
| Sens 3 | 94% | nd | 92% | 96% | nd | 97% | 94% | nd | 93% |
| Spec 3 | 10% | nd | 11% | 0% | nd | 0% | 8% | nd | 9% |
| Cutoff 4 | 34.2 | nd | 29.5 | 34.2 | nd | 29.5 | 34.2 | nd | 29.5 |
| Sens 4 | 19% | nd | 23% | 25% | nd | 31% | 24% | nd | 33% |
| Spec 4 | 70% | nd | 70% | 70% | nd | 70% | 70% | nd | 70% |
| Cutoff 5 | 56.3 | nd | 42.1 | 56.3 | nd | 42.1 | 56.3 | nd | 42.1 |
| Sens 5 | 19% | nd | 15% | 7% | nd | 10% | 12% | nd | 20% |
| Spec 5 | 80% | nd | 80% | 80% | nd | 80% | 80% | nd | 80% |
| Cutoff 6 | 130 | nd | 91.3 | 130 | nd | 91.3 | 130 | nd | 91.3 |
| Sens 6 | 6% | nd | 8% | 7% | nd | 7% | 12% | nd | 13% |
| Spec 6 | 90% | nd | 90% | 90% | nd | 90% | 90% | nd | 90% |
| OR Quart 2 | 1.0 | nd | 1.5 | 1.0 | nd | 0.84 | 1.8 | nd | 0.75 |
| p Value | 1.0 | nd | 0.65 | 1.0 | nd | 0.77 | 0.45 | nd | 0.72 |
| 95% CI of OR Quart2 | 0.19 | nd | 0.25 | 0.30 | nd | 0.26 | 0.40 | nd | 0.16 |
| | 5.2 | nd | 9.5 | 3.3 | nd | 2.7 | 7.7 | nd | 3.5 |
| OR Quart 3 | 1.7 | nd | 1.5 | 1.2 | nd | 1.0 | 1.4 | nd | 0.75 |
| p Value | 0.47 | nd | 0.65 | 0.77 | nd | 1.0 | 0.68 | nd | 0.72 |
| 95% CI of OR Quart3 | 0.39 | nd | 0.25 | 0.38 | nd | 0.33 | 0.30 | nd | 0.16 |
| | 7.6 | nd | 9.5 | 3.8 | nd | 3.1 | 6.5 | nd | 3.5 |
| OR Quart 4 | 1.7 | nd | 2.7 | 1.6 | nd | 1.4 | 1.8 | nd | 1.3 |
| p Value | 0.47 | nd | 0.25 | 0.41 | nd | 0.56 | 0.45 | nd | 0.71 |
| 95% CI of OR Quart4 | 0.39 | nd | 0.50 | 0.53 | nd | 0.47 | 0.40 | nd | 0.33 |
| | 7.6 | nd | 15 | 4.8 | nd | 4.0 | 7.7 | nd | 5.1 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

C—C motif chemokine 21

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 430 | 582 | 430 | 463 | 430 | 546 |
| Average | 696 | 778 | 696 | 767 | 696 | 786 |
| Stdev | 1120 | 708 | 1120 | 699 | 1120 | 782 |
| p(t-test) | | 0.77 | | 0.75 | | 0.75 |
| Min | 0.303 | 69.7 | 0.303 | 3.47 | 0.303 | 56.1 |
| Max | 12300 | 2620 | 12300 | 2760 | 12300 | 2860 |
| n (Samp) | 217 | 16 | 217 | 28 | 217 | 17 |
| n (Patient) | 133 | 16 | 133 | 28 | 133 | 17 |
| UO only | | | | | | |
| Median | 442 | 474 | 442 | 608 | 442 | 546 |
| Average | 715 | 587 | 715 | 756 | 715 | 692 |
| Stdev | 1170 | 440 | 1170 | 604 | 1170 | 590 |
| p(t-test) | | 0.69 | | 0.85 | | 0.94 |
| Min | 0.303 | 69.7 | 0.303 | 3.47 | 0.303 | 61.1 |
| Max | 12300 | 1320 | 12300 | 2540 | 12300 | 2450 |
| n (Samp) | 199 | 13 | 199 | 29 | 199 | 15 |
| n (Patient) | 118 | 13 | 118 | 29 | 118 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.57 | nd | 0.52 | 0.58 | nd | 0.60 | 0.57 | nd | 0.57 |
| SE | 0.077 | nd | 0.084 | 0.059 | nd | 0.059 | 0.075 | nd | 0.079 |
| p | 0.39 | nd | 0.83 | 0.18 | nd | 0.095 | 0.35 | nd | 0.41 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 277 | nd | 231 | 355 | nd | 355 | 428 | nd | 354 |
| Sens 1 | 75% | nd | 77% | 71% | nd | 72% | 71% | nd | 73% |
| Spec 1 | 31% | nd | 25% | 41% | nd | 41% | 50% | nd | 41% |
| Cutoff 2 | 231 | nd | 105 | 287 | nd | 287 | 227 | nd | 261 |
| Sens 2 | 81% | nd | 85% | 82% | nd | 83% | 82% | nd | 80% |
| Spec 2 | 24% | nd | 10% | 33% | nd | 34% | 23% | nd | 29% |
| Cutoff 3 | 103 | nd | 103 | 204 | nd | 204 | 56.1 | nd | 204 |
| Sens 3 | 94% | nd | 92% | 93% | nd | 93% | 94% | nd | 93% |
| Spec 3 | 10% | nd | 10% | 19% | nd | 19% | 7% | nd | 19% |
| Cutoff 4 | 672 | nd | 677 | 672 | nd | 677 | 672 | nd | 677 |
| Sens 4 | 50% | nd | 46% | 43% | nd | 48% | 35% | nd | 33% |
| Spec 4 | 71% | nd | 70% | 71% | nd | 70% | 71% | nd | 70% |
| Cutoff 5 | 832 | nd | 843 | 832 | nd | 843 | 832 | nd | 843 |
| Sens 5 | 44% | nd | 23% | 32% | nd | 38% | 24% | nd | 20% |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Spec 5 | 80% | nd | 80% | nd | 80% | nd |
| Cutoff 6 | 1250 | nd | 1360 | nd | 1250 | nd |
| Sens 6 | 19% | nd | 0% | nd | 14% | nd |
| Spec 6 | 90% | nd | 90% | nd | 90% | nd |
| OR Quart | 20.74 | nd | 0.48 | nd | 2.2 | nd |
| p Value | 0.70 | nd | 0.41 | nd | 0.23 | nd |
| 95% CI of OR Quan2 | 0.16 | nd | 0.084 | nd | 0.61 | nd |
| | 3.4 | nd | 2.7 | nd | 7.6 | nd |
| OR Quart 3 | 0.48 | nd | 2.7 | nd | 1.6 | nd |
| p Value | 0.41 | nd | 0.41 | nd | 0.51 | nd |
| 95% CI of OR Quart3 | 0.085 | nd | 0.084 | nd | 0.42 | nd |
| | 2.7 | nd | 2.7 | nd | 5.8 | nd |
| OR Quart 4 | 1.8 | nd | 1.3 | nd | 5.0 | nd |
| p Value | 0.36 | nd | 0.73 | nd | 3.5 | nd |
| 95% CI of OR Quart4 | 0.50 | nd | 0.32 | nd | 0.039 | nd |
| | 6.6 | nd | 5.0 | nd | 1.1 | nd |
| OR Quart4 | | | | | 12 | nd |

Spec 5 80% nd
Cutoff 6 1250 nd 1360 7%
Sens 6 14% 90%
Spec 6 90% 0.64
OR Quart 2.2 0.63
p Value 0.23 0.10
95% CI of OR Quan2 0.61 4.0
7.6 2.1
OR Quart 3 1.6 0.30
p Value 0.51 0.50
95% CI of OR Quart3 0.42 9.0
5.8 1.3
OR Quart 4 1.2 0.72
p Value 0.75 0.28
95% CI of OR Quart4 0.32 6.3
4.9

C—C motif chemokine 27

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 314 | 412 | 314 | 337 | 314 | 410 |
| Average | 362 | 442 | 362 | 369 | 362 | 402 |
| Stdev | 191 | 138 | 191 | 191 | 191 | 140 |
| p(t-test) | | 0.10 | | 0.84 | | 0.39 |
| Min | 29.4 | 236 | 29.4 | 80.3 | 29.4 | 144 |
| Max | 973 | 756 | 973 | 935 | 973 | 698 |
| n (Samp) | 217 | 16 | 217 | 28 | 217 | 17 |
| n (Patient) | 133 | 16 | 133 | 28 | 133 | 17 |
| UO only | | | | | | |
| Median | 337 | 467 | 337 | 345 | 337 | 372 |
| Average | 373 | 462 | 373 | 373 | 373 | 372 |
| Stdev | 193 | 140 | 193 | 184 | 193 | 153 |
| p(t-test) | | 0.10 | | 1.00 | | 0.99 |
| Min | 29.4 | 277 | 29.4 | 80.3 | 29.4 | 144 |
| Max | 973 | 756 | 973 | 935 | 973 | 698 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.67 | nd | 0.68 | 0.53 | nd | 0.51 | 0.60 | nd | 0.53 |
| SE | 0.076 | nd | 0.084 | 0.059 | nd | 0.058 | 0.075 | nd | 0.078 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| p | 0.026 |  | 0.032 |  | 0.67 |  | 0.80 |  | 0.16 |  | 0.74 |
| nCohort 1 | 217 | nd | 199 | nd | 217 | nd | 199 | nd | 217 | nd | 199 |
| nCohort 2 | 16 | nd | 13 | nd | 28 | nd | 29 | nd | 17 | nd | 15 |
| Cutoff | 357 | nd | 357 | nd | 285 | nd | 285 | nd | 338 | nd | 274 |
| Sens 1 | 75% | nd | 77% | nd | 71% | nd | 72% | nd | 71% | nd | 73% |
| Spec 1 | 57% | nd | 55% | nd | 40% | nd | 38% | nd | 54% | nd | 37% |
| Cutoff 2 | 330 | nd | 330 | nd | 221 | nd | 232 | nd | 274 | nd | 273 |
| Sens 2 | 81% | nd | 85% | nd | 82% | nd | 83% | nd | 82% | nd | 80% |
| Spec 2 | 53% | nd | 50% | nd | 24% | nd | 23% | nd | 38% | nd | 37% |
| Cutoff 3 | 277 | nd | 289 | nd | 132 | nd | 132 | nd | 232 | nd | 148 |
| Sens 3 | 94% | nd | 92% | nd | 93% | nd | 93% | nd | 94% | nd | 93% |
| Spec 3 | 39% | nd | 41% | nd | 6% | nd | 6% | nd | 26% | nd | 9% |
| Cutoff 4 | 419 | nd | 450 | nd | 419 | nd | 450 | nd | 419 | nd | 450 |
| Sens 4 | 50% | nd | 54% | nd | 36% | nd | 21% | nd | 41% | nd | 33% |
| Spec 4 | 70% | nd | 70% | nd | 70% | nd | 70% | nd | 70% | nd | 70% |
| Cutoff 5 | 501 | nd | 501 | nd | 501 | nd | 511 | nd | 501 | nd | 511 |
| Sens 5 | 31% | nd | 38% | nd | 14% | nd | 14% | nd | 18% | nd | 13% |
| Spec 5 | 80% | nd | 80% | nd | 80% | nd | 80% | nd | 80% | nd | 80% |
| Cutoff 6 | 660 | nd | 665 | nd | 660 | nd | 665 | nd | 660 | nd | 665 |
| Sens 6 | 6% | nd | 8% | nd | 11% | nd | 10% | nd | 6% | nd | 7% |
| Spec 6 | 90% | nd | 90% | nd | 90% | nd | 90% | nd | 90% | nd | 90% |
| OR Quart 2 | 2.0 | nd | >3.2 | nd | 0.82 | nd | 1.0 | nd | 1.5 | nd | 0.98 |
| p Value | 0.57 | nd | <0.32 | nd | 0.75 | nd | 1.0 | nd | 0.66 | nd | 0.98 |
| 95% CI of | 0.18 | nd | >0.32 | nd | 0.24 | nd | 0.33 | nd | 0.24 | nd | 0.19 |
| OR Quart2 | 23 | nd | na | nd | 2.8 | nd | 3.1 | nd | 9.3 | nd | 5.1 |
| OR Quart 3 | 9.1 | nd | >5.5 | nd | 2.0 | nd | 1.5 | nd | 3.8 | nd | 2.1 |
| p Value | 0.040 | nd | <0.12 | nd | 0.20 | nd | 0.43 | nd | 0.10 | nd | 0.30 |
| 95% CI of | 1.1 | nd | >0.62 | nd | 0.69 | nd | 0.53 | nd | 0.76 | nd | 0.50 |
| OR Quart3 | 75 | nd | na | nd | 5.9 | nd | 4.3 | nd | 19 | nd | 9.0 |
| OR Quart 4 | 5.3 | nd | >5.5 | nd | 0.98 | nd | 0.69 | nd | 2.6 | nd | 0.98 |
| p Value | 0.13 | nd | <0.12 | nd | 0.98 | nd | 0.54 | nd | 0.27 | nd | 0.98 |
| 95% CI of | 0.60 | nd | >0.62 | nd | 0.30 | nd | 0.20 | nd | 0.48 | nd | 0.19 |
| OR Quart4 | 47 | nd | na | nd | 3.2 | nd | 2.3 | nd | 14 | nd | 5.1 |

Vascular endothelial growth factor receptor 1

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO |  |  |  |  |  |  |
| Median | 750 | 551 | 750 | 867 | 750 | 829 |
| Average | 1430 | 2860 | 1430 | 1540 | 1430 | 1350 |
| Stdev | 3750 | 9060 | 3750 | 1970 | 3750 | 1750 |
| p(t-test) |  | 0.20 |  | 0.88 |  | 0.93 |
| Min | 73.4 | 152 | 73.4 | 166 | 73.4 | 80.7 |
| Max | 50500 | 36800 | 50500 | 9150 | 50500 | 7250 |
| n (Samp) | 217 | 16 | 217 | 28 | 217 | 17 |
| n (Patient) | 133 | 16 | 133 | 28 | 133 | 17 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | UO only | 0 hr prior to AKI stage | | | 24 hr prior to AKI stage | | | 48 hr prior to AKI stage | | |
|---|---|---|---|---|---|---|---|---|---|---|
| | | sCr or UO | sCr only | UO only | sCr or UO | sCr only | UO only | sCr or UO | sCr only | UO only |
| Median | 750 | | 542 | 750 | 754 | | 750 | 829 | | 750 |
| Average | 1470 | | 560 | 1470 | 2440 | | 1470 | 1990 | | 1470 |
| Stdev | 3920 | | 327 | 3920 | 6730 | | 3920 | 2700 | | 3920 |
| p(t-test) | | | 0.40 | | 0.26 | | | 0.62 | | |
| Min | 73.4 | | 152 | 73.4 | 166 | | 73.4 | 332 | | 73.4 |
| Max | 50500 | | 1290 | 50500 | 36800 | | 50500 | 9150 | | 50500 |
| n (Samp) | 199 | | 13 | 199 | 29 | | 199 | 15 | | 199 |
| n (Patient) | 118 | | 13 | 118 | 29 | | 118 | 15 | | 118 |
| AUC | | 0.38 | nd | 0.33 | 0.57 | nd | 0.56 | 0.51 | nd | 0.55 |
| SE | | 0.077 | nd | 0.084 | 0.059 | nd | 0.059 | 0.073 | nd | 0.079 |
| P | | 0.13 | nd | 0.042 | 0.26 | nd | 0.31 | 0.93 | nd | 0.50 |
| nCohort 1 | | 217 | nd | 199 | 217 | nd | 199 | 217 | nd | 199 |
| nCohort 2 | | 16 | nd | 13 | 28 | nd | 29 | 17 | nd | 15 |
| Cutoff 1 | | 369 | nd | 311 | 551 | nd | 551 | 570 | nd | 559 |
| Sens 1 | | 75% | nd | 77% | 71% | nd | 72% | 71% | nd | 73% |
| Spec 1 | | 15% | nd | 12% | 36% | nd | 38% | 38% | nd | 39% |
| Cutoff 2 | | 311 | nd | 259 | 455 | nd | 455 | 340 | nd | 402 |
| Sens 2 | | 81% | nd | 85% | 82% | nd | 83% | 82% | nd | 80% |
| Spec 2 | | 10% | nd | 9% | 28% | nd | 29% | 13% | nd | 23% |
| Cutoff 3 | | 173 | nd | 173 | 404 | nd | 404 | 326 | nd | 326 |
| Sens 3 | | 94% | nd | 92% | 93% | nd | 93% | 94% | nd | 100% |
| Spec 3 | | 2% | nd | 2% | 22% | nd | 24% | 12% | nd | 13% |
| Cutoff 4 | | 1160 | nd | 1170 | 1160 | nd | 1170 | 1160 | nd | 1170 |
| Sens 4 | | 19% | nd | 8% | 43% | nd | 38% | 24% | nd | 33% |
| Spec 4 | | 70% | nd | 70% | 70% | nd | 70% | 70% | nd | 70% |
| Cutoff 5 | | 1490 | nd | 1540 | 1490 | nd | 1540 | 1490 | nd | 1540 |
| Sens 5 | | 6% | nd | 0% | 36% | nd | 34% | 24% | nd | 33% |
| Spec 5 | | 80% | nd | 80% | 80% | nd | 80% | 80% | nd | 80% |
| Cutoff 6 | | 2440 | nd | 2570 | 2440 | nd | 2570 | 2440 | nd | 2570 |
| Sens 6 | | 6% | nd | 0% | 11% | nd | 10% | 12% | nd | 20% |
| Spec 6 | | 90% | nd | 90% | 90% | nd | 90% | 90% | nd | 90% |
| OR Quart | | 24.3 | nd | >3.2 | 1.7 | nd | 2.0 | 0.57 | nd | 0.72 |
| p Value | | 0.20 | nd | <0.32 | 0.38 | nd | 0.26 | 0.45 | nd | 0.68 |
| 95% CI of | | 0.47 | nd | <0.32 | 0.52 | nd | 0.61 | 0.13 | nd | 0.15 |
| OR Quart2 | | 40 | nd | na | 5.5 | nd | 6.2 | 2.5 | nd | 3.4 |
| OR Quart 3 | | 6.7 | nd | >5.5 | 1.0 | nd | 1.0 | 1.0 | nd | 0.74 |
| 95% CI of | | 0.083 | nd | <0.12 | 1.0 | nd | 1.0 | 1.0 | nd | 0.70 |
| p Value | | 0.78 | nd | >0.62 | 0.27 | nd | 0.27 | 0.27 | nd | 0.16 |
| OR Quart3 | | 57 | nd | na | 3.6 | nd | 3.7 | 3.7 | nd | 3.5 |
| OR Quart 4 | | 5.5 | nd | >5.5 | 2.2 | nd | 2.2 | 0.77 | nd | 1.2 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | 0 hr prior to AKI stage | | 24 hr prior to AKI stage | | 48 hr prior to AKI stage | |
|---|---|---|---|---|---|---|
| p Value | 0.13 | nd | 0.19 | nd | 0.17 | 0.75 |
| 95% CI of OR Quart4 | 0.62 | nd | 0.69 | nd | 0.71 | 0.32 |
| | 48 | nd | 6.7 | nd | 6.9 | 4.9 |
| | | | | | 0.71 | 0.71 |
| | | | | | 0.20 | |
| | | | | | 3.0 | |

SL cytokine

| | 0 hr prior to AKI stage | | | 24 hr prior to AKI stage | | | 48 hr prior to AKI stage | | |
|---|---|---|---|---|---|---|---|---|---|
| | Cohort 1 | | Cohort 2 | Cohort 1 | | Cohort 2 | Cohort 1 | | Cohort 2 |
| sCr or UO | | | | | | | | | |
| Median | 0.0548 | | 0.0548 | 0.0548 | | 0.114 | 0.0548 | | 0.0548 |
| Average | 8.74 | | 7.85 | 8.74 | | 3.88 | 8.74 | | 14.7 |
| Stdev | 38.6 | | 21.9 | 38.6 | | 10.2 | 38.6 | | 42.2 |
| p(t-test) | | | 0.93 | | | 0.51 | | | 0.55 |
| Min | 0.0206 | | 0.0206 | 0.0206 | | 0.0206 | 0.0206 | | 0.0206 |
| Max | 400 | | 80.6 | 400 | | 45.3 | 400 | | 163 |
| n (Samp) | 217 | | 16 | 217 | | 28 | 217 | | 17 |
| n (Patient) | 133 | | 16 | 133 | | 28 | 133 | | 17 |
| UO only | | | | | | | | | |
| Median | 0.0548 | | 0.0548 | 0.0548 | | 0.114 | 0.0548 | | 0.0275 |
| Average | 9.35 | | 6.52 | 9.35 | | 3.89 | 9.35 | | 16.2 |
| Stdev | 40.2 | | 22.3 | 40.2 | | 10.00 | 40.2 | | 44.8 |
| p(t-test) | 0.80 | | 0.47 | 0.53 | | | | | |
| Min | 0.0206 | | 0.0275 | 0.0206 | | 0.0206 | 0.0206 | | 0.0206 |
| Max | 400 | | 80.6 | 400 | | 45.3 | 400 | | 163 |
| n (Samp) | 199 | | 13 | 199 | | 29 | 199 | | 15 |
| n (Patient) | 118 | | 13 | 118 | | 29 | 118 | | 15 |

| | 0 hr prior to AKI stage | | | 24 hr prior to AKI stage | | | 48 hr prior to AKI stage | | |
|---|---|---|---|---|---|---|---|---|---|
| | sCr or UO | UO only | sCr only | sCr or UO | UO only | sCr only | sCr or UO | UO only | sCr only |
| AUC | 0.48 | 0.48 | nd | 0.60 | 0.62 | nd | 0.45 | 0.38 | nd |
| SE | 0.076 | 0.084 | nd | 0.060 | 0.059 | nd | 0.074 | 0.080 | nd |
| p | 0.81 | 0.78 | nd | 0.085 | 0.04 | nd | 0.53 | 0.15 | nd |
| nCohort 1 | 217 | 199 | nd | 217 | 199 | nd | 217 | 199 | nd |
| nCohort 2 | 16 | 13 | nd | 28 | 29 | nd | 17 | 15 | nd |
| Cutoff 1 | 0.0206 | 0.0206 | nd | 0.0486 | 0.0486 | nd | 0.0206 | 0 | nd |
| Sens 1 | 94% | 100% | nd | 79% | 79% | nd | 71% | 100% | nd |
| Spec 1 | 16% | 16% | nd | 35% | 36% | nd | 16% | 0% | nd |
| Cutoff 2 | 0.0206 | 0.0206 | nd | 0.0206 | 0.0206 | nd | 0 | 0 | nd |
| Sens 2 | 94% | 100% | nd | 93% | 93% | nd | 100% | 100% | nd |
| Spec 2 | 16% | 16% | nd | 16% | 16% | nd | 0% | 0% | nd |
| Cutoff 3 | 0.0206 | 0.0206 | nd | 0.0206 | 0.0206 | nd | 0 | 0 | nd |
| Sens 3 | 94% | 100% | nd | 93% | 93% | nd | 100% | 100% | nd |
| Spec 3 | 16% | 16% | nd | 16% | 16% | nd | 0% | 0% | nd |
| Cutoff 4 | 0.114 | 0.114 | nd | 0.114 | 0.114 | nd | 0.114 | 0.114 | nd |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| Sens 4 | 19% | nd | 15% | nd | 24% | 24% |
| Spec 4 | 82% | nd | 82% | nd | 81% | 82% |
| Cutoff 5 | 0.114 | nd | 0.114 | nd | 0.114 | 0.114 |
| Sens 5 | 19% | nd | 15% | nd | 24% | 24% |
| Spec 5 | 82% | nd | 82% | nd | 81% | 82% |
| Cutoff 6 | 16.7 | nd | 16.7 | nd | 18.9 | 16.7 |
| Sens 6 | 12% | nd | 8% | nd | 10% | 12% |
| Spec 6 | 90% | nd | 90% | nd | 90% | 90% |
| OR Quart 2 | 1.4 | nd | 1.5 | nd | 0 | 1.0 |
| p Value | 0.68 | nd | 0.65 | nd | na | 0.98 |
| 95% CI of OR Quart2 | 0.30 | nd | 0.51 | nd | na | 0.24 |
|  | 6.5 | nd | 4.2 | nd | na | 4.3 |
| OR Quart 3 | 2.6 | nd | 2.2 | nd | 1.4 | 0.48 |
| p Value | 0.19 | nd | 0.23 | nd | 0.57 | 0.41 |
| 95% CI of OR Quart3 | 0.63 | nd | 0.61 | nd | 0.45 | 0.085 |
|  | 10 | nd | 7.6 | nd | 4.3 | 2.7 |
| OR Quart 4 | 0.67 | nd | 2.7 | nd | 3.0 | 1.9 |
| p Value | 0.66 | nd | 0.49 | nd | 0.035 | 0.33 |
| 95% CI of OR Quart4 | 0.11 | nd | 0.11 | nd | 1.1 | 0.52 |
|  | 4.1 | nd | 0.81 | nd | 8.5 | 6.8 |
|  | | | 9.3 | | | |

Immunoglobulin G3

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO |  |  |  |  |  |  |
| Median | 539000 | 889000 | 539000 | 671000 | 539000 | 468000 |
| Average | 699000 | 795000 | 699000 | 970000 | 699000 | 605000 |
| Stdev | 488000 | 565000 | 488000 | 829000 | 488000 | 358000 |
| p(t-test) |  | 0.57 |  | 0.029 |  | 0.59 |
| Min | 94000 | 204000 | 94000 | 210000 | 94000 | 231000 |
| Max | 2930000 | 2030000 | 2930000 | 3750000 | 2930000 | 1250000 |
| n (Samp) | 205 | 9 | 205 | 20 | 205 | 8 |
| n (Patient) | 127 | 9 | 127 | 20 | 127 | 8 |
| UO only |  |  |  |  |  |  |
| Median | 526000 | 889000 | 526000 | 671000 | 526000 | 386000 |
| Average | 688000 | 795000 | 688000 | 933000 | 688000 | 613000 |
| Stdev | 479000 | 565000 | 479000 | 826000 | 479000 | 386000 |
| p(t-test) |  | 0.52 |  | 0.68 |  |  |
| Min | 94000 | 204000 | 94000 | 210000 | 94000 | 231000 |
| Max | 2930000 | 2030000 | 2930000 | 3750000 | 2930000 | 1250000 |
| n (Samp) | 191 | 9 | 191 | 18 | 191 | 7 |
| n (Patient) | 113 | 9 | 113 | 18 | 113 | 7 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.54 | nd | 0.54 | 0.61 | nd | 0.61 | 0.44 | nd | 0.43 |
| SE | 0.10 | nd | 0.10 | 0.070 | nd | 0.073 | 0.11 | nd | 0.11 |
| p | 0.72 | nd | 0.69 | 0.10 | nd | 0.14 | 0.55 | nd | 0.56 |
| nCohort 1 | 205 | nd | 191 | 205 | nd | 191 | 205 | nd | 191 |
| nCohort 2 | 9 | nd | 9 | 20 | nd | 18 | 8 | nd | 7 |
| Cutoff 1 | 319000 | nd | 319000 | 559000 | nd | 559000 | 344000 | nd | 344000 |
| Sens 1 | 78% | nd | 78% | 70% | nd | 72% | 75% | nd | 71% |
| Spec 1 | 10% | nd | 12% | 52% | nd | 54% | 14% | nd | 16% |
| Cutoff 2 | 277000 | nd | 277000 | 526000 | nd | 526000 | 342000 | nd | 342000 |
| Sens 2 | 89% | nd | 89% | 80% | nd | 83% | 88% | nd | 86% |
| Spec 2 | 5% | nd | 6% | 48% | nd | 50% | 14% | nd | 16% |
| Cutoff 3 | 200000 | nd | 200000 | 244000 | nd | 213000 | 213000 | nd | 213000 |
| Sens 3 | 100% | nd | 100% | 90% | nd | 94% | 100% | nd | 100% |
| Spec 3 | 2% | nd | 2% | 3% | nd | 3% | 2% | nd | 3% |
| Cutoff 4 | 755000 | nd | 755000 | 755000 | nd | 755000 | 755000 | nd | 755000 |
| Sens 4 | 56% | nd | 56% | 45% | nd | 44% | 38% | nd | 43% |
| Spec 4 | 70% | nd | 70% | 70% | nd | 70% | 70% | nd | 70% |
| Cutoff 5 | 931000 | nd | 943000 | 931000 | nd | 943000 | 931000 | nd | 943000 |
| Sens 5 | 33% | nd | 33% | 35% | nd | 33% | 25% | nd | 29% |
| Spec 5 | 80% | nd | 80% | 80% | nd | 80% | 80% | nd | 80% |
| Cutoff 6 | 1260000 | nd | 1220000 | 1260000 | nd | 1220000 | 1260000 | nd | 1220000 |
| Sens 6 | 11% | nd | 11% | 20% | nd | 17% | 0% | nd | 14% |
| Spec 6 | 90% | nd | 90% | 90% | nd | 90% | 90% | nd | 90% |
| OR Quart | 20.31 | nd | 0.32 | 1.0 | nd | 0.32 | 1.0 | nd | 0.50 |
| p Value | 0.32 | nd | 0.33 | 1.0 | nd | 0.33 | 0.98 | nd | 0.58 |
| 95% CI of OR Quart2 | 0.032 | nd | 0.032 | 0.19 | nd | 0.032 | 0.14 | nd | 0.044 |
| OR Quart 3 | 3.1 | nd | 3.2 | 5.2 | nd | 3.2 | 7.5 | nd | 5.7 |
| p Value | 0 | nd | 0 | 2.1 | nd | 2.5 | 0.50 | nd | 0.49 |
| 95% CI of OR Quart3 | na | nd | na | 0.31 | nd | 0.20 | 0.58 | nd | 0.57 |
| OR Quart 4 | na | nd | na | 0.50 | nd | 0.62 | 0.044 | nd | 0.043 |
| p Value | 1.7 | nd | 1.7 | 8.9 | nd | 10 | 5.7 | nd | 5.6 |
| 95% CI of OR Quart4 | 0.48 | nd | 0.47 | 2.9 | nd | 2.5 | 1.6 | nd | 1.6 |
| OR Quart4 | 0.39 | nd | 0.39 | 0.13 | nd | 0.21 | 0.63 | nd | 0.63 |
|  | 7.5 | nd | 7.7 | 0.72 | nd | 0.61 | 0.25 | nd | 0.25 |
|  |  |  |  | 11 |  | 10 | 9.7 |  | 9.8 |

Interleukin-1 receptor type I

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 | sCr or UO

|  | | | | | | |
|---|---|---|---|---|---|---|
| Median | 61.8 | 61.9 | 61.8 | 66.2 | 61.8 | 56.0 |
| Average | 72.2 | 71.0 | 72.2 | 68.5 | 72.2 | 63.6 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | | | | | |
|---|---|---|---|---|---|
| Stdev | 52.2 | | 52.2 | 22.2 | 25.0 |
| p(t-test) | | | | 0.72 | 0.50 |
| Min | 25.4 | | 25.4 | 34.6 | 38.7 |
| Max | 502 | | 502 | 123 | 133 |
| n (Samp) | 217 | | 217 | 28 | 17 |
| n (Patient) | 133 | | 133 | 28 | 17 |
| UO only | | | | | |
| Median | 63.3 | | 63.3 | 65.6 | 56.5 |
| Average | 74.5 | | 74.5 | 68.0 | 66.4 |
| Stdev | 54.0 | | 54.0 | 22.2 | 25.9 |
| p(t-test) | | | | 0.53 | 0.57 |
| Min | 25.8 | | 25.8 | 34.6 | 38.7 |
| Max | 502 | | 502 | 123 | 133 |
| n (Samp) | 199 | | 199 | 29 | 15 |
| n (Patient) | 118 | | 118 | 29 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | nd | 0.50 | 0.55 | nd | 0.51 | 0.45 | nd | 0.47 |
| SE | 0.076 | nd | 0.083 | 0.059 | nd | 0.058 | 0.074 | nd | 0.079 |
| p | 0.67 | nd | 0.98 | 0.44 | nd | 0.80 | 0.54 | nd | 0.72 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 50.1 | nd | 50.1 | 53.7 | nd | 53.0 | 51.0 | nd | 51.0 |
| Sens 1 | 75% | nd | 77% | 71% | nd | 72% | 71% | nd | 73% |
| Spec 1 | 27% | nd | 24% | 31% | nd | 27% | 27% | nd | 24% |
| Cutoff 2 | 49.8 | nd | 49.8 | 47.6 | nd | 47.4 | 39.9 | nd | 45.5 |
| Sens 2 | 81% | nd | 85% | 82% | nd | 83% | 82% | nd | 80% |
| Spec 2 | 24% | nd | 21% | 21% | nd | 18% | 9% | nd | 17% |
| Cutoff 3 | 47.1 | nd | 49.1 | 41.4 | nd | 41.4 | 38.7 | nd | 38.7 |
| Sens 3 | 94% | nd | 92% | 93% | nd | 93% | 94% | nd | 93% |
| Spec 3 | 20% | nd | 20% | 11% | nd | 8% | 9% | nd | 7% |
| Cutoff 4 | 72.1 | nd | 74.6 | 72.1 | nd | 74.6 | 72.1 | nd | 74.6 |
| Sens 4 | 31% | nd | 31% | 39% | nd | 34% | 29% | nd | 40% |
| Spec 4 | 70% | nd | 70% | 70% | nd | 70% | 70% | nd | 70% |
| Cutoff 5 | 83.6 | nd | 84.6 | 83.6 | nd | 84.6 | 83.6 | nd | 84.6 |
| Sens 5 | 31% | nd | 31% | 25% | nd | 28% | 24% | nd | 27% |
| Spec 5 | 80% | nd | 80% | 80% | nd | 80% | 80% | nd | 80% |
| Cutoff 6 | 96.4 | nd | 96.4 | 96.4 | nd | 96.4 | 96.4 | nd | 96.4 |
| Sens 6 | 25% | nd | 31% | 7% | nd | 7% | 6% | nd | 7% |
| Spec 6 | 91% | nd | 90% | 91% | nd | 90% | 91% | nd | 90% |
| OR Quart | 1.0 | nd | 0.74 | 1.0 | nd | 1.2 | 0.75 | nd | 0.75 |
| p Value | 0.24 | nd | 0.70 | 0.30 | nd | 0.77 | 0.71 | nd | 0.72 |
| 95% CI of | 4.2 | nd | 0.16 | 3.3 | nd | 0.37 | 0.16 | nd | 0.16 |
| OR Quart2 | 0.74 | nd | 3.5 | 1.4 | nd | 3.8 | 3.5 | nd | 3.5 |
| OR Quart 3 | 0.74 | nd | 0.48 | 0.48 | nd | 1.4 | 1.3 | nd | 0.74 |
| p Value | 0.70 | nd | 0.41 | 0.57 | nd | 0.57 | 0.73 | nd | 0.70 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| 95% CI of OR Quart3 | 0.16 | nd | 0.084 | 0.45 | 0.32 | 0.16 |
| OR Quart3 | 3.4 | nd | 2.7 | 4.3 | 5.0 | 3.5 |
| p Value | 41.2 | nd | 1.0 | 1.4 | 1.4 | 1.3 |
| 95% CI of OR Quart4 | 0.75 | nd | 1.0 | 0.57 | 0.71 | 0.71 |
| | 0.32 | nd | 0.24 | 0.45 | 0.33 | 0.33 |
| OR Quart4 | 4.9 | nd | 4.2 | 4.2 | 5.1 | 5.1 |

Interleukin-20

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 5.54 | 3.83 | 5.54 | 12.1 | 5.54 | 50.0 |
| Average | 99.0 | 110 | 99.0 | 60.2 | 99.0 | 123 |
| Stdev | 594 | 274 | 594 | 141 | 594 | 265 |
| p(t-test) | | 0.94 | | 0.73 | | 0.87 |
| Min | 0.990 | 0.990 | 0.990 | 0.990 | 0.990 | 0.990 |
| Max | 8230 | 1090 | 8230 | 732 | 8230 | 1100 |
| n (Samp) | 217 | 16 | 217 | 28 | 217 | 17 |
| n (Patient) | 133 | 16 | 133 | 28 | 133 | 17 |
| UO only | | | | | | |
| Median | 5.54 | 0.995 | 5.54 | 12.1 | 5.54 | 50.0 |
| Average | 97.7 | 38.7 | 97.7 | 36.1 | 97.7 | 62.0 |
| Stdev | 619 | 90.1 | 619 | 52.0 | 619 | 87.0 |
| p(t-test) | | 0.73 | | 0.59 | | 0.82 |
| Min | 0.990 | 0.990 | 0.990 | 0.990 | 0.990 | 0.990 |
| Max | 8230 | 318 | 8230 | 247 | 8230 | 353 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | UO only | sCr only | sCr or UO | UO only | sCr only | sCr or UO | UO only | sCr only |
| AUC | 0.48 | 0.42 | nd | 0.57 | 0.59 | nd | 0.63 | 0.63 | nd |
| SE | 0.076 | 0.085 | nd | 0.059 | 0.059 | nd | 0.075 | 0.080 | nd |
| p | 0.78 | 0.34 | nd | 0.23 | 0.11 | nd | 0.087 | 0.094 | nd |
| nCohort 1 | 217 | 199 | nd | 217 | 199 | nd | 217 | 199 | nd |
| nCohort 2 | 16 | 13 | nd | 28 | 29 | nd | 17 | 15 | nd |
| Cutoff 1 | 0.990 | 0.990 | nd | 5.54 | 3.83 | nd | 21.4 | 5.54 | nd |
| Sens 1 | 81% | 77% | nd | 71% | 76% | nd | 71% | 73% | nd |
| Spec 1 | 19% | 21% | nd | 54% | 48% | nd | 64% | 58% | nd |
| Cutoff 2 | 0.990 | 0 | nd | 2.41 | 2.41 | nd | 2.41 | 2.41 | nd |
| Sens 2 | 81% | 100% | nd | 82% | 83% | nd | 82% | 80% | nd |
| Spec 2 | 19% | 0% | nd | 37% | 41% | nd | 37% | 41% | nd |
| Cutoff 3 | 0 | 0 | nd | 0.990 | 0.990 | nd | 0.990 | 0.990 | nd |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Sens 3 | 100% | nd | 93% | nd | 94% | nd | 93% |
| Spec 3 | 0% | nd | 21% | nd | 19% | nd | 21% |
| Cutoff 4 | 50.0 | nd | 45.2 | nd | 50.0 | nd | 45.2 |
| Sens 4 | 38% | nd | 31% | nd | 47% | nd | 53% |
| Spec 4 | 71% | nd | 71% | nd | 71% | nd | 71% |
| Cutoff 5 | 99.9 | nd | 88.1 | nd | 99.9 | nd | 88.1 |
| Sens 5 | 19% | nd | 14% | nd | 18% | nd | 13% |
| Spec 5 | 83% | nd | 80% | nd | 83% | nd | 80% |
| Cutoff 6 | 171 | nd | 141 | nd | 171 | nd | 141 |
| Sens 6 | 12% | nd | 3% | nd | 12% | nd | 7% |
| Spec 6 | 90% | nd | 90% | nd | 90% | nd | 90% |
| OR Quart | 20.49 | nd | 0.58 | nd | 3.1 | nd | 3.1 |
| 95% CI of p Value | 0.42 | nd | 0.47 | nd | 0.34 | nd | 0.34 |
| OR Quart2 | 0.086 | nd | 0.13 | nd | 0.31 | nd | 0.31 |
| 95% CI of | 2.8 | nd | 2.5 | nd | 30 | nd | 30 |
| OR Quart 3 | 1.9 | nd | 3.4 | nd | 12 | nd | 6.6 |
| p Value | 0.33 | nd | 0.029 | nd | 0.020 | nd | 0.085 |
| 95% CI of | 0.52 | nd | 1.1 | nd | 1.5 | nd | 0.77 |
| OR Quart3 | 6.8 | nd | 10 | nd | 96 | nd | 57 |
| OR Quart 4 | 0.75 | nd | 1.5 | nd | 3.1 | nd | 5.3 |
| p Value | 0.71 | nd | 0.54 | nd | 0.34 | nd | 0.13 |
| 95% CI of | 0.16 | nd | 0.43 | nd | 0.31 | nd | 0.60 |
| OR Quart4 | 3.5 | nd | 4.9 | nd | 30 | nd | 47 |

Interleukin-29

|  | 0 hr prior to AKI stage | | 24 hr prior to AKI stage | | 48 hr prior to AK stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 25.8 | 75.0 | 25.8 | 37.6 | 25.8 | 119 |
| Average | 164 | 267 | 164 | 75.7 | 164 | 138 |
| Stdev | 880 | 772 | 880 | 115 | 880 | 169 |
| p(t-test) |  | 0.65 |  | 0.60 |  | 0.91 |
| Min | 0.690 | 2.46 | 0.690 | 0.690 | 0.690 | 1.65 |
| Max | 10500 | 3150 | 10500 | 453 | 10500 | 735 |
| n (Samp) | 217 | 16 | 217 | 28 | 217 | 17 |
| n (Patient) | 133 | 16 | 133 | 28 | 133 | 17 |
| UO only |  |  |  |  |  |  |
| Median | 25.8 | 59.3 | 25.8 | 49.5 | 25.8 | 119 |
| Average | 175 | 60.3 | 175 | 55.8 | 175 | 126 |
| Stdev | 919 | 49.9 | 919 | 59.7 | 919 | 116 |
| p(t-test) | 0.65 | 0.49 | 0.83 |  |  |  |
| Min | 0.690 | 2.46 | 0.690 | 0.690 | 0.690 | 1.65 |
| Max | 10500 | 157 | 10500 | 211 | 10500 | 453 |
| n (Samp) | 199 | 13 | 199 | 29 | 199 | 15 |
| n (Patient) | 118 | 13 | 118 | 29 | 118 | 15 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | nd | 0.56 | 0.47 | nd | 0.46 | 0.70 | nd | 0.69 |
| SE | 0.077 | nd | 0.085 | 0.059 | nd | 0.058 | 0.073 | nd | 0.078 |
| p | 0.087 | nd | 0.51 | 0.60 | nd | 0.51 | 0.0049 | nd | 0.013 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 51.5 | nd | 2.05 | 1.31 | nd | 1.31 | 79.3 | nd | 79.3 |
| Sens 1 | 75% | nd | 100% | 71% | nd | 72% | 71% | nd | 73% |
| Spec 1 | 59% | nd | 20% | 18% | nd | 16% | 68% | nd | 67% |
| Cutoff 2 | 2.05 | nd | 2.05 | 0 | nd | 0 | 49.5 | nd | 49.5 |
| Sens 2 | 100% | nd | 100% | 100% | nd | 100% | 82% | nd | 80% |
| Spec 2 | 21% | nd | 20% | 0 | nd | 0 | 55% | nd | 54% |
| Cutoff 3 | 2.05 | nd | 2.05 | 0 | nd | 0 | 2.05 | nd | 2.05 |
| Sens 3 | 100% | nd | 100% | 100% | nd | 100% | 94% | nd | 93% |
| Spec 3 | 21% | nd | 20% | 0 | nd | 0 | 21% | nd | 20% |
| Cutoff 4 | 80.9 | nd | 80.9 | 80.9 | nd | 80.9 | 80.9 | nd | 80.9 |
| Sens 4 | 38% | nd | 23% | 36% | nd | 34% | 59% | nd | 60% |
| Spec 4 | 73% | nd | 73% | 73% | nd | 73% | 73% | nd | 73% |
| Cutoff 5 | 108 | nd | 119 | 108 | nd | 119 | 108 | nd | 119 |
| Sens 5 | 31% | nd | 15% | 21% | nd | 17% | 53% | nd | 47% |
| Spec 5 | 80% | nd | 81% | 80% | nd | 81% | 80% | nd | 81% |
| Cutoff 6 | 181 | nd | 197 | 181 | nd | 197 | 181 | nd | 197 |
| Sens 6 | 6% | nd | 0% | 11% | nd | 3% | 12% | nd | 13% |
| Spec 6 | 90% | nd | 91% | 90% | nd | 91% | 90% | nd | 91% |
| OR Quart 2 | 1.0 | nd | 0.32 | 0.74 | nd | 0.86 | 0.48 | nd | 2.0 |
| p Value | 1.0 | nd | 0.33 | 0.59 | nd | 0.78 | 0.56 | nd | 0.58 |
| 95% CI of OR Quart2 | 0.14 | nd | 0.032 | 0.24 | nd | 0.29 | 0.043 | nd | 0.18 |
| | 7.3 | nd | 3.2 | 2.3 | nd | 2.5 | 5.5 | nd | 23 |
| OR Quart 3 | 3.8 | nd | 2.5 | 0.60 | nd | 0.59 | 2.6 | nd | 4.2 |
| p Value | 0.10 | nd | 0.20 | 0.40 | nd | 0.38 | 0.26 | nd | 0.20 |
| 95% CI of OR Quart3 | 0.76 | nd | 0.62 | 0.19 | nd | 0.18 | 0.49 | nd | 0.46 |
| | 19 | nd | 10 | 2.0 | nd | 1.9 | 14 | nd | 39 |
| OR Quart 4 | 2.6 | nd | 0.65 | 1.2 | nd | 1.1 | 5.0 | nd | 9.0 |
| p Value | 0.27 | nd | 0.65 | 0.77 | nd | 0.79 | 0.045 | nd | 0.041 |
| 95% CI of OR Quart4 | 0.48 | nd | 0.10 | 0.42 | nd | 0.41 | 1.0 | nd | 1.1 |
| | 14 | nd | 4.1 | 3.3 | nd | 3.2 | 24 | nd | 75 |

Interleukin-7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.131 | 0.774 | 0.131 | 0.0775 | 0.131 | 2.44 |
| Average | 4.85 | 2.83 | 4.85 | 2.05 | 4.85 | 3.73 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | | | | | |
|---|---|---|---|---|---|
| Stdev | 18.2 | | 18.2 | 2.87 | 18.2 | 5.41 |
| p(t-test) | | | | 0.42 | | 0.80 |
| Min | 0.00806 | | 0.00806 | 0.00806 | 0.00806 | 0.00806 |
| Max | 153 | | 153 | 10.0 | 153 | 20.7 |
| n (Samp) | 217 | | 217 | 28 | 217 | 17 |
| n (Patient) | 133 | | 133 | 28 | 133 | 17 |

UO only

| | | | | | |
|---|---|---|---|---|---|
| Median | 0.0293 | | 0.0293 | 0.0301 | 0.0293 | 0.679 |
| Average | 4.53 | | 4.53 | 2.02 | 4.53 | 4.24 |
| Stdev | 18.7 | | 18.7 | 2.90 | 18.7 | 6.00 |
| p(t-test) | | | | 0.47 | | 0.95 |
| Min | 0.00806 | | 0.00806 | 0.00806 | 0.00806 | 0.00806 |
| Max | 153 | | 153 | 10.0 | 153 | 20.7 |
| n (Samp) | 199 | | 199 | 29 | 199 | 15 |
| n (Patient) | 118 | | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | nd | 0.46 | 0.53 | nd | 0.56 | 0.57 | nd | 0.59 |
| SE | 0.076 | nd | 0.084 | 0.059 | nd | 0.059 | 0.075 | nd | 0.080 |
| P | 0.84 | nd | 0.62 | 0.56 | nd | 0.27 | 0.32 | nd | 0.26 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 0.0119 | nd | 0.0119 | 0.0245 | nd | 0.0245 | 0.0163 | nd | 0.0163 |
| Sens 1 | 81% | nd | 77% | 71% | nd | 72% | 76% | nd | 73% |
| Spec 1 | 18% | nd | 21% | 41% | nd | 45% | 37% | nd | 41% |
| Cutoff 2 | 0.0119 | nd | 0 | 0.0119 | nd | 0.0119 | 0.0119 | nd | 0.0119 |
| Sens 2 | 81% | nd | 100% | 89% | nd | 90% | 82% | nd | 80% |
| Spec 2 | 18% | nd | 0% | 18% | nd | 21% | 18% | nd | 21% |
| Cutoff 3 | 0 | nd | 0 | 0 | nd | 0 | 0 | nd | 0 |
| Sens 3 | 100% | nd | 100% | 100% | nd | 100% | 100% | nd | 100% |
| Spec 3 | 0% | nd | 0% | 0% | nd | 0% | 0% | nd | 0% |
| Cutoff 4 | 2.41 | nd | 2.13 | 2.41 | nd | 2.13 | 2.41 | nd | 2.13 |
| Sens 4 | 38% | nd | 31% | 36% | nd | 38% | 53% | nd | 47% |
| Spec 4 | 70% | nd | 71% | 70% | nd | 71% | 70% | nd | 71% |
| Cutoff 5 | 4.20 | nd | 3.59 | 4.20 | nd | 3.59 | 4.20 | nd | 3.59 |
| Sens 5 | 31% | nd | 15% | 25% | nd | 24% | 29% | nd | 40% |
| Spec 5 | 80% | nd | 80% | 80% | nd | 80% | 80% | nd | 80% |
| Cutoff 6 | 8.05 | nd | 6.62 | 8.05 | nd | 6.62 | 8.05 | nd | 6.62 |
| Sens 6 | 19% | nd | 8% | 7% | nd | 10% | 12% | nd | 27% |
| Spec 6 | 90% | nd | 90% | 90% | nd | 90% | 90% | nd | 90% |
| OR Quart | 20.58 | nd | 1.5 | 4.7 | nd | 2.0 | 1.3 | nd | 1.3 |
| p Value | 0.47 | nd | 0.65 | 0.021 | nd | 0.26 | 0.71 | nd | 0.72 |
| 95% CI of | 0.13 | nd | 0.25 | 1.3 | nd | 0.61 | 0.29 | nd | 0.28 |
| OR Quart2 | 2.5 | nd | 9.5 | 18 | nd | 6.2 | 6.2 | nd | 6.3 |
| OR Quart | 30.58 | nd | 2.7 | 2.1 | nd | 1.5 | 1.4 | nd | 0.65 |
| p Value | 0.47 | nd | 0.26 | 0.31 | nd | 0.54 | 0.70 | nd | 0.65 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| 95% CI of OR Quart3 | 0.13 | nd | 0.49 | 0.50 | 0.43 | nd | 0.29 | 0.10 |
| OR Quart | 2.5 | nd | 14 | 8.9 | 4.9 | nd | 6.4 | 4.1 |
| p Value | 40.98 | nd | 1.5 | 2.5 | 1.7 | nd | 2.1 | 2.1 |
| 95% CI of OR Quart4 | 0.98 | nd | 0.65 | 0.21 | 0.38 | nd | 0.32 | 0.32 |
|  | 0.27 | nd | 0.25 | 0.61 | 0.52 | nd | 0.49 | 0.49 |
|  | 3.6 | nd | 9.5 | 10.0 | 5.5 | nd | 8.7 | 8.8 |

Platelet-derived growth factor subunit A (dimer)

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 1290 | 912 | 1290 | 1100 | 1290 | 2520 |
| Average | 2700 | 1240 | 2700 | 3700 | 2700 | 2720 |
| Stdev | 3350 | 1600 | 3350 | 9540 | 3350 | 2210 |
| p(t-test) | 0.268 | 0.085 | 0.268 | 0.24 | 0.268 | 0.98 |
| Min | 17600 | 15.3 | 17600 | 62.9 | 17600 | 5.98 |
| Max | 281 | 6630 | 281 | 51400 | 281 | 6840 |
| n (Samp) | 159 | 16 | 159 | 28 | 159 | 20 |
| n (Patient) |  | 16 |  | 28 |  | 20 |
| sCr only |  |  |  |  |  |  |
| Median | nd | nd | nd | nd | 1180 | 2710 |
| Average | nd | nd | nd | nd | 2520 | 3090 |
| Stdev | nd | nd | nd | nd | 3190 | 2290 |
| p(t-test) | nd | nd | nd | nd | 0.268 | 0.66 |
| Min | nd | nd | nd | nd | 17600 | 283 |
| Max | nd | nd | nd | nd | 352 | 6840 |
| n (Samp) | nd | nd | nd | nd | 192 | 6 |
| n (Patient) |  |  |  |  |  | 6 |
| UO only |  |  |  |  |  |  |
| Median | 1060 | 900 | 1060 | 778 | 1060 | 1900 |
| Average | 2380 | 883 | 2380 | 2120 | 2380 | 2350 |
| Stdev | 3160 | 763 | 3160 | 2560 | 3160 | 2110 |
| p(t-test) | 0.268 | 0.089 | 0.268 | 0.69 | 0.268 | 0.97 |
| Min | 17600 | 15.3 | 17600 | 62.9 | 17600 | 5.98 |
| Max | 257 | 2230 | 257 | 10300 | 257 | 6600 |
| n (Samp) | 139 | 13 | 139 | 26 | 139 | 17 |
| n (Patient) |  | 13 |  | 26 |  | 17 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.40 | nd | 0.39 | 0.51 | nd | 0.52 | 0.56 | 0.64 | 0.55 |
| SE | 0.077 | nd | 0.085 | 0.058 | nd | 0.060 | 0.069 | 0.12 | 0.074 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| P | 0.18 | 0.19 | 0.86 | 0.75 | 0.36 | 0.26 | 0.46 |
|---|---|---|---|---|---|---|---|
| nCohort 1 | 281 | 257 | 281 | 257 | 281 | 352 | 257 |
| nCohort 2 | 16 | 13 | 28 | 26 | 20 | 6 | 17 |
| Cutoff 1 | 367 | 312 | 555 | 431 | 1550 | 1590 | 468 |
| Sens 1 | 75% | 77% | 71% | 73% | 70% | 83% | 71% |
| Spec 1 | 30% | 28% | 35% | 33% | 53% | 56% | 35% |
| Cutoff 2 | 312 | 87.1 | 418 | 384 | 438 | 1590 | 418 |
| Sens 2 | 81% | 85% | 82% | 81% | 80% | 83% | 82% |
| Spec 2 | 26% | 12% | 31% | 32% | 31% | 56% | 33% |
| Cutoff 3 | 38.2 | 38.2 | 281 | 281 | 236 | 281 | 50.5 |
| Sens 3 | 94% | 92% | 93% | 92% | 90% | 100% | 94% |
| Spec 3 | 6% | 6% | 23% | 25% | 22% | 24% | 9% |
| Cutoff 4 | 3420 | 2690 | 3420 | 2690 | 3420 | 2970 | 2690 |
| Sens 4 | 6% | 0% | 25% | 35% | 35% | 33% | 41% |
| Spec 4 | 70% | 70% | 70% | 70% | 70% | 70% | 70% |
| Cutoff 5 | 4680 | 4200 | 4680 | 4200 | 4680 | 4540 | 4200 |
| Sens 5 | 6% | 0% | 18% | 15% | 25% | 17% | 24% |
| Spec 5 | 80% | 80% | 80% | 80% | 80% | 80% | 80% |
| Cutoff 6 | 7350 | 6630 | 7350 | 6630 | 7350 | 6910 | 6630 |
| Sens 6 | 0% | 0% | 7% | 8% | 0% | 0% | 0% |
| Spec 6 | 90% | 90% | 90% | 90% | 90% | 90% | 90% |
| OR Quart | 24.2 | >5.5 | 4.6 | 4.1 | 1.0 | 0 | 1.3 |
| p Value | 0.20 | <0.13 | 0.023 | 0.037 | 1.0 | na | 0.71 |
| 95% CI of | 0.46 | >0.62 | 1.2 | 1.1 | 0.20 | na | 0.29 |
| OR Quart2 | 39 | na | 17 | 15 | 5.1 | na | 6.2 |
| OR Quart | 39.0 | >5.4 | 2.5 | 2.1 | 2.9 | 3.1 | 1.7 |
| p Value | 0.041 | <0.13 | 0.20 | 0.32 | 0.13 | 0.34 | 0.47 |
| 95% CI of | 1.1 | >0.61 | 0.61 | 0.49 | 0.73 | 0.31 | 0.39 |
| OR Quart3 | 74 | na | 9.9 | 8.6 | 11 | 30 | 7.5 |
| OR Quart | 3.1 | >3.2 | 2.1 | 2.1 | 2.1 | 2.0 | 1.7 |
| p Value | 0.33 | <0.32 | 0.32 | 0.32 | 0.32 | 0.57 | 0.48 |
| 95% CI of | 0.32 | >0.32 | 0.50 | 0.49 | 0.50 | 0.18 | 0.39 |
| OR Quart4 | 31 | na | 8.5 | 8.6 | 8.5 | 22 | 7.4 |

Platelet-derived growth factor A

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 4540 | 2980 | 4540 | 3720 | 4540 | 5040 |
| Average | 9580 | 7050 | 9580 | 17100 | 9580 | 13900 |
| Stdev | 13100 | 9270 | 13100 | 40900 | 13100 | 23400 |
| p(t-test) | | 0.45 | | 0.030 | | 0.18 |
| Min | 1.99 | 9.75 | 1.99 | 10.5 | 1.99 | 9.75 |
| Max | 94900 | 30000 | 94900 | 170000 | 94900 | 103000 |
| n (Samp) | 281 | 16 | 281 | 28 | 281 | 20 |
| n (Patient) | 159 | 16 | 159 | 28 | 159 | 20 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

sCr only

|  | | |
|---|---|---|
| Median | nd | 8830 |
| Average | nd | 9330 |
| Stdev | nd | 5600 |
| p(t-test) | nd | 0.93 |
| Min | nd | 3570 |
| Max | nd | 18800 |
| n (Samp) | nd | 6 |
| n (Patient) | nd | 6 |

UO only

|  | | |
|---|---|---|
| Median | 3960 | 4720 |
| Average | 8890 | 14000 |
| Stdev | 12400 | 25400 |
| p(t-test) | 1.99 | 0.064 |
| Min | 1.99 | 9.75 |
| Max | 94900 | 103000 |
| n (Samp) | 352 | 257 |
| n (Patient) | 192 | 17 | sCr or UO

|  | | |
|---|---|---|
| Median | 3920 | 3920 |
| Average | 8130 | 8130 |
| Stdev | 11400 | 11400 |
| p(t-test) |  | 1.99 |
| Min | 1.99 | 9.75 |
| Max | 88200 | 88200 |
| n (Samp) | 257 | 257 |
| n (Patient) | 139 | 139 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.44 | nd | 0.44 | 0.48 | nd | 0.48 | 0.55 | 0.66 | 0.54 |
| SE | 0.076 | nd | 0.084 | 0.058 | nd | 0.060 | 0.068 | 0.12 | 0.074 |
| P | 0.42 | nd | 0.45 | 0.78 | nd | 0.76 | 0.48 | 0.19 | 0.56 |
| nCohort 1 | 281 | nd | 257 | 281 | nd | 257 | 281 | 352 | 257 |
| nCohort 2 | 16 | nd | 13 | 28 | nd | 26 | 20 | 6 | 17 |
| Cutoff 1 | 1020 | nd | 689 | 1990 | nd | 1600 | 2730 | 4000 | 2490 |
| Sens 1 | 75% | nd | 77% | 75% | nd | 73% | 70% | 83% | 71% |
| Spec 1 | 20% | nd | 19% | 31% | nd | 30% | 38% | 50% | 37% |
| Cutoff 2 | 689 | nd | 333 | 1220 | nd | 1220 | 1700 | 4000 | 1400 |
| Sens 2 | 81% | nd | 85% | 82% | nd | 81% | 80% | 83% | 82% |
| Spec 2 | 17% | nd | 12% | 26% | nd | 28% | 30% | 50% | 28% |
| Cutoff 3 | 190 | nd | 190 | 303 | nd | 303 | 430 | 3550 | 333 |
| Sens 3 | 94% | nd | 92% | 93% | nd | 92% | 90% | 100% | 94% |
| Spec 3 | 10% | nd | 11% | 10% | nd | 11% | 13% | 47% | 12% |
| Cutoff 4 | 10000 | nd | 8230 | 10000 | nd | 8230 | 10000 | 9060 | 8230 |
| Sens 4 | 25% | nd | 23% | 21% | nd | 27% | 40% | 33% | 35% |
| Spec 4 | 70% | nd | 70% | 70% | nd | 70% | 70% | 70% | 70% |
| Cutoff 5 | 16000 | nd | 12800 | 16000 | nd | 12800 | 16000 | 14200 | 12800 |
| Sens 5 | 25% | nd | 23% | 18% | nd | 19% | 20% | 17% | 29% |
| Spec 5 | 80% | nd | 80% | 80% | nd | 80% | 80% | 80% | 80% |
| Cutoff 6 | 25000 | nd | 21300 | 25000 | nd | 21300 | 25000 | 24700 | 21300 |
| Sens 6 | 6% | nd | 8% | 14% | nd | 15% | 15% | 0% | 18% |
| Spec 6 | 90% | nd | 90% | 90% | nd | 90% | 90% | 90% | 90% |
| OR Quart | 20.49 | nd | 0.67 | 1.0 | nd | 1.2 | 2.1 | >2.0 | 1.3 |
| p Value | 0.42 | nd | 0.66 | 0.98 | nd | 0.75 | 0.31 | <0.57 | 0.71 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| 95% CI of Quart2 | 0.088 | nd | 0.11 | 0.31 | 0.35 | >0.18 |
| OR Quart2 | 2.8 | nd | 4.1 | 3.3 | 4.2 | na |
| OR Quart 3 | 1.3 | nd | 1.0 | 2.0 | 2.2 | >3.1 |
| p Value | 0.72 | nd | 1.0 | 0.20 | 0.18 | <0.33 |
| 95% CI of Quart3 | 0.33 | nd | 0.19 | 0.70 | 0.70 | >0.32 |
| OR Quart3 | 5.0 | nd | 5.1 | 5.7 | 6.7 | na |
| OR Quart 4 | 1.3 | nd | 1.7 | 0.83 | 1.0 | >1.0 |
| p Value | 0.72 | nd | 0.46 | 0.77 | 0.98 | <1.0 |
| 95% CI of Quart4 | 0.33 | nd | 0.40 | 0.24 | 0.28 | >0.062 |
| OR Quart4 | 5.0 | nd | 7.6 | 2.9 | 3.7 | na |

Cohort 2 (right column): 0.29, 6.2, 1.4, 0.70, 0.29, 6.3, 2.1, 0.32, 0.49, 8.6

Thymic stromal lymphopoietin

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.0181 | 0.998 | 0.0181 | 0.232 | 0.0181 | 1.55 |
| Average | 109 | 160 | 109 | 99.1 | 109 | 1330 |
| Stdev | 1360 | 534 | 1360 | 410 | 1360 | 4840 |
| p(t-test) |  | 0.88 |  | 0.97 |  | 0.0086 |
| Min | 0.00640 | 0.00640 | 0.00640 | 0.00640 | 0.00640 | 0.00640 |
| Max | 20000 | 2140 | 20000 | 2170 | 20000 | 20000 |
| n (Samp) | 216 | 16 | 216 | 28 | 216 | 17 |
| n (Patient) | 132 | 16 | 132 | 28 | 132 | 17 |
| UO only | | | | | | |
| Median | 0.0181 | 0.190 | 0.0181 | 0.637 | 0.0181 | 1.55 |
| Average | 118 | 175 | 118 | 88.1 | 118 | 1490 |
| Stdev | 1420 | 592 | 1420 | 402 | 1420 | 5150 |
| p(t-test) |  | 0.89 |  | 0.91 |  | 0.0081 |
| Min | 0.00640 | 0.00640 | 0.00640 | 0.00640 | 0.00640 | 0.00640 |
| Max | 20000 | 2140 | 20000 | 2170 | 20000 | 20000 |
| n (Samp) | 198 | 13 | 198 | 29 | 198 | 15 |
| n (Patient) | 117 | 113 | 117 | 29 | 117 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.62 | nd | 0.59 | 0.58 | nd | 0.59 | 0.60 | nd | 0.58 |
| SE | 0.077 | nd | 0.085 | 0.059 | nd | 0.059 | 0.075 | nd | 0.080 |
| p | 0.13 | nd | 0.28 | 0.19 | nd | 0.11 | 0.20 | nd | 0.35 |
| nCohort 1 | 216 | nd | 198 | 216 | nd | 198 | 216 | nd | 198 |
| nCohort 2 | 16 | nd | 13 | 28 | nd | 29 | 17 | nd | 15 |
| Cutoff 1 | 0.0150 | nd | 0.0150 | 0.0150 | nd | 0.0150 | 0.0174 | nd | 0.0150 |
| Sens 1 | 88% | nd | 85% | 71% | nd | 76% | 71% | nd | 73% |
| Spec 1 | 34% | nd | 34% | 34% | nd | 34% | 48% | nd | 34% |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | | | | | | | |
|---|---|---|---|---|---|---|---|
| Cutoff 2 | 0.0150 | nd | 0.0129 | 0.0129 | nd | 0.0123 | 0.0123 |
| Sens 2 | 88% | nd | 89% | 93% | nd | 88% | 87% |
| Spec 2 | 34% | nd | 21% | 22% | nd | 14% | 15% |
| Cutoff 3 | 0 | nd | 0.0123 | 0.0129 | nd | 0 | 0 |
| Sens 3 | 100% | nd | 96% | 93% | nd | 100% | 100% |
| Spec 3 | 0% | nd | 14% | 22% | nd | 0% | 0% |
| Cutoff 4 | 2.68 | nd | 2.68 | 2.68 | nd | 2.68 | 2.68 |
| Sens 4 | 44% | nd | 43% | 41% | nd | 47% | 47% |
| Spec 4 | 70% | nd | 70% | 70% | nd | 70% | 70% |
| Cutoff 5 | 6.32 | nd | 6.32 | 7.30 | nd | 6.32 | 7.30 |
| Sens 5 | 31% | nd | 21% | 21% | nd | 24% | 20% |
| Spec 5 | 80% | nd | 80% | 80% | nd | 80% | 80% |
| Cutoff 6 | 18.0 | nd | 18.0 | 18.0 | nd | 18.0 | 18.0 |
| Sens 6 | 25% | nd | 18% | 17% | nd | 24% | 20% |
| Spec 6 | 90% | nd | 90% | 90% | nd | 90% | 90% |
| OR Quart 2 | 1.5 | nd | 1.8 | 1.2 | nd | 0.24 | 0.24 |
| p Value | 0.65 | nd | 0.35 | 0.77 | nd | 0.20 | 0.20 |
| 95% CI of OR Quart2 | 0.25, 9.5 | nd | 0.51, 6.7 | 0.34, 4.2 | nd | 0.026, 2.2 | 0.025, 2.2 |
| OR Quart 3 | 2.1 | nd | 2.2 | 1.9 | nd | 1.3 | 1.0 |
| p Value | 0.41 | nd | 0.23 | 0.27 | nd | 0.73 | 1.0 |
| 95% CI of OR Quart3 | 0.36, 12 | nd | 0.61, 7.6 | 0.60, 6.1 | nd | 0.32, 5.0 | 0.24, 4.2 |
| OR Quart 4 | 3.8 | nd | 2.5 | 1.9 | nd | 1.8 | 1.5 |
| p Value | 0.10 | nd | 0.15 | 0.27 | nd | 0.36 | 0.53 |
| 95% CI of OR Quart4 | 0.76, 19 | nd | 0.72, 8.5 | 0.60, 6.1 | nd | 0.50, 6.6 | 0.41, 5.8 |

TABLE 7

Comparison of marker levels in EDTA samples collected within 12
hours of reaching stage R from Cohort 1 (patients that reached, but did not progress
beyond, RIFLE stage R) and from Cohort 2 (patients that reached RIFLE stage I or F).

| | C—C motif chemokine 21 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 478 | 699 | nd | nd | 400 | 732 |
| Average | 666 | 841 | nd | nd | 546 | 836 |
| Stdev | 655 | 685 | nd | nd | 434 | 658 |
| p(t-test) | | 0.35 | nd | nd | | 0.080 |
| Min | 83.1 | 226 | nd | nd | 83.1 | 226 |
| Max | 3130 | 2540 | nd | nd | 2230 | 2450 |
| n (Samp) | 41 | 19 | nd | nd | 31 | 15 |
| n (Patient) | 41 | 19 | nd | nd | 31 | 15 |

| | At Enrollment | | |
|---|---|---|---|
| | sCr or UO | sCr only | UO only |
| AUC | 0.61 | nd | 0.65 |
| SE | 0.080 | nd | 0.090 |
| p | 0.16 | nd | 0.093 |
| nCohort 1 | 41 | nd | 31 |
| nCohort 2 | 19 | nd | 15 |
| Cutoff 1 | 355 | nd | 354 |
| Sens 1 | 74% | nd | 73% |
| Spec 1 | 39% | nd | 45% |
| Cutoff 2 | 294 | nd | 294 |
| Sens 2 | 84% | nd | 80% |
| Spec 2 | 32% | nd | 35% |
| Cutoff 3 | 272 | nd | 272 |
| Sens 3 | 95% | nd | 93% |
| Spec 3 | 24% | nd | 29% |
| Cutoff 4 | 614 | nd | 602 |
| Sens 4 | 53% | nd | 53% |
| Spec 4 | 71% | nd | 71% |
| Cutoff 5 | 866 | nd | 785 |
| Sens 5 | 37% | nd | 47% |
| Spec 5 | 80% | nd | 81% |
| Cutoff 6 | 1360 | nd | 903 |
| Sens 6 | 16% | nd | 40% |
| Spec 6 | 90% | nd | 90% |
| OR Quart 2 | 2.7 | nd | 3.2 |
| p Value | 0.24 | nd | 0.23 |
| 95% CI of OR Quart2 | 0.52 14 | nd | 0.47 22 |
| OR Quart 3 | 1.0 | nd | 1.0 |
| p Value | 1.0 | nd | 1.0 |
| 95% CI of OR Quart3 | 0.17 6.0 | nd | 0.11 8.7 |
| OR Quart 4 | 3.5 | nd | 4.5 |
| p Value | 0.13 | nd | 0.12 |
| 95% CI of OR Quart4 | 0.69 18 | nd | 0.67 30 |

| | Interleukin-20 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 5.54 | 45.2 | nd | nd | 5.54 | 45.2 |
| Average | 50.9 | 55.4 | nd | nd | 53.8 | 61.7 |
| Stdev | 86.1 | 79.9 | nd | nd | 93.6 | 88.1 |
| p(t-test) | | 0.85 | nd | nd | | 0.78 |
| Min | 0.990 | 0.995 | nd | nd | 0.990 | 0.995 |
| Max | 412 | 353 | nd | nd | 412 | 353 |
| n (Samp) | 41 | 19 | nd | nd | 31 | 15 |
| n (Patient) | 41 | 19 | nd | nd | 31 | 15 |

| | At Enrollment | | |
|---|---|---|---|
| | sCr or UO | sCr only | UO only |
| AUC | 0.64 | nd | 0.65 |
| SE | 0.080 | nd | 0.090 |

TABLE 7-continued

Comparison of marker levels in EDTA samples collected within 12 hours of reaching stage R from Cohort 1 (patients that reached, but did not progress beyond, RIFLE stage R) and from Cohort 2 (patients that reached RIFLE stage I or F).

| | | | | | |
|---|---|---|---|---|---|
| p | 0.081 | | nd | | 0.10 |
| nCohort 1 | 41 | | nd | | 31 |
| nCohort 2 | 19 | | nd | | 15 |
| Cutoff 1 | 5.54 | | nd | | 5.54 |
| Sens 1 | 84% | | nd | | 87% |
| Spec 1 | 54% | | nd | | 58% |
| Cutoff 2 | 5.54 | | nd | | 5.54 |
| Sens 2 | 84% | | nd | | 87% |
| Spec 2 | 54% | | nd | | 58% |
| Cutoff 3 | 0.990 | | nd | | 0.990 |
| Sens 3 | 100% | | nd | | 100% |
| Spec 3 | 20% | | nd | | 19% |
| Cutoff 4 | 50.0 | | nd | | 37.9 |
| Sens 4 | 32% | | nd | | 53% |
| Spec 4 | 71% | | nd | | 71% |
| Cutoff 5 | 99.9 | | nd | | 99.9 |
| Sens 5 | 21% | | nd | | 7% |
| Spec 5 | 80% | | nd | | 81% |
| Cutoff 6 | 173 | | nd | | 173 |
| Sens 6 | 5% | | nd | | 7% |
| Spec 6 | 90% | | nd | | 90% |
| OR Quart 2 | 3.2 | | nd | | 0.90 |
| p Value | 0.21 | | nd | | 0.92 |
| 95% CI of | 0.52 | | nd | | 0.10 |
| OR Quart2 | 20 | | nd | | 7.8 |
| OR Quart 3 | 5.7 | | nd | | 7.9 |
| p Value | 0.059 | | nd | | 0.039 |
| 95% CI of | 0.94 | | nd | | 1.1 |
| OR Quart3 | 34 | | nd | | 56 |
| OR Quart 4 | 3.2 | | nd | | 2.2 |
| p Value | 0.21 | | nd | | 0.41 |
| 95% CI of | 0.52 | | nd | | 0.32 |
| OR Quart4 | 20 | | nd | | 16 |

TABLE 8

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| C—C motif chemokine 1 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2.06 | 2.77 | 2.06 | 2.55 | 2.06 | 2.73 |
| Average | 3.93 | 4.27 | 3.93 | 4.17 | 3.93 | 4.61 |
| Stdev | 9.16 | 4.74 | 9.16 | 4.79 | 9.16 | 5.94 |
| p(t-test) | | 0.90 | | 0.93 | | 0.85 |
| Min | 0.00857 | 1.12 | 0.00857 | 1.12 | 0.00857 | 1.26 |
| Max | 62.2 | 18.0 | 62.2 | 18.0 | 62.2 | 18.0 |
| n (Samp) | 64 | 12 | 64 | 12 | 64 | 7 |
| n (Patient) | 64 | 12 | 64 | 12 | 64 | 7 |
| sCr only | | | | | | |
| Median | 2.09 | 2.77 | 2.09 | 2.27 | nd | nd |
| Average | 4.01 | 3.27 | 4.01 | 3.07 | nd | nd |
| Stdev | 8.24 | 2.55 | 8.24 | 2.64 | nd | nd |
| p(t-test) | | 0.83 | | 0.78 | nd | nd |
| Min | 0.00857 | 1.12 | 0.00857 | 1.12 | nd | nd |
| Max | 62.2 | 8.28 | 62.2 | 8.28 | nd | nd |
| n (Samp) | 131 | 6 | 131 | 6 | nd | nd |
| n (Patient) | 131 | 6 | 131 | 6 | nd | nd |
| UO only | | | | | | |
| Median | 2.09 | 2.81 | 2.09 | 2.81 | 2.09 | 2.81 |
| Average | 4.11 | 4.66 | 4.11 | 4.66 | 4.11 | 5.07 |
| Stdev | 9.21 | 5.50 | 9.21 | 5.50 | 9.21 | 6.36 |
| p(t-test) | | 0.87 | | 0.87 | | 0.80 |

TABLE 8-continued

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.

| | | | | | | | | | |
|---|---|---|---|---|---|---|---|---|---|
| Min | 0.00857 | 1.37 | 0.00857 | 1.37 | 0.00857 | | 1.26 | | |
| Max | 62.2 | 18.0 | 62.2 | 18.0 | 62.2 | | 18.0 | | |
| n (Samp) | 63 | 8 | 63 | 8 | 63 | | 6 | | |
| n (Patient) | 63 | 8 | 63 | 8 | 63 | | 6 | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.57 | 0.63 | 0.61 | 0.52 | 0.63 | 0.62 | nd | 0.63 |
| SE | 0.093 | 0.12 | 0.11 | 0.093 | 0.12 | 0.11 | 0.12 | nd | 0.13 |
| p | 0.16 | 0.55 | 0.25 | 0.25 | 0.85 | 0.25 | 0.31 | nd | 0.32 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 1.79 | 1.79 | 2.28 | 1.58 | 1.55 | 2.28 | 2.28 | nd | 2.28 |
| Sens 1 | 75% | 83% | 75% | 75% | 83% | 75% | 71% | nd | 83% |
| Spec 1 | 41% | 39% | 56% | 39% | 34% | 56% | 58% | nd | 56% |
| Cutoff 2 | 1.55 | 1.79 | 1.55 | 1.55 | 1.55 | 1.55 | 1.79 | nd | 2.28 |
| Sens 2 | 83% | 83% | 88% | 83% | 83% | 88% | 86% | nd | 83% |
| Spec 2 | 39% | 39% | 37% | 39% | 34% | 37% | 41% | nd | 56% |
| Cutoff 3 | 1.32 | 1.10 | 1.32 | 1.32 | 1.10 | 1.32 | 1.26 | nd | 1.26 |
| Sens 3 | 92% | 100% | 100% | 92% | 100% | 100% | 100% | nd | 100% |
| Spec 3 | 34% | 21% | 32% | 34% | 21% | 32% | 31% | nd | 29% |
| Cutoff 4 | 3.19 | 3.30 | 3.30 | 3.19 | 3.30 | 3.30 | 3.19 | nd | 3.30 |
| Sens 4 | 25% | 17% | 25% | 25% | 17% | 25% | 14% | nd | 17% |
| Spec 4 | 70% | 70% | 71% | 70% | 70% | 71% | 70% | nd | 71% |
| Cutoff 5 | 4.33 | 4.23 | 4.57 | 4.33 | 4.23 | 4.57 | 4.33 | nd | 4.57 |
| Sens 5 | 25% | 17% | 25% | 25% | 17% | 25% | 14% | nd | 17% |
| Spec 5 | 81% | 80% | 81% | 81% | 80% | 81% | 81% | nd | 81% |
| Cutoff 6 | 6.00 | 7.18 | 6.77 | 6.00 | 7.18 | 6.77 | 6.00 | nd | 6.77 |
| Sens 6 | 17% | 17% | 12% | 17% | 17% | 12% | 14% | nd | 17% |
| Spec 6 | 91% | 90% | 90% | 91% | 90% | 90% | 91% | nd | 90% |
| OR Quart | 23.4 | 1.0 | >2.1 | 4.8 | 2.1 | >2.1 | >2.1 | nd | >1.1 |
| p Value | 0.31 | 1.0 | <0.55 | 0.18 | 0.56 | <0.55 | <0.55 | nd | <0.97 |
| 95% CI of | 0.32 | 0.060 | >0.18 | 0.48 | 0.18 | >0.18 | >0.18 | nd | >0.061 |
| OR Quart2 | 36 | 17 | na | 48 | 24 | na | na | nd | na |
| OR Quart 3 | 6.4 | 3.2 | >4.9 | 4.8 | 2.1 | >4.9 | >4.9 | nd | >5.2 |
| p Value | 0.11 | 0.33 | <0.18 | 0.18 | 0.56 | <0.18 | <0.18 | nd | <0.16 |
| 95% CI of | 0.67 | 0.32 | >0.49 | 0.48 | 0.18 | >0.49 | >0.49 | nd | >0.52 |
| OR Quart3 | 61 | 32 | na | 48 | 24 | na | na | nd | na |
| OR Quart 4 | 3.4 | 0.97 | >2.1 | 3.4 | 0.97 | >2.1 | >1.0 | nd | >1.0 |
| p Value | 0.31 | 0.98 | <0.55 | 0.31 | 0.98 | <0.55 | <1.0 | nd | <1.0 |
| 95% CI of | 0.32 | 0.058 | >0.18 | 0.32 | 0.058 | >0.18 | >0.058 | nd | >0.058 |
| OR Quart4 | 36 | 16 | na | 36 | 16 | na | na | nd | na |

C—C motif chemokine 17

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 24.7 | 31.1 | 24.7 | 31.1 | 24.7 | 31.5 |
| Average | 45.0 | 48.2 | 45.0 | 48.2 | 45.0 | 60.4 |
| Stdev | 52.8 | 73.3 | 52.8 | 73.3 | 52.8 | 95.2 |
| p(t-test) | | 0.86 | | 0.86 | | 0.51 |
| Min | 2.50 | 0.819 | 2.50 | 0.819 | 2.50 | 0.819 |
| Max | 258 | 273 | 258 | 273 | 258 | 273 |
| n (Samp) | 64 | 12 | 64 | 12 | 64 | 7 |
| n (Patient) | 64 | 12 | 64 | 12 | 64 | 7 |
| sCr only | | | | | | |
| Median | 25.3 | 25.4 | 25.3 | 25.4 | nd | nd |
| Average | 47.8 | 62.9 | 47.8 | 62.9 | nd | nd |
| Stdev | 83.5 | 105 | 83.5 | 105 | nd | nd |
| p(t-test) | | 0.67 | | 0.67 | nd | nd |
| Min | 0.0212 | 0.819 | 0.0212 | 0.819 | nd | nd |
| Max | 737 | 273 | 737 | 273 | nd | nd |
| n (Samp) | 131 | 6 | 131 | 6 | nd | nd |
| n (Patient) | 131 | 6 | 131 | 6 | nd | nd |
| UO only | | | | | | |
| Median | 20.6 | 32.2 | 20.6 | 32.2 | 20.6 | 30.0 |
| Average | 41.0 | 31.6 | 41.0 | 31.6 | 41.0 | 25.0 |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | | | |
|---|---|---|---|---|---|---|---|---|---|
| Stdev | 54.3 | 21.4 | 54.3 | | 21.4 | 54.3 | | 18.8 | |
| p(t-test) | | 0.63 | | | 0.63 | | | 0.48 | |
| Min | 2.50 | 0.819 | 2.50 | | 0.819 | 2.50 | | 0.819 | |
| Max | 285 | 65.4 | 285 | | 65.4 | 285 | | 51.0 | |
| n (Samp) | 63 | 8 | 63 | | 8 | 63 | | 6 | |
| n (Patient) | 63 | 8 | 63 | | 8 | 63 | | 6 | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.46 | 0.54 | 0.49 | 0.46 | 0.54 | 0.49 | nd | 0.46 |
| SE | 0.092 | 0.12 | 0.11 | 0.092 | 0.12 | 0.11 | 0.12 | nd | 0.13 |
| P | 0.88 | 0.77 | 0.75 | 0.88 | 0.77 | 0.75 | 0.95 | nd | 0.75 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 18.9 | 0.819 | 28.2 | 18.9 | 0.819 | 28.2 | 25.6 | nd | 5.21 |
| Sens 1 | 75% | 83% | 75% | 75% | 83% | 75% | 71% | nd | 83% |
| Spec 1 | 42% | 2% | 62% | 42% | 2% | 62% | 53% | nd | 8% |
| Cutoff 2 | 5.21 | 0.819 | 5.21 | 5.21 | 0.819 | 5.21 | 5.21 | nd | 5.21 |
| Sens 2 | 83% | 83% | 88% | 83% | 83% | 88% | 86% | nd | 83% |
| Spec 2 | 8% | 2% | 8% | 8% | 2% | 8% | 8% | nd | 8% |
| Cutoff 3 | 0.819 | 0.0212 | 0 | 0.819 | 0.0212 | 0 | 0 | nd | 0 |
| Sens 3 | 92% | 100% | 100% | 92% | 100% | 100% | 100% | nd | 100% |
| Spec 3 | 0% | 1% | 0% | 0% | 1% | 0% | 0% | nd | 0% |
| Cutoff 4 | 48.8 | 38.8 | 36.3 | 48.8 | 38.8 | 36.3 | 48.8 | nd | 36.3 |
| Sens 4 | 25% | 33% | 38% | 25% | 33% | 38% | 29% | nd | 17% |
| Spec 4 | 70% | 70% | 71% | 70% | 70% | 71% | 70% | nd | 71% |
| Cutoff 5 | 72.7 | 54.3 | 61.5 | 72.7 | 54.3 | 61.5 | 72.7 | nd | 61.5 |
| Sens 5 | 8% | 17% | 12% | 8% | 17% | 12% | 14% | nd | 0% |
| Spec 5 | 81% | 80% | 81% | 81% | 80% | 81% | 81% | nd | 81% |
| Cutoff 6 | 114 | 98.8 | 93.6 | 114 | 98.8 | 93.6 | 114 | nd | 93.6 |
| Sens 6 | 8% | 17% | 0% | 8% | 17% | 0% | 14% | nd | 0% |
| Spec 6 | 91% | 90% | 90% | 91% | 90% | 90% | 91% | nd | 90% |
| OR Quart | 23.9 | 0.50 | 0 | 3.9 | 0.50 | 0 | 4.9 | nd | 3.6 |
| p Value | 0.13 | 0.58 | na | 0.13 | 0.58 | na | 0.18 | nd | 0.29 |
| 95% CI of | 0.68 | 0.043 | na | 0.68 | 0.043 | na | 0.49 | nd | 0.34 |
| OR Quart2 | 23 | 5.8 | na | 23 | 5.8 | na | 49 | nd | 39 |
| OR Quart 3 | 0.47 | 0.50 | 2.1 | 0.47 | 0.50 | 2.1 | 0 | nd | 0 |
| p Value | 0.55 | 0.58 | 0.42 | 0.55 | 0.58 | 0.42 | na | nd | na |
| 95% CI of | 0.039 | 0.043 | 0.34 | 0.039 | 0.043 | 0.34 | na | nd | na |
| OR Quart3 | 5.7 | 5.8 | 14 | 5.7 | 5.8 | 14 | na | nd | na |
| OR Quart 4 | 1.6 | 1.0 | 0.94 | 1.6 | 1.0 | 0.94 | 2.3 | nd | 2.3 |
| p Value | 0.63 | 0.98 | 0.95 | 0.63 | 0.98 | 0.95 | 0.52 | nd | 0.52 |
| 95% CI of | 0.23 | 0.14 | 0.12 | 0.23 | 0.14 | 0.12 | 0.19 | nd | 0.19 |
| OR Quart4 | 11 | 7.8 | 7.5 | 11 | 7.8 | 7.5 | 28 | nd | 28 |

C—C motif chemokine 21

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 474 | 849 | 474 | 798 | 474 | 832 |
| Average | 923 | 2300 | 923 | 2180 | 923 | 1110 |
| Stdev | 1760 | 4460 | 1760 | 4490 | 1760 | 628 |
| p(t-test) | | 0.067 | | 0.096 | | 0.78 |
| Min | 0.947 | 171 | 0.947 | 171 | 0.947 | 470 |
| Max | 12300 | 16300 | 12300 | 16300 | 12300 | 2060 |
| n (Samp) | 65 | 12 | 65 | 12 | 65 | 7 |
| n (Patient) | 65 | 12 | 65 | 12 | 65 | 7 |
| sCr only | | | | | | |
| Median | 524 | 730 | 524 | 555 | nd | nd |
| Average | 842 | 904 | 842 | 657 | nd | nd |
| Stdev | 1370 | 632 | 1370 | 455 | nd | nd |
| p(t-test) | | 0.91 | | 0.74 | nd | nd |
| Min | 0.947 | 171 | 0.947 | 171 | nd | nd |
| Max | 12300 | 1850 | 12300 | 1460 | nd | nd |
| n (Samp) | 132 | 6 | 132 | 6 | nd | nd |
| n (Patient) | 132 | 6 | 132 | 6 | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| UO only | | | | | | |
|---|---|---|---|---|---|---|
| Median | 511 | 1170 | 511 | 1170 | 511 | 1150 |
| Average | 1010 | 3060 | 1010 | 3060 | 1010 | 1210 |
| Stdev | 1800 | 5390 | 1800 | 5390 | 1800 | 617 |
| p(t-test) | | 0.026 | | 0.026 | | 0.78 |
| Min | 0.947 | 470 | 0.947 | 470 | 0.947 | 470 |
| Max | 12300 | 16300 | 12300 | 16300 | 12300 | 2060 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.72 | 0.62 | 0.78 | 0.68 | 0.52 | 0.78 | 0.74 | nd | 0.75 |
| SE | 0.088 | 0.12 | 0.10 | 0.091 | 0.12 | 0.10 | 0.11 | nd | 0.12 |
| p | 0.013 | 0.33 | 0.0053 | 0.054 | 0.84 | 0.0053 | 0.035 | nd | 0.038 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 615 | 474 | 815 | 474 | 355 | 815 | 726 | nd | 726 |
| Sens 1 | 75% | 83% | 75% | 75% | 83% | 75% | 71% | nd | 83% |
| Spec 1 | 63% | 46% | 72% | 51% | 34% | 72% | 71% | nd | 67% |
| Cutoff 2 | 474 | 474 | 726 | 442 | 355 | 726 | 474 | nd | 726 |
| Sens 2 | 83% | 83% | 88% | 83% | 83% | 88% | 86% | nd | 83% |
| Spec 2 | 51% | 46% | 67% | 49% | 34% | 67% | 51% | nd | 67% |
| Cutoff 3 | 442 | 168 | 455 | 339 | 168 | 455 | 442 | nd | 455 |
| Sens 3 | 92% | 100% | 100% | 92% | 100% | 100% | 100% | nd | 100% |
| Spec 3 | 49% | 14% | 48% | 38% | 14% | 48% | 49% | nd | 48% |
| Cutoff 4 | 726 | 821 | 786 | 726 | 821 | 786 | 726 | nd | 786 |
| Sens 4 | 67% | 50% | 75% | 58% | 33% | 75% | 71% | nd | 67% |
| Spec 4 | 71% | 70% | 70% | 71% | 70% | 70% | 71% | nd | 70% |
| Cutoff 5 | 933 | 1050 | 1170 | 933 | 1050 | 1170 | 933 | nd | 1170 |
| Sens 5 | 42% | 33% | 50% | 33% | 17% | 50% | 43% | nd | 50% |
| Spec 5 | 80% | 80% | 81% | 80% | 80% | 81% | 80% | nd | 81% |
| Cutoff 6 | 1560 | 1520 | 2520 | 1560 | 1520 | 2520 | 1560 | nd | 2520 |
| Sens 6 | 33% | 17% | 12% | 25% | 0% | 12% | 29% | nd | 0% |
| Spec 6 | 91% | 90% | 91% | 91% | 90% | 91% | 91% | nd | 91% |
| OR Quart | 22.1 | 0.97 | >1.1 | 3.4 | 2.0 | >1.1 | >2.2 | nd | >1.0 |
| p Value | 0.55 | 0.98 | <0.97 | 0.31 | 0.58 | <0.97 | <0.52 | nd | <1.0 |
| 95% CI of | 0.18 | 0.058 | >0.061 | 0.32 | 0.17 | >0.061 | >0.19 | nd | >0.058 |
| OR Quart2 | 26 | 16 | na | 36 | 23 | na | na | nd | na |
| OR Quart 3 | 4.8 | 2.1 | >3.6 | 3.4 | 2.1 | >3.6 | >2.2 | nd | >2.3 |
| p Value | 0.18 | 0.56 | <0.29 | 0.31 | 0.56 | <0.29 | <0.52 | nd | <0.52 |
| 95% CI of | 0.48 | 0.18 | >0.34 | 0.32 | 0.18 | >0.34 | >0.19 | nd | >0.19 |
| OR Quart3 | 48 | 24 | na | 36 | 24 | na | na | nd | na |
| OR Quart 4 | 6.0 | 2.0 | >5.1 | 6.0 | 0.97 | >5.1 | >3.6 | nd | >3.4 |
| p Value | 0.12 | 0.58 | <0.16 | 0.12 | 0.98 | <0.16 | <0.29 | nd | <0.31 |
| 95% CI of | 0.63 | 0.17 | >0.52 | 0.63 | 0.058 | >0.52 | >0.34 | nd | >0.32 |
| OR Quart4 | 57 | 23 | na | 57 | 16 | na | na | nd | na |

C—C motif chemokine 27

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 300 | 404 | 300 | 404 | 300 | 459 |
| Average | 352 | 445 | 352 | 438 | 352 | 559 |
| Stdev | 217 | 260 | 217 | 267 | 217 | 281 |
| p(t-test) | | 0.19 | | 0.23 | | 0.022 |
| Min | 29.4 | 129 | 29.4 | 129 | 29.4 | 144 |
| Max | 973 | 935 | 973 | 935 | 973 | 935 |
| n (Samp) | 65 | 12 | 65 | 12 | 65 | 7 |
| n (Patient) | 65 | 12 | 65 | 12 | 65 | 7 |
| sCr only | | | | | | |
| Median | 318 | 337 | 318 | 337 | nd | nd |
| Average | 355 | 377 | 355 | 362 | nd | nd |
| Stdev | 195 | 221 | 195 | 234 | nd | nd |
| p(t-test) | | 0.79 | | 0.93 | nd | nd |
| Min | 29.4 | 129 | 29.4 | 129 | nd | nd |
| Max | 973 | 761 | 973 | 761 | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | |
|---|---|---|---|---|---|---|---|
| n (Samp) | 132 | 6 | 132 | 6 | | nd | nd |
| n (Patient) | 132 | 6 | 132 | 6 | | nd | nd |
| UO only | | | | | | | |
| Median | 307 | 418 | 307 | 418 | | 307 | 589 |
| Average | 389 | 530 | 389 | 530 | | 389 | 576 |
| Stdev | 237 | 271 | 237 | 271 | | 237 | 304 |
| p(t-test) | | 0.12 | | 0.12 | | | 0.076 |
| Min | 29.4 | 144 | 29.4 | 144 | | 29.4 | 144 |
| Max | 973 | 935 | 973 | 935 | | 973 | 935 |
| n (Samp) | 64 | 8 | 64 | 8 | | 64 | 6 |
| n (Patient) | 64 | 8 | 64 | 8 | | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.53 | 0.68 | 0.60 | 0.50 | 0.68 | 0.73 | nd | 0.69 |
| SE | 0.093 | 0.12 | 0.11 | 0.093 | 0.12 | 0.11 | 0.11 | nd | 0.12 |
| p | 0.22 | 0.83 | 0.11 | 0.30 | 1.00 | 0.11 | 0.039 | nd | 0.12 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 273 | 232 | 389 | 273 | 148 | 389 | 413 | nd | 389 |
| Sens 1 | 75% | 83% | 75% | 75% | 83% | 75% | 71% | nd | 83% |
| Spec 1 | 45% | 28% | 64% | 45% | 12% | 64% | 72% | nd | 64% |
| Cutoff 2 | 227 | 232 | 359 | 148 | 148 | 359 | 389 | nd | 389 |
| Sens 2 | 83% | 83% | 88% | 83% | 83% | 88% | 86% | nd | 83% |
| Spec 2 | 34% | 28% | 59% | 14% | 12% | 59% | 69% | nd | 64% |
| Cutoff 3 | 129 | 120 | 118 | 129 | 120 | 118 | 118 | nd | 118 |
| Sens 3 | 92% | 100% | 100% | 92% | 100% | 100% | 100% | nd | 100% |
| Spec 3 | 11% | 10% | 8% | 11% | 10% | 8% | 11% | nd | 8% |
| Cutoff 4 | 396 | 413 | 488 | 396 | 413 | 488 | 396 | nd | 488 |
| Sens 4 | 50% | 33% | 38% | 50% | 33% | 38% | 71% | nd | 50% |
| Spec 4 | 71% | 70% | 70% | 71% | 70% | 70% | 71% | nd | 70% |
| Cutoff 5 | 489 | 489 | 621 | 489 | 489 | 621 | 489 | nd | 621 |
| Sens 5 | 25% | 17% | 38% | 25% | 17% | 38% | 43% | nd | 50% |
| Spec 5 | 80% | 80% | 81% | 80% | 80% | 81% | 80% | nd | 81% |
| Cutoff 6 | 675 | 665 | 789 | 675 | 665 | 789 | 675 | nd | 789 |
| Sens 6 | 25% | 17% | 25% | 25% | 17% | 25% | 43% | nd | 33% |
| Spec 6 | 91% | 90% | 91% | 91% | 90% | 91% | 91% | nd | 91% |
| OR Quart | 21.0 | 2.0 | 0 | 0.30 | 0.50 | 0 | 0 | nd | 0 |
| p Value | 1.0 | 0.58 | na | 0.31 | 0.58 | na | na | nd | na |
| 95% CI of | 0.13 | 0.17 | na | 0.028 | 0.043 | na | na | nd | na |
| OR Quart2 | 7.9 | 23 | na | 3.1 | 5.8 | na | na | nd | na |
| OR Quart 3 | 3.0 | 1.0 | 4.9 | 1.9 | 0.49 | 4.9 | 3.4 | nd | 2.1 |
| p Value | 0.22 | 1.0 | 0.18 | 0.43 | 0.56 | 0.18 | 0.31 | nd | 0.55 |
| 95% CI of | 0.51 | 0.060 | 0.49 | 0.38 | 0.042 | 0.49 | 0.32 | nd | 0.17 |
| OR Quart3 | 18 | 17 | 49 | 9.4 | 5.6 | 49 | 36 | nd | 26 |
| OR Quart 4 | 1.5 | 2.0 | 3.4 | 0.94 | 1.0 | 3.4 | 3.4 | nd | 3.2 |
| p Value | 0.68 | 0.58 | 0.31 | 0.95 | 0.98 | 0.31 | 0.31 | nd | 0.34 |
| 95% CI of | 0.22 | .17 | 0.32 | 0.17 | 0.14 | 0.32 | 0.32 | nd | 0.30 |
| OR Quart4 | 10 | 23 | 36 | 5.4 | 7.8 | 36 | 36 | nd | 34 |

Vascular endothelial growth factor receptor 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 890 | 1020 | 890 | 1020 | 890 | 765 |
| Average | 1320 | 4720 | 1320 | 2420 | 1320 | 1740 |
| Stdev | 1680 | 10300 | 1680 | 2930 | 1680 | 2390 |
| p(t-test) | | 0.013 | | 0.072 | | 0.54 |
| Min | 254 | 110 | 254 | 110 | 254 | 110 |
| Max | 12800 | 36800 | 12800 | 9150 | 12800 | 6930 |
| n (Samp) | 65 | 12 | 65 | 12 | 65 | 7 |
| n (Patient) | 65 | 12 | 65 | 12 | 65 | 7 |
| sCr only | | | | | | |
| Median | 937 | 685 | 937 | 685 | nd | nd |
| Average | 1540 | 6630 | 1540 | 2020 | nd | nd |
| Stdev | 2060 | 14800 | 2060 | 3510 | nd | nd |
| p(t-test) | | 6.3E−4 | | 0.59 | nd | nd |

TABLE 8-continued

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.

|  |  |  |  |  |  |  |
|---|---|---|---|---|---|---|
| Min | 254 | 110 | 254 | 110 | nd | nd |
| Max | 15600 | 36800 | 15600 | 9150 | nd | nd |
| n (Samp) | 132 | 6 | 132 | 6 | nd | nd |
| n (Patient) | 132 | 6 | 132 | 6 | nd | nd |
| UO only |  |  |  |  |  |  |
| Median | 941 | 1320 | 941 | 1320 | 941 | 1210 |
| Average | 1430 | 2180 | 1430 | 2180 | 1430 | 1980 |
| Stdev | 1720 | 2400 | 1720 | 2400 | 1720 | 2530 |
| p(t-test) |  | 0.27 |  | 0.27 |  | 0.48 |
| Min | 254 | 110 | 254 | 110 | 254 | 110 |
| Max | 12800 | 6930 | 12800 | 6930 | 12800 | 6930 |
| n (Samp) | 64 | 8 | 64 | 8 | 64 | 6 |
| n (Patient) | 64 | 8 | 64 | 8 | 64 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.57 | 0.37 | 0.55 | 0.57 | 0.37 | 0.55 | 0.46 | nd | 0.50 |
| SE | 0.093 | 0.12 | 0.11 | 0.093 | 0.12 | 0.11 | 0.12 | nd | 0.12 |
| p | 0.47 | 0.32 | 0.67 | 0.47 | 0.30 | 0.67 | 0.76 | nd | 1.00 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 685 | 338 | 685 | 685 | 338 | 685 | 455 | nd | 455 |
| Sens 1 | 75% | 83% | 75% | 75% | 83% | 75% | 71% | nd | 83% |
| Spec 1 | 37% | 5% | 34% | 37% | 5% | 34% | 15% | nd | 12% |
| Cutoff 2 | 455 | 338 | 455 | 455 | 338 | 455 | 338 | nd | 455 |
| Sens 2 | 83% | 83% | 88% | 83% | 83% | 88% | 86% | nd | 83% |
| Spec 2 | 15% | 5% | 12% | 15% | 5% | 12% | 8% | nd | 12% |
| Cutoff 3 | 338 | 0 | 0 | 338 | 0 | 0 | 0 | nd | 0 |
| Sens 3 | 92% | 100% | 100% | 92% | 100% | 100% | 100% | nd | 100% |
| Spec 3 | 8% | 0% | 0% | 8% | 0% | 0% | 0% | nd | 0% |
| Cutoff 4 | 1180 | 1410 | 1440 | 1180 | 1410 | 1440 | 1180 | nd | 1440 |
| Sens 4 | 42% | 17% | 50% | 42% | 17% | 50% | 43% | nd | 50% |
| Spec 4 | 71% | 70% | 70% | 71% | 70% | 70% | 71% | nd | 70% |
| Cutoff 5 | 1710 | 1820 | 2060 | 1710 | 1820 | 2060 | 1710 | nd | 2060 |
| Sens 5 | 42% | 17% | 25% | 42% | 17% | 25% | 29% | nd | 17% |
| Spec 5 | 80% | 80% | 81% | 80% | 80% | 81% | 80% | nd | 81% |
| Cutoff 6 | 2440 | 2620 | 2620 | 2440 | 2620 | 2620 | 2440 | nd | 2620 |
| Sens 6 | 25% | 17% | 25% | 25% | 17% | 25% | 14% | nd | 17% |
| Spec 6 | 91% | 90% | 91% | 91% | 90% | 91% | 91% | nd | 91% |
| OR Quart 2 | 0.63 | 1.0 | 1.0 | 0.63 | 1.0 | 1.0 | 0 | nd | 0.44 |
| p Value | 0.63 | 0.98 | 1.0 | 0.63 | 0.98 | 1.0 | na | nd | 0.52 |
| 95% CI of | 0.092 | 0.062 | 0.13 | 0.092 | 0.062 | 0.13 | na | nd | 0.036 |
| OR Quart2 | 4.3 | 17 | 8.0 | 4.3 | 17 | 8.0 | na | nd | 5.4 |
| OR Quart 3 | 0.63 | 1.0 | 0 | 0.63 | 1.0 | 0 | 0.29 | nd | 0.47 |
| p Value | 0.63 | 1.0 | na | 0.63 | 1.0 | na | 0.31 | nd | 0.55 |
| 95% CI of | 0.092 | 0.060 | na | 0.092 | 0.060 | na | 0.028 | nd | 0.038 |
| OR Quart3 | 4.3 | 17 | na | 4.3 | 17 | na | 3.1 | nd | 5.7 |
| OR Quart 4 | 1.8 | 3.3 | 2.3 | 1.8 | 3.3 | 2.3 | 1.0 | nd | 0.94 |
| p Value | 0.48 | 0.31 | 0.38 | 0.48 | 0.31 | 0.38 | 1.0 | nd | 0.95 |
| 95% CI of | 0.36 | 0.32 | 0.36 | 0.36 | 0.32 | 0.36 | 0.17 | nd | 0.12 |
| OR Quart4 | 8.8 | 33 | 14 | 8.8 | 33 | 14 | 5.8 | nd | 7.5 |

SL cytokine

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 0.0696 | 0.114 | 0.0696 | 0.114 | 0.0696 | 0.114 |
| Average | 13.0 | 22.9 | 13.0 | 22.9 | 13.0 | 23.4 |
| Stdev | 51.8 | 52.8 | 51.8 | 52.8 | 51.8 | 61.8 |
| p(t-test) |  | 0.55 |  | 0.55 |  | 0.62 |
| Min | 0.0206 | 0.0206 | 0.0206 | 0.0206 | 0.0206 | 0.0206 |
| Max | 400 | 163 | 400 | 163 | 400 | 163 |
| n (Samp) | 65 | 12 | 65 | 12 | 65 | 7 |
| n (Patient) | 65 | 12 | 65 | 12 | 65 | 7 |
| sCr only |  |  |  |  |  |  |
| Median | 0.0696 | 0.0921 | 0.0696 | 0.0921 | nd | nd |
| Average | 14.3 | 0.0814 | 14.3 | 0.0814 | nd | nd |

TABLE 8-continued

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.

|  |  |  |  |  |  |  |
|---|---|---|---|---|---|---|
| Stdev | 50.6 | 0.0396 | 50.6 | 0.0396 | nd | nd |
| p(t-test) |  | 0.49 |  | 0.49 | nd | nd |
| Min | 0.0206 | 0.0206 | 0.0206 | 0.0206 | nd | nd |
| Max | 400 | 0.114 | 400 | 0.114 | nd | nd |
| n (Samp) | 132 | 6 | 132 | 6 | nd | nd |
| n (Patient) | 132 | 6 | 132 | 6 | nd | nd |
| UO only |  |  |  |  |  |  |
| Median | 0.114 | 2.13 | 0.114 | 2.13 | 0.114 | 0.114 |
| Average | 14.1 | 34.3 | 14.1 | 34.3 | 14.1 | 27.3 |
| Stdev | 52.3 | 62.8 | 52.3 | 62.8 | 52.3 | 66.7 |
| p(t-test) |  | 0.32 |  | 0.32 |  | 0.56 |
| Min | 0.0206 | 0.0696 | 0.0206 | 0.0696 | 0.0206 | 0.0206 |
| Max | 400 | 163 | 400 | 163 | 400 | 163 |
| n (Samp) | 64 | 8 | 64 | 8 | 64 | 6 |
| n (Patient) | 64 | 8 | 64 | 8 | 64 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.62 | 0.46 | 0.72 | 0.62 | 0.46 | 0.72 | 0.52 | nd | 0.56 |
| SE | 0.093 | 0.12 | 0.11 | 0.093 | 0.12 | 0.11 | 0.12 | nd | 0.13 |
| p | 0.18 | 0.77 | 0.041 | 0.18 | 0.77 | 0.041 | 0.84 | nd | 0.66 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 0.0696 | 0.0486 | 0.0696 | 0.0696 | 0.0486 | 0.0696 | 0.0548 | nd | 0.0548 |
| Sens 1 | 75% | 83% | 88% | 75% | 83% | 88% | 71% | nd | 83% |
| Spec 1 | 52% | 21% | 48% | 52% | 21% | 48% | 34% | nd | 38% |
| Cutoff 2 | 0.0548 | 0.0486 | 0.0696 | 0.0548 | 0.0486 | 0.0696 | 0.0486 | nd | 0.0548 |
| Sens 2 | 83% | 83% | 88% | 83% | 83% | 88% | 86% | nd | 83% |
| Spec 2 | 34% | 21% | 48% | 34% | 21% | 48% | 15% | nd | 38% |
| Cutoff 3 | 0.0486 | 0 | 0.0548 | 0.0486 | 0 | 0.0548 | 0 | nd | 0 |
| Sens 3 | 92% | 100% | 100% | 92% | 100% | 100% | 100% | nd | 100% |
| Spec 3 | 15% | 0% | 38% | 15% | 0% | 38% | 0% | nd | 0% |
| Cutoff 4 | 0.114 | 0.114 | 0.114 | 0.114 | 0.114 | 0.114 | 0.114 | nd | 0.114 |
| Sens 4 | 33% | 0% | 50% | 33% | 0% | 50% | 14% | nd | 17% |
| Spec 4 | 77% | 75% | 75% | 77% | 75% | 75% | 77% | nd | 75% |
| Cutoff 5 | 8.22 | 7.12 | 14.1 | 8.22 | 7.12 | 14.1 | 8.22 | nd | 14.1 |
| Sens 5 | 17% | 0% | 25% | 17% | 0% | 25% | 14% | nd | 17% |
| Spec 5 | 80% | 80% | 81% | 80% | 80% | 81% | 80% | nd | 81% |
| Cutoff 6 | 28.3 | 27.5 | 42.7 | 28.3 | 27.5 | 42.7 | 28.3 | nd | 42.7 |
| Sens 6 | 17% | 0% | 25% | 17% | 0% | 25% | 14% | nd | 17% |
| Spec 6 | 91% | 90% | 91% | 91% | 90% | 91% | 91% | nd | 91% |
| OR Quart | 21.0 | >3.4 | >5.1 | 1.0 | >3.4 | >5.1 | 0.47 | nd | 3.2 |
| p Value | 1.0 | <0.30 | <0.16 | 1.0 | <0.30 | <0.16 | 0.55 | nd | 0.34 |
| 95% CI of | 0.13 | >0.33 | >0.52 | 0.13 | >0.33 | >0.52 | 0.039 | nd | 0.30 |
| OR Quart2 | 7.9 | na | na | 7.9 | na | na | 5.7 | nd | 34 |
| OR Quart 3 | 2.3 | >2.1 | >2.2 | 2.3 | >2.1 | >2.2 | 1.6 | nd | 0 |
| p Value | 0.38 | <0.55 | <0.52 | 0.38 | <0.55 | <0.52 | 0.63 | nd | na |
| 95% CI of | 0.36 | >0.18 | >0.19 | 0.36 | >0.18 | >0.19 | 0.23 | nd | na |
| OR Quart3 | 14 | na | na | 14 | na | na | 11 | nd | na |
| OR Quart 4 | 2.1 | >1.1 | >2.2 | 2.1 | >1.1 | >2.2 | 0.47 | nd | 2.0 |
| p Value | 0.42 | <0.97 | <0.52 | 0.42 | <0.97 | <0.52 | 0.55 | nd | 0.59 |
| 95% CI of | 0.34 | >0.064 | >0.19 | 0.34 | >0.064 | >0.19 | 0.039 | nd | 0.16 |
| OR Quart4 | 13 | na | na | 13 | na | na | 5.7 | nd | 24 |

| Interleukin-1 receptor type I | | | | | |
|---|---|---|---|---|---|
| 0 hr prior to AKI stage | | 24 hr prior to AKI stage | | 48 hr prior to AKI stage | |
| Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 62.9 | 83.0 | 62.9 | 79.9 | 62.9 | 65.7 |
| Average | 75.4 | 86.0 | 75.4 | 85.1 | 75.4 | 75.4 |
| Stdev | 68.7 | 29.7 | 68.7 | 29.8 | 68.7 | 26.2 |
| p(t-test) |  | 0.60 |  | 0.64 |  | 1.00 |
| Min | 25.4 | 52.5 | 25.4 | 52.5 | 25.4 | 51.4 |
| Max | 502 | 134 | 502 | 134 | 502 | 123 |
| n (Samp) | 65 | 12 | 65 | 12 | 65 | 7 |
| n (Patient) | 65 | 12 | 65 | 12 | 65 | 7 |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

sCr only

| | | | | | | |
|---|---|---|---|---|---|---|
| Median | 64.7 | 83.0 | 64.7 | 79.9 | nd | nd |
| Average | 76.0 | 84.4 | 76.0 | 82.6 | nd | nd |
| Stdev | 56.0 | 27.8 | 56.0 | 27.9 | nd | nd |
| p(t-test) | | 0.72 | | 0.77 | nd | nd |
| Min | 25.4 | 52.7 | 25.4 | 52.7 | nd | nd |
| Max | 502 | 134 | 502 | 134 | nd | nd |
| n (Samp) | 132 | 6 | 132 | 6 | nd | nd |
| n (Patient) | 132 | 6 | 132 | 6 | nd | nd |

UO only

| | | | | | | |
|---|---|---|---|---|---|---|
| Median | 65.3 | 74.3 | 65.3 | 74.3 | 65.3 | 74.3 |
| Average | 82.8 | 84.2 | 82.8 | 84.2 | 82.8 | 79.2 |
| Stdev | 74.2 | 29.7 | 74.2 | 29.7 | 74.2 | 26.5 |
| p(t-test) | | 0.96 | | 0.96 | | 0.91 |
| Min | 31.7 | 52.5 | 31.7 | 52.5 | 31.7 | 51.4 |
| Max | 502 | 132 | 502 | 132 | 502 | 123 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.69 | 0.65 | 0.63 | 0.68 | 0.64 | 0.63 | 0.59 | nd | 0.60 |
| SE | 0.090 | 0.12 | 0.11 | 0.091 | 0.12 | 0.11 | 0.12 | nd | 0.13 |
| P | 0.034 | 0.21 | 0.24 | 0.043 | 0.26 | 0.24 | 0.45 | nd | 0.45 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 64.9 | 65.6 | 64.9 | 64.9 | 65.6 | 64.9 | 57.0 | nd | 58.3 |
| Sens 1 | 75% | 83% | 75% | 75% | 83% | 75% | 71% | nd | 83% |
| Spec 1 | 58% | 52% | 50% | 58% | 52% | 50% | 42% | nd | 34% |
| Cutoff 2 | 57.0 | 65.6 | 58.3 | 57.0 | 65.6 | 58.3 | 52.2 | nd | 58.3 |
| Sens 2 | 83% | 83% | 88% | 83% | 83% | 88% | 86% | nd | 83% |
| Spec 2 | 42% | 52% | 34% | 42% | 52% | 34% | 25% | nd | 34% |
| Cutoff 3 | 52.5 | 52.2 | 51.6 | 52.5 | 52.2 | 51.6 | 50.0 | nd | 50.0 |
| Sens 3 | 92% | 100% | 100% | 92% | 100% | 100% | 100% | nd | 100% |
| Spec 3 | 25% | 25% | 16% | 25% | 25% | 16% | 22% | nd | 14% |
| Cutoff 4 | 72.4 | 81.6 | 81.5 | 72.4 | 81.6 | 81.5 | 72.4 | nd | 81.5 |
| Sens 4 | 58% | 67% | 50% | 58% | 50% | 50% | 43% | nd | 50% |
| Spec 4 | 71% | 70% | 72% | 71% | 70% | 72% | 71% | nd | 72% |
| Cutoff 5 | 84.8 | 89.6 | 85.9 | 84.8 | 89.6 | 85.9 | 84.8 | nd | 85.9 |
| Sens 5 | 42% | 17% | 38% | 33% | 17% | 38% | 29% | nd | 33% |
| Spec 5 | 80% | 80% | 81% | 80% | 80% | 81% | 80% | nd | 81% |
| Cutoff 6 | 96.4 | 105 | 96.4 | 96.4 | 105 | 96.4 | 96.4 | nd | 96.4 |
| Sens 6 | 25% | 17% | 25% | 25% | 17% | 25% | 14% | nd | 17% |
| Spec 6 | 92% | 90% | 92% | 92% | 90% | 92% | 92% | nd | 92% |
| OR Quart | 20.47 | 0 | 3.4 | 0.47 | 0 | 3.4 | 0.47 | nd | 2.0 |
| p Value | 0.55 | na | 0.31 | 0.55 | na | 0.31 | 0.55 | nd | 0.59 |
| 95% CI of | 0.039 | na | 0.32 | 0.039 | na | 0.32 | 0.039 | nd | 0.16 |
| OR Quart2 | 5.7 | na | 36 | 5.7 | na | 36 | 5.7 | nd | 24 |
| OR Quart 3 | 1.6 | 3.2 | 1.0 | 1.6 | 4.4 | 1.0 | 0.47 | nd | 1.0 |
| p Value | 0.63 | 0.33 | 1.0 | 0.63 | 0.20 | 1.0 | 0.55 | nd | 1.0 |
| 95% CI of | 0.23 | 0.32 | 0.058 | 0.23 | 0.47 | 0.058 | 0.039 | nd | 0.057 |
| OR Quart3 | 11 | 32 | 17 | 11 | 42 | 17 | 5.7 | nd | 17 |
| OR Quart 4 | 3.6 | 2.0 | 3.4 | 3.6 | 0.97 | 3.4 | 1.6 | nd | 2.0 |
| p Value | 0.15 | 0.58 | 0.31 | 0.15 | 0.98 | 0.31 | 0.63 | nd | 0.59 |
| 95% CI of | 0.63 | 0.17 | 0.32 | 0.63 | 0.058 | 0.32 | 0.23 | nd | 0.16 |
| OR Quart4 | 21 | 23 | 36 | 21 | 16 | 36 | 11 | nd | 24 |

Interleukin-29

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 25.8 | 134 | 25.8 | 134 | 25.8 | 61.9 |
| Average | 349 | 1020 | 349 | 1020 | 349 | 115 |
| Stdev | 1580 | 2960 | 1580 | 2960 | 1580 | 117 |
| p(t-test) | | 0.25 | | 0.25 | | 0.70 |
| Min | 0.690 | 0.690 | 0.690 | 0.690 | 0.690 | 0.690 |
| Max | 10500 | 10400 | 10500 | 10400 | 10500 | 276 |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

|  |  |  |  |  |  |  |
|---|---|---|---|---|---|---|
| n (Samp) | 65 | 12 | 65 | 12 | 65 | 7 |
| n (Patient) | 65 | 12 | 65 | 12 | 65 | 7 |
| sCr only |  |  |  |  |  |  |
| Median | 50.0 | 202 | 50.0 | 202 | nd | nd |
| Average | 221 | 219 | 221 | 219 | nd | nd |
| Stdev | 1110 | 177 | 1110 | 177 | nd | nd |
| p(t-test) |  | 1.00 |  | 1.00 | nd | nd |
| Min | 0.690 | 25.8 | 0.690 | 25.8 | nd | nd |
| Max | 10500 | 453 | 10500 | 453 | nd | nd |
| n (Samp) | 132 | 6 | 132 | 6 | nd | nd |
| n (Patient) | 132 | 6 | 132 | 6 | nd | nd |
| UO only |  |  |  |  |  |  |
| Median | 23.2 | 114 | 23.2 | 114 | 23.2 | 56.0 |
| Average | 355 | 1410 | 355 | 1410 | 355 | 111 |
| Stdev | 1590 | 3640 | 1590 | 3640 | 1590 | 127 |
| p(t-test) |  | 0.14 |  | 0.14 |  | 0.71 |
| Min | 0.690 | 0.690 | 0.690 | 0.690 | 0.690 | 0.690 |
| Max | 10500 | 10400 | 10500 | 10400 | 10500 | 276 |
| n (Samp) | 64 | 8 | 64 | 8 | 64 | 6 |
| n (Patient) | 64 | 8 | 64 | 8 | 64 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.77 | 0.77 | 0.74 | 0.77 | 0.77 | 0.74 | 0.66 | nd | 0.62 |
| SE | 0.084 | 0.11 | 0.11 | 0.084 | 0.11 | 0.11 | 0.12 | nd | 0.13 |
| P | 0.0012 | 0.017 | 0.025 | 0.0012 | 0.017 | 0.025 | 0.18 | nd | 0.36 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 59.3 | 49.5 | 59.3 | 59.3 | 49.5 | 59.3 | 26.3 | nd | 4.53 |
| Sens 1 | 75% | 83% | 75% | 75% | 83% | 75% | 71% | nd | 83% |
| Spec 1 | 69% | 49% | 67% | 69% | 49% | 67% | 62% | nd | 39% |
| Cutoff 2 | 26.3 | 49.5 | 25.8 | 26.3 | 49.5 | 25.8 | 4.53 | nd | 4.53 |
| Sens 2 | 83% | 83% | 88% | 83% | 83% | 88% | 86% | nd | 83% |
| Spec 2 | 62% | 49% | 61% | 62% | 49% | 61% | 40% | nd | 39% |
| Cutoff 3 | 20.7 | 20.7 | 0 | 20.7 | 20.7 | 0 | 0 | nd | 0 |
| Sens 3 | 92% | 100% | 100% | 92% | 100% | 100% | 100% | nd | 100% |
| Spec 3 | 49% | 42% | 0% | 49% | 42% | 0% | 0% | nd | 0% |
| Cutoff 4 | 80.3 | 108 | 80.9 | 80.3 | 108 | 80.9 | 80.3 | nd | 80.9 |
| Sens 4 | 67% | 67% | 62% | 67% | 67% | 62% | 43% | nd | 33% |
| Spec 4 | 71% | 73% | 72% | 71% | 73% | 72% | 71% | nd | 72% |
| Cutoff 5 | 108 | 128 | 108 | 108 | 128 | 108 | 108 | nd | 108 |
| Sens 5 | 58% | 67% | 50% | 58% | 67% | 50% | 43% | nd | 33% |
| Spec 5 | 82% | 80% | 81% | 82% | 80% | 81% | 82% | nd | 81% |
| Cutoff 6 | 180 | 197 | 185 | 180 | 197 | 185 | 180 | nd | 185 |
| Sens 6 | 42% | 50% | 38% | 42% | 50% | 38% | 29% | nd | 33% |
| Spec 6 | 91% | 91% | 91% | 91% | 91% | 91% | 91% | nd | 91% |
| OR Quart | 21.0 | >2.1 | 0 | 1.0 | >2.1 | 0 | 1.0 | nd | 0.94 |
| p Value | 1.0 | <0.56 | na | 1.0 | <0.56 | na | 1.0 | nd | 0.97 |
| 95% CI of | 0.058 | >0.18 | na | 0.058 | >0.18 | na | 0.058 | nd | 0.054 |
| OR Quart2 | 17 | na | na | 17 | na | na | 17 | nd | 16 |
| OR Quart 3 | 3.4 | >0 | 3.4 | 3.4 | >0 | 3.4 | 2.1 | nd | 2.1 |
| p Value | 0.31 | <na | 0.31 | 0.31 | <na | 0.31 | 0.55 | nd | 0.55 |
| 95% CI of | 0.32 | >na | 0.32 | 0.32 | >na | 0.32 | 0.18 | nd | 0.17 |
| OR Quart3 | 36 | na | 36 | 36 | na | 36 | 26 | nd | 26 |
| OR Quart 4 | 9.7 | >4.4 | 4.9 | 9.7 | >4.4 | 4.9 | 3.4 | nd | 2.0 |
| p Value | 0.044 | <0.20 | 0.18 | 0.044 | <0.20 | 0.18 | 0.31 | nd | 0.59 |
| 95% CI of | 1.1 | >0.46 | 0.49 | 1.1 | >0.46 | 0.49 | 0.32 | nd | 0.16 |
| OR Quart4 | 89 | na | 49 | 89 | na | 49 | 36 | nd | 24 |

| Interleukin-7 | | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO |  |  |  |  |  |  |
| Median | 1.47 | 5.75 | 1.47 | 5.75 | 1.47 | 4.33 |
| Average | 10.0 | 7.76 | 10.0 | 7.76 | 10.0 | 3.96 |
| Stdev | 31.3 | 7.83 | 31.3 | 7.83 | 31.3 | 3.61 |
| p(t-test) |  | 0.80 |  | 0.80 |  | 0.61 |

TABLE 8-continued

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.

|  |  |  |  |  |  |  |
|---|---|---|---|---|---|---|
| Min | 0.0119 | 0.0293 | 0.0119 | 0.0293 | 0.0119 | 0.0293 |
| Max | 153 | 22.9 | 153 | 22.9 | 153 | 10.7 |
| n (Samp) | 65 | 12 | 65 | 12 | 65 | 7 |
| n (Patient) | 65 | 12 | 65 | 12 | 65 | 7 |
| sCr only |  |  |  |  |  |  |
| Median | 1.64 | 7.40 | 1.64 | 7.40 | nd | nd |
| Average | 7.00 | 8.58 | 7.00 | 8.58 | nd | nd |
| Stdev | 22.6 | 8.13 | 22.6 | 8.13 | nd | nd |
| p(t-test) |  | 0.87 |  | 0.87 | nd | nd |
| Min | 0.00806 | 0.0293 | 0.00806 | 0.0293 | nd | nd |
| Max | 153 | 22.9 | 153 | 22.9 | nd | nd |
| n (Samp) | 132 | 6 | 132 | 6 | nd | nd |
| n (Patient) | 132 | 6 | 132 | 6 | nd | nd |
| UO only |  |  |  |  |  |  |
| Median | 0.815 | 4.55 | 0.815 | 4.55 | 0.815 | 3.68 |
| Average | 9.67 | 6.18 | 9.67 | 6.18 | 9.67 | 2.84 |
| Stdev | 31.6 | 7.09 | 31.6 | 7.09 | 31.6 | 2.27 |
| p(t-test) |  | 0.76 |  | 0.76 |  | 0.60 |
| Min | 0.0119 | 0.0293 | 0.0119 | 0.0293 | 0.0119 | 0.0293 |
| Max | 153 | 22.2 | 153 | 22.2 | 153 | 4.81 |
| n (Samp) | 64 | 8 | 64 | 8 | 64 | 6 |
| n (Patient) | 64 | 8 | 64 | 8 | 64 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.69 | 0.73 | 0.70 | 0.69 | 0.73 | 0.70 | 0.62 | nd | 0.63 |
| SE | 0.090 | 0.12 | 0.11 | 0.090 | 0.12 | 0.11 | 0.12 | nd | 0.13 |
| p | 0.039 | 0.058 | 0.063 | 0.039 | 0.058 | 0.063 | 0.31 | nd | 0.31 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 2.88 | 3.02 | 3.02 | 2.88 | 3.02 | 3.02 | 2.88 | nd | 0.0245 |
| Sens 1 | 75% | 83% | 75% | 75% | 83% | 75% | 71% | nd | 100% |
| Spec 1 | 65% | 61% | 70% | 65% | 61% | 70% | 65% | nd | 27% |
| Cutoff 2 | 0.0245 | 3.02 | 0.0245 | 0.0245 | 3.02 | 0.0245 | 0.0245 | nd | 0.0245 |
| Sens 2 | 100% | 83% | 100% | 100% | 83% | 100% | 100% | nd | 100% |
| Spec 2 | 25% | 61% | 27% | 25% | 61% | 27% | 25% | nd | 27% |
| Cutoff 3 | 0.0245 | 0.0245 | 0.0245 | 0.0245 | 0.0245 | 0.0245 | 0.0245 | nd | 0.0245 |
| Sens 3 | 100% | 100% | 100% | 100% | 100% | 100% | 100% | nd | 100% |
| Spec 3 | 25% | 23% | 27% | 25% | 23% | 27% | 25% | nd | 27% |
| Cutoff 4 | 3.77 | 4.33 | 3.02 | 3.77 | 4.33 | 3.02 | 3.77 | nd | 3.02 |
| Sens 4 | 67% | 67% | 75% | 67% | 67% | 75% | 57% | nd | 67% |
| Spec 4 | 72% | 71% | 70% | 72% | 71% | 70% | 72% | nd | 70% |
| Cutoff 5 | 7.46 | 6.46 | 4.45 | 7.46 | 6.46 | 4.45 | 7.46 | nd | 4.45 |
| Sens 5 | 42% | 50% | 50% | 42% | 50% | 50% | 14% | nd | 33% |
| Spec 5 | 80% | 80% | 81% | 80% | 80% | 81% | 80% | nd | 81% |
| Cutoff 6 | 11.3 | 10.0 | 10.2 | 11.3 | 10.0 | 10.2 | 11.3 | nd | 10.2 |
| Sens 6 | 17% | 33% | 12% | 17% | 33% | 12% | 0% | nd | 0% |
| Spec 6 | 91% | 90% | 91% | 91% | 90% | 91% | 91% | nd | 91% |
| OR Quart 2 | 2.1 | >1.0 | >2.2 | 2.1 | >1.0 | >2.2 | 1.0 | nd | >2.1 |
| p Value | 0.55 | <1.0 | <0.52 | 0.55 | <1.0 | <0.52 | 1.0 | nd | <0.55 |
| 95% CI of | 0.18 | >0.060 | >0.19 | 0.18 | >0.060 | >0.19 | 0.058 | nd | >0.18 |
| OR Quart2 | 26 | na | na | 26 | na | na | 17 | nd | na |
| OR Quart 3 | 4.8 | >2.1 | >1.1 | 4.8 | >2.1 | >1.1 | 4.9 | nd | >1.1 |
| p Value | 0.18 | <0.55 | <0.97 | 0.18 | <0.55 | <0.97 | 0.18 | nd | <0.97 |
| 95% CI of | 0.48 | >0.18 | >0.061 | 0.48 | >0.18 | >0.061 | 0.49 | nd | >0.061 |
| OR Quart3 | 48 | na | na | 48 | na | na | 49 | nd | na |
| OR Quart 4 | 6.0 | >3.2 | >6.9 | 6.0 | >3.2 | >6.9 | 1.0 | nd | >3.4 |
| p Value | 0.12 | <0.33 | <0.094 | 0.12 | <0.33 | <0.094 | 1.0 | nd | <0.31 |
| 95% CI of | 0.63 | >0.32 | >0.72 | 0.63 | >0.32 | >0.72 | 0.058 | nd | >0.32 |
| OR Quart4 | 57 | na | na | 57 | na | na | 17 | nd | na |

Platelet-derived growth factor subunit A (dimer)

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 2370 | 5180 | 2370 | 5180 | nd | nd |
| Average | 3290 | 4860 | 3290 | 4860 | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

|  | 3170 | 3230 | 3170 | 3230 | nd | nd |
|---|---|---|---|---|---|---|
| Stdev | 3170 | 3230 | 3170 | 3230 | nd | nd |
| p(t-test) |  | 0.19 |  | 0.19 | nd | nd |
| Min | 48.5 | 810 | 48.5 | 810 | nd | nd |
| Max | 13500 | 10300 | 13500 | 10300 | nd | nd |
| n (Samp) | 86 | 8 | 86 | 8 | nd | nd |
| n (Patient) | 86 | 8 | 86 | 8 | nd | nd |
| UO only |  |  |  |  |  |  |
| Median | 1890 | 5180 | 1890 | 5180 | nd | nd |
| Average | 2540 | 5020 | 2540 | 5020 | nd | nd |
| Stdev | 2450 | 3210 | 2450 | 3210 | nd | nd |
| p(t-test) |  | 0.021 |  | 0.021 | nd | nd |
| Min | 48.5 | 810 | 48.5 | 810 | nd | nd |
| Max | 12100 | 10300 | 12100 | 10300 | nd | nd |
| n (Samp) | 79 | 6 | 79 | 6 | nd | nd |
| n (Patient) | 79 | 6 | 79 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.68 | nd | 0.78 | 0.68 | nd | 0.78 | nd | nd | nd |
| SE | 0.11 | nd | 0.11 | 0.11 | nd | 0.11 | nd | nd | nd |
| p | 0.093 | nd | 0.015 | 0.093 | nd | 0.015 | nd | nd | nd |
| nCohort 1 | 86 | nd | 79 | 86 | nd | 79 | nd | nd | nd |
| nCohort 2 | 8 | nd | 6 | 8 | nd | 6 | nd | nd | nd |
| Cutoff 1 | 2690 | nd | 2690 | 2690 | nd | 2690 | nd | nd | nd |
| Sens 1 | 75% | nd | 83% | 75% | nd | 83% | nd | nd | nd |
| Spec 1 | 55% | nd | 65% | 55% | nd | 65% | nd | nd | nd |
| Cutoff 2 | 1020 | nd | 2690 | 1020 | nd | 2690 | nd | nd | nd |
| Sens 2 | 88% | nd | 83% | 88% | nd | 83% | nd | nd | nd |
| Spec 2 | 31% | nd | 65% | 31% | nd | 65% | nd | nd | nd |
| Cutoff 3 | 748 | nd | 796 | 748 | nd | 796 | nd | nd | nd |
| Sens 3 | 100% | nd | 100% | 100% | nd | 100% | nd | nd | nd |
| Spec 3 | 28% | nd | 34% | 28% | nd | 34% | nd | nd | nd |
| Cutoff 4 | 4280 | nd | 3500 | 4280 | nd | 3500 | nd | nd | nd |
| Sens 4 | 62% | nd | 67% | 62% | nd | 67% | nd | nd | nd |
| Spec 4 | 71% | nd | 71% | 71% | nd | 71% | nd | nd | nd |
| Cutoff 5 | 5070 | nd | 4370 | 5070 | nd | 4370 | nd | nd | nd |
| Sens 5 | 62% | nd | 67% | 62% | nd | 67% | nd | nd | nd |
| Spec 5 | 80% | nd | 81% | 80% | nd | 81% | nd | nd | nd |
| Cutoff 6 | 8710 | nd | 6230 | 8710 | nd | 6230 | nd | nd | nd |
| Sens 6 | 12% | nd | 17% | 12% | nd | 17% | nd | nd | nd |
| Spec 6 | 91% | nd | 91% | 91% | nd | 91% | nd | nd | nd |
| OR Quart 2 | >2.1 | nd | >1.0 | >2.1 | nd | >1.0 | nd | nd | nd |
| p Value | <0.56 | nd | <0.97 | <0.56 | nd | <0.97 | nd | nd | nd |
| 95% CI of | >0.18 | nd | >0.061 | >0.18 | nd | >0.061 | nd | nd | nd |
| OR Quart2 | na | nd | na | na | nd | na | nd | nd | nd |
| OR Quart 3 | >1.0 | nd | >1.0 | >1.0 | nd | >1.0 | nd | nd | nd |
| p Value | <0.98 | nd | <0.97 | <0.98 | nd | <0.97 | nd | nd | nd |
| 95% CI of | >0.062 | nd | >0.061 | >0.062 | nd | >0.061 | nd | nd | nd |
| OR Quart3 | na | nd | na | na | nd | na | nd | nd | nd |
| OR Quart 4 | >6.1 | nd | >4.7 | >6.1 | nd | >4.7 | nd | nd | nd |
| p Value | <0.11 | nd | <0.19 | <0.11 | nd | <0.19 | nd | nd | nd |
| 95% CI of | >0.65 | nd | >0.48 | >0.65 | nd | >0.48 | nd | nd | nd |
| OR Quart4 | na | nd | na | na | nd | na | nd | nd | nd |

| Platelet-derived growth factor A | | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO |  |  |  |  |  |  |
| Median | 7810 | 11200 | 7810 | 11200 | nd | nd |
| Average | 12000 | 32900 | 12000 | 32900 | nd | nd |
| Stdev | 14800 | 49400 | 14800 | 49400 | nd | nd |
| p(t-test) |  | 0.0050 |  | 0.0050 | nd | nd |
| Min | 2.22 | 1110 | 2.22 | 1110 | nd | nd |
| Max | 94900 | 148000 | 94900 | 148000 | nd | nd |
| n (Samp) | 86 | 8 | 86 | 8 | nd | nd |
| n (Patient) | 86 | 8 | 86 | 8 | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

UO only

| | | | | | | |
|---|---|---|---|---|---|---|
| Median | 5900 | 11200 | 5900 | 11200 | nd | nd |
| Average | 8830 | 18400 | 8830 | 18400 | nd | nd |
| Stdev | 10000 | 18200 | 10000 | 18200 | nd | nd |
| p(t-test) | | 0.038 | | 0.038 | nd | nd |
| Min | 2.22 | 1110 | 2.22 | 1110 | nd | nd |
| Max | 49900 | 49500 | 49900 | 49500 | nd | nd |
| n (Samp) | 79 | 6 | 79 | 6 | nd | nd |
| n (Patient) | 79 | 6 | 79 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | nd | 0.68 | 0.64 | nd | 0.68 | nd | nd | nd |
| SE | 0.11 | nd | 0.12 | 0.11 | nd | 0.12 | nd | nd | nd |
| p | 0.21 | nd | 0.16 | 0.21 | nd | 0.16 | nd | nd | nd |
| nCohort 1 | 86 | nd | 79 | 86 | nd | 79 | nd | nd | nd |
| nCohort 2 | 8 | nd | 6 | 8 | nd | 6 | nd | nd | nd |
| Cutoff 1 | 6240 | nd | 6240 | 6240 | nd | 6240 | nd | nd | nd |
| Sens 1 | 75% | nd | 83% | 75% | nd | 83% | nd | nd | nd |
| Spec 1 | 44% | nd | 54% | 44% | nd | 54% | nd | nd | nd |
| Cutoff 2 | 4720 | nd | 6240 | 4720 | nd | 6240 | nd | nd | nd |
| Sens 2 | 88% | nd | 83% | 88% | nd | 83% | nd | nd | nd |
| Spec 2 | 40% | nd | 54% | 40% | nd | 54% | nd | nd | nd |
| Cutoff 3 | 1080 | nd | 1080 | 1080 | nd | 1080 | nd | nd | nd |
| Sens 3 | 100% | nd | 100% | 100% | nd | 100% | nd | nd | nd |
| Spec 3 | 10% | nd | 11% | 10% | nd | 11% | nd | nd | nd |
| Cutoff 4 | 13300 | nd | 9950 | 13300 | nd | 9950 | nd | nd | nd |
| Sens 4 | 50% | nd | 50% | 50% | nd | 50% | nd | nd | nd |
| Spec 4 | 71% | nd | 71% | 71% | nd | 71% | nd | nd | nd |
| Cutoff 5 | 18000 | nd | 13600 | 18000 | nd | 13600 | nd | nd | nd |
| Sens 5 | 38% | nd | 50% | 38% | nd | 50% | nd | nd | nd |
| Spec 5 | 80% | nd | 81% | 80% | nd | 81% | nd | nd | nd |
| Cutoff 6 | 30600 | nd | 23800 | 30600 | nd | 23800 | nd | nd | nd |
| Sens 6 | 25% | nd | 33% | 25% | nd | 33% | nd | nd | nd |
| Spec 6 | 91% | nd | 91% | 91% | nd | 91% | nd | nd | nd |
| OR Quart | 22.0 | nd | 0 | 2.0 | nd | 0 | nd | nd | nd |
| p Value | 0.58 | nd | na | 0.58 | nd | na | nd | nd | nd |
| 95% CI of | 0.17 | nd | na | 0.17 | nd | na | nd | nd | nd |
| OR Quart2 | 24 | nd | na | 24 | nd | na | nd | nd | nd |
| OR Quart | 32.1 | nd | 2.1 | 2.1 | nd | 2.1 | nd | nd | nd |
| p Value | 0.56 | nd | 0.56 | 0.56 | nd | 0.56 | nd | nd | nd |
| 95% CI of | 0.18 | nd | 0.18 | 0.18 | nd | 0.18 | nd | nd | nd |
| OR Quart3 | 25 | nd | 25 | 25 | nd | 25 | nd | nd | nd |
| OR Quart 4 | 3.1 | nd | 3.2 | 3.1 | nd | 3.2 | nd | nd | nd |
| p Value | 0.34 | nd | 0.34 | 0.34 | nd | 0.34 | nd | nd | nd |
| 95% CI of | 0.30 | nd | 0.30 | 0.30 | nd | 0.30 | nd | nd | nd |
| OR Quart4 | 33 | nd | 33 | 33 | nd | 33 | nd | nd | nd |

Thymic stromal lymphopoietin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 0.0181 | 4.05 | 0.0181 | 4.05 | 0.0181 | 3.86 |
| Average | 327 | 1690 | 327 | 1690 | 327 | 17.0 |
| Stdev | 2500 | 5770 | 2500 | 5770 | 2500 | 38.7 |
| p(t-test) | | 0.18 | | 0.18 | | 0.75 |
| Min | 0.0123 | 0.0150 | 0.0123 | 0.0129 | 0.0123 | 0.0167 |
| Max | 20000 | 20000 | 20000 | 20000 | 20000 | 105 |
| n (Samp) | 64 | 12 | 64 | 12 | 64 | 7 |
| n (Patient) | 64 | 12 | 64 | 12 | 64 | 7 | sCr only

| | | | | | | |
|---|---|---|---|---|---|---|
| Median | 0.623 | 0.912 | 0.623 | 0.0174 | nd | nd |
| Average | 333 | 5.74 | 333 | 5.44 | nd | nd |
| Stdev | 2470 | 11.4 | 2470 | 11.5 | nd | nd |
| p(t-test) | | 0.75 | | 0.75 | nd | nd |
| Min | 0.0123 | 0.0150 | 0.0123 | 0.0129 | nd | nd |
| Max | 20000 | 28.7 | 20000 | 28.7 | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

|  |  |  |  |  |  |  |
|---|---|---|---|---|---|---|
| n (Samp) | 131 | 6 | 131 | 6 | nd | nd |
| n (Patient) | 131 | 6 | 131 | 6 | nd | nd |
| UO only |  |  |  |  |  |  |
| Median | 0.0181 | 5.28 | 0.0181 | 5.28 | 0.0181 | 4.05 |
| Average | 345 | 2530 | 345 | 2530 | 345 | 19.9 |
| Stdev | 2520 | 7060 | 2520 | 7060 | 2520 | 41.5 |
| p(t-test) |  | 0.081 |  | 0.081 |  | 0.75 |
| Min | 0.0129 | 0.0181 | 0.0129 | 0.0181 | 0.0129 | 0.0181 |
| Max | 20000 | 20000 | 20000 | 20000 | 20000 | 105 |
| n (Samp) | 63 | 8 | 63 | 8 | 63 | 6 |
| n (Patient) | 63 | 8 | 63 | 8 | 63 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.70 | 0.51 | 0.78 | 0.65 | 0.42 | 0.78 | 0.67 | nd | 0.72 |
| SE | 0.090 | 0.12 | 0.10 | 0.092 | 0.12 | 0.10 | 0.12 | nd | 0.12 |
| p | 0.026 | 0.94 | 0.0054 | 0.10 | 0.52 | 0.0054 | 0.14 | nd | 0.073 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 0.0181 | 0.0150 | 3.13 | 0.0167 | 0.0129 | 3.13 | 0.0181 | nd | 0.0181 |
| Sens 1 | 75% | 83% | 75% | 75% | 83% | 75% | 71% | nd | 83% |
| Spec 1 | 53% | 27% | 76% | 44% | 8% | 76% | 53% | nd | 54% |
| Cutoff 2 | 0.0167 | 0.0150 | 0.0181 | 0.0150 | 0.0129 | 0.0181 | 0.0167 | nd | 0.0181 |
| Sens 2 | 83% | 83% | 88% | 83% | 83% | 88% | 86% | nd | 83% |
| Spec 2 | 44% | 27% | 54% | 31% | 8% | 54% | 44% | nd | 54% |
| Cutoff 3 | 0.0150 | 0.0129 | 0.0167 | 0.0129 | 0.0123 | 0.0167 | 0.0150 | nd | 0.0167 |
| Sens 3 | 92% | 100% | 100% | 92% | 100% | 100% | 100% | nd | 100% |
| Spec 3 | 31% | 8% | 48% | 8% | 1% | 48% | 31% | nd | 48% |
| Cutoff 4 | 2.45 | 5.02 | 2.68 | 2.45 | 5.02 | 2.68 | 2.45 | nd | 2.68 |
| Sens 4 | 58% | 17% | 75% | 58% | 17% | 75% | 57% | nd | 67% |
| Spec 4 | 70% | 71% | 71% | 70% | 71% | 71% | 70% | nd | 71% |
| Cutoff 5 | 5.40 | 7.30 | 6.32 | 5.40 | 7.30 | 6.32 | 5.40 | nd | 6.32 |
| Sens 5 | 42% | 17% | 38% | 42% | 17% | 38% | 29% | nd | 17% |
| Spec 5 | 81% | 80% | 81% | 81% | 80% | 81% | 81% | nd | 81% |
| Cutoff 6 | 21.9 | 21.5 | 30.2 | 21.9 | 21.5 | 30.2 | 21.9 | nd | 30.2 |
| Sens 6 | 33% | 17% | 38% | 33% | 17% | 38% | 14% | nd | 17% |
| Spec 6 | 91% | 90% | 90% | 91% | 90% | 90% | 91% | nd | 90% |
| OR Quart 2 | >3.6 | 2.1 | >1.0 | 1.0 | 1.0 | >1.0 | >2.1 | nd | >1.1 |
| p Value | <0.29 | 0.56 | <1.0 | 0.98 | 0.98 | <1.0 | <0.55 | nd | <0.97 |
| 95% CI of | >0.34 | 0.18 | >0.058 | 0.13 | 0.062 | >0.058 | >0.18 | nd | >0.061 |
| OR Quart2 | na | 24 | na | 7.9 | 17 | na | na | nd | na |
| OR Quart 3 | >5.1 | 2.1 | >3.4 | 1.6 | 3.3 | >3.4 | >2.1 | nd | >2.3 |
| p Value | <0.17 | 0.56 | <0.31 | 0.63 | 0.31 | <0.31 | <0.55 | nd | <0.52 |
| 95% CI of | >0.51 | 0.18 | >0.32 | 0.23 | 0.32 | >0.32 | >0.18 | nd | >0.19 |
| OR Quart3 | na | 24 | na | 11 | 33 | na | na | nd | na |
| OR Quart 4 | >6.8 | 0.97 | >4.9 | 3.0 | 1.0 | >4.9 | >3.4 | nd | >3.4 |
| p Value | <0.096 | 0.98 | <0.18 | 0.22 | 0.98 | <0.18 | <0.31 | nd | <0.31 |
| 95% CI of | >0.71 | 0.058 | >0.49 | 0.51 | 0.062 | >0.49 | >0.32 | nd | >0.32 |
| OR Quart4 | na | 16 | na | 18 | 17 | na | na | nd | na |

TABLE 9

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| C-C motif chemokine 1 | | | | | | |
|---|---|---|---|---|---|---|
|  | 0 hr prior to AKI stage | | 24 hr prior to AKI stage | | 48 hr prior to AKI stage | |
| sCr or U0 | Cohort 1 | Cohort 2 | Cohort 1 | Cohort 2 | Cohort 1 | Cohort 2 |
| Median | 0.0140 | 0.0224 | 0.0140 | 2.18 | 0.0140 | 0.0146 |
| Average | 1.19 | 5.95 | 1.19 | 6.06 | 1.19 | 2.56 |
| Stdev | 9.13 | 12.0 | 9.13 | 9.25 | 9.13 | 5.53 |
| p(t-test) |  | 0.016 |  | 0.018 |  | 0.64 |
| Min | 0.00501 | 0.00547 | 0.00501 | 0.00547 | 0.00501 | 0.0105 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Max | 228 | 49.3 | 228 | 35.4 | 228 | 17.3 |
| n (Samp) | 1275 | 22 | 1275 | 20 | 1275 | 10 |
| n (Patient) | 452 | 22 | 452 | 20 | 452 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0140 | 0.0145 | nd | nd | nd | nd |
| Average | 1.25 | 6.53 | nd | nd | nd | nd |
| Stdev | 8.96 | 10.3 | nd | nd | nd | nd |
| p(t-test) | | 0.097 | nd | nd | nd | nd |
| Min | 0.00501 | 0.00547 | nd | nd | nd | nd |
| Max | 228 | 26.5 | nd | nd | nd | nd |
| n (Samp) | 1339 | 8 | nd | nd | nd | nd |
| n (Patient) | 467 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0140 | 0.770 | 0.0140 | 2.88 | 0.0140 | 0.0151 |
| Average | 1.41 | 5.20 | 1.41 | 5.99 | 1.41 | 2.79 |
| Stdev | 9.87 | 7.63 | 9.87 | 9.40 | 9.87 | 6.45 |
| p(t-test) | | 0.15 | | 0.045 | | 0.71 |
| Min | 0.00501 | 0.00547 | 0.00501 | 0.00547 | 0.00501 | 0.0140 |
| Max | 228 | 26.5 | 228 | 35.4 | 228 | 17.3 |
| n (Samp) | 1122 | 14 | 1122 | 19 | 1122 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.70 | 0.58 | 0.78 | 0.76 | nd | 0.76 |
| SE | 0.063 | 0.11 | 0.073 | 0.063 | nd | 0.065 |
| P | 0.0019 | 0.45 | 1.0E−4 | 3.0E−5 | nd | 7.8E−5 |
| nCohort 1 | 1275 | 1339 | 1122 | 1275 | nd | 1122 |
| nCohort 2 | 22 | 8 | 14 | 20 | nd | 19 |
| Cutoff 1 | 0.0150 | 0.0116 | 0.0183 | 0.0216 | nd | 0.0183 |
| Sens 1 | 77% | 75% | 71% | 70% | nd | 74% |
| Spec 1 | 60% | 38% | 64% | 71% | nd | 64% |
| Cutoff 2 | 0.0134 | 0.00679 | 0.0151 | 0.0151 | nd | 0.00997 |
| Sens 2 | 82% | 88% | 86% | 80% | nd | 84% |
| Spec 2 | 48% | 15% | 62% | 63% | nd | 29% |
| Cutoff 3 | 0.00679 | 0.00501 | 0.0150 | 0.00764 | nd | 0.00764 |
| Sens 3 | 91% | 100% | 93% | 95% | nd | 95% |
| Spec 3 | 15% | 4% | 58% | 19% | nd | 19% |
| Cutoff 4 | 0.0192 | 0.0223 | 0.0223 | 0.0192 | nd | 0.0223 |
| Sens 4 | 55% | 38% | 64% | 70% | nd | 68% |
| Spec 4 | 70% | 74% | 74% | 70% | nd | 74% |
| Cutoff 5 | 0.0250 | 0.0250 | 0.0250 | 0.0250 | nd | 0.0250 |
| Sens 5 | 41% | 38% | 57% | 65% | nd | 68% |
| Spec 5 | 83% | 82% | 83% | 83% | nd | 83% |
| Cutoff 6 | 0.581 | 0.967 | 0.652 | 0.581 | nd | 0.652 |
| Sens 6 | 41% | 38% | 57% | 55% | nd | 58% |
| Spec 6 | 90% | 90% | 90% | 90% | nd | 90% |
| OR Quart 2 | 0.33 | 1.00 | 0 | 0.33 | nd | 0.33 |
| p Value | 0.34 | 1.00 | na | 0.34 | nd | 0.34 |
| 95% CI of | 0.034 | 0.14 | na | 0.034 | nd | 0.034 |
| OR Quart2 | 3.2 | 7.1 | na | 3.2 | nd | 3.2 |
| OR Quart 3 | 2.4 | 0.50 | 4.0 | 1.00 | nd | 0.66 |
| p Value | 0.22 | 0.57 | 0.21 | 1.00 | nd | 0.66 |
| 95% CI of | 0.61 | 0.045 | 0.45 | 0.20 | nd | 0.11 |
| OR Quart3 | 9.2 | 5.5 | 36 | 5.0 | nd | 4.0 |
| OR Quart 4 | 3.7 | 1.5 | 9.3 | 4.5 | nd | 4.5 |
| p Value | 0.044 | 0.66 | 0.035 | 0.021 | nd | 0.020 |
| 95% CI of | 1.0 | 0.25 | 1.2 | 1.3 | nd | 1.3 |
| OR Quart4 | 14 | 9.0 | 74 | 16 | nd | 16 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  | 48 hr prior to AKI stage | | |
|---|---|---|---|
|  | sCr or UO | sCr only | UO only |
| AUC | 0.68 | nd | 0.68 |
| SE | 0.094 | nd | 0.11 |
| P | 0.062 | nd | 0.10 |
| nCohort 1 | 1275 | nd | 1122 |
| nCohort 2 | 10 | nd | 7 |
| Cutoff 1 | 0.0140 | nd | 0.0141 |
| Sens 1 | 70% | nd | 71% |
| Spec 1 | 56% | nd | 58% |
| Cutoff 2 | 0.0140 | nd | 0.0140 |
| Sens 2 | 90% | nd | 100% |
| Spec 2 | 52% | nd | 50% |
| Cutoff 3 | 0.0140 | nd | 0.0140 |
| Sens 3 | 90% | nd | 100% |
| Spec 3 | 52% | nd | 50% |
| Cutoff 4 | 0.0192 | nd | 0.0223 |
| Sens 4 | 30% | nd | 29% |
| Spec 4 | 70% | nd | 74% |
| Cutoff 5 | 0.0250 | nd | 0.0250 |
| Sens 5 | 30% | nd | 29% |
| Spec 5 | 83% | nd | 83% |
| Cutoff 6 | 0.581 | nd | 0.652 |
| Sens 6 | 30% | nd | 29% |
| Spec 6 | 90% | nd | 90% |
| OR Quart 2 | >1.0 | nd | >0 |
| p Value | <1.00 | nd | <na |
| 95% CI of | >0.062 | nd | >na |
| OR Quart2 | na | nd | na |
| OR Quart 3 | >6.1 | nd | >5.1 |
| p Value | <0.095 | nd | <0.14 |
| 95% CI of | >0.73 | nd | >0.59 |
| OR Quart3 | na | nd | na |
| OR Quart 4 | >3.0 | nd | >2.0 |
| p Value | <0.34 | nd | <0.57 |
| 95% CI of | >0.31 | nd | >0.18 |
| OR Quart4 | na | nd | na |

C-C motif chemokine 17

| sCr or UO | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 0.00507 | 0.0115 | 0.00507 | 0.0130 | 0.00507 | 0.00780 |
| Average | 0.284 | 1.23 | 0.284 | 0.579 | 0.284 | 0.186 |
| Stdev | 2.11 | 4.10 | 2.11 | 1.43 | 2.11 | 0.380 |
| p(t-test) |  | 0.041 |  | 0.53 |  | 0.88 |
| Min | 0.00114 | 0.00241 | 0.00114 | 0.00114 | 0.00114 | 0.00114 |
| Max | 56.6 | 19.4 | 56.6 | 6.36 | 56.6 | 0.966 |
| n (Samp) | 1275 | 22 | 1275 | 20 | 1275 | 10 |
| n (Patient) | 452 | 22 | 452 | 20 | 452 | 10 |

| sCr only | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 0.00507 | 0.00635 | nd | nd | nd | nd |
| Average | 0.332 | 0.116 | nd | nd | nd | nd |
| Stdev | 2.26 | 0.268 | nd | nd | nd | nd |
| p(t-test) |  | 0.79 | nd | nd | nd | nd |
| Min | 0.00114 | 0.00241 | nd | nd | nd | nd |
| Max | 56.6 | 0.771 | nd | nd | nd | nd |
| n (Samp) | 1339 | 8 | nd | nd | nd | nd |
| n (Patient) | 467 | 8 | nd | nd | nd | nd |

| UO only | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 0.00507 | 0.0990 | 0.00507 | 0.0130 | 0.00507 | 0.0106 |
| Average | 0.308 | 2.46 | 0.308 | 1.71 | 0.308 | 0.263 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Stdev | 2.23 | 7.10 | 2.23 | 4.53 | 2.23 | 0.439 |
| p(t-test) | | 6.8E−4 | | 0.0081 | | 0.96 |
| Min | 0.00114 | 0.00246 | 0.00114 | 0.00114 | 0.00114 | 0.00114 |
| Max | 56.6 | 26.9 | 56.6 | 19.4 | 56.6 | 0.966 |
| n (Samp) | 1122 | 14 | 1122 | 19 | 1122 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.66 | 0.51 | 0.74 | 0.69 | nd | 0.71 |
| SE | 0.064 | 0.10 | 0.077 | 0.066 | nd | 0.067 |
| p | 0.012 | 0.90 | 0.0015 | 0.0033 | nd | 0.0015 |
| nCohort 1 | 1275 | 1339 | 1122 | 1275 | nd | 1122 |
| nCohort 2 | 22 | 8 | 14 | 20 | nd | 19 |
| Cutoff 1 | 0.00503 | 0.00309 | 0.0109 | 0.00869 | nd | 0.00869 |
| Sens 1 | 73% | 75% | 79% | 70% | nd | 74% |
| Spec 1 | 49% | 26% | 68% | 56% | nd | 55% |
| Cutoff 2 | 0.00442 | 0.00304 | 0.00503 | 0.00443 | nd | 0.00442 |
| Sens 2 | 82% | 88% | 86% | 80% | nd | 89% |
| Spec 2 | 38% | 19% | 49% | 41% | nd | 37% |
| Cutoff 3 | 0.00304 | 0.00114 | 0.00442 | 0.00442 | nd | 0.00388 |
| Sens 3 | 91% | 100% | 93% | 90% | nd | 95% |
| Spec 3 | 19% | 4% | 37% | 38% | nd | 30% |
| Cutoff 4 | 0.0114 | 0.0114 | 0.0114 | 0.0114 | nd | 0.0114 |
| Sens 4 | 50% | 38% | 57% | 55% | nd | 58% |
| Spec 4 | 71% | 70% | 70% | 71% | nd | 70% |
| Cutoff 5 | 0.0162 | 0.0162 | 0.0162 | 0.0162 | nd | 0.0162 |
| Sens 5 | 41% | 25% | 50% | 45% | nd | 47% |
| Spec 5 | 84% | 82% | 83% | 84% | nd | 83% |
| Cutoff 6 | 0.265 | 0.391 | 0.320 | 0.265 | nd | 0.320 |
| Sens 6 | 32% | 12% | 43% | 30% | nd | 37% |
| Spec 6 | 90% | 90% | 90% | 90% | nd | 90% |
| OR Quart 2 | 1.0 | 0.50 | 1.0 | 5.0 | nd | 4.0 |
| p Value | 1.0 | 0.57 | 1.0 | 0.14 | nd | 0.21 |
| 95% CI of OR Quart2 | 0.20 5.0 | 0.045 5.5 | 0.062 16 | 0.59 43 | nd nd | 0.45 36 |
| OR Quart 3 | 2.4 | 1.5 | 5.1 | 3.0 | nd | 3.0 |
| p Value | 0.22 | 0.66 | 0.14 | 0.34 | nd | 0.34 |
| 95% CI of OR Quart3 | 0.61 9.2 | 0.25 9.0 | 0.59 44 | 0.31 29 | nd nd | 0.31 29 |
| OR Quart 4 | 3.0 | 1.00 | 7.2 | 11 | nd | 11 |
| p Value | 0.097 | 1.00 | 0.067 | 0.021 | nd | 0.020 |
| 95% CI of OR Quart4 | 0.82 11 | 0.14 7.1 | 0.87 59 | 1.5 88 | nd nd | 1.5 89 |

| | 48 hr prior to AKI stage | | |
|---|---|---|---|
| | sCr or UO | sCr only | UO only |
| AUC | 0.55 | nd | 0.61 |
| SE | 0.094 | nd | 0.11 |
| p | 0.57 | nd | 0.35 |
| nCohort 1 | 1275 | nd | 1122 |
| nCohort 2 | 10 | nd | 7 |
| Cutoff 1 | 0.00449 | nd | 0.00449 |
| Sens 1 | 70% | nd | 86% |
| Spec 1 | 45% | nd | 46% |
| Cutoff 2 | 0.00388 | nd | 0.00449 |
| Sens 2 | 80% | nd | 86% |
| Spec 2 | 30% | nd | 46% |
| Cutoff 3 | 0.00308 | nd | 0 |
| Sens 3 | 90% | nd | 100% |
| Spec 3 | 23% | nd | 0% |
| Cutoff 4 | 0.0114 | nd | 0.0114 |
| Sens 4 | 30% | nd | 43% |
| Spec 4 | 71% | nd | 70% |
| Cutoff 5 | 0.0162 | nd | 0.0162 |
| Sens 5 | 20% | nd | 29% |
| Spec 5 | 84% | nd | 83% |
| Cutoff 6 | 0.265 | nd | 0.320 |
| Sens 6 | 20% | nd | 29% |
| Spec 6 | 90% | nd | 90% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| OR Quart 2 | 4.0 | nd | 2.0 |
| p Value | 0.21 | nd | 0.57 |
| 95% CI of | 0.45 | nd | 0.18 |
| OR Quart2 | 36 | nd | 22 |
| OR Quart 3 | 3.0 | nd | 2.0 |
| p Value | 0.34 | nd | 0.57 |
| 95% CI of | 0.31 | nd | 0.18 |
| OR Quart3 | 29 | nd | 22 |
| OR Quart 4 | 2.0 | nd | 2.0 |
| p Value | 0.57 | nd | 0.57 |
| 95% Cl of | 0.18 | nd | 0.18 |
| OR Quart4 | 22 | nd | 22 |

C-C motif chemokine 21

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1.77 | 81.2 | 1.77 | 34.1 | 1.77 | 7.76 |
| Average | 361 | 215 | 361 | 254 | 361 | 60.1 |
| Stdev | 2510 | 351 | 2510 | 561 | 2510 | 99.5 |
| p(t-test) | | 0.79 | | 0.85 | | 0.70 |
| Min | 0.327 | 0.879 | 0.327 | 0.327 | 0.327 | 0.939 |
| Max | 36200 | 1580 | 36200 | 2190 | 36200 | 259 |
| n (Samp) | 1275 | 22 | 1275 | 20 | 1275 | 10 |
| n (Patient) | 452 | 22 | 452 | 20 | 452 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1.77 | 56.4 | nd | nd | nd | nd |
| Average | 349 | 125 | nd | nd | nd | nd |
| Stdev | 2450 | 170 | nd | nd | nd | nd |
| p(t-test) | | 0.80 | nd | nd | nd | nd |
| Min | 0.327 | 0.879 | nd | nd | nd | nd |
| Max | 36200 | 473 | nd | nd | nd | nd |
| n (Samp) | 1339 | 8 | nd | nd | nd | nd |
| n (Patient) | 467 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1.77 | 52.0 | 1.77 | 45.0 | 1.77 | 7.82 |
| Average | 397 | 475 | 397 | 277 | 397 | 52.5 |
| Stdev | 2670 | 911 | 2670 | 581 | 2670 | 96.0 |
| p(t-test) | | 0.91 | | 0.84 | | 0.73 |
| Min | 0.327 | 0.879 | 0.327 | 0.327 | 0.327 | 0.979 |
| Max | 36200 | 3280 | 36200 | 2240 | 36200 | 259 |
| n (Samp) | 1122 | 14 | 1122 | 19 | 1122 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.73 | 0.66 | 0.74 | 0.67 | nd | 0.68 |
| SE | 0.062 | 0.11 | 0.077 | 0.067 | nd | 0.068 |
| P | 1.9E−4 | 0.13 | 0.0018 | 0.012 | nd | 0.0080 |
| nCohort 1 | 1275 | 1339 | 1122 | 1275 | nd | 1122 |
| nCohort 2 | 22 | 8 | 14 | 20 | nd | 19 |
| Cutoff 1 | 1.79 | 1.77 | 23.1 | 1.78 | nd | 1.78 |
| Sens 1 | 77% | 75% | 71% | 80% | nd | 84% |
| Spec 1 | 57% | 52% | 73% | 54% | nd | 55% |
| Cutoff 2 | 1.36 | 0.979 | 1.36 | 1.78 | nd | 1.78 |
| Sens 2 | 82% | 88% | 86% | 80% | nd | 84% |
| Spec 2 | 46% | 30% | 46% | 54% | nd | 55% |
| Cutoff 3 | 0.979 | 0.832 | 0.979 | 0.979 | nd | 0 |
| Sens 3 | 91% | 100% | 93% | 90% | nd | 100% |
| Spec 3 | 34% | 18% | 34% | 34% | nd | 0% |
| Cutoff 4 | 13.0 | 17.1 | 12.9 | 13.0 | nd | 12.9 |
| Sens 4 | 64% | 50% | 71% | 55% | nd | 58% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Spec 4 | 70% | 71% | 70% | 70% | nd | 70% |
| Cutoff 5 | 46.1 | 51.4 | 54.1 | 46.1 | nd | 54.1 |
| Sens 5 | 55% | 50% | 50% | 45% | nd | 47% |
| Spec 5 | 80% | 80% | 80% | 80% | nd | 80% |
| Cutoff 6 | 208 | 213 | 225 | 208 | nd | 225 |
| Sens 6 | 36% | 25% | 43% | 25% | nd | 26% |
| Spec 6 | 90% | 90% | 90% | 90% | nd | 90% |
| OR Quart 2 | 4.0 | 1.00 | 2.0 | 1.00 | nd | 0.50 |
| p Value | 0.21 | 1.00 | 0.57 | 1.00 | nd | 0.57 |
| 95% CI of OR Quart2 | 0.45 36 | 0.062 16 | 0.18 22 | 0.14 7.1 | nd nd | 0.045 5.5 |
| OR Quart 3 | 4.0 | 2.0 | 2.0 | 2.5 | nd | 3.0 |
| p Value | 0.21 | 0.57 | 0.57 | 0.27 | nd | 0.18 |
| 95% CI of OR Quart3 | 0.45 36 | 0.18 22 | 0.18 22 | 0.48 13 | nd nd | 0.61 15 |
| OR Quart 4 | 13 | 4.0 | 9.3 | 5.6 | nd | 5.1 |
| p Value | 0.012 | 0.21 | 0.035 | 0.025 | nd | 0.036 |
| 95% CI of OR Quart4 | 1.8 100 | 0.45 36 | 1.2 74 | 1.2 26 | nd nd | 1.1 24 |

| | 48 hr prior to AKI stage | | |
|---|---|---|---|
| | sCr or UO | sCr only | UO only |
| AUC | 0.59 | nd | 0.58 |
| SE | 0.095 | nd | 0.11 |
| P | 0.36 | nd | 0.47 |
| nCohort 1 | 1275 | nd | 1122 |
| nCohort 2 | 10 | nd | 7 |
| Cutoff 1 | 0.979 | nd | 0.979 |
| Sens 1 | 80% | nd | 86% |
| Spec 1 | 34% | nd | 34% |
| Cutoff 2 | 0.979 | nd | 0.979 |
| Sens 2 | 80% | nd | 86% |
| Spec 2 | 34% | nd | 34% |
| Cutoff 3 | 0.939 | nd | 0.939 |
| Sens 3 | 90% | nd | 100% |
| Spec 3 | 28% | nd | 28% |
| Cutoff 4 | 13.0 | nd | 12.9 |
| Sens 4 | 30% | nd | 29% |
| Spec 4 | 70% | nd | 70% |
| Cutoff 5 | 46.1 | nd | 54.1 |
| Sens 5 | 30% | nd | 29% |
| Spec 5 | 80% | nd | 80% |
| Cutoff 6 | 208 | nd | 225 |
| Sens 6 | 20% | nd | 14% |
| Spec 6 | 90% | nd | 90% |
| OR Quart 2 | 3.0 | nd | >3.0 |
| p Value | 0.34 | nd | <0.34 |
| 95% CI of | 0.31 | nd | >0.31 |
| OR Quart2 | 29 | nd | na |
| OR Quart 3 | 3.0 | nd | >2.0 |
| p Value | 0.34 | nd | <0.57 |
| 95% CI of | 0.31 | nd | >0.18 |
| OR Quart3 | 29 | nd | na |
| OR Quart 4 | 3.0 | nd | >2.0 |
| p Value | 0.34 | nd | <0.57 |
| 95% CI of | 0.31 | nd | >0.18 |
| OR Quart4 | 29 | nd | na |

| C-C motif chemokine 27 | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 2.00 | 4.09 | 2.00 | 4.47 | 2.00 | 1.90 |
| Average | 3.87 | 11.2 | 3.87 | 12.2 | 3.87 | 8.55 |
| Stdev | 10.4 | 25.3 | 10.4 | 25.8 | 10.4 | 17.6 |
| p(t-test) | | 0.0015 | | 6.4E−4 | | 0.16 |
| Min | 0.00255 | 0.00898 | 0.00255 | 0.00333 | 0.00255 | 0.00333 |
| Max | 230 | 118 | 230 | 109 | 230 | 57.4 |

TABLE 9-continued

Comparison of marker levels in urine samples collected from
Cohort 1 (patients that did not progress beyond RIFLE stage 0, R, or I)
and in urine samples collected from Cohort 2 (subjects who progress
to RIFLE stage F) at 0, 24 hours, and 48 hours prior to the subject
reaching RIFLE stage I.

| | | | | | | |
|---|---|---|---|---|---|---|
| n (Samp) | 1274 | 22 | 1274 | 20 | 1274 | 10 |
| n (Patient) | 452 | 22 | 452 | 20 | 452 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 2.06 | 4.41 | nd | nd | nd | nd |
| Average | 4.32 | 3.69 | nd | nd | nd | nd |
| Stdev | 11.7 | 2.96 | nd | nd | nd | nd |
| p(t-test) | | 0.88 | nd | nd | nd | nd |
| Min | 0.00255 | 0.00898 | nd | nd | nd | nd |
| Max | 230 | 7.60 | nd | nd | nd | nd |
| n (Samp) | 1338 | 8 | nd | nd | nd | nd |
| n (Patient) | 467 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 2.06 | 4.92 | 2.06 | 4.91 | 2.06 | 6.16 |
| Average | 4.09 | 31.8 | 4.09 | 23.5 | 4.09 | 11.8 |
| Stdev | 10.9 | 65.9 | 10.9 | 49.8 | 10.9 | 20.5 |
| p(t-test) | | 4.6E−15 | | 3.7E−11 | | 0.066 |
| Min | 0.00255 | 0.00898 | 0.00255 | 0.00333 | 0.00255 | 0.0100 |
| Max | 230 | 234 | 230 | 198 | 230 | 57.4 |
| n (Samp) | 1121 | 14 | 1121 | 19 | 1121 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.63 | 0.59 | 0.69 | 0.62 | nd | 0.66 |
| SE | 0.064 | 0.11 | 0.079 | 0.068 | nd | 0.069 |
| P | 0.050 | 0.38 | 0.018 | 0.073 | nd | 0.024 |
| nCohort 1 | 1274 | 1338 | 1121 | 1274 | nd | 1121 |
| nCohort 2 | 22 | 8 | 14 | 20 | nd | 19 |
| Cutoff 1 | 0.933 | 0.825 | 2.22 | 1.65 | nd | 1.65 |
| Sens 1 | 73% | 75% | 71% | 70% | nd | 74% |
| Spec 1 | 34% | 31% | 52% | 45% | nd | 45% |
| Cutoff 2 | 0.386 | 0.265 | 0.933 | 0.315 | nd | 0.315 |
| Sens 2 | 82% | 88% | 86% | 80% | nd | 84% |
| Spec 2 | 23% | 21% | 34% | 22% | nd | 23% |
| Cutoff 3 | 0.0337 | 0.00883 | 0.0337 | 0.00983 | nd | 0.00255 |
| Sens 3 | 91% | 100% | 93% | 90% | nd | 100% |
| Spec 3 | 18% | 8% | 19% | 11% | nd | 0% |
| Cutoff 4 | 3.54 | 3.65 | 3.69 | 3.54 | nd | 3.69 |
| Sens 4 | 55% | 62% | 57% | 55% | nd | 58% |
| Spec 4 | 70% | 70% | 70% | 70% | nd | 70% |
| Cutoff 5 | 4.63 | 4.87 | 4.91 | 4.63 | nd | 4.91 |
| Sens 5 | 45% | 38% | 50% | 50% | nd | 53% |
| Spec 5 | 80% | 80% | 80% | 80% | nd | 80% |
| Cutoff 6 | 7.18 | 7.78 | 7.78 | 7.18 | nd | 7.78 |
| Sens 6 | 23% | 0% | 36% | 35% | nd | 37% |
| Spec 6 | 90% | 90% | 90% | 90% | nd | 90% |
| OR Quart 2 | 0.40 | 0.50 | 1.00 | 0.40 | nd | 0.75 |
| p Value | 0.27 | 0.57 | 1.00 | 0.27 | nd | 0.70 |
| 95% CI of | 0.076 | 0.045 | 0.14 | 0.076 | nd | 0.17 |
| OR Quart2 | 2.1 | 5.5 | 7.1 | 2.1 | nd | 3.4 |
| OR Quart 3 | 0.80 | 0.50 | 1.00 | 0.40 | nd | 0.25 |
| p Value | 0.74 | 0.57 | 1.00 | 0.27 | nd | 0.21 |
| 95% CI of | 0.21 | 0.045 | 0.14 | 0.076 | nd | 0.027 |
| OR Quart3 | 3.0 | 5.5 | 7.1 | 2.1 | nd | 2.2 |
| OR Quart 4 | 2.2 | 2.0 | 4.1 | 2.2 | nd | 2.8 |
| p Value | 0.14 | 0.42 | 0.077 | 0.14 | nd | 0.079 |
| 95% CI of | 0.77 | 0.36 | 0.86 | 0.77 | nd | 0.89 |
| OR Quart4 | 6.5 | 11 | 19 | 6.5 | nd | 9.0 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  |  | 48 hr prior to AKI stage | | |
|---|---|---|---|---|
|  |  | sCr or UO | sCr only | UO only |
|  | AUC | 0.51 | nd | 0.61 |
|  | SE | 0.092 | nd | 0.11 |
|  | P | 0.94 | nd | 0.33 |
|  | nCohort 1 | 1274 | nd | 1121 |
|  | nCohort 2 | 10 | nd | 7 |
|  | Cutoff 1 | 0.0105 | nd | 0.903 |
|  | Sens 1 | 70% | nd | 71% |
|  | Spec 1 | 13% | nd | 33% |
|  | Cutoff 2 | 0.0100 | nd | 0.0100 |
|  | Sens 2 | 80% | nd | 86% |
|  | Spec 2 | 13% | nd | 13% |
|  | Cutoff 3 | 0.00986 | nd | 0.00986 |
|  | Sens 3 | 90% | nd | 100% |
|  | Spec 3 | 12% | nd | 12% |
|  | Cutoff 4 | 3.54 | nd | 3.69 |
|  | Sens 4 | 40% | nd | 57% |
|  | Spec 4 | 70% | nd | 70% |
|  | Cutoff 5 | 4.63 | nd | 4.91 |
|  | Sens 5 | 40% | nd | 57% |
|  | Spec 5 | 80% | nd | 80% |
|  | Cutoff 6 | 7.18 | nd | 7.78 |
|  | Sens 6 | 30% | nd | 43% |
|  | Spec 6 | 90% | nd | 90% |
|  | OR Quart 2 | 0.25 | nd | 0.50 |
|  | p Value | 0.21 | nd | 0.57 |
|  | 95% CI of OR Quart2 | 0.028 2.2 | nd nd | 0.045 5.5 |
|  | OR Quart 3 | 0.25 | nd | 0 |
|  | p Value | 0.21 | nd | na |
|  | 95% CI of OR Quart3 | 0.028 2.2 | nd nd | na na |
|  | OR Quart 4 | 1.0 | nd | 2.0 |
|  | p Value | 1.0 | nd | 0.42 |
|  | 95% CI of OR Quart4 | 0.25 4.0 | nd nd | 0.37 11 |

Vascular endothelial growth factor receptor 1

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 11.2 | 160 | 11.2 | 80.3 | 11.2 | 38.1 |
| Average | 66.2 | 165 | 66.2 | 404 | 66.2 | 64.9 |
| Stdev | 287 | 146 | 287 | 1140 | 287 | 79.7 |
| p(t-test) |  | 0.18 |  | 6.5E−5 |  | 0.99 |
| Min | 0.169 | 0.242 | 0.169 | 0.169 | 0.169 | 0.169 |
| Max | 6850 | 432 | 6850 | 4630 | 6850 | 219 |
| n (Samp) | 652 | 15 | 652 | 16 | 652 | 7 |
| n (Patient) | 297 | 15 | 297 | 16 | 297 | 7 |

|  | 0 hr prior to AKI stage | | 24 hr prior to AKI stage | | 48 hr prior to AK stage | |
|---|---|---|---|---|---|---|
| UO only | Cohort 1 | Cohort 2 | Cohort 1 | Cohort 2 | Cohort 1 | Cohort 2 |
| Median | 13.6 | 244 | 13.6 | 94.6 | nd | nd |
| Average | 68.6 | 241 | 68.6 | 478 | nd | nd |
| Stdev | 299 | 188 | 299 | 1260 | nd | nd |
| p(t-test) |  | 0.086 |  | 2.7E−5 | nd | nd |
| Min | 0.169 | 0.454 | 0.169 | 0.169 | nd | nd |
| Max | 6850 | 605 | 6850 | 4630 | nd | nd |
| n (Samp) | 596 | 9 | 596 | 13 | nd | nd |
| n (Patient) | 262 | 9 | 262 | 13 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.74 | nd | 0.83 | 0.72 | nd | 0.72 |
| SE | 0.075 | nd | 0.085 | 0.073 | nd | 0.081 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| p | 0.0015 | nd | 1.3E-4 | 0.0025 | nd | 0.0081 |
| nCohort 1 | 652 | nd | 596 | 652 | nd | 596 |
| nCohort 2 | 15 | nd | 9 | 16 | nd | 13 |
| Cutoff 1 | 36.8 | nd | 116 | 37.3 | nd | 37.3 |
| Sens 1 | 73% | nd | 78% | 75% | nd | 77% |
| Spec 1 | 62% | nd | 85% | 63% | nd | 61% |
| Cutoff 2 | 33.8 | nd | 36.8 | 19.5 | nd | 19.5 |
| Sens 2 | 80% | nd | 89% | 81% | nd | 85% |
| Spec 2 | 59% | nd | 60% | 53% | nd | 51% |
| Cutoff 3 | 0.429 | nd | 0.429 | 0.521 | nd | 0.521 |
| Sens 3 | 93% | nd | 100% | 94% | nd | 92% |
| Spec 3 | 19% | nd | 18% | 32% | nd | 32% |
| Cutoff 4 | 54.1 | nd | 58.5 | 54.1 | nd | 58.5 |
| Sens 4 | 67% | nd | 78% | 69% | nd | 62% |
| Spec 4 | 70% | nd | 70% | 70% | nd | 70% |
| Cutoff 5 | 93.9 | nd | 93.9 | 93.9 | nd | 93.9 |
| Sens 5 | 60% | nd | 78% | 50% | nd | 54% |
| Spec 5 | 81% | nd | 81% | 81% | nd | 81% |
| Cutoff 6 | 164 | nd | 164 | 164 | nd | 164 |
| Sens 6 | 47% | nd | 67% | 25% | nd | 31% |
| Spec 6 | 90% | nd | 90% | 90% | nd | 90% |
| OR Quart 2 | 0.49 | nd | 0 | 1.0 | nd | 1.0 |
| p Value | 0.57 | nd | na | 1.0 | nd | 1.0 |
| 95% CI of | 0.044 | nd | na | 0.062 | nd | 0.062 |
| OR Quart2 | 5.5 | nd | na | 16 | nd | 16 |
| OR Quart 3 | 1.5 | nd | 1.0 | 6.2 | nd | 4.1 |
| p Value | 0.66 | nd | 1.0 | 0.093 | nd | 0.21 |
| 95% CI of | 0.25 | nd | 0.062 | 0.74 | nd | 0.45 |
| OR Quart3 | 9.1 | nd | 16 | 52 | nd | 37 |
| OR Quart 4 | 4.7 | nd | 7.2 | 8.4 | nd | 7.2 |
| p Value | 0.051 | nd | 0.066 | 0.047 | nd | 0.066 |
| 95% CI of | 0.99 | nd | 0.88 | 1.0 | nd | 0.88 |
| OR Quart4 | 22 | nd | 60 | 68 | nd | 60 |

| | 48 hr prior to AKI stage | | |
|---|---|---|---|
| | sCr or UO | sCr only | UO only |
| AUC | 0.55 | nd | nd |
| SE | 0.11 | nd | nd |
| p | 0.63 | nd | nd |
| nCohort 1 | 652 | nd | nd |
| nCohort 2 | 7 | nd | nd |
| Cutoff 1 | 6.41 | nd | nd |
| Sens 1 | 71% | nd | nd |
| Spec 1 | 45% | nd | nd |
| Cutoff 2 | 0.429 | nd | nd |
| Sens 2 | 86% | nd | nd |
| Spec 2 | 19% | nd | nd |
| Cutoff 3 | 0 | nd | nd |
| Sens 3 | 100% | nd | nd |
| Spec 3 | 0% | nd | nd |
| Cutoff 4 | 54.1 | nd | nd |
| Sens 4 | 43% | nd | nd |
| Spec 4 | 70% | nd | nd |
| Cutoff 5 | 93.9 | nd | nd |
| Sens 5 | 29% | nd | nd |
| Spec 5 | 81% | nd | nd |
| Cutoff 6 | 164 | nd | nd |
| Sens 6 | 14% | nd | nd |
| Spec 6 | 90% | nd | nd |
| OR Quart 2 | 0.49 | nd | nd |
| p Value | 0.57 | nd | nd |
| 95% CI of | 0.044 | nd | nd |
| OR Quart2 | 5.5 | nd | nd |
| OR Quart 3 | 0.49 | nd | nd |
| p Value | 0.57 | nd | nd |
| 95% CI of | 0.044 | nd | nd |
| OR Quart3 | 5.5 | nd | nd |
| OR Quart 4 | 1.5 | nd | nd |
| p Value | 0.66 | nd | nd |
| 95% CI of | 0.25 | nd | nd |
| OR Quart4 | 9.1 | nd | nd |

TABLE 9-continued

Comparison of marker levels in urine samples collected from
Cohort 1 (patients that did not progress beyond RIFLE stage 0, R, or I)
and in urine samples collected from Cohort 2 (subjects who progress
to RIFLE stage F) at 0, 24 hours, and 48 hours prior to the subject
reaching RIFLE stage I.

SL cytokine

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0627 | 0.100 | 0.0627 | 0.0952 | 0.0627 | 0.0869 |
| Average | 1.27 | 10.2 | 1.27 | 6.94 | 1.27 | 0.905 |
| Stdev | 17.9 | 21.2 | 17.9 | 13.2 | 17.9 | 2.55 |
| p(t-test) | | 0.021 | | 0.16 | | 0.95 |
| Min | 0.0336 | 0.0449 | 0.0336 | 0.0537 | 0.0336 | 0.0336 |
| Max | 527 | 68.6 | 527 | 45.6 | 527 | 8.15 |
| n (Samp) | 1277 | 22 | 1277 | 20 | 1277 | 10 |
| n (Patient) | 452 | 22 | 452 | 20 | 452 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0627 | 0.100 | nd | nd | nd | nd |
| Average | 1.74 | 2.44 | nd | nd | nd | nd |
| Stdev | 19.0 | 6.61 | nd | nd | nd | nd |
| p(t-test) | | 0.92 | nd | nd | nd | nd |
| Min | 0.0336 | 0.0511 | nd | nd | nd | nd |
| Max | 527 | 18.8 | nd | nd | nd | nd |
| n (Samp) | 1341 | 8 | nd | nd | nd | nd |
| n (Patient) | 467 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0627 | 0.288 | 0.0627 | 0.0908 | 0.0627 | 0.0869 |
| Average | 1.33 | 12.3 | 1.33 | 7.29 | 1.33 | 1.24 |
| Stdev | 19.0 | 23.0 | 19.0 | 13.4 | 19.0 | 3.05 |
| p(t-test) | | 0.032 | | 0.17 | | 0.99 |
| Min | 0.0336 | 0.0449 | 0.0336 | 0.0449 | 0.0336 | 0.0336 |
| Max | 527 | 68.6 | 527 | 45.6 | 527 | 8.15 |
| n (Samp) | 1124 | 14 | 1124 | 19 | 1124 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.71 | 0.69 | 0.74 | 0.74 | nd | 0.68 |
| SE | 0.063 | 0.10 | 0.077 | 0.064 | nd | 0.068 |
| p | 9.5E−4 | 0.071 | 0.0018 | 1.3E−4 | nd | 0.0084 |
| nCohort 1 | 1277 | 1341 | 1124 | 1277 | nd | 1124 |
| nCohort 2 | 22 | 8 | 14 | 20 | nd | 19 |
| Cutoff 1 | 0.0845 | 0.0845 | 0.0847 | 0.0878 | nd | 0.0847 |
| Sens 1 | 73% | 75% | 71% | 75% | nd | 74% |
| Spec 1 | 57% | 56% | 60% | 65% | nd | 60% |
| Cutoff 2 | 0.0651 | 0.0651 | 0.0527 | 0.0847 | nd | 0.0569 |
| Sens 2 | 82% | 88% | 93% | 85% | nd | 89% |
| Spec 2 | 51% | 51% | 25% | 60% | nd | 30% |
| Cutoff 3 | 0.0487 | 0.0487 | 0.0527 | 0.0569 | nd | 0.0527 |
| Sens 3 | 91% | 100% | 93% | 95% | nd | 95% |
| Spec 3 | 17% | 17% | 25% | 30% | nd | 25% |
| Cutoff 4 | 0.0914 | 0.0914 | 0.0914 | 0.0914 | nd | 0.0914 |
| Sens 4 | 50% | 50% | 57% | 50% | nd | 42% |
| Spec 4 | 72% | 72% | 71% | 72% | nd | 71% |
| Cutoff 5 | 0.109 | 0.109 | 0.109 | 0.109 | nd | 0.109 |
| Sens 5 | 45% | 25% | 57% | 45% | nd | 37% |
| Spec 5 | 82% | 81% | 81% | 82% | nd | 81% |
| Cutoff 6 | 0.175 | 0.188 | 0.186 | 0.175 | nd | 0.186 |
| Sens 6 | 45% | 25% | 57% | 40% | nd | 37% |
| Spec 6 | 90% | 94% | 90% | 90% | nd | 90% |
| OR Quart 2 | 0.33 | 0 | 2.0 | >3.0 | nd | 4.0 |
| p Value | 0.34 | na | 0.57 | <0.34 | nd | 0.21 |
| 95% CI of | 0.034 | na | 0.18 | >0.31 | nd | 0.45 |
| OR Quart2 | 3.2 | na | 22 | na | nd | 36 |
| OR Quart 3 | 2.4 | 3.0 | 3.0 | >8.2 | nd | 7.1 |
| p Value | 0.22 | 0.34 | 0.34 | <0.048 | nd | 0.067 |

TABLE 9-continued

Comparison of marker levels in urine samples collected from
Cohort 1 (patients that did not progress beyond RIFLE stage 0, R, or I)
and in urine samples collected from Cohort 2 (subjects who progress
to RIFLE stage F) at 0, 24 hours, and 48 hours prior to the subject
reaching RIFLE stage I.

| | | | | | | |
|---|---|---|---|---|---|---|
| 95% CI of | 0.60 | 0.31 | 0.31 | >1.0 | nd | 0.87 |
| OR Quart3 | 9.2 | 29 | 29 | na | nd | 58 |
| OR Quart 4 | 3.7 | 4.0 | 8.2 | >9.2 | nd | 7.1 |
| p Value | 0.044 | 0.21 | 0.048 | <0.036 | nd | 0.067 |
| 95% CI of | 1.0 | 0.45 | 1.0 | >1.2 | nd | 0.87 |
| OR Quart4 | 14 | 36 | 66 | na | nd | 58 |

| | | 48 hr prior to AKI stage | | |
|---|---|---|---|---|
| | | sCr or UO | sCr only | UO only |
| | AUC | 0.54 | nd | 0.55 |
| | SE | 0.094 | nd | 0.11 |
| | p | 0.67 | nd | 0.66 |
| | nCohort 1 | 1277 | nd | 1124 |
| | nCohort 2 | 10 | nd | 7 |
| | Cutoff 1 | 0.0569 | nd | 0.0847 |
| | Sens 1 | 70% | nd | 71% |
| | Spec 1 | 30% | nd | 60% |
| | Cutoff 2 | 0.0514 | nd | 0 |
| | Sens 2 | 80% | nd | 100% |
| | Spec 2 | 21% | nd | 0% |
| | Cutoff 3 | 0 | nd | 0 |
| | Sens 3 | 100% | nd | 100% |
| | Spec 3 | 0% | nd | 0% |
| | Cutoff 4 | 0.0914 | nd | 0.0914 |
| | Sens 4 | 30% | nd | 29% |
| | Spec 4 | 72% | nd | 71% |
| | Cutoff 5 | 0.109 | nd | 0.109 |
| | Sens 5 | 30% | nd | 29% |
| | Spec 5 | 82% | nd | 81% |
| | Cutoff 6 | 0.175 | nd | 0.186 |
| | Sens 6 | 20% | nd | 14% |
| | Spec 6 | 90% | nd | 90% |
| | OR Quart 2 | 0.33 | nd | 0 |
| | p Value | 0.34 | nd | na |
| | 95% CI of | 0.034 | nd | na |
| | OR Quart2 | 3.2 | nd | na |
| | OR Quart 3 | 1.00 | nd | 1.5 |
| | p Value | 1.00 | nd | 0.66 |
| | 95% CI of | 0.20 | nd | 0.25 |
| | OR Quart3 | 5.0 | nd | 9.0 |
| | OR Quart 4 | 1.00 | nd | 1.00 |
| | p Value | 1.00 | nd | 1.00 |
| | 95% CI of | 0.20 | nd | 0.14 |
| | OR Quart4 | 5.0 | nd | 7.1 |

Immunoglogulin G3

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 99.4 | 222 | 99.4 | 274 | 99.4 | 188 |
| Average | 204 | 445 | 204 | 430 | 204 | 286 |
| Stdev | 288 | 467 | 288 | 394 | 288 | 342 |
| p(t-test) | | 1.3E−4 | | 5.5E−4 | | 0.37 |
| Min | 0.833 | 34.7 | 0.833 | 51.9 | 0.833 | 2.02 |
| Max | 1200 | 1200 | 1200 | 1200 | 1200 | 1200 |
| n (Samp) | 1268 | 22 | 1268 | 20 | 1268 | 10 |
| n (Patient) | 449 | 22 | 449 | 20 | 449 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 104 | 214 | nd | nd | nd | nd |
| Average | 216 | 531 | nd | nd | nd | nd |
| Stdev | 302 | 557 | nd | nd | nd | nd |
| p(t-test) | | 0.0035 | nd | nd | nd | nd |
| Min | 0.833 | 34.7 | nd | nd | nd | nd |
| Max | 1200 | 1200 | nd | nd | nd | nd |

TABLE 9-continued

Comparison of marker levels in urine samples collected from
Cohort 1 (patients that did not progress beyond RIFLE stage 0, R, or I)
and in urine samples collected from Cohort 2 (subjects who progress
to RIFLE stage F) at 0, 24 hours, and 48 hours prior to the subject
reaching RIFLE stage I.

| | | | | | | |
|---|---|---|---|---|---|---|
| n (Samp) | 1332 | 8 | nd | nd | nd | nd |
| n (Patient) | 464 | 8 | nd | nd | nd | nd |

| | 0 hr prior to AKI stage | | 24 hr prior to AKI stage | | 48 hr prior to AK stage | |
|---|---|---|---|---|---|---|
| UO only | Cohort 1 | Cohort 2 | Cohort 1 | Cohort 2 | Cohort 1 | Cohort 2 |
| Median | 102 | 292 | 102 | 326 | 102 | 236 |
| Average | 207 | 539 | 207 | 558 | 207 | 370 |
| Stdev | 290 | 499 | 290 | 443 | 290 | 379 |
| p(t-test) | | 2.8E-5 | | 2.7E-7 | | 0.14 |
| Min | 0.833 | 53.3 | 0.833 | 51.9 | 0.833 | 118 |
| Max | 1200 | 1200 | 1200 | 1200 | 1200 | 1200 |
| n (Samp) | 1114 | 14 | 1114 | 19 | 1114 | 7 |
| n (Patient) | 359 | 14 | 359 | 19 | 359 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.70 | 0.68 | 0.74 | 0.75 | nd | 0.81 |
| SE | 0.063 | 0.10 | 0.077 | 0.064 | nd | 0.061 |
| P | 0.0013 | 0.078 | 0.0016 | 8.5E-5 | nd | 3.4E-7 |
| nCohort 1 | 1268 | 1332 | 1114 | 1268 | nd | 1114 |
| nCohort 2 | 22 | 8 | 14 | 20 | nd | 19 |
| Cutoff 1 | 136 | 98.1 | 182 | 211 | nd | 234 |
| Sens 1 | 73% | 75% | 71% | 70% | nd | 74% |
| Spec 1 | 60% | 48% | 70% | 75% | nd | 76% |
| Cutoff 2 | 90.6 | 90.6 | 66.3 | 150 | nd | 185 |
| Sens 2 | 82% | 88% | 86% | 80% | nd | 84% |
| Spec 2 | 47% | 45% | 36% | 64% | nd | 71% |
| Cutoff 3 | 60.1 | 34.6 | 59.9 | 76.6 | nd | 95.7 |
| Sens 3 | 91% | 100% | 93% | 90% | nd | 95% |
| Spec 3 | 33% | 17% | 33% | 42% | nd | 48% |
| Cutoff 4 | 178 | 191 | 182 | 178 | nd | 182 |
| Sens 4 | 64% | 62% | 71% | 75% | nd | 84% |
| Spec 4 | 70% | 70% | 70% | 70% | nd | 70% |
| Cutoff 5 | 269 | 278 | 274 | 269 | nd | 274 |
| Sens 5 | 36% | 38% | 50% | 55% | nd | 63% |
| Spec 5 | 80% | 80% | 80% | 80% | nd | 80% |
| Cutoff 6 | 441 | 512 | 440 | 441 | nd | 440 |
| Sens 6 | 27% | 38% | 36% | 30% | nd | 42% |
| Spec 6 | 90% | 90% | 90% | 90% | nd | 90% |
| OR Quart 2 | 5.0 | 2.0 | >3.0 | >4.1 | nd | >2.0 |
| p Value | 0.14 | 0.57 | <0.34 | <0.21 | nd | <0.57 |
| 95% CI of OR Quart2 | 0.59 | 0.18 | >0.31 | >0.45 | nd | >0.18 |
| | 43 | 22 | na | na | nd | na |
| OR Quart 3 | 4.0 | 2.0 | >3.0 | >3.0 | nd | >3.0 |
| p Value | 0.21 | 0.57 | <0.34 | <0.34 | nd | <0.34 |
| 95% CI of OR Quart3 | 0.45 | 0.18 | >0.31 | >0.31 | nd | >0.31 |
| | 36 | 22 | na | na | nd | na |
| OR Quart 4 | 12 | 3.0 | >8.2 | >14 | nd | >15 |
| p Value | 0.016 | 0.34 | <0.048 | <0.012 | nd | <0.0097 |
| 95% CI of OR Quart4 | 1.6 | 0.31 | >1.0 | >1.8 | nd | >1.9 |
| | 96 | 29 | na | na | nd | na |

| | 48 hr prior to AKI stage | | |
|---|---|---|---|
| | sCr or UO | sCr only | UO only |
| AUC | 0.64 | nd | 0.76 |
| SE | 0.095 | nd | 0.11 |
| P | 0.13 | nd | 0.014 |
| nCohort 1 | 1268 | nd | 1114 |
| nCohort 2 | 10 | nd | 7 |
| Cutoff 1 | 147 | nd | 163 |
| Sens 1 | 70% | nd | 71% |
| Spec 1 | 64% | nd | 67% |
| Cutoff 2 | 117 | nd | 147 |
| Sens 2 | 80% | nd | 86% |
| Spec 2 | 55% | nd | 63% |
| Cutoff 3 | 58.2 | nd | 117 |
| Sens 3 | 90% | nd | 100% |
| Spec 3 | 32% | nd | 54% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  |  |  |
|---|---|---|
| Cutoff 4 | 178 | nd | 182 |
| Sens 4 | 50% | nd | 57% |
| Spec 4 | 70% | nd | 70% |
| Cutoff 5 | 269 | nd | 274 |
| Sens 5 | 30% | nd | 43% |
| Spec 5 | 80% | nd | 80% |
| Cutoff 6 | 441 | nd | 440 |
| Sens 6 | 10% | nd | 14% |
| Spec 6 | 90% | nd | 90% |
| OR Quart 2 | 1.00 | nd | >0 |
| p Value | 1.00 | nd | <na |
| 95% CI of OR Quart2 | 0.062 16 | nd nd | >na na |
| OR Quart 3 | 4.0 | nd | >3.0 |
| p Value | 0.21 | nd | <0.34 |
| 95% CI of OR Quart3 | 0.45 36 | nd nd | >0.31 na |
| OR Quart 4 | 4.0 | nd | >4.0 |
| p Value | 0.21 | nd | <0.21 |
| 95% CI of OR Quart4 | 0.45 36 | nd nd | >0.45 na |

Interleukin-1 receptor type I

| sCr or UO | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 5.15 | 4.97 | 5.15 | 6.60 | 5.15 | 9.18 |
| Average | 5.84 | 7.62 | 5.84 | 12.3 | 5.84 | 6.53 |
| Stdev | 5.07 | 7.42 | 5.07 | 18.3 | 5.07 | 6.22 |
| p(t-test) |  | 0.19 |  | 8.6E−6 |  | 0.72 |
| Min | 0.0141 | 0.0200 | 0.0141 | 1.40 | 0.0141 | 0.0147 |
| Max | 37.1 | 29.6 | 37.1 | 78.1 | 37.1 | 14.7 |
| n (Samp) | 657 | 15 | 657 | 16 | 657 | 7 |
| n (Patient) | 300 | 15 | 300 | 16 | 300 | 7 |

| UO only | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 5.34 | 10.2 | 5.34 | 6.63 | nd | nd |
| Average | 5.99 | 10.4 | 5.99 | 13.7 | nd | nd |
| Stdev | 5.10 | 8.65 | 5.10 | 20.3 | nd | nd |
| p(t-test) |  | 0.011 |  | 3.0E−6 | nd | nd |
| Min | 0.0141 | 0.0200 | 0.0141 | 1.40 | nd | nd |
| Max | 37.1 | 29.6 | 37.1 | 78.1 | nd | nd |
| n (Samp) | 599 | 9 | 599 | 13 | nd | nd |
| n (Patient) | 263 | 9 | 263 | 13 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.56 | nd | 0.67 | 0.64 | nd | 0.64 |
| SE | 0.078 | nd | 0.100 | 0.076 | nd | 0.084 |
| p | 0.43 | nd | 0.095 | 0.065 | nd | 0.099 |
| nCohort 1 | 657 | nd | 599 | 657 | nd | 599 |
| nCohort 2 | 15 | nd | 9 | 16 | nd | 13 |
| Cutoff 1 | 3.03 | nd | 4.81 | 5.95 | nd | 3.17 |
| Sens 1 | 73% | nd | 78% | 75% | nd | 85% |
| Spec 1 | 36% | nd | 47% | 56% | nd | 35% |
| Cutoff 2 | 2.68 | nd | 3.03 | 3.17 | nd | 3.17 |
| Sens 2 | 80% | nd | 89% | 88% | nd | 85% |
| Spec 2 | 33% | nd | 34% | 37% | nd | 35% |
| Cutoff 3 | 0.0213 | nd | 0.0179 | 1.97 | nd | 1.97 |
| Sens 3 | 93% | nd | 100% | 94% | nd | 92% |
| Spec 3 | 5% | nd | 2% | 26% | nd | 24% |
| Cutoff 4 | 8.08 | nd | 8.09 | 8.08 | nd | 8.09 |
| Sens 4 | 40% | nd | 56% | 31% | nd | 38% |
| Spec 4 | 70% | nd | 70% | 70% | nd | 70% |
| Cutoff 5 | 9.31 | nd | 9.31 | 9.31 | nd | 9.31 |
| Sens 5 | 40% | nd | 56% | 31% | nd | 38% |
| Spec 5 | 80% | nd | 80% | 80% | nd | 80% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Cutoff 6 | 11.5 | nd | 11.5 | 11.5 | nd | 11.5 |
| Sens 6 | 20% | nd | 44% | 25% | nd | 31% |
| Spec 6 | 90% | nd | 90% | 90% | nd | 90% |
| OR Quart 2 | 3.1 | nd | 2.0 | 3.0 | nd | 1.0 |
| p Value | 0.17 | nd | 0.57 | 0.34 | nd | 1.0 |
| 95% CI of OR Quart2 | 0.61 15 | nd | 0.18 22 | 0.31 29 | nd | 0.14 7.2 |
| OR Quart 3 | 0.50 | nd | 1.0 | 7.3 | nd | 2.0 |
| p Value | 0.57 | nd | 1.0 | 0.065 | nd | 0.42 |
| 95% CI of OR Quart3 | 0.045 5.5 | nd | 0.062 16 | 0.88 60 | nd | 0.37 11 |
| OR Quart 4 | 3.1 | nd | 5.1 | 5.1 | nd | 2.6 |
| p Value | 0.17 | nd | 0.14 | 0.14 | nd | 0.27 |
| 95% CI of OR Quart4 | 0.61 15 | nd | 0.59 44 | 0.59 44 | nd | 0.49 13 |

| | | 48 hr prior to AKI stage | | |
|---|---|---|---|---|
| | | sCr or UO | sCr only | UO only |
| | AUC | 0.52 | nd | nd |
| | SE | 0.11 | nd | nd |
| | p | 0.86 | nd | nd |
| | nCohort 1 | 657 | nd | nd |
| | nCohort 2 | 7 | nd | nd |
| | Cutoff 1 | 0.289 | nd | nd |
| | Sens 1 | 71% | nd | nd |
| | Spec 1 | 14% | nd | nd |
| | Cutoff 2 | 0.0179 | nd | nd |
| | Sens 2 | 86% | nd | nd |
| | Spec 2 | 2% | nd | nd |
| | Cutoff 3 | 0.0141 | nd | nd |
| | Sens 3 | 100% | nd | nd |
| | Spec 3 | 0% | nd | nd |
| | Cutoff 4 | 8.08 | nd | nd |
| | Sens 4 | 57% | nd | nd |
| | Spec 4 | 70% | nd | nd |
| | Cutoff 5 | 9.31 | nd | nd |
| | Sens 5 | 43% | nd | nd |
| | Spec 5 | 80% | nd | nd |
| | Cutoff 6 | 11.5 | nd | nd |
| | Sens 6 | 14% | nd | nd |
| | Spec 6 | 90% | nd | nd |
| | OR Quart 2 | 0 | nd | nd |
| | p Value | na | nd | nd |
| | 95% CI of OR Quart2 | na na | nd | nd |
| | OR Quart 3 | 0 | nd | nd |
| | p Value | na | nd | nd |
| | 95% CI of OR Quart3 | na na | nd | nd |
| | OR Quart 4 | 1.3 | nd | nd |
| | p Value | 0.70 | nd | nd |
| | 95% CI of OR Quart4 | 0.30 6.1 | nd | nd |

| | Interleukin-20 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 9.54 | 32.3 | 9.54 | 182 | 9.54 | 10.4 |
| Average | 74.9 | 1 1 1 | 74.9 | 218 | 74.9 | 73.7 |
| Stdev | 122 | 143 | 122 | 268 | 122 | 165 |
| p(t-test) | | 0.17 | | 5.1E−7 | | 0.98 |
| Min | 0.368 | 0.488 | 0.368 | 0.541 | 0.368 | 0.541 |
| Max | 811 | 414 | 811 | 1080 | 811 | 534 |
| n (Samp) | 1274 | 22 | 1274 | 20 | 1274 | 10 |
| n (Patient) | 452 | 22 | 452 | 20 | 452 | 10 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 9.54 | 58.5 | nd | nd | nd | nd |
| Average | 75.8 | 110 | nd | nd | nd | nd |
| Stdev | 126 | 130 | nd | nd | nd | nd |
| p(t-test) | | 0.44 | nd | nd | nd | nd |
| Min | 0.368 | 1.33 | nd | nd | nd | nd |
| Max | 1080 | 356 | nd | nd | nd | nd |
| n (Samp) | 1338 | 8 | nd | nd | nd | nd |
| n (Patient) | 467 | 8 | nd | nd | nd | nd |

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 9.54 | 23.6 | 9.54 | 125 | 9.54 | 1.37 |
| Average | 74.7 | 94.3 | 74.7 | 185 | 74.7 | 20.7 |
| Stdev | 121 | 133 | 121 | 264 | 121 | 35.1 |
| p(t-test) | | 0.55 | | 1.3E−4 | | 0.24 |
| Min | 0.368 | 0.412 | 0.368 | 0.488 | 0.368 | 0.541 |
| Max | 811 | 414 | 811 | 1080 | 811 | 96.5 |
| n (Samp) | 1121 | 14 | 1121 | 19 | 1121 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.59 | 0.65 | 0.56 | 0.67 | nd | 0.60 |
| SE | 0.064 | 0.11 | 0.080 | 0.067 | nd | 0.069 |
| P | 0.16 | 0.16 | 0.45 | 0.011 | nd | 0.16 |
| nCohort 1 | 1274 | 1338 | 1121 | 1274 | nd | 1121 |
| nCohort 2 | 22 | 8 | 14 | 20 | nd | 19 |
| Cutoff 1 | 1.56 | 19.9 | 1.56 | 1.56 | nd | 1.33 |
| Sens 1 | 77% | 75% | 79% | 70% | nd | 79% |
| Spec 1 | 37% | 58% | 36% | 37% | nd | 23% |
| Cutoff 2 | 1.37 | 3.07 | 1.33 | 1.37 | nd | 0.898 |
| Sens 2 | 82% | 88% | 86% | 80% | nd | 84% |
| Spec 2 | 28% | 43% | 23% | 28% | nd | 16% |
| Cutoff 3 | 1.32 | 1.32 | 1.32 | 1.33 | nd | 0.488 |
| Sens 3 | 95% | 100% | 93% | 90% | nd | 95% |
| Spec 3 | 22% | 21% | 21% | 24% | nd | 9% |
| Cutoff 4 | 85.6 | 85.6 | 85.6 | 85.6 | nd | 85.6 |
| Sens 4 | 41% | 38% | 43% | 60% | nd | 53% |
| Spec 4 | 70% | 70% | 70% | 70% | nd | 70% |
| Cutoff 5 | 149 | 153 | 153 | 149 | nd | 153 |
| Sens 5 | 32% | 25% | 14% | 55% | nd | 42% |
| Spec 5 | 80% | 82% | 82% | 80% | nd | 82% |
| Cutoff 6 | 233 | 234 | 235 | 233 | nd | 235 |
| Sens 6 | 23% | 25% | 14% | 35% | nd | 26% |
| Spec 6 | 90% | 90% | 90% | 90% | nd | 90% |
| OR Quart 2 | 1.3 | 1.00 | 1.00 | 2.5 | nd | 0.60 |
| p Value | 0.74 | 1.00 | 1.00 | 0.27 | nd | 0.48 |
| 95% CI of OR Quart2 | 0.33 | 0.062 | 0.20 | 0.48 | nd | 0.14 |
| | 4.7 | 16 | 5.0 | 13 | nd | 2.5 |
| OR Quart 3 | 1.3 | 3.0 | 1.00 | 0.50 | nd | 0.20 |
| p Value | 0.74 | 0.34 | 1.00 | 0.57 | nd | 0.14 |
| 95% CI of OR Quart3 | 0.33 | 0.31 | 0.20 | 0.045 | nd | 0.023 |
| | 4.7 | 29 | 5.0 | 5.5 | nd | 1.7 |
| OR Quart 4 | 2.0 | 3.0 | 1.7 | 6.2 | nd | 2.0 |
| p Value | 0.25 | 0.34 | 0.48 | 0.018 | nd | 0.20 |
| 95% CI of OR Quart4 | 0.60 | 0.31 | 0.40 | 1.4 | nd | 0.69 |
| | 6.8 | 29 | 7.1 | 28 | nd | 6.0 |

| | 48 hr prior to AKI stage | | |
|---|---|---|---|
| | sCr or UO | sCr only | UO only |
| AUC | 0.47 | nd | 0.37 |
| SE | 0.093 | nd | 0.11 |
| p | 0.73 | nd | 0.24 |
| nCohort 1 | 1274 | nd | 1121 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| nCohort 2 | 10 | nd | 7 |
| Cutoff 1 | 1.33 | nd | 1.33 |
| Sens 1 | 80% | nd | 71% |
| Spec 1 | 24% | nd | 23% |
| Cutoff 2 | 1.33 | nd | 0.488 |
| Sens 2 | 80% | nd | 100% |
| Spec 2 | 24% | nd | 9% |
| Cutoff 3 | 0.488 | nd | 0.488 |
| Sens 3 | 100% | nd | 100% |
| Spec 3 | 9% | nd | 9% |
| Cutoff 4 | 85.6 | nd | 85.6 |
| Sens 4 | 20% | nd | 14% |
| Spec 4 | 70% | nd | 70% |
| Cutoff 5 | 149 | nd | 153 |
| Sens 5 | 10% | nd | 0% |
| Spec 5 | 80% | nd | 82% |
| Cutoff 6 | 233 | nd | 235 |
| Sens 6 | 10% | nd | 0% |
| Spec 6 | 90% | nd | 90% |
| OR Quart 2 | 4.0 | nd | >3.0 |
| p Value | 0.21 | nd | <0.34 |
| 95% CI of OR Quart2 | 0.45 | nd | >0.31 |
| | 36 | nd | na |
| OR Quart 3 | 3.0 | nd | >2.0 |
| p Value | 0.34 | nd | <0.57 |
| 95% CI of OR Quart3 | 0.31 | nd | >0.18 |
| | 29 | nd | na |
| OR Quart 4 | 2.0 | nd | >2.0 |
| p Value | 0.57 | nd | <0.57 |
| 95% CI of OR Quart4 | 0.18 | nd | >0.18 |
| | 22 | nd | na |

Interleukin-29

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 34.7 | 94.4 | 34.7 | 126 | 34.7 | 34.8 |
| Average | 76.8 | 162 | 76.8 | 164 | 76.8 | 93.3 |
| Stdev | 102 | 165 | 102 | 154 | 102 | 153 |
| p(t-test) | | 1.3E−4 | | 2.6E−4 | | 0.61 |
| Min | 0.114 | 16.2 | 0.114 | 7.55 | 0.114 | 0.170 |
| Max | 675 | 635 | 675 | 613 | 675 | 510 |
| n (Samp) | 1275 | 22 | 1275 | 19 | 1275 | 10 |
| n (Patient) | 452 | 22 | 452 | 19 | 452 | 10 |

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 37.9 | 59.5 | nd | nd | nd | nd |
| Average | 82.2 | 114 | nd | nd | nd | nd |
| Stdev | 110 | 143 | nd | nd | nd | nd |
| p(t-test) | | 0.41 | nd | nd | nd | nd |
| Min | 0.114 | 16.2 | nd | nd | nd | nd |
| Max | 827 | 423 | nd | nd | nd | nd |
| n (Samp) | 1338 | 8 | nd | nd | nd | nd |
| n (Patient) | 467 | 8 | nd | nd | nd | nd |

| UO only | 0 hr prior to AKI stage | | 24 hr prior to AKI stage | | 48 hr prior to AK stage | |
|---|---|---|---|---|---|---|
| | Cohort 1 | Cohort 2 | Cohort 1 | Cohort 2 | Cohort 1 | Cohort 2 |
| Median | 38.9 | 157 | 38.9 | 137 | 38.9 | 100 |
| Average | 79.9 | 227 | 79.9 | 174 | 79.9 | 129 |
| Stdev | 102 | 207 | 102 | 159 | 102 | 175 |
| p(t-test) | | 1.7E−7 | | 1.3E−4 | | 0.21 |
| Min | 0.114 | 24.4 | 0.114 | 7.55 | 0.114 | 0.170 |
| Max | 675 | 635 | 675 | 613 | 675 | 510 |
| n (Samp) | 1121 | 14 | 1121 | 18 | 1121 | 7 |
| n (Patient) | 362 | 14 | 362 | 18 | 362 | 7 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.71 | 0.61 | 0.77 | 0.73 | nd | 0.73 |
| SE | 0.063 | 0.11 | 0.074 | 0.067 | nd | 0.068 |
| p | 9.1E−4 | 0.32 | 2.1E−4 | 6.1E−4 | nd | 9.1E−4 |
| nCohort 1 | 1275 | 1338 | 1121 | 1275 | nd | 1121 |
| nCohon 2 | 22 | 8 | 14 | 19 | nd | 18 |
| Cutoff 1 | 50.4 | 19.5 | 86.1 | 49.5 | nd | 54.1 |
| Sens 1 | 73% | 75% | 71% | 74% | nd | 72% |
| Spec 1 | 59% | 38% | 68% | 58% | nd | 58% |
| Cutoff 2 | 24.4 | 16.3 | 76.8 | 32.3 | nd | 32.3 |
| Sens 2 | 82% | 88% | 86% | 84% | nd | 83% |
| Spec 2 | 42% | 35% | 64% | 49% | nd | 46% |
| Cutoff 3 | 19.5 | 16.2 | 24.4 | 25.5 | nd | 25.5 |
| Sens 3 | 91% | 100% | 93% | 95% | nd | 94% |
| Spec 3 | 39% | 34% | 39% | 45% | nd | 42% |
| Cutoff 4 | 91.9 | 99.2 | 99.2 | 91.9 | nd | 99.2 |
| Sens 4 | 50% | 25% | 64% | 63% | nd | 61% |
| Spec 4 | 71% | 70% | 70% | 71% | nd | 70% |
| Cutoff 5 | 139 | 150 | 143 | 139 | nd | 143 |
| Sens 5 | 41% | 25% | 50% | 47% | nd | 50% |
| Spec 5 | 81% | 80% | 80% | 81% | nd | 80% |
| Cutoff 6 | 211 | 218 | 211 | 211 | nd | 211 |
| Sens 6 | 27% | 25% | 36% | 21% | nd | 28% |
| Spec 6 | 90% | 90% | 90% | 90% | nd | 90% |
| OR Quart 2 | >5.1 | >3.0 | >2.0 | >4.0 | nd | >4.0 |
| p Value | <0.14 | <0.34 | <0.57 | <0.21 | nd | <0.21 |
| 95% CI of OR Quart2 | >0.59 na | >0.31 na | >0.18 na | >0.45 na | nd nd | >0.45 na |
| OR Quart 3 | >7.2 | >3.0 | >4.0 | >4.1 | nd | >4.0 |
| p Value | <0.066 | <0.34 | <0.21 | <0.21 | nd | <0.21 |
| 95% CI of OR Quart3 | >0.88 na | >0.31 na | >0.45 na | >0.45 na | nd nd | >0.45 na |
| OR Quart 4 | >10 | >2.0 | >8.2 | >11 | nd | >10 |
| p Value | <0.027 | <0.57 | <0.048 | <0.020 | nd | <0.026 |
| 95% CI of OR Quart4 | >1.3 na | >0.18 na | >1.0 na | >1.5 na | nd nd | >1.3 na |

| | 48 hr prior to AKI stage | | |
|---|---|---|---|
| | sCr or UO | sCr only | UO only |
| AUC | 0.50 | nd | 0.58 |
| SE | 0.092 | nd | 0.11 |
| p | 0.96 | nd | 0.49 |
| nCohort 1 | 1275 | nd | 1121 |
| nCohort 2 | 10 | nd | 7 |
| Cutoff 1 | 14.2 | nd | 46.5 |
| Sens 1 | 70% | nd | 71% |
| Spec 1 | 34% | nd | 54% |
| Cutoff 2 | 7.90 | nd | 14.2 |
| Sens 2 | 80% | nd | 86% |
| Spec 2 | 28% | nd | 31% |
| Cutoff 3 | 2.78 | nd | 0.158 |
| Sens 3 | 90% | nd | 100% |
| Spec 3 | 23% | nd | 2% |
| Cutoff 4 | 91.9 | nd | 99.2 |
| Sens 4 | 40% | nd | 57% |
| Spec 4 | 71% | nd | 70% |
| Cutoff 5 | 139 | nd | 143 |
| Sens 5 | 10% | nd | 14% |
| Spec 5 | 81% | nd | 80% |
| Cutoff 6 | 211 | nd | 211 |
| Sens 6 | 10% | nd | 14% |
| Spec 6 | 90% | nd | 90% |
| OR Quart 2 | 1.5 | nd | 1.0 |
| p Value | 0.66 | nd | 1.0 |
| 95% CI of OR Quart2 | 0.25 9.1 | nd nd | 0.062 16 |
| OR Quart 3 | 1.5 | nd | 4.0 |
| p Value | 0.66 | nd | 0.21 |
| 95% CI of | 0.25 | nd | 0.45 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  |  |  |  |
|---|---|---|---|
| OR Quart3 | 9.1 | nd | 36 |
| OR Quart 4 | 1.00 | nd | 1.0 |
| p Value | 1.00 | nd | 1.0 |
| 95% CI of | 0.14 | nd | 0.062 |
| OR Quart4 | 7.1 | nd | 16 |

Interleukin-7

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0110 | 0.0128 | 0.0110 | 0.0226 | 0.0110 | 0.0121 |
| Average | 0.296 | 0.560 | 0.296 | 1.99 | 0.296 | 0.199 |
| Stdev | 2.81 | 2.15 | 2.81 | 7.16 | 2.81 | 0.576 |
| p(t-test) | | 0.66 | | 0.010 | | 0.91 |
| Min | 0.00316 | 0.00451 | 0.00316 | 0.00316 | 0.00316 | 0.00316 |
| Max | 64.2 | 9.95 | 64.2 | 31.8 | 64.2 | 1.84 |
| n (Samp) | 1275 | 22 | 1275 | 20 | 1275 | 10 |
| n (Patient) | 452 | 22 | 452 | 20 | 452 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0110 | 0.0127 | nd | nd | nd | nd |
| Average | 0.325 | 1.27 | nd | nd | nd | nd |
| Stdev | 2.89 | 3.55 | nd | nd | nd | nd |
| p(t-test) | | 0.36 | nd | nd | nd | nd |
| Min | 0.00316 | 0.00487 | nd | nd | nd | nd |
| Max | 64.2 | 10.1 | nd | nd | nd | nd |
| n (Samp) | 1339 | 8 | nd | nd | nd | nd |
| n (Patient) | 467 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0115 | 0.0107 | 0.0115 | 0.0226 | 0.0115 | 0.0244 |
| Average | 0.279 | 0.161 | 0.279 | 2.09 | 0.279 | 0.280 |
| Stdev | 2.36 | 0.560 | 2.36 | 7.34 | 2.36 | 0.687 |
| p(t-test) | | 0.85 | | 0.0020 | | 1.00 |
| Min | 0.00316 | 0.00451 | 0.00316 | 0.00316 | 0.00316 | 0.00316 |
| Max | 64.2 | 2.11 | 64.2 | 31.8 | 64.2 | 1.84 |
| n (Samp) | 1122 | 14 | 1122 | 19 | 1122 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.52 | 0.53 | 0.44 | 0.68 | nd | 0.61 |
| SE | 0.063 | 0.10 | 0.080 | 0.067 | nd | 0.069 |
| P | 0.75 | 0.77 | 0.43 | 0.0063 | nd | 0.11 |
| nCohort 1 | 1275 | 1339 | 1122 | 1275 | nd | 1122 |
| nCohort 2 | 22 | 8 | 14 | 20 | nd | 19 |
| Cutoff 1 | 0.00822 | 0.00822 | 0.00822 | 0.0127 | nd | 0.0107 |
| Sens 1 | 77% | 75% | 71% | 70% | nd | 74% |
| Spec 1 | 30% | 29% | 28% | 59% | nd | 46% |
| Cutoff 2 | 0.00801 | 0.00801 | 0.00451 | 0.0107 | nd | 0.00822 |
| Sens 2 | 82% | 88% | 86% | 85% | nd | 84% |
| Spec 2 | 26% | 25% | 7% | 47% | nd | 28% |
| Cutoff 3 | 0.00451 | 0.00451 | 0.00316 | 0.0105 | nd | 0.00451 |
| Sens 3 | 95% | 100% | 100% | 90% | nd | 95% |
| Spec 3 | 9% | 9% | 3% | 42% | nd | 7% |
| Cutoff 4 | 0.0156 | 0.0156 | 0.0156 | 0.0156 | nd | 0.0156 |
| Sens 4 | 27% | 25% | 21% | 60% | nd | 53% |
| Spec 4 | 71% | 71% | 70% | 71% | nd | 70% |
| Cutoff 5 | 0.0268 | 0.0294 | 0.0288 | 0.0268 | nd | 0.0288 |
| Sens 5 | 14% | 12% | 14% | 35% | nd | 32% |
| Spec 5 | 80% | 80% | 80% | 80% | nd | 80% |
| Cutoff 6 | 0.0478 | 0.0478 | 0.0478 | 0.0478 | nd | 0.0478 |
| Sens 6 | 9% | 12% | 7% | 15% | nd | 16% |
| Spec 6 | 93% | 92% | 93% | 93% | nd | 93% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| OR Quart 2 | 1.3 | 2.0 | 1.0 | 4.0 | nd | 1.3 |
| p Value | 0.74 | 0.57 | 1.0 | 0.21 | nd | 0.70 |
| 95% CI of | 0.33 | 0.18 | 0.20 | 0.45 | nd | 0.30 |
| OR Quart2 | 4.7 | 22 | 5.0 | 36 | nd | 6.0 |
| OR Quart 3 | 2.0 | 3.0 | 1.3 | 8.2 | nd | 2.0 |
| p Value | 0.25 | 0.34 | 0.70 | 0.049 | nd | 0.32 |
| 95% CI of | 0.60 | 0.31 | 0.30 | 1.0 | nd | 0.50 |
| OR Quart3 | 6.8 | 29 | 6.0 | 66 | nd | 8.2 |
| OR Quart 4 | 1.2 | 2.0 | 1.3 | 7.1 | nd | 2.0 |
| p Value | 0.74 | 0.57 | 0.70 | 0.067 | nd | 0.33 |
| 95% CI of | 0.33 | 0.18 | 0.30 | 0.87 | nd | 0.50 |
| OR Quart4 | 4.7 | 22 | 6.0 | 58 | nd | 8.1 |

| | 48 hr prior to AKI stage | | |
|---|---|---|---|
| | sCr or UO | sCr only | UO only |
| AUC | 0.53 | nd | 0.57 |
| SE | 0.093 | nd | 0.11 |
| p | 0.76 | nd | 0.52 |
| nCohort 1 | 1275 | nd | 1122 |
| nCohort 2 | 10 | nd | 7 |
| Cutoff 1 | 0.0107 | nd | 0.0110 |
| Sens 1 | 70% | nd | 71% |
| Spec 1 | 47% | nd | 50% |
| Cutoff 2 | 0.00487 | nd | 0 |
| Sens 2 | 80% | nd | 100% |
| Spec 2 | 13% | nd | 0% |
| Cutoff 3 | 0 | nd | 0 |
| Sens 3 | 100% | nd | 100% |
| Spec 3 | 0% | nd | 0% |
| Cutoff 4 | 0.0156 | nd | 0.0156 |
| Sens 4 | 40% | nd | 57% |
| Spec 4 | 71% | nd | 70% |
| Cutoff 5 | 0.0268 | nd | 0.0288 |
| Sens 5 | 30% | nd | 43% |
| Spec 5 | 80% | nd | 80% |
| Cutoff 6 | 0.0478 | nd | 0.0478 |
| Sens 6 | 10% | nd | 14% |
| Spec 6 | 93% | nd | 93% |
| OR Quart 2 | 0.33 | nd | 0.50 |
| p Value | 0.34 | nd | 0.57 |
| 95% CI of | 0.034 | nd | 0.045 |
| OR Quart2 | 3.2 | nd | 5.5 |
| OR Quart 3 | 0.66 | nd | 0.50 |
| p Value | 0.66 | nd | 0.57 |
| 95% CI of | 0.11 | nd | 0.045 |
| OR Quart3 | 4.0 | nd | 5.5 |
| OR Quart 4 | 1.3 | nd | 1.5 |
| p Value | 0.71 | nd | 0.66 |
| 95% CI of | 0.30 | nd | 0.25 |
| OR Quart4 | 6.0 | nd | 9.0 |

Matrix metalloproteinase-9:Metalloproteinase inhibitor 2 complex

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 280 | 24000 | 280 | 1330 | nd | nd |
| Average | 3930 | 13900 | 3930 | 5610 | nd | nd |
| Stdev | 8350 | 12600 | 8350 | 9720 | nd | nd |
| p(t-test) | | 0.0022 | | 0.53 | nd | nd |
| Min | 0.227 | 31.4 | 0.227 | 103 | nd | nd |
| Max | 24000 | 24000 | 24000 | 24000 | nd | nd |
| n (Samp) | 331 | 7 | 331 | 10 | nd | nd |
| n (Patient) | 192 | 7 | 192 | 10 | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | nd | nd | 267 | 1820 | nd | nd |
| Average | nd | nd | 3470 | 6850 | nd | nd |

TABLE 9-continued

Comparison of marker levels in urine samples collected from
Cohort 1 (patients that did not progress beyond RIFLE stage 0, R, or I)
and in urine samples collected from Cohort 2 (subjects who progress
to RIFLE stage F) at 0, 24 hours, and 48 hours prior to the subject
reaching RIFLE stage I.

| | | | | | | |
|---|---|---|---|---|---|---|
| Stdev | nd | nd | 7850 | 10600 | nd | nd |
| p(t-test) | nd | nd | | 0.23 | nd | nd |
| Min | nd | nd | 0.227 | 103 | nd | nd |
| Max | nd | nd | 24000 | 24000 | nd | nd |
| n (Samp) | nd | nd | 289 | 8 | nd | nd |
| n (Patient) | nd | nd | 161 | 8 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.73 | nd | nd | 0.70 | nd | 0.73 |
| SE | 0.11 | nd | nd | 0.094 | nd | 0.10 |
| p | 0.038 | nd | nd | 0.037 | nd | 0.025 |
| nCohort 1 | 331 | nd | nd | 331 | nd | 289 |
| nCohort 2 | 7 | nd | nd | 10 | nd | 8 |
| Cutoff 1 | 578 | nd | nd | 712 | nd | 712 |
| Sens 1 | 71% | nd | nd | 70% | nd | 75% |
| Spec 1 | 67% | nd | nd | 70% | nd | 71% |
| Cutoff 2 | 398 | nd | nd | 280 | nd | 280 |
| Sens 2 | 86% | nd | nd | 80% | nd | 88% |
| Spec 2 | 56% | nd | nd | 50% | nd | 52% |
| Cutoff 3 | 29.2 | nd | nd | 242 | nd | 102 |
| Sens 3 | 100% | nd | nd | 90% | nd | 100% |
| Spec 3 | 15% | nd | nd | 45% | nd | 28% |
| Cutoff 4 | 716 | nd | nd | 716 | nd | 697 |
| Sens 4 | 57% | nd | nd | 60% | nd | 75% |
| Spec 4 | 70% | nd | nd | 70% | nd | 70% |
| Cutoff 5 | 1650 | nd | nd | 1650 | nd | 1380 |
| Sens 5 | 57% | nd | nd | 40% | nd | 62% |
| Spec 5 | 80% | nd | nd | 80% | nd | 80% |
| Cutoff 6 | 24000 | nd | nd | 24000 | nd | 24000 |
| Sens 6 | 0% | nd | nd | 0% | nd | 0% |
| Spec 6 | 100% | nd | nd | 100% | nd | 100% |
| OR Quart 2 | 0 | nd | nd | >3.1 | nd | >1.0 |
| p Value | na | nd | nd | <0.33 | nd | <0.99 |
| 95% CI of OR Quart2 | na | nd | nd | >0.32 | nd | >0.062 |
| | na | nd | nd | na | nd | na |
| OR Quart 3 | 2.0 | nd | nd | >1.0 | nd | >2.1 |
| p Value | 0.57 | nd | nd | <0.99 | nd | <0.56 |
| 95% CI of OR Quart3 | 0.18 | nd | nd | >0.062 | nd | >0.18 |
| | 23 | nd | nd | na | nd | na |
| OR Quart4 | 4.1 | nd | nd | >6.4 | nd | >5.3 |
| p Value | 0.21 | nd | nd | <0.090 | nd | <0.13 |
| 95% CI of OR Quart4 | 0.45 | nd | nd | >0.75 | nd | >0.60 |
| | 37 | nd | nd | na | nd | na |

| | 48 hr prior to AKI stage | | |
|---|---|---|---|
| | sCr or UO | sCr only | UO only |
| AUC | nd | nd | nd |
| SE | nd | nd | nd |
| p | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  |  |  |  |
|---|---|---|---|
| OR Quart 2 | nd | nd | nd |
| p Value | nd | nd | nd |
| 95% CI of | nd | nd | nd |
| OR Quart2 | nd | nd | nd |
| OR Quart 3 | nd | nd | nd |
| p Value | nd | nd | nd |
| 95% CI of | nd | nd | nd |
| OR Quart3 | nd | nd | nd |
| OR Quart 4 | nd | nd | nd |
| p Value | nd | nd | nd |
| 95% CI of | nd | nd | nd |
| OR Quart4 | nd | nd | nd |

Platelet-derived growth factor subunit A (dimer)

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 89.6 | 141 | 89.6 | 299 | 89.6 | 154 |
| Average | 139 | 1150 | 139 | 809 | 139 | 184 |
| Stdev | 193 | 4240 | 193 | 1880 | 193 | 207 |
| p(t-test) |  | 4.4E−16 |  | 1.2E−22 |  | 0.46 |
| Min | 0.994 | 14.9 | 0.994 | 11.9 | 0.994 | 5.73 |
| Max | 4020 | 20000 | 4020 | 8310 | 4020 | 730 |
| n (Samp) | 1273 | 22 | 1273 | 20 | 1273 | 10 |
| n (Patient) | 451 | 22 | 451 | 20 | 451 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 92.5 | 87.1 | nd | nd | nd | nd |
| Average | 168 | 529 | nd | nd | nd | nd |
| Stdev | 626 | 1260 | nd | nd | nd | nd |
| p(t-test) |  | 0.11 | nd | nd | nd | nd |
| Min | 0.994 | 14.9 | nd | nd | nd | nd |
| Max | 20000 | 3640 | nd | nd | nd | nd |
| n (Samp) | 1337 | 8 | nd | nd | nd | nd |
| n (Patient) | 466 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 89.6 | 159 | 89.6 | 300 | 89.6 | 160 |
| Average | 136 | 1770 | 136 | 960 | 136 | 208 |
| Stdev | 191 | 5300 | 191 | 1950 | 191 | 240 |
| p(t-test) |  | 3.8E−23 |  | 6.4E−29 |  | 0.32 |
| Min | 1.31 | 29.0 | 1.31 | 11.9 | 1.31 | 29.1 |
| Max | 4020 | 20000 | 4020 | 8310 | 4020 | 730 |
| n (Samp) | 1119 | 14 | 1119 | 19 | 1119 | 7 |
| n (Patient) | 361 | 14 | 361 | 19 | 361 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.60 | 0.48 | 0.65 | 0.78 | nd | 0.79 |
| SE | 0.064 | 0.10 | 0.080 | 0.062 | nd | 0.063 |
| P | 0.11 | 0.82 | 0.056 | 6.1E−6 | nd | 4.2E−6 |
| nCohort 1 | 1273 | 1337 | 1119 | 1273 | nd | 1119 |
| nCohort 2 | 22 | 8 | 14 | 20 | nd | 19 |
| Cutoff 1 | 55.1 | 36.4 | 76.2 | 144 | nd | 139 |
| Sens 1 | 73% | 75% | 71% | 70% | nd | 74% |
| Spec 1 | 33% | 22% | 44% | 70% | nd | 69% |
| Cutoff 2 | 47.6 | 30.3 | 53.7 | 125 | nd | 118 |
| Sens 2 | 82% | 88% | 86% | 80% | nd | 84% |
| Spec 2 | 28% | 18% | 32% | 65% | nd | 62% |
| Cutoff 3 | 30.3 | 14.8 | 47.6 | 102 | nd | 35.1 |
| Sens 3 | 91% | 100% | 93% | 90% | nd | 95% |
| Spec 3 | 18% | 7% | 28% | 56% | nd | 22% |
| Cutoff 4 | 143 | 151 | 142 | 143 | nd | 142 |
| Sens 4 | 45% | 25% | 57% | 70% | nd | 68% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Spec 4 | 70% | 70% | 70% | 70% | nd | 70% |
| Cutoff 5 | 203 | 212 | 200 | 203 | nd | 200 |
| Sens 5 | 27% | 12% | 36% | 60% | nd | 63% |
| Spec 5 | 80% | 80% | 80% | 80% | nd | 80% |
| Cutoff 6 | 293 | 304 | 289 | 293 | nd | 289 |
| Sens 6 | 18% | 12% | 29% | 55% | nd | 58% |
| Spec 6 | 90% | 90% | 90% | 90% | nd | 90% |
| OR Quart 2 | 1.00 | 1.0 | 4.0 | 0 | nd | 0 |
| p Value | 1.00 | 1.00 | 0.21 | na | nd | na |
| 95% CI of | 0.25 | 0.14 | 0.45 | na | nd | na |
| OR Quart2 | 4.0 | 7.2 | 36 | na | nd | na |
| OR Quart 3 | 1.5 | 0.50 | 3.0 | 2.5 | nd | 2.5 |
| p Value | 0.53 | 0.57 | 0.34 | 0.27 | nd | 0.27 |
| 95% CI of | 0.42 | 0.045 | 0.31 | 0.49 | nd | 0.49 |
| OR Quart3 | 5.4 | 5.5 | 29 | 13 | nd | 13 |
| OR Quart 4 | 2.0 | 1.5 | 6.1 | 6.7 | nd | 6.2 |
| p Value | 0.26 | 0.65 | 0.096 | 0.013 | nd | 0.018 |
| 95% CI of | 0.60 | 0.25 | 0.73 | 1.5 | nd | 1.4 |
| OR Quart4 | 6.8 | 9.1 | 51 | 30 | nd | 28 |

| | | 48 hr prior to AKI stage | | |
|---|---|---|---|---|
| | | sCr or UO | sCr only | UO only |
| | AUC | 0.59 | nd | 0.62 |
| | SE | 0.095 | nd | 0.11 |
| | p | 0.36 | nd | 0.31 |
| | nCohort 1 | 1273 | nd | 1119 |
| | nCohort 2 | 10 | nd | 7 |
| | Cutoff 1 | 114 | nd | 114 |
| | Sens 1 | 70% | nd | 71% |
| | Spec 1 | 61% | nd | 61% |
| | Cutoff 2 | 38.8 | nd | 38.8 |
| | Sens 2 | 80% | nd | 86% |
| | Spec 2 | 23% | nd | 24% |
| | Cutoff 3 | 28.9 | nd | 28.9 |
| | Sens 3 | 90% | nd | 100% |
| | Spec 3 | 17% | nd | 17% |
| | Cutoff 4 | 143 | nd | 142 |
| | Sens 4 | 60% | nd | 57% |
| | Spec 4 | 70% | nd | 70% |
| | Cutoff 5 | 203 | nd | 200 |
| | Sens 5 | 30% | nd | 29% |
| | Spec 5 | 80% | nd | 80% |
| | Cutoff 6 | 293 | nd | 289 |
| | Sens 6 | 10% | nd | 14% |
| | Spec 6 | 90% | nd | 90% |
| | OR Quart 2 | 0 | nd | 0 |
| | p Value | na | nd | na |
| | 95% CI of | na | nd | na |
| | OR Quart2 | na | nd | na |
| | OR Quart 3 | 1.3 | nd | 1.5 |
| | p Value | 0.71 | nd | 0.66 |
| | 95% CI of | 0.30 | nd | 0.25 |
| | OR Quart3 | 6.0 | nd | 9.1 |
| | OR Quart 4 | 1.00 | nd | 1.00 |
| | p Value | 1.00 | nd | 1.00 |
| | 95% CI of | 0.20 | nd | 0.14 |
| | OR Quart4 | 5.0 | nd | 7.1 |

Platelet-derived growth factor A

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 3.43 | 8.82 | 3.43 | 22.0 | 3.43 | 11.6 |
| Average | 27.1 | 340 | 27.1 | 285 | 27.1 | 39.4 |
| Stdev | 311 | 1460 | 311 | 1080 | 311 | 84.5 |
| p(t-test) | | 5.6E−5 | | 6.6E−4 | | 0.90 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Min | 0.0141 | 0.0450 | 0.0141 | 0.0450 | 0.0141 | 0.0161 |
| Max | 10600 | 6850 | 10600 | 4860 | 10600 | 277 |
| n (Samp) | 1273 | 22 | 1273 | 20 | 1273 | 10 |
| n (Patient) | 451 | 22 | 451 | 20 | 451 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 3.53 | 15.3 | nd | nd | nd | nd |
| Average | 42.7 | 34.4 | nd | nd | nd | nd |
| Stdev | 408 | 58.2 | nd | nd | nd | nd |
| p(t-test) | | 0.95 | nd | nd | nd | nd |
| Min | 0.0141 | 0.156 | nd | nd | nd | nd |
| Max | 10600 | 174 | nd | nd | nd | nd |
| n (Samp) | 1337 | 8 | nd | nd | nd | nd |
| n (Patient) | 466 | 8 | nd | nd | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3.53 | 15.5 | 3.53 | 23.3 | 3.53 | 15.6 |
| Average | 20.1 | 349 | 20.1 | 663 | 20.1 | 52.3 |
| Stdev | 104 | 1120 | 104 | 1860 | 104 | 100 |
| p(t-test) | | 2.5E-14 | | 3.6E-26 | | 0.41 |
| Min | 0.0141 | 0.0450 | 0.0141 | 0.0450 | 0.0141 | 0.0161 |
| Max | 2250 | 4230 | 2250 | 6850 | 2250 | 277 |
| n (Samp) | 1119 | 14 | 1119 | 19 | 1119 | 7 |
| n (Patient) | 361 | 14 | 361 | 19 | 361 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.65 | 0.68 | 0.64 | 0.74 | nd | 0.74 |
| SE | 0.064 | 0.11 | 0.081 | 0.064 | nd | 0.066 |
| p | 0.019 | 0.085 | 0.086 | 2.2E-4 | nd | 3.7E-4 |
| nCohort 1 | 1273 | 1337 | 1119 | 1273 | nd | 1119 |
| nCohort 2 | 22 | 8 | 14 | 20 | nd | 19 |
| Cutoff 1 | 1.72 | 4.61 | 0.756 | 16.2 | nd | 7.33 |
| Sens 1 | 73% | 75% | 79% | 70% | nd | 74% |
| Spec 1 | 40% | 55% | 34% | 83% | nd | 63% |
| Cutoff 2 | 0.756 | 0.756 | 0.661 | 3.40 | nd | 2.26 |
| Sens 2 | 82% | 88% | 86% | 80% | nd | 84% |
| Spec 2 | 33% | 33% | 34% | 49% | nd | 43% |
| Cutoff 3 | 0.257 | 0.143 | 0.257 | 0.257 | nd | 0.0604 |
| Sens 3 | 91% | 100% | 93% | 90% | nd | 95% |
| Spec 3 | 29% | 26% | 29% | 29% | nd | 10% |
| Cutoff 4 | 9.40 | 10.3 | 9.92 | 9.40 | nd | 9.92 |
| Sens 4 | 50% | 62% | 50% | 70% | nd | 68% |
| Spec 4 | 71% | 70% | 70% | 71% | nd | 70% |
| Cutoff 5 | 15.3 | 15.9 | 15.8 | 15.3 | nd | 15.8 |
| Sens 5 | 45% | 50% | 50% | 70% | nd | 68% |
| Spec 5 | 80% | 80% | 81% | 80% | nd | 81% |
| Cutoff 6 | 30.7 | 35.0 | 31.2 | 30.7 | nd | 31.2 |
| Sens 6 | 27% | 25% | 43% | 35% | nd | 37% |
| Spec 6 | 90% | 90% | 90% | 90% | nd | 90% |
| OR Quart 2 | 7.1 | >2.0 | 6.1 | 1.5 | nd | 1.5 |
| p Value | 0.067 | <0.57 | 0.095 | 0.66 | nd | 0.66 |
| 95% CI of | 0.87 | >0.18 | 0.73 | 0.25 | nd | 0.25 |
| OR Quart2 | 58 | na | 51 | 9.1 | nd | 9.0 |
| OR Quart 3 | 4.0 | >2.0 | 0 | 0.50 | nd | 0.50 |
| p Value | 0.21 | <0.57 | na | 0.57 | nd | 0.57 |
| 95% CI of | 0.45 | >0.18 | na | 0.045 | nd | 0.045 |
| OR Quart3 | 36 | na | na | 5.5 | nd | 5.5 |
| OR Quart 4 | 10 | >4.0 | 7.1 | 7.2 | nd | 6.7 |
| p Value | 0.027 | <0.21 | 0.067 | 0.0092 | nd | 0.013 |
| 95% CI of | 1.3 | >0.45 | 0.87 | 1.6 | nd | 1.5 |
| OR Quart4 | 81 | na | 58 | 32 | nd | 30 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

|  |  | 48 hr prior to AKI stage | | |
|---|---|---|---|---|
|  |  | sCr or UO | sCr only | UO only |
|  | AUC | 0.61 | nd | 0.62 |
|  | SE | 0.095 | nd | 0.11 |
|  | p | 0.25 | nd | 0.30 |
|  | nCohort 1 | 1273 | nd | 1119 |
|  | nCohort 2 | 10 | nd | 7 |
|  | Cutoff 1 | 6.35 | nd | 6.35 |
|  | Sens 1 | 70% | nd | 71% |
|  | Spec 1 | 62% | nd | 61% |
|  | Cutoff 2 | 0.123 | nd | 0.0604 |
|  | Sens 2 | 80% | nd | 86% |
|  | Spec 2 | 23% | nd | 10% |
|  | Cutoff 3 | 0.0604 | nd | 0.0141 |
|  | Sens 3 | 90% | nd | 100% |
|  | Spec 3 | 9% | nd | 1% |
|  | Cutoff 4 | 9.40 | nd | 9.92 |
|  | Sens 4 | 50% | nd | 57% |
|  | Spec 4 | 71% | nd | 70% |
|  | Cutoff 5 | 15.3 | nd | 15.8 |
|  | Sens 5 | 50% | nd | 43% |
|  | Spec 5 | 80% | nd | 81% |
|  | Cutoff 6 | 30.7 | nd | 31.2 |
|  | Sens 6 | 20% | nd | 29% |
|  | Spec 6 | 90% | nd | 90% |
|  | OR Quart 2 | 0.50 | nd | 0 |
|  | p Value | 0.57 | nd | na |
|  | 95% CI of | 0.045 | nd | na |
|  | OR Quart2 | 5.5 | nd | na |
|  | OR Quart 3 | 1.00 | nd | 0.50 |
|  | p Value | 1.00 | nd | 0.57 |
|  | 95% CI of | 0.14 | nd | 0.045 |
|  | OR Quart3 | 7.1 | nd | 5.5 |
|  | OR Quart 4 | 2.5 | nd | 2.0 |
|  | p Value | 0.27 | nd | 0.42 |
|  | 95% CI of | 0.48 | nd | 0.36 |
|  | OR Quart4 | 13 | nd | 11 |

Thymic stromal lymphopoietin

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 73.5 | 36.8 | 73.5 | 46.2 | 73.5 | 61.6 |
| Average | 94.1 | 62.1 | 94.1 | 50.0 | 94.1 | 75.9 |
| Stdev | 80.9 | 75.2 | 80.9 | 33.1 | 80.9 | 71.9 |
| p(t-test) |  | 0.066 |  | 0.015 |  | 0.48 |
| Min | 0.00579 | 0.00694 | 0.00579 | 4.01 | 0.00579 | 14.3 |
| Max | 695 | 356 | 695 | 143 | 695 | 266 |
| n (Samp) | 1272 | 22 | 1272 | 20 | 1272 | 10 |
| n (Patient) | 452 | 22 | 452 | 20 | 452 | 10 |

|  | 0 hr prior to AKI stage | | 24 hr prior to AKI stage | | 48 hr prior to AK stage | |
|---|---|---|---|---|---|---|
| sCr only | Cohort 1 | Cohort 2 | Cohort 1 | Cohort 2 | Cohort 1 | Cohort 2 |
| Median | 72.6 | 38.1 | nd | nd | nd | nd |
| Average | 92.4 | 90.3 | nd | nd | nd | nd |
| Stdev | 79.6 | 116 | nd | nd | nd | nd |
| p(t-test) |  | 0.94 | nd | nd | nd | nd |
| Min | 0.00579 | 10.2 | nd | nd | nd | nd |
| Max | 695 | 356 | nd | nd | nd | nd |
| n (Samp) | 1336 | 8 | nd | nd | nd | nd |
| n (Patient) | 467 | 8 | nd | nd | nd | nd |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 73.2 | 33.2 | 73.2 | 43.1 | 73.2 | 82.9 |
| Average | 95.4 | 44.0 | 95.4 | 43.7 | 95.4 | 87.6 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Stdev | 82.9 | 34.2 | 82.9 | 25.8 | 82.9 | 84.0 |
| p(t-test) | | 0.021 | | 0.0068 | | 0.80 |
| Min | 0.00579 | 0.00694 | 0.00579 | 4.01 | 0.00579 | 14.3 |
| Max | 695 | 135 | 695 | 92.1 | 695 | 266 |
| n (Samp) | 1119 | 14 | 1119 | 19 | 1119 | 7 |
| n (Patient) | 362 | 14 | 362 | 19 | 362 | 7 |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.32 | 0.39 | 0.27 | 0.31 | nd | 0.28 |
| SE | 0.064 | 0.11 | 0.077 | 0.067 | nd | 0.067 |
| P | 0.0045 | 0.30 | 0.0027 | 0.0052 | nd | 8.6E−4 |
| nCohort 1 | 1272 | 1336 | 1119 | 1272 | nd | 1119 |
| nCohort 2 | 22 | 8 | 14 | 20 | nd | 19 |
| Cutoff 1 | 29.7 | 32.8 | 30.0 | 31.1 | nd | 28.3 |
| Sens 1 | 73% | 75% | 71% | 70% | nd | 74% |
| Spec 1 | 17% | 19% | 17% | 18% | nd | 16% |
| Cutoff 2 | 25.8 | 30.0 | 22.5 | 29.5 | nd | 17.0 |
| Sens 2 | 82% | 88% | 86% | 80% | nd | 84% |
| Spec 2 | 14% | 17% | 12% | 17% | nd | 9% |
| Cutoff 3 | 22.5 | 10.0 | 1.07 | 10.0 | nd | 5.43 |
| Sens 3 | 91% | 100% | 93% | 90% | nd | 95% |
| Spec 3 | 12% | 6% | 2% | 5% | nd | 3% |
| Cutoff 4 | 111 | 109 | 111 | 111 | nd | 111 |
| Sens 4 | 14% | 25% | 7% | 5% | nd | 0% |
| Spec 4 | 70% | 70% | 70% | 70% | nd | 70% |
| Cutoff 5 | 139 | 137 | 141 | 139 | nd | 141 |
| Sens 5 | 9% | 25% | 0% | 5% | nd | 0% |
| Spec 5 | 80% | 80% | 80% | 80% | nd | 80% |
| Cutoff 6 | 192 | 190 | 198 | 192 | nd | 198 |
| Sens 6 | 5% | 12% | 0% | 0% | nd | 0% |
| Spec 6 | 90% | 90% | 90% | 90% | nd | 90% |
| OR Quart 2 | 0.33 | 0 | 1.0 | 3.0 | nd | >3.0 |
| p Value | 0.34 | na | 1.00 | 0.34 | nd | <0.34 |
| 95% CI of OR Quart2 | 0.034 | na | 0.062 | 0.31 | nd | >0.31 |
| | 3.2 | na | 16 | 29 | nd | na |
| OR Quart 3 | 1.7 | 0.50 | 3.0 | 9.2 | nd | >8.2 |
| p Value | 0.48 | 0.57 | 0.34 | 0.036 | nd | <0.048 |
| 95% CI of OR Quart3 | 0.40 | 0.045 | 0.31 | 1.2 | nd | >1.0 |
| | 7.1 | 5.5 | 29 | 73 | nd | na |
| OR Quart 4 | 4.5 | 2.5 | 9.3 | 7.1 | nd | >8.3 |
| p Value | 0.020 | 0.27 | 0.035 | 0.067 | nd | <0.047 |
| 95% CI of OR Quart4 | 1.3 | 0.49 | 1.2 | 0.87 | nd | >1.0 |
| | 16 | 13 | 74 | 58 | nd | na |

| | 48 hr prior to AKI stage | | |
|---|---|---|---|
| | sCr or UO | sCr only | UO only |
| AUC | 0.41 | nd | 0.46 |
| SE | 0.095 | nd | 0.11 |
| p | 0.37 | nd | 0.71 |
| nCohort 1 | 1272 | nd | 1119 |
| nCohort 2 | 10 | nd | 7 |
| Cutoff 1 | 50.7 | nd | 50.7 |
| Sens 1 | 70% | nd | 71% |
| Spec 1 | 32% | nd | 32% |
| Cutoff 2 | 25.3 | nd | 25.3 |
| Sens 2 | 80% | nd | 86% |
| Spec 2 | 14% | nd | 14% |
| Cutoff 3 | 23.0 | nd | 14.2 |
| Sens 3 | 90% | nd | 100% |
| Spec 3 | 12% | nd | 8% |
| Cutoff 4 | 111 | nd | 111 |
| Sens 4 | 10% | nd | 14% |
| Spec 4 | 70% | nd | 70% |
| Cutoff 5 | 139 | nd | 141 |
| Sens 5 | 10% | nd | 14% |
| Spec 5 | 80% | nd | 80% |
| Cutoff 6 | 192 | nd | 198 |
| Sens 6 | 10% | nd | 14% |
| Spec 6 | 90% | nd | 90% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| OR Quart 2 | 3.0 | nd | 3.0 |
| p Value | 0.34 | nd | 0.34 |
| 95% CI of OR Quart2 | 0.31 29 | nd nd | 0.31 29 |
| OR Quart 3 | 3.0 | nd | 1.0 |
| p Value | 0.34 | nd | 1.0 |
| 95% CI of OR Quart3 | 0.31 29 | nd nd | 0.062 16 |
| OR Quart 4 | 3.0 | nd | 2.0 |
| p Value | 0.34 | nd | 0.57 |
| 95% CI of OR Quart4 | 0.31 29 | nd nd | 0.18 22 |

TABLE 10

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | C-C motif chemokine 1 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | nd | nd | 1.89 | 2.10 | nd | nd |
| Average | nd | nd | 3.61 | 2.22 | nd | nd |
| Stdev | nd | nd | 13.4 | 0.654 | nd | nd |
| p(t-test) | nd | nd | | 0.80 | nd | nd |
| Min | nd | nd | 0.00552 | 1.58 | nd | nd |
| Max | nd | nd | 212 | 3.19 | nd | nd |
| n (Samp) | nd | nd | 297 | 6 | nd | nd |
| n (Patient) | nd | nd | 166 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.56 | nd | nd |
| SE | nd | nd | nd | 0.12 | nd | nd |
| P | nd | nd | nd | 0.61 | nd | nd |
| nCohort 1 | nd | nd | nd | 297 | nd | nd |
| nCohort 2 | nd | nd | nd | 6 | nd | nd |
| Cutoff 1 | nd | nd | nd | 1.63 | nd | nd |
| Sens 1 | nd | nd | nd | 83% | nd | nd |
| Spec 1 | nd | nd | nd | 45% | nd | nd |
| Cutoff 2 | nd | nd | nd | 1.63 | nd | nd |
| Sens 2 | nd | nd | nd | 83% | nd | nd |
| Spec 2 | nd | nd | nd | 45% | nd | nd |
| Cutoff 3 | nd | nd | nd | 1.55 | nd | nd |
| Sens 3 | nd | nd | nd | 100% | nd | nd |
| Spec 3 | nd | nd | nd | 43% | nd | nd |
| Cutoff 4 | nd | nd | nd | 2.90 | nd | nd |
| Sens 4 | nd | nd | nd | 17% | nd | nd |
| Spec 4 | nd | nd | nd | 70% | nd | nd |
| Cutoff 5 | nd | nd | nd | 3.70 | nd | nd |
| Sens 5 | nd | nd | nd | 0% | nd | nd |
| Spec 5 | nd | nd | nd | 80% | nd | nd |
| Cutoff 6 | nd | nd | nd | 6.12 | nd | nd |
| Sens 6 | nd | nd | nd | 0% | nd | nd |
| Spec 6 | nd | nd | nd | 90% | nd | nd |
| OR Quart 2 | nd | nd | nd | >3.1 | nd | nd |
| p Value | nd | nd | nd | <0.33 | nd | nd |
| 95% CI of OR Quart2 | nd | nd | nd | >0.31 na | nd | nd |
| OR Quart 3 | nd | nd | nd | >3.1 | nd | nd |
| p Value | nd | nd | nd | <0.33 | nd | nd |
| 95% CI of OR Quart3 | nd | nd | nd | >0.31 na | nd | nd |
| OR Quart 4 | nd | nd | nd | >0 | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| p Value | nd | nd | nd | <na | nd | nd |
| 95% CI of | nd | nd | nd | >na | nd | nd |
| OR Quart4 | nd | nd | nd | na | nd | nd |

| | | 48 hr prior to AKI stage | | |
|---|---|---|---|---|
| | | sCr or UO | sCr only | UO only |
| | AUC | nd | nd | nd |
| | SE | nd | nd | nd |
| | P | nd | nd | nd |
| | nCohort 1 | nd | nd | nd |
| | nCohort 2 | nd | nd | nd |
| | Cutoff 1 | nd | nd | nd |
| | Sens 1 | nd | nd | nd |
| | Spec 1 | nd | nd | nd |
| | Cutoff 2 | nd | nd | nd |
| | Sens 2 | nd | nd | nd |
| | Spec 2 | nd | nd | nd |
| | Cutoff 3 | nd | nd | nd |
| | Sens 3 | nd | nd | nd |
| | Spec 3 | nd | nd | nd |
| | Cutoff 4 | nd | nd | nd |
| | Sens 4 | nd | nd | nd |
| | Spec 4 | nd | nd | nd |
| | Cutoff 5 | nd | nd | nd |
| | Sens 5 | nd | nd | nd |
| | Spec 5 | nd | nd | nd |
| | Cutoff 6 | nd | nd | nd |
| | Sens 6 | nd | nd | nd |
| | Spec 6 | nd | nd | nd |
| | OR Quart 2 | nd | nd | nd |
| | p Value | nd | nd | nd |
| | 95% CI of | nd | nd | nd |
| | OR Quart2 | nd | nd | nd |
| | OR Quart 3 | nd | nd | nd |
| | p Value | nd | nd | nd |
| | 95% CI of | nd | nd | nd |
| | OR Quart3 | nd | nd | nd |
| | OR Quart 4 | nd | nd | nd |
| | p Value | nd | nd | nd |
| | 95% CI of | nd | nd | nd |
| | OR Quart4 | nd | nd | nd |

C-C motif chemokine 17

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 18.0 | 27.5 | nd | nd |
| Average | nd | nd | 50.2 | 63.6 | nd | nd |
| Stdev | nd | nd | 110 | 103 | nd | nd |
| p(t-test) | nd | nd | | 0.77 | nd | nd |
| Min | nd | nd | 0.0212 | 0.819 | nd | nd |
| Max | nd | nd | 1010 | 273 | nd | nd |
| n (Samp) | nd | nd | 297 | 6 | nd | nd |
| n (Patient) | nd | nd | 166 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.59 | nd | nd |
| SE | nd | nd | nd | 0.12 | nd | nd |
| p | nd | nd | nd | 0.47 | nd | nd |
| nCohort 1 | nd | nd | nd | 297 | nd | nd |
| nCohort 2 | nd | nd | nd | 6 | nd | nd |
| Cutoff 1 | nd | nd | nd | 20.0 | nd | nd |
| Sens 1 | nd | nd | nd | 83% | nd | nd |
| Spec 1 | nd | nd | nd | 55% | nd | nd |
| Cutoff 2 | nd | nd | nd | 20.0 | nd | nd |
| Sens 2 | nd | nd | nd | 83% | nd | nd |
| Spec 2 | nd | nd | nd | 55% | nd | nd |
| Cutoff 3 | nd | nd | nd | 0.0212 | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Sens 3 | nd | nd | nd | 100% | nd | nd |
| Spec 3 | nd | nd | nd | 1% | nd | nd |
| Cutoff 4 | nd | nd | nd | 31.5 | nd | nd |
| Sens 4 | nd | nd | nd | 33% | nd | nd |
| Spec 4 | nd | nd | nd | 70% | nd | nd |
| Cutoff 5 | nd | nd | nd | 48.3 | nd | nd |
| Sens 5 | nd | nd | nd | 17% | nd | nd |
| Spec 5 | nd | nd | nd | 80% | nd | nd |
| Cutoff 6 | nd | nd | nd | 115 | nd | nd |
| Sens 6 | nd | nd | nd | 17% | nd | nd |
| Spec 6 | nd | nd | nd | 90% | nd | nd |
| OR Quart 2 | nd | nd | nd | 0 | nd | nd |
| p Value | nd | nd | nd | na | nd | nd |
| 95% CI of OR Quart2 | nd | nd | nd | na | nd | nd |
| | nd | nd | nd | na | nd | nd |
| OR Quart 3 | nd | nd | nd | 4.1 | nd | nd |
| p Value | nd | nd | nd | 0.21 | nd | nd |
| 95% CI of OR Quart3 | nd | nd | nd | 0.45 | nd | nd |
| | nd | nd | nd | 38 | nd | nd |
| OR Quart 4 | nd | nd | nd | 0.99 | nd | nd |
| p Value | nd | nd | nd | 0.99 | nd | nd |
| 95% CI of OR Quart4 | nd | nd | nd | 0.061 | nd | nd |
| | nd | nd | nd | 16 | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |
| OR Quart 3 | nd | nd | nd |
| p Value | nd | nd | nd |
| 95% CI of OR Quart3 | nd | nd | nd |
| OR Quart 4 | nd | nd | nd |
| p Value | nd | nd | nd |
| 95% CI of OR Quart4 | nd | nd | nd |

C-C motif chemokine 21

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 455 | 593 | nd | nd |
| Average | nd | nd | 695 | 915 | nd | nd |
| Stdev | nd | nd | 1020 | 693 | nd | nd |
| p(t-test) | nd | nd | | 0.60 | nd | nd |
| Min | nd | nd | 0.303 | 369 | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

| | | | | | | |
|---|---|---|---|---|---|---|
| Max | nd | nd | 12300 | 2060 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.66 | nd | nd |
| SE | nd | nd | nd | 0.12 | nd | nd |
| p | nd | nd | nd | 0.21 | nd | nd |
| nCohort 1 | nd | nd | nd | 298 | nd | nd |
| nCohort 2 | nd | nd | nd | 6 | nd | nd |
| Cutoff 1 | nd | nd | nd | 410 | nd | nd |
| Sens 1 | nd | nd | nd | 83% | nd | nd |
| Spec 1 | nd | nd | nd | 46% | nd | nd |
| Cutoff 2 | nd | nd | nd | 410 | nd | nd |
| Sens 2 | nd | nd | nd | 83% | nd | nd |
| Spec 2 | nd | nd | nd | 46% | nd | nd |
| Cutoff 3 | nd | nd | nd | 359 | nd | nd |
| Sens 3 | nd | nd | nd | 100% | nd | nd |
| Spec 3 | nd | nd | nd | 41% | nd | nd |
| Cutoff 4 | nd | nd | nd | 716 | nd | nd |
| Sens 4 | nd | nd | nd | 33% | nd | nd |
| Spec 4 | nd | nd | nd | 70% | nd | nd |
| Cutoff 5 | nd | nd | nd | 888 | nd | nd |
| Sens 5 | nd | nd | nd | 33% | nd | nd |
| Spec 5 | nd | nd | nd | 80% | nd | nd |
| Cutoff 6 | nd | nd | nd | 1290 | nd | nd |
| Sens 6 | nd | nd | nd | 33% | nd | nd |
| Spec 6 | nd | nd | nd | 90% | nd | nd |
| OR Quart 2 | nd | nd | nd | >2.1 | nd | nd |
| p Value | nd | nd | nd | <0.56 | nd | nd |
| 95% CI of OR Quart2 | nd | nd | nd | >0.18 na | nd | nd |
| OR Quart 3 | nd | nd | nd | >2.1 | nd | nd |
| p Value | nd | nd | nd | <0.56 | nd | nd |
| 95% CI of OR Quart3 | nd | nd | nd | >0.18 na | nd | nd |
| OR Quart 4 | nd | nd | nd | >2.1 | nd | nd |
| p Value | nd | nd | nd | <0.56 | nd | nd |
| 95% CI of OR Quart4 | nd | nd | nd | >0.18 na | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nci | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

|  |  | OR Quart 3 | nd | nd | nd |
|---|---|---|---|---|---|
|  |  | p Value | nd | nd | nd |
|  |  | 95% CI of | nd | nd | nd |
|  |  | OR Quart3 |  |  |  |
|  |  | OR Quart 4 | nd | nd | nd |
|  |  | p Value | nd | nd | nd |
|  |  | 95% CI of | nd | nd | nd |
|  |  | OR Quart4 |  |  |  |

C-C motif chemokine 27

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohor 2 | Cohort 1 | Cohort 2 |
| Median | nd | nd | 346 | 380 | nd | nd |
| Average | nd | nd | 372 | 399 | nd | nd |
| Stdev | nd | nd | 183 | 290 | nd | nd |
| p(t-test) | nd | nd |  | 0.72 | nd | nd. |
| Min | nd | nd | 29.4 | 134 | nd | nd |
| Max | nd | nd | 973 | 935 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.49 | nd | nd |
| SE | nd | nd | nd | 0.12 | nd | nd |
| p | nd | nd | nd | 0.96 | nd | nd |
| nCohort 1 | nd | nd | nd | 298 | nd | nd |
| nCohort 2 | nd | nd | nd | 6 | nd | nd |
| Cutoff 1 | nd | nd | nd | 148 | nd | nd |
| Sens 1 | nd | nd | nd | 83% | nd | nd |
| Spec 1 | nd | nd | nd | 8% | nd | nd |
| Cutoff 2 | nd | nd | nd | 148 | nd | nd |
| Sens 2 | nd | nd | nd | 83% | nd | nd |
| Spec 2 | nd | nd | nd | 8% | nd | nd |
| Cutoff 3 | nd | nd | nd | 132 | nd | nd |
| Sens 3 | nd | nd | nd | 100% | nd | nd |
| Spec 3 | nd | nd | nd | 7% | nd | nd |
| Cutoff 4 | nd | nd | nd | 450 | nd | nd |
| Sens 4 | nd | nd | nd | 17% | nd | nd |
| Spec 4 | nd | nd | nd | 70% | nd | nd |
| Cutoff 5 | nd | nd | nd | 509 | nd | nd |
| Sens 5 | nd | nd | nd | 17% | nd | nd |
| Spec 5 | nd | nd | nd | 80% | nd | nd |
| Cutoff 6 | nd | nd | nd | 620 | nd | nd |
| Sens 6 | nd | nd | nd | 17% | nd | nd |
| Spec 6 | nd | nd | nd | 90% | nd | nd |
| OR Quart 2 | nd | nd | nd | 3.1 | nd | nd |
| p Value | nd | nd | nd | 0.33 | nd | nd |
| 95% CI of OR Quart2 | nd | nd | nd | 0.31 30 | nd | nd |
| OR Quart 3 | nd | nd | nd | 0 | nd | nd |
| p Value | nd | nd | nd | na | nd | nd |
| 95% CI of OR Quart3 | nd | nd | nd | na na | nd | nd |
| OR Quart 4 | nd | nd | nd | 2.0 | nd | nd |
| p Value | nd | nd | nd | 0.57 | nd | nd |
| 95% CI of OR Quart4 | nd | nd | nd | 0.18 23 | nd | nd |

|  | 48 hr prior to AKI stage | | |
|---|---|---|---|
|  | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

|  | Spec 1 | nd | nd | nd |
|---|---|---|---|---|
|  | Cutoff 2 | nd | nd | nd |
|  | Sens 2 | nd | nd | nd |
|  | Spec 2 | nd | nd | nd |
|  | Cutoff 3 | nd | nd | nd |
|  | Sens 3 | nd | nd | nd |
|  | Spec 3 | nd | nd | nd |
|  | Cutoff 4 | nd | nd | nd |
|  | Sens 4 | nd | nd | nd |
|  | Spec 4 | nd | nd | nd |
|  | Cutoff 5 | nd | nd | nd |
|  | Sens 5 | nd | nd | nd |
|  | Spec 5 | nd | nd | nd |
|  | Cutoff 6 | nd | nd | nd |
|  | Sens 6 | nd | nd | nd |
|  | Spec 6 | nd | nd | nd |
|  | OR Quart 2 | nd | nd | nd |
|  | p Value | nd | nd | nd |
|  | 95% CI of OR Quart2 | nd | nd | nd |
|  | OR Quart 3 | nd | nd | nd |
|  | p Value | nd | nd | nd |
|  | 95% CI of OR Quart3 | nd | nd | nd |
|  | OR Quart 4 | nd | nd | nd |
|  | p Value | nd | nd | nd |
|  | 95% CI of OR Quart4 | nd | nd | nd |

Vascular endothelial growth factor receptor 1

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 750 | 1910 | nd | nd |
| Average | nd | nd | 1340 | 3420 | nd | nd |
| Stdev | nd | nd | 3280 | 3720 | nd | nd |
| p(t-test) | nd | nd |  | 0.13 | nd | nd |
| Min | nd | nd | 73.4 | 166 | nd | nd |
| Max | nd | nd | 50500 | 9150 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.66 | nd | nd |
| SE | nd | nd | nd | 0.12 | nd | nd |
| P | nd | nd | nd | 0.18 | nd | nd |
| nCohort 1 | nd | nd | nd | 298 | nd | nd |
| nCohort 2 | nd | nd | nd | 6 | nd | nd |
| Cutoff 1 | nd | nd | nd | 455 | nd | nd |
| Sens 1 | nd | nd | nd | 83% | nd | nd |
| Spec 1 | nd | nd | nd | 28% | nd | nd |
| Cutoff 2 | nd | nd | nd | 455 | nd | nd |
| Sens 2 | nd | nd | nd | 83% | nd | nd |
| Spec 2 | nd | nd | nd | 28% | nd | nd |
| Cutoff 3 | nd | nd | nd | 162 | nd | nd |
| Sens 3 | nd | nd | nd | 100% | nd | nd |
| Spec 3 | nd | nd | nd | 2% | nd | nd |
| Cutoff 4 | nd | nd | nd | 1120 | nd | nd |
| Sens 4 | nd | nd | nd | 67% | nd | nd |
| Spec 4 | nd | nd | nd | 70% | nd | nd |
| Cutoff 5 | nd | nd | nd | 1460 | nd | nd |
| Sens 5 | nd | nd | nd | 67% | nd | nd |
| Spec 5 | nd | nd | nd | 80% | nd | nd |
| Cutoff 6 | nd | nd | nd | 2390 | nd | nd |
| Sens 6 | nd | nd | nd | 33% | nd | nd |
| Spec 6 | nd | nd | nd | 90% | nd | nd |
| OR Quart 2 | nd | nd | nd | 1.0 | nd | nd |
| p Value | nd | nd | nd | 1.0 | nd | nd |
| 95% CI of OR Quart2 | nd | nd | nd | 0.061 16 | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

| | | | | | | |
|---|---|---|---|---|---|---|
| OR Quart 3 | nd | nd | nd | 0 | nd | nd |
| p Value | nd | nd | nd | na | nd | nd |
| 95% CI of | nd | nd | nd | na | nd | nd |
| OR Quart3 | nd | nd | nd | na | nd | nd |
| OR Quart 4 | nd | nd | nd | 4.2 | nd | nd |
| p Value | nd | nd | nd | 0.21 | nd | nd |
| 95% CI of | nd | nd | nd | 0.45 | nd | nd |
| OR Quart4 | nd | nd | nd | 38 | nd | nd |

| | | 48 hr prior to AKI stage | | |
|---|---|---|---|---|
| | | sCr or UO | sCr only | UO only |
| | AUC | nd | nd | nd |
| | SE | nd | nd | nd |
| | P | nd | nd | nd |
| | nCohort 1 | nd | nd | nd |
| | nCohort 2 | nd | nd | nd |
| | Cutoff 1 | nd | nd | nd |
| | Sens 1 | nd | nd | nd |
| | Spec 1 | nd | nd | nd |
| | Cutoff 2 | nd | nd | nd |
| | Sens 2 | nd | nd | nd |
| | Spec 2 | nd | nd | nd |
| | Cutoff 3 | nd | nd | nd |
| | Sens 3 | nd | nd | nd |
| | Spec 3 | nd | nd | nd |
| | Cutoff 4 | nd | nd | nd |
| | Sens 4 | nd | nd | nd |
| | Spec 4 | nd | nd | nd |
| | Cutoff 5 | nd | nd | nd |
| | Sens 5 | nd | nd | nd |
| | Spec 5 | nd | nd | nd |
| | Cutoff 6 | nd | nd | nd |
| | Sens 6 | nd | nd | nd |
| | Spec 6 | nd | nd | nd |
| | OR Quart 2 | nd | nd | nd |
| | p Value | nd | nd | nd |
| | 95% CI of | nd | nd | nd |
| | OR Quart2 | nd | nd | nd |
| | OR Quart 3 | nd | nd | nd |
| | p Value | nd | nd | nd |
| | 95% CI of | nd | nd | nd |
| | OR Quart3 | nd | nd | nd |
| | OR Quart 4 | nd | nd | nd |
| | p Value | nd | nd | nd |
| | 95% CI of | nd | nd | nd |
| | OR Quart4 | nd | nd | nd |

SL cytokine

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 0.0548 | 0.114 | nd | nd |
| Average | nd | nd | 7.42 | 0.946 | nd | nd |
| Stdev | nd | nd | 33.7 | 2.11 | nd | nd |
| p(t-test) | nd | nd | | 0.64 | nd | nd |
| Min | nd | nd | 0.0206 | 0.0206 | nd | nd |
| Max | nd | nd | 400 | 5.26 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.62 | nd | nd |
| SE | nd | nd | nd | 0.12 | nd | nd |
| p | nd | nd | nd | 0.34 | nd | nd |
| nCohort 1 | nd | nd | nd | 298 | nd | nd |
| nCohort 2 | nd | nd | nd | 6 | nd | nd |
| Cutoff 1 | nd | nd | nd | 0.0486 | nd | nd |
| Sens 1 | nd | nd | nd | 83% | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| Spec 1 | nd | nd | nd | 38% | nd | nd |
| Cutoff 2 | nd | nd | nd | 0.0486 | nd | nd |
| Sens 2 | nd | nd | nd | 83% | nd | nd |
| Spec 2 | nd | nd | nd | 38% | nd | nd |
| Cutoff 3 | nd | nd | nd | 0 | nd | nd |
| Sens 3 | nd | nd | nd | 100% | nd | nd |
| Spec 3 | nd | nd | nd | 0% | nd | nd |
| Cutoff 4 | nd | nd | nd | 0.0696 | nd | nd |
| Sens 4 | nd | nd | nd | 67% | nd | nd |
| Spec 4 | nd | nd | nd | 70% | nd | nd |
| Cutoff 5 | nd | nd | nd | 0.114 | nd | nd |
| Sens 5 | nd | nd | nd | 17% | nd | nd |
| Spec 5 | nd | nd | nd | 83% | nd | nd |
| Cutoff 6 | nd | nd | nd | 15.7 | nd | nd |
| Sens 6 | nd | nd | nd | 0% | nd | nd |
| Spec 6 | nd | nd | nd | 90% | nd | nd |
| OR Quart 2 | nd | nd | nd | 0 | nd | nd |
| p Value | nd | nd | nd | na | nd | nd |
| 95% CI of OR Quart2 | nd | nd | nd | na | nd | nd |
| OR Quart 3 | nd | nd | nd | 2.0 | nd | nd |
| p Value | nd | nd | nd | 0.57 | nd | nd |
| 95% CI of OR Quart3 | nd | nd | nd | 0.18 23 | nd | nd |
| OR Quart 4 | nd | nd | nd | 3.1 | nd | nd |
| p Value | nd | nd | nd | 0.33 | nd | nd |
| 95% CI of OR Quart4 | nd | nd | nd | 0.31 30 | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |
| OR Quart 3 | nd | nd | nd |
| p Value | nd | nd | nd |
| 95% CI of OR Quart3 | nd | nd | nd |
| OR Quart 4 | nd | nd | nd |
| p Value | nd | nd | nd |
| 95% CI of OR Quart4 | nd | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

Interleukin-1 receptor type I

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 62.2 | 65.7 | nd | nd |
| Average | nd | nd | 71.1 | 72.1 | nd | nd |
| Stdev | nd | nd | 46.3 | 26.9 | nd | nd |
| p(t-test) | nd | nd | | 0.96 | nd | nd |
| Min | nd | nd | 25.4 | 45.7 | nd | nd |
| Max | nd | nd | 502 | 123 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.57 | nd | nd |
| SE | nd | nd | nd | 0.12 | nd | nd |
| p | nd | nd | nd | 0.60 | nd | nd |
| nCohort 1 | nd | nd | nd | 298 | nd | nd |
| nCohort 2 | nd | nd | nd | 6 | nd | nd |
| Cutoff 1 | nd | nd | nd | 56.2 | nd | nd |
| Sens 1 | nd | nd | nd | 83% | nd | nd |
| Spec 1 | nd | nd | nd | 39% | nd | nd |
| Cutoff 2 | nd | nd | nd | 56.2 | nd | nd |
| Sens 2 | nd | nd | nd | 83% | nd | nd |
| Spec 2 | nd | nd | nd | 39% | nd | nd |
| Cutoff 3 | nd | nd | nd | 45.5 | nd | nd |
| Sens 3 | nd | nd | nd | 100% | nd | nd |
| Spec 3 | nd | nd | nd | 17% | nd | nd |
| Cutoff 4 | nd | nd | nd | 72.5 | nd | nd |
| Sens 4 | nd | nd | nd | 33% | nd | nd |
| Spec 4 | nd | nd | nd | 70% | nd | nd |
| Cutoff 5 | nd | nd | nd | 84.6 | nd | nd |
| Sens 5 | nd | nd | nd | 17% | nd | nd |
| Spec 5 | nd | nd | nd | 80% | nd | nd |
| Cutoff 6 | nd | nd | nd | 96.4 | nd | nd |
| Sens 6 | nd | nd | nd | 17% | nd | nd |
| Spec 6 | nd | nd | nd | 90% | nd | nd |
| OR Quart 2 | nd | nd | nd | 1.0 | nd | nd |
| p Value | nd | nd | nd | 1.0 | nd | nd |
| 95% CI of OR Quart2 | nd | nd | nd | 0.061 16 | nd | nd |
| OR Quart 3 | nd | nd | nd | 3.1 | nd | nd |
| p Value | nd | nd | nd | 0.33 | nd | nd |
| 95% CI of OR Quart3 | nd | nd | nd | 0.31 30 | nd | nd |
| OR Quart 4 | nd | nd | nd | 1.0 | nd | nd |
| p Value | nd | nd | nd | 1.0 | nd | nd |
| 95% CI of OR Quart4 | nd | nd | nd | 0.061 16 | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

|  | Spec 4 | nd | nd | nd |
|---|---|---|---|---|
|  | Cutoff 5 | nd | nd | nd |
|  | Sens 5 | nd | nd | nd |
|  | Spec 5 | nd | nd | nd |
|  | Cutoff 6 | nd | nd | nd |
|  | Sens 6 | nd | nd | nd |
|  | Spec 6 | nd | nd | nd |
|  | OR Quart 2 | nd | nd | nd |
|  | p Value | nd | nd | nd |
|  | 95% CI of OR Quart2 | nd | nd | nd |
|  | OR Quart 3 | nd | nd | nd |
|  | p Value | nd | nd | nd |
|  | 95% CI of OR Quart3 | nd | nd | nd |
|  | OR Quart 4 | nd | nd | nd |
|  | p Value | nd | nd | nd |
|  | 95% CI of OR Quart4 | nd | nd | nd |

Interleukin-20

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 5.54 | 12.1 | nd | nd |
| Average | nd | nd | 92.9 | 36.0 | nd | nd |
| Stdev | nd | nd | 516 | 42.6 | nd | nd |
| p(t-test) | nd | nd |  | 0.79 | nd | nd |
| Min | nd | nd | 0.990 | 0.990 | nd | nd |
| Max | nd | nd | 8230 | 104 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.56 | nd | nd |
| SE | nd | nd | nd | 0.12 | nd | nd |
| p | nd | nd | nd | 0.61 | nd | nd |
| nCohort 1 | nd | nd | nd | 298 | nd | nd |
| nCohort 2 | nd | nd | nd | 6 | nd | nd |
| Cutoff 1 | nd | nd | nd | 6.98 | nd | nd |
| Sens 1 | nd | nd | nd | 83% | nd | nd |
| Spec 1 | nd | nd | nd | 52% | nd | nd |
| Cutoff 2 | nd | nd | nd | 6.98 | nd | nd |
| Sens 2 | nd | nd | nd | 83% | nd | nd |
| Spec 2 | nd | nd | nd | 52% | nd | nd |
| Cutoff 3 | nd | nd | nd | 0 | nd | nd |
| Sens 3 | nd | nd | nd | 100% | nd | nd |
| Spec 3 | nd | nd | nd | 0% | nd | nd |
| Cutoff 4 | nd | nd | nd | 50.0 | nd | nd |
| Sens 4 | nd | nd | nd | 33% | nd | nd |
| Spec 4 | nd | nd | nd | 70% | nd | nd |
| Cutoff 5 | nd | nd | nd | 99.9 | nd | nd |
| Sens 5 | nd | nd | nd | 17% | nd | nd |
| Spec 5 | nd | nd | nd | 81% | nd | nd |
| Cutoff 6 | nd | nd | nd | 171 | nd | nd |
| Sens 6 | nd | nd | nd | 0% | nd | nd |
| Spec 6 | nd | nd | nd | 90% | nd | nd |
| OR Quart 2 | nd | nd | nd | 0 | nd | nd |
| p Value | nd | nd | nd | na | nd | nd |
| 95% CI of OR Quart2 | nd | nd | nd | na | nd | nd |
| OR Quart 3 | nd | nd | nd | 4.2 | nd | nd |
| p Value | nd | nd | nd | 0.21 | nd | nd |
| 95% CI of OR Quart3 | nd | nd | nd | 0.45 | nd | nd |
| OR Quart 4 | nd | nd | nd | 1.0 | nd | nd |
| p Value | nd | nd | nd | 1.0 | nd | nd |
| 95% CI of OR Quart4 | nd | nd | nd | 0.061 | nd | nd |
|  | nd | nd | nd | 16 | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

|  | 48 hr prior to AKI stage | | |
|---|---|---|---|
|  | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |
| OR Quart 3 | nd | nd | nd |
| p Value | nd | nd | nd |
| 95% CI of OR Quart3 | nd | nd | nd |
| OR Quart 4 | nd | nd | nd |
| p Value | nd | nd | nd |
| 95% CI of OR Quart4 | nd | nd | nd |

Interleukin-29

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 49.5 | 56.0 | nd | nd |
| Average | nd | nd | 153 | 113 | nd | nd |
| Stdev | nd | nd | 774 | 169 | nd | nd |
| p(t-test) | nd | nd |  | 0.90 | nd | nd |
| Min | nd | nd | 0.690 | 0.690 | nd | nd |
| Max | nd | nd | 10500 | 453 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.55 | nd | nd |
| SE | nd | nd | nd | 0.12 | nd | nd |
| p | nd | nd | nd | 0.71 | nd | nd |
| nCohort 1 | nd | nd | nd | 298 | nd | nd |
| nCohort 2 | nd | nd | nd | 6 | nd | nd |
| Cutoff 1 | nd | nd | nd | 15.6 | nd | nd |
| Sens 1 | nd | nd | nd | 83% | nd | nd |
| Spec 1 | nd | nd | nd | 40% | nd | nd |
| Cutoff 2 | nd | nd | nd | 15.6 | nd | nd |
| Sens 2 | nd | nd | nd | 83% | nd | nd |
| Spec 2 | nd | nd | nd | 40% | nd | nd |
| Cutoff 3 | nd | nd | nd | 0 | nd | nd |
| Sens 3 | nd | nd | nd | 100% | nd | nd |
| Spec 3 | nd | nd | nd | 0% | nd | nd |
| Cutoff 4 | nd | nd | nd | 80.9 | nd | nd |
| Sens 4 | nd | nd | nd | 33% | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

| | | | | | | |
|---|---|---|---|---|---|---|
| Spec 4 | nd | nd | nd | 71% | nd | nd |
| Cutoff 5 | nd | nd | nd | 119 | nd | nd |
| Sens 5 | nd | nd | nd | 17% | nd | nd |
| Spec 5 | nd | nd | nd | 81% | nd | nd |
| Cutoff 6 | nd | nd | nd | 185 | nd | nd |
| Sens 6 | nd | nd | nd | 17% | nd | nd |
| Spec 6 | nd | nd | nd | 90% | nd | nd |
| OR Quart 2 | nd | nd | nd | 1.0 | nd | nd |
| p Value | nd | nd | nd | 1.0 | nd | nd |
| 95% CI of | nd | nd | nd | 0.061 | nd | nd |
| OR Quart2 | nd | nd | nd | 16 | nd | nd |
| OR Quart 3 | nd | nd | nd | 3.1 | nd | nd |
| p Value | nd | nd | nd | 0.33 | nd | nd |
| 95% CI of | nd | nd | nd | 0.31 | nd | nd |
| OR Quart3 | nd | nd | nd | 30 | nd | nd |
| OR Quart 4 | nd | nd | nd | 1.0 | nd | nd |
| p Value | nd | nd | nd | 1.0 | nd | nd |
| 95% CI of | nd | nd | nd | 0.061 | nd | nd |
| OR Quart4 | nd | nd | nd | 16 | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of | nd | nd | nd |
| OR Quart2 | nd | nd | nd |
| OR Quart 3 | nd | nd | nd |
| p Value | nd | nd | nd |
| 95% CI of | nd | nd | nd |
| OR Quart3 | nd | nd | nd |
| OR Quart 4 | nd | nd | nd |
| p Value | nd | nd | nd |
| 95% CI of | nd | nd | nd |
| OR Quart4 | nd | nd | nd |

| | Interleukin-7 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | nd | nd | 0.0297 | 4.21 | nd | nd |
| Average | nd | nd | 4.02 | 4.48 | nd | nd |
| Stdev | nd | nd | 15.7 | 4.21 | nd | nd |
| p(t-test) | nd | nd | | 0.94 | nd | nd |
| Min | nd | nd | 0.00806 | 0.0293 | nd | nd |
| Max | nd | nd | 153 | 10.0 | nd | nd |
| n (Samp) | nd | nd | 298 | 6 | nd | nd |
| n (Patient) | nd | nd | 167 | 6 | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.73 | nd | nd |
| SE | nd | nd | nd | 0.12 | nd | nd |
| p | nd | nd | nd | 0.052 | nd | nd |
| nCohort 1 | nd | nd | nd | 298 | nd | nd |
| nCohort 2 | nd | nd | nd | 6 | nd | nd |
| Cutoff 1 | nd | nd | nd | 0.0245 | nd | nd |
| Sens 1 | nd | nd | nd | 100% | nd | nd |
| Spec 1 | nd | nd | nd | 43% | nd | nd |
| Cutoff 2 | nd | nd | nd | 0.0245 | nd | nd |
| Sens 2 | nd | nd | nd | 100% | nd | nd |
| Spec 2 | nd | nd | nd | 43% | nd | nd |
| Cutoff 3 | nd | nd | nd | 0.0245 | nd | nd |
| Sens 3 | nd | nd | nd | 100% | nd | nd |
| Spec 3 | nd | nd | nd | 43% | nd | nd |
| Cutoff 4 | nd | nd | nd | 2.44 | nd | nd |
| Sens 4 | nd | nd | nd | 67% | nd | nd |
| Spec 4 | nd | nd | nd | 70% | nd | nd |
| Cutoff 5 | nd | nd | nd | 3.90 | nd | nd |
| Sens 5 | nd | nd | nd | 50% | nd | nd |
| Spec 5 | nd | nd | nd | 80% | nd | nd |
| Cutoff 6 | nd | nd | nd | 7.46 | nd | nd |
| Sens 6 | nd | nd | nd | 33% | nd | nd |
| Spec 6 | nd | nd | nd | 90% | nd | nd |
| OR Quart 2 | nd | nd | nd | >2.1 | nd | nd |
| p Value | nd | nd | nd | <0.56 | nd | nd |
| 95% CI of OR Quart2 | nd | nd | nd | >0.18 | nd | nd |
|  | nd | nd | nd | na | nd | nd |
| OR Quart 3 | nd | nd | nd | >1.0 | nd | nd |
| p Value | nd | nd | nd | <0.99 | nd | nd |
| 95% CI of OR Quart3 | nd | nd | nd | >0.062 | nd | nd |
|  | nd | nd | nd | na | nd | nd |
| OR Quart 4 | nd | nd | nd | >3.1 | nd | nd |
| p Value | nd | nd | nd | <0.33 | nd | nd |
| 95% CI of OR Quart4 | nd | nd | nd | >0.32 | nd | nd |
|  | nd | nd | nd | na | nd | nd |

|  | 48 hr prior to AKI stage | | |
|---|---|---|---|
|  | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |
| OR Quart 3 | nd | nd | nd |
| p Value | nd | nd | nd |
| 95% CI of OR Quart3 | nd | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

|  | OR Quart 4 | nd | nd | nd |
|---|---|---|---|---|
|  | p Value | nd | nd | nd |
|  | 95% CI of | nd | nd | nd |
|  | OR Quart4 | nd | nd | nd |

Platelet-derived growth factor subunit A (dimer)

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 1240 | 2840 | nd | nd |
| Average | nd | nd | 2630 | 3320 | nd | nd |
| Stdev | nd | nd | 4060 | 2530 | nd | nd |
| p(t-test) | nd | nd |  | 0.68 | nd | nd |
| Min | nd | nd | 0.268 | 810 | nd | nd |
| Max | nd | nd | 51400 | 7610 | nd | nd |
| n (Samp) | nd | nd | 366 | 6 | nd | nd |
| n (Patient) | nd | nd | 196 | 6 | nd | nd |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | nd | nd | nd | 0.67 | nd | nd |
| SE | nd | nd | nd | 0.12 | nd | nd |
| P | nd | nd | nd | 0.16 | nd | nd |
| nCohort 1 | nd | nd | nd | 366 | nd | nd |
| nCohort 2 | nd | nd | nd | 6 | nd | nd |
| Cutoff 1 | nd | nd | nd | 1120 | nd | nd |
| Sens 1 | nd | nd | nd | 83% | nd | nd |
| Spec 1 | nd | nd | nd | 48% | nd | nd |
| Cutoff 2 | nd | nd | nd | 1120 | nd | nd |
| Sens 2 | nd | nd | nd | 83% | nd | nd |
| Spec 2 | nd | nd | nd | 48% | nd | nd |
| Cutoff 3 | nd | nd | nd | 800 | nd | nd |
| Sens 3 | nd | nd | nd | 100% | nd | nd |
| Spec 3 | nd | nd | nd | 43% | nd | nd |
| Cutoff 4 | nd | nd | nd | 2830 | nd | nd |
| Sens 4 | nd | nd | nd | 50% | nd | nd |
| Spec 4 | nd | nd | nd | 70% | nd | nd |
| Cutoff 5 | nd | nd | nd | 4530 | nd | nd |
| Sens 5 | nd | nd | nd | 33% | nd | nd |
| Spec 5 | nd | nd | nd | 80% | nd | nd |
| Cutoff 6 | nd | nd | nd | 6930 | nd | nd |
| Sens 6 | nd | nd | nd | 17% | nd | nd |
| Spec 6 | nd | nd | nd | 90% | nd | nd |
| OR Quart 2 | nd | nd | nd | >2.0 | nd | nd |
| p Value | nd | nd | nd | <0.56 | nd | nd |
| 95% CI of | nd | nd | nd | >0.18 | nd | nd |
| OR Quart2 | nd | nd | nd | na | nd | nd |
| OR Quart 3 | nd | nd | nd | >2.0 | nd | nd |
| p Value | nd | nd | nd | <0.56 | nd | nd |
| 95% CI of | nd | nd | nd | >0.18 | nd | nd |
| OR Quart3 | nd | nd | nd | na | nd | nd |
| OR Quart 4 | nd | nd | nd | >2.0 | nd | nd |
| p Value | nd | nd | nd | <0.56 | nd | nd |
| 95% CI of | nd | nd | nd | >0.18 | nd | nd |
| OR Quart4 | nd | nd | nd | na | nd | nd |

|  | 48 hr prior to AKI stage | | |
|---|---|---|---|
|  | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

|  |  |  |  |
|---|---|---|---|
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of OR Quart2 | nd | nd | nd |
| OR Quart 3 | nd | nd | nd |
| p Value | nd | nd | nd |
| 95% CI of OR Quart3 | nd | nd | nd |
| OR Quart 4 | nd | nd | nd |
| p Value | nd | nd | nd |
| 95% CI of OR Quart4 | nd | nd | nd |

Platelet-derived growth factor A

|  | 0 hr prior to AKI stage | | 24 hr prior to AKI stage | | 48hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 4120 | 6700 | nd | nd |
| Average | nd | nd | 9280 | 32200 | nd | nd |
| Stdev | nd | nd | 14900 | 57600 | nd | nd |
| p(t-test) | nd | nd |  | 6.6E−4 | nd | nd |
| Min | nd | nd | 1.99 | 1110 | nd | nd |
| Max | nd | nd | 170000 | 148000 | nd | nd |
| n (Samp) | nd | nd | 366 | 6 | nd | nd |
| n (Patient) | nd | nd | 196 | 6 | nd | nd |

|  | 0 hr prior to AKI stage | | | 24 hr prior to AKI stage | | |
|---|---|---|---|---|---|---|
| sCr or UO | sCr or UO | sCr only | UO only | sCr or UO | sCr only | UO only |
| AUC | nd | nd | nd | 0.64 | nd | nd |
| SE | nd | nd | nd | 0.12 | nd | nd |
| p | nd | nd | nd | 0.24 | nd | nd |
| nCohort 1 | nd | nd | nd | 366 | nd | nd |
| nCohort 2 | nd | nd | nd | 6 | nd | nd |
| Cutoff 1 | nd | nd | nd | 3820 | nd | nd |
| Sens 1 | nd | nd | nd | 83% | nd | nd |
| Spec 1 | nd | nd | nd | 48% | nd | nd |
| Cutoff 2 | nd | nd | nd | 3820 | nd | nd |
| Sens 2 | nd | nd | nd | 83% | nd | nd |
| Spec 2 | nd | nd | nd | 48% | nd | nd |
| Cutoff 3 | nd | nd | nd | 1080 | nd | nd |
| Sens 3 | nd | nd | nd | 100% | nd | nd |
| Spec 3 | nd | nd | nd | 23% | nd | nd |
| Cutoff 4 | nd | nd | nd | 9400 | nd | nd |
| Sens 4 | nd | nd | nd | 33% | nd | nd |
| Spec 4 | nd | nd | nd | 70% | nd | nd |
| Cutoff 5 | nd | nd | nd | 14200 | nd | nd |
| Sens 5 | nd | nd | nd | 33% | nd | nd |
| Spec 5 | nd | nd | nd | 80% | nd | nd |
| Cutoff 6 | nd | nd | nd | 23800 | nd | nd |
| Sens 6 | nd | nd | nd | 33% | nd | nd |
| Spec 6 | nd | nd | nd | 90% | nd | nd |
| OR Quart 2 | nd | nd | nd | 1.0 | nd | nd |
| p Value | nd | nd | nd | 1.0 | nd | nd |
| 95% CI of OR Quart2 | nd | nd | nd | 0.062 16 | nd | nd |
| OR Quart 3 | nd | nd | nd | 2.0 | nd | nd |
| p Value | nd | nd | nd | 0.57 | nd | nd |
| 95% CI of OR Quart3 | nd | nd | nd | 0.18 23 | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | |
|---|---|---|---|---|---|---|
| OR Quart 4 | nd | nd | nd | 2.0 | nd | nd |
| p Value | nd | nd | nd | 0.57 | nd | nd |
| 95% CI of | nd | nd | nd | 0.18 | nd | nd |
| OR Quart4 | nd | nd | nd | 23 | nd | nd |

| | | 48 hr prior to AKI stage | | |
|---|---|---|---|---|
| | | sCr or UO | sCr only | UO only |
| | AUC | nd | nd | nd |
| | SE | nd | nd | nd |
| | P | nd | nd | nd |
| | nCohort 1 | nd | nd | nd |
| | nCohort 2 | nd | nd | nd |
| | Cutoff 1 | nd | nd | nd |
| | Sens 1 | nd | nd | nd |
| | Spec 1 | nd | nd | nd |
| | Cutoff 2 | nd | nd | nd |
| | Sens 2 | nd | nd | nd |
| | Spec 2 | nd | nd | nd |
| | Cutoff 3 | nd | nd | nd |
| | Sens 3 | nd | nd | nd |
| | Spec 3 | nd | nd | nd |
| | Cutoff 4 | nd | nd | nd |
| | Sens 4 | nd | nd | nd |
| | Spec 4 | nd | nd | nd |
| | Cutoff 5 | nd | nd | nd |
| | Sens 5 | nd | nd | nd |
| | Spec 5 | nd | nd | nd |
| | Cutoff 6 | nd | nd | nd |
| | Sens 6 | nd | nd | nd |
| | Spec 6 | nd | nd | nd |
| | OR Quart 2 | nd | nd | nd |
| | p Value | nd | nd | nd |
| | 95% CI of | nd | nd | nd |
| | OR Quart2 | nd | nd | nd |
| | OR Quart 3 | nd | nd | nd |
| | p Value | nd | nd | nd |
| | 95% CI of | nd | nd | nd |
| | OR Quart3 | nd | nd | nd |
| | OR Quart 4 | nd | nd | nd |
| | p Value | nd | nd | nd |
| | 95% CI of | nd | nd | nd |
| | OR Quart4 | nd | nd | nd |

Thymic stromal lymphopoietin

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 0.0181 | 2.02 | nd | nd |
| Average | nd | nd | 172 | 23.6 | nd | nd |
| Stdev | nd | nd | 1650 | 53.7 | nd | nd |
| p(t-test) | nd | nd | | 0.83 | nd | nd |
| Min | nd | nd | 0.00640 | 0.0129 | nd | nd |
| Max | nd | nd | 20000 | 133 | nd | nd |
| n (Samp) | nd | nd | 297 | 6 | nd | nd |
| n (Patient) | nd | nd | 166 | 6 | nd | nd |

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | nd | nd | nd | 0.58 | nd | nd |
| SE | nd | nd | nd | 0.12 | nd | nd |
| P | nd | nd | nd | 0.52 | nd | nd |
| nCohort 1 | nd | nd | nd | 297 | nd | nd |
| nCohort 2 | nd | nd | nd | 6 | nd | nd |
| Cutoff 1 | nd | nd | nd | 0.0150 | nd | nd |
| Sens 1 | nd | nd | nd | 83% | nd | nd |
| Spec 1 | nd | nd | nd | 32% | nd | nd |
| Cutoff 2 | nd | nd | nd | 0.0150 | nd | nd |
| Sens 2 | nd | nd | nd | 83% | nd | nd |
| Spec 2 | nd | nd | nd | 32% | nd | nd |

TABLE 10-continued

Comparison of marker levels in EDTA samples collected from
Cohort 1 (patients that did not progress beyond RIFLE stage 0, R, or I) and in EDTA
samples collected from Cohort 2 (subjects who progress to RIFLE stage F) at 0, 24 hours,
and 48 hours prior to the subject reaching RIFLE stage I.

| | | | | | | |
|---|---|---|---|---|---|---|
| Cutoff 3 | nd | nd | nd | 0.0123 | nd | nd |
| Sens 3 | nd | nd | nd | 100% | nd | nd |
| Spec 3 | nd | nd | nd | 13% | nd | nd |
| Cutoff 4 | nd | nd | nd | 3.32 | nd | nd |
| Sens 4 | nd | nd | nd | 50% | nd | nd |
| Spec 4 | nd | nd | nd | 70% | nd | nd |
| Cutoff 5 | nd | nd | nd | 6.16 | nd | nd |
| Sens 5 | nd | nd | nd | 17% | nd | nd |
| Spec 5 | nd | nd | nd | 80% | nd | nd |
| Cutoff 6 | nd | nd | nd | 19.4 | nd | nd |
| Sens 6 | nd | nd | nd | 17% | nd | nd |
| Spec 6 | nd | nd | nd | 90% | nd | nd |
| OR Quart 2 | nd | nd | nd | 0.99 | nd | nd |
| p Value | nd | nd | nd | 0.99 | nd | nd |
| 95% CI of | nd | nd | nd | 0.061 | nd | nd |
| OR Quart2 | nd | nd | nd | 16 | nd | nd |
| OR Quart 3 | nd | nd | nd | 3.0 | nd | nd |
| p Value | nd | nd | nd | 0.34 | nd | nd |
| 95% CI of | nd | nd | nd | 0.31 | nd | nd |
| OR Quart3 | nd | nd | nd | 30 | nd | nd |
| OR Quart 4 | nd | nd | nd | 0.99 | nd | nd |
| p Value | nd | nd | nd | 0.99 | nd | nd |
| 95% CI of | nd | nd | nd | 0.061 | nd | nd |
| OR Quart4 | nd | nd | nd | 16 | nd | nd |

| | 48 hr prior to AKI stage | | |
|---|---|---|---|
| | sCr or UO | sCr only | UO only |
| AUC | nd | nd | nd |
| SE | nd | nd | nd |
| P | nd | nd | nd |
| nCohort 1 | nd | nd | nd |
| nCohort 2 | nd | nd | nd |
| Cutoff 1 | nd | nd | nd |
| Sens 1 | nd | nd | nd |
| Spec 1 | nd | nd | nd |
| Cutoff 2 | nd | nd | nd |
| Sens 2 | nd | nd | nd |
| Spec 2 | nd | nd | nd |
| Cutoff 3 | nd | nd | nd |
| Sens 3 | nd | nd | nd |
| Spec 3 | nd | nd | nd |
| Cutoff 4 | nd | nd | nd |
| Sens 4 | nd | nd | nd |
| Spec 4 | nd | nd | nd |
| Cutoff 5 | nd | nd | nd |
| Sens 5 | nd | nd | nd |
| Spec 5 | nd | nd | nd |
| Cutoff 6 | nd | nd | nd |
| Sens 6 | nd | nd | nd |
| Spec 6 | nd | nd | nd |
| OR Quart 2 | nd | nd | nd |
| p Value | nd | nd | nd |
| 95% CI of | nd | nd | nd |
| OR Quart2 | nd | nd | nd |
| OR Quart 3 | nd | nd | nd |
| p Value | nd | nd | nd |
| 95% CI of | nd | nd | nd |
| OR Quart3 | nd | nd | nd |
| OR Quart 4 | nd | nd | nd |
| p Value | nd | nd | nd |
| 95% CI of | nd | nd | nd |
| OR Quart4 | nd | nd | nd |

TABLE 11

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | C-C motif chemokine 1 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0132 | 0.0141 | 0.0140 | 0.0163 | 0.0140 | 0.0141 |
| Average | 1.38 | 2.46 | 1.38 | 6.11 | 1.82 | 2.56 |
| Stdev | 13.1 | 7.49 | 12.2 | 13.3 | 14.9 | 7.83 |
| p(t-test) | | 0.45 | | 0.093 | | 0.67 |
| Min | 0.00501 | 0.00501 | 0.00501 | 0.00547 | 0.00501 | 0.00501 |
| Max | 228 | 49.3 | 228 | 49.3 | 228 | 49.3 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.59 | 0.60 | 0.57 |
| SE | 0.034 | 0.068 | 0.037 |
| p | 0.0087 | 0.15 | 0.044 |
| nCohort 1 | 383 | 451 | 297 |
| nCohort 2 | 92 | 20 | 79 |
| Cutoff 1 | 0.0112 | 0.0105 | 0.0114 |
| Sens 1 | 72% | 75% | 71% |
| Spec 1 | 42% | 33% | 39% |
| Cutoff 2 | 0.00908 | 0.00908 | 0.00851 |
| Sens 2 | 82% | 85% | 81% |
| Spec 2 | 20% | 20% | 18% |
| Cutoff 3 | 0.00679 | 0.00764 | 0.00637 |
| Sens 3 | 90% | 90% | 91% |
| Spec 3 | 15% | 16% | 9% |
| Cutoff 4 | 0.0186 | 0.0186 | 0.0206 |
| Sens 4 | 40% | 45% | 41% |
| Spec 4 | 72% | 71% | 70% |
| Cutoff 5 | 0.0224 | 0.0224 | 0.0224 |
| Sens 5 | 32% | 35% | 34% |
| Spec 5 | 83% | 81% | 81% |
| Cutoff 6 | 0.351 | 0.552 | 0.475 |
| Sens 6 | 22% | 35% | 23% |
| Spec 6 | 90% | 90% | 90% |
| OR Quart 2 | 0.49 | 0.79 | 0.52 |
| p Value | 0.064 | 0.72 | 0.11 |
| 95% CI of OR Quart 2 | 0.23 | 0.21 | 0.23 |
| | 1.0 | 3.0 | 1.2 |
| OR Quart 3 | 1.0 | 0.39 | 1.1 |
| p Value | 0.89 | 0.26 | 0.72 |
| 95% CI of OR Quart 3 | 0.55 | 0.073 | 0.56 |
| | 2.0 | 2.0 | 2.3 |
| OR Quart 4 | 1.8 | 1.8 | 1.7 |
| p Value | 0.054 | 0.28 | 0.13 |
| 95% CI of OR Quart 4 | 0.99 | 0.60 | 0.86 |
| | 3.3 | 5.7 | 3.3 |

| | C-C motif chemokine 17 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.00507 | 0.00919 | 0.00507 | 0.00823 | 0.00507 | 0.00953 |
| Average | 0.421 | 0.954 | 0.479 | 1.67 | 0.494 | 1.07 |
| Stdev | 3.40 | 3.10 | 3.30 | 4.47 | 3.82 | 3.32 |
| p(t-test) | | 0.17 | | 0.12 | | 0.22 |
| Min | 0.00114 | 0.00114 | 0.00114 | 0.00114 | 0.00114 | 0.00114 |
| Max | 56.6 | 20.4 | 56.6 | 19.4 | 56.6 | 20.4 |
| n (Samp) | 383 | 92 | 451 | 20 | 297 | 79 |
| n (Patient) | 383 | 92 | 451 | 20 | 297 | 79 |

TABLE 11-continued

Comparison of marker levels in enroll urine samples collected from
Cohort 1 (patients that did not progress beyond RIFLE stage 0 or R
within 48 hrs) and in enroll urine samples collected from Cohort 2
(subjects reaching RIFLE stage I or F within 48 hrs). Enroll samples
from patients already at RIFLE stage I or F were included in Cohort 2.

| | At Enrollment | | |
|---|---|---|---|
| | sCr or UO | sCr only | UO only |
| AUC | 0.57 | 0.54 | 0.59 |
| SE | 0.034 | 0.067 | 0.037 |
| p | 0.037 | 0.56 | 0.020 |
| nCohort 1 | 383 | 451 | 297 |
| nCohort 2 | 92 | 20 | 79 |
| Cutoff 1 | 0.00442 | 0.00309 | 0.00442 |
| Sens 1 | 71% | 70% | 73% |
| Spec 1 | 33% | 24% | 31% |
| Cutoff 2 | 0.00308 | 0.00304 | 0.00309 |
| Sens 2 | 83% | 80% | 84% |
| Spec 2 | 23% | 20% | 26% |
| Cutoff 3 | 0.00241 | 0.00114 | 0.00304 |
| Sens 3 | 91% | 95% | 91% |
| Spec 3 | 6% | 4% | 21% |
| Cutoff 4 | 0.0117 | 0.0117 | 0.0121 |
| Sens 4 | 34% | 40% | 34% |
| Spec 4 | 71% | 71% | 72% |
| Cutoff 5 | 0.0162 | 0.0162 | 0.0162 |
| Sens 5 | 29% | 40% | 30% |
| Spec 5 | 83% | 81% | 81% |
| Cutoff 6 | 0.391 | 0.717 | 0.490 |
| Sens 6 | 25% | 30% | 27% |
| Spec 6 | 90% | 90% | 90% |
| OR Quart 2 | 0.87 | 0.48 | 0.79 |
| p Value | 0.70 | 0.31 | 0.56 |
| 95% CI of | 0.44 | 0.12 | 0.37 |
| OR Quart 2 | 1.7 | 2.0 | 1.7 |
| OR Quart 3 | 1.3 | 0.48 | 1.6 |
| p Value | 0.43 | 0.31 | 0.22 |
| 95% CI of | 0.68 | 0.12 | 0.77 |
| OR Quart 3 | 2.5 | 2.0 | 3.1 |
| OR Quart 4 | 1.6 | 1.3 | 1.6 |
| p Value | 0.16 | 0.59 | 0.22 |
| 95% CI of | 0.83 | 0.45 | 0.77 |
| OR Quart 4 | 3.0 | 4.0 | 3.1 |

| | C-C motif chemokine 21 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 1.23 | 7.23 | 1.60 | 54.8 | 1.23 | 7.71 |
| Average | 301 | 183 | 271 | 444 | 377 | 164 |
| Stdev | 2220 | 466 | 2050 | 768 | 2520 | 425 |
| p(t-test) | | 0.61 | | 0.71 | | 0.46 |
| Min | 0.327 | 0.327 | 0.327 | 0.979 | 0.327 | 0.327 |
| Max | 36200 | 2240 | 36200 | 2240 | 36200 | 2240 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.61 | 0.72 | 0.61 |
| SE | 0.034 | 0.066 | 0.037 |
| p | 8.8E-4 | 6.0E-4 | 0.0037 |
| nCohort 1 | 383 | 451 | 297 |
| nCohort 2 | 92 | 20 | 79 |
| Cutoff 1 | 1.20 | 1.79 | 1.20 |
| Sens 1 | 71% | 70% | 71% |
| Spec 1 | 47% | 57% | 45% |
| Cutoff 2 | 0.979 | 1.36 | 0.922 |
| Sens 2 | 80% | 80% | 85% |
| Spec 2 | 34% | 49% | 24% |
| Cutoff 3 | 0.879 | 1.07 | 0.762 |
| Sens 3 | 90% | 90% | 94% |
| Spec 3 | 25% | 39% | 19% |
| Cutoff 4 | 12.9 | 13.0 | 12.5 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Sens 4 | 42% | 55% | 44% |
| Spec 4 | 71% | 70% | 70% |
| Cutoff 5 | 41.8 | 42.5 | 34.1 |
| Sens 5 | 32% | 50% | 34% |
| Spec 5 | 80% | 80% | 80% |
| Cutoff 6 | 194 | 194 | 257 |
| Sens 6 | 17% | 35% | 14% |
| Spec 6 | 90% | 90% | 90% |
| OR Quart 2 | 0.92 | >5.2 | 0.65 |
| p Value | 0.83 | <0.14 | 0.30 |
| 95% CI of | 0.43 | >0.60 | 0.28 |
| OR Quart 2 | 2.0 | na | 1.5 |
| OR Quart 3 | 2.0 | >4.1 | 1.5 |
| p Value | 0.051 | <0.21 | 0.28 |
| 95% CI of | 1.00 | >0.45 | 0.73 |
| OR Quart 3 | 3.9 | na | 3.1 |
| OR Quart 4 | 2.4 | >12 | 2.3 |
| p Value | 0.0081 | <0.018 | 0.019 |
| 95% CI of | 1.3 | >1.5 | 1.1 |
| OR Quart 4 | 4.7 | na | 4.6 |

C-C motif chemokine 27

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 1.92 | 3.65 | 2.08 | 3.76 | 1.91 | 3.84 |
| Average | 3.56 | 9.79 | 4.20 | 17.5 | 3.79 | 10.7 |
| Stdev | 9.77 | 25.3 | 11.2 | 44.6 | 10.7 | 27.1 |
| p(t-test) | | 1.7E−4 | | 4.5E−5 | | 5.0E−4 |
| Min | 0.00255 | 0.00333 | 0.00255 | 0.0149 | 0.00255 | 0.00333 |
| Max | 155 | 198 | 155 | 198 | 155 | 198 |
| n (Samp) | 383 | 92 | 451 | 20 | 297 | 79 |
| n (Patient) | 383 | 92 | 451 | 20 | 297 | 79 |

At Enrollment

| | sCr or UO | sCr only | UO only |
|---|---|---|---|
| AUC | 0.63 | 0.65 | 0.64 |
| SE | 0.034 | 0.068 | 0.037 |
| p | 7.8E−5 | 0.031 | 1.1E−4 |
| nCohort 1 | 383 | 451 | 297 |
| nCohort 2 | 92 | 20 | 79 |
| Cutoff 1 | 1.26 | 1.54 | 1.77 |
| Sens 1 | 71% | 70% | 71% |
| Spec 1 | 39% | 42% | 47% |
| Cutoff 2 | 0.697 | 0.804 | 0.753 |
| Sens 2 | 80% | 80% | 81% |
| Spec 2 | 29% | 30% | 30% |
| Cutoff 3 | 0.0144 | 0.521 | 0.0100 |
| Sens 3 | 90% | 90% | 91% |
| Spec 3 | 17% | 24% | 16% |
| Cutoff 4 | 3.33 | 3.61 | 3.46 |
| Sens 4 | 54% | 55% | 54% |
| Spec 4 | 70% | 70% | 70% |
| Cutoff 5 | 4.28 | 4.61 | 4.54 |
| Sens 5 | 39% | 40% | 39% |
| Spec 5 | 80% | 80% | 80% |
| Cutoff 6 | 5.96 | 6.72 | 6.35 |
| Sens 6 | 30% | 35% | 30% |
| Spec 6 | 90% | 90% | 90% |
| OR Quart 2 | 1.1 | 1.7 | 1.1 |
| p Value | 0.73 | 0.48 | 0.84 |
| 95% CI of | 0.55 | 0.39 | 0.48 |
| OR Quart 2 | 2.4 | 7.2 | 2.5 |
| OR Quart 3 | 1.2 | 0.99 | 1.6 |
| p Value | 0.60 | 0.99 | 0.25 |
| 95% CI of | 0.59 | 0.20 | 0.73 |
| OR Quart 3 | 2.5 | 5.0 | 3.4 |
| OR Quart 4 | 3.1 | 3.1 | 3.4 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| p Value | 6.4E−4 | 0.093 | 9.8E−4 |
| 95% CI of | 1.6 | 0.83 | 1.6 |
| OR Quart 4 | 6.0 | 12 | 6.9 |

Vascular endothelial growth factor receptor 1

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 8.05 | 65.7 | 10.1 | 62.8 | 6.11 | 71.3 |
| Average | 48.0 | 201 | 76.7 | 153 | 48.4 | 213 |
| Stdev | 88.3 | 625 | 313 | 167 | 91.5 | 674 |
| p(t-test) | | 0.0011 | | 0.44 | | 0.0022 |
| Min | 0.169 | 0.169 | 0.169 | 0.242 | 0.169 | 0.169 |
| Max | 659 | 4630 | 4630 | 438 | 659 | 4630 |
| n (Samp) | 194 | 55 | 237 | 10 | 170 | 47 |
| n (Patient) | 194 | 55 | 237 | 10 | 170 | 47 |

At Enrollment

| | sCr or UO | sCr only | UO only |
|---|---|---|---|
| AUC | 0.68 | 0.70 | 0.68 |
| SE | 0.043 | 0.094 | 0.047 |
| p | 3.5E−5 | 0.037 | 1.3E−4 |
| nCohort 1 | 194 | 237 | 170 |
| nCohort 2 | 55 | 10 | 47 |
| Cutoff 1 | 31.0 | 56.1 | 31.0 |
| Sens 1 | 71% | 70% | 70% |
| Spec 1 | 64% | 68% | 64% |
| Cutoff 2 | 3.16 | 43.2 | 3.16 |
| Sens 2 | 80% | 80% | 81% |
| Spec 2 | 44% | 63% | 46% |
| Cutoff 3 | 0.215 | 0.521 | 0.215 |
| Sens 3 | 95% | 90% | 94% |
| Spec 3 | 6% | 33% | 6% |
| Cutoff 4 | 53.5 | 59.8 | 54.1 |
| Sens 4 | 58% | 50% | 57% |
| Spec 4 | 70% | 70% | 71% |
| Cutoff 5 | 81.0 | 102 | 71.6 |
| Sens 5 | 42% | 40% | 49% |
| Spec 5 | 80% | 80% | 80% |
| Cutoff 6 | 149 | 178 | 133 |
| Sens 6 | 29% | 40% | 30% |
| Spec 6 | 90% | 90% | 90% |
| OR Quart 2 | 0.86 | 0.98 | 0.84 |
| p Value | 0.78 | 0.99 | 0.77 |
| 95% CI of | 0.29 | 0.060 | 0.26 |
| OR Quart 2 | 2.5 | 16 | 2.7 |
| OR Quart 3 | 2.3 | 4.1 | 1.9 |
| p Value | 0.074 | 0.21 | 0.21 |
| 95% CI of | 0.92 | 0.45 | 0.69 |
| OR Quart 3 | 6.0 | 38 | 5.3 |
| OR Quart 4 | 4.2 | 4.1 | 4.5 |
| p Value | 0.0019 | 0.21 | 0.0022 |
| 95% CI of | 1.7 | 0.45 | 1.7 |
| OR Quart 4 | 10 | 38 | 12 |

SL cytokine

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0624 | 0.0797 | 0.0624 | 0.0952 | 0.0625 | 0.0744 |
| Average | 1.76 | 4.79 | 1.78 | 15.6 | 2.23 | 4.42 |
| Stdev | 27.2 | 23.3 | 25.2 | 47.2 | 30.9 | 24.3 |
| p(t-test) | | 0.32 | | 0.022 | | 0.56 |
| Min | 0.0336 | 0.0336 | 0.0336 | 0.0449 | 0.0336 | 0.0336 |
| Max | 527 | 207 | 527 | 207 | 527 | 207 |
| n (Samp) | 385 | 92 | 453 | 20 | 298 | 79 |
| n (Patient) | 385 | 92 | 453 | 20 | 298 | 79 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | At Enrollment | | |
|---|---|---|---|
| | sCr or UO | sCr only | UO only |
| AUC | 0.57 | 0.65 | 0.53 |
| SE | 0.034 | 0.068 | 0.037 |
| p | 0.052 | 0.026 | 0.35 |
| nCohort 1 | 385 | 453 | 298 |
| nCohort 2 | 92 | 20 | 79 |
| Cutoff 1 | 0.0518 | 0.0651 | 0.0518 |
| Sens 1 | 76% | 70% | 76% |
| Spec 1 | 27% | 54% | 26% |
| Cutoff 2 | 0.0511 | 0.0518 | 0.0511 |
| Sens 2 | 83% | 80% | 84% |
| Spec 2 | 24% | 26% | 21% |
| Cutoff 3 | 0.0445 | 0.0487 | 0.0336 |
| Sens 3 | 90% | 95% | 96% |
| Spec 3 | 10% | 20% | 6% |
| Cutoff 4 | 0.0908 | 0.0914 | 0.0997 |
| Sens 4 | 36% | 50% | 33% |
| Spec 4 | 70% | 71% | 76% |
| Cutoff 5 | 0.100 | 0.109 | 0.125 |
| Sens 5 | 32% | 40% | 22% |
| Spec 5 | 80% | 80% | 86% |
| Cutoff 6 | 0.154 | 0.186 | 0.170 |
| Sens 6 | 21% | 30% | 19% |
| Spec 6 | 90% | 91% | 90% |
| OR Quart 2 | 0.82 | 0.49 | 0.87 |
| p Value | 0.59 | 0.42 | 0.71 |
| 95% CI of | 0.41 | 0.088 | 0.42 |
| OR Quart 2 | 1.7 | 2.7 | 1.8 |
| OR Quart 3 | 1.2 | 1.5 | 0.93 |
| p Value | 0.61 | 0.52 | 0.85 |
| 95% CI of | 0.61 | 0.42 | 0.46 |
| OR Quart 3 | 2.3 | 5.6 | 1.9 |
| OR Quart 4 | 1.8 | 2.1 | 1.4 |
| p Value | 0.067 | 0.25 | 0.32 |
| 95% CI of | 0.96 | 0.60 | 0.71 |
| OR Quart 4 | 3.4 | 7.0 | 2.8 |

| | Immunoglogulin G3 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 99.3 | 180 | 109 | 204 | 102 | 187 |
| Average | 210 | 403 | 238 | 455 | 212 | 425 |
| Stdev | 296 | 446 | 329 | 480 | 294 | 457 |
| p(t-test) | | 7.2E−7 | | 0.0051 | | 7.9E−7 |
| Min | 0.833 | 2.02 | 0.833 | 8.91 | 0.833 | 2.02 |
| Max | 1200 | 1200 | 1200 | 1200 | 1200 | 1200 |
| n (Samp) | 379 | 92 | 447 | 20 | 292 | 79 |
| n (Patient) | 379 | 92 | 447 | 20 | 292 | 79 |

| | At Enrollment | | |
|---|---|---|---|
| | sCr or UO | sCr only | UO only |
| AUC | 0.63 | 0.65 | 0.64 |
| SE | 0.034 | 0.068 | 0.037 |
| p | 1.5E−4 | 0.031 | 2.3E−4 |
| nCohort 1 | 379 | 447 | 292 |
| nCohort 2 | 92 | 20 | 79 |
| Cutoff 1 | 87.0 | 121 | 87.2 |
| Sens 1 | 71% | 70% | 71% |
| Spec 1 | 45% | 54% | 43% |
| Cutoff 2 | 53.3 | 76.3 | 53.3 |
| Sens 2 | 80% | 80% | 81% |
| Spec 2 | 29% | 39% | 28% |
| Cutoff 3 | 34.6 | 40.8 | 32.5 |
| Sens 3 | 90% | 90% | 91% |
| Spec 3 | 18% | 20% | 15% |
| Cutoff 4 | 171 | 195 | 175 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Sens 4 | 51% | 55% | 53% |
| Spec 4 | 70% | 70% | 70% |
| Cutoff 5 | 274 | 312 | 280 |
| Sens 5 | 39% | 40% | 41% |
| Spec 5 | 80% | 80% | 80% |
| Cutoff 6 | 520 | 792 | 520 |
| Sens 6 | 28% | 30% | 30% |
| Spec 6 | 90% | 90% | 90% |
| OR Quart 2 | 1.1 | 0.99 | 0.99 |
| p Value | 0.73 | 0.99 | 0.98 |
| 95% CI of | 0.55 | 0.20 | 0.44 |
| OR Quart 2 | 2.4 | 5.0 | 2.2 |
| OR Quart 3 | 1.4 | 1.7 | 1.4 |
| p Value | 0.30 | 0.48 | 0.36 |
| 95% CI of | 0.72 | 0.39 | 0.67 |
| OR Quart 3 | 2.9 | 7.2 | 3.1 |
| OR Quart 4 | 2.8 | 3.1 | 2.9 |
| p Value | 0.0024 | 0.093 | 0.0031 |
| 95% CI of | 1.4 | 0.83 | 1.4 |
| OR Quart 4 | 5.3 | 12 | 6.0 |

Interleukin-1 receptor type I

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 4.11 | 7.01 | 5.06 | 6.10 | 4.02 | 7.43 |
| Average | 4.91 | 9.66 | 5.89 | 6.25 | 4.73 | 10.3 |
| Stdev | 4.26 | 11.5 | 6.91 | 4.37 | 4.20 | 12.2 |
| p(t-test) | | 3.3E−6 | | 0.87 | | 9.8E−7 |
| Min | 0.0141 | 0.0147 | 0.0141 | 0.0214 | 0.0141 | 0.0147 |
| Max | 21.7 | 78.1 | 78.1 | 14.1 | 21.7 | 78.1 |
| n (Samp) | 197 | 55 | 240 | 10 | 172 | 47 |
| n (Patient) | 197 | 55 | 240 | 10 | 172 | 47 |

| | At Enrollment | | |
|---|---|---|---|
| | sCr or UO | sCr only | UO only |
| AUC | 0.67 | 0.56 | 0.70 |
| SE | 0.044 | 0.096 | 0.046 |
| p | 7.2E−5 | 0.51 | 9.2E−6 |
| nCohort 1 | 197 | 240 | 172 |
| nCohort 2 | 55 | 10 | 47 |
| Cutoff 1 | 5.31 | 4.81 | 5.40 |
| Sens 1 | 71% | 70% | 70% |
| Spec 1 | 56% | 48% | 59% |
| Cutoff 2 | 4.02 | 3.99 | 4.02 |
| Sens 2 | 80% | 80% | 83% |
| Spec 2 | 50% | 42% | 52% |
| Cutoff 3 | 0.203 | 0.143 | 0.694 |
| Sens 3 | 91% | 90% | 91% |
| Spec 3 | 17% | 15% | 24% |
| Cutoff 4 | 7.11 | 7.41 | 7.03 |
| Sens 4 | 49% | 30% | 51% |
| Spec 4 | 70% | 70% | 70% |
| Cutoff 5 | 8.31 | 8.95 | 8.08 |
| Sens 5 | 42% | 30% | 45% |
| Spec 5 | 80% | 80% | 81% |
| Cutoff 6 | 10.3 | 11.3 | 10.1 |
| Sens 6 | 31% | 10% | 36% |
| Spec 6 | 90% | 90% | 90% |
| OR Quart 2 | 1.0 | 0.98 | 0.98 |
| p Value | 1.0 | 0.99 | 0.97 |
| 95% CI of | 0.35 | 0.13 | 0.30 |
| OR Quart 2 | 2.9 | 7.2 | 3.3 |
| OR Quart 3 | 2.3 | 1.5 | 2.7 |
| p Value | 0.074 | 0.65 | 0.059 |
| 95% CI of | 0.92 | 0.25 | 0.96 |
| OR Quart 3 | 6.0 | 9.5 | 7.8 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| OR Quart 4 | 4.0 | 1.5 | 4.9 |
| p Value | 0.0028 | 0.66 | 0.0019 |
| 95% CI of | 1.6 | 0.24 | 1.8 |
| OR Quart 4 | 9.7 | 9.3 | 14 |

Interleukin-29

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 25.4 | 79.1 | 29.8 | 96.6 | 34.8 | 78.9 |
| Average | 67.9 | 125 | 76.4 | 135 | 71.9 | 124 |
| Stdev | 99.7 | 131 | 108 | 124 | 97.0 | 130 |
| p(t-test) | | 4.4E−6 | | 0.019 | | 1.1E−4 |
| Min | 0.114 | 0.173 | 0.114 | 0.187 | 0.114 | 0.173 |
| Max | 612 | 510 | 612 | 429 | 554 | 510 |
| n (Samp) | 385 | 91 | 452 | 20 | 298 | 78 |
| n (Patient) | 385 | 91 | 452 | 20 | 298 | 78 |

At Enrollment

| | sCr or UO | sCr only | UO only |
|---|---|---|---|
| AUC | 0.68 | 0.70 | 0.65 |
| SE | 0.033 | 0.067 | 0.037 |
| p | 1.5E−7 | 0.0032 | 5.9E−5 |
| nCohort 1 | 385 | 452 | 298 |
| nCohort 2 | 91 | 20 | 78 |
| Cutoff 1 | 32.3 | 69.7 | 32.1 |
| Sens 1 | 70% | 70% | 71% |
| Spec 1 | 55% | 66% | 49% |
| Cutoff 2 | 16.3 | 39.1 | 16.2 |
| Sens 2 | 80% | 80% | 81% |
| Spec 2 | 44% | 55% | 38% |
| Cutoff 3 | 3.91 | 19.5 | 2.79 |
| Sens 3 | 90% | 90% | 91% |
| Spec 3 | 30% | 43% | 24% |
| Cutoff 4 | 72.8 | 81.7 | 80.7 |
| Sens 4 | 55% | 60% | 47% |
| Spec 4 | 70% | 70% | 70% |
| Cutoff 5 | 112 | 135 | 126 |
| Sens 5 | 42% | 35% | 36% |
| Spec 5 | 80% | 80% | 81% |
| Cutoff 6 | 205 | 222 | 205 |
| Sens 6 | 21% | 15% | 21% |
| Spec 6 | 90% | 90% | 91% |
| OR Quart 2 | 2.6 | 2.0 | 2.1 |
| p Value | 0.029 | 0.57 | 0.096 |
| 95% CI of | 1.1 | 0.18 | 0.88 |
| OR Quart 2 | 6.3 | 23 | 5.0 |
| OR Quart 3 | 3.9 | 9.7 | 2.7 |
| p Value | 0.0015 | 0.033 | 0.020 |
| 95% CI of | 1.7 | 1.2 | 1.2 |
| OR Quart 3 | 9.0 | 78 | 6.3 |
| OR Quart 4 | 6.5 | 8.5 | 4.6 |
| p Value | 6.5E−6 | 0.045 | 2.0E−4 |
| 95% CI of | 2.9 | 1.0 | 2.1 |
| OR Quart 4 | 15 | 69 | 10 |

Interleukin-7

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0110 | 0.0118 | 0.0110 | 0.0125 | 0.0125 | 0.0110 |
| Average | 0.474 | 0.635 | 0.497 | 0.725 | 0.398 | 0.611 |
| Stdev | 4.66 | 3.54 | 4.55 | 2.37 | 3.90 | 3.66 |
| p(t-test) | | 0.76 | | 0.82 | | 0.66 |
| Min | 0.00316 | 0.00316 | 0.00316 | 0.00316 | 0.00316 | 0.00316 |
| Max | 64.2 | 31.8 | 64.2 | 9.95 | 64.2 | 31.8 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | | | | |
|---|---|---|---|---|---|---|
| n (Samp) | 385 | 92 | 453 | 20 | 298 | 79 |
| n (Patient) | 385 | 92 | 453 | 20 | 298 | 79 |

| | At Enrollment | | |
|---|---|---|---|
| | sCr or UO | sCr only | UO only |
| AUC | 0.53 | 0.55 | 0.49 |
| SE | 0.034 | 0.068 | 0.037 |
| p | 0.45 | 0.48 | 0.81 |
| nCohort 1 | 385 | 453 | 298 |
| nCohort 2 | 92 | 20 | 79 |
| Cutoff 1 | 0.00822 | 0.0105 | 0.00822 |
| Sens 1 | 74% | 70% | 72% |
| Spec 1 | 34% | 41% | 31% |
| Cutoff 2 | 0.00584 | 0.00742 | 0.00517 |
| Sens 2 | 82% | 85% | 84% |
| Spec 2 | 26% | 31% | 22% |
| Cutoff 3 | 0.00487 | 0.00584 | 0.00487 |
| Sens 3 | 92% | 90% | 91% |
| Spec 3 | 22% | 25% | 18% |
| Cutoff 4 | 0.0174 | 0.0174 | 0.0226 |
| Sens 4 | 28% | 30% | 20% |
| Spec 4 | 70% | 71% | 72% |
| Cutoff 5 | 0.0315 | 0.0315 | 0.0315 |
| Sens 5 | 12% | 10% | 13% |
| Spec 5 | 84% | 84% | 82% |
| Cutoff 6 | 0.0478 | 0.0478 | 0.0478 |
| Sens 6 | 10% | 10% | 10% |
| Spec 6 | 93% | 92% | 92% |
| OR Quart 2 | 1.8 | 2.6 | 1.3 |
| p Value | 0.097 | 0.27 | 0.44 |
| 95% CI of | 0.90 | 0.49 | 0.64 |
| OR Quart 2 | 3.4 | 13 | 2.8 |
| OR Quart 3 | 1.8 | 4.8 | 1.9 |
| p Value | 0.097 | 0.048 | 0.076 |
| 95% CI of | 0.90 | 1.0 | 0.94 |
| OR Quart 3 | 3.4 | 23 | 3.8 |
| OR Quart 4 | 1.3 | 2.0 | 1.1 |
| p Value | 0.50 | 0.42 | 0.82 |
| 95% CI of | 0.63 | 0.36 | 0.51 |
| OR Quart 4 | 9.6 | 11 | 2.3 |

Matrix metalloproteinase-9: Metalloproteinase inhibitor 2 complex

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 180 | 1620 | nd | nd | 176 | 1620 |
| Average | 2890 | 8670 | nd | nd | 2400 | 8360 |
| Stdev | 7400 | 11100 | nd | nd | 6720 | 11000 |
| p(t-test) | | 0.0020 | nd | nd | | 0.0015 |
| Min | 0.227 | 3.10 | nd | nd | 0.227 | 3.10 |
| Max | 24000 | 24000 | nd | nd | 24000 | 24000 |
| n (Samp) | 111 | 24 | nd | nd | 92 | 22 |
| n (Patient) | 111 | 24 | nd | nd | 92 | 22 |

| | At Enrollment | | |
|---|---|---|---|
| | sCr or UO | sCr only | UO only |
| AUC | 0.76 | nd | 0.78 |
| SE | 0.060 | nd | 0.062 |
| p | 1.0E−5 | nd | 8.1E−6 |
| nCohort 1 | 111 | nd | 92 |
| nCohort 2 | 24 | nd | 22 |
| Cutoff 1 | 708 | nd | 697 |
| Sens 1 | 71% | nd | 73% |
| Spec 1 | 77% | nd | 78% |
| Cutoff 2 | 217 | nd | 443 |
| Sens 2 | 83% | nd | 82% |
| Spec 2 | 56% | nd | 71% |
| Cutoff 3 | 94.3 | nd | 91.9 |

TABLE 11-continued

Comparison of marker levels in enroll urine samples collected from
Cohort 1 (patients that did not progress beyond RIFLE stage 0 or R
within 48 hrs) and in enroll urine samples collected from Cohort 2
(subjects reaching RIFLE stage I or F within 48 hrs). Enroll samples
from patients already at RIFLE stage I or F were included in Cohort 2.

| | | | |
|---|---|---|---|
| Sens 3 | 92% | nd | 91% |
| Spec 3 | 36% | nd | 36% |
| Cutoff 4 | 496 | nd | 443 |
| Sens 4 | 75% | nd | 82% |
| Spec 4 | 70% | nd | 71% |
| Cutoff 5 | 783 | nd | 762 |
| Sens 5 | 67% | nd | 68% |
| Spec 5 | 80% | nd | 80% |
| Cutoff 6 | 24000 | nd | 2320 |
| Sens 6 | 0% | nd | 36% |
| Spec 6 | 100% | nd | 90% |
| OR Quart 2 | 4.3 | nd | 3.1 |
| p Value | 0.21 | nd | 0.34 |
| 95% CI of OR Quart 2 | 0.45 | nd | 0.30 |
|  | 40 | nd | 32 |
| OR Quart 3 | 4.3 | nd | 4.5 |
| p Value | 0.21 | nd | 0.19 |
| 95% CI of OR Quart 3 | 0.45 | nd | 0.47 |
|  | 40 | nd | 43 |
| OR Quart 4 | 25 | nd | 25 |
| p Value | 0.0026 | nd | 0.0029 |
| 95% CI of OR Quart 4 | 3.1 | nd | 3.0 |
|  | 210 | nd | 210 |

Platelet-derived growth factor subunit A (dimer)

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 89.0 | 139 | 89.9 | 231 | 90.2 | 133 |
| Average | 144 | 360 | 173 | 484 | 140 | 370 |
| Stdev | 183 | 950 | 446 | 594 | 166 | 1020 |
| p(t-test) | | 4.0E−5 | | 0.0028 | | 2.4E−4 |
| Min | 0.994 | 3.46 | 0.994 | 14.9 | 3.01 | 3.46 |
| Max | 1830 | 8310 | 8310 | 2480 | 1190 | 8310 |
| n (Samp) | 383 | 92 | 451 | 20 | 296 | 79 |
| n (Patient) | 383 | 92 | 451 | 20 | 296 | 79 |

At Enrollment

| | sCr or UO | sCr only | UO only |
|---|---|---|---|
| AUC | 0.60 | 0.78 | 0.58 |
| SE | 0.034 | 0.062 | 0.037 |
| p | 0.0022 | 8.0E−6 | 0.024 |
| nCohort 1 | 383 | 451 | 296 |
| nCohort 2 | 92 | 20 | 79 |
| Cutoff 1 | 66.6 | 140 | 61.9 |
| Sens 1 | 71% | 70% | 71% |
| Spec 1 | 37% | 67% | 36% |
| Cutoff 2 | 43.6 | 133 | 34.3 |
| Sens 2 | 80% | 80% | 81% |
| Spec 2 | 26% | 66% | 21% |
| Cutoff 3 | 22.3 | 104 | 14.6 |
| Sens 3 | 90% | 90% | 91% |
| Spec 3 | 11% | 55% | 8% |
| Cutoff 4 | 148 | 159 | 151 |
| Sens 4 | 48% | 65% | 44% |
| Spec 4 | 70% | 70% | 70% |
| Cutoff 5 | 209 | 215 | 204 |
| Sens 5 | 36% | 55% | 34% |
| Spec 5 | 80% | 80% | 80% |
| Cutoff 6 | 317 | 341 | 322 |
| Sens 6 | 24% | 40% | 22% |
| Spec 6 | 90% | 90% | 90% |
| OR Quart 2 | 0.86 | 0.99 | 0.85 |
| p Value | 0.69 | 1.00 | 0.67 |
| 95% CI of OR Quart 2 | 0.42 | 0.061 | 0.40 |
|  | 1.8 | 16 | 1.8 |
| OR Quart 3 | 1.3 | 6.2 | 1.1 |
| p Value | 0.41 | 0.093 | 0.88 |
| 95% CI of OR Quart 3 | 0.68 | 0.74 | 0.51 |
|  | 2.6 | 52 | 2.2 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| OR Quart 4 | 2.3 | 13 | 2.0 |
| p Value | 0.0099 | 0.014 | 0.048 |
| 95% CI of | 1.2 | 1.7 | 1.0 |
| OR Quart 4 | 4.4 | 100 | 4.0 |

Platelet-derived growth factor A

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 3.02 | 5.34 | 3.33 | 15.5 | 3.16 | 5.36 |
| Average | 47.0 | 175 | 54.3 | 479 | 22.6 | 201 |
| Stdev | 550 | 896 | 556 | 1580 | 127 | 966 |
| p(t-test) | | 0.082 | | 0.0033 | | 0.0022 |
| Min | 0.0141 | 0.0184 | 0.0141 | 0.0625 | 0.0141 | 0.0184 |
| Max | 10600 | 6850 | 10600 | 6850 | 2000 | 6850 |
| n (Samp) | 383 | 92 | 451 | 20 | 296 | 79 |
| n (Patient) | 383 | 92 | 451 | 20 | 296 | 79 |

At Enrollment

| | sCr or UO | sCr only | UO only |
|---|---|---|---|
| AUC | 0.57 | 0.68 | 0.55 |
| SE | 0.034 | 0.067 | 0.037 |
| p | 0.042 | 0.0082 | 0.14 |
| nCohort 1 | 383 | 451 | 296 |
| nCohort 2 | 92 | 20 | 79 |
| Cutoff 1 | 0.156 | 4.61 | 0.156 |
| Sens 1 | 72% | 70% | 71% |
| Spec 1 | 27% | 61% | 26% |
| Cutoff 2 | 0.123 | 0.156 | 0.0828 |
| Sens 2 | 80% | 80% | 82% |
| Spec 2 | 23% | 27% | 16% |
| Cutoff 3 | 0.0604 | 0.143 | 0.0568 |
| Sens 3 | 90% | 90% | 91% |
| Spec 3 | 7% | 26% | 6% |
| Cutoff 4 | 7.78 | 9.13 | 8.62 |
| Sens 4 | 43% | 55% | 42% |
| Spec 4 | 71% | 71% | 70% |
| Cutoff 5 | 14.1 | 15.6 | 14.2 |
| Sens 5 | 35% | 50% | 34% |
| Spec 5 | 80% | 80% | 80% |
| Cutoff 6 | 29.8 | 32.0 | 31.0 |
| Sens 6 | 23% | 35% | 20% |
| Spec 6 | 90% | 90% | 91% |
| OR Quart 2 | 0.64 | 1.5 | 0.52 |
| p Value | 0.21 | 0.66 | 0.088 |
| 95% CI of | 0.32 | 0.25 | 0.24 |
| OR Quart 2 | 1.3 | 9.1 | 1.1 |
| OR Quart 3 | 0.83 | 2.5 | 0.71 |
| p Value | 0.59 | 0.27 | 0.35 |
| 95% CI of | 0.43 | 0.48 | 0.35 |
| OR Quart 3 | 1.6 | 13 | 1.4 |
| OR Quart 4 | 1.6 | 5.3 | 1.3 |
| p Value | 0.14 | 0.033 | 0.43 |
| 95% CI of | 0.86 | 1.1 | 0.68 |
| OR Quan4 | 2.9 | 25 | 2.5 |

Thymic stromal lymphopoietin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 71.2 | 58.6 | 68.6 | 39.4 | 70.0 | 59.7 |
| Average | 92.4 | 72.3 | 88.9 | 72.0 | 94.5 | 72.5 |
| Stdev | 79.2 | 62.4 | 75.9 | 82.4 | 81.6 | 64.0 |
| p(t-test) | | 0.023 | | 0.33 | | 0.027 |
| Min | 0.00642 | 0.0121 | 0.00642 | 4.47 | 0.00667 | 0.0121 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

|  | | | | | | |
|---|---|---|---|---|---|---|
| Max | 559 | 356 | 559 | 356 | 559 | 356 |
| n (Samp) | 382 | 92 | 450 | 20 | 296 | 79 |
| n (Patient) | 382 | 92 | 450 | 20 | 296 | 79 |

| | At Enrollment | | |
|---|---|---|---|
| | sCr or UO | sCr only | UO only |
| AUC | 0.41 | 0.37 | 0.40 |
| SE | 0.034 | 0.068 | 0.037 |
| p | 0.0077 | 0.055 | 0.010 |
| nCohort 1 | 382 | 450 | 296 |
| nCohort 2 | 92 | 20 | 79 |
| Cutoff 1 | 37.1 | 29.0 | 42.6 |
| Sens 1 | 71% | 70% | 71% |
| Spec 1 | 19% | 14% | 23% |
| Cutoff 2 | 29.0 | 25.8 | 28.3 |
| Sens 2 | 80% | 80% | 81% |
| Spec 2 | 14% | 12% | 12% |
| Cutoff 3 | 22.0 | 22.0 | 20.7 |
| Sens 3 | 90% | 90% | 91% |
| Spec 3 | 10% | 10% | 8% |
| Cutoff 4 | 107 | 99.4 | 111 |
| Sens 4 | 16% | 25% | 14% |
| Spec 4 | 70% | 70% | 70% |
| Cutoff 5 | 134 | 132 | 137 |
| Sens 5 | 12% | 15% | 11% |
| Spec 5 | 80% | 80% | 80% |
| Cutoff 6 | 184 | 177 | 189 |
| Sens 6 | 8% | 10% | 8% |
| Spec 6 | 90% | 90% | 90% |
| OR Quart 2 | 2.3 | 1.0 | 2.6 |
| p Value | 0.031 | 0.99 | 0.023 |
| 95% CI of | 1.1 | 0.20 | 1.1 |
| OR Quart 2 | 4.8 | 5.1 | 5.8 |
| OR Quart 3 | 2.6 | 1.0 | 2.6 |
| p Value | 0.010 | 1.0 | 0.023 |
| 95% CI of | 1.3 | 0.20 | 1.1 |
| OR Quart 3 | 5.5 | 5.1 | 5.8 |
| OR Quart 4 | 2.9 | 4.0 | 3.1 |
| p Value | 0.0041 | 0.038 | 0.0057 |
| 95% CI of | 1.4 | 1.1 | 1.4 |
| OR Quart 4 | 6.0 | 15 | 6.9 |

TABLE 12

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | C-C motif chemokine 1 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 1.82 | 2.81 | 1.99 | 1.58 | 1.82 | 3.04 |
| Average | 5.08 | 3.85 | 4.73 | 5.91 | 5.34 | 4.10 |
| Stdev | 22.3 | 4.47 | 20.3 | 7.67 | 23.4 | 4.72 |
| p(t-test) | | 0.78 | | 0.88 | | 0.81 |
| Min | 0.00831 | 0.00831 | 0.00831 | 0.486 | 0.00831 | 0.00831 |
| Max | 212 | 21.9 | 212 | 21.9 | 212 | 21.9 |
| n (Samp) | 89 | 26 | 108 | 7 | 81 | 22 |
| n (Patient) | 89 | 26 | 108 | 7 | 81 | 22 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | At Enrollment | | |
|---|---|---|---|
| | sCr or UO | sCr only | UO only |
| AUC | 0.56 | 0.56 | 0.58 |
| SE | 0.065 | 0.12 | 0.071 |
| p | 0.40 | 0.61 | 0.27 |
| nCohort 1 | 89 | 108 | 81 |
| nCohort 2 | 26 | 7 | 22 |
| Cutoff 1 | 1.32 | 1.32 | 1.47 |
| Sens 1 | 73% | 71% | 73% |
| Spec 1 | 31% | 31% | 38% |
| Cutoff 2 | 1.06 | 1.06 | 1.15 |
| Sens 2 | 81% | 86% | 82% |
| Spec 2 | 22% | 22% | 25% |
| Cutoff 3 | 0 | 0.305 | 0 |
| Sens 3 | 100% | 100% | 100% |
| Spec 3 | 0% | 16% | 0% |
| Cutoff 4 | 3.24 | 3.44 | 3.22 |
| Sens 4 | 42% | 43% | 45% |
| Spec 4 | 71% | 70% | 70% |
| Cutoff 5 | 4.51 | 4.33 | 4.51 |
| Sens 5 | 23% | 43% | 23% |
| Spec 5 | 81% | 81% | 80% |
| Cutoff 6 | 6.98 | 7.03 | 6.98 |
| Sens 6 | 19% | 29% | 23% |
| Spec 6 | 91% | 91% | 90% |
| OR Quart 2 | 0.76 | 0.96 | 0.95 |
| p Value | 0.69 | 0.97 | 0.95 |
| 95% CI of | 0.20 | 0.13 | 0.21 |
| OR Quart 2 | 2.9 | 7.4 | 4.3 |
| OR Quart 3 | 1.2 | 0 | 1.9 |
| p Value | 0.81 | na | 0.35 |
| 95% CI of | 0.34 | na | 0.49 |
| OR Quart 3 | 4.0 | na | 7.7 |
| OR Quart 4 | 1.4 | 1.5 | 1.9 |
| p Value | 0.59 | 0.67 | 0.35 |
| 95% CI of | 0.41 | 0.23 | 0.49 |
| OR Quart 4 | 4.7 | 9.7 | 7.7 |

| | C-C motif chemokine 17 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 20.3 | 18.3 | 20.2 | 20.0 | 18.9 | 14.9 |
| Average | 59.9 | 25.6 | 54.2 | 21.0 | 56.8 | 25.8 |
| Stdev | 135 | 31.2 | 124 | 13.1 | 138 | 33.9 |
| p(t-test) | | 0.20 | | 0.48 | | 0.30 |
| Min | 2.05 | 0.0212 | 0.0212 | 1.98 | 2.05 | 0.0212 |
| Max | 1010 | 160 | 1010 | 37.0 | 1010 | 160 |
| n (Samp) | 89 | 26 | 108 | 7 | 81 | 22 |
| n (Patient) | 89 | 26 | 108 | 7 | 81 | 22 |

| | At Enrollment | | |
|---|---|---|---|
| | sCr or UO | sCr only | UO only |
| AUC | 0.44 | 0.47 | 0.44 |
| SE | 0.065 | 0.11 | 0.071 |
| p | 0.36 | 0.79 | 0.40 |
| nCohort 1 | 89 | 108 | 81 |
| nCohort 2 | 26 | 7 | 22 |
| Cutoff 1 | 9.84 | 14.1 | 9.76 |
| Sens 1 | 73% | 71% | 73% |
| Spec 1 | 27% | 38% | 28% |
| Cutoff 2 | 5.21 | 9.76 | 4.20 |
| Sens 2 | 81% | 86% | 82% |
| Spec 2 | 9% | 27% | 7% |
| Cutoff 3 | 0.0212 | 0.819 | 0.0212 |
| Sens 3 | 96% | 100% | 95% |
| Spec 3 | 0% | 3% | 0% |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| Cutoff 4 | 34.4 | 32.3 | 31.5 |
|---|---|---|---|
| Sens 4 | 19% | 29% | 23% |
| Spec 4 | 71% | 70% | 70% |
| Cutoff 5 | 44.9 | 42.0 | 39.6 |
| Sens 5 | 12% | 0% | 18% |
| Spec 5 | 81% | 81% | 80% |
| Cutoff 6 | 130 | 124 | 122 |
| Sens 6 | 4% | 0% | 5% |
| Spec 6 | 91% | 91% | 90% |
| OR Quart 2 | 1.5 | 2.1 | 1.0 |
| p Value | 0.52 | 0.56 | 1.0 |
| 95% CI of | 0.42 | 0.18 | 0.25 |
| OR Quart 2 | 5.5 | 24 | 4.0 |
| OR Quart 3 | 1.8 | 3.2 | 1.3 |
| p Value | 0.35 | 0.32 | 0.73 |
| 95% CI of | 0.52 | 0.32 | 0.33 |
| OR Quart 3 | 6.5 | 33 | 4.8 |
| OR Quart 4 | 1.3 | 1.0 | 1.3 |
| p Value | 0.69 | 0.98 | 0.68 |
| 95% CI of | 0.35 | 0.062 | 0.35 |
| OR Quart 4 | 4.9 | 17 | 5.1 |

C-C motif chemokine 21

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 414 | 785 | 482 | 672 | 414 | 816 |
| Average | 671 | 1160 | 706 | 1930 | 683 | 1160 |
| Stdev | 897 | 1530 | 850 | 2800 | 929 | 1610 |
| p(t-test) | | 0.043 | | 0.0033 | | 0.073 |
| Min | 0.947 | 171 | 0.947 | 171 | 0.947 | 171 |
| Max | 5980 | 7950 | 5980 | 7950 | 5980 | 7950 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.69 | 0.65 | 0.69 |
| SE | 0.063 | 0.12 | 0.068 |
| p | 0.0029 | 0.20 | 0.0063 |
| nCohort 1 | 90 | 109 | 82 |
| nCohort 2 | 26 | 7 | 22 |
| Cutoff 1 | 478 | 611 | 478 |
| Sens 1 | 73% | 71% | 73% |
| Spec 1 | 54% | 61% | 55% |
| Cutoff 2 | 354 | 354 | 287 |
| Sens 2 | 81% | 86% | 82% |
| Spec 2 | 42% | 39% | 35% |
| Cutoff 3 | 257 | 168 | 257 |
| Sens 3 | 92% | 100% | 91% |
| Spec 3 | 33% | 16% | 32% |
| Cutoff 4 | 684 | 764 | 684 |
| Sens 4 | 58% | 43% | 64% |
| Spec 4 | 70% | 71% | 71% |
| Cutoff 5 | 832 | 933 | 832 |
| Sens 5 | 42% | 29% | 45% |
| Spec 5 | 80% | 81% | 80% |
| Cutoff 6 | 1250 | 1460 | 1380 |
| Sens 6 | 19% | 29% | 18% |
| Spec 6 | 90% | 91% | 90% |
| OR Quart 2 | 3.5 | 1.0 | 2.9 |
| p Value | 0.15 | 1.0 | 0.24 |
| 95% CI of | 0.65 | 0.060 | 0.50 |
| OR Quart 2 | 19 | 17 | 16 |
| OR Quart 3 | 4.3 | 2.1 | 2.9 |
| p Value | 0.087 | 0.56 | 0.24 |
| 95% CI of | 0.81 | 0.18 | 0.50 |
| OR Quart 3 | 23 | 24 | 16 |
| OR Quart 4 | 8.2 | 3.2 | 7.5 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| p Value | 0.011 | 0.32 | 0.016 |
| 95% CI of | 1.6 | 0.32 | 1.4 |
| OR Quart 4 | 42 | 33 | 39 |

C-C motif chemokine 27

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 297 | 355 | 306 | 294 | 301 | 378 |
| Average | 340 | 372 | 345 | 374 | 341 | 397 |
| Stdev | 182 | 187 | 176 | 283 | 186 | 188 |
| p(t-test) | | 0.42 | | 0.69 | | 0.21 |
| Min | 29.4 | 129 | 29.4 | 129 | 29.4 | 144 |
| Max | 973 | 968 | 973 | 968 | 973 | 968 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.56 | 0.49 | 0.60 |
| SE | 0.065 | 0.11 | 0.071 |
| p | 0.40 | 0.90 | 0.17 |
| nCohort 1 | 90 | 109 | 82 |
| nCohort 2 | 26 | 7 | 22 |
| Cutoff 1 | 275 | 281 | 277 |
| Sens 1 | 73% | 71% | 73% |
| Spec 1 | 43% | 44% | 45% |
| Cutoff 2 | 228 | 144 | 257 |
| Sens 2 | 81% | 86% | 82% |
| Spec 2 | 31% | 7% | 44% |
| Cutoff 3 | 144 | 96.5 | 221 |
| Sens 3 | 92% | 100% | 91% |
| Spec 3 | 8% | 6% | 28% |
| Cutoff 4 | 404 | 412 | 405 |
| Sens 4 | 38% | 29% | 45% |
| Spec 4 | 70% | 71% | 71% |
| Cutoff 5 | 502 | 502 | 502 |
| Sens 5 | 15% | 14% | 18% |
| Spec 5 | 80% | 81% | 80% |
| Cutoff 6 | 600 | 600 | 616 |
| Sens 6 | 8% | 14% | 9% |
| Spec 6 | 90% | 91% | 90% |
| OR Quart 2 | 2.0 | 2.1 | 1.8 |
| p Value | 0.32 | 0.56 | 0.45 |
| 95% CI of | 0.51 | 0.18 | 0.39 |
| OR Quart 2 | 7.7 | 24 | 8.6 |
| OR Quart 3 | 2.8 | 2.1 | 3.4 |
| p Value | 0.12 | 0.56 | 0.10 |
| 95% CI of | 0.75 | 0.18 | 0.79 |
| OR Quart 3 | 10 | 24 | 15 |
| OR Quart 4 | 1.6 | 2.1 | 2.3 |
| p Value | 0.49 | 0.56 | 0.28 |
| 95% CI of | 0.41 | 0.18 | 0.51 |
| OR Quart 4 | 6.5 | 24 | 10 |

Vascular endothelial growth factor receptor 1

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 876 | 729 | 782 | 1130 | 902 | 681 |
| Average | 1290 | 1400 | 1260 | 2160 | 1400 | 1110 |
| Stdev | 1360 | 2030 | 1380 | 3090 | 1650 | 1390 |
| p(t-test) | | 0.74 | | 0.13 | | 0.44 |
| Min | 51.7 | 277 | 51.7 | 701 | 162 | 277 |
| Max | 10800 | 9150 | 10800 | 9150 | 10800 | 6930 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | | | | |
|---|---|---|---|---|---|---|
| n (Samp) | 90 | 26 | 109 | 7 | 82 | 22 |
| n (Patient) | 90 | 26 | 109 | 7 | 82 | 22 |

At Enrollment

| | sCr or UO | sCr only | UO only |
|---|---|---|---|
| AUC | 0.45 | 0.61 | 0.42 |
| SE | 0.065 | 0.12 | 0.071 |
| p | 0.46 | 0.35 | 0.23 |
| nCohort 1 | 90 | 109 | 82 |
| nCohort 2 | 26 | 7 | 22 |
| Cutoff 1 | 559 | 890 | 481 |
| Sens 1 | 73% | 71% | 73% |
| Spec 1 | 26% | 54% | 22% |
| Cutoff 2 | 448 | 754 | 412 |
| Sens 2 | 81% | 86% | 82% |
| Spec 2 | 21% | 46% | 17% |
| Cutoff 3 | 348 | 662 | 348 |
| Sens 3 | 92% | 100% | 91% |
| Spec 3 | 12% | 39% | 11% |
| Cutoff 4 | 1460 | 1440 | 1460 |
| Sens 4 | 19% | 14% | 18% |
| Spec 4 | 70% | 71% | 71% |
| Cutoff 5 | 1770 | 1710 | 1810 |
| Sens 5 | 12% | 14% | 9% |
| Spec 5 | 80% | 81% | 80% |
| Cutoff 6 | 2560 | 2560 | 2670 |
| Sens 6 | 8% | 14% | 5% |
| Spec 6 | 90% | 91% | 90% |
| OR Quart 2 | 2.0 | >2.1 | 1.0 |
| p Value | 0.32 | <0.54 | 1.0 |
| 95% CI of | 0.51 | >0.18 | 0.22 |
| OR Quart 2 | 7.7 | na | 4.5 |
| OR Quart 3 | 2.4 | >4.6 | 2.0 |
| p Value | 0.20 | <0.18 | 0.31 |
| 95% CI of | 0.63 | >0.49 | 0.51 |
| OR Quart 3 | 9.0 | na | 8.0 |
| OR Quart 4 | 2.0 | >1.0 | 2.0 |
| p Value | 0.32 | <0.98 | 0.31 |
| 95% CI of | 0.51 | >0.062 | 0.51 |
| OR Quart 4 | 7.7 | na | 8.0 |

SL cytokine

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0548 | 0.0622 | 0.0548 | 0.114 | 0.0548 | 0.0548 |
| Average | 8.73 | 5.74 | 8.18 | 6.27 | 9.24 | 6.78 |
| Stdev | 28.5 | 16.3 | 26.8 | 14.7 | 29.6 | 17.6 |
| p(t-test) | | 0.61 | | 0.85 | | 0.71 |
| Min | 0.0206 | 0.0206 | 0.0206 | 0.0206 | 0.0206 | 0.0206 |
| Max | 172 | 72.9 | 172 | 39.3 | 172 | 72.9 |
| n (Samp) | 90 | 26 | 109 | 7 | 82 | 22 |
| n (Patient) | 90 | 26 | 109 | 7 | 82 | 22 |

At Enrollment

| | sCr or UO | sCr only | UO only |
|---|---|---|---|
| AUC | 0.47 | 0.63 | 0.47 |
| SE | 0.065 | 0.12 | 0.070 |
| p | 0.65 | 0.26 | 0.64 |
| nCohort 1 | 90 | 109 | 82 |
| nCohort 2 | 26 | 7 | 22 |
| Cutoff 1 | 0.0206 | 0.0622 | 0.0206 |
| Sens 1 | 81% | 86% | 82% |
| Spec 1 | 17% | 55% | 16% |
| Cutoff 2 | 0.0206 | 0.0622 | 0.0206 |
| Sens 2 | 81% | 86% | 82% |
| Spec 2 | 17% | 55% | 16% |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| Cutoff 3 | 0 | 0 | 0 |
| Sens 3 | 100% | 100% | 100% |
| Spec 3 | 0% | 0% | 0% |
| Cutoff 4 | 0.114 | 0.114 | 0.114 |
| Sens 4 | 19% | 29% | 23% |
| Spec 4 | 79% | 80% | 79% |
| Cutoff 5 | 0.666 | 0.666 | 4.84 |
| Sens 5 | 19% | 29% | 18% |
| Spec 5 | 80% | 81% | 80% |
| Cutoff 6 | 19.6 | 23.0 | 19.6 |
| Sens 6 | 12% | 14% | 14% |
| Spec 6 | 90% | 91% | 90% |
| OR Quart 2 | 1.8 | 0 | 1.0 |
| p Value | 0.35 | na | 1.0 |
| 95% CI of | 0.52 | na | 0.25 |
| OR Quart 2 | 6.5 | na | 4.0 |
| OR Quart 3 | 1.5 | 4.5 | 1.3 |
| p Value | 0.52 | 0.19 | 0.73 |
| 95% CI of | 0.42 | 0.47 | 0.33 |
| OR Quart 3 | 5.5 | 43 | 4.8 |
| OR Quart 4 | 1.3 | 2.1 | 1.3 |
| p Value | 0.74 | 0.56 | 0.73 |
| 95% CI of | 0.34 | 0.18 | 0.33 |
| OR Quart 4 | 4.7 | 24 | 4.8 |

Immunoglogulin G3

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 605000 | 560000 | nd | nd | 600000 | 560000 |
| Average | 729000 | 880000 | nd | nd | 726000 | 880000 |
| Stdev | 484000 | 871000 | nd | nd | 492000 | 871000 |
| p(t-test) | | 0.32 | nd | nd | | 0.33 |
| Min | 94000 | 210000 | nd | nd | 94000 | 210000 |
| Max | 2930000 | 3750000 | nd | nd | 2930000 | 3750000 |
| n (Samp) | 81 | 17 | nd | nd | 74 | 17 |
| n (Patient) | 81 | 17 | nd | nd | 74 | 17 |

At Enrollment

| | sCr or UO | sCr only | UO only |
|---|---|---|---|
| AUC | 0.50 | nd | 0.50 |
| SE | 0.077 | nd | 0.078 |
| p | 0.99 | nd | 0.95 |
| nCohort 1 | 81 | nd | 74 |
| nCohort 2 | 17 | nd | 17 |
| Cutoff 1 | 385000 | nd | 385000 |
| Sens 1 | 71% | nd | 71% |
| Spec 1 | 23% | nd | 24% |
| Cutoff 2 | 327000 | nd | 327000 |
| Sens 2 | 82% | nd | 82% |
| Spec 2 | 16% | nd | 18% |
| Cutoff 3 | 244000 | nd | 244000 |
| Sens 3 | 94% | nd | 94% |
| Spec 3 | 4% | nd | 4% |
| Cutoff 4 | 826000 | nd | 833000 |
| Sens 4 | 29% | nd | 29% |
| Spec 4 | 70% | nd | 70% |
| Cutoff 5 | 960000 | nd | 1030000 |
| Sens 5 | 29% | nd | 24% |
| Spec 5 | 80% | nd | 81% |
| Cutoff 6 | 1300000 | nd | 1300000 |
| Sens 6 | 24% | nd | 24% |
| Spec 6 | 90% | nd | 91% |
| OR Quart 2 | 0.57 | nd | 0.72 |
| p Value | 0.48 | nd | 0.66 |
| 95% CI of | 0.12 | nd | 0.16 |
| OR Quart 2 | 2.7 | nd | 3.1 |
| OR Quart 3 | 0.76 | nd | 0.51 |
| p Value | 0.71 | nd | 0.40 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

|  | | | | | | |
|---|---|---|---|---|---|---|
| 95% CI of | 0.18 | | nd | | 0.11 | |
| OR Quart 3 | 3.2 | | nd | | 2.5 | |
| OR Quart 4 | 1.1 | | nd | | 0.94 | |
| p Value | 0.94 | | nd | | 0.94 | |
| 95% CI of | 0.26 | | nd | | 0.23 | |
| OR Quart 4 | 4.2 | | nd | | 3.9 | |

Interleukin-1 receptor type I

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 61.4 | 6,4.6 | 61.3 | 76.9 | 63.1 | 61.5 |
| Average | 69.7 | 70.6 | 68.8 | 87.1 | 71.5 | 70.8 |
| Stdev | 40.3 | 29.4 | 37.9 | 37.6 | 41.3 | 31.6 |
| p(t-test) |  | 0.92 |  | 0.22 |  | 0.94 |
| Min | 25.4 | 39.2 | 25.4 | 50.8 | 29.0 | 39.2 |
| Max | 315 | 144 | 315 | 144 | 315 | 144 |
| n (Samp) | 90 | 26 | 109 | 7 | 82 | 22 |
| n (Patient) | 90 | 26 | 109 | 7 | 82 | 22 |

At Enrollment

|  | sCr or UO | sCr only | UO only |
|---|---|---|---|
| AUC | 0.53 | 0.68 | 0.49 |
| SE | 0.065 | 0.11 | 0.070 |
| p | 0.68 | 0.12 | 0.88 |
| nCohort 1 | 90 | 109 | 82 |
| nCohort 2 | 26 | 7 | 22 |
| Cutoff 1 | 51.2 | 66.9 | 51.2 |
| Sens 1 | 73% | 71% | 73% |
| Spec 1 | 31% | 62% | 28% |
| Cutoff 2 | 50.3 | 52.2 | 47.8 |
| Sens 2 | 81% | 86% | 82% |
| Spec 2 | 31% | 33% | 21% |
| Cutoff 3 | 39.6 | 50.3 | 39.6 |
| Sens 3 | 92% | 100% | 91% |
| Spec 3 | 10% | 30% | 9% |
| Cutoff 4 | 72.2 | 72.1 | 75.6 |
| Sens 4 | 31% | 57% | 27% |
| Spec 4 | 70% | 71% | 71% |
| Cutoff 5 | 83.6 | 84.6 | 84.6 |
| Sens 5 | 23% | 29% | 27% |
| Spec 5 | 80% | 81% | 80% |
| Cutoff 6 | 87.9 | 96.4 | 87.9 |
| Sens 6 | 19% | 29% | 23% |
| Spec 6 | 90% | 91% | 90% |
| OR Quart 2 | 1.5 | >2.1 | 0.79 |
| p Value | 0.52 | <0.54 | 0.73 |
| 95% CI of | 0.42 | >0.18 | 0.21 |
| OR Quart 2 | 5.5 | na | 3.0 |
| OR Quart 3 | 1.5 | >2.1 | 1.0 |
| p Value | 0.52 | <0.54 | 1.0 |
| 95% CI of | 0.42 | >0.18 | 0.28 |
| OR Quart 3 | 5.5 | na | 3.6 |
| OR Quart 4 | 1.5 | >3.3 | 0.79 |
| p Value | 0.52 | <0.31 | 0.73 |
| 95% CI of | 0.42 | >0.33 | 0.21 |
| OR Quart 4 | 5.5 | na | 3.0 |

Interleukin-29

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 . |
| Median | 25.8 | 107 | 49.5 | 380 | 25.8 | 107 |
| Average | 98.1 | 165 | 96.0 | 378 | 105 | 139 |
| Stdev | 211 | 224 | 193 | 353 | 222 | 193 |
| p(t-test) |  | 0.17 |  | 6.0E−4 |  | 0.51 |
| Min | 0.690 | 0.690 | 0.690 | 2.06 | 0.690 | 0.690 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | | | | |
|---|---|---|---|---|---|---|
| Max | 1520 | 917 | 1520 | 917 | 1520 | 917 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.66 | 0.76 | 0.65 |
| SE | 0.064 | 0.11 | 0.070 |
| p | 0.014 | 0.015 | 0.035 |
| nCohort 1 | 90 | 109 | 82 |
| nCohort 2 | 26 | 7 | 22 |
| Cutoff 1 | 49.5 | 131 | 49.5 |
| Sens 1 | 73% | 71% | 77% |
| Spec 1 | 56% | 81% | 55% |
| Cutoff 2 | 20.7 | 20.7 | 46.8 |
| Sens 2 | 81% | 86% | 82% |
| Spec 2 | 43% | 39% | 54% |
| Cutoff 3 | 2.06 | 1.65 | 1.65 |
| Sens 3 | 92% | 100% | 95% |
| Spec 3 | 22% | 19% | 20% |
| Cutoff 4 | 80.3 | 80.9 | 80.9 |
| Sens 4 | 54% | 71% | 55% |
| Spec 4 | 70% | 71% | 73% |
| Cutoff 5 | 131 | 131 | 134 |
| Sens 5 | 31% | 71% | 23% |
| Spec 5 | 80% | 81% | 82% |
| Cutoff 6 | 197 | 197 | 197 |
| Sens 6 | 19% | 57% | 14% |
| Spec 6 | 90% | 91% | 90% |
| OR Quart 2 | 1.0 | 1.0 | 1.0 |
| p Value | 1.0 | 1.0 | 1.0 |
| 95% CI of OR Quart 2 | 0.22 | 0.060 | 0.18 |
| | 4.4 | 17 | 5.5 |
| OR Quart 3 | 2.4 | 0 | 3.4 |
| p Value | 0.20 | na | 0.10 |
| 95% CI of OR Quart 3 | 0.63 | na | 0.79 |
| | 9.0 | na | 15 |
| OR Quart 4 | 3.3 | 5.8 | 3.4 |
| p Value | 0.073 | 0.12 | 0.10 |
| 95% CI of OR Quart 4 | 0.89 | 0.64 | 0.79 |
| | 12 | 53 | 15 |

| | Interleukin-7 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0293 | 0.239 | 0.0293 | 3.15 | 0.0293 | 0.0293 |
| Average | 5.12 | 3.06 | 4.54 | 6.50 | 4.83 | 3.00 |
| Stdev | 17.7 | 5.16 | 16.2 | 8.07 | 17.9 | 5.35 |
| p(t-test) | | 0.56 | | 0.75 | | 0.64 |
| Min | 0.00806 | 0.00806 | 0.00806 | 0.0293 | 0.00806 | 0.00806 |
| Max | 153 | 22.9 | 153 | 22.9 | 153 | 22.9 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.52 | 0.74 | 0.51 |
| SE | 0.065 | 0.11 | 0.070 |
| p | 0.80 | 0.030 | 0.93 |
| nCohort 1 | 90 | 109 | 82 |
| nCohort 2 | 26 | 7 | 22 |
| Cutoff 1 | 0.0144 | 2.20 | 0.0119 |
| Sens 1 | 73% | 71% | 77% |
| Spec 1 | 34% | 68% | 16% |
| Cutoff 2 | 0.0119 | 0.131 | 0.00806 |
| Sens 2 | 81% | 86% | 82% |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

|  |  |  |  |
|---|---|---|---|
| Spec 2 | 14% | 55% | 13% |
| Cutoff 3 | 0 | 0.0245 | 0 |
| Sens 3 | 100% | 100% | 100% |
| Spec 3 | 0% | 40% | 0% |
| Cutoff 4 | 2.39 | 2.59 | 2.25 |
| Sens 4 | 38% | 57% | 36% |
| Spec 4 | 70% | 71% | 71% |
| Cutoff 5 | 3.83 | 3.95 | 3.83 |
| Sens 5 | 27% | 43% | 27% |
| Spec 5 | 80% | 81% | 80% |
| Cutoff 6 | 8.54 | 8.54 | 8.54 |
| Sens 6 | 12% | 29% | 9% |
| Spec 6 | 90% | 91% | 90% |
| OR Quart 2 | 1.2 | >1.0 | 0.79 |
| p Value | 0.75 | <0.98 | 0.73 |
| 95% CI of | 0.35 | >0.062 | 0.21 |
| OR Quart 2 | 4.2 | na | 3.0 |
| OR Quart 3 | 1.0 | >3.3 | 0.79 |
| p Value | 1.0 | <0.31 | 0.73 |
| 95% CI of | 0.28 | >0.33 | 0.21 |
| OR Quart 3 | 3.6 | na | 3.0 |
| OR Quart 4 | 1.2 | >3.3 | 1.0 |
| p Value | 0.75 | <0.31 | 1.0 |
| 95% CI of | 0.35 | >0.33 | 0.28 |
| OR Quart 4 | 4.2 | na | 3.6 |

Platelet-derived growth factor subunit A (dimer)

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 1140 | 939 | nd | nd | 964 | 747 |
| Average | 2380 | 2000 | nd | nd | 2160 | 2080 |
| Stdev | 2880 | 2330 | nd | nd | 2730 | 2460 |
| p(t-test) |  | 0.51 | nd | nd |  | 0.89 |
| Min | 5.98 | 5.98 | nd | nd | 5.98 | 5.98 |
| Max | 12300 | 10300 | nd | nd | 12300 | 10300 |
| n (Samp) | 109 | 28 | nd | nd | 98 | 25 |
| n (Patient) | 109 | 28 | nd | nd | 98 | 25 |

At Enrollment

|  | sCr or UO | sCr only | UO only |
|---|---|---|---|
| AUC | 0.50 | nd | 0.52 |
| SE | 0.061 | nd | 0.065 |
| p | 0.95 | nd | 0.80 |
| nCohort 1 | 109 | nd | 98 |
| nCohort 2 | 28 | nd | 25 |
| Cutoff 1 | 508 | nd | 456 |
| Sens 1 | 71% | nd | 172% |
| Spec 1 | 34% | nd | 36% |
| Cutoff 2 | 376 | nd | 376 |
| Sens 2 | 82% | nd | 80% |
| Spec 2 | 30% | nd | 33% |
| Cutoff 3 | 155 | nd | 155 |
| Sens 3 | 93% | nd | 92% |
| Spec 3 | 15% | nd | 15% |
| Cutoff 4 | 2710 | nd | 2470 |
| Sens 4 | 25% | nd | 32% |
| Spec 4 | 71% | nd | 70% |
| Cutoff 5 | 4550 | nd | 3710 |
| Sens 5 | 18% | nd | 20% |
| Spec 5 | 81% | nd | 81% |
| Cutoff 6 | 7080 | nd | 5390 |
| Sens 6 | 4% | nd | 4% |
| Spec 6 | 91% | nd | 91% |
| OR Quart 2 | 1.0 | nd | 3.1 |
| p Value | 0.95 | nd | 0.087 |
| 95% CI of | 0.32 | nd | 0.85 |
| OR Quart 2 | 3.4 | nd | 11 |
| OR Quart 3 | 1.7 | nd | 0.96 |

TABLE 12-continued

Comparison of marker levels in enroll EDTA samples
collected from Cohort 1 (patients that did not progress beyond
RIFLE stage 0 or R within 48 hrs) and in enroll EDTA
samples collected from Cohort 2 (subjects reaching RIFLE
stage I or F within 48 hrs). Enroll samples from patients already
at stage I or F were included in Cohort 2.

| | | | |
|---|---|---|---|
| p Value | 0.37 | nd | 0.96 |
| 95% CI of | 0.55 | nd | 0.22 |
| OR Quart 3 | 5.1 | nd | 4.3 |
| OR Quart 4 | 0.53 | nd | 1.9 |
| p Value | 0.36 | nd | 0.35 |
| 95% CI of | 0.14 | nd | 0.49 |
| OR Quart 4 | 2.0 | nd | 7.3 |

Platelet-derived growth factor A

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 4290 | 3800 | nd | nd | 3770 | 3220 |
| Average | 9010 | 10300 | nd | nd | 7920 | 11000 |
| Stdev | 13200 | 21000 | nd | nd | 10300 | 22200 |
| p(t-test) | | 0.69 | nd | nd | | 0.31 |
| Min | 3.72 | 9.75 | nd | nd | 3.72 | 9.75 |
| Max | 94900 | 103000 | nd | nd | 54100 | 103000 |
| n (Samp) | 109 | 28 | nd | nd | 98 | 25 |
| n (Patient) | 109 | 28 | nd | nd | 98 | 25 |

At Enrollment

| | sCr or UO | sCr only | UO only |
|---|---|---|---|
| AUC | 0.47 | nd | 0.48 |
| SE | 0.062 | nd | 0.065 |
| p | 0.62 | nd | 0.78 |
| nCohort 1 | 109 | nd | 98 |
| nCohort 2 | 28 | nd | 25 |
| Cutoff 1 | 1700 | nd | 1470 |
| Sens 1 | 71% | nd | 72% |
| Spec 1 | 30% | nd | 29% |
| Cutoff 2 | 1220 | nd | 1220 |
| Sens 2 | 82% | nd | 80% |
| Spec 2 | 26% | nd | 28% |
| Cutoff 3 | 333 | nd | 333 |
| Sens 3 | 93% | rid | 92% |
| Spec 3 | 10% | nd | 11% |
| Cutoff 4 | 9820 | nd | 8330 |
| Sens 4 | 21% | nd | 32% |
| Spec 4 | 71% | nd | 70% |
| Cutoff 5 | 13900 | nd | 12400 |
| Sens 5 | 11% | nd | 16% |
| Spec 5 | 81% | nd | 81% |
| Cutoff 6 | 22900 | nd | 21500 |
| Sens 6 | 11% | nd | 12% |
| Spec 6 | 91% | nd | 91% |
| OR Quart 2 | 1.3 | nd | 0.80 |
| p Value | 0.71 | nd | 0.74 |
| 95% CI of | 0.37 | nd | 0.22 |
| OR Quart 2 | 4.2 | nd | 3.0 |
| OR Quart 3 | 1.7 | nd | 1.7 |
| p Value | 0.35 | nd | 0.38 |
| 95% CI of | 0.54 | nd | 0.52 |
| OR Quart 3 | 5.6 | nd | 5.6 |
| OR Quart 4 | 1.0 | nd | 0.83 |
| p Value | 0.96 | nd | 0.79 |
| 95% CI of | 0.30 | nd | 0.22 |
| OR Quart 4 | 3.6 | nd | 3.1 |

Thymic stromal lymphopoietin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0181 | 4.77 | 0.630 | 9.16 | 0.183 | 4.77 |
| Average | 260 | 28.1 | 217 | 59.5 | 285 | 18.5 |
| Stdev | 2130 | 66.6 | 1930 | 115 | 2230 | 34.6 |
| p(t-test) | | 0.58 | | 0.83 | | 0.58 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | | | | |
|---|---|---|---|---|---|---|
| Min | 0.00640 | 0.00640 | 0.00640 | 0.0129 | 0.00640 | 0.00640 |
| Max | 20000 | 314 | 20000 | 314 | 20000 | 126 |
| n (Samp) | 89 | 26 | 108 | 7 | 81 | 22 |
| n (Patient) | 89 | 26 | 108 | 7 | 81 | 22 |

| | At Enrollment | | |
|---|---|---|---|
| | sCr or UO | sCr only | UO only |
| AUC | 0.62 | 0.67 | 0.63 |
| SE | 0.065 | 0.12 | 0.070 |
| p | 0.067 | 0.15 | 0.066 |
| nCohort 1 | 89 | 108 | 81 |
| nCohort 2 | 26 | 7 | 22 |
| Cutoff 1 | 0.0174 | 1.06 | 1.06 |
| Sens 1 | 73% | 71% | 73% |
| Spec 1 | 47% | 56% | 60% |
| Cutoff 2 | 0.0123 | 0.0129 | 0.0123 |
| Sens 2 | 88% | 86% | 86% |
| Spec 2 | 9% | 18% | 9% |
| Cutoff 3 | 0 | 0.0123 | 0 |
| Sens 3 | 100% | 100% | 100% |
| Spec 3 | 0% | 10% | 0% |
| Cutoff 4 | 4.05 | 4.64 | 3.13 |
| Sens 4 | 58% | 57% | 64% |
| Spec 4 | 71% | 70% | 70% |
| Cutoff 5 | 6.92 | 6.92 | 6.92 |
| Sens 5 | 31% | 57% | 27% |
| Spec 5 | 81% | 81% | 80% |
| Cutoff 6 | 17.1 | 18.0 | 17.1 |
| Sens 6 | 27% | 43% | 27% |
| Spec 6 | 91% | 91% | 90% |
| OR Quart 2 | 0.27 | 0.96 | 0.16 |
| p Value | 0.13 | 0.98 | 0.11 |
| 95% CI of | 0.050 | 0.057 | 0.017 |
| OR Quart 2 | 1.5 | 16 | 1.5 |
| OR Quart 3 | 1.2 | 0.96 | 1.5 |
| p Value | 0.81 | 0.98 | 0.56 |
| 95% CI of | 0.34 | 0.057 | 0.40 |
| OR Quart 3 | 4.0 | 16 | 5.5 |
| OR Quart 4 | 2.2 | 4.3 | 2.1 |
| p Value | 0.18 | 0.20 | 0.25 |
| 95% CI of | 0.69 | 0.45 | 0.59 |
| OR Quart 4 | 7.2 | 41 | 7.5 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating renal status in a subject and treating the subject based on the evaluation, the method comprising:
    performing an assay configured to detect matrix metalloproteinase-9:tissue inhibitor of metalloproteinase 2 (MMP9:TIMP2) complex in a body fluid sample obtained from the subject to generate an assay result;
    correlating the assay result to an increased risk of having acute kidney injury within 7 days of the time at which the sample is obtained from the subject when the assay result is above a predetermined threshold; and
    treating the subject having the increased risk of having acute kidney injury within 7 days with a compatible treatment regimen, wherein the compatible treatment regimen comprises one or more of initiating renal replacement therapy, withdrawing delivery of compounds that are known to be damaging to the kidney, delaying procedures that are known to be damaging to the kidney, modifying diuretic administration, and monitoring and optimizing hemodynamics and fluid administration.

2. The method of claim 1, wherein the increased risk of having acute kidney injury within 7 days is an increased risk of having RIFLE stage I or F or AKIN stage II or III acute kidney injury within 7 days.

3. The method of claim 1, wherein the increased risk of having acute kidney injury within 7 days is an increased risk of having RIFLE F or AKIN stage III acute kidney injury within 7 days.

4. The method of claim 1, wherein said assay result is a measured concentration of MMP9:TIMP2 complex.

5. The method of claim 1, wherein said correlating step comprises correlating the assay result to an increased risk of the subject having acute kidney injury within 48 hours of the time at which the sample is obtained.

6. The method of claim 1, wherein said correlating step comprises correlating the assay result to an increased risk of the subject having acute kidney injury within 24 hours of the time at which the sample is obtained.

7. The method of claim 1, wherein said correlating step comprises correlating the assay result to an increased risk of the subject having acute kidney injury within 12 hours of the time at which the sample is obtained.

8. The method according to claim 1, wherein the subject is in RIFLE stage 0 or R or AKIN stage I at the time at which the sample is obtained.

9. The method of claim 1, wherein the body fluid sample comprises a urine sample, whole blood sample, serum sample, or plasma sample.

10. The method of claim 1, wherein the increased risk of having acute kidney injury within 7 days is an increased risk of having future acute kidney injury.

11. The method of claim 1, wherein the correlating step comprises determining that the subject currently has acute kidney injury.

12. The method of claim 1, wherein the acute kidney injury is prerenal acute kidney injury.

13. The method of claim 1, wherein the compatible treatment regimen comprises monitoring and optimizing hemodynamics and fluid administration, and wherein monitoring and optimizing hemodynamics and fluid administration comprises monitoring one or more of extracellular fluid (ECF) volume depletion, cardiac output, and systemic vascular resistance.

14. A method of detecting a marker of acute kidney injury in a subject under clinical evaluation for kidney injury, the method comprising
    performing an assay to detect a level of matrix metalloproteinase-9:tissue inhibitor of metalloproteinase 2 (MMP9:TIMP2) complex within a urine, whole blood, plasma, or serum sample obtained from the subject.

15. The method of claim 14, wherein the sample is obtained within 7 days after an acute medical event which predisposes the subject for developing acute kidney injury.

16. The method of claim 15, wherein the acute medical event comprises shock, sepsis, hemorrhage, an ischemic surgery, myocardial infarction, cardiac tamponade, increased intra-abdominal pressure with acute decompensated heart failure, ischemia, pulmonary embolism, pancreatitis, a burn, excessive diuresis, major trauma, or anaphylaxis.

17. The method of claim 15, wherein the acute medical event comprises exposure to an NSAID, a cyclosporine, tacrolimus, an aminoglycoside, foscarnet, ethylene glycol, hemoglobin, myoglobin, ifosfamide, a heavy metal, methotrexate, radiopaque contrast media, streptozotocin, an antihypertensive drug, an ACE-inhibitor, an angiotensin II receptor blocker, an anesthetic, a β-lactam, a sulfonamide, ciprofloxacin, a thiazide diuretic, furosemide, phenytoin, allopurinol, triamterene, acyclovir, or indinavir.

18. The method of claim 14, further comprising measuring a volume of urine output, urine flow rate, serum creatinine, or urine creatinine when the sample is obtained or within 7 days after the sample is obtained.

19. The method of claim 14, wherein the subject has an existing diagnosis of one or more of congestive heart failure, preeclampsia, eclampsia, diabetes mellitus, hypertension, coronary artery disease, aneurism, chronic obstructive pulmonary disease, pulmonary hypertension, hypotension, shock, sepsis, liver failure, hypercalcemia, lymphoma, sarcoidosis, leukemia, a ureteral obstruction, a bladder obstruction, proteinuria, renal insufficiency, glomerular filtration below the normal range, cirrhosis, serum creatinine above the normal range, chronic kidney disease, hepatorenal syndrome, renal artery obstruction, renal vein thrombosis, crescentic glomerulonephritis, polyarteritis nodosa, Wegener's granulomatosis, Goodpasture's syndrome, Lupus glomerulonephritis, postinfectious glomerulonephritis, cryoglobulinemic glomerulonephritis, pyelonephritis, papillary necrosis, tubular precipitation injury to renal function, reduced renal function, and acute kidney injury; or wherein the subject is on positive-pressure mechanical ventilation.

20. A method of treating a subject for acute kidney injury, the method comprising:
  selecting the subject for treatment based on the subject's having a matrix metalloproteinase-9:tissue inhibitor of metalloproteinase 2 (MMP9:TIMP2) complex level in a body fluid sample being above a predetermined threshold indicating an increased risk of having acute kidney injury within 7 days from the time the sample was obtained; and
  treating the subject with a compatible treatment regimen, wherein the compatible treatment regimen comprises one or more of initiating renal replacement therapy, withdrawing delivery of compounds that are known to be damaging to the kidney, delaying procedures that are known to be damaging to the kidney, modifying diuretic administration, and monitoring kidney reperfusion.

* * * * *